US008779237B2

(12) United States Patent
Hatzfeld

(10) Patent No.: US 8,779,237 B2
(45) Date of Patent: Jul. 15, 2014

(54) PLANTS HAVING ENHANCED YIELD-RELATED TRAITS AND A METHOD FOR MAKING THE SAME

(75) Inventor: Yves Hatzfeld, Lille (FR)

(73) Assignee: BASF Plant Science GmbH, Ludwigshafen (DE)

( * ) Notice: Subject to any disclaimer, the term of this patent is extended or adjusted under 35 U.S.C. 154(b) by 366 days.

(21) Appl. No.: 13/000,067

(22) PCT Filed: Jun. 22, 2009

(86) PCT No.: PCT/EP2009/057722

§ 371 (c)(1), (2), (4) Date: Dec. 20, 2010

(87) PCT Pub. No.: WO2009/156360

PCT Pub. Date: Dec. 30, 2009

(65) Prior Publication Data

US 2011/0107464 A1 May 5, 2011

Related U.S. Application Data

(60) Provisional application No. 61/075,909, filed on Jun. 26, 2008, provisional application No. 61/076,178, filed on Jun. 27, 2008, provisional application No. 61/076,158, filed on Jun. 27, 2008, provisional application No. 61/078,471, filed on Jul. 7, 2008.

(30) Foreign Application Priority Data

| | | |
|---|---|---|
| Jun. 26, 2008 | (EP) | 08159089 |
| Jun. 26, 2008 | (EP) | 08159093 |
| Jun. 26, 2008 | (EP) | 08159099 |
| Jul. 4, 2008 | (EP) | 08159746 |

(51) Int. Cl.
*A01H 1/00* (2006.01)

(52) U.S. Cl.
USPC .......... 800/290; 800/298

(58) Field of Classification Search
None
See application file for complete search history.

(56) References Cited

U.S. PATENT DOCUMENTS

| | | | |
|---|---|---|---|
| 6,921,848 | B2 | 7/2005 | Chory et al. |
| 7,262,057 | B2 | 8/2007 | Torne Cubiro et al. |
| 2006/0005266 | A1 | 1/2006 | Torne Cubiro et al. |
| 2008/0148432 | A1 | 6/2008 | Abad |
| 2010/0092606 | A1 | 4/2010 | Torne Cubiro et al. |

FOREIGN PATENT DOCUMENTS

WO WO-03/102128 A1 12/2003

OTHER PUBLICATIONS

Schneider et al, 1997, Development, 124:1780-1798.*

Sugimoto-Shirasu et al, 2005, PNAS, 102: 18736-18741.*

Schneider et al, 1998, Genes Dev., 12:2013-2021.*

Hirel et al, 2007, J. Experimental Botany, 58:2369-2387.*

Sylvia de Pater et al, 1992, The Plant Journal, 2:837-844.*

Botstein, D., et al., "Construction of a Genetic Linkage Map in Man Using Restriction Fragment Length Polymorphisms," Am. J. Hum. Genet., 1980, vol. 32, pp. 314-331.

Claparols, M. I., et al., "Transgenic Rice as a Vehicle for the Production of the Industrial Enzyme Transglutaminase," Transgenic Research, 2004, vol. 13, pp. 195-199.

He, J.-X., et al., "BZR1 Is a Transcriptional Repressor with Dual Roles in Brassinosteroid Homeostasis and Growth Responses," Science, 2005, vol. 307, pp. 1634-1638.

Rushton, P. J., et al., "Tobacco Transcription Factors: Novel Insights into Transcriptional Regulation in the Solanaceae," Plant Physiology, 2008, vol. 147, pp. 280-295.

Schellmann, S., et al., "Triptychon and Caprice Mediate Lateral Inhibition During Trichome and Root Hair Patterning in *Arabidopsis*," The EMBO Journal, 2002, vol. 21, No. 19, pp. 5036-5046.

Villalobos, E., et al., "Molecular Cloning and Characterization of a Maize Transglutaminase Complementary DNA," Gene, 2004, vol. 336, pp. 93-104.

Wang, Z.-Y., et al., "The Brassinosteroid Signal Transduction Pathway," Cell Research, 2006, vol. 16, pp. 427-434.

Xue, G.-P., "A CELD-Fusion Method for Rapid Determination of the DNA-Binding Sequence Specificity of Novel Plant DNA-Binding Proteins," The Plant Journal, 2005, vol. 41, pp. 638-649.

Schneider, K., et al., "The Root Hairless 1 Gene Encodes a Nuclear Protein Required for Root Hair Initiation in *Arabidopsis*", Genes Dev., 1998, vol. 12, No. 13, pp. 2013-2021.

Sugimoto-Shirasu, K., et al., "RHL1 Is an Essential Component of the Plant DNA Topoisomerase VI Complex and Is Required for Ploidy-Dependent Cell Growth", Proc. Natl. Acad. Sci. U.S.A., 2005, vol. 102, No. 51, pp. 18736-18741.

* cited by examiner

*Primary Examiner* — Ashwin Mehta
*Assistant Examiner* — Jason Deveau Rosen
(74) *Attorney, Agent, or Firm* — Novak Druce Connolly Bove + Quigg LLP

(57) ABSTRACT

The present invention relates generally to the field of molecular biology and concerns a method for enhancing various plant yield-related traits by modulating expression in a plant of a nucleic acid encoding a RHL1 (Root Hairless 1). The present invention also concerns plants having modulated expression of a nucleic acid encoding a RHL1, which plants have enhanced various plant yield-related relative to corresponding wild type plants or other control plants. The invention also provides constructs useful in the methods of the invention.

21 Claims, 66 Drawing Sheets

MVRASSSKKGGSKGGDKDDAESKQRKRLKTLALDNQLLSDSP
AKSHSSLKPSKQVLKHHGTDIIRKSQRKNRFLFSFPGLLAPI
SAATIGDLDRLSTKNPVLYLNFPQGRMKLFGTILYPKNRYLT
LQFSRGGKNVLCDDYFDNMIVFSESWWIGTKEENPEEARLDF
PKELAQAENTEFDFQGGAGGAASVKKLASPEIGSQPTETDSP
EVDNEDVLSEDGEFLDDKIQVTPPVQLTPPVQVTPVRQSQRN
SGKKFNFAETSSEASSGESEGNTSDEDEKPLLEPESSTRSRE
ESQDGNGITASASKLPEELPAKREKLKSKDSKLVQATLSNLF
KKAEEKTAGTSKAKSSSKA

FIGURE 1

```
CLUSTAL W (1.83)

O.sativa_Os07g07580                --------------------------------------------------
O.sativa_Os06g51380                --------------------------------------------------
Z.mays_TA180670                    MAVFSASKAVSDESAFRVAGRVFVFVSSRLVPNTRTRHADTRIVPPNFCS
A.formosa_TA10038                  --------------------------------------------------
V.vinifera_GSVIVT00027050001       --------------------------------------------------
M.domestica_TA43921                --------------------------------------------------
S.tuberosum_TA36268                --------------------------------------------------
p.trichocarpa_scaff_IV.277         --------------------------------------------------
A.thaliana_AT1G48380.1             --------------------------------------------------
P.patens_74926                     --------------------------------------------------
P.patens_173149                    --------------------------------------------------


O.sativa_Os07g07580                -----------------------------MVKKKE---AGDAEAD-----
O.sativa_Os06g51380                -----------------------------MVKKKP---AGDAEAD-----
Z.mays_TA180670                    EISSSRLISLFQSITSSNLYPKPYTGGRGMVKKAVSTAPADAEAD-----
A.formosa_TA10038                  -----------------------------MVRATS---KKIEND------
V.vinifera_GSVIVT00027050001       -----------------------------MVRVS----KKNENGG--VSE
M.domestica_TA43921                -----------------------------MARTSSSKKRKHEDDEGAEAE
S.tuberosum_TA36268                -----------------------------MARGG----KKAANGE-----
p.trichocarpa_scaff_IV.277         -----------------------------MVKSKK---TEASNSN----R
A.thaliana_AT1G48380.1             -----------------------------MVRASSS--KKGGSKG--GDK
P.patens_74926                     -----------------------------MGKKK-VEEVSQTKEE-----
P.patens_173149                    -----------------------------MGKKKQVEEVSQTKED-----
                                                                * :          .
```

FIGURE 2

```
O.sativa_Os07g07580           ------ERRRLRSLAFSNGLLQRGEPAAPRSALAPSTAVSRLQGRDIVRR
O.sativa_Os06g51380           ------ERRRLRSLAFSNGLLQRGEPAAPRSALAPSTAVSRLQGRDIVRR
Z.mays_TA180670               ------ERRRLRSLAFSNGLLQRGDPAAPRAPLAPAAAVTRLQGRDVVRR
A.formosa_TA10038             ------DDRSRLKKLALSRNLLSQ-TPSKPSSTLSLSKTVLKHHGKDIMKK
V.vinifera_GSVIVT00027050001  LNPEAEERKRKKLAFSKNLLSD-TPSKAFSALSPSKTVIKHHGKDILKK
M.domestica_TA43921           AEPEVAQRKRLKALAFSNNQLSE-IPAKPRAPLTPSNGVLKQHGKDIVKK
S.tuberosum_TA36268           SNPDMEEKKRLKKLAISKQMVSE-NPSRDNNSLNPSKTVIKHHGKDILRK
p.trichocarpa_scaff_IV.277    ENPDVLERKRLKKLAITNNIVSD-AQVKAPYSLNPSKTVAKHHGKDIIRK
A.thaliana_AT1G48380.1        DDAESKQRKRLKTLALDNQLLSD-SPAKSHSSLKPSKQVLKHHGTDIIRK
P.patens_74926                -KTLAKESKRLRELALTSGLLSE-KKAVPDAPMHPHSGIVRCDGKDICKK
P.patens_173149               -KSLEKQSKKLRELARSCGLVSE-KKALPAEALRPKWGIVKCDGKDICKK
                                   :       * * :           .              * ::  :*

O.sativa_Os07g07580           GGQRKSRFLFSFPGLLAPAAAASGGRVGELADLGTKNPLLYLDFPQ----
O.sativa_Os06g51380           GGQRKSRFLFSFPGLLAPAAAASGGRVGELADLGTKNPLLYLDFPQ----
Z.mays_TA180670               GGQRKSRYLFSFPGLLAP--AASGGRVGELADLGTKNPLLYLEFPQ----
A.formosa_TA10038             S-QRKNRFLFSFPGLLGP--ITGG-KVGELKDLGTMKPILYLDFPQ----
V.vinifera_GSVIVT00027050001  S-QRKNRFLFSFPGLLAP--IAGG-KIGELKDLGTKNPILYLDFPQ----
M.domestica_TA43921           S-QRKNKFLFSFPGLLAP--IGGG-KIGDLKDLDTKNPVLYLQFPL----
S.tuberosum_TA36268           S-QRKNRFLFSLPGLLAP--VSGG-KIGELKDLGTKNPILYLDFPQ----
p.trichocarpa_scaff_IV.277    S-QRKNRFLFSFPGLLAP--INGGGKIGELKDLSSKNPVLYLDFPQ----
A.thaliana_AT1G48380.1        S-QRKNRFLFSFPGLLAP--ISAA-TIGDLDRLSTKNPVLYLNFPQ----
P.patens_74926                G-HRKNKYLFSFPGLVAP---VAVGKFGDLTQLDTKNPILYVDFLQASRA
P.patens_173149               G-HRKNKYLFSFPGLVAP---VSGGKFGELTQLDSRNPILYIDFPQ----
                              . :**:*:***:***:.*     .   .*  *..::*:**::* :
```

FIGURE 2 (continued)

```
O.sativa_Os07g07580                 ----GRMKLLGTHVYPKNKYLTLQMSRSTKGVVCEDVFESLIVFSEAWWI
O.sativa_Os06g51380                 ----VSYIYLSIPSGEDEAVGDACVPQEQVSDTADDVFESLIVFSEAWWI
Z.mays_TA180670                     ----GRMKLFGTHVYPKNKYLTLQMTRSAKGVVCEDVFESLIVFSEAWWV
A.formosa_TA10038                   ----GRVKMFGTIVYPKNRYLTLHFSKGGKNVMCEDHFDNMVVFSDAWWI
V.vinifera_GSVIVT00027050001        ----GQMKLFGTIVYPKNRYLTLHFSRGGKNVMCEDYFDNMIVFSDAWWI
M.domestica_TA43921                 ----GQMKLFGTLVFPKNRYLTMQFPKGGKSVMCEDYFDNMIVFSDAWWI
S.tuberosum_TA36268                 ----GQMKLFGTIVYPKNGYLTMQFSRGGKNVVCEDYLDNMIVFSDAWWI
p.trichocarpa_scaff_IV.277          ----GQMKLFGTILHPKNRYLTLQFSRSGKNVMCEDYFDHMIIFSEAWWI
A.thaliana_AT1G48380.1              ----GRMKLFGTILYPKNRYLTLQFSRGGKNVLCDDYFDNMIVFSESWWI
P.patens_74926                      FAQTGRLKLFGTIVYSKNKYITLNFVRGAGSIQCEDIFENLVVFSDAWWI
P.patens_173149                     ----GRLKLFGTIVYPINKYITMNFVRGAGSILCEDLFESMVVFPEAWWV
                                             :.      :      . :   .  .:* :: :::*.::**:

O.sativa_Os07g07580                 GTKEE-NPQELKLDFPKEFQNDGAVADSDFKG--GAGASCDEAVTINKPP
O.sativa_Os06g51380                 GTKEEENPQELKLDFPKEFQNDEAVADSDFKG--GAGASCDEAVSINKPP
Z.mays_TA180670                     GTKED-NPEELKLEFPKEFQNDGTTADCDFRG--GAGGAIDEATGS-KAG
A.formosa_TA10038                   GTKDE-NPEEVQLEFPKNLIKGK-HTDADFKGGAGAGATSEQKPGPNKPR
V.vinifera_GSVIVT00027050001        GRKEE-NPEEARLEFPKELSEGQ-SVEYDFKG--GAGMASDSKQGVNKPE
M.domestica_TA43921                 GTKDE-NPE-AQLDFPKELTEGQ-HSEFDFQG--GAGSTSAKKQSDSKNE
S.tuberosum_TA36268                 GRKDE-NPEEARLEFPKELNVQQEKSECDFKG--GAGATCVQKRSTSECG
p.trichocarpa_scaff_IV.277          GTKEE-NPEELKLDFPNELFEGK-GVECDFKG--GAGAGSVNKQVLQKSG
A.thaliana_AT1G48380.1              GTKEE-NPEEARLDFPKELAQAE-NTEFDFQGG-AGGAASVKKLASPEIG
P.patens_74926                      GTKEE-NPDELRLEMPLDFQQER-HAVYDFAG--GAGKPRNIKDDVDVQD
P.patens_173149                     GKKEE-NPDELRLDMPLDLQQEK-HQVYDFTG--GAGEPRDSRKYGDVQP
                                    * *:: **:  :*::* ::        ** *  ..*
```

FIGURE 2 (continued)

```
O.sativa_Os07g07580           KETTTGSLSPKIESDIDSSEDSDLKD--------------EDNTQ-------
O.sativa_Os06g51380           KETTTGSLSPKIESDIDSSEDSDLKD--------------EDNTQ-------
Z.mays_TA180670               KEIAE-PRSPKFASDDDAPEDSNHKD--------------ENNTQ-------
A.formosa_TA10038             -KEYVETETPSTDVEDVSEDFDSLN---------------EKNKD-------
V.vinifera_GSVIVT00027050001  -MKYVEPQSPKPELEDDLSGEDSLKD--------------VVEMTPK-----
M.domestica_TA43921           -TTYVEEYSPHNKVEDNLSD--------------------EENNE-------
S.tuberosum_TA36268           -VKHVEQQSPEHEQEELLSESQ------------------NDSKE-------
p.trichocarpa_scaff_IV.277    GTKYVKEESPETELDDDLSDDN------------------NDFKD-------
A.thaliana_AT1G48380.1        -SQPTETDSPEVDNEDVLSEDGEFLDDKIQVTPPVQLTP-------------
P.patens_74926                SQLELVQVSELESSKQCTPKGQLKMDRWLFQKKPSENKTLEKSFESNAKT--
P.patens_173149               IQSELVQETQLDSSKLSTPKAQVS---------------QRKPSEK----IP
                                .               .                 .               **

O.sativa_Os07g07580           ----------------STSQAPSVRQSARTAGKALK-YTEISSGD
O.sativa_Os06g51380           ----------------STSQAPSVRQSARTAGKALK-YTEISSGD
Z.mays_TA180670               ----------------TMSGTP-VRQSARNAGKTLKRYTDLSSGG
A.formosa_TA10038             ----------------LMEVLP-VRSSTRTAGRKFK-FTEPSSVD
V.vinifera_GSVIVT00027050001  ----------------DVEVTP-VRHSQRTAGKTFN-FAEASSGD
M.domestica_TA43921           ----------------LMKATP-VRHSARTAGKKFK-FGEASSGD
S.tuberosum_TA36268           ----------------FIELTP-SRRSARAAGKKIN-FAEVSSGD
p.trichocarpa_scaff_IV.277    ----------------LNETTP-IRQSARTSGKKFK-FTEVSSGD
A.thaliana_AT1G48380.1        ----------------PVQVTP-VRQSQRNSGKKFN-FAETSSEA
P.patens_74926                KPKNASEWESDEDEE--GFVNLGDAPTPSRQSARIAEKKHS-YAESSSEE
P.patens_173149               KHKVVSEWESDDDDDDPGFAIVGAAPTPSRQSARTAGKKYS-YAESSSEE
                                                    *   *   *     **  :   **
```

FIGURE 2 (continued)

```
O.sativa_Os07g07580                 DSSDNDDE----------------IDVPEDMDEK-VKSPAVKNESQSEDI
O.sativa_Os06g51380                 DSSDNDDE----------------IDVPEDMDEK-MKSPAVKNESQSEDI
Z.mays_TA180670                     ESSDNNNE----------------TDISEDLDDKEVESPEIKDEIESEDV
A.formosa_TA10038                   NSTESD------------------SDSSK----VRKGVKQTLDDETEDAS
V.vinifera_GSVIVT00027050001        DSVENDGNISDGQENSGSATPESGNEDAE----ARTGATTQIQESAGAAT
M.domestica_TA43921                 DSAESD------------------TPSAE----GRR--------------
S.tuberosum_TA36268                 ELVDNEVE----------------SSEGE----EKTGSDILCDETVVQSQ
p.trichocarpa_scaff_IV.277          DSAERSPDALG-------------VEEEE----EEEEEKKVKTNMSSGLD
A.thaliana_AT1G48380.1              SSGESEGN---------------TSDEDEKPLLEPESSTRSREESQDGNG
P.patens_74926                      NQTDGSDEHDRADAELRDP---RDKTVNK--LFNDVEDGFLAPESQISQM
P.patens_173149                     NLSDDADESDDLDGKQGES---RSKAANKAIEFEDADDTLLVPESQASKK
                                    .  :                        :

O.sativa_Os07g07580                 KPADSSA-------------------------------------------
O.sativa_Os06g51380                 KPADWSA-------------------------------------------
Z.mays_TA180670                     KPADSSA-------------------------------------------
A.formosa_TA10038                   LVGHAID-------------------------------------------
V.vinifera_GSVIVT00027050001        KSRKRLS-------------------------------------------
M.domestica_TA43921                 --------------------------------------------------
S.tuberosum_TA36268                 VTGKITA-------------------------------------------
p.trichocarpa_scaff_IV.277          IESESSR-------------------------------------------
A.thaliana_AT1G48380.1              ITASASK-------------------------------------------
P.patens_74926                      DLADMVTDRCVWNVVYDSIPLSFFPGCCRIRSPCVFHERCVQFTNSLKFT
P.patens_173149                     DVTDAVD-----------------------KNPSTNMTITIDEHDDEEAS
```

FIGURE 2 (continued)

```
O.sativa_Os07g07580              ----------QPISAKKEPLVQATLSSMFKKAEEKKRCTRSPKGSPATKG
O.sativa_Os06g51380              ----------QPISAKKEPLVQATLSSMFKKAEEKK-------------G
Z.mays_TA180670                  ----------ISLSSKKEPLVQATLSSMFIRAEEKKRSTRSPKGSPATKG
A.formosa_TA10038                ----------NPNVAT--KQIY-------PNKSSSLLFQ-----------
V.vinifera_GSVIVT00027050001     ----------QATISTLFKKVEEQKTSRTPRKSSSAKASAQKTDSRKAPE
M.domestica_TA43921              --------------------------------------------------
S.tuberosum_TA36268              ----------LAETASKSKKSARTKQSSLVQATISTMFK--KVDKLVTPD
p.trichocarpa_scaff_IV.277       ----------EGNHLSEQIQASITKSKKLSESAASVTIPKENLYNSHGSL
A.thaliana_AT1G48380.1           ----------LPEELPAKREKLKSKDSKLVQATLSNLFKKAEEKTAGTSK
P.patens_74926                   ANLVYMKTYIVCHAVSPQTSVPKTSASGMILSTSVLADLTANTIGAGSKQ
P.patens_173149                  A---------IDHLAMSQTRAPST-AGDMLLSTSVQAVANASTTGAGSRQ

O.sativa_Os07g07580              PAAKKQRASPEEKH-------------PTGKKSGKCSSK-----------
O.sativa_Os06g51380              PAAKKQRASPEEKH-------------PTGKKSAGRSQKRRKTQVEDDKI
Z.mays_TA180670                  AAAKKQRASPMAKQ-------------PAGIKKVSGTRGKKKPKVGEDEI
A.formosa_TA10038                --------------------------------------------------
V.vinifera_GSVIVT00027050001     HGKKRKVIEETKSE-------------IDISTESEQSDEEKKTSRTPRKS
M.domestica_TA43921              --------------------------------------------------
S.tuberosum_TA36268              RVSQRKTRKSTNKG-------------ESNTECGSTMPDHVGTSQGEDDI
p.trichocarpa_scaff_IV.277       VQSTISTLFKKVQE-------------KKKVVEKVRFDNFEANS------
A.thaliana_AT1G48380.1           AKSSSKA-------------------------------------------
P.patens_74926                   SSLSAFFMKSSEKSTLDNDDAGKEDENVTPKDEMESVLPCTPPDINDSKR
P.patens_173149                  STLSTFFLKSSEKEKVKN---------VEPQNSVVDIG-FTRTYQREKLT
```

FIGURE 2 (continued)

```
O.sativa_Os07g07580                SVVRSI--------------------------------------------
O.sativa_Os06g51380                EVLSSSSQDNNVDDDSDEDWAE----------------------------
Z.mays_TA180670                    EELSSSSQDNDADDDSDEDWAE----------------------------
A.formosa_TA10038                  --------------------------------------------------
V.vinifera_GSVIVT00027050001       SSTKVSARKTDARKAQGPRKRRKVIEETKSEIDISTEGEQSDNPTSDASV
M.domestica_TA43921                --------------------------------------------------
S.tuberosum_TA36268                EELSSSSKDTEASDEDWAA-------------------------------
p.trichocarpa_scaff_IV.277         --------------------------------------------------
A.thaliana_AT1G48380.1             --------------------------------------------------
P.patens_74926                     KRKSTPDGKRNSRDDMNISRVDNLPPAFSDNCRVGTGGNGYHIEGAAVNT
P.patens_173149                    KLQSTFDKGRAAEDDENVASKTEVESVLP---FTPPESNGSKRKRKAPSE

O.sativa_Os07g07580                --------------------------------------------
O.sativa_Os06g51380                --------------------------------------------
Z.mays_TA180670                    --------------------------------------------
A.formosa_TA10038                  --------------------------------------------
V.vinifera_GSVIVT00027050001       RVYKRKMKSPAA--------------------------------
M.domestica_TA43921                --------------------------------------------
S.tuberosum_TA36268                --------------------------------------------
p.trichocarpa_scaff_IV.277         --------------------------------------------
A.thaliana_AT1G48380.1             --------------------------------------------
P.patens_74926                     GTMLTKQSNVHNVATLFYGPQNKSYTSCENYALFFMFCHAFGK-
P.patens_173149                    RKQISKGVEGKGKTPVKRRKKIAEDKEPRAKDQLILVSDDSDSS
```

FIGURE 2 (continued)

```
                         1                                                    50
Orysa_TGase      (1)  ---------  YH Q   R---   SG   D A P A----------S   G
Sorbi_TGase      (1)  ---------     H   LT-A    A   H    A----------K
Sacof_TGase      (1)  ---------   R H   LT-A    A        A----------S
Zeama_TGase 2    (1)  ---------     H   LT-A    A        A----------S
Zeama_TGase 3    (1)  ---------     H   LT-A    A        A----------S
Zeama_tgz15      (1)  ---------     H   LT-G    A        A----------S
Zeama_tgz21      (1)  ---------     H   LT-G    A        A----------S
Poptr_TGase      (1)  ------MSARR  IRPTLEGRVI   GM    P P----------HH
Lyces_TGase      (1)  MGSKGRGPPPNI  RPPP ------  GM  YPD  GPPTHNPP---PVDFPP
Horvu_TGase      (1)  MGSKGRMPPSY  HRP P SGSG PPHGM  HRDP GP  MHPPP---GPGPYP
Orysa_TGase 2    (1)  MGSKGRAPPPY  HR---  -A----HKM  HRDP GG ---APG---MPGPFP
Arath_TGase      (1)  MESKGRIHPSH  HMRRPLPG--P  GC  AHPE   GNHGAIPPSAAQGVYP
Picsi_TGAse      (1)  MAGRNRLPAHPLK  GPR  MPPMREGPYA  GPGPLPPHPGLVEEIRDGPFG
    Consensus    (1)              MAHRG LDGL  AQAPALMRHGSFAAG           LSS

                         51                                                  100
Orysa_TGase     (29)  RQ   DRAATA    EK    EQ A    L R N  RL      H    LR
Sorbi_TGase     (35)  HS   Q-SSST  M E      MQ A V  L  N  RL      H    LR
Sacof_TGase     (31)  HS   Q-SSST  M  S     MQ A V  L M N  RL      H    LR
Zeama_TGase 2   (31)  HS   E-SSST  M E      MQ A V  L   N  RL     H    LR
Zeama_TGase 3   (31)  HS   E-SSST  M E      MQ A V  L M N  RL     H    LR
Zeama_tgz15     (31)  RS   Q-SSST  M E      MQ   V  L   N  RL     H    LR
Zeama_tgz21     (31)  RS   Q-SSST  M E      MQ  T V  L T N  RL     H    LR
Poptr_TGase     (34)  SE    S----RSDL  EHRF  AQ A DI  Q AGDN  RIVT  HM ALRE  LAAAQ
Lyces_TGase     (42)  FDR   P----PP   I EQ  IGA HI  MQ  TT  N RL  ATH  TLRR  LAAAQ
Horvu_TGase     (48)  YDM   P----PP   I EQ  VQC C  IQ  AV  N ERL  T H  SLRKELAAAQ
Orysa_TGase 2   (37)  YDM  AAAAPPP I EQ   MA RG  LQ  AV  N DRL  M HDSLRKELAAAQ
Arath_TGase     (49)  FNM   P----PP  VM  Q  FVA HC  LQR  AI  N  R GG HGS LR ELAAAQ
Picsi_TGAse     (51)  RG   GP-LPPHPAL  E    A HQ  IQG  LV N RL  A H  ALR  ELASAQ
    Consensus   (51)     PL  SSS  LEMLENKLAMQTA EVEKLIMENQRLASSHVVLRQDIVDTE
COILED COIL           XXXXXXXXXXXXXXXXXXXXXXXXXXXXXXXXXXXXXXXXXXXXXXXXXX

                         101                                                 150
Orysa_TGase     (79)   E Q  A      L       MHM    M  M     E      QA  DA      Q V
Sorbi_TGase     (84)   E Q    T    E       LQ              E      H   DA      Q V
Sacof_TGase     (80)   E Q    T    SE      LQ              E      H   DA      Q V
Zeama_TGase 2   (80)   E Q    T    GE      LH              E      H   DA      Q V
Zeama_TGase 3   (80)   E Q    T         LH                 E      H   DA      Q V
Zeama_tgz15     (80)   E  Q   T    E      LQ               EV  H  NV N         QM
Zeama_tgz21     (80)   E  Q   T    E      LQ               EV  H  NV N         QM
Poptr_TGase     (80)  QE  MQRLKA  IRSI    SS IQ    V   DK AK  EK     RA EN   D KQA V
Lyces_TGase     (88)  H   Q  LHVQ ET  KANREQETKG  SDK  SRI E LQAAES  I    PQAQG
Horvu_TGase     (94)  QE  QRLQAQGEAAKAAEEQEM  G    DKAAK E   LK YES   AD QQA T
Orysa_TGase 2   (87)  QE A QRLQAQGQAAMAAEEQEA  GI  DKVAK E   LKARDP  A  QQA A
Arath_TGase     (95)  H  IQ  HAQ T SMK  R FQRMMG A KVAK  ETE QKSEA   L MQ QARA
Picsi_TGAse    (100)  Q  LQ HMNHMAANM  ADKEHH  E  YDKSMKLE  NLRANEPM A  MQ LRA
    Consensus  (101)  KEMQMIR HLGEVQTETDL IRDLLERIRLMEADI SGDAVKKELHQVHM
COILED COIL           XXXXXXXXXXXXXXXXXXXXXXXXXXXXXXXXXXXXXXXXXXXXXXXXXX
```

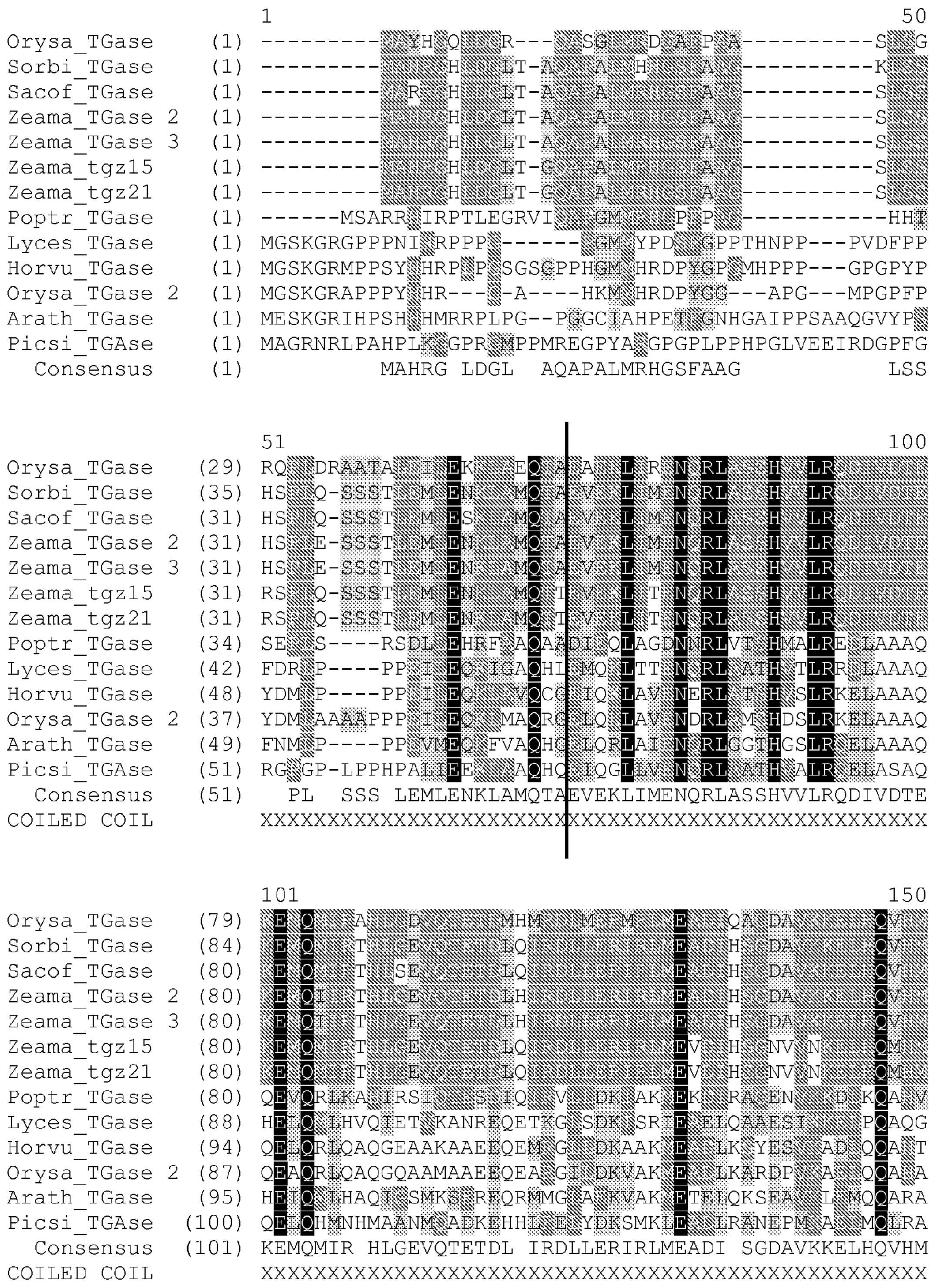

FIGURE 7

```
                        151                                                200
Orysa_TGase   (129)  ...........MDK....H.FG--SK......T...G....D
Sorbi_TGase   (134)  ........T....IEN.I..L..SG.G...........G...E.H
Sacof_TGase   (130)  ........T....ILN....H.I.PG.G..........G...E.H
Zeama_TGase 2 (130)  .........T..TED.N...L..SG.S...........G...E.L
Zeama_TGase 3 (130)  .........T..TED.....L..SG.S...........G...E.L
Zeama_tgz15   (130)  .........T...IED.V..L..SG.N..........S..R.E.H
Zeama_tgz21   (130)  .........T...IED.....L..SG.N..........S..R.E.H
Poptr_TGase   (130)  .QN.VK.R.E.AT.IQQASH..IHT--.V..I.DH...ENS.HELK
Lyces_TGase   (138)  .RT.FAAR.E.VTKIQML.QD..RAH.--.VLHI.R...ES.K.YD
Horvu_TGase   (144)  .QN.AAAR.H.SA.VQKIN..RNFG--.AQQ..A.M.D..AA.Q.YD
Orysa_TGase 2 (137)  .QG.VVAR.Q.AA.TQKLS.D..RNLG--.AQQ..A.V..R.AA.Q.YD
Arath_TGase   (145)  .RS.VVAREE.MSKVHQL.Q...SRS--.VQQI.A.MS..EN..QEYD
Picsi_TGAse   (150)  DNQKMGAIR..EM.A.VQAL.QL.VRAR.--.MQQ.VGAMR..IESMHQEL.D
  Consensus   (151)  EAKRLI ERQMLTL EIE VTKELQKLSA  D KSLPELLAELDGLRKEH
CALCIUM BINDIING                     XXXXXXXXXXXXXXXXXXXXXXXXXXXXXXXXX
COILED COIL          XXXXXXXXXXXXXXXXXXXXXXXXXXXXXXXXXXXXXXXXXXXXXX

                        201                                                250
Orysa_TGase   (177)  S.R.A...E...I..E.......N.M.M...D..L.A....N...K.V
Sorbi_TGase   (184)  N.R.Q..E...I..E.......N.M..Q...L.G....N..T.R
Sacof_TGase   (180)  N.R.Q..E...I..E.......N.M..Q...L.G....N..T.R
Zeama_TGase 2 (180)  N.R.Q..E...I..E.......N.M.M.Q...L.G....N..T.R
Zeama_TGase 3 (180)  N.R.Q..E....I.E.......N.M.M.Q...L.G....N..T.R
Zeama_tgz15   (180)  N.R.Q..E...V.......N.M..Q...L.V....N..R..
Zeama_tgz21   (180)  N.R.Q..E...V.A......N.M..Q...L.V....N..R..
Poptr_TGase   (178)  R.RAT...E.GL.IEK.E...A..QN..GMAR.M.NL.V.LN..T..R.
Lyces_TGase   (186)  QC.R.TY..C.RKLYSDH.E.SLQV..KNYM.MSR..V...L..AEL.NTSNSDRQ
Horvu_TGase   (192)  H..RAAY...E.RKLKMDHSE.SLQVTKTNYD.MVT..L...L..AELTN.STNIDRS
Orysa_TGase 2 (185)  H..RATY...E.RKLRMDHSE.SLQV.KRNYD..MVA.LD..L..AELMN.TANIDRG
Arath_TGase   (193)  QC.RATY.L.E.KFYNDH.LE.SLQA..KNYM.MAR.V...L.QAQLM.N.NANSDRR
Picsi_TGAse   (198)  RA.R.TAI..E.KARAD..LE.GQA...KN..ISMAR.V...L..AEL.N.DK.GRV
  Consensus   (201)  NLRS  FEYEKNTNIKQVEQMRTMEMNLITMTKEAEKLRADVANAERRAQA
COILED COIL          XXXXXXXXXXXXXXXXXXXXXXXXXXXXXXXXXXXXXXXXXXXXXX

                        251                                                300
Orysa_TGase   (227)  A..Q.VAAQ...V.H.....AA------------------------QAVA
Sorbi_TGase   (234)  A..Q.AAH.-.Q.......TA------------------------QATA
Sacof_TGase   (230)  A..Q.AAH...Q.......TA------------------------QATA
Zeama_TGase 2 (230)  V..K.TGH...Q.......TA------------------------QATA
Zeama_TGase 3 (230)  V..K.TGH...Q.......TA------------------------QATA
Zeama_tgz15   (230)  A..Q.AAH...Q.------------------------------QLKLPR
Zeama_tgz21   (230)  A..Q.AAH...Q.------------------------------QLKLPR
Poptr_TGase   (228)  PNQYIG..Y.NPDG------------------YGRPFVH.MGVGPA..EGIIPY
Lyces_TGase   (236)  TG.GPYGG---------------------------.STGYNE.ND.A.TNNYAT
Horvu_TGase   (242)  -----------------------------GTLYNP.N.LAQKDG..TSGR--
Orysa_TGase 2 (235)  GMPFICCSIFFTTIFGSIYRNHTMRHFLCVGMLYNT.NTAQKDD..APSLPV
Arath_TGase   (243)  .G.GPY.G--------------------------------N.I.N..EIDAS.GHQS-
Picsi_TGAse   (248)  .ANPGGAY.GN---------------------------YGG..EMGY.SGGAYG
  Consensus   (251)  AAA  AAAHAAG AQVTASQPGTA
COILED COIL          XXXXXXXXXXXXXXXX
```

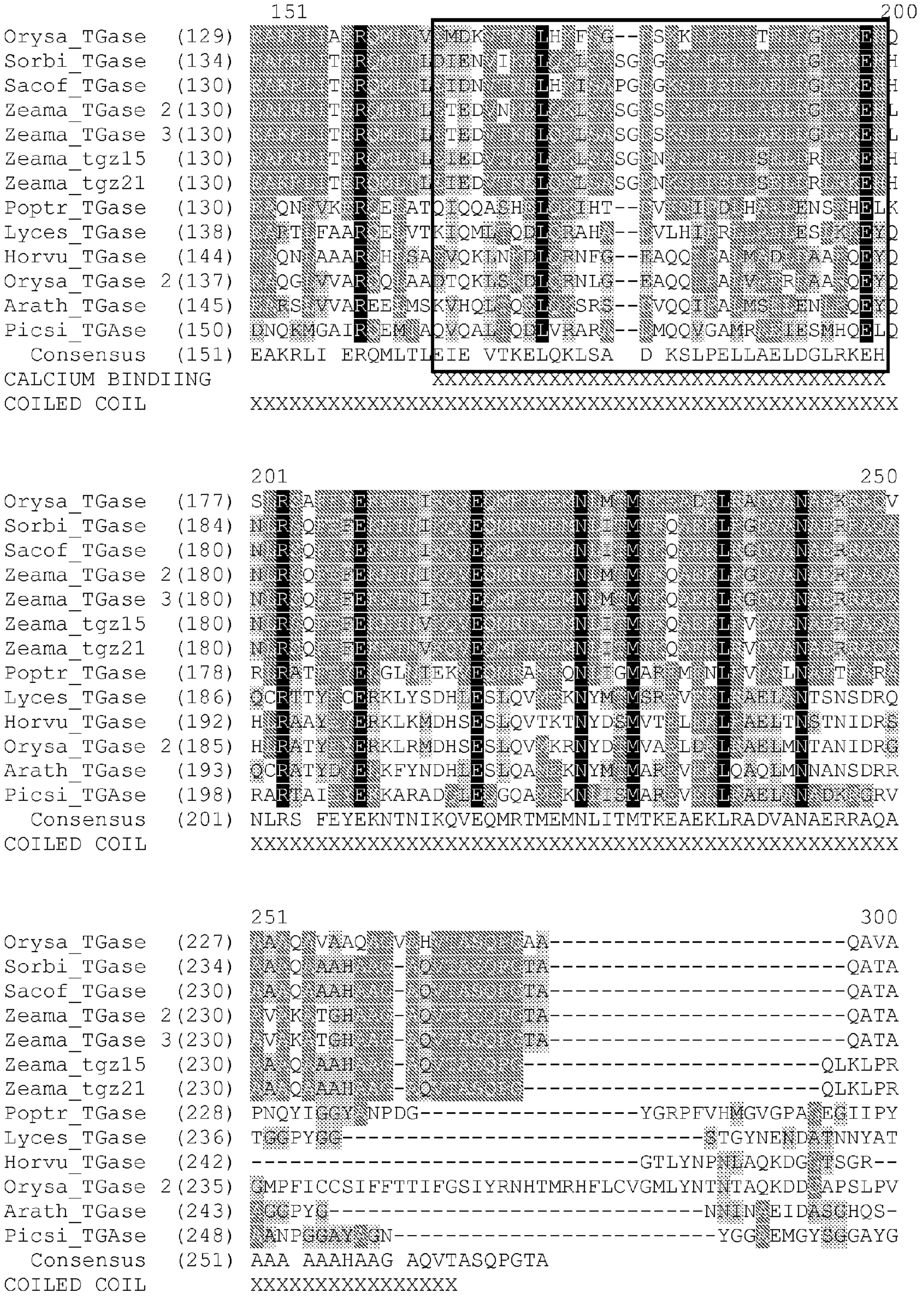

FIGURE 7 (continued)

```
                      301                                              350
Orysa_TGase    (254) VPA S-NP SS FTGH SAYHQG TQA VYQQ------------------
Sorbi_TGase    (260) VSA ATDP A  YASY SAYQQG -QAAAYQQGAQA--------------
Sacof_TGase    (256) VSA ATDP A  YASY SAYQQG -QA AYQQGAQA--------------
Zeama_TGase 2  (256) VPA ATDP A  YASY PAYQQG -QA AYQQGAQA AYQQGAQAGAYQQ
Zeama_TGase 3  (256) VPA ATDP A  YASY PAYQQG -QA AYQQGAQA TYQQGAGT-----
Zeama_tgz15    (256) FQQQQPQTHMQVHIPATPLHISREPRL HISRVLRL YISREPRLGHISR
Zeama_tgz21    (256) FQQQQPQTHMQVHIPATPLHISREPRL HISRVLRL YISREPRLGHISR
Poptr_TGase    (261) NSSNSVVSNV FGGAAMSTTGGV QWV PFDPSHAR -------------
Lyces_TGase    (258) GQNIYADG GVYQGRGSVPTGTN GGVPAVDSPQVGAQSVP---------
Horvu_TGase    (260) -HS YDGG G  QART PG-MPDPLSGSPAGTAPLS YDP----------
Orysa_TGase 2  (285) GQI YDSG GA QGRT PAGLGDSLSGNPAGTAPRT FDP----------
Arath_TGase    (263) -GNGYYEDAF PQGYI QPVAGN TGPNSVVG------------------
Picsi_TGAse    (273) DGYGVHPAQG  ESGGQYGAGAAPWGAYEMQRSHVRR-------------
  Consensus    (301)   AA    YAGA A  P AY   A  AG        G

                      351                                              400
Orysa_TGase    (285) -----GTT----------------------------------QVGAYQQ-
Sorbi_TGase    (295) ----------------------------------------AAYQQGAQAG
Sacof_TGase    (291) ---------------------------------------- AYQQGTQAG
Zeama_TGase 2  (305) GGQDGAYQQGAQAGAYQQGAQAGAYQQGAQAGAYQQGAQA AYQQGAQAG
Zeama_TGase 3  (300) ------------QAGAYQQ----------------G-AQA AYQQGAQAG
Zeama_tgz15    (306) EPRLGHISRGARMGHISRGLRLGHISREPRLGHISREPRL HISRVLRLG
Zeama_tgz21    (306) EPRLGHISRGARMGHISRGLRLGHISREPRLGHISREPRL HISRVLRLG
Poptr_TGase    (298) --------------------------------------------------
Lyces_TGase    (299) -------------------------------------PSNRPPYDTSNMS
Horvu_TGase    (298) -------------------SR------------------- NAYETSRLA
Orysa_TGase 2  (325) -------------------SR------------------- NMYDASRIA
Arath_TGase    (294) --------------------------------------------------
Picsi_TGAse    (310) --------------------------------------------------
  Consensus    (351)                                         G        G

                      401                                              450
Orysa_TGase    (295) --------------------------------------------------
Sorbi_TGase    (305) AYQ-----------------------------------------------
Sacof_TGase    (301) AYQ-----------------------------------------------
Zeama_TGase 2  (355) AYQ-----------------------------------------------
Zeama_TGase 3  (321) AYQ-----------------------------------------------
Zeama_tgz15    (356) HIS-----------------------------------------------
Zeama_tgz21    (356) HISRVLRLGYISREPRLGHISREPRLGHISRGARMGHISRGLRLGHISRE
Poptr_TGase    (298) --------------------------------------------------
Lyces_TGase    (312) GYDAQRG-------------------------------------------
Horvu_TGase    (310) RV------------------------------------------------
Orysa_TGase 2  (337) SFS-----------------------------------------------
Arath_TGase    (294) --------------------------------------------------
Picsi_TGAse    (310) --------------------------------------------------
  Consensus    (401)
```

FIGURE 7 (continued)

```
                   451                                               500
Orysa_TGase   (295) -----------------------------------------------STQAAA
Sorbi_TGase   (308) -----Q-----------AAQAGAYQQGAQAGAYQQGAQVAAYQHGTQAAA
Sacof_TGase   (304) -----L-----------A----------------------AYQQGTQAAA
Zeama_TGase 2(358) -----Q-----------AAQSGAYQQGAQAGAYQQGAQDAAYQQGAQDAA
Zeama_TGase 3(324) -----Q-----------AAQSGAYQQGAQAGAYQQGAQDAAYQQGAQDAA
Zeama_tgz15   (359) -------REPRLGHISRGPSLGHISRGPRLGHISREPRMGHISREPRMGH
Zeama_tgz21   (406) PRLGHISREPRLGHISRGPSLGHISRGPRLGHISREPRMGHISREPRMGH
Poptr_TGase   (298) --------------------------------------------------
Lyces_TGase   (319) ---------------IRGPVGHGYEAQMGSSGPGYDAQRGSGLAAYEAQR
Horvu_TGase   (312) ------------HDASRGATGYDSLKVAGYDTSRMPALGAQTAAPTAHGS
Orysa_TGase 2(340) ------SSKAGGHDASRGAAGYNSLKGAGYDPSKAPALGAQATAAAAHGS
Arath_TGase   (294) ----------------------------------------AAQYPYQGVT
Picsi_TGAse   (310) --------------------------------------------------
  Consensus   (451)                  G                      G        GA

                  501                                          550
Orysa_TGase   (302) YAYPTY-----------DAATAYQMHAAQANAYAGYPGYPVAAATQAALP
Sorbi_TGase   (342) YQQGNQ-----------AGAYTYAYDAATAYAYAGYSGYP--AAAQSAVP
Sacof_TGase   (316) YQKGNQ-----------AGTYTYAYDAATAYTYAGYSGYPIAAAQKAVP
Zeama_TGase 2(392) YQQGAQ-----------AGAYNYAYDAGTAYAYAGYSGYPVAAAQSAVP
Zeama_TGase 3(358) YQQGAQ-----------AGAYNYAYDAGTAYAYAGYSGYPVAAAQSAVP
Zeama_tgz15   (402) ISRVLR-----------LEHTTMLMMLARLMHMQVTLAIQLQATRKVQCP
Zeama_tgz21   (456) ISRVLR-----------LEHTTMLMMLARLMHMQVTLAIQLQATRKVQCP
Poptr_TGase   (298) --------------------------------------------------
Lyces_TGase   (354) GHGYDR------------------GPGYDAQRAAGYEAYRGPGYDAYGAP
Horvu_TGase   (350) SAGYYG-------------------SAQVPPSYASG-PVSSSSGGATTAR
Orysa_TGase 2(384) SADYYGSNQATPPSYAWGQAASAYGSAQVPQSHASGPPVQSTSGSATTAR
Arath_TGase   (304) QPGYFP--------------------------------QRPGYNFPRGP
Picsi_TGAse   (310) --------------------------------------------------
  Consensus   (501)                           AA    YA   G    GY     P

                   551                                               600
Orysa_TGase   (341) GYPSAYAAPQGPISSG------VATDVASMYGAISSGGYGAGVVGSSGGA
Sorbi_TGase   (379) NYS--YAVPPGPSSG-------ATTEAASMYGAAGSGGYGTAQVGPSGAT
Sacof_TGase   (355) NYS--YAVPPGPSSG-------AATDAASLYGAAGSGGYGTGQVGPSGVT
Zeama_TGase 2(431) NYS--YAAPPGPTSSG-----AATNAAGGQYGAVGSGGYGTGQVGPSGGT
Zeama_TGase 3(397) NYS--YAAPPGPTSSG-----AATNAAGGQYGAVGSGGYGTGQVGPSGGT
Zeama_tgz15   (441) TIPMLHLRSQGAAVQLRTPQEASMGQLVVLDILLGKFSRAVALQMQRKHL
Zeama_tgz21   (495) TIPMLHLRSQGAAVQLRTPQEASMGQLVVLDILLGKFSRAVALQMQRKHL
Poptr_TGase   (298) --------------------------------------------------
Lyces_TGase   (386) VYDPSKGSNYDASSKG-------GVATQGQVAPIGNGPPGAAPSPGHIGP
Horvu_TGase   (380) PHGSAQGLSSYGQTQA---PSSYAHTQIPPSYGLAQGSSHFGPTGGGPY
Orysa_TGase 2(434) NFGSAQGLPSYAHAQE---QPSYGHAQLPSSYGLAQGSFGFAPAGGVGPY
Arath_TGase   (321) PGS-------------------YDPTTRLPTGPYGGPFGPGPSNNTPYA
Picsi_TGAse   (310) --------------------------------------------------
  Consensus   (551)  Y    YA    Q   S                 ALG  A  YP  G   Q   S
```

FIGURE 7 (continued)

```
                         601                                     644
Orysa_TGase  (385) ANAGQAP------- TY -VA  PTRAGQR--------------
Sorbi_TGase  (420) ANA QPPPPPPP-A PY -ST  QTRGAQR--------------
Sacof_TGase  (396) ANA QPPSSPLX-T PY -ST  QTRGAQR--------------
Zeama_TGase 2(474) ANA QAPPPPPPPA PY PST  QTRGAQR--------------
Zeama_TGase 3(440) ANA QAPPPPPPPA PY PST  QTRGAQR--------------
Zeama_tgz15  (491) LLHHHRQHHIPPAHMTK EEPR KIWDVNQMDVCHAHLLSRQIW
Zeama_tgz21  (545) LLHHHRQHHIPPAHMTK EEPR KIWDVNQMDVCHAHLLSRQIW
Poptr_TGase  (298) --------------------------------------------
Lyces_TGase  (429) GYD SAQGGNPARR------------------------------
Horvu_TGase  (427) GLS RPQAYGSAQA PNTGGA QTPHGRR---------------
Orysa_TGase 2(481) GSG QPPQYGAGQA TN GSA QAPHGRK---------------
Arath_TGase  (351) GTHGNPSRR-----------------------------------
Picsi_TGAse  (310) --------------------------------------------
  Consensus  (601) A  AQ        A  P   YD   G Q
```

FIGURE 7 (continued)

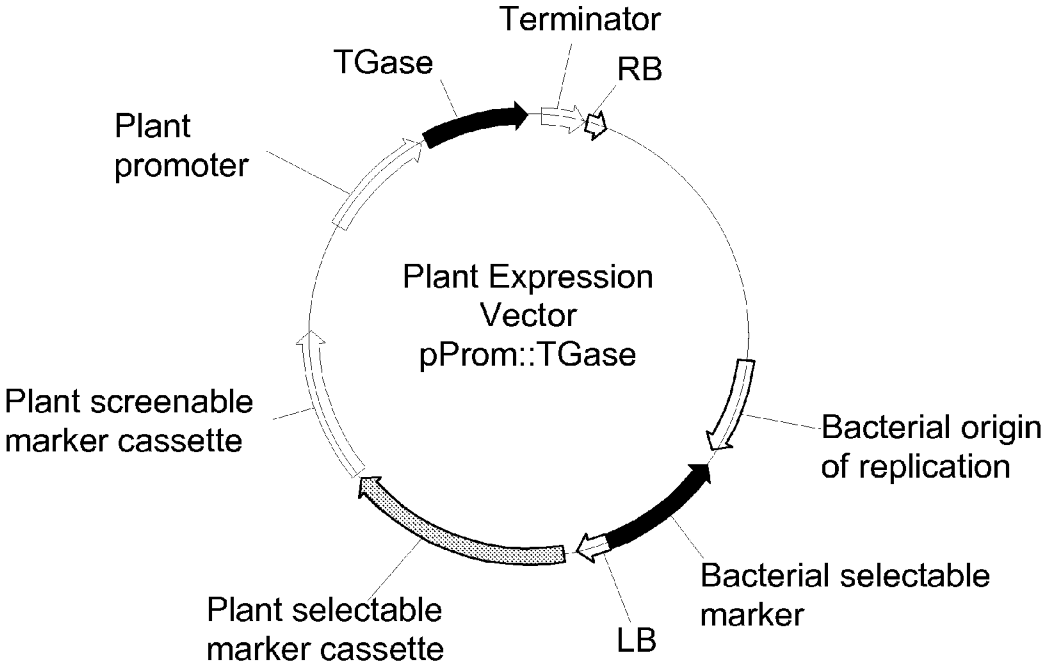

FIGURE 8

MDNTDRRRRRKQHKIALHDSEEVSSIELEFINMTEQ

<u>EEDLIFRMYRLVGDRWDLIAGRVPGRQPEEI</u>ERYWI

<u>Motif 1</u>

MRNSEGFADKRRQLHSSSHKHTKPHRPRFSIYPS

FIGURE 9

```
CLUSTAL 2.0.11 multiple sequence alignment

A.sativa_CN818591                   --------------------------------------------------
L.multiflorum_AU249134              --------------------------------------------------
A.capillaris_DV853805               --------------------------------------------------
A.capillaris_DV859458               --------------------------------------------------
H.vulgare_TC189825                  --------------------------------------------------
T.aestivum_BE412359                 --------------------------------------------------
O.minuta_CB884361                   --------------------------------------------------
O.sativa_LOC_Os01g43230.2           --------------------------------------------------
S.bicolor_Sb03g028170.1             --------------------------------------------------
Z.mays_TC409725                     --------------------------------------------------
T.androssowii_TA2313_189785         --------------------------------------------------
Triphysaria_sp_TC9313               --------------------------------------------------
S.tuberosum_CV505951                --------------------------------------------------
P.tremula_TA11725_113636            --------------------------------------------------
P.trichocarpa_594467                --------------------------------------------------
P.trichocarpa_562293                --------------------------------------------------
B.gymnorrhiza_TA2541_39984          --------------------------------------------------
M.esculenta_TA9427_3983             --------------------------------------------------
P.persica_BU039343                  --------------------------------------------------
V.vinifera_GSVIVT00026045001        --------------------------------------------------
L.tulipifera_CV004984               --------------------------------------------------
G.hirsutum_TC121748                 --------------------------------------------------
E.esula_DV121180                    --------------------------------------------------
M.domestica_TC17597                 --------------------------------------------------
P.tremula_BU888423                  --------------------------------------------------
P.trichocarpa_568212                --------------------------------------------------
G.hirsutum_DW508052                 --------------------------------------------------
G.hirsutum_TC116960                 --------------------------------------------------
V.vinifera_GSVIVT00006915001        --------------------------------------------------
J.hindsii_x_regia_TA1295_43229      --------------------------------------------------
G.max_8223                          --------------------------------------------------
P.vulgaris_CV538421                 --------------------------------------------------
C.tetragonoloba_EG990179            --------------------------------------------------
G.max_29139                         --------------------------------------------------
G.soja_TA4526_3848                  --------------------------------------------------
L.japonicus_CB827663                --------------------------------------------------
C.canephora_DV693718                --------------------------------------------------
P.hybrida_EB175070                  --------------------------------------------------
```

FIGURE 10

```
I.nil_TC6509                          --------------------------------------------------
L.saligna_DW052030                    --------------------------------------------------
A.hypogaea_CD038483                   --------------------------------------------------
P.tremula_TA7610_113636               --------------------------------------------------
P.equestris_CB034844                  --------------------------------------------------
V.vinifera_GSVIVT00010755001          --------------------------------------------------
P.pinaster_CT579117                   --------------------------------------------------
P.taeda_DR096185                      --------------------------------------------------
P.sitchensis_TA16538_3332             --------------------------------------------------
A.thaliana_At1g01380_CPC-like_        --------------------------------------------------
B.napus_EV055366                      --------------------------------------------------
A.thaliana_At4g01060_CPC-like_        --------------------------------------------------
A.thaliana_At2g46410_CPC-like_        --------------------------------------------------
B.napus_TC92601                       --------------------------------------------------
A.thaliana_At5g53200_CPC-like_        --------------------------------------------------
B.napus_EE451172                      --------------------------------------------------
J.hindsii_x_regia_EL893054            --------------------------------------------------
G.hirsutum_TC102183                   --------------------------------------------------
P.trichocarpa_807368                  --------------------------------------------------
M.esculenta_DV443286                  --------------------------------------------------
P.tremula_DN497189                    --------------------------------------------------
P.trichocarpa_674550                  --------------------------------------------------
C.longa_DY390653                      --------------------------------------------------
A.thaliana_At2g30420_CPC-like_        --------------------------------------------------
B.napus_CD843377                      --------------------------------------------------
B.napus_TC95812                       --------------------------------------------------
G.max_Glyma11g02060.1                 --------------------------------------------------
M.truncatula_CT033771_17.4            --------------------------------------------------
L.serriola_DW108811                   --------------------------------------------------
S.miltiorrhiza_CV166339               --------------------------------------------------
S.miltiorrhiza_TA1626_226208          --------------------------------------------------
P.glauca_DR564374                     --------------------------------------------------
P.sitchensis_TA17447_3332             --------------------------------------------------
P.pinaster_TA6535_71647               --------------------------------------------------
P.menziesii_TA3655_3357               --------------------------------------------------
A.thaliana_At1g71030_CPC-like_        --------------------------------------------------
A.thaliana_At1g18960_CPC-like_        --------------------------------------------------
A.thaliana_At1g09710_CPC-like_        MVANNNTSSNRRKRIITEGDIATLLLRYDMETILRMLQEISYCSETKMDW
A.thaliana_At1g58220_CPC-like_        MVDNSNN--KKRKEFISEADIATLLQRYDTVTILKLLQEMAYYAEAKMNW
```

FIGURE 10 (continued)

```
A.sativa_CN818591                    --------------------------------------------------
L.multiflorum_AU249134               --------------------------------------------------
A.capillaris_DV853805                --------------------------------------------------
A.capillaris_DV859458                --------------------------------------------------
H.vulgare_TC189825                   --------------------------------------------------
T.aestivum_BE412359                  --------------------------------------------------
O.minuta_CB884361                    --------------------------------------------------
O.sativa_LOC_Os01g43230.2            --------------------------------------------------
S.bicolor_Sb03g028170.1              --------------------------------------------------
Z.mays_TC409725                      --------------------------------------------------
T.androssowii_TA2313_189785          --------------------------------------------------
Triphysaria_sp_TC9313                --------------------------------------------------
S.tuberosum_CV505951                 --------------------------------------------------
P.tremula_TA11725_113636             --------------------------------------------------
P.trichocarpa_594467                 --------------------------------------------------
P.trichocarpa_562293                 --------------------------------------------------
B.gymnorrhiza_TA2541_39984           --------------------------------------------------
M.esculenta_TA9427_3983              --------------------------------------------------
P.persica_BU039343                   --------------------------------------------------
V.vinifera_GSVIVT00026045001         --------------------------------------------------
L.tulipifera_CV004984                --------------------------------------------------
G.hirsutum_TC121748                  --------------------------------------------------
E.esula_DV121180                     --------------------------------------------------
M.domestica_TC17597                  --------------------------------------------------
P.tremula_BU888423                   --------------------------------------------------
P.trichocarpa_568212                 --------------------------------------------------
G.hirsutum_DW508052                  --------------------------------------------------
G.hirsutum_TC116960                  --------------------------------------------------
V.vinifera_GSVIVT00006915001         --------------------------------------------------
J.hindsii_x_regia_TA1295_43229       --------------------------------------------------
G.max_8223                           --------------------------------------------------
P.vulgaris_CV538421                  --------------------------------------------------
C.tetragonoloba_EG990179             --------------------------------------------------
G.max_29139                          --------------------------------------------------
G.soja_TA4526_3848                   --------------------------------------------------
L.japonicus_CB827663                 --------------------------------------------------
C.canephora_DV693718                 --------------------------------------------------
P.hybrida_EB175070                   --------------------------------------------------
```

FIGURE 10 (continued)

| | |
|---|---|
| I.nil_TC6509 | -------------------------------------------------- |
| L.saligna_DW052030 | -------------------------------------------------- |
| A.hypogaea_CD038483 | -------------------------------------------------- |
| P.tremula_TA7610_113636 | -------------------------------------------------- |
| P.equestris_CB034844 | -------------------------------------------------- |
| V.vinifera_GSVIVT00010755001 | -------------------------------------------------- |
| P.pinaster_CT579117 | -------------------------------------------------- |
| P.taeda_DR096185 | -------------------------------------------------- |
| P.sitchensis_TA16538_3332 | -------------------------------------------------- |
| A.thaliana_At1g01380_CPC-like_ | -------------------------------------------------- |
| B.napus_EV055366 | -------------------------------------------------- |
| A.thaliana_At4g01060_CPC-like_ | -------------------------------------------------- |
| A.thaliana_At2g46410_CPC-like_ | -------------------------------------------------- |
| B.napus_TC92601 | -------------------------------------------------- |
| A.thaliana_At5g53200_CPC-like_ | -------------------------------------------------- |
| B.napus_EE451172 | -------------------------------------------------- |
| J.hindsii_x_regia_EL893054 | -------------------------------------------------- |
| G.hirsutum_TC102183 | -------------------------------------------------- |
| P.trichocarpa_807368 | -------------------------------------------------- |
| M.esculenta_DV443286 | -------------------------------------------------- |
| P.tremula_DN497189 | -------------------------------------------------- |
| P.trichocarpa_674550 | -------------------------------------------------- |
| C.longa_DY390653 | -------------------------------------------------- |
| A.thaliana_At2g30420_CPC-like_ | -------------------------------------------------- |
| B.napus_CD843377 | -------------------------------------------------- |
| B.napus_TC95812 | -------------------------------------------------- |
| G.max_Glyma11g02060.1 | -------------------------------------------------- |
| M.truncatula_CT033771_17.4 | -------------------------------------------------- |
| L.serriola_DW108811 | -------------------------------------------------- |
| S.miltiorrhiza_CV166339 | -------------------------------------------------- |
| S.miltiorrhiza_TA1626_226208 | -------------------------------------------------- |
| P.glauca_DR564374 | -------------------------------------------------- |
| P.sitchensis_TA17447_3332 | -------------------------------------------------- |
| P.pinaster_TA6535_71647 | -------------------------------------------------- |
| P.menziesii_TA3655_3357 | -------------------------------------------------- |
| A.thaliana_At1g71030_CPC-like_ | -------------------------------------------------- |
| A.thaliana_At1g18960_CPC-like_ | -------------------------------------------------- |
| A.thaliana_At1g09710_CPC-like_ | NALVKKTTTGITNAREYQLLWRHLSYRHPLLPVEDDALPLDDDSDMECEL |
| A.thaliana_At1g58220_CPC-like_ | NELVKKTSTGITSAREYQLLWRHLAYRDSLVPVGNNARVLDDDSDMECEL |

FIGURE 10 (continued)

```
A.sativa_CN818591                 ------------------------------------------------M
L.multiflorum_AU249134            -----------------------------------------MLSSRKDM
A.capillaris_DV853805             ------------------------------------------------M
A.capillaris_DV859458             ------------------------------------------------M
H.vulgare_TC189825                ------------------------------------------------M
T.aestivum_BE412359               ------------------------------------------------M
O.minuta_CB884361                 ----------------------------------------------MDS
O.sativa_LOC_Os01g43230.2         ----------------------------------------------MDS
S.bicolor_Sb03g028170.1           ----------------------------------------------MDS
Z.mays_TC409725                   ----------------------------------------------MDS
T.androssowii_TA2313_189785       ------------------------------------------------M
Triphysaria_sp_TC9313             ------------------------------------------------M
S.tuberosum_CV505951              ------------------------------------------------M
P.tremula_TA11725_113636          ------------------------------------------------M
P.trichocarpa_594467              ------------------------------------------------M
P.trichocarpa_562293              ------------------------------------------------M
B.gymnorrhiza_TA2541_39984        ------------------------------------------------M
M.esculenta_TA9427_3983           ------------------------------------------------M
P.persica_BU039343                ------------------------------------------------M
V.vinifera_GSVIVT00026045001      ------------------------------------------------M
L.tulipifera_CV004984             ------------------------------------------------M
G.hirsutum_TC121748               ------------------------------------------------M
E.esula_DV121180                  ------------------------------------------------M
M.domestica_TC17597               ------------------------------------------------M
P.tremula_BU888423                ------------------------------------------------M
P.trichocarpa_568212              ------------------------------------------------M
G.hirsutum_DW508052               ------------------------------------------------M
G.hirsutum_TC116960               ------------------------------------------------M
V.vinifera_GSVIVT00006915001      ------------------------------------------------M
J.hindsii_x_regia_TA1295_43229    ------------------------------------------------M
G.max_8223                        ------------------------------------------------M
P.vulgaris_CV538421               ------------------------------------------------M
C.tetragonoloba_EG990179          -------------------------------------------------
G.max_29139                       ------------------------------------------------M
G.soja_TA4526_3848                ------------------------------------------------M
L.japonicus_CB827663              ------------------------------------------------M
C.canephora_DV693718              ------------------------------------------------M
P.hybrida_EB175070                ------------------------------------------------M
```

FIGURE 10 (continued)

| | |
|---|---|
| I.nil_TC6509 | -------------------------------------------------M |
| L.saligna_DW052030 | -------------------------------------------------M |
| A.hypogaea_CD038483 | -------------------------------------------------- |
| P.tremula_TA7610_113636 | -------------------------------------------------M |
| P.equestris_CB034844 | -------------------------------------------------M |
| V.vinifera_GSVIVT00010755001 | -------------------------------------------------M |
| P.pinaster_CT579117 | -----------------------------------------------MDR |
| P.taeda_DR096185 | -----------------------------------------------MDR |
| P.sitchensis_TA16538_3332 | -----------------------------------------------MDV |
| A.thaliana_At1g01380_CPC-like_ | -------------------------------------------------M |
| B.napus_EV055366 | -------------------------------------------------M |
| A.thaliana_At4g01060_CPC-like_ | -------------------------------------------------M |
| A.thaliana_At2g46410_CPC-like_ | ----------------------------------------MFRSDKAEKM |
| B.napus_TC92601 | -------------------------------------------------M |
| A.thaliana_At5g53200_CPC-like_ | ----------------------------------------------MDNT |
| B.napus_EE451172 | ----------------------------------------------MDNT |
| J.hindsii_x_regia_EL893054 | ----------------------------------------------MD-- |
| G.hirsutum_TC102183 | -------------------------------------------------M |
| P.trichocarpa_807368 | -------------------------------------------------M |
| M.esculenta_DV443286 | -------------------------------------------------M |
| P.tremula_DN497189 | ----------------------------------------------MESM |
| P.trichocarpa_674550 | ----------------------------------------------MESM |
| C.longa_DY390653 | -------------------------------------------------M |
| A.thaliana_At2g30420_CPC-like_ | ----------------------------------------------MDNT |
| B.napus_CD843377 | -------------------------------------------------M |
| B.napus_TC95812 | -------------------------------------------------M |
| G.max_Glyma11g02060.1 | -------------------------------------------------- |
| M.truncatula_CT033771_17.4 | ----------------------------------------MEEKRRSHSQ |
| L.serriola_DW108811 | -------------------------------------------------- |
| S.miltiorrhiza_CV166339 | -------------------------------------------------M |
| S.miltiorrhiza_TA1626_226208 | -------------------------------------------------M |
| P.glauca_DR564374 | -------------------------------------------------M |
| P.sitchensis_TA17447_3332 | -------------------------------------------------M |
| P.pinaster_TA6535_71647 | -----------------------------------------MARSSSLSM |
| P.menziesii_TA3655_3357 | -------------------------------------------------M |
| A.thaliana_At1g71030_CPC-like_ | -------------------------------------------------M |
| A.thaliana_At1g18960_CPC-like_ | -------------------------------------MVRSCSSKSKNPW |
| A.thaliana_At1g09710_CPC-like_ | EASPAVSHEASVEAIAHVKVMAASYVLSESDILDDSTVEAPLTINIPYAL |
| A.thaliana_At1g58220_CPC-like_ | EASPGVSVDVVTEAVAHVKVMAASYVPSESDIPEDSTVEAPLTINIPYSL |

FIGURE 10 (continued)

```
A.sativa_CN818591                  SSKSLA-----KNFKTMG------VHEAK------------EVNSTAQHF
L.multiflorum_AU249134             SSKSLA-----KNSKTMG------VHEAK------------EVTSTTQHF
A.capillaris_DV853805              SSGSLV-----KNSKTMG------VHEAK------------EVNGTSQHF
A.capillaris_DV859458              SSESLA-----KNSKIMA------IHETK------------GNNTTAQHF
H.vulgare_TC189825                 SSKSLG-----KNSKIMS------GRERK------------EVNSNAKHF
T.aestivum_BE412359                SSESLG-----KNSKIMG------GRERK------------EVNSTAKHF
O.minuta_CB884361                  SSGSQG-----KNSKTSD------GCETK------------EVNSTALNF
O.sativa_LOC_Os01g43230.2          SSGSQG-----KNSKTSD------GCETK------------EVNNTAQNF
S.bicolor_Sb03g028170.1            SSGSQD-----KKSKGND------RREAK------------EANGTAQHF
Z.mays_TC409725                    SSGSQD-----KKFRDND------RPEAK------------EANSTAQHL
T.androssowii_TA2313_189785        KIRS-I-----PQSTAT------KSLSRN---------------------
Triphysaria_sp_TC9313              ADDQ-L-----QKPSATN----DNAIDGNKDDKV---VAESPSIVDDSKQ
S.tuberosum_CV505951               GALQGL-----LGIGNGI----DKAFEAKKEE---------------SSK
P.tremula_TA11725_113636           ADLD--------HSSSD-----DNSVDSR------------EETSQD-SK
P.trichocarpa_594467               ADLD--------HSSSD-----DNSVDSR------------EETSQD-SK
P.trichocarpa_562293               ADSD--------HSSSD-----DLSVDSR------------D-TSQD-SK
B.gymnorrhiza_TA2541_39984         ADVD--------NSSVD-----EFSVDSR------------EESSQD-SK
M.esculenta_TA9427_3983            ADLD--------HSSSD-----DVSVDSR------------EESSQE-SK
P.persica_BU039343                 ADLD--------HSTSD-----DNSVDSR------------EESSQD-SK
V.vinifera_GSVIVT00026045001       ADLD--------HS-SD-----GSSLDSR------------EGSSQD-SK
L.tulipifera_CV004984              ADLD--------HS-SE-----DVSDDS-------------QGTSQD-SK
G.hirsutum_TC121748                ADMD--------GS----------SVDSK------------EESSED-SK
E.esula_DV121180                   ADSE--------HSSTS----DEIYLDYQD-----------EQSHEY-SK
M.domestica_TC17597                ADSE--------HSS-S----DDTFSDSR------------EKSTEK-SE
P.tremula_BU888423                 ADSE--------HSSSD----ETFAYSREETSQ---------ETSQE-SR
P.trichocarpa_568212               ADSE--------HSSSD----ETFVYSRE-------------ETSKE-SK
G.hirsutum_DW508052                ADSQ--------HSSSG----KTYVNSQDFSSE--------EETNEE-SK
G.hirsutum_TC116960                AESE--------YSSS-----ENASTDSNSIA---------EQSKQD-LE
V.vinifera_GSVIVT00006915001       ADSE--------YSTSN----DTSCVDSQ------------EQSSQE-AK
J.hindsii_x_regia_TA1295_43229     ADSQ--------NSSSNGVRNETPSNDTFADSRS-------EETSEA-SK
G.max_8223                         ADSD--------LSSSQ------ISTHST------------DSGNRGSSK
P.vulgaris_CV538421                ADSN--------TSSTQ------TSSHSS------------DSGKRGTSK
C.tetragonoloba_EG990179           --MD--------RSSDD------VSADSS------------EQRSQG-SK
G.max_29139                        ADID--------RSFDNN-----VSAVST------------EKSSQV-SD
G.soja_TA4526_3848                 TDID--------RSSDN------VSSDSI------------EKSSQV-SD
L.japonicus_CB827663               ADRE--------HSSDN------VSADST------------EKSSQA-SN
C.canephora_DV693718               ADSD--------QSTTL----NEKSVGSQE------------DKSQD-SE
P.hybrida_EB175070                 ADKG--------QSSSS----VNTPADSQDGVAPR--MLVSGKTSKV-AE
```

FIGURE 10 (continued)

```
I.nil_TC6509                      ADLD-------NSSTCG-----EAEACVEI--------TEVEVTSQDSNK
L.saligna_DW052030                ANLD-------KYSTSN-----DTS-------------THTRGPSNQESR
A.hypogaea_CD038483               -----------------------------------------MRQEEEPTM
P.tremula_TA7610_113636           AGSGHT-----SNNTNQ-----DT---------------KAAKSNQDSNL
P.equestris_CB034844              S------------------------------------------------K
V.vinifera_GSVIVT00010755001      SPLVRT-----PKVPTQ-----HPSLSSSCSLIW---VCSGSEETAKDSK
P.pinaster_CT579117               ADTDED-----RLSSSH------KEVEEA------------GKER--TSS
P.taeda_DR096185                  ADTDED-----RLSSSH------KEVEEA------------GEERR-TRS
P.sitchensis_TA16538_3332         QDLQQQ-------SSEG------ESDSQG------------GRSRQGLCD
A.thaliana_At1g01380_CPC-like_    NTQRKS-----KHLKTNP---TIVASSSE------------EVSSLEWEE
B.napus_EV055366                  DKQRKS-----KHPKTNAYA-TIVSSSSE------------EVSSLEWEE
A.thaliana_At4g01060_CPC-like_    DNHRRT-----KQPKTNS----IVTSSSEG----------TEVSSLEWEV
A.thaliana_At2g46410_CPC-like_    DKRRR------RQSKAKA-------SCSE------------EVSSIEWEA
B.napus_TC92601                   DRRRR------RQSKAKA-------SCSE------------EVSSIEWEA
A.thaliana_At5g53200_CPC-like_    DRRRRR-----KQHKIAL-------HDS------------EEVSSIEWEF
B.napus_EE451172                  DRRRRR-----KQHKVTL-------HDS------------EEVSSIEWEF
J.hindsii_x_regia_EL893054        -KRPRK-----QAKSTKS-------STS------------EEVSSIEWEF
G.hirsutum_TC102183               DKRDRK------QAKTGS-------CCS------------EEVSSTEWEF
P.trichocarpa_807368              DRRRKK------QAKTTS-------CCSE-----------QEVSSIEWEF
M.esculenta_DV443286              DRRRKK------QSKAAT-------PRS------------EEVSSIEWEF
P.tremula_DN497189                DRRRRR-----KQPKINS-------SES------------EEVSSIEWEF
P.trichocarpa_674550              DRRRRRRR---KQAKINN-------SGS------------EEVSSIEWEF
C.longa_DY390653                  ERRRKK-------QRRSS-------DDSE-----------EEVNSVEWQS
A.thaliana_At2g30420_CPC-like_    NRLRLRRGPSLRQTKFTR-------SRYDS----------EEVSSIEWEF
B.napus_CD843377                  DSTYRR----------QR-------HNS------------EEVCSVKWDF
B.napus_TC95812                   DSTYRR----------QR-------HNS------------EEVCSVKWDF
G.max_Glyma11g02060.1             ---------------MST-------TATTT----------SEVSSNEWKV
M.truncatula_CT033771_17.4        NKANIS-------PNTSQ-------TSEAG----------GEVSSTEWEF
L.serriola_DW108811               ----------------MK-------HNSEF----------EEVSSRKWEF
S.miltiorrhiza_CV166339           DKCRQK-------QIKIR-------KYPLC----------EEVSSIEWEF
S.miltiorrhiza_TA1626_226208      DKCSS----------TQK-------HPKIQ----------NEASSLEWEF
P.glauca_DR564374                 EKNVYC---------SSA------ILEYDT----------EEGSSLDWEC
P.sitchensis_TA17447_3332         EKNVYC---------SSA------ILEYDT----------EEGSSLDWEC
P.pinaster_TA6535_71647           EKNMYC---------SST------LLEYDT----------EEGSSLDWEC
P.menziesii_TA3655_3357           EKNVYC---------STS------ILEYDT----------EEGSSLDWEC
A.thaliana_At1g71030_CPC-like_    NKTRLR-----ALSPPSG-----MQHRKRCRLRG------RNYVRPEVKQ
A.thaliana_At1g18960_CPC-like_    TNEEDTTQKFVFASASKNGCAAPKKIGLRRCG-KS--CRVRKTDHSGTKH
A.thaliana_At1g09710_CPC-like_    PEGSQEPSESPWSSRGMNINFPVCLQKVTSTEGMNGNGSAGISMAFRRKR
A.thaliana_At1g58220_CPC-like_    HRGPQEPSDSYWSSRGMNITFPVFLPKAA--EGHNGNGLA-SSLAPRKRR
```

FIGURE 10 (continued)

```
A.sativa_CN818591                  VDFTEAEEDLVFRMHRLVGNR-WELIA-GRIPG-RTAKEVEMFWAKKHR-
L.multiflorum_AU249134             VDFTEAEEDLVFRMHRLVGNR-WELIA-GRIPG-RTAGEVEMFWAKKQK-
A.capillaris_DV853805              VDFTEAEENLVFRMHRLVGTR-WELIA-GEIPG-RTAKEVEMFWAKKPR-
A.capillaris_DV859458              VDFTEAEEDLVFRMHRLVGNR-WELIA-GRIPG-RTAKEVEMFWAKKHQ-
H.vulgare_TC189825                 VDFTEAEEDLVFRMHRLVGNR-WELIA-GRIPG-RTAEEVEMFWAKKHQ-
T.aestivum_BE412359                VDFTEAEEDLVFRMHRLVGNR-WELIA-GRIPG-RTAEEVEMFWAKRHQ-
O.minuta_CB884361                  IHFTEEEEDLVFRMHRLVGNR-WELIA-GRIPG-RTAKEVEMFWAIKHQ-
O.sativa_LOC_Os01g43230.2          VHFTEEEEDLVFRMHRLVGNR-WELIA-GRIPG-RTAKEVEMFWAVKHQ-
S.bicolor_Sb03g028170.1            VDFTEAEEDLVSRMHRLVGNR-WEIIA-GRIPG-RTAEEVEMFWSKKHQ-
Z.mays_TC409725                    VDFTEAEEDLVSRMHRLVGNR-WEIIA-GRIPG-RTAEEVEMFWSKKYQ-
T.androssowii_TA2313_189785        --FSEDEETLITRMFNLVGER-WSLIA-GRIPG-RTAEEIEKYWTSRYY-
Triphysaria_sp_TC9313              LEITEDEETLINRMYNLVGER-WSLIA-GRIPG-RSAEEIEKYWNFRPQ-
S.tuberosum_CV505951               LEFSQDEEILITKMFNLVGER-WSLIA-GRIPG-RTAEEIEKYWNSRNS-
P.tremula_TA11725_113636           LEFSEDEETLITRMYNLAGER-WPLIA-GRIPG-RTAEEIEKYWTSRYS-
P.trichocarpa_594467               LEFSEDEETLITRMYNLVGER-WPLIA-GRIPG-RTAEEIEKYWTSRYS-
P.trichocarpa_562293               LEFSEDEETLITRMYNLVGER-WTLIA-GRIPG-RTAEEIEKYWTSRYS-
B.gymnorrhiza_TA2541_39984         LEFSEDEETLITRMYNLVGER-WPLIA-GRIPG-RTAEEIEKYWTSRYS-
M.esculenta_TA9427_3983            LEFTEDEETLITRMYNLVGER-WPLIA-GRIPG-RTAEEIEKYWNSRFS-
P.persica_BU039343                 LHFSEDEETLITRMFNLVGER-WSLIA-GRIPG-RSAEEIEKYWTSRYS-
V.vinifera_GSVIVT00026045001       LEFSEDEETLITRMFNLVGER-WSLIA-GRIPG-RTAEEIEKYWTSRYS-
L.tulipifera_CV004984              LEFTEDEQTLIERMFNLLGER-WSLIA-GRIPG-RTAEEIEKYWTSRYS-
G.hirsutum_TC121748                LDFSEDEETLIIRMFNLVGER-WSLIA-GRIPG-RTAEEIQKYWASRFS-
E.esula_DV121180                   QEFSEDEEELVIRMYNLVGER-WHLIA-GRIPG-RTADEIEKYWNSRYS-
M.domestica_TC17597                LQFSEDEEALIIRMYNLVGER-WALIA-GRIPG-RTAEEIEKYWTSTHS-
P.tremula_BU888423                 LEFSEDEETLIIRMFNLVGER-WSLIA-GRIPG-RTAEEIEKYWNTRYS-
P.trichocarpa_568212               LEFSEDEETLIIRMFNLVGER-WSLIA-GRIPG-RTAEEIEKYWNTRYS-
G.hirsutum_DW508052                LKFSEDEETLIIRMFNLVGER-WALIA-GRIPG-RTAEEIEEYWNTRYS-
G.hirsutum_TC116960                LQFSEDEETLVIRMFNLVGER-WGLIA-GRIPG-RTAEEIEKYWNTRYS-
V.vinifera_GSVIVT00006915001       LEFSEDEETLIIRMFNLVGER-WALIA-GRIPG-RTAEDIEKYWNSRYS-
J.hindsii_x_regia_TA1295_43229     LEFSEDEEMLIIRMFNLVGER-WSLIA-GRIPG-RTAEEIEKYWTSRYS-
G.max_8223                         VEFSEDEETLIIRMYKLVGER-WSIIA-GRIPG-RTAEEIEKYWTSRFS-
P.vulgaris_CV538421                VEFSEDEETLITRMYKLVGKR-WSLIA-GRIPG-RTAEEIEKYWTSKLS-
C.tetragonoloba_EG990179           VEFSEDEETLIIRMYKLVGKR-WPLIA-GRIPG-RTAEEIEKFWNSRFS-
G.max_29139                        VEFSEAEEILIAMVYNLVGER-WSLIA-GRIPG-RTAEEIEKYWTSRFS-
G.soja_TA4526_3848                 VEFSEAEEILIAMVYNLVGER-WSLIA-GRIPG-RTAEEIEKYWTSRFS-
L.japonicus_CB827663               VEFSEDEEILITMVYNLVGER-WSLIA-GRIPG-RTAEEIEKYWTSRYS-
C.canephora_DV693718               LHFSEDEEILIIRMFNLVGKR-WSLIA-GRIPG-RTAKEIEEYWNTRSA-
P.hybrida_EB175070                 IKFSEEEEDLIIRMYNLVGER-WSLIA-GRIPG-RSAEEIEKYWNTRSS-
```

FIGURE 10 (continued)

```
I.nil_TC6509                       LVFSVDEEALVVRMYNLVGER-WSLIA-GRIPG-RSAEEIEKYWNSTHS-
L.saligna_DW052030                 VHFSEDEKTLITRMYKLVGER-WSLIA-GRIPG-RSAEEIEKYWTSKYSR
A.hypogaea_CD038483                LEFSEDEEDLVARMFRLVGKR-WSLIA-GRIPG-RTAQEIEKYWSSKCAF
P.tremula_TA7610_113636            QDFSEDEENLIARMFGLVGKR-WSLIA-GRIPG-RTAEEIEKYWTSK---
P.equestris_CB034844               PNFTEEEDDLIARMYKLVGDR-WSLIA-GRIPG-RTSEEIENYWKSK---
V.vinifera_GSVIVT00010755001       VEFSEDEETLIARMFRLVGDR-WNLIA-GRIPG-RSAEEIKKYWTSK---
P.pinaster_CT579117                TNINEDEEDLIIRLHKLVGDR-WSLIA-GRIPG-RTPEEIEKYWKSRKQE
P.taeda_DR096185                   TNMNEDEEDLIIRLHKLLGER-WSLIA-GRIPG-RTPEEIEKYWKSRKQE
P.sitchensis_TA16538_3332          SDISADEEDLIIRLHKLLGDR-WALIA-GRLPW-RTTEEIEKYWKMRSQE
A.thaliana_At1g01380_CPC-like_     IAMAQEEEDLICRMYKLVGER-WDLIA-GRIPG-RTAEEIERFWVMKN--
B.napus_EV055366                   IAMTQEEEDLICRMYKLVGER-WDLIT-GRIPG-RTAQVIERFWVMKN--
A.thaliana_At4g01060_CPC-like_     VNMSQEEEDLVSRMHKLVGDR-WELIA-GRIPG-RTAGEIERFWVMKN--
A.thaliana_At2g46410_CPC-like_     VKMSEEEEDLISRMYKLVGDR-WELIA-GRIPG-RTPEEIERYWLMKHGV
B.napus_TC92601                    VKMTEEEEDLISRMYKLVGDR-WELIA-GRIPG-RTPEEIERYWLMKHGV
A.thaliana_At5g53200_CPC-like_     INMTEQEEDLIFRMYRLVGDR-WDLIA-GRVPG-RQPEEIERYWIMRNSE
B.napus_EE451172                   INMTEQEEDLIFRMHRLVGDR-WDLIA-GRVPG-RQPEEIERYWIMRNSD
J.hindsii_x_regia_EL893054         IKMTEQEEDLIFRMYKLVGDR-WDLIA-GRVPG-RKPEEIERFWIMRHGE
G.hirsutum_TC102183                INMSEQEEDLIYRMYKLVGDR-WGLIA-GRIPG-QKAEEIERFWIMRHGE
P.trichocarpa_807368               INMSEQEEDLIYRMHNLVGDR-WALIA-GRIPG-RKAEEIERFWLMRHGE
M.esculenta_DV443286               INMSEQEEDLIYRMYKLVGDR-WALIA-GRIPG-RKAEEIERFWIMRHGE
P.tremula_DN497189                 INMSEQEEDLIYRMHKLVGER-WDLIA-GRIPG-RKAEEIERFWIMKHRE
P.trichocarpa_674550               IDMSEQEEDLIYRMYRLVGER-WDLVA-GRIPG-RKAEEIERFWIMKHRE
C.longa_DY390653                   ISMTEQEEDLICRMYRLVGDR-WDLIA-GRVPG-RKPEEIERFWIMRHRQ
A.thaliana_At2g30420_CPC-like_     ISMTEQEEDLISRMYRLVGNR-WDLIA-GRVVG-RKANEIERYWIMRNSD
B.napus_CD843377                   IKMSQQEEDLILRMYRLVGDR-WEIIA-GRVPA-KKSCG-DREILDHEKQ
B.napus_TC95812                    IKMSQQEEDLILRMYRLVGDR-WEIIA-GRVPG-RKAVEIERYWIMRNNT
G.max_Glyma11g02060.1              IHMSEQEEDLIRRMYKLVGDK-WNLIA-GRIPS-RKAEEIERFWIMRHGD
M.truncatula_CT033771_17.4         IEMSEQEEDLIRRMYDLVGDR-WNLIA-GRIPG-RKAEEIERFWIMRHTD
L.serriola_DW108811                INMSEQEEDIIYRMHKLAGNR-WDLIA-GRISG-RNPEEIERFWLMRHSE
S.miltiorrhiza_CV166339            VNMTDQEEDIINRMHKLVGDR-WGLIA-GRLPG-RKAEEIERFWLMRNSD
S.miltiorrhiza_TA1626_226208       IKMTEQEEDIICRMHKLVGDK-WELIA-GRIPG-RSAEEIERFWLMRNGD
P.glauca_DR564374                  -DMSEEEEDLILRMYKLVGNK-WSLIA-GRIPG-RKAEEIERYWAMRTQQ
P.sitchensis_TA17447_3332          -DMSEEEEDLILRMYKLVGNK-WSLIA-GRIPG-RKAEEIERYWAMRTQQ
P.pinaster_TA6535_71647            -DMSEEEEDLILRMYKLIGNK-WSLIA-GRIPG-RKAEEIERYWAMRTQQ
P.menziesii_TA3655_3357            -DMSEEEEDLILRMYKLIGNK-WSLIA-GRIPG-RKAEEIERYWAMRTQQ
A.thaliana_At1g71030_CPC-like_     RNFSKDEDDLILKLHALLGNR-WSLIA-GRLPG-RTDNEVRIHWETYLKR
A.thaliana_At1g18960_CPC-like_     ESFTSEDEDLIIKMHAAMGSR-WQLIA-QHLPG-KTEEEVKMFWNTKLKK
A.thaliana_At1g09710_CPC-like_     KRWSAEEDEELFAAVKRCGEGNWAHIVKGDFRGERTASQLSQRWALIRKR
A.thaliana_At1g58220_CPC-like_     KKWSAEEDEELIAAVKRHGEGSWALISKEEFEGERTASQLSQRWGAIRRR
                                         :.  :       *   *  :    .   :
```

FIGURE 10 (continued)

```
A.sativa_CN818591                    -----------EQ-------------------------------------
L.multiflorum_AU249134               -----------EQ-------------------------------------
A.capillaris_DV853805                -----------EQ-------------------------------------
A.capillaris_DV859458                -----------EQ-------------------------------------
H.vulgare_TC189825                   -----------DQ-------------------------------------
T.aestivum_BE412359                  -----------DQ-------------------------------------
O.minuta_CB884361                    -----------DT-------------------------------------
O.sativa_LOC_Os01g43230.2            -----------NT-------------------------------------
S.bicolor_Sb03g028170.1              -----------ER-------------------------------------
Z.mays_TC409725                      -----------ER-------------------------------------
T.androssowii_TA2313_189785          ----------TSR-------------------------------------
Triphysaria_sp_TC9313                ----------STLKQLLDNAILVVDNQP----------------------
S.tuberosum_CV505951                 ----------TSQ-------------------------------------
P.tremula_TA11725_113636             ----------TSQ-------------------------------------
P.trichocarpa_594467                 ----------TSQ-------------------------------------
P.trichocarpa_562293                 ----------TSQ-------------------------------------
B.gymnorrhiza_TA2541_39984           ----------TSQ-------------------------------------
M.esculenta_TA9427_3983              ----------SSQ-------------------------------------
P.persica_BU039343                   ----------TSE-------------------------------------
V.vinifera_GSVIVT00026045001         ----------SSE-------------------------------------
L.tulipifera_CV004984                ----------SSE-------------------------------------
G.hirsutum_TC121748                  ----------YNNPMPNLS-------------------------------
E.esula_DV121180                     ----------TSA-------------------------------------
M.domestica_TC17597                  ----------TSQ-------------------------------------
P.tremula_BU888423                   ----------TSE-------------------------------------
P.trichocarpa_568212                 ----------TSE-------------------------------------
G.hirsutum_DW508052                  ----------TRKDIFKERGQI----------------------------
G.hirsutum_TC116960                  ----------TSQ-------------------------------------
V.vinifera_GSVIVT00006915001         ----------TSE-------------------------------------
J.hindsii_x_regia_TA1295_43229       ----------TSEMK-----------------------------------
G.max_8223                           ----------GSSE------------------------------------
P.vulgaris_CV538421                  ----------SSSK------------------------------------
C.tetragonoloba_EG990179             ----------NSK-------------------------------------
G.max_29139                          ----------TSQ-------------------------------------
G.soja_TA4526_3848                   ----------TSQ-------------------------------------
L.japonicus_CB827663                 ----------TSE-------------------------------------
C.canephora_DV693718                 ----------TSP-------------------------------------
P.hybrida_EB175070                   ----------TSQ-------------------------------------
```

FIGURE 10 (continued)

| | |
|---|---|
| I.nil_TC6509 | ----------TSHQ------------------------------------ |
| L.saligna_DW052030 | ----------TNDQM----------------------------------- |
| A.hypogaea_CD038483 | PSD-----QCSSSA------------------------------------ |
| P.tremula_TA7610_113636 | --------QRSSKER----------------------------------- |
| P.equestris_CB034844 | --------NSTSST------------------------------------ |
| V.vinifera_GSVIVT00010755001 | --------SVSSSTKQHD-------------------------------- |
| P.pinaster_CT579117 | ----------NSKRKRGK-------------------------------- |
| P.taeda_DR096185 | ----------NSKRKRGK-------------------------------- |
| P.sitchensis_TA16538_3332 | ----------IDQSSD---------------------------------- |
| A.thaliana_At1g01380_CPC-like_ | ------------HRRSQLR------------------------------- |
| B.napus_EV055366 | ------------HRRA---------------------------------- |
| A.thaliana_At4g01060_CPC-like_ | -------------------------------------------------- |
| A.thaliana_At2g46410_CPC-like_ | V--------FANRRRDFFRK------------------------------ |
| B.napus_TC92601 | V--------FANRPRDFVRR------------------------------ |
| A.thaliana_At5g53200_CPC-like_ | G--------FADKRRQLH-SSSHKHTKPHRPRFSIYPS------------ |
| B.napus_EE451172 | G--------FAEKRRQLHHSSSHKSTKPHRPRFSIYPS------------ |
| J.hindsii_x_regia_EL893054 | V--------FAQKR-----DAAAKN-------YS---------------- |
| G.hirsutum_TC102183 | L--------FAKRRRELKMRHGSV-------------------------- |
| P.trichocarpa_807368 | G--------FASRRREQKRCHS---------------------------- |
| M.esculenta_DV443286 | G--------FAGRRKELKKSKC---------------------------- |
| P.tremula_DN497189 | G--------FAGNGKLYNEVKSRTSS------------------------ |
| P.trichocarpa_674550 | G--------FAEKRRLHSKAKSKTYR------------------------ |
| C.longa_DY390653 | ----------DSRRRSSFASHAK--------------------------- |
| A.thaliana_At2g30420_CPC-like_ | Y--------FSHKRRRLNNSPFFSTSPLNLQENLKL-------------- |
| B.napus_CD843377 | H--------TCPPSIFQILTSFLCCASHVCFKCYIFISKTKN-------- |
| B.napus_TC95812 | H--------FLPPS-----SKF---------------------------- |
| G.max_Glyma11g02060.1 | ------A--FSVKRH----RSKAQDS------------------------ |
| M.truncatula_CT033771_17.4 | ------A--FSAKRK----K------------------------------ |
| L.serriola_DW108811 | ------A--YEDLRK----RVKS--------------------------- |
| S.miltiorrhiza_CV166339 | ------N--FTDKRKEYHRRQKS--------------------------- |
| S.miltiorrhiza_TA1626_226208 | ERKRKAN--NIERAPPLHVRVSSAD------------------------- |
| P.glauca_DR564374 | LCGGHGA-IFTNKKQTANMISIQYRINGCNDVEVNS-------------- |
| P.sitchensis_TA17447_3332 | LCGGHGA-IFTNKKQTANMISIQYRINGCNDVEVNS-------------- |
| P.pinaster_TA6535_71647 | LCGGHDA-ILTKKQQKTNMISIQYRINGPNDVEVNS-------------- |
| P.menziesii_TA3655_3357 | FCGSHGATIFASNKQMGNMISIPYHINGCNDVEVHS-------------- |
| A.thaliana_At1g71030_CPC-like_ | KLVKMGIDPTNHRLHHHTNYISRRHLHSSHKEHETKIISDQSSSVSESCG |
| A.thaliana_At1g18960_CPC-like_ | KLSEMGIDHVTHRPFSHVLAEYGNINGGGNLNPNPSNQAGSLGRNHSLND |
| A.thaliana_At1g09710_CPC-like_ | CHTSTSVSQCGLQGTEAKLAVNHALSLALGNRPPSNKLAIGLMPTTSSCT |
| A.thaliana_At1g58220_CPC-like_ | TDTSNTSTQTGLQRTEAQMAANRALSLAVGNRLPSKKLAVGMTPMLSSGT |

FIGURE 10 (continued)

```
A.sativa_CN818591                   --------------------------------------------------
L.multiflorum_AU249134              --------------------------------------------------
A.capillaris_DV853805               --------------------------------------------------
A.capillaris_DV859458               --------------------------------------------------
H.vulgare_TC189825                  --------------------------------------------------
T.aestivum_BE412359                 --------------------------------------------------
O.minuta_CB884361                   --------------------------------------------------
O.sativa_LOC_Os01g43230.2           --------------------------------------------------
S.bicolor_Sb03g028170.1             --------------------------------------------------
Z.mays_TC409725                     --------------------------------------------------
T.androssowii_TA2313_189785         --------------------------------------------------
Triphysaria_sp_TC9313               --------------------------------------------------
S.tuberosum_CV505951                --------------------------------------------------
P.tremula_TA11725_113636            --------------------------------------------------
P.trichocarpa_594467                --------------------------------------------------
P.trichocarpa_562293                --------------------------------------------------
B.gymnorrhiza_TA2541_39984          --------------------------------------------------
M.esculenta_TA9427_3983             --------------------------------------------------
P.persica_BU039343                  --------------------------------------------------
V.vinifera_GSVIVT00026045001        --------------------------------------------------
L.tulipifera_CV004984               --------------------------------------------------
G.hirsutum_TC121748                 --------------------------------------------------
E.esula_DV121180                    --------------------------------------------------
M.domestica_TC17597                 --------------------------------------------------
P.tremula_BU888423                  --------------------------------------------------
P.trichocarpa_568212                --------------------------------------------------
G.hirsutum_DW508052                 --------------------------------------------------
G.hirsutum_TC116960                 --------------------------------------------------
V.vinifera_GSVIVT00006915001        --------------------------------------------------
J.hindsii_x_regia_TA1295_43229      --------------------------------------------------
G.max_8223                          --------------------------------------------------
P.vulgaris_CV538421                 --------------------------------------------------
C.tetragonoloba_EG990179            --------------------------------------------------
G.max_29139                         --------------------------------------------------
G.soja_TA4526_3848                  --------------------------------------------------
L.japonicus_CB827663                --------------------------------------------------
C.canephora_DV693718                --------------------------------------------------
P.hybrida_EB175070                  --------------------------------------------------
```

FIGURE 10 (continued)

| | |
|---|---|
| I.nil_TC6509 | -------------------------------------------------- |
| L.saligna_DW052030 | -------------------------------------------------- |
| A.hypogaea_CD038483 | -------------------------------------------------- |
| P.tremula_TA7610_113636 | -------------------------------------------------- |
| P.equestris_CB034844 | -------------------------------------------------- |
| V.vinifera_GSVIVT00010755001 | -------------------------------------------------- |
| P.pinaster_CT579117 | -------------------------------------------------- |
| P.taeda_DR096185 | -------------------------------------------------- |
| P.sitchensis_TA16538_3332 | -------------------------------------------------- |
| A.thaliana_At1g01380_CPC-like_ | -------------------------------------------------- |
| B.napus_EV055366 | -------------------------------------------------- |
| A.thaliana_At4g01060_CPC-like_ | -------------------------------------------------- |
| A.thaliana_At2g46410_CPC-like_ | -------------------------------------------------- |
| B.napus_TC92601 | -------------------------------------------------- |
| A.thaliana_At5g53200_CPC-like_ | -------------------------------------------------- |
| B.napus_EE451172 | -------------------------------------------------- |
| J.hindsii_x_regia_EL893054 | -------------------------------------------------- |
| G.hirsutum_TC102183 | -------------------------------------------------- |
| P.trichocarpa_807368 | -------------------------------------------------- |
| M.esculenta_DV443286 | -------------------------------------------------- |
| P.tremula_DN497189 | -------------------------------------------------- |
| P.trichocarpa_674550 | -------------------------------------------------- |
| C.longa_DY390653 | -------------------------------------------------- |
| A.thaliana_At2g30420_CPC-like_ | -------------------------------------------------- |
| B.napus_CD843377 | -------------------------------------------------- |
| B.napus_TC95812 | -------------------------------------------------- |
| G.max_Glyma11g02060.1 | -------------------------------------------------- |
| M.truncatula_CT033771_17.4 | -------------------------------------------------- |
| L.serriola_DW108811 | -------------------------------------------------- |
| S.miltiorrhiza_CV166339 | -------------------------------------------------- |
| S.miltiorrhiza_TA1626_226208 | -------------------------------------------------- |
| P.glauca_DR564374 | -------------------------------------------------- |
| P.sitchensis_TA17447_3332 | -------------------------------------------------- |
| P.pinaster_TA6535_71647 | -------------------------------------------------- |
| P.menziesii_TA3655_3357 | -------------------------------------------------- |
| A.thaliana_At1g71030_CPC-like_ | VTILPIPSTNCSEDSTSTGRSHLPDLNIGLIPAVTSLPALCLQDSSESST |
| A.thaliana_At1g18960_CPC-like_ | DGHQQQPNDSGDLMFHLQAIKLMTDSSNQVKPESTFVYASSSSSNSSPPL |
| A.thaliana_At1g09710_CPC-like_ | ITETEANGGSSS---QGQQQSKPIVQALPRAGTSLPAAKSRV-VKKTTAS |
| A.thaliana_At1g58220_CPC-like_ | IKGAQANGASSGSTLQGQQQPQPQIQALSRATTSVPVAKSRVPVKKTTGN |

FIGURE 10 (continued)

```
A.sativa_CN818591                   --------------------------------------------------
L.multiflorum_AU249134              --------------------------------------------------
A.capillaris_DV853805               --------------------------------------------------
A.capillaris_DV859458               --------------------------------------------------
H.vulgare_TC189825                  --------------------------------------------------
T.aestivum_BE412359                 --------------------------------------------------
O.minuta_CB884361                   --------------------------------------------------
O.sativa_LOC_Os01g43230.2           --------------------------------------------------
S.bicolor_Sb03g028170.1             --------------------------------------------------
Z.mays_TC409725                     --------------------------------------------------
T.androssowii_TA2313_189785         --------------------------------------------------
Triphysaria_sp_TC9313               --------------------------------------------------
S.tuberosum_CV505951                --------------------------------------------------
P.tremula_TA11725_113636            --------------------------------------------------
P.trichocarpa_594467                --------------------------------------------------
P.trichocarpa_562293                --------------------------------------------------
B.gymnorrhiza_TA2541_39984          --------------------------------------------------
M.esculenta_TA9427_3983             --------------------------------------------------
P.persica_BU039343                  --------------------------------------------------
V.vinifera_GSVIVT00026045001        --------------------------------------------------
L.tulipifera_CV004984               --------------------------------------------------
G.hirsutum_TC121748                 --------------------------------------------------
E.esula_DV121180                    --------------------------------------------------
M.domestica_TC17597                 --------------------------------------------------
P.tremula_BU888423                  --------------------------------------------------
P.trichocarpa_568212                --------------------------------------------------
G.hirsutum_DW508052                 --------------------------------------------------
G.hirsutum_TC116960                 --------------------------------------------------
V.vinifera_GSVIVT00006915001        --------------------------------------------------
J.hindsii_x_regia_TA1295_43229      --------------------------------------------------
G.max_8223                          --------------------------------------------------
P.vulgaris_CV538421                 --------------------------------------------------
C.tetragonoloba_EG990179            --------------------------------------------------
G.max_29139                         --------------------------------------------------
G.soja_TA4526_3848                  --------------------------------------------------
L.japonicus_CB827663                --------------------------------------------------
C.canephora_DV693718                --------------------------------------------------
P.hybrida_EB175070                  --------------------------------------------------
```

FIGURE 10 (continued)

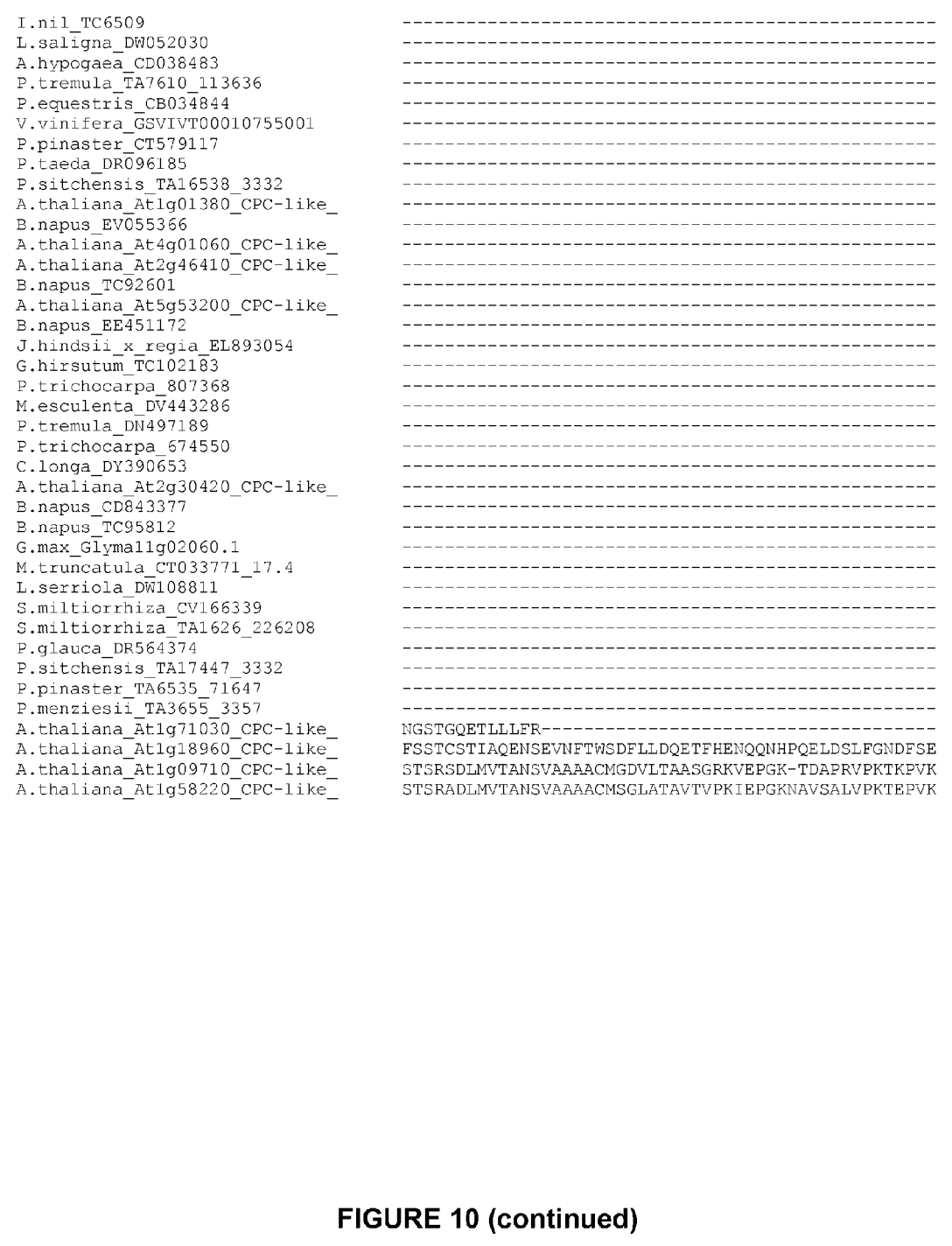

```
I.nil_TC6509                          --------------------------------------------------
L.saligna_DW052030                    --------------------------------------------------
A.hypogaea_CD038483                   --------------------------------------------------
P.tremula_TA7610_113636               --------------------------------------------------
P.equestris_CB034844                  --------------------------------------------------
V.vinifera_GSVIVT00010755001          --------------------------------------------------
P.pinaster_CT579117                   --------------------------------------------------
P.taeda_DR096185                      --------------------------------------------------
P.sitchensis_TA16538_3332             --------------------------------------------------
A.thaliana_At1g01380_CPC-like_        --------------------------------------------------
B.napus_EV055366                      --------------------------------------------------
A.thaliana_At4g01060_CPC-like_        --------------------------------------------------
A.thaliana_At2g46410_CPC-like_        --------------------------------------------------
B.napus_TC92601                       --------------------------------------------------
A.thaliana_At5g53200_CPC-like_        --------------------------------------------------
B.napus_EE451172                      --------------------------------------------------
J.hindsii_x_regia_EL893054            --------------------------------------------------
G.hirsutum_TC102183                   --------------------------------------------------
P.trichocarpa_807368                  --------------------------------------------------
M.esculenta_DV443286                  --------------------------------------------------
P.tremula_DN497189                    --------------------------------------------------
P.trichocarpa_674550                  --------------------------------------------------
C.longa_DY390653                      --------------------------------------------------
A.thaliana_At2g30420_CPC-like_        --------------------------------------------------
B.napus_CD843377                      --------------------------------------------------
B.napus_TC95812                       --------------------------------------------------
G.max_Glyma11g02060.1                 --------------------------------------------------
M.truncatula_CT033771_17.4            --------------------------------------------------
L.serriola_DW108811                   --------------------------------------------------
S.miltiorrhiza_CV166339               --------------------------------------------------
S.miltiorrhiza_TA1626_226208          --------------------------------------------------
P.glauca_DR564374                     --------------------------------------------------
P.sitchensis_TA17447_3332             --------------------------------------------------
P.pinaster_TA6535_71647               --------------------------------------------------
P.menziesii_TA3655_3357               --------------------------------------------------
A.thaliana_At1g71030_CPC-like_        NGSTGQETLLLFR-------------------------------------
A.thaliana_At1g18960_CPC-like_        FSSTCSTIAQENSEVNFTWSDFLLDQETFHENQQNHPQELDSLFGNDFSE
A.thaliana_At1g09710_CPC-like_        STSRSDLMVTANSVAAAACMGDVLTAASGRKVEPGK-TDAPRVPKTKPVK
A.thaliana_At1g58220_CPC-like_        STSRADLMVTANSVAAAACMSGLATAVTVPKIEPGKNAVSALVPKTEPVK
```

FIGURE 10 (continued)

```
A.sativa_CN818591                    --------------------------------------------------
L.multiflorum_AU249134               --------------------------------------------------
A.capillaris_DV853805                --------------------------------------------------
A.capillaris_DV859458                --------------------------------------------------
H.vulgare_TC189825                   --------------------------------------------------
T.aestivum_BE412359                  --------------------------------------------------
O.minuta_CB884361                    --------------------------------------------------
O.sativa_LOC_Os01g43230.2            --------------------------------------------------
S.bicolor_Sb03g028170.1              --------------------------------------------------
Z.mays_TC409725                      --------------------------------------------------
T.androssowii_TA2313_189785          --------------------------------------------------
Triphysaria_sp_TC9313                --------------------------------------------------
S.tuberosum_CV505951                 --------------------------------------------------
P.tremula_TA11725_113636             --------------------------------------------------
P.trichocarpa_594467                 --------------------------------------------------
P.trichocarpa_562293                 --------------------------------------------------
B.gymnorrhiza_TA2541_39984           --------------------------------------------------
M.esculenta_TA9427_3983              --------------------------------------------------
P.persica_BU039343                   --------------------------------------------------
V.vinifera_GSVIVT00026045001         --------------------------------------------------
L.tulipifera_CV004984                --------------------------------------------------
G.hirsutum_TC121748                  --------------------------------------------------
E.esula_DV121180                     --------------------------------------------------
M.domestica_TC17597                  --------------------------------------------------
P.tremula_BU888423                   --------------------------------------------------
P.trichocarpa_568212                 --------------------------------------------------
G.hirsutum_DW508052                  --------------------------------------------------
G.hirsutum_TC116960                  --------------------------------------------------
V.vinifera_GSVIVT00006915001         --------------------------------------------------
J.hindsii_x_regia_TA1295_43229       --------------------------------------------------
G.max_8223                           --------------------------------------------------
P.vulgaris_CV538421                  --------------------------------------------------
C.tetragonoloba_EG990179             --------------------------------------------------
G.max_29139                          --------------------------------------------------
G.soja_TA4526_3848                   --------------------------------------------------
L.japonicus_CB827663                 --------------------------------------------------
C.canephora_DV693718                 --------------------------------------------------
P.hybrida_EB175070                   --------------------------------------------------
```

FIGURE 10 (continued)

```
I.nil_TC6509                          --------------------------------------------------
L.saligna_DW052030                    --------------------------------------------------
A.hypogaea_CD038483                   --------------------------------------------------
P.tremula_TA7610_113636               --------------------------------------------------
P.equestris_CB034844                  --------------------------------------------------
V.vinifera_GSVIVT00010755001          --------------------------------------------------
P.pinaster_CT579117                   --------------------------------------------------
P.taeda_DR096185                      --------------------------------------------------
P.sitchensis_TA16538_3332             --------------------------------------------------
A.thaliana_At1g01380_CPC-like_        --------------------------------------------------
B.napus_EV055366                      --------------------------------------------------
A.thaliana_At4g01060_CPC-like_        --------------------------------------------------
A.thaliana_At2g46410_CPC-like_        --------------------------------------------------
B.napus_TC92601                       --------------------------------------------------
A.thaliana_At5g53200_CPC-like_        --------------------------------------------------
B.napus_EE451172                      --------------------------------------------------
J.hindsii_x_regia_EL893054            --------------------------------------------------
G.hirsutum_TC102183                   --------------------------------------------------
P.trichocarpa_807368                  --------------------------------------------------
M.esculenta_DV443286                  --------------------------------------------------
P.tremula_DN497189                    --------------------------------------------------
P.trichocarpa_674550                  --------------------------------------------------
C.longa_DY390653                      --------------------------------------------------
A.thaliana_At2g30420_CPC-like_        --------------------------------------------------
B.napus_CD843377                      --------------------------------------------------
B.napus_TC95812                       --------------------------------------------------
G.max_Glyma11g02060.1                 --------------------------------------------------
M.truncatula_CT033771_17.4            --------------------------------------------------
L.serriola_DW108811                   --------------------------------------------------
S.miltiorrhiza_CV166339               --------------------------------------------------
S.miltiorrhiza_TA1626_226208          --------------------------------------------------
P.glauca_DR564374                     --------------------------------------------------
P.sitchensis_TA17447_3332             --------------------------------------------------
P.pinaster_TA6535_71647               --------------------------------------------------
P.menziesii_TA3655_3357               --------------------------------------------------
A.thaliana_At1g71030_CPC-like_        --------------------------------------------------
A.thaliana_At1g18960_CPC-like_        VTAATMANTSTVPSQIEEESLSNGFVESIIAKEKEFFLGFPSYLEQPFHF
A.thaliana_At1g09710_CPC-like_        HASTVCMPQPS---------------------------------------
A.thaliana_At1g58220_CPC-like_        TASTVSMPRPSGISSALNTEPVKTAVAASLPRSSGIISAPKVEPVKTAAS
```

FIGURE 10 (continued)

```
A.sativa_CN818591                    --------------------------------------------------
L.multiflorum_AU249134               --------------------------------------------------
A.capillaris_DV853805                --------------------------------------------------
A.capillaris_DV859458                --------------------------------------------------
H.vulgare_TC189825                   --------------------------------------------------
T.aestivum_BE412359                  --------------------------------------------------
O.minuta_CB884361                    --------------------------------------------------
O.sativa_LOC_Os01g43230.2            --------------------------------------------------
S.bicolor_Sb03g028170.1              --------------------------------------------------
Z.mays_TC409725                      --------------------------------------------------
T.androssowii_TA2313_189785          --------------------------------------------------
Triphysaria_sp_TC9313                --------------------------------------------------
S.tuberosum_CV505951                 --------------------------------------------------
P.tremula_TA11725_113636             --------------------------------------------------
P.trichocarpa_594467                 --------------------------------------------------
P.trichocarpa_562293                 --------------------------------------------------
B.gymnorrhiza_TA2541_39984           --------------------------------------------------
M.esculenta_TA9427_3983              --------------------------------------------------
P.persica_BU039343                   --------------------------------------------------
V.vinifera_GSVIVT00026045001         --------------------------------------------------
L.tulipifera_CV004984                --------------------------------------------------
G.hirsutum_TC121748                  --------------------------------------------------
E.esula_DV121180                     --------------------------------------------------
M.domestica_TC17597                  --------------------------------------------------
P.tremula_BU888423                   --------------------------------------------------
P.trichocarpa_568212                 --------------------------------------------------
G.hirsutum_DW508052                  --------------------------------------------------
G.hirsutum_TC116960                  --------------------------------------------------
V.vinifera_GSVIVT00006915001         --------------------------------------------------
J.hindsii_x_regia_TA1295_43229       --------------------------------------------------
G.max_8223                           --------------------------------------------------
P.vulgaris_CV538421                  --------------------------------------------------
C.tetragonoloba_EG990179             --------------------------------------------------
G.max_29139                          --------------------------------------------------
G.soja_TA4526_3848                   --------------------------------------------------
L.japonicus_CB827663                 --------------------------------------------------
C.canephora_DV693718                 --------------------------------------------------
P.hybrida_EB175070                   --------------------------------------------------
```

FIGURE 10 (continued)

```
I.nil_TC6509                          --------------------------------------------------
L.saligna_DW052030                    --------------------------------------------------
A.hypogaea_CD038483                   --------------------------------------------------
P.tremula_TA7610_113636               --------------------------------------------------
P.equestris_CB034844                  --------------------------------------------------
V.vinifera_GSVIVT00010755001          --------------------------------------------------
P.pinaster_CT579117                   --------------------------------------------------
P.taeda_DR096185                      --------------------------------------------------
P.sitchensis_TA16538_3332             --------------------------------------------------
A.thaliana_At1g01380_CPC-like_        --------------------------------------------------
B.napus_EV055366                      --------------------------------------------------
A.thaliana_At4g01060_CPC-like_        --------------------------------------------------
A.thaliana_At2g46410_CPC-like_        --------------------------------------------------
B.napus_TC92601                       --------------------------------------------------
A.thaliana_At5g53200_CPC-like_        --------------------------------------------------
B.napus_EE451172                      --------------------------------------------------
J.hindsii_x_regia_EL893054            --------------------------------------------------
G.hirsutum_TC102183                   --------------------------------------------------
P.trichocarpa_807368                  --------------------------------------------------
M.esculenta_DV443286                  --------------------------------------------------
P.tremula_DN497189                    --------------------------------------------------
P.trichocarpa_674550                  --------------------------------------------------
C.longa_DY390653                      --------------------------------------------------
A.thaliana_At2g30420_CPC-like_        --------------------------------------------------
B.napus_CD843377                      --------------------------------------------------
B.napus_TC95812                       --------------------------------------------------
G.max_Glyma11g02060.1                 --------------------------------------------------
M.truncatula_CT033771_17.4            --------------------------------------------------
L.serriola_DW108811                   --------------------------------------------------
S.miltiorrhiza_CV166339               --------------------------------------------------
S.miltiorrhiza_TA1626_226208          --------------------------------------------------
P.glauca_DR564374                     --------------------------------------------------
P.sitchensis_TA17447_3332             --------------------------------------------------
P.pinaster_TA6535_71647               --------------------------------------------------
P.menziesii_TA3655_3357               --------------------------------------------------
A.thaliana_At1g71030_CPC-like_        --------------------------------------------------
A.thaliana_At1g18960_CPC-like_        --------------------------------------------------
A.thaliana_At1g09710_CPC-like_        --------GSLSMPKVEPG---------------------------TSVA
A.thaliana_At1g58220_CPC-like_        AASLPRPSGMISAPKVEPVKTTASVASLPRPSGIISAPKAEPVKTAASAA
```

FIGURE 10 (continued)

```
A.sativa_CN818591                    --------------------------------------------------
L.multiflorum_AU249134               --------------------------------------------------
A.capillaris_DV853805                --------------------------------------------------
A.capillaris_DV859458                --------------------------------------------------
H.vulgare_TC189825                   --------------------------------------------------
T.aestivum_BE412359                  --------------------------------------------------
O.minuta_CB884361                    --------------------------------------------------
O.sativa_LOC_Os01g43230.2            --------------------------------------------------
S.bicolor_Sb03g028170.1              --------------------------------------------------
Z.mays_TC409725                      --------------------------------------------------
T.androssowii_TA2313_189785          --------------------------------------------------
Triphysaria_sp_TC9313                --------------------------------------------------
S.tuberosum_CV505951                 --------------------------------------------------
P.tremula_TA11725_113636             --------------------------------------------------
P.trichocarpa_594467                 --------------------------------------------------
P.trichocarpa_562293                 --------------------------------------------------
B.gymnorrhiza_TA2541_39984           --------------------------------------------------
M.esculenta_TA9427_3983              --------------------------------------------------
P.persica_BU039343                   --------------------------------------------------
V.vinifera_GSVIVT00026045001         --------------------------------------------------
L.tulipifera_CV004984                --------------------------------------------------
G.hirsutum_TC121748                  --------------------------------------------------
E.esula_DV121180                     --------------------------------------------------
M.domestica_TC17597                  --------------------------------------------------
P.tremula_BU888423                   --------------------------------------------------
P.trichocarpa_568212                 --------------------------------------------------
G.hirsutum_DW508052                  --------------------------------------------------
G.hirsutum_TC116960                  --------------------------------------------------
V.vinifera_GSVIVT00006915001         --------------------------------------------------
J.hindsii_x_regia_TA1295_43229       --------------------------------------------------
G.max_8223                           --------------------------------------------------
P.vulgaris_CV538421                  --------------------------------------------------
C.tetragonoloba_EG990179             --------------------------------------------------
G.max_29139                          --------------------------------------------------
G.soja_TA4526_3848                   --------------------------------------------------
L.japonicus_CB827663                 --------------------------------------------------
C.canephora_DV693718                 --------------------------------------------------
P.hybrida_EB175070                   --------------------------------------------------
```

FIGURE 10 (continued)

```
I.nil_TC6509                        --------------------------------------------------
L.saligna_DW052030                  --------------------------------------------------
A.hypogaea_CD038483                 --------------------------------------------------
P.tremula_TA7610_113636             --------------------------------------------------
P.equestris_CB034844                --------------------------------------------------
V.vinifera_GSVIVT00010755001        --------------------------------------------------
P.pinaster_CT579117                 --------------------------------------------------
P.taeda_DR096185                    --------------------------------------------------
P.sitchensis_TA16538_3332           --------------------------------------------------
A.thaliana_At1g01380_CPC-like_      --------------------------------------------------
B.napus_EV055366                    --------------------------------------------------
A.thaliana_At4g01060_CPC-like_      --------------------------------------------------
A.thaliana_At2g46410_CPC-like_      --------------------------------------------------
B.napus_TC92601                     --------------------------------------------------
A.thaliana_At5g53200_CPC-like_      --------------------------------------------------
B.napus_EE451172                    --------------------------------------------------
J.hindsii_x_regia_EL893054          --------------------------------------------------
G.hirsutum_TC102183                 --------------------------------------------------
P.trichocarpa_807368                --------------------------------------------------
M.esculenta_DV443286                --------------------------------------------------
P.tremula_DN497189                  --------------------------------------------------
P.trichocarpa_674550                --------------------------------------------------
C.longa_DY390653                    --------------------------------------------------
A.thaliana_At2g30420_CPC-like_      --------------------------------------------------
B.napus_CD843377                    --------------------------------------------------
B.napus_TC95812                     --------------------------------------------------
G.max_Glyma11g02060.1               --------------------------------------------------
M.truncatula_CT033771_17.4          --------------------------------------------------
L.serriola_DW108811                 --------------------------------------------------
S.miltiorrhiza_CV166339             --------------------------------------------------
S.miltiorrhiza_TA1626_226208        --------------------------------------------------
P.glauca_DR564374                   --------------------------------------------------
P.sitchensis_TA17447_3332           --------------------------------------------------
P.pinaster_TA6535_71647             --------------------------------------------------
P.menziesii_TA3655_3357             --------------------------------------------------
A.thaliana_At1g71030_CPC-like_      --------------------------------------------------
A.thaliana_At1g18960_CPC-like_      --------------------------------------------------
A.thaliana_At1g09710_CPC-like_      AS------------------------------------------------
A.thaliana_At1g58220_CPC-like_      SSPRPSGMISAPKVESVKTTASMPRPSGIISAPKAELVKSAASAASLPCT
```

FIGURE 10 (continued)

```
A.sativa_CN818591                   --------------------------------------------------
L.multiflorum_AU249134              --------------------------------------------------
A.capillaris_DV853805               --------------------------------------------------
A.capillaris_DV859458               --------------------------------------------------
H.vulgare_TC189825                  --------------------------------------------------
T.aestivum_BE412359                 --------------------------------------------------
O.minuta_CB884361                   --------------------------------------------------
O.sativa_LOC_Os01g43230.2           --------------------------------------------------
S.bicolor_Sb03g028170.1             --------------------------------------------------
Z.mays_TC409725                     --------------------------------------------------
T.androssowii_TA2313_189785         --------------------------------------------------
Triphysaria_sp_TC9313               --------------------------------------------------
S.tuberosum_CV505951                --------------------------------------------------
P.tremula_TA11725_113636            --------------------------------------------------
P.trichocarpa_594467                --------------------------------------------------
P.trichocarpa_562293                --------------------------------------------------
B.gymnorrhiza_TA2541_39984          --------------------------------------------------
M.esculenta_TA9427_3983             --------------------------------------------------
P.persica_BU039343                  --------------------------------------------------
V.vinifera_GSVIVT00026045001        --------------------------------------------------
L.tulipifera_CV004984               --------------------------------------------------
G.hirsutum_TC121748                 --------------------------------------------------
E.esula_DV121180                    --------------------------------------------------
M.domestica_TC17597                 --------------------------------------------------
P.tremula_BU888423                  --------------------------------------------------
P.trichocarpa_568212                --------------------------------------------------
G.hirsutum_DW508052                 --------------------------------------------------
G.hirsutum_TC116960                 --------------------------------------------------
V.vinifera_GSVIVT00006915001        --------------------------------------------------
J.hindsii_x_regia_TA1295_43229      --------------------------------------------------
G.max_8223                          --------------------------------------------------
P.vulgaris_CV538421                 --------------------------------------------------
C.tetragonoloba_EG990179            --------------------------------------------------
G.max_29139                         --------------------------------------------------
G.soja_TA4526_3848                  --------------------------------------------------
L.japonicus_CB827663                --------------------------------------------------
C.canephora_DV693718                --------------------------------------------------
P.hybrida_EB175070                  --------------------------------------------------
```

FIGURE 10 (continued)

```
I.nil_TC6509                      --------------------------------------------------
L.saligna_DW052030                --------------------------------------------------
A.hypogaea_CD038483               --------------------------------------------------
P.tremula_TA7610_113636           --------------------------------------------------
P.equestris_CB034844              --------------------------------------------------
V.vinifera_GSVIVT00010755001      --------------------------------------------------
P.pinaster_CT579117               --------------------------------------------------
P.taeda_DR096185                  --------------------------------------------------
P.sitchensis_TA16538_3332         --------------------------------------------------
A.thaliana_At1g01380_CPC-like_    --------------------------------------------------
B.napus_EV055366                  --------------------------------------------------
A.thaliana_At4g01060_CPC-like_    --------------------------------------------------
A.thaliana_At2g46410_CPC-like_    --------------------------------------------------
B.napus_TC92601                   --------------------------------------------------
A.thaliana_At5g53200_CPC-like_    --------------------------------------------------
B.napus_EE451172                  --------------------------------------------------
J.hindsii_x_regia_EL893054        --------------------------------------------------
G.hirsutum_TC102183               --------------------------------------------------
P.trichocarpa_807368              --------------------------------------------------
M.esculenta_DV443286              --------------------------------------------------
P.tremula_DN497189                --------------------------------------------------
P.trichocarpa_674550              --------------------------------------------------
C.longa_DY390653                  --------------------------------------------------
A.thaliana_At2g30420_CPC-like_    --------------------------------------------------
B.napus_CD843377                  --------------------------------------------------
B.napus_TC95812                   --------------------------------------------------
G.max_Glyma11g02060.1             --------------------------------------------------
M.truncatula_CT033771_17.4        --------------------------------------------------
L.serriola_DW108811               --------------------------------------------------
S.miltiorrhiza_CV166339           --------------------------------------------------
S.miltiorrhiza_TA1626_226208      --------------------------------------------------
P.glauca_DR564374                 --------------------------------------------------
P.sitchensis_TA17447_3332         --------------------------------------------------
P.pinaster_TA6535_71647           --------------------------------------------------
P.menziesii_TA3655_3357           --------------------------------------------------
A.thaliana_At1g71030_CPC-like_    --------------------------------------------------
A.thaliana_At1g18960_CPC-like_    --------------------------------------------------
A.thaliana_At1g09710_CPC-like_    --------------------------------------------------
A.thaliana_At1g58220_CPC-like_    SGIISSPKAELVKSAASAASFPRPSSMLSAPKADPVKIVPAAATNTKSVG
```

FIGURE 10 (continued)

```
A.sativa_CN818591                     --------------------------------------------------
L.multiflorum_AU249134                --------------------------------------------------
A.capillaris_DV853805                 --------------------------------------------------
A.capillaris_DV859458                 --------------------------------------------------
H.vulgare_TC189825                    --------------------------------------------------
T.aestivum_BE412359                   --------------------------------------------------
O.minuta_CB884361                     --------------------------------------------------
O.sativa_LOC_Os01g43230.2             --------------------------------------------------
S.bicolor_Sb03g028170.1               --------------------------------------------------
Z.mays_TC409725                       --------------------------------------------------
T.androssowii_TA2313_189785           --------------------------------------------------
Triphysaria_sp_TC9313                 --------------------------------------------------
S.tuberosum_CV505951                  --------------------------------------------------
P.tremula_TA11725_113636              --------------------------------------------------
P.trichocarpa_594467                  --------------------------------------------------
P.trichocarpa_562293                  --------------------------------------------------
B.gymnorrhiza_TA2541_39984            --------------------------------------------------
M.esculenta_TA9427_3983               --------------------------------------------------
P.persica_BU039343                    --------------------------------------------------
V.vinifera_GSVIVT00026045001          --------------------------------------------------
L.tulipifera_CV004984                 --------------------------------------------------
G.hirsutum_TC121748                   --------------------------------------------------
E.esula_DV121180                      --------------------------------------------------
M.domestica_TC17597                   --------------------------------------------------
P.tremula_BU888423                    --------------------------------------------------
P.trichocarpa_568212                  --------------------------------------------------
G.hirsutum_DW508052                   --------------------------------------------------
G.hirsutum_TC116960                   --------------------------------------------------
V.vinifera_GSVIVT00006915001          --------------------------------------------------
J.hindsii_x_regia_TA1295_43229        --------------------------------------------------
G.max_8223                            --------------------------------------------------
P.vulgaris_CV538421                   --------------------------------------------------
C.tetragonoloba_EG990179              --------------------------------------------------
G.max_29139                           --------------------------------------------------
G.soja_TA4526_3848                    --------------------------------------------------
L.japonicus_CB827663                  --------------------------------------------------
C.canephora_DV693718                  --------------------------------------------------
P.hybrida_EB175070                    --------------------------------------------------
```

FIGURE 10 (continued)

```
I.nil_TC6509                        --------------------------------------------------
L.saligna_DW052030                  --------------------------------------------------
A.hypogaea_CD038483                 --------------------------------------------------
P.tremula_TA7610_113636             --------------------------------------------------
P.equestris_CB034844                --------------------------------------------------
V.vinifera_GSVIVT00010755001        --------------------------------------------------
P.pinaster_CT579117                 --------------------------------------------------
P.taeda_DR096185                    --------------------------------------------------
P.sitchensis_TA16538_3332           --------------------------------------------------
A.thaliana_At1g01380_CPC-like_      --------------------------------------------------
B.napus_EV055366                    --------------------------------------------------
A.thaliana_At4g01060_CPC-like_      --------------------------------------------------
A.thaliana_At2g46410_CPC-like_      --------------------------------------------------
B.napus_TC92601                     --------------------------------------------------
A.thaliana_At5g53200_CPC-like_      --------------------------------------------------
B.napus_EE451172                    --------------------------------------------------
J.hindsii_x_regia_EL893054          --------------------------------------------------
G.hirsutum_TC102183                 --------------------------------------------------
P.trichocarpa_807368                --------------------------------------------------
M.esculenta_DV443286                --------------------------------------------------
P.tremula_DN497189                  --------------------------------------------------
P.trichocarpa_674550                --------------------------------------------------
C.longa_DY390653                    --------------------------------------------------
A.thaliana_At2g30420_CPC-like_      --------------------------------------------------
B.napus_CD843377                    --------------------------------------------------
B.napus_TC95812                     --------------------------------------------------
G.max_Glyma11g02060.1               --------------------------------------------------
M.truncatula_CT033771_17.4          --------------------------------------------------
L.serriola_DW108811                 --------------------------------------------------
S.miltiorrhiza_CV166339             --------------------------------------------------
S.miltiorrhiza_TA1626_226208        --------------------------------------------------
P.glauca_DR564374                   --------------------------------------------------
P.sitchensis_TA17447_3332           --------------------------------------------------
P.pinaster_TA6535_71647             --------------------------------------------------
P.menziesii_TA3655_3357             --------------------------------------------------
A.thaliana_At1g71030_CPC-like_      --------------------------------------------------
A.thaliana_At1g18960_CPC-like_      --------------------------------------------------
A.thaliana_At1g09710_CPC-like_      ---IRSLANGKLKPVMASSSSNKPPLIAPRSEGSSMLSASAPLASLS-RI
A.thaliana_At1g58220_CPC-like_      PLNLRHAVNGSPNHTIPSSPFTKPLHMAPLSKGSTIQSNSVPPSFASSRL
```

FIGURE 10 (continued)

```
A.sativa_CN818591                    --------------------------------------------------
L.multiflorum_AU249134               --------------------------------------------------
A.capillaris_DV853805                --------------------------------------------------
A.capillaris_DV859458                --------------------------------------------------
H.vulgare_TC189825                   --------------------------------------------------
T.aestivum_BE412359                  --------------------------------------------------
O.minuta_CB884361                    --------------------------------------------------
O.sativa_LOC_Os01g43230.2            --------------------------------------------------
S.bicolor_Sb03g028170.1              --------------------------------------------------
Z.mays_TC409725                      --------------------------------------------------
T.androssowii_TA2313_189785          --------------------------------------------------
Triphysaria_sp_TC9313                --------------------------------------------------
S.tuberosum_CV505951                 --------------------------------------------------
P.tremula_TA11725_113636             --------------------------------------------------
P.trichocarpa_594467                 --------------------------------------------------
P.trichocarpa_562293                 --------------------------------------------------
B.gymnorrhiza_TA2541_39984           --------------------------------------------------
M.esculenta_TA9427_3983              --------------------------------------------------
P.persica_BU039343                   --------------------------------------------------
V.vinifera_GSVIVT00026045001         --------------------------------------------------
L.tulipifera_CV004984                --------------------------------------------------
G.hirsutum_TC121748                  --------------------------------------------------
E.esula_DV121180                     --------------------------------------------------
M.domestica_TC17597                  --------------------------------------------------
P.tremula_BU888423                   --------------------------------------------------
P.trichocarpa_568212                 --------------------------------------------------
G.hirsutum_DW508052                  --------------------------------------------------
G.hirsutum_TC116960                  --------------------------------------------------
V.vinifera_GSVIVT00006915001         --------------------------------------------------
J.hindsii_x_regia_TA1295_43229       --------------------------------------------------
G.max_8223                           --------------------------------------------------
P.vulgaris_CV538421                  --------------------------------------------------
C.tetragonoloba_EG990179             --------------------------------------------------
G.max_29139                          --------------------------------------------------
G.soja_TA4526_3848                   --------------------------------------------------
L.japonicus_CB827663                 --------------------------------------------------
C.canephora_DV693718                 --------------------------------------------------
P.hybrida_EB175070                   --------------------------------------------------
```

FIGURE 10 (continued)

```
I.nil_TC6509                        --------------------------------------------------
L.saligna_DW052030                  --------------------------------------------------
A.hypogaea_CD038483                 --------------------------------------------------
P.tremula_TA7610_113636             --------------------------------------------------
P.equestris_CB034844                --------------------------------------------------
V.vinifera_GSVIVT00010755001        --------------------------------------------------
P.pinaster_CT579117                 --------------------------------------------------
P.taeda_DR096185                    --------------------------------------------------
P.sitchensis_TA16538_3332           --------------------------------------------------
A.thaliana_At1g01380_CPC-like_      --------------------------------------------------
B.napus_EV055366                    --------------------------------------------------
A.thaliana_At4g01060_CPC-like_      --------------------------------------------------
A.thaliana_At2g46410_CPC-like_      --------------------------------------------------
B.napus_TC92601                     --------------------------------------------------
A.thaliana_At5g53200_CPC-like_      --------------------------------------------------
B.napus_EE451172                    --------------------------------------------------
J.hindsii_x_regia_EL893054          --------------------------------------------------
G.hirsutum_TC102183                 --------------------------------------------------
P.trichocarpa_807368                --------------------------------------------------
M.esculenta_DV443286                --------------------------------------------------
P.tremula_DN497189                  --------------------------------------------------
P.trichocarpa_674550                --------------------------------------------------
C.longa_DY390653                    --------------------------------------------------
A.thaliana_At2g30420_CPC-like_      --------------------------------------------------
B.napus_CD843377                    --------------------------------------------------
B.napus_TC95812                     --------------------------------------------------
G.max_Glyma11g02060.1               --------------------------------------------------
M.truncatula_CT033771_17.4          --------------------------------------------------
L.serriola_DW108811                 --------------------------------------------------
S.miltiorrhiza_CV166339             --------------------------------------------------
S.miltiorrhiza_TA1626_226208        --------------------------------------------------
P.glauca_DR564374                   --------------------------------------------------
P.sitchensis_TA17447_3332           --------------------------------------------------
P.pinaster_TA6535_71647             --------------------------------------------------
P.menziesii_TA3655_3357             --------------------------------------------------
A.thaliana_At1g71030_CPC-like_      --------------------------------------------------
A.thaliana_At1g18960_CPC-like_      --------------------------------------------------
A.thaliana_At1g09710_CPC-like_      VSNQRVFAGSVP------------------------ATEIVTCKPDGGQK
A.thaliana_At1g58220_CPC-like_      VPTQRAPAATVVTPQKPSVVAAATVVTPQKPSVGAAATVVTPQKPSVGAA
```

FIGURE 10 (continued)

```
A.sativa_CN818591                    --------------------------------------------------
L.multiflorum_AU249134               --------------------------------------------------
A.capillaris_DV853805                --------------------------------------------------
A.capillaris_DV859458                --------------------------------------------------
H.vulgare_TC189825                   --------------------------------------------------
T.aestivum_BE412359                  --------------------------------------------------
O.minuta_CB884361                    --------------------------------------------------
O.sativa_LOC_Os01g43230.2            --------------------------------------------------
S.bicolor_Sb03g028170.1              --------------------------------------------------
Z.mays_TC409725                      --------------------------------------------------
T.androssowii_TA2313_189785          --------------------------------------------------
Triphysaria_sp_TC9313                --------------------------------------------------
S.tuberosum_CV505951                 --------------------------------------------------
P.tremula_TA11725_113636             --------------------------------------------------
P.trichocarpa_594467                 --------------------------------------------------
P.trichocarpa_562293                 --------------------------------------------------
B.gymnorrhiza_TA2541_39984           --------------------------------------------------
M.esculenta_TA9427_3983              --------------------------------------------------
P.persica_BU039343                   --------------------------------------------------
V.vinifera_GSVIVT00026045001         --------------------------------------------------
L.tulipifera_CV004984                --------------------------------------------------
G.hirsutum_TC121748                  --------------------------------------------------
E.esula_DV121180                     --------------------------------------------------
M.domestica_TC17597                  --------------------------------------------------
P.tremula_BU888423                   --------------------------------------------------
P.trichocarpa_568212                 --------------------------------------------------
G.hirsutum_DW508052                  --------------------------------------------------
G.hirsutum_TC116960                  --------------------------------------------------
V.vinifera_GSVIVT00006915001         --------------------------------------------------
J.hindsii_x_regia_TA1295_43229       --------------------------------------------------
G.max_8223                           --------------------------------------------------
P.vulgaris_CV538421                  --------------------------------------------------
C.tetragonoloba_EG990179             --------------------------------------------------
G.max_29139                          --------------------------------------------------
G.soja_TA4526_3848                   --------------------------------------------------
L.japonicus_CB827663                 --------------------------------------------------
C.canephora_DV693718                 --------------------------------------------------
P.hybrida_EB175070                   --------------------------------------------------
```

FIGURE 10 (continued)

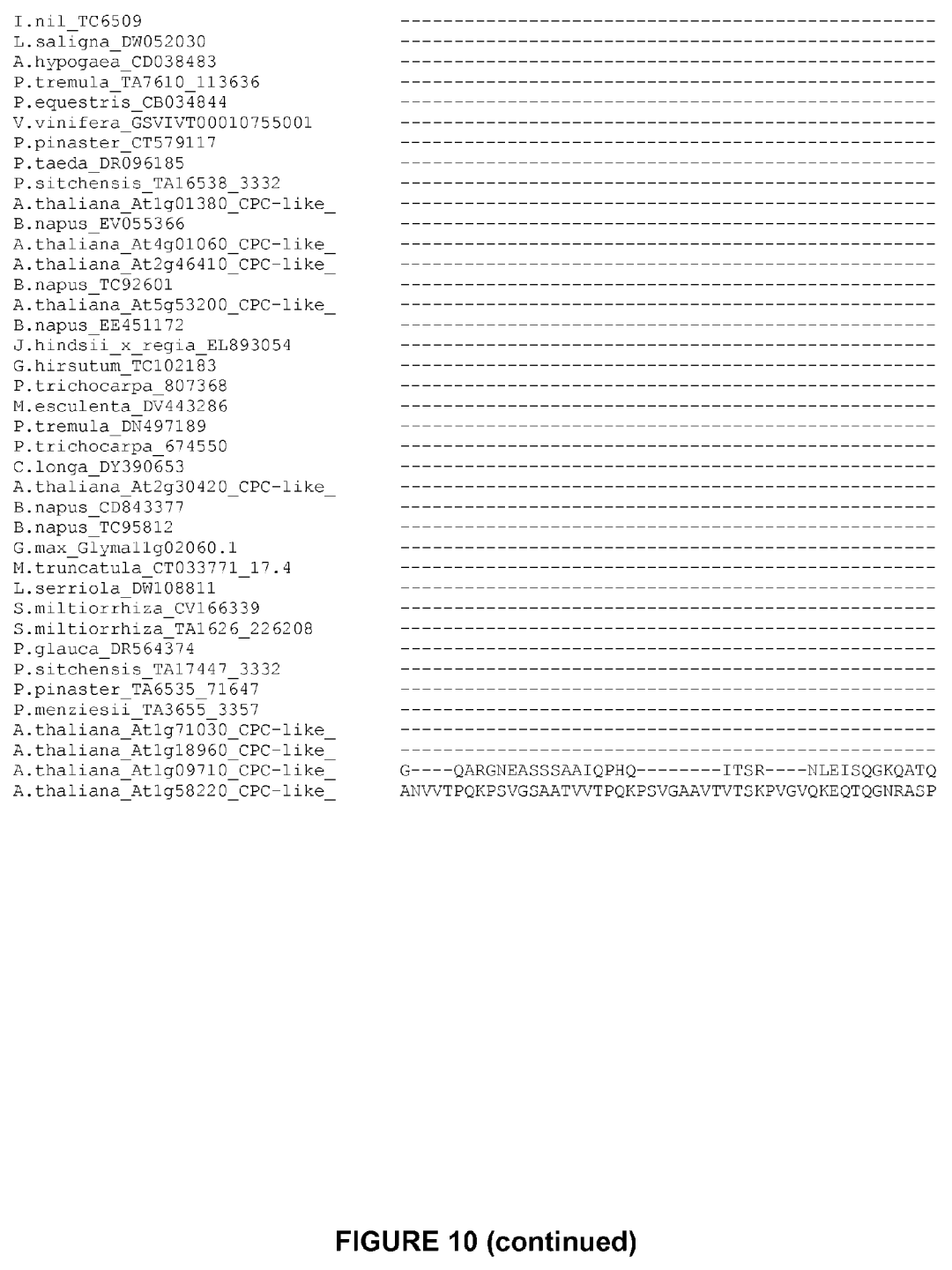

```
I.nil_TC6509                            --------------------------------------------------
L.saligna_DW052030                      --------------------------------------------------
A.hypogaea_CD038483                     --------------------------------------------------
P.tremula_TA7610_113636                 --------------------------------------------------
P.equestris_CB034844                    --------------------------------------------------
V.vinifera_GSVIVT00010755001            --------------------------------------------------
P.pinaster_CT579117                     --------------------------------------------------
P.taeda_DR096185                        --------------------------------------------------
P.sitchensis_TA16538_3332               --------------------------------------------------
A.thaliana_At1g01380_CPC-like_          --------------------------------------------------
B.napus_EV055366                        --------------------------------------------------
A.thaliana_At4g01060_CPC-like_          --------------------------------------------------
A.thaliana_At2g46410_CPC-like_          --------------------------------------------------
B.napus_TC92601                         --------------------------------------------------
A.thaliana_At5g53200_CPC-like_          --------------------------------------------------
B.napus_EE451172                        --------------------------------------------------
J.hindsii_x_regia_EL893054              --------------------------------------------------
G.hirsutum_TC102183                     --------------------------------------------------
P.trichocarpa_807368                    --------------------------------------------------
M.esculenta_DV443286                    --------------------------------------------------
P.tremula_DN497189                      --------------------------------------------------
P.trichocarpa_674550                    --------------------------------------------------
C.longa_DY390653                        --------------------------------------------------
A.thaliana_At2g30420_CPC-like_          --------------------------------------------------
B.napus_CD843377                        --------------------------------------------------
B.napus_TC95812                         --------------------------------------------------
G.max_Glyma11g02060.1                   --------------------------------------------------
M.truncatula_CT033771_17.4              --------------------------------------------------
L.serriola_DW108811                     --------------------------------------------------
S.miltiorrhiza_CV166339                 --------------------------------------------------
S.miltiorrhiza_TA1626_226208            --------------------------------------------------
P.glauca_DR564374                       --------------------------------------------------
P.sitchensis_TA17447_3332               --------------------------------------------------
P.pinaster_TA6535_71647                 --------------------------------------------------
P.menziesii_TA3655_3357                 --------------------------------------------------
A.thaliana_At1g71030_CPC-like_          --------------------------------------------------
A.thaliana_At1g18960_CPC-like_          --------------------------------------------------
A.thaliana_At1g09710_CPC-like_          G----QARGNEASSSAAIQPHQ--------ITSR----NLEISQGKQATQ
A.thaliana_At1g58220_CPC-like_          ANVVTPQKPSVGSAATVVTPQKPSVGAAVTVTSKPVGVQKEQTQGNRASP
```

FIGURE 10 (continued)

```
A.sativa_CN818591                   --------------------------------------------------
L.multiflorum_AU249134              --------------------------------------------------
A.capillaris_DV853805               --------------------------------------------------
A.capillaris_DV859458               --------------------------------------------------
H.vulgare_TC189825                  --------------------------------------------------
T.aestivum_BE412359                 --------------------------------------------------
O.minuta_CB884361                   --------------------------------------------------
O.sativa_LOC_Os01g43230.2           --------------------------------------------------
S.bicolor_Sb03g028170.1             --------------------------------------------------
Z.mays_TC409725                     --------------------------------------------------
T.androssowii_TA2313_189785         --------------------------------------------------
Triphysaria_sp_TC9313               --------------------------------------------------
S.tuberosum_CV505951                --------------------------------------------------
P.tremula_TA11725_113636            --------------------------------------------------
P.trichocarpa_594467                --------------------------------------------------
P.trichocarpa_562293                --------------------------------------------------
B.gymnorrhiza_TA2541_39984          --------------------------------------------------
M.esculenta_TA9427_3983             --------------------------------------------------
P.persica_BU039343                  --------------------------------------------------
V.vinifera_GSVIVT00026045001        --------------------------------------------------
L.tulipifera_CV004984               --------------------------------------------------
G.hirsutum_TC121748                 --------------------------------------------------
E.esula_DV121180                    --------------------------------------------------
M.domestica_TC17597                 --------------------------------------------------
P.tremula_BU888423                  --------------------------------------------------
P.trichocarpa_568212                --------------------------------------------------
G.hirsutum_DW508052                 --------------------------------------------------
G.hirsutum_TC116960                 --------------------------------------------------
V.vinifera_GSVIVT00006915001        --------------------------------------------------
J.hindsii_x_regia_TA1295_43229      --------------------------------------------------
G.max_8223                          --------------------------------------------------
P.vulgaris_CV538421                 --------------------------------------------------
C.tetragonoloba_EG990179            --------------------------------------------------
G.max_29139                         --------------------------------------------------
G.soja_TA4526_3848                  --------------------------------------------------
L.japonicus_CB827663                --------------------------------------------------
C.canephora_DV693718                --------------------------------------------------
P.hybrida_EB175070                  --------------------------------------------------
```

FIGURE 10 (continued)

```
I.nil_TC6509                          --------------------------------------------------
L.saligna_DW052030                    --------------------------------------------------
A.hypogaea_CD038483                   --------------------------------------------------
P.tremula_TA7610_113636               --------------------------------------------------
P.equestris_CB034844                  --------------------------------------------------
V.vinifera_GSVIVT00010755001          --------------------------------------------------
P.pinaster_CT579117                   --------------------------------------------------
P.taeda_DR096185                      --------------------------------------------------
P.sitchensis_TA16538_3332             --------------------------------------------------
A.thaliana_At1g01380_CPC-like_        --------------------------------------------------
B.napus_EV055366                      --------------------------------------------------
A.thaliana_At4g01060_CPC-like_        --------------------------------------------------
A.thaliana_At2g46410_CPC-like_        --------------------------------------------------
B.napus_TC92601                       --------------------------------------------------
A.thaliana_At5g53200_CPC-like_        --------------------------------------------------
B.napus_EE451172                      --------------------------------------------------
J.hindsii_x_regia_EL893054            --------------------------------------------------
G.hirsutum_TC102183                   --------------------------------------------------
P.trichocarpa_807368                  --------------------------------------------------
M.esculenta_DV443286                  --------------------------------------------------
P.tremula_DN497189                    --------------------------------------------------
P.trichocarpa_674550                  --------------------------------------------------
C.longa_DY390653                      --------------------------------------------------
A.thaliana_At2g30420_CPC-like_        --------------------------------------------------
B.napus_CD843377                      --------------------------------------------------
B.napus_TC95812                       --------------------------------------------------
G.max_Glyma11g02060.1                 --------------------------------------------------
M.truncatula_CT033771_17.4            --------------------------------------------------
L.serriola_DW108811                   --------------------------------------------------
S.miltiorrhiza_CV166339               --------------------------------------------------
S.miltiorrhiza_TA1626_226208          --------------------------------------------------
P.glauca_DR564374                     --------------------------------------------------
P.sitchensis_TA17447_3332             --------------------------------------------------
P.pinaster_TA6535_71647               --------------------------------------------------
P.menziesii_TA3655_3357               --------------------------------------------------
A.thaliana_At1g71030_CPC-like_        --------------------------------------------------
A.thaliana_At1g18960_CPC-like_        --------------------------------------------------
A.thaliana_At1g09710_CPC-like_        AQSPNLLPRKVPVVR--------TAVHCATNQKLMDKPSDQTVVPIRGAG
A.thaliana_At1g58220_CPC-like_        LVTATLPPNKTIPANSVIGTAKAVAAKVETPPSLMPK-KNEVVGSCTDKS
```

FIGURE 10 (continued)

```
A.sativa_CN818591                      ----------------------------------------
L.multiflorum_AU249134                 ----------------------------------------
A.capillaris_DV853805                  ----------------------------------------
A.capillaris_DV859458                  ----------------------------------------
H.vulgare_TC189825                     ----------------------------------------
T.aestivum_BE412359                    ----------------------------------------
O.minuta_CB884361                      ----------------------------------------
O.sativa_LOC_Os01g43230.2              ----------------------------------------
S.bicolor_Sb03g028170.1                ----------------------------------------
Z.mays_TC409725                        ----------------------------------------
T.androssowii_TA2313_189785            ----------------------------------------
Triphysaria_sp_TC9313                  ----------------------------------------
S.tuberosum_CV505951                   ----------------------------------------
P.tremula_TA11725_113636               ----------------------------------------
P.trichocarpa_594467                   ----------------------------------------
P.trichocarpa_562293                   ----------------------------------------
B.gymnorrhiza_TA2541_39984             ----------------------------------------
M.esculenta_TA9427_3983                ----------------------------------------
P.persica_BU039343                     ----------------------------------------
V.vinifera_GSVIVT00026045001           ----------------------------------------
L.tulipifera_CV004984                  ----------------------------------------
G.hirsutum_TC121748                    ----------------------------------------
E.esula_DV121180                       ----------------------------------------
M.domestica_TC17597                    ----------------------------------------
P.tremula_BU888423                     ----------------------------------------
P.trichocarpa_568212                   ----------------------------------------
G.hirsutum_DW508052                    ----------------------------------------
G.hirsutum_TC116960                    ----------------------------------------
V.vinifera_GSVIVT00006915001           ----------------------------------------
J.hindsii_x_regia_TA1295_43229         ----------------------------------------
G.max_8223                             ----------------------------------------
P.vulgaris_CV538421                    ----------------------------------------
C.tetragonoloba_EG990179               ----------------------------------------
G.max_29139                            ----------------------------------------
G.soja_TA4526_3848                     ----------------------------------------
L.japonicus_CB827663                   ----------------------------------------
C.canephora_DV693718                   ----------------------------------------
P.hybrida_EB175070                     ----------------------------------------
```

FIGURE 10 (continued)

```
I.nil_TC6509                          ----------------------------------------
L.saligna_DW052030                    ----------------------------------------
A.hypogaea_CD038483                   ----------------------------------------
P.tremula_TA7610_113636               ----------------------------------------
P.equestris_CB034844                  ----------------------------------------
V.vinifera_GSVIVT00010755001          ----------------------------------------
P.pinaster_CT579117                   ----------------------------------------
P.taeda_DR096185                      ----------------------------------------
P.sitchensis_TA16538_3332             ----------------------------------------
A.thaliana_At1g01380_CPC-like_        ----------------------------------------
B.napus_EV055366                      ----------------------------------------
A.thaliana_At4g01060_CPC-like_        ----------------------------------------
A.thaliana_At2g46410_CPC-like_        ----------------------------------------
B.napus_TC92601                       ----------------------------------------
A.thaliana_At5g53200_CPC-like_        ----------------------------------------
B.napus_EE451172                      ----------------------------------------
J.hindsii_x_regia_EL893054            ----------------------------------------
G.hirsutum_TC102183                   ----------------------------------------
P.trichocarpa_807368                  ----------------------------------------
M.esculenta_DV443286                  ----------------------------------------
P.tremula_DN497189                    ----------------------------------------
P.trichocarpa_674550                  ----------------------------------------
C.longa_DY390653                      ----------------------------------------
A.thaliana_At2g30420_CPC-like_        ----------------------------------------
B.napus_CD843377                      ----------------------------------------
B.napus_TC95812                       ----------------------------------------
G.max_Glyma11g02060.1                 ----------------------------------------
M.truncatula_CT033771_17.4            ----------------------------------------
L.serriola_DW108811                   ----------------------------------------
S.miltiorrhiza_CV166339               ----------------------------------------
S.miltiorrhiza_TA1626_226208          ----------------------------------------
P.glauca_DR564374                     ----------------------------------------
P.sitchensis_TA17447_3332             ----------------------------------------
P.pinaster_TA6535_71647               ----------------------------------------
P.menziesii_TA3655_3357               ----------------------------------------
A.thaliana_At1g71030_CPC-like_        ----------------------------------------
A.thaliana_At1g18960_CPC-like_        ----------------------------------------
A.thaliana_At1g09710_CPC-like_        SQSKAKGEVNSKVGPVIKVSSVCGKPLEVATVAGTGQGV-
A.thaliana_At1g58220_CPC-like_        SLDKPPEKESTTTVSPLAVAATKSKPKDEATVTGTGLKEL
```

FIGURE 10 (continued)

```
                            101                                              150
        AT1G19350.1     (1) --------------------------------------------------
        AT1G75080.1     (1) --------------------------------------------------
    Pt_scaff_40.175     (1) --------------------------------------------------
   Pt_scaff_II.1237     (1) --------------------------------------------------
         Gm 1762729     (1) --------------------------------------------------
     Mt_TA28179_3880    (1) --------------------------------------------------
           Le LAT61     (1) --------------------------------------------------
     Le_TA51962_4081    (1) --------------------------------------------------
    Vv_TA44770_29760    (1) --------------------------------------------------
        AT3G50750.1     (1) --------------------------------------------------
         Gm 1768381     (1) --------------------------------------------------
         Gm 1768507     (1) --------------------------------------------------
     Mt_TA21345_3880    (1) --------------------------------------------------
     Pt_scaff_57.215    (1) --------------------------------------------------
  Pt_scaff_VII.1038     (1) --------------------------------------------------
        Le_DB718708     (1) --------------------------------------------------
     Le_TA37112_4081    (1) --------------------------------------------------
       Os07g0580500     (1) --------------------------------------------------
        Zm_AY107201     (1) --------------------------------------------------
        AT4G36780.1     (1) --------------------------------------------------
       Os02g0129600     (1) ---------------------------MSLKHPHSPVLDGDPPPHRRPRG
        Zm_EE158804     (1) ----------------------------------------MQQAGLADDD
    Zm_TA189809_4577    (1) ----------------------------------------MQQAGLADDD
           Pp 82495     (1) --------------------------------------------------
           Pp 17189     (1) --------------------------------------------------
          Pp 172161   (101) FKGAALVMMVEFLREGWVDLTCVRTRKRAAGVLSEGGSGSFRVASPHARA
       Ps WS0287_023    (1) --------------------------------------------------
     Hv_TA37786_4513    (1) --------------------------------------------------
       Os01g0203000     (1) --------------------------------------------------
    Zm_TA178991_4577    (1) --------------------------------------------------
       Os06g0552300     (1) --------------------------------------------------
    Zm_TA175044_4577    (1) --------------------------------------------------
        AT1G78700.1     (1) --------------------------------------------------
        AT4G18890.1     (1) --------------------------------------------------
     Pt_scaff_IV.340    (1) --------------------------------------------------
     Pt_scaff_XI.678    (1) --------------------------------------------------
         Gm 1765606     (1) --------------------------------------------------
        Mt_BF635822     (1) --------------------------------------------------
      Pt WS01123_K11    (1) --------------------------------------------------
     Pt_scaff_178.36    (1) --------------------------------------------------
     Pt_scaff_XI.792    (1) --------------------------------------------------
        Sl FC26BA11     (1) --------------------------------------------------
          Consensus   (101)
```

FIGURE 12

```
                           151                                              200
        AT1G19350.1    (1) ---------------------------MTSDGATSTSAAAAAAAMAT---
        AT1G75080.1    (1) ---------------------------MTSDGATSTSAAAAAAAAAA---
    Pt_scaff_40.175    (1) ---------------------------MTSDGATST--S-AAMAAAT---
   Pt_scaff_II.1237    (1) ---------------------------MTSDGATST--S-AAAAATT---
         Gm 1762729    (1) ---------------------------MADDGATSAATS-----------
   Mt_TA28179_3880     (1) ---------------------------MASDGATSAANS-----------
          Le LAT61     (1) --------------------------MMWEAGESPASSSAGAGAGGSGGA
   Le_TA51962_4081     (1) ---------------------------MWEAGESPASSSAGAGAGGSGGA
  Vv_TA44770_29760     (1) ---------------------------MTSERTPTR----------R---
        AT3G50750.1    (1) ---------------------------MTASGGGSTAATG----------
         Gm 1768381    (1) ---------------------------MTGGGSTGR--------------
         Gm 1768507    (1) ---------------------------MTGGGSTGR--------------
   Mt_TA21345_3880     (1) ---------------------------MTGGGSSGR--------------
    Pt_scaff_57.215    (1) ---------------------------MTAGGSSAR--------------
  Pt_scaff_VII.1038    (1) ---------------------------MTAGGSSGR--------------
        Le_DB718708    (1) -----------------------MTAGTGGGGSSGR--------------
   Le_TA37112_4081     (1) -----------------------MTAGTGGGGSSGR--------------
     Os07g0580500      (1) --------------------------MTSGAAAAGR--------------
        Zm_AY107201    (1) --------------------MTSGSAAAAAVGGLGR--------------
        AT4G36780.1    (1) ---------------------------MAAGGGGGGGGS-----------
     Os02g0129600     (24) LVSTPPPPAVAADTSPSPSPSPAAPPPRRRGGGGGGG-------------
        Zm_EE158804   (11) DEEIWVKEEDDEEEEDGYYMDPRSPAVWTPGGRAGGTSN-----------
  Zm_TA189809_4577    (11) DEEIWVKEEDDEEEEDGYYMDPRSPAVWTPGGRAGGTSN-----------
           Pp 82495    (1) -MQVGDRSFEQGESSEVRKCTVRGCIKSTSGPWIVRRPPGKGQS------
           Pp 17189    (1) ---------------------------MTSGTR-----------------
          Pp 172161  (151) TPLFGGCFVVPEPVLYRPSCLGSKIGDMTSGTR-----------------
     Ps WS0287_023     (1) ---------------------------MTSGSR-----------------
   Hv_TA37786_4513     (1) --MATGGGGG-----------ADFGAAGGAGGR-----------------
     Os01g0203000      (1) --MATGGGGGGGGMGGGGVGGGAGAAGVGVGGR-----------------
  Zm_TA178991_4577     (1) --MASGGGGG--------------LGAAGAGGR-----------------
     Os06g0552300      (1) --MTNGAGGG-------------GGGGGLGGTR-----------------
  Zm_TA175044_4577     (1) --MTSGAGGA-------------AAG--IGGTR-----------------
        AT1G78700.1    (1) ---------------------------MTSGTR-----------------
        AT4G18890.1    (1) ---------------------------MTSGTR-----------------
    Pt_scaff_IV.340    (1) ---------------------------MTSGTR-----------------
    Pt_scaff_XI.678    (1) ---------------------------MTSGTR-----------------
         Gm 1765606    (1) ---------------------------MTSVAR-----------------
        Mt_BF635822    (1) ---------------------------MTSGTR-----------------
    Pt WS01123_K11     (1) ---------------------------MTSGTR-----------------
    Pt_scaff_178.36    (1) ---------------------------MTSGTR-----------------
    Pt_scaff_XI.792    (1) ---------------------------MTSGTR-----------------
        Sl FC26BA11    (1) ---------------------------MTSGTR-----------------
          Consensus  (151)                            MTSGG
```

FIGURE 12 (continued)

```
                             201                                               250
       AT1G19350.1    (21)   --------------RR-KPSWRERENNRRRERRRRAVAAKIYTGLRAQGN
       AT1G75080.1    (21)   --------------ARRKPSWRERENNRRRERRRRAVAAKIYTGLRAQGD
   Pt_scaff_40.175    (18)   --------------RR-KPSWRERENNRRRERRRRAIAAKIFTGLRAQGN
  Pt_scaff_II.1237    (18)   --------------RR-KPSWRERENNRRRERRRRAIAAKIFTGLRAQGN
        Gm_1762729    (13)   --------------RR-KPSWRERENNRRRERRRRAIAAKIYSGLRAQGN
  Mt_TA28179_3880     (13)   --------------SRRKPSWRERENNRRRERRRRAIAAKIYAGLRSQGN
          Le_LAT61    (25)   GVGLPESGGGGGGGRR-KPSWRERENNRRRERRRRAVAAKIYTGLRAQGN
  Le_TA51962_4081     (24)   GVGLPESGGGGGGGRR-KPSWRERENNRRRERRRRAVAAKIYTGLRAQGN
 Vv_TA44770_29760     (11)   -----------------KASWKERENNMRRERRRRAIAAKIYAGLRAQGN
       AT3G50750.1    (14)   ----------------RMPTWKERENNKKRERRRRAIAAKIFTGLRSQGN
        Gm_1768381    (10)   -----------------LPTWKERENNKRRERRRRAIAAKIYTGLRAQGN
        Gm_1768507    (10)   -----------------LPTWKERENNKRRERRRRAIAAKIYTGLRAQGN
  Mt_TA21345_3880     (10)   -----------------LPTWKERENNKRRERRRRAIAAKIYSGLRAQGN
   Pt_scaff_57.215    (10)   -----------------LPTWKERENNMRRERRRRAIAAKIYTGLRTQGN
Pt_scaff_VII.1038     (10)   -----------------LPTWKERENNKRRERRRRAIAAKIYTGLRTQGN
      Le_DB718708     (14)   -----------------LPTWKERENNKRRERRRRAIAAKIFTGLRTQGN
  Le_TA37112_4081     (14)   -----------------LPTWKERENNKRRERRRRAIAAKIFTGLRTQGN
     Os07g0580500     (11)   -----------------TPTWKERENNKRRERRRRAIAAKIFTGLRALGN
      Zm_AY107201     (17)   -----------------TPTWKERENNKRRERRRRAIAAKIFTGLRALGN
       AT4G36780.1    (13)   -------------SSGRTPTWKERENNKKRERRRRAITAKIYSGLRAQGN
     Os02g0129600     (61)   ----------------EREREREKERTKLRERHRRAITSRMLSGLRQHGN
      Zm_EE158804     (50)   ----------------RRRAREEKERTKMRERQRRAITGRILAGLRQHGN
 Zm_TA189809_4577     (50)   ----------------RRRAREEKERTKMRERQRRAITGRILAGLRQHGN
          Pp_82495    (44)   ----------TAPAVLRMPSARERENNKRRERRRRAIAAKIFAGLRAHGN
          Pp_17189     (7)   -----------------LPTWKERENNKRRERRRRAIAAKIFAGLRLYGN
         Pp_172161   (184)   -----------------LPTWKERENNKRRERRRRAIAAKIFAGLRLYGN
    Ps_WS0287_023      (7)   -----------------LPTWKERENNKKRERRRRAIAAKIYAGLRMYGN
  Hv_TA37786_4513     (21)   -----------------MPTWRERENNKRRERRRRAIAAKIFSGLRAHGG
     Os01g0203000     (32)   -----------------MPTWRERENNKRRERRRRAIAAKIFAGLRAHGG
 Zm_TA178991_4577     (18)   -----------------MPTWRERENNKRRERRRRAIAAKIFAGLRAHGG
     Os06g0552300     (19)   -----------------VPTWRERENNRRRERRRRAIAAKIYAGLRAYGN
 Zm_TA175044_4577     (17)   -----------------VPTWRERENNRRRERRRRAIAAKIFAGLRAYGN
       AT1G78700.1     (7)   -----------------MPTWRERENNKRRERRRRAIAAKIFTGLRMYGN
       AT4G18890.1     (7)   -----------------TPTWKERENNKRRERRRRAIAAKIFAGLRIHGN
   Pt_scaff_IV.340     (7)   -----------------MPTWKERENNKRRERRRRAIAAKIYSGLRMYGN
   Pt_scaff_XI.678     (7)   -----------------MPTWKERENNKRRERRRRAIAAKIYAGLRMYGS
        Gm_1765606     (7)   -----------------QPTWKERENNKRRERRRRAIAAKIFSGLRMYGN
       Mt_BF635822     (7)   -----------------LPTWKERENNKRRERRRRAIAAKIFSGLRMYGN
    Pt_WS01123_K11     (7)   -----------------LPTWKERENNKRRERRRRAIAAKIFSGLRMYGN
   Pt_scaff_178.36     (7)   -----------------LPTWKERENNKRRERRRRAIAAKIFSGLRMYGN
   Pt_scaff_XI.792     (7)   -----------------LPTWKERENNKRRERRRRAIAAKIFSGLRMYGN
        Sl_FC26BA11     (7)   -----------------MPTWKERENNKRRERRRKAIAAKIFAGLRMYGN
         Consensus   (201)                    LPTWKERENNKRRERRRRAIAAKIFTGLRAYGN
```

FIGURE 12 (continued)

```
                              251                                               300
         AT1G19350.1   (56)  YNLPKHCDNNEVLKALCSEAGWVVEEDGTTYRK-----------------
         AT1G75080.1   (57)  YNLPKHCDNNEVLKALCVEAGWVVEEDGTTYRK-----------------
     Pt_scaff_40.175   (53)  YNLPKYCDNNEVLKALCAEAGWVVEEDGTTYRK-----------------
    Pt_scaff_II.1237   (53)  YNLPKYCDNNEVLKALCAEAGWVVEEDGTTYRK-----------------
          Gm_1762729   (48)  FNLPKHCDNNEVLKALCAEAGWCVEEDGTTYRK-----------------
     Mt_TA28179_3880   (49)  YNLPKHCDNNEVLKALCAEAGWTVEEDGTTYRR-----------------
            Le_LAT61   (74)  YNLPKHCDNNEVLKALCTEAGWIVEPDGTTYRK-----------------
     Le_TA51962_4081   (73)  YNLPKHCDNNEVLKALCTEAGWIVEPDGTTYRK-----------------
    Vv_TA44770_29760   (44)  YRLPKHCDNNEVLKALCSEAGWTVEDDGTTYRK-----------------
         AT3G50750.1   (48)  YKLPKHCDNNEVLKALCLEAGWIVHEDGTTYRK-----------------
          Gm_1768381   (43)  YKLPKHCDNNEVLKALCAEAGWIVEEDGTTYRK-----------------
          Gm_1768507   (43)  YKLPKHCDNNEVLKALCAEAGWIVEEDGTTYRK-----------------
     Mt_TA21345_3880   (43)  FKLPKHCDNNEVLKALCSEAGWIVEEDGTTYRK-----------------
     Pt_scaff_57.215   (43)  YKLPKHCDNNEVLKALCAEAGWIVEEDGTTYRK-----------------
   Pt_scaff_VII.1038   (43)  FKLPKHCDNNEVLKALCAEAGWIVEEDGTTYRK-----------------
         Le_DB718708   (47)  FKLPKHCDNNEVLKALCIEAGWIVEDDGTTYRK-----------------
     Le_TA37112_4081   (47)  FKLPKHCDNNEVLKALCIEAGWIVEDDGTTYRK-----------------
        Os07g0580500   (44)  YNLPKHCDNNEVLKALCREAGWVVEDDGTTYRK-----------------
         Zm_AY107201   (50)  YKLPKHCDNNEVLKALCREAGWVVEDDGTTYRK-----------------
         AT4G36780.1   (50)  YKLPKHCDNNEVLKALCLEAGWIVEDDGTTYRK-----------------
        Os02g0129600   (95)  FPLPARADMNDVLAALARAAGWTVHPDGTTFRAS----------------
         Zm_EE158804   (84)  YRLRARADINEVIAALAREAGWVVLPDGTTFPS-----------------
   Zm_TA189809_4577    (84)  YRLRARADINEVIAALAREAGWVVLPDGTTFPS-----------------
            Pp_82495   (84)  YCLPKHADHNEVLKALCQEAGWQVEEDGTIFRKNSFRAVHPVIQRIVEAK
            Pp_17189   (40)  YKLPKHCDNNEVLKALCVEAGWTVEEDGTTYRK-----------------
           Pp_172161  (217)  YKLPKHCDNNEVLKALCVEAGWTVEEDGTTYRK-----------------
       Ps_WS0287_023   (40)  YKLPKHCDNNEVLKALCAEAGWMVEEDGTTYRK-----------------
     Hv_TA37786_4513   (54)  YKLPKHCDNNEVLKALCNEAGWVVEPDGTTYRK-----------------
        Os01g0203000   (65)  YKLPKHCDNNEVLKALCNEAGWVVEPDGTTYRK-----------------
    Zm_TA178991_4577   (51)  YKLPKHCDNNEVLKALCNEAGWVVEPDGTTYRQ-----------------
        Os06g0552300   (52)  YNLPKHCDNNEVLKALCNEAGWTVEPDGTTYRK-----------------
    Zm_TA175044_4577   (50)  YNLPKHCDNNEVLKALCNEAGWTVEPDGTTYRK-----------------
         AT1G78700.1   (40)  YELPKHCDNNEVLKALCNEAGWIVEPDGTTYRK-----------------
         AT4G18890.1   (40)  FKLPKHCDNNEVLKALCNEAGWTVEDDGTTYRK-----------------
     Pt_scaff_IV.340   (40)  YKLPKHCDNNEVLKALCKEAGWTVEEDGTTYRK-----------------
     Pt_scaff_XI.678   (40)  YKLPKHCDNNEVLKALCNEAGWTVEEDGTTYRK-----------------
          Gm_1765606   (40)  YKLPKHCDNNEVLKALCNEAGWTVEADGTTYRK-----------------
         Mt_BF635822   (40)  FRLPKHCDNNEVLKAPCNEAGWTVEPDGTTYRK-----------------
     Pt_WS01123_K11    (40)  YKLPKHCDNNEVLKALCNEAGWTVEPDGTTFRK-----------------
     Pt_scaff_178.36   (40)  YKLPKHCDNNEVLKALCNEAGWTVEPDGTTFRK-----------------
     Pt_scaff_XI.792   (40)  FKLPKHCDNNEVLKALCNEAGWAVEPDGTTYRK-----------------
         Sl_FC26BA11   (40)  YQLPKHCDNNEVLKALCNEAGWTVEPDGTTYRK-----------------
           Consensus  (251)  YKLPKHCDNNEVLKALC EAGWIVEEDGTTYRK
```

FIGURE 12 (continued)

```
                            301                                              350
       AT1G19350.1    (89)  --------GHKPLP-GDMAGSSSRATPYSS-HNQSPLSSTFDSPILSYQV
       AT1G75080.1    (90)  --------GCKPLP-GEIAGTSSRVTPYSS-QNQSPLSSAFQSPIPSYQV
    Pt_scaff_40.175   (86)  --------GHRPPP-IEIVGTSTRVTPYSS-QNPSPLSSLFPSPIPSYQA
   Pt_scaff_II.1237   (86)  --------GHRPPP-IEIVGSSMRVTPYSS-QNPSPLSSSFPSPIPSYQV
        Gm_1762729    (81)  --------GCKPPL-ANGAGSSMRNITFSSSQNPSPLSSSFPSPIPSYQV
   Mt_TA28179_3880    (82)  --------GSRAETPGDGAGNFNRNNPFSS-QNLSPLSSSFPSPIPSYQV
          Le_LAT61   (107)  --------GCKPTP-MEIGGTSTNITPSSS-RHPSPPSSYFASPIPSYQP
   Le_TA51962_4081   (106)  --------GCKPTP-MEIGGTSTNITPSSS-RHPSPPSSYFASPIPSYQP
  Vv_TA44770_29760    (77)  --------GCKPPPSTEIAGTSTNNTPCSS-QKPSPPSSSFPSAFASYQP
       AT3G50750.1    (81)  --------GSRPT---------ETTVPCSS-IQLSPQSSAFQSPIPSYQA
        Gm_1768381    (76)  --------GCKRPSASEIGGTVANISACSS-IQPSPQSSSYPSPVPSYHA
        Gm_1768507    (76)  --------GCKRP-TSEIGGTPLNLSACSS-IQASPQSSSYPSPVPSYHA
   Mt_TA21345_3880    (76)  --------GSKRPLPNEMGGTPTNMSACSS-MQPSPQSSSFPSPQSSSFP
    Pt_scaff_57.215   (76)  --------GCKPP-PSEIAGMPANISACSS-IQPSPQSSNFASPVPSYHA
  Pt_scaff_VII.1038   (76)  --------GCKPP-PTEIAGTPTNISACSS-IQPSPQSSNFPSPVASYHA
       Le_DB718708    (80)  --------GHRPP-PIENGCVSMNISASSS-IQPSPMSSSFPSPVPSYHA
   Le_TA37112_4081    (80)  --------GHRPP-PIENGCVSMNISASSS-IQPSPMSSSFPSPVPSYHA
      Os07g0580500    (77)  --------GCKPPPSS-AGGASVGMSPCSSTQLLSAPSSSFPSPVPSYHA
       Zm_AY107201    (83)  --------GCKPPPG--------MMSPCSSSQLLSAPSSSFPSPVPSYHA
       AT4G36780.1    (83)  --------GFSHQH----QIFQELLQTSAQIHQSNQVHNHQLFQVLHLRT
      Os02g0129600   (129)  ---------SQP-------LHPPTPQSPGIFHVNSVETPSFTSVLNSYAI
       Zm_EE158804   (117)  --------SSSFAAVAAQPPRPVMVAAASPSATPLALPASSALPLRGIAP
   Zm_TA189809_4577  (117)  --------SSSFAAVAAQVVMSFHECGGNVGDDISIPLPHWVIEIGRSNP
          Pp_82495   (134)  PIRTVQLISLQMQHSIVRQFIRNQQQGSQPPSREVTTAHNTPEGTPSYER
          Pp_17189    (73)  --------GSKPP--------AQPMEVCTSPSEVSPTNSYPGATDGTSLI
         Pp_172161   (250)  --------GSKPP--------AQPMEVCTSPSEASPTSSYPGAAEGTSLI
     Ps_WS0287_023    (73)  --------GCKP---------TERIEVAG-SSSVSPASSYHPSPAPSYQP
    Hv_TA37786_4513   (87)  --------GCRP---------AERMDGIGCSVSPSPCSSYQPSPRASYNA
      Os01g0203000    (98)  --------GYKP---------PERMEVIGCSVSPSPCSSYQPSPRASYNA
   Zm_TA178991_4577   (84)  --------GSKP---------MERMDPIGCSVSPSPCSSYQPSPRASYNA
      Os06g0552300    (85)  --------GCKPPQ-------AERPDPIGRSASPSPCSSYQPSPRASYNP
   Zm_TA175044_4577   (83)  --------GCKPLA-------TERPDPIGRSASPSPCSSYQPSPRASYNP
       AT1G78700.1    (73)  --------GCSR-P-------VERMEIGGGSATASPCSSYQPSPCASYNP
       AT4G18890.1    (73)  --------GCKP---------MDRMDLMNGSTSASPCSSYQHSPRASYNP
    Pt_scaff_IV.340   (73)  --------GCKP---------VERMDIMGGSASASPCSSYHRSPCASYNP
    Pt_scaff_XI.678   (73)  --------GCKP---------VERMDIIGGSASASPCSSYHQSPCASYNP
        Gm_1765606    (73)  --------GCKP-P-------VERMDIVGGSAAASPCSSYHPSPCASYNP
       Mt_BF635822    (73)  --------GCKP---------LENMDMVGGSSAASPCSSYHPSP------
     Pt_WS01123_K11   (73)  --------GCKP---------VERMDILGVSATTSPCSSYHPSPCASYNP
    Pt_scaff_178.36   (73)  --------GCKP---------VERMDILGVSATTSPCSSYHPSPCASYNP
    Pt_scaff_XI.792   (73)  --------GCKP---------AEHMDIIGGSATASPCSSYLPSPCASYNP
       Sl_FC26BA11    (73)  --------GCKP---------MERLDFLGGSTSLSPCSSYQPSPFTSNNP
         Consensus   (301)          GCKP            M   SS    SP SSYFPSPI SYN
```

FIGURE 12 (continued)

```
                          351                                                400
       AT1G19350.1  (129) SPSSSSFPSPSRVGDPHN----------ISTIFPFLRNGG----------
       AT1G75080.1  (130) SPSSSSFPSPS-RGEPNNN--------MSSTFFPFLRNGG----------
    Pt_scaff_40.175  (126) SPSSSSFPSPT---RGDNN--------ASSNLLPFLRS-A----------
   Pt_scaff_II.1237  (126) SPSSSSFPSPT---RGDNN--------VSSNLLPFLQS-A----------
        Gm 1762729  (122) SPSSSSFPSPFR-LDVDKD--------NVSNLIPYIRN------------
   Mt_TA28179_3880  (123) SPSSSSFPSPS---RMDAN-------NNASNYIPYART-MF---------
          Le LAT61  (147) SPTSSSFPSPS---RADAN--------MLSHPYSFLQN-V----------
   Le_TA51962_4081  (146) SPTSSSFPSPS---RADAN--------MSSHPYSFLQN-V----------
  Vv_TA44770_29760  (118) SPSSSNLSFMD------AN--------ASLNLLPFLYK-S----------
       AT3G50750.1  (113) SPSSSSYPSPT---RFDPN-------QSSTYLIPYLQN-LA---------
        Gm 1768381  (117) SPTSSSFPSPT---RIDGN-------HPSSFLIPFIRNITS---------
        Gm 1768507  (116) SPTSSSFPSPT---RIDGN-------HPSSFLIPFIRNITS---------
   Mt_TA21345_3880  (117) SPIPSYPTSPT---RMDGIT------NPSSFLLPFIRNITS---------
   Pt_scaff_57.215  (116) SPSSSSFPSPT---CFDGN--------SSTYLLPFLRNIAS---------
  Pt_scaff_VII.1038  (116) SPTSSSFPSPS---RFDGN--------PSTYLLPFLRNIAS---------
        Le_DB718708  (120) SPTSSSFPSPS---RCDGN--------PSSYILPFLHNLAS---------
   Le_TA37112_4081  (120) SPTSSSFPSPS---RCDGN--------PSSYILPFLHNLAS---------
      Os07g0580500  (118) SPASSSFPSPS---RIDNP--------SASCLLPFLRG------------
       Zm_AY107201  (117) SPASSSFPSPT---RLDHG--------SGSNT------------------
       AT4G36780.1  (121) TEVQSHHPSRVHLAMTETLLHTFFFRSYTTSLLRFLLTFH----------
      Os02g0129600  (163) GTPLDSQASMLQTDDSLSP-------SSLDSVVVADQSIKNEK-------
       Zm_EE158804  (159) VAARPISHRPAPAFALLLPPRAAAASRSPADDVPDGNSSHLLAVPVPVPM
  Zm_TA189809_4577  (159) DIYFTDRAGRRNTECLSWGVDKERVLQGRTAVEVYFDFMRSFRVEFDEYF
          Pp 82495  (184) SFKSDTSPSTSCSQAGQTSDEPTCTARSGGAEVRHLGRISVDSQFEDKRQ
          Pp 17189  (107) PWLKGLSSNGGSGAATPS----------SSAGLPPLHVMHG---------
         Pp 172161  (284) PWLKGLSSNGGSGTATPS----------SSAGLPPLHVMHG---------
      Ps WS0287_023  (105) SPASSSFASPASSSFEPAG------TGAANSLIPWLKNLSSSS----SAS
   Hv_TA37786_4513  (120) SPTSSSFPSGASSPFLPH-SNNMVNGVDATPILPWLQTFSN------SNK
      Os01g0203000  (131) SPTSSSFPSGASSPFLPH-PNNMANGVDGNPILPWLKTLSNSP---SSKK
  Zm_TA178991_4577  (117) SPTSSSFPSGASSPFLP--PNEMPNGIDGNPILPWLKTFSNGT---PSKK
      Os06g0552300  (120) SPASSSFPSSGSSSHITIGGNSLIGGVEGSSLIPWLKTLPLSSSYASSSK
  Zm_TA175044_4577  (118) SAASSSFPSSGSSSHITLGGSNFMGGVEGSSLIPWLKNLSSSSSFASSSK
       AT1G78700.1  (107) SPGSSNFMSPASSSFAN------LTSGDGQSLIPWLKHLSTTSSSSASSS
       AT4G18890.1  (106) SPSSSSFPSPTN------------PFGDANSLIPWLKNLSSNS---PSKL
    Pt_scaff_IV.340  (106) SPASSSFPSPVSSHYAAN--ANG--NADPNSLIPWLKNLSSGS---SSAS
    Pt_scaff_XI.678  (106) SPASSSFPSPVSSRYAAN--GNGNVDADANSLIPWLRNLSSGS---SSAS
        Gm 1765606  (107) SPGSSCLPSPRASPFPPN------PNADGNSLIPWLKNLSSGS---SSAS
       Mt_BF635822  (100) --GSSSFPSPSSSPYAAN------RNADGNSLIPWLKNLSTAS---SSGS
     Pt WS01123_K11  (106) SPGSSSFPSPASSSYAAN------ANMDCNSLIPWLKNLSSAS---SSAS
    Pt_scaff_178.36  (106) SPGSSSFPSPASSSYAAN------ANMDCNSLIPWLKNLSSAS---SSAS
    Pt_scaff_XI.792  (106) SPGSSSFPSPVSSSYAAN------ANLDDNSLLPWLKNLSSAS---SSK-
        Sl FC26BA11  (106) SPASSSFPSPASSSYAAN------LNMDGKSLIPWLKNLSSGS---SSAS
         Consensus  (351) SP SSSFPSP                 SS LIPFLKNLS
```

FIGURE 12 (continued)

```
                           401                                               450
        AT1G19350.1  (159) --IPSSLPPLRISNSAPVTPPVSSPTS--RNPKPLPTWESFTKQSMSMAA
        AT1G75080.1  (161) --IPSSLPSLRISNSCPVTPPVSSPTS--KNPKPLPNWESIAKQSMAIA-
     Pt_scaff_40.175  (154) --IPLSLPPLRISNSAPVTPPLSSPTS--RNPKPIPNWDFIAKQSMASF-
    Pt_scaff_II.1237  (154) --IPLSLPPLRISNSAPVTPPLSSPTS--RNPKPIPNWDFIAKQSMASF-
          Gm 1762729  (151) --ASLSLPPLRISNSAPVTPPLSSPTS--RNPKPIPTWESIAKESMASFS
    Mt_TA28179_3880  (153) --PNMSLPPLRISNSAPVTPPVS---------------------------
            Le LAT61  (175) --VPSSLPPLRISNSAPVTPPLSSPT---RHPKQTFNLETLAKESMFALN
    Le_TA51962_4081  (174) --VPSSLPPLRISNSAPVTPPLSSPT---RHPKQTFNLETLAKETMFALN
   Vv_TA44770_29760  (143) --IPSSLPPLRISNSAPVTPPISSPTS--RVPMPKPNWESLAKESMASIH
        AT3G50750.1  (143) --SSGNLAPLRISNSAPVTPPISSPR---RSNPRLPRWQS----S-----
          Gm 1768381  (148) --IPANLPPLRISNSAPVTPPLSSPR----SSKRKADFDSL--HN----A
          Gm 1768507  (147) --IPANLPPLRISNSAPVTPPLSSPR----SSKRKADFD-----------
    Mt_TA21345_3880  (149) --IPTNLPPLRISNSAPVTPPLSSPR----SSKRKADFESL--CNGSFNS
     Pt_scaff_57.215  (146) --IPTNLPPLRISNSAPVTPPRSSPTC--RSSKRKVDWESL--SNGS-LN
   Pt_scaff_VII.1038  (146) --IPTNLPPLRISNSAPVTPPLSSPTS--RGSKRKADWESL--SNGT-LN
         Le_DB718708  (150) --IPSTLPPLRISXSAPVTPPLSSPTR--RSKPPKPLWESL--SX-VPXN
    Le_TA37112_4081  (150) --IPSTLPPLRISNSAPVTPPLSSPTR--RSKPPKPLWESL--SR-VPLN
       Os07g0580500  (145) ---LPNLPPLRVSSSAPVTPPLSSPTASRPPKIRKPDWDVDP--------
         Zm_AY107201  (138) --------------------------------------------------
         AT4G36780.1  (161) ------------LLEYPTVRL------------------------------
       Os02g0129600  (199) YGNSDSVSSLNCLENHQLTRASAALAGDYTRTPYIPVYASLPMG---IIN
         Zm_EE158804  (209) DPAAAEDVPVAKQLQVPDVSPRPP--------------------------
   Zm_TA189809_4577  (209) EDGIISEIEIGLGACGELRYPSYPAKHG-WKYPGIGEFQCYDRYLQKSLR
            Pp 82495  (234) --RCDPLSNFKTVVAFPSAVQARNPNPNSRDPKNRAGPKSVAGFLLPEQT
            Pp 17189  (138) -----------GSSSAPVTPPLSSPTHR--GPPVKPDWDHIKETDHHPHG
           Pp 172161  (315) -----------GSSSAPVTPPLSSPTHR--GPPVKPDWDHIKDADHHSHG
       Ps WS0287_023  (145) SS--GRLIHGGGSISAPVTPPLSSPTG--RGARAKLDWDAMVKAVANESN
    Hv_TA37786_4513  (163) RPHLPPLLIHGGSISAPVTPPLSSPTA--RTPRMKTDWDESVIQPPWHGS
       Os01g0203000  (177) HPQLPPLLIHGGSISAPVTPPLSSPTA--RTPRMKTDWDESNVQPTWTGS
   Zm_TA178991_4577  (162) HPLLPPLLIHGGSISAPVTPPLSSPSA--RTPRMKTDWDEAAVQPPWHGA
       Os06g0552300  (170) FPQLHHLYFNGGSISAPVTPPSSSP-T--RTPRLRTDWENASVQPPWASA
   Zm_TA175044_4577  (168) FPQLHHLYFNGGSISAPVTPPSSSP-T--RTPRIKTDWENPSVQPPWAGA
        AT1G78700.1  (151) SRLPNYLYIPGGSISAPVTPPLSSPTA--RTPRMNTDWQQLN---NS---
        AT4G18890.1  (141) P------FFHGNSISAPVTPPLAR--------------------------
     Pt_scaff_IV.340  (149) PKHPHHLFIHTGSISAPVTPPLSSPTA--RTPRTKNDWDDAAAGQSWMGQ
     Pt_scaff_XI.678  (151) PKHPNHLFIHTGSISAPVTPPLSSPTA--RTPRTRNDWDDPAAGQSWMGQ
          Gm 1765606  (148) SSKLPQLYIPNGSISAPVTPPISSPSS--RKPRIKADWEDLSTRPAAWGG
         Mt_BF635822  (139) SPKLPHPYFHSGSISAPVTPPLSSPTS-----------------------
     Pt WS01123_K11  (147) SSKFPHLYIHGGSISAPVTPPLSSPTA--RTARIKADWEDQSIRPGWGGQ
     Pt_scaff_178.36  (147) SSKFPHLYIHGGSISAPVTPPLSSPTA--RTARIKADWEDQSIRPGWGGQ
     Pt_scaff_XI.792  (146) ---LPHLYIHGGSISAPVTPPLSSPTA--RTPRIKTGWEDQPIHPGWCGQ
         Sl FC26BA11  (147) SSKLPNFHIHTGSISAPVTPPFSSPTA--RTPRIKTDAG-------WAGF
           Consensus  (401)       L  L  S SAPVTPPLSSPT   R PR K DWE
```

FIGURE 12 (continued)

```
                             451                                            500
        AT1G19350.1  (205)  KQSMT--------SLNYPFYAVSAPASPTHHR------------------
        AT1G75080.1  (206)  KQSMA--------SFNYPFYAVSAPASPTHRH------------------
     Pt_scaff_40.175  (199)  -------------SY--PFNAVSAPASPTHR-------------------
    Pt_scaff_II.1237  (199)  -------------SY--PFNAVSAPASPTHR-------------------
          Gm 1762729  (197)  -------------YP---FFAASAPASPTHR-------------------
   Mt_TA28179_3880  (174)  --------------------------------------------------
           Le LAT61  (220)  -------------IP---FFAASAPASPTRV-------------------
    Le_TA51962_4081  (219)  -------------IP---FLAASAPASPTRG-------------------
   Vv_TA44770_29760  (189)  --------------HHYPIFAASAPASPSRC-------------------
        AT3G50750.1  (179)  ------------------NFPVSAPSSPTRRL------------------
         Gm 1768381  (186)  -------------SLRHPLFDTSAPSSPSRR-------------------
         Gm 1768507  (180)  -------------SLRHPLFATSAPSSPTRR-------------------
    Mt_TA21345_3880  (191)  -------------SFRHPLFATSAPSSPSRR-------------------
     Pt_scaff_57.215  (189)  -------------SFRHPLFAASAPSSPTRR-------------------
   Pt_scaff_VII.1038  (189)  -------------SLHHPLLAASAPSSPTRR-------------------
        Le_DB718708  (193)  -------------SFQHPLFAASAPSSPTRR-------------------
    Le_TA37112_4081  (193)  -------------SFQHPLFAASAPSSPTRR-------------------
       Os07g0580500  (184)  --------------FRHPFFAVSAPASPTRGR------------------
        Zm_AY107201  (138)  --------------------------------------------------
        AT4G36780.1  (170)  --------------------------------------------------
       Os02g0129600  (246)  -------------SHCQLIDPEGIRAELMHLKSLN---------------
        Zm_EE158804  (233)  --------------------------------------------------
  Zm_TA189809_4577  (258)  KAAEARGHTIWARGPDNAGHYNSEPNLTGFFCDGGDYDSYYGRFF-----
           Pp 82495  (282)  VRLHHVGNLNDPPVPGAEDIAEVCTALAVKNEWETTQGTAGVLYSGGQTV
           Pp 17189  (175)  FPPTGTPTWNHHPFLAAAAAAAQAAASNQSHLRPGYCDTPDGART-----
          Pp 172161  (352)  FPPSGPPTWNHHPFLAAAAAAAQAAASNQSHLRPGYCDTPDGART-----
      Ps WS0287_023  (191)  DCPNSGFSTPVSPWSNYPFVASSTPASPGRHAEMATQLSNAVVDK-----
    Hv_TA37786_4513  (211)  NSP---------------CVVNSTPPSPGRQ----------MVPD-----
       Os01g0203000  (225)  NSP---------------CVVNSTPPSPGRT----------MLPD-----
   Zm_TA178991_4577  (210)  SSP---------------TIVNSTPPSPGRP----------IAPD-----
       Os06g0552300  (217)  NYT---------------SLPNSTPPSPGHK----------IAPD-----
   Zm_TA175044_4577  (215)  NYA---------------SLPNSQPPSPGHQ----------VAPD-----
        AT1G78700.1  (193)  ------------------FFVSSTPPSPTRQ----------IIPD-----
        AT4G18890.1  (159)  ----------------------SP--TRDQV----------TIPD-----
     Pt_scaff_IV.340  (197)  NYSFM-----------PSSMPSSTPPSPGRH----------VLPD-----
     Pt_scaff_XI.678  (199)  NYSFL-----------PSSMPSSTPPSPGRQ----------VLPD-----
         Gm 1765606  (196)  PAYT--------------FLPSSTPPSPGR-----------QVAE-----
        Mt_BF635822  (166)  --------------------------------------------------
     Pt WS01123_K11  (195)  HYS---------------FLPSSTPPSPGRQ----------IVPD-----
    Pt_scaff_178.36  (195)  HYS---------------FLPSSTPPSPGRQ----------IVPD-----
     Pt_scaff_XI.792  (191)  HY-----------------LPSSTPPSPGRQ----------IVPD-----
        Sl FC26BA11  (188)  RYP---------------YLPSSTPASPGRQ----------NFIN-----
          Consensus  (451)                        S PASP R
```

FIGURE 12 (continued)

```
                              501                                               550
        AT1G19350.1   (229)   ---------------QFHAPATIPEC---------DESDSSTVD--SGHW
        AT1G75080.1   (230)   ---------------QFHTPATIPEC---------DESDSSTVD--SGHW
     Pt_scaff_40.175  (215)   ---------------QFHAPATIPEC---------DESDTSTVE--SGQW
   Pt_scaff_II.1237   (215)   ---------------QFHAPATIPEC---------DESDSSTVE--SGQW
         Gm 1762729   (212)   ---------------HLYTPPTIPEC---------DESDTSTGE--SGQW
     Mt_TA28179_3880  (174)   --------------------------------------------------
          Le LAT61    (235)   ---------------QRFTPPTIPEC---------DESDSSTID--SGQW
     Le_TA51962_4081  (234)   ---------------QRFTPPTIPEC---------DESDSSTID--SGQW
   Vv_TA44770_29760   (206)   ---------------QYIAPATIPEY---------EESDTSTVE--SGQW
        AT3G50750.1   (193)   ---------------HHYTS--IPEC---------DESDVSTVD--SCRW
         Gm 1768381   (204)   ---------------HHLATSTIPEC---------DESDASTVDSASGRW
         Gm 1768507   (198)   ---------------HHVATSTIPEC---------DESDASTVDSASGRW
     Mt_TA21345_3880  (209)   ---------------NHLPPSTIPEC---------DESDASTVD--SGRW
     Pt_scaff_57.215  (207)   ---------------PHLTPATIPEC---------DESDASTVD--SGRW
  Pt_scaff_VII.1038   (207)   ---------------HHLTPATIPEC---------DESDASTVD--SGRW
        Le_DB718708   (211)   ---------------XXSX------------------------LLQFXXX
     Le_TA37112_4081  (211)   ---------------RYSKPATIPEC-----------DESDAASVESARW
       Os07g0580500   (202)   ---------------RLEHPDTIPEC---------DESDVSTVD--SGRW
        Zm_AY107201   (138)   --------------------------------------------------
        AT4G36780.1   (170)   --------------------------------------------------
       Os02g0129600   (268)   -----------------VDGVIVDCWWGIVEAWIPHKYEWSGYRDLFGII
        Zm_EE158804   (233)   --------------------------------------------------
   Zm_TA189809_4577   (303)   --------------LSWYSQALVDHADRVLMLARLAFEGTNIAVKVSGVH
           Pp 82495   (332)   GQTYIVSCASEKDTSDCFERVSVTAGHDRFSHDPLVADMMDCVDLGQQLE
           Pp 17189   (220)   --------------PIEEGDSEISPEA-------ALEFATVCGSNSSKWA
          Pp 172161   (397)   --------------PIEEAESEISPGT-------ALEFATVCGSNSSKWA
       Ps WS0287_023  (236)   --------------GRWMGGIRMMAFP-------SAGPSSPTFNLLTPAA
     Hv_TA37786_4513  (231)   --------------PAWLAGIQISST---------S-PSSPTFSLMSSNP
       Os01g0203000   (245)   --------------PAWLAGIQISST---------S-PSSPTFSLVSSNP
   Zm_TA178991_4577   (230)   --------------PAWLAGIQISST---------S-PNSPTFSLVSTNP
       Os06g0552300   (237)   --------------PAWLSGFQISSA---------G-PSSPTYNLVSPNP
   Zm_TA175044_4577   (235)   --------------PAWLAGFQISSA---------G-PSSPTYSLVAPNP
        AT1G78700.1   (210)   --------------SEWFSGIQLAQS---------V-PASPTFSLVSQNP
        AT4G18890.1   (170)   --------------SGWLSGMQTPQS---------G-PSSPTFSLVSRNP
     Pt_scaff_IV.340  (221)   --------------SGWLAGIQIPQS---------G-PSSPTFSLVSRNP
     Pt_scaff_XI.678  (223)   --------------SGWLAGIQIPQS---------G-PSSPTFSLVSRNP
         Gm 1765606   (216)   --------------TDWFSKIRIPQVG-------LT-PTSPTFSLVSSNP
        Mt_BF635822   (166)   --------------------------------------------------
      Pt WS01123_K11  (215)   --------------PEWFRGIRIPQG---------G-PTSPTFSLVASNP
     Pt_scaff_178.36  (215)   --------------PEWFRGVRMPQG---------G-PTSPTFSLVASNP
     Pt_scaff_XI.792  (209)   --------------PGWFAGIRLPQG---------G-PTSPTFSLVASNP
        Sl FC26BA11   (208)   --------------AECFAGISGPPS--------------PTYSLVSPNP
          Consensus   (501)                   W     IP               S T    S
```

FIGURE 12 (continued)

```
                         551                                              600
       AT1G19350.1 (253) ISFQKFAQQQPF---------SASMVPTSPTFNLVKPAPQQLSP------
       AT1G75080.1 (254) ISFQKFAQQQPF---------SASMVPTSPTFNLVKPAPQQMSP------
   Pt_scaff_40.175 (239) ISFQKFA---PS---------VAAAMPTSPTYNLVIPVAQQIS-------
  Pt_scaff_II.1237 (239) ISFQKFA---PS---------VAAAMPTSPTYNLVKPVARQIL-------
        Gm_1762729 (236) VKFQAFAP-------------SSSVLPISPTFNLVKPVIPHRMP------
   Mt_TA28179_3880 (174) --------------------------------------------------
          Le_LAT61 (259) INFQKYASN---------------V-PPSPTFNLVKPVPQPLR-------
   Le_TA51962_4081 (258) INFQKYASN---------------V-PPSPTFNLVKPVPQPLR-------
  Vv_TA44770_29760 (230) VSFQTFAR---------------HLAPLPPTFNLMKPVAQKIS-------
       AT3G50750.1 (215) GNFQSVNVSQTC---------P-----PSPTFNLVGKSVSSVG-------
        Gm_1768381 (230) VSFQVQTTMAAA---------P-----PSPTFNLMKPAMQQIAAQ-----
        Gm_1768507 (224) VSFQVQTTMVAA---------AAAA-PPSPTFNLMKPAMQQIAAQ-----
   Mt_TA21345_3880 (233) VSFQTTTAHGAA---------P-----PSPTFNLMKPAMQITPQSSMDMK
   Pt_scaff_57.215 (231) LSFQAVAPQVAP---------P------SPTFNLVKPVDQQCAFQIG--V
 Pt_scaff_VII.1038 (231) VSFLAGAPHVAP---------P------SPTFNLVKPVAQQSGFQDG--V
       Le_DB718708 (222) MSLXPXX-------------------------------------------
   Le_TA37112_4081 (235) VSFQTVAAPTSP---------T---------FNLVKPLPQQNILLDALSG
      Os07g0580500 (226) ISFQMATT-----------------APTSPTYNLVNPGASTSNS------
       Zm_AY107201 (138) --------------------------------------------------
       AT4G36780.1 (170) --------------------------------------------------
      Os02g0129600 (301) KEFKLKVQAVLSFHG--------SGETGSGGVSLPKWVMEIAQ-------
       Zm_EE158804 (233) --------------------------------------------------
  Zm_TA189809_4577 (339) WWYKTASHAAELT-------AGFYNPCNRDGYAPIAAVLKKYDAALNFTC
          Pp_82495 (382) CGRRKRFLEHQSKQLEYDQLNPYLNVHMNGDSSVVSQVQRQTQDPDPGKH
          Pp_17189 (249) NGVRVRTSSEGRL-------LSGMAGLGPFPSANSDSPLETFSHPWRNPM
         Pp_172161 (426) NGVRVRTSSGGRL-------LGGMAGLGPFPSANNDSPLETFSHAWRNPM
     Ps_WS0287_023 (265) QLQHGLATEGG-------------RLWTPGQSGVSSPCNNRAG-------
   Hv_TA37786_4513 (257) FSVFKEAIPGG----------GSSRMCTPGQSGTCSPVIPG---------
      Os01g0203000 (271) FSVFKDAILVG---------NNSSRMCTPGQSGTCSPAIPG---------
  Zm_TA178991_4577 (256) FGVFKESIPVGGG-------DSSMRMCTPGQSGACSPAIPG---------
      Os06g0552300 (263) FGIFKEAIAST------------SRVCTPGQSGTCSPVMGG---------
  Zm_TA175044_4577 (261) FGIFKETIVST------------SRMCTPGQSGTCSPVMGG---------
       AT1G78700.1 (236) FGFKEEAASAAGG-------GGGSRMWTPGQSGTCSPAIPPG--------
       AT4G18890.1 (196) FFDKEAFKMGD----------CNSPMWTPGQSGNCSPAIPAG--------
   Pt_scaff_IV.340 (247) FGFREEALSG-----------AGSRMWTPGQSGTCSPAIPAG--------
   Pt_scaff_XI.678 (249) FGFKEEALSG-----------AGSRMWTPGQSGTCSPAVPAG--------
        Gm_1765606 (244) FGFKEDAMGGS----------GSRMWTTPGASGTCSPAVAAG--------
       Mt_BF635822 (166) --------------------------------------------------
    Pt_WS01123_K11 (241) FGFKEEAFGGGGS-------NGGSRMWTPGQSGTCSPAIAAG--------
   Pt_scaff_178.36 (241) FGFKEEAFGGGGS-------NGGSRMWTPGQSGTCSPAIAAG--------
   Pt_scaff_XI.792 (235) FGFKEEALAG-----------GGSRMWTPGQSGTCSPAIAAG--------
       Sl_FC26BA11 (230) FGFKMDGLSRG-----------GSRMCTPGQSGACSPAIAAG--------
         Consensus (551)   F   A                             P I
```

FIGURE 12 (continued)

```
                              601                                              650
      AT1G19350.1   (288)    --------NTAAIQEIGQSSEFKFENS-----------------------
      AT1G75080.1   (289)    --------NTAAFQEIGQSSEFKFENS-----------------------
  Pt_scaff_40.175   (270)    --------SSNLVKESAVPMDFEFGSE-----------------------
 Pt_scaff_II.1237   (270)    --------SNNLVKDNGMSMDFEFGSE-----------------------
       Gm 1762729   (267)    --------DNSIQVMRTSSE--EFG-V-----------------------
  Mt_TA28179_3880   (174)    --------------------------------------------------
         Le LAT61   (286)    --------PNDMITDKGKSIDFDFENV-----------------------
  Le_TA51962_4081   (285)    --------PNDMITDKGKSIDFDFENV-----------------------
 Vv_TA44770_29760   (258)    --------PDGATKEKGITPELEIGSA-----------------------
      AT3G50750.1   (244)    ------------------------VDV-----------------------
       Gm 1768381   (261)    ---EGMLWGSVAERVRG-GSDFDFENG-----------------------
       Gm 1768507   (259)    ---EGMQWGSVAERGRG-GSDFDFENG-----------------------
  Mt_TA21345_3880   (269)    HMNEAMQWSAGSATERGRGSDFDFENGR----------------------
  Pt_scaff_57.215   (264)    DRHEGLSWGVAAERGRG--AEFEFENC-----------------------
Pt_scaff_VII.1038   (264)    DRHGGLSWGAAAERGRG--AEFEFENC-----------------------
      Le_DB718708   (229)    --------------------------------------------------
  Le_TA37112_4081   (267)    ---HGMVGWGETAAQKGHGAEFDFESC-----------------------
     Os07g0580500   (253)    --------MEIEGTAGRGGAEFEFDKG-----------------------
      Zm_AY107201   (138)    --------------------------------------------------
      AT4G36780.1   (170)    --------------------------------------------------
     Os02g0129600   (336)    ---ENQDVFFTDREGRRNMECLSWGIDKER--------------------
      Zm_EE158804   (233)    --------------------------------------------------
 Zm_TA189809_4577   (382)    VELRTMDQHEVYPEAFADPEGLVWQVLNAAWDAGIQVASENALPCYDRDG
         Pp 82495   (432)    YTLFPEAADLLNQSQREQGDQYSCITHEMVDVTG--------QAYKSLKD
         Pp 17189   (292)    QKSISMPVSPVSSRMKGSFGDRLGRCPSELEFP------------GAVQG
        Pp 172161   (469)    QKSISMPVSPVSSRMKGSFGDRLGRCPSELELS------------GAVQG
    Ps WS0287_023   (295)    ---EEERLLPPFQEGMDASDEFAFGSVA----------------------
  Hv_TA37786_4513   (288)    ---MARHPDVHMMDVVS--DEFAFGSSTNGVAQ------------QATAG
     Os01g0203000   (303)    ---MAPHPDIHMMDAVS--DEFAFGSSTN--GG------------HQAAG
 Zm_TA178991_4577   (290)    ---MPRHSDVHMMDVVS--DEFAFGSSTN--GA------------QQAAG
     Os06g0552300   (292)    ---MPAHHDVQMVDGAP--DDFAFGSSSN--GN------------NESPG
 Zm_TA175044_4577   (290)    ---APIHHDVQMADGAP--DDFAFGSSSN--GN------------NESPG
      AT1G78700.1   (271)    ---ADQTADVPMSEAVAP-PEFAFGSNTN--------------------G
      AT4G18890.1   (228)    ---VDQNSDVPMADGMT--AEFAFGCNAM-----------------AANG
  Pt_scaff_IV.340   (278)    ---IDQTADVPMSDSMA--AEFAFGSN--------------------AAG
  Pt_scaff_XI.678   (280)    ---IDQTADVPMADSMA--AEFAFGSN--------------------TAG
       Gm 1765606   (276)    ---SENTSDIPMAEAVS--DEFAFGSSSS--------------------G
      Mt_BF635822   (166)    --------------------------------------------------
   Pt WS01123_K11   (276)    ---SDHTADIPMAEIS---DEFAFRCNAT--------------------G
  Pt_scaff_178.36   (276)    ---SDHTADIPMAEIS---DEFAFRCNAT--------------------G
  Pt_scaff_XI.792   (266)    ---SDQTADIPMAEVIS--DEFAFRCNAT--------------------G
      Sl FC26BA11   (261)    ---LDHNADVPMAEVMIS-DEFAFGSN--------------------VAG
        Consensus   (601)                        EF F
```

FIGURE 12 (continued)

```
                            651                                                700
       AT1G19350.1  (307) QVKPWEGERIHDVAME------DLELTLGNGKAHS---------------
       AT1G75080.1  (308) QVKPWEGERIHDVGME------DLELTLGNGKARG---------------
     Pt_scaff_40.175  (289) QVKPWEGERIHEVGLD------DLELTLGSGKAQS---------------
    Pt_scaff_II.1237  (289) QVKPWEGERIHEVGLD------DLELTLGGGKARS---------------
        Gm 1762729  (283) QVKPWVGEKIHEVALD------DLELTLGSGKVRS---------------
    Mt_TA28179_3880  (174) --------------------------------------------------
          Le LAT61  (305) SVKAWEGERIHDVGFD------DLELTLGSGNARI---------------
    Le_TA51962_4081  (304) SVKAWEGERIHDVGFD------DLELTLGSGNARI---------------
   Vv_TA44770_29760  (277) QVKPWEGERIHEIGLD------DLELTLGSGKSRSKG-------------
       AT3G50750.1  (247) SVKPWEGEKIHDVGID------DLELTLGHNTKGRG--------------
        Gm 1768381  (284) RVKPWEGERIHEVGMD------DLELTLGVGKA-----------------
        Gm 1768507  (282) RVKPWEGERIHEVGMD------DLELTLGVGKA-----------------
    Mt_TA21345_3880  (297) VVKPWEGERIHEVGME------ELELTLGFGKA-----------------
     Pt_scaff_57.215  (289) RVKPWEGERIHEIGVD------DLELTLGSGKVHGQASIDDLAWERSNK-
   Pt_scaff_VII.1038  (289) RVKPWEGERIHEIGVD------DLELTLGGGKARG---------------
        Le_DB718708  (229) --------------------------------------------------
    Le_TA37112_4081  (291) KVKAWEGERIHEVAVD------DLELTLGSAKARA---------------
       Os07g0580500  (272) RVTPWEGERIHEVAAE------ELELTLGVGAK-----------------
        Zm_AY107201  (138) --------------------------------------------------
       AT4G36780.1  (170) --------------------------------------------------
       Os02g0129600  (363) VLRGRTGIEVLGHPWRILIS----GAFIWNSET-----------------
        Zm_EE158804  (233) --------------------------------------------------
   Zm_TA189809_4577  (432) FNKILENAKPLNDPDGRHLL-GFTYLRLGKDLFERPNFFEFERFIKRMHG
          Pp 82495  (474) GLCLWSGRDGASVSTGSTRL-SLHPAAAAASTTASNRGGASIISLQHKKV
          Pp 17189  (330) LGSLWDG--LAPEVGGKMKL-PADDLELKL--------------------
         Pp 172161  (507) LGSLWELDGVVPEVGAKRKL-PADDLELKLIAGGLVPIATEVVQVKLWVF
     Ps WS0287_023  (320) -VKPWQGERIHEECGGEIGS-DDLELTLGSFSSSSSKLRSDREPLFSVKE
    Hv_TA37786_4513  (321) LVRAWEGERIHEDSGS-----DELELTLGSTRTRS---------------
       Os01g0203000  (334) LVRAWEGERIHEDSGS-----DDLELTLGSSRTRAAA-------------
   Zm_TA178991_4577  (321) LVRAWEGERIHEDSGS-----DDLELTLKL--------------------
       Os06g0552300  (323) LVKAWEGERIHEECAS-----DELELTLGSSKTRADPS------------
   Zm_TA175044_4577  (321) LVKAWEGERIHEECASDE---HELELTLGSSKTRADPS------------
       AT1G78700.1  (297) LVKAWEGERIHEESGS-----DDLELTLGNSSTR----------------
       AT4G18890.1  (256) MVKPWEGERIHGECVS-----DDLELTLGNSRTR----------------
     Pt_scaff_IV.340  (303) LVKPWEGERIHEECVS-----DDLELTLGNSNTR----------------
     Pt_scaff_XI.678  (305) LVKPWEGERIHEECVS-----DDLELTLGNSSTR----------------
        Gm 1765606  (301) LVNAWKGERIHEASFG-T---DDLELTLGSSKTRLLHK------------
        Mt_BF635822  (166) --------------------------------------------------
     Pt WS01123_K11  (300) LVKPWEGERIHEECGS-----DDLELTLGNSRTR----------------
     Pt_scaff_178.36  (300) LVKPWEGERIHEECGS-----DDLELTLGNSRTR-TIAKMKIPE------
     Pt_scaff_XI.792  (291) LVKPWEGERIHEECGS-----DDLELTLGNSRTR----------------
       Sl FC26BA11  (287) MVKPWEGERIHEDCVP-----DDLELTLGSSKTR-NLEVCKQAELALIDV
         Consensus  (651)  VKPWEGERIHE          DLELTLG  K R
```

FIGURE 12 (continued)

```
                             701                                              750
       AT1G19350.1  (336) --------------------------------------------------
       AT1G75080.1  (337) --------------------------------------------------
    Pt_scaff_40.175  (318) --------------------------------------------------
   Pt_scaff_II.1237  (318) --------------------------------------------------
        Gm 1762729  (312) --------------------------------------------------
    Mt_TA28179_3880  (174) --------------------------------------------------
          Le LAT61  (334) --------------------------------------------------
    Le_TA51962_4081  (333) --------------------------------------------------
   Vv_TA44770_29760  (308) --------------------------------------------------
       AT3G50750.1  (277) --------------------------------------------------
        Gm 1768381  (311) --------------------------------------------------
        Gm 1768507  (309) --------------------------------------------------
    Mt_TA21345_3880  (324) --------------------------------------------------
    Pt_scaff_57.215  (332) --------------------------------------------------
  Pt_scaff_VII.1038  (318) --------------------------------------------------
       Le_DB718708  (229) --------------------------------------------------
    Le_TA37112_4081  (320) --------------------------------------------------
      Os07g0580500  (299) --------------------------------------------------
       Zm_AY107201  (138) --------------------------------------------------
       AT4G36780.1  (170) --------------------------------------------------
      Os02g0129600  (392) --------------------------------------------------
       Zm_EE158804  (233) --------------------------------------------------
   Zm_TA189809_4577  (481) EAVLDLQV------------------------------------------
          Pp 82495  (523) DADEDIVKDIADDLTLTLCTSVRHTHTPESSRVV----------------
          Pp 17189  (357) --------------------------------------------------
         Pp 172161  (556) QAVHLKDVGLVSVVYFVGLHLLEPLHEGALYSSTTLILQFNAVKSALFVS
     Ps WS0287_023  (368) --------------------------------------------------
    Hv_TA37786_4513  (351) --------------------------------------------------
      Os01g0203000  (366) --------------------------------------------------
   Zm_TA178991_4577  (346) --------------------------------------------------
      Os06g0552300  (356) --------------------------------------------------
   Zm_TA175044_4577  (356) --------------------------------------------------
       AT1G78700.1  (326) --------------------------------------------------
       AT4G18890.1  (285) --------------------------------------------------
    Pt_scaff_IV.340  (332) --------------------------------------------------
    Pt_scaff_XI.678  (334) --------------------------------------------------
        Gm 1765606  (335) --------------------------------------------------
       Mt_BF635822  (166) --------------------------------------------------
    Pt WS01123_K11  (329) --------------------------------------------------
    Pt_scaff_178.36  (338) --------------------------------------------------
    Pt_scaff_XI.792  (320) --------------------------------------------------
       Sl FC26BA11  (331) KVRQSTGLC-----------------------------------------
         Consensus  (701)
```

FIGURE 12 (continued)

SEQUENCE LISTING

<160> NUMBER OF SEQ ID NOS: 328

<210> SEQ ID NO 1
<211> LENGTH: 1359
<212> TYPE: DNA
<213> ORGANISM: Arabidopsis thaliana

<400> SEQUENCE: 1
gacaaagaca tttaaaagaa gaattttcga agaaaaatta gagagagtag aagaagcaga 60
agcagtaatg gtacgagctt catcgtcgaa gaaaggagga tcaaaaggag gagacaaaga 120
cgacgcagag tcaaaacaga ggaagagatt aaaaacccta gctctcgata accaattgct 180
ctctgattct ccggcgaaat ctcattcctc tctcaaacct tcaaagcaag ttctcaaaca 240
ccatggcacc gacatcatcc gcaaatctca gcgcaagaat cgctttctct tctccttccc 300
tggtcttctc gctcctatct ccgccgctac catcggcgat ctcgatcgat tatctaccaa 360
aaaccctgtc ctctacctta atttcccaca gggtcgtatg aaactttttg gaacgatttt 420
gtatccgaag aacagatact tgactcttca attctctaga ggaggcaaaa atgtcttatg 480
tgatgattat tttgataaca tgattgtgtt ctctgagtca tggtggattg ggacaaaaga 540
ggagaatcca gaagaagctc gtcttgattt ccctaaagaa ctagctcagg cagagaatac 600
tgagtttgat ttccaaggcg gtgctggagg agcagcttcg gtgaagaagc tggcgagtcc 660
tgaaattggt agccaaccaa cagagacaga ctcacctgaa gttgacaacg aggatgtttt 720
gtctgaggat ggagaattct tggacgataa gatccaagta acaccaccag ttcaattaac 780
accaccagtc caagtaactc cggtccgaca gtctcagaga aattctggga agaaattcaa 840
ctttgcagaa acttcctcag aggcctcctc tggtgaaagt gaaggcaata catctgatga 900
agatgagaaa cctctgttgg aacctgaatc ttcaacaaga agtcgtgagg aatctcaaga 960
tggtaatggt attactgcat ctgcaagcaa gttgcctgaa gaacttccgg ctaaaaggga 1020
aaaactaaag agcaaagaca gtaagctcgt tcaagctact ttgtctaacc ttttcaagaa 1080
agctgaggag aaaacagctg gaacttccaa ggctaaatca tcctcaaaag cttaaagaaa 1140
tcttttccag aagaaaatag aggtctgttg tttctttgct gtgagaatga acagttttta 1200
gttcttttag gtatgtttgt gtgagaaatt gctacaagac tgatgtattc atcatgcagt 1260
tggataatgt attcattatg cttattcgat agtttgtgtt catcgagcta tgtataaatc 1320
atctctgctc tttttaatac aacaaactgt ctccatcta 1359

<210> SEQ ID NO 2
<211> LENGTH: 355
<212> TYPE: PRT
<213> ORGANISM: Arabidopsis thaliana

<400> SEQUENCE: 2

Met Val Arg Ala Ser Ser Ser Lys Lys Gly Gly Ser Lys Gly Gly Asp
1 5 10 15

Lys Asp Asp Ala Glu Ser Lys Gln Arg Lys Arg Leu Lys Thr Leu Ala
20 25 30

Leu Asp Asn Gln Leu Leu Ser Asp Ser Pro Ala Lys Ser His Ser Ser
35 40 45

Leu Lys Pro Ser Lys Gln Val Leu Lys His His Gly Thr Asp Ile Ile
50 55 60

Arg Lys Ser Gln Arg Lys Asn Arg Phe Leu Phe Ser Phe Pro Gly Leu
65 70 75 80

```
Leu Ala Pro Ile Ser Ala Ala Thr Ile Gly Asp Leu Asp Arg Leu Ser
                85                  90                  95

Thr Lys Asn Pro Val Leu Tyr Leu Asn Phe Pro Gln Gly Arg Met Lys
            100                 105                 110

Leu Phe Gly Thr Ile Leu Tyr Pro Lys Asn Arg Tyr Leu Thr Leu Gln
        115                 120                 125

Phe Ser Arg Gly Gly Lys Asn Val Leu Cys Asp Asp Tyr Phe Asp Asn
    130                 135                 140

Met Ile Val Phe Ser Glu Ser Trp Trp Ile Gly Thr Lys Glu Glu Asn
145                 150                 155                 160

Pro Glu Glu Ala Arg Leu Asp Phe Pro Lys Glu Leu Ala Gln Ala Glu
                165                 170                 175

Asn Thr Glu Phe Asp Phe Gln Gly Gly Ala Gly Gly Ala Ala Ser Val
            180                 185                 190

Lys Lys Leu Ala Ser Pro Glu Ile Gly Ser Gln Pro Thr Glu Thr Asp
        195                 200                 205

Ser Pro Glu Val Asp Asn Glu Asp Val Leu Ser Glu Asp Gly Glu Phe
    210                 215                 220

Leu Asp Asp Lys Ile Gln Val Thr Pro Pro Val Gln Leu Thr Pro Pro
225                 230                 235                 240

Val Gln Val Thr Pro Val Arg Gln Ser Gln Arg Asn Ser Gly Lys Lys
                245                 250                 255

Phe Asn Phe Ala Glu Thr Ser Ser Glu Ala Ser Ser Gly Glu Ser Glu
            260                 265                 270

Gly Asn Thr Ser Asp Glu Asp Glu Lys Pro Leu Leu Glu Pro Glu Ser
        275                 280                 285

Ser Thr Arg Ser Arg Glu Glu Ser Gln Asp Gly Asn Gly Ile Thr Ala
    290                 295                 300

Ser Ala Ser Lys Leu Pro Glu Glu Leu Pro Ala Lys Arg Glu Lys Leu
305                 310                 315                 320

Lys Ser Lys Asp Ser Lys Leu Val Gln Ala Thr Leu Ser Asn Leu Phe
                325                 330                 335

Lys Lys Ala Glu Glu Lys Thr Ala Gly Thr Ser Lys Ala Lys Ser Ser
            340                 345                 350

Ser Lys Ala
        355
```

<210> SEQ ID NO 3
<211> LENGTH: 674
<212> TYPE: DNA
<213> ORGANISM: Populus trichocarpa

<400> SEQUENCE: 3

```
acatcatcat caaagaactt ttttaaaaaa atggtgaaat ccaagaaaac agaagccagc     60

aattctaaca gggaaaaccc ggatgtgtta gagagaaaaa gactgaaaaa gcttgcaata    120

accaacaaca tagtatcaga cacacaagtc agatatatta ggaaatctca aagaaaaaac    180

aggtacttgc cttcatttcc tggtcttctt gctcctgtca atggtggtgg caagattggc    240

gagctcaaag acttgtcctc taaaagccct gttctttacc tcgattttcg tcagctgaca    300

ttgcaattct ctaggagtgg aaagaatgtt atgtgtgagg attattttga tcacatgatt    360

gtattttctg aggcatggtg gattggaacg aaagaagaga acccggagga attgaaactt    420

gattttctta aggaactgtt tgaggagggg caggagcatg tagttgataa aagtggtggg    480

acaaaatatg tgaaagaaga gtctcctgaa acagagcttg atgatgatga taacaaatat    540
```

```
ttgaaaggtt tgaaggaagt tatgccaatt cggcagcatg caagaactct gtaaaaatat    600

gttttaaaaa tatttttgaa agaaattaat attttttaa ttttttttac ttcaaattaa    660

tatttttta gatc                                                      674


<210> SEQ ID NO 4
<211> LENGTH: 187
<212> TYPE: PRT
<213> ORGANISM: Populus trichocarpa

<400> SEQUENCE: 4

Met Val Lys Ser Lys Lys Thr Glu Ala Ser Asn Ser Asn Arg Glu Asn
1               5                   10                  15

Pro Asp Val Leu Glu Arg Lys Arg Leu Lys Lys Leu Ala Ile Thr Asn
            20                  25                  30

Asn Ile Val Ser Asp Thr Gln Val Arg Tyr Ile Arg Lys Ser Gln Arg
        35                  40                  45

Lys Asn Arg Tyr Leu Pro Ser Phe Pro Gly Leu Leu Ala Pro Val Asn
    50                  55                  60

Gly Gly Gly Lys Ile Gly Glu Leu Lys Asp Leu Ser Ser Lys Ser Pro
65                  70                  75                  80

Val Leu Tyr Leu Asp Phe Arg Gln Leu Thr Leu Gln Phe Ser Arg Ser
                85                  90                  95

Gly Lys Asn Val Met Cys Glu Asp Tyr Phe Asp His Met Ile Val Phe
            100                 105                 110

Ser Glu Ala Trp Trp Ile Gly Thr Lys Glu Glu Asn Pro Glu Glu Leu
        115                 120                 125

Lys Leu Asp Phe Leu Lys Glu Leu Phe Glu Glu Gly Gln Glu His Val
    130                 135                 140

Val Asp Lys Ser Gly Gly Thr Lys Tyr Val Lys Glu Glu Ser Pro Glu
145                 150                 155                 160

Thr Glu Leu Asp Asp Asp Asp Asn Lys Tyr Leu Lys Gly Leu Lys Glu
                165                 170                 175

Val Met Pro Ile Arg Gln His Ala Arg Thr Leu
            180                 185


<210> SEQ ID NO 5
<211> LENGTH: 332
<212> TYPE: DNA
<213> ORGANISM: Populus trichocarpa

<400> SEQUENCE: 5

ttacagcaac cccctcttaa atctaaataa atgcagagaa aacacaaaga gcatttgaat     60

caatgtagaa ggaaatctca aagaaaaaac aggtacttgc cttcatttcc tggtcttctt    120

gctcctgtca atggtggtgg caagattggc gagctcaaag acttgtcctc taaaagccct    180

gttctttacc tcgattttcg tcagggacgg atgaagctgc ttgggactgt tgtgtatcca    240

aaaaacagat agctgacatt gcaattctct aggagtggaa agaatgttat gtgtgaggat    300

tattttgatc acatggtttc tttctttctt gt                                  332


<210> SEQ ID NO 6
<211> LENGTH: 100
<212> TYPE: PRT
<213> ORGANISM: Populus trichocarpa

<400> SEQUENCE: 6
```

-continued

```
Met Gln Arg Lys His Lys Glu His Leu Asn Gln Cys Arg Arg Lys Ser
1               5                   10                  15

Gln Arg Lys Asn Arg Tyr Leu Pro Ser Phe Pro Gly Leu Leu Ala Pro
            20                  25                  30

Val Asn Gly Gly Gly Lys Ile Gly Glu Leu Lys Asp Leu Ser Ser Lys
        35                  40                  45

Ser Pro Val Leu Tyr Leu Asp Phe Arg Gln Gly Arg Met Lys Leu Leu
    50                  55                  60

Gly Thr Val Val Tyr Pro Lys Asn Arg Leu Thr Leu Gln Phe Ser Arg
65                  70                  75                  80

Ser Gly Lys Asn Val Met Cys Glu Asp Tyr Phe Asp His Met Val Ser
                85                  90                  95

Phe Phe Leu Val
            100
```

<210> SEQ ID NO 7
<211> LENGTH: 1202
<212> TYPE: DNA
<213> ORGANISM: Populus trichocarpa

<400> SEQUENCE: 7

```
atcttcatcg tcaaagagaa gggaaaaaaa atggtgaaat ccaagaagac agaagccagc     60

aattctaaca gagaaaaccc ggatgtgtta gagagaaaaa gattgaaaaa acttgccata    120

accaacaaca tagtatcaga cgcacaagtc aaggctccat attcattgaa cccatcaaaa    180

actgttgcaa aacaccatgg taaagatatt attaggaaat ctcaaagaaa gaacaggttt    240

ttgttttcat ttcctggtct tcttgcacct attaatggag gtggcaagat tggcgagctc    300

aaagacttgt cctctaaaaa ccctgttctt tacctcgatt ttcctcaggg acagatgaag    360

ctgtttggga caattttgca tccaaagaat agatatttga cattgcaatt ctctaggagt    420

ggaaagaatg ttatgtgtga ggattatttt gatcacatga ttatattttc tgaggcatgg    480

tggattggaa cgaaagaaga gaacccggaa gaattgaaac ttgattttcc caacgaactg    540

tttgagggaa aaggtgttga atgtgatttt aaaggtgggg caggagcagg atctgtcaat    600

aagcaagtac ttcaaaagag tggtggaacc aaatatgtaa aagaagagtc tcctgaaact    660

gagcttgatg atgatttatc agatgataac aatgatttta aagatttgaa tgaaactaca    720

ccaattcggc aatctgcaag aacttctggg aaaaaattca agtttactga agtttcctcg    780

ggagatgatt ctgctgaaag aagtcctgat gccttggggg tggaggagga ggaggaggag    840

gaggaggaaa agaaagtgaa aactaacatg tcctctggtc ttgacattga aagtgaaagt    900

tctagagaag ggaatcatct ttctgagcaa attcaagcat ctataaccaa atctaaaaag    960

ctttctgagt ctgctgcttc agtgacgata cctaaggaaa acttgtataa tagtcatggt   1020

tcacttgttc agtcaaccat atccacgctg ttcaagaaag tgcaggaaaa gaagaaagtg   1080

gtggaaaagg ttaggtttga caactttgag gctaatagct aaatatgccg tctagtcaga   1140

acttgttgag aggctataat ctgtagtatt ttgctgcagt cactgaatag aaccatatag   1200

gt                                                                  1202
```

<210> SEQ ID NO 8
<211> LENGTH: 363
<212> TYPE: PRT
<213> ORGANISM: Populus trichocarpa

<400> SEQUENCE: 8

-continued

```
Met Val Lys Ser Lys Lys Thr Glu Ala Ser Asn Ser Asn Arg Glu Asn
1               5                   10                  15

Pro Asp Val Leu Glu Arg Lys Arg Leu Lys Lys Leu Ala Ile Thr Asn
            20                  25                  30

Asn Ile Val Ser Asp Ala Gln Val Lys Ala Pro Tyr Ser Leu Asn Pro
        35                  40                  45

Ser Lys Thr Val Ala Lys His His Gly Lys Asp Ile Ile Arg Lys Ser
    50                  55                  60

Gln Arg Lys Asn Arg Phe Leu Phe Ser Phe Pro Gly Leu Leu Ala Pro
65                  70                  75                  80

Ile Asn Gly Gly Gly Lys Ile Gly Glu Leu Lys Asp Leu Ser Ser Lys
                85                  90                  95

Asn Pro Val Leu Tyr Leu Asp Phe Pro Gln Gly Gln Met Lys Leu Phe
            100                 105                 110

Gly Thr Ile Leu His Pro Lys Asn Arg Tyr Leu Thr Leu Gln Phe Ser
        115                 120                 125

Arg Ser Gly Lys Asn Val Met Cys Glu Asp Tyr Phe Asp His Met Ile
    130                 135                 140

Ile Phe Ser Glu Ala Trp Trp Ile Gly Thr Lys Glu Glu Asn Pro Glu
145                 150                 155                 160

Glu Leu Lys Leu Asp Phe Pro Asn Glu Leu Phe Glu Gly Lys Gly Val
                165                 170                 175

Glu Cys Asp Phe Lys Gly Gly Ala Gly Ala Gly Ser Val Asn Lys Gln
            180                 185                 190

Val Leu Gln Lys Ser Gly Gly Thr Lys Tyr Val Lys Glu Glu Ser Pro
        195                 200                 205

Glu Thr Glu Leu Asp Asp Asp Leu Ser Asp Asp Asn Asn Asp Phe Lys
    210                 215                 220

Asp Leu Asn Glu Thr Thr Pro Ile Arg Gln Ser Ala Arg Thr Ser Gly
225                 230                 235                 240

Lys Lys Phe Lys Phe Thr Glu Val Ser Ser Gly Asp Asp Ser Ala Glu
                245                 250                 255

Arg Ser Pro Asp Ala Leu Gly Val Glu Glu Glu Glu Glu Glu Glu Glu
            260                 265                 270

Glu Lys Lys Val Lys Thr Asn Met Ser Ser Gly Leu Asp Ile Glu Ser
        275                 280                 285

Glu Ser Ser Arg Glu Gly Asn His Leu Ser Glu Gln Ile Gln Ala Ser
    290                 295                 300

Ile Thr Lys Ser Lys Lys Leu Ser Glu Ser Ala Ala Ser Val Thr Ile
305                 310                 315                 320

Pro Lys Glu Asn Leu Tyr Asn Ser His Gly Ser Leu Val Gln Ser Thr
                325                 330                 335

Ile Ser Thr Leu Phe Lys Lys Val Gln Glu Lys Lys Lys Val Val Glu
            340                 345                 350

Lys Val Arg Phe Asp Asn Phe Glu Ala Asn Ser
        355                 360
```

<210> SEQ ID NO 9
<211> LENGTH: 2170
<212> TYPE: DNA
<213> ORGANISM: Populus trichocarpa

<400> SEQUENCE: 9
gaggcgtaaa gtagtgcagg caaggcgaga agggcaagaa ggaggaggga ggagggatgg 60

-continued

```
tgaagaagaa ggaggccggc gatgcggagg ccgacgagcg gcgccgcctc cgctccctcg    120
ccttctctaa tggcttactc cagcgcgggg agccggcggc gccgcgctcg gcgctcgcgc    180
cctccactgc cgtgtcgcgg ctgcagggcc gcgacatcgt gcgccgcggc gggcagcgca    240
agagccgctt cctcttctca ttccccggcc tcctcgcgcc cgcggctgct gcctcgggcg    300
gccgcgtcgg cgagctcgct gatcttggca ccaaaaatcc tctgctctac ctcgacttcc    360
cacaggggag gatgaagctg ttggggacgc atgtgtaccc caagaacaag tatctgacac    420
tgcagatgag caggtccacc aagggcgttg tctgcgagga cgtcttcgag agcctgattg    480
ttttttctga agcctggtgg attggaacaa aagaagaaaa cccacaagaa ctgaaactgg    540
attttccaaa agagttccag aatgatgggg ctgttgcaga ttctgatttt aaaggtggag    600
caggtgcttc ctgtgatgaa gctgttacca tcaataaacc gccaaaggaa accaccacag    660
gatccctttc cccaaagatt gaatctgaca ttgattcttc cgaggattca gaccttaagg    720
acgaggataa cacacaaagc actagtcaag caccttcagt taggcagtct gctagaactg    780
ctgggaaagc cttgaagtat actgagatat cctctggaga cgattcatct gataatgacg    840
atgagattga tgtccctgag gacatggatg agaaggtgaa gagtccggca gttaagaatg    900
aatcccaaag tgaagacatt aaacctgcag attcatctgc gcagcctatc tcagctaaga    960
aggagccact cgttcaggct actctgtcta gcatgtttaa aaaagcagaa gaaaaaaaga   1020
gatgtactag aagcccgaaa ggatctccag caacaaaagg acctgctgct aagaagcagc   1080
gagcaagtcc agaggaaaaa catccaacag ggaagaagag tggtaagtgc agtagcaagt   1140
ctgttgttag aagcatctaa tagaccttgg tgcgattaca tttgttttaa gcctctgaag   1200
gccttcttca atggagaaga cttgttctaa aataatccaa aggctttggg aggcttactt   1260
gagaagcttt cagcttttgt ctatgtaagg ggcatttaaa atattaatcc atttcatgaa   1320
gctttaggac catctcaagc ctgtcgaatc ggaataaatg atggaattaa catctattgt   1380
ggtggctcta tactaaatat gctatttgaa ttttacaaga cttgatattg ctgggtaaaa   1440
gctgtgatgc atggggggaa acaaatgcat tttagtggct cttagtgcaa tgtgcaacga   1500
tctatcagct tttctttaac tgagtacatc agtacatgtt agtgttcttc atatgaagct   1560
gacaattgta tttacatgga tgtagctggc agaagtcaga aaaagagaaa aacacaggta   1620
gaagatgacg aaattgaagt gctctcaagt tcctcccagg ataacaatgt ggacgatgat   1680
agcgatgaag actgggctga gtgatgtgca gctgaagttg aaaggaatgt agcactcggt   1740
gatgaagagt gaaggatgca agattgtggg caattgtttt cttttggggc aatatcacaa   1800
ttgatgtgtt tgaggagctt aggttctgac ctgaccattg atgagatata tcatcatagt   1860
cttttcatcg tactggtgaa attgaaaacc gagaagtgtg atctgttagc actagattta   1920
ttatttattt gacttgttgt aatgtaacat aaacaagagc tgataaatca ttgttagggt   1980
ctgcaatgca aattagtacg gcaattgcag atataaacta taccattgat gaagaaaatg   2040
attgttgtgt atttatttat ggtattgata aattaaacgg ttttatctga acaactgaga   2100
gggtcctggg gcttaaggca aacaggcctg tttttgtaag agaaaaagct gaccccgagc   2160
ttgtatgttc                                                          2170
```

<210> SEQ ID NO 10
<211> LENGTH: 367
<212> TYPE: PRT
<213> ORGANISM: Populus trichocarpa

<400> SEQUENCE: 10

-continued

```
Met Val Lys Lys Lys Glu Ala Gly Asp Ala Glu Ala Asp Glu Arg Arg
1               5                   10                  15

Arg Leu Arg Ser Leu Ala Phe Ser Asn Gly Leu Leu Gln Arg Gly Glu
            20                  25                  30

Pro Ala Ala Pro Arg Ser Ala Leu Ala Pro Ser Thr Ala Val Ser Arg
        35                  40                  45

Leu Gln Gly Arg Asp Ile Val Arg Arg Gly Gly Gln Arg Lys Ser Arg
    50                  55                  60

Phe Leu Phe Ser Phe Pro Gly Leu Leu Ala Pro Ala Ala Ala Ala Ser
65                  70                  75                  80

Gly Gly Arg Val Gly Glu Leu Ala Asp Leu Gly Thr Lys Asn Pro Leu
                85                  90                  95

Leu Tyr Leu Asp Phe Pro Gln Gly Arg Met Lys Leu Leu Gly Thr His
            100                 105                 110

Val Tyr Pro Lys Asn Lys Tyr Leu Thr Leu Gln Met Ser Arg Ser Thr
        115                 120                 125

Lys Gly Val Val Cys Glu Asp Val Phe Glu Ser Leu Ile Val Phe Ser
    130                 135                 140

Glu Ala Trp Trp Ile Gly Thr Lys Glu Glu Asn Pro Gln Glu Leu Lys
145                 150                 155                 160

Leu Asp Phe Pro Lys Glu Phe Gln Asn Asp Gly Ala Val Ala Asp Ser
                165                 170                 175

Asp Phe Lys Gly Gly Ala Gly Ala Ser Cys Asp Glu Ala Val Thr Ile
            180                 185                 190

Asn Lys Pro Pro Lys Glu Thr Thr Thr Gly Ser Leu Ser Pro Lys Ile
        195                 200                 205

Glu Ser Asp Ile Asp Ser Ser Glu Asp Ser Asp Leu Lys Asp Glu Asp
    210                 215                 220

Asn Thr Gln Ser Thr Ser Gln Ala Pro Ser Val Arg Gln Ser Ala Arg
225                 230                 235                 240

Thr Ala Gly Lys Ala Leu Lys Tyr Thr Glu Ile Ser Ser Gly Asp Asp
                245                 250                 255

Ser Ser Asp Asn Asp Asp Glu Ile Asp Val Pro Glu Asp Met Asp Glu
            260                 265                 270

Lys Val Lys Ser Pro Ala Val Lys Asn Glu Ser Gln Ser Glu Asp Ile
        275                 280                 285

Lys Pro Ala Asp Ser Ser Ala Gln Pro Ile Ser Ala Lys Lys Glu Pro
    290                 295                 300

Leu Val Gln Ala Thr Leu Ser Ser Met Phe Lys Lys Ala Glu Glu Lys
305                 310                 315                 320

Lys Arg Cys Thr Arg Ser Pro Lys Gly Ser Pro Ala Thr Lys Gly Pro
                325                 330                 335

Ala Ala Lys Lys Gln Arg Ala Ser Pro Glu Glu Lys His Pro Thr Gly
            340                 345                 350

Lys Lys Ser Gly Lys Cys Ser Ser Lys Ser Val Val Arg Ser Ile
        355                 360                 365
```

<210> SEQ ID NO 11
<211> LENGTH: 1511
<212> TYPE: DNA
<213> ORGANISM: Oryza sativa

<400> SEQUENCE: 11

```
atggtgaaga agaagccggc cggcgatgcg gaggccgacg agcggcgccg cctccgctcc      60
```

```
ctcgccttct ctaatggctt actccagcgc ggggagccgg cggcgccgcg ctcggctctc    120

gcgccctcca ctgccgtgtc gcggctgcag ggccgcgaca tcgtgcgccg cggcgggcag    180

cgcaagagcc gcttcctctt ctccttcccc ggcctcctcg cgcccgcggc tgctgcctcg    240

ggcggccgcg tcggcgagct cgctgatctt ggcaccaaaa atcctctgct ctacctcgac    300

ttcccacagg tatcctatat ctatctatct attccgtcag gggaggatga agctgttggg    360

gacgcatgtg taccccaaga acaagtatct gacactgcag atgacgtctt cgagagcctg    420

attgtttttt ctgaagcctg gtggattgga acaaaagaag aagaaaaccc acaagaactg    480

aaactggatt ttccaaaaga gttccagaat gatgaggcgg ttgcagattc tgattttaaa    540

ggtggagcag gtgcttcctg tgatgaagct gtttccatca ataaaccgcc aaaggaaacc    600

accacaggat ccctttcccc taagattgaa tctgacattg attcttccga ggattcagac    660

cttaaggacg aggataacac acaaagcact agtcaagcac cttcagttag gcagtctgct    720

agaactgctg ggaaagcctt gaagtatact gagatatcat ctggagacga ttcatctgat    780

aatgacgatg agattgatgt ccctgaggac atggatgaga agatgaagag tccagcagtt    840

aagaatgaat cccaaagtga agacattaaa cctgcagatt ggtctgcgca gcctatctca    900

gctaagaagg agccactcgt tcaggccact ctgtctagca tgtttaaaaa agcagaagaa    960

aaaaaaggac ctgctgctaa gaagcagcga gcaagtccag aggaaaaaca tccaacaggg   1020

aagaagagtg ctggcagaag tcagaaaagg agaaaaacac aggtagaaga tgacaaaatt   1080

gaagtgctct caagttcctc ccaggataac aacgtggacg atgatagcga tgaggactgg   1140

gctgagtgat gtgcagctga agttgaaagg aatgatgcaa gattgtgggc aattcttttc   1200

tttgggggcg atatcacaat tgatgtgttt gaggagctta ggttctggcc tgaccattga   1260

tgagatatat catcatagtc ttttcatcgc actggtgaaa ttgaaaaccg agaagtcgtg   1320

tgatctgtta gcactagatt tattatttat ttgacttgtt gtaatgtaac ataaacaaga   1380

gctgataaat cattgttagg gtctgcaatg caaattagta ctgcaattac agatataaac   1440

tataccattg atgaagaaaa tgattgttgt gtatttattt atggtattga taaattaaac   1500

ggttttatct g                                                         1511
```

<210> SEQ ID NO 12
<211> LENGTH: 382
<212> TYPE: PRT
<213> ORGANISM: Oryza sativa

<400> SEQUENCE: 12

```
Met Val Lys Lys Lys Pro Ala Gly Asp Ala Glu Ala Asp Glu Arg Arg
1               5                   10                  15

Arg Leu Arg Ser Leu Ala Phe Ser Asn Gly Leu Leu Gln Arg Gly Glu
            20                  25                  30

Pro Ala Ala Pro Arg Ser Ala Leu Ala Pro Ser Thr Ala Val Ser Arg
        35                  40                  45

Leu Gln Gly Arg Asp Ile Val Arg Arg Gly Gly Gln Arg Lys Ser Arg
    50                  55                  60

Phe Leu Phe Ser Phe Pro Gly Leu Leu Ala Pro Ala Ala Ala Ala Ser
65                  70                  75                  80

Gly Gly Arg Val Gly Glu Leu Ala Asp Leu Gly Thr Lys Asn Pro Leu
                85                  90                  95

Leu Tyr Leu Asp Phe Pro Gln Val Ser Tyr Ile Tyr Leu Ser Ile Pro
            100                 105                 110
```

```
Ser Gly Glu Asp Glu Ala Val Gly Asp Ala Cys Val Pro Gln Glu Gln
        115                 120                 125

Val Ser Asp Thr Ala Asp Asp Val Phe Glu Ser Leu Ile Val Phe Ser
    130                 135                 140

Glu Ala Trp Trp Ile Gly Thr Lys Glu Glu Glu Asn Pro Gln Glu Leu
145                 150                 155                 160

Lys Leu Asp Phe Pro Lys Glu Phe Gln Asn Asp Glu Ala Val Ala Asp
                165                 170                 175

Ser Asp Phe Lys Gly Gly Ala Gly Ala Ser Cys Asp Glu Ala Val Ser
            180                 185                 190

Ile Asn Lys Pro Pro Lys Glu Thr Thr Thr Gly Ser Leu Ser Pro Lys
        195                 200                 205

Ile Glu Ser Asp Ile Asp Ser Ser Glu Asp Ser Asp Leu Lys Asp Glu
    210                 215                 220

Asp Asn Thr Gln Ser Thr Ser Gln Ala Pro Ser Val Arg Gln Ser Ala
225                 230                 235                 240

Arg Thr Ala Gly Lys Ala Leu Lys Tyr Thr Glu Ile Ser Ser Gly Asp
                245                 250                 255

Asp Ser Ser Asp Asn Asp Asp Glu Ile Asp Val Pro Glu Asp Met Asp
            260                 265                 270

Glu Lys Met Lys Ser Pro Ala Val Lys Asn Glu Ser Gln Ser Glu Asp
        275                 280                 285

Ile Lys Pro Ala Asp Trp Ser Ala Gln Pro Ile Ser Ala Lys Lys Glu
    290                 295                 300

Pro Leu Val Gln Ala Thr Leu Ser Ser Met Phe Lys Lys Ala Glu Glu
305                 310                 315                 320

Lys Lys Gly Pro Ala Ala Lys Lys Gln Arg Ala Ser Pro Glu Glu Lys
                325                 330                 335

His Pro Thr Gly Lys Lys Ser Ala Gly Arg Ser Gln Lys Arg Arg Lys
            340                 345                 350

Thr Gln Val Glu Asp Asp Lys Ile Glu Val Leu Ser Ser Ser Ser Gln
        355                 360                 365

Asp Asn Asn Val Asp Asp Asp Ser Asp Glu Asp Trp Ala Glu
    370                 375                 380
```

<210> SEQ ID NO 13
<211> LENGTH: 1965
<212> TYPE: DNA
<213> ORGANISM: Oryza sativa

<400> SEQUENCE: 13

```
ctcgcatggc cgttttttca gcgtcgaagg cggtctcgga tgaatccgct ttccgtgtgg      60

ccggtagagt cttcgtcttc gtctcgtctc gtctcgtccc aaacacgcga acgcgacacg     120

ccgacacccg tatcgtacca cctaactttt gctccgagat ctcctcctcc cgtctcatca     180

gtcttttcca atcaatcacc agctcaaact tgtacccaaa accctacacc ggagggagag     240

ggatggtcaa gaaagccgtc tccaccgcgc cagcagacgc cgaggccgac gagcgccgcc     300

gcctccgctc gctcgccttc tccaacggcc tgctccagcg aggcgacccc gcggcgccgc     360

gggcgccgct cgcgccggcg gctgccgtca cgcgcctaca gggccgcgac gtcgtccgcc     420

gtggcggcca gcgaaagagc cgctacctct tctccttccc tggcctcctc gcgccagcag     480

cctcgggtgg ccgggtcgga gagctcgccg acctcgggac caagaacccc ctgctgtacc     540

tcgagttccc acagggaagg atgaagctct tcgggacgca cgtttacccc aagaacaagt     600
```

```
acctcacgct gcagatgacc aggtcggcca agggcgtcgt ctgtgaggac gtctttgaga    660

gcctgattgt gttttctgaa gcctggtggg tgggaacaaa agaagataat ccggaagagc    720

tcaaacttga gtttccaaaa gaattccaaa atgatggcac gacagcagac tgtgatttca    780

gaggtggtgc aggtggtgcc atcgatgaag caactggaag caaagctgga aaggaaattg    840

cagaacctcg ttccccaaag tttgcatctg atgacgatgc tcctgaggat tcaaatcata    900

aggatgagaa taacacacag actatgagtg gaacaccagt tagacagtct gctaggaatg    960

cagggaaaac cttgaaaagg tacacagact tatcttctgg aggtgaatcg tctgacaata   1020

ataatgaaac tgatatatct gaggacttgg atgataagga ggtggagagt ccagaaatta   1080

aggacgagat tgaaagcgaa gatgtcaaac ccgcagattc ttcagcaatt tccctctcta   1140

gcaagaagga gcctcttgtt caggctactt tgtctagcat gtttataagg gcagaagaaa   1200

aaaagagatc tacaaggagt cctaaagggt cccctgcaac caaaggtgct gctgctaaga   1260

agcagcgagc aagtccaatg gcaaaacagc cagcagggat caagaaggtt agcggaactc   1320

ggggaaagaa aaaaccaaag gtgggagaag atgaaatcga agagctctca agttcctccc   1380

aggataacga cgcagatgat gatagtgacg aggactgggc cgaataatgc gatggtacag   1440

acgacggata ggttgggccg ttggggaagc atatgcataa ttgatgtgcg gctgaagaga   1500

aggatggatt gggggatggc acagaaactg cctgttttca tggactggtt tggctggtca   1560

tgtctgacga cggatctaga atatggaata tcctgatctg ttgtcaagct gagtccatga   1620

aacgttggtt gatgaaacat tagttagtca gaagcgggtt tgtttgtagt taggaactag   1680

gaacacacac acccgaggtt gtgatggggt tgcatacttg gactagccat tcccattcat   1740

ctgtctgtac tctgttcgac tgttcctttg tgtggctcac acctgttgtg tttctgatgg   1800

tggtcatttc tccagccagg ggcaaagaac acactgcgtt tcgctgatcc tttaattcag   1860

acccatagtc cttttttttt tttcagcaca ttctgatgtg gctctttgta ttgcagactg   1920

tatcatggta tcagattggt ttcgacttga aacccctctc tcttc                   1965
```

<210> SEQ ID NO 14
<211> LENGTH: 473
<212> TYPE: PRT
<213> ORGANISM: Oryza sativa

<400> SEQUENCE: 14

```
Met Ala Val Phe Ser Ala Ser Lys Ala Val Ser Asp Glu Ser Ala Phe
1               5                   10                  15

Arg Val Ala Gly Arg Val Phe Val Phe Val Ser Ser Arg Leu Val Pro
            20                  25                  30

Asn Thr Arg Thr Arg His Ala Asp Thr Arg Ile Val Pro Pro Asn Phe
        35                  40                  45

Cys Ser Glu Ile Ser Ser Ser Arg Leu Ile Ser Leu Phe Gln Ser Ile
    50                  55                  60

Thr Ser Ser Asn Leu Tyr Pro Lys Pro Tyr Thr Gly Gly Arg Gly Met
65                  70                  75                  80

Val Lys Lys Ala Val Ser Thr Ala Pro Ala Asp Ala Glu Ala Asp Glu
                85                  90                  95

Arg Arg Arg Leu Arg Ser Leu Ala Phe Ser Asn Gly Leu Leu Gln Arg
            100                 105                 110

Gly Asp Pro Ala Ala Pro Arg Ala Pro Leu Ala Pro Ala Ala Ala Val
        115                 120                 125
```

-continued

```
Thr Arg Leu Gln Gly Arg Asp Val Val Arg Arg Gly Gly Gln Arg Lys
    130                 135                 140

Ser Arg Tyr Leu Phe Ser Phe Pro Gly Leu Leu Ala Pro Ala Ala Ser
145                 150                 155                 160

Gly Gly Arg Val Gly Glu Leu Ala Asp Leu Gly Thr Lys Asn Pro Leu
                165                 170                 175

Leu Tyr Leu Glu Phe Pro Gln Gly Arg Met Lys Leu Phe Gly Thr His
            180                 185                 190

Val Tyr Pro Lys Asn Lys Tyr Leu Thr Leu Gln Met Thr Arg Ser Ala
        195                 200                 205

Lys Gly Val Val Cys Glu Asp Val Phe Glu Ser Leu Ile Val Phe Ser
    210                 215                 220

Glu Ala Trp Trp Val Gly Thr Lys Glu Asp Asn Pro Glu Glu Leu Lys
225                 230                 235                 240

Leu Glu Phe Pro Lys Glu Phe Gln Asn Asp Gly Thr Thr Ala Asp Cys
                245                 250                 255

Asp Phe Arg Gly Gly Ala Gly Gly Ala Ile Asp Glu Ala Thr Gly Ser
            260                 265                 270

Lys Ala Gly Lys Glu Ile Ala Glu Pro Arg Ser Pro Lys Phe Ala Ser
        275                 280                 285

Asp Asp Asp Ala Pro Glu Asp Ser Asn His Lys Asp Glu Asn Asn Thr
    290                 295                 300

Gln Thr Met Ser Gly Thr Pro Val Arg Gln Ser Ala Arg Asn Ala Gly
305                 310                 315                 320

Lys Thr Leu Lys Arg Tyr Thr Asp Leu Ser Ser Gly Gly Glu Ser Ser
                325                 330                 335

Asp Asn Asn Asn Glu Thr Asp Ile Ser Glu Asp Leu Asp Asp Lys Glu
            340                 345                 350

Val Glu Ser Pro Glu Ile Lys Asp Glu Ile Glu Ser Glu Asp Val Lys
        355                 360                 365

Pro Ala Asp Ser Ser Ala Ile Ser Leu Ser Ser Lys Lys Glu Pro Leu
    370                 375                 380

Val Gln Ala Thr Leu Ser Ser Met Phe Ile Arg Ala Glu Glu Lys Lys
385                 390                 395                 400

Arg Ser Thr Arg Ser Pro Lys Gly Ser Pro Ala Thr Lys Gly Ala Ala
                405                 410                 415

Ala Lys Lys Gln Arg Ala Ser Pro Met Ala Lys Gln Pro Ala Gly Ile
            420                 425                 430

Lys Lys Val Ser Gly Thr Arg Gly Lys Lys Lys Pro Lys Val Gly Glu
        435                 440                 445

Asp Glu Ile Glu Glu Leu Ser Ser Ser Ser Gln Asp Asn Asp Ala Asp
    450                 455                 460

Asp Asp Ser Asp Glu Asp Trp Ala Glu
465                 470
```

<210> SEQ ID NO 15
<211> LENGTH: 1363
<212> TYPE: DNA
<213> ORGANISM: Aquilegia formosa

<400> SEQUENCE: 15

```
tcgctgttgc ctgaacaact gaactgaaca cgatggttcg agctacgtcg aagaagatag     60

agaacgacga cgatcgaagt agactaaaaa agcttgctct atcacgaaat ctcctttcgc    120

aaactccttc gaaaccttct tctacactat cactatcgaa aacagttctc aaacaccatg    180
```

```
gtaaagatat aatgaagaaa tcacagagaa agaacagatt tctttttca tttcctggtc     240
ttcttggtcc tattactggt ggtaaggttg gtgaactgaa ggatttagga acaatgaagc     300
caattcttta tctcgatttc cctcagggaa gggtgaaaat gtttggtaca atagtttatc     360
ccaagaacag gtacttgacg ctgcatttct ctaaaggagg gaagaatgtg atgtgtgaag     420
atcattttga taacatggtt gttttctcag acgcatggtg gattgggaca aaagatgaga     480
atccagaaga ggttcaactc gaatttccta agaacctgat taagggtaag catacagacg     540
ctgattttaa aggtggagcc ggtgctggtg ccacatctga acaaaaacca ggtcctaaca     600
agcctagaaa agaatatgtt gaaacagaga ctcctagtac tgatgtagaa gatgtttctg     660
aggattttga ttccttaaat gaaaagaata aggatttgat ggaagtactg ccagttcgat     720
cttctaccag aacagctggg agaaaattca agtttacaga accttcatca gtagataatt     780
ctactgaaag tgactctgac tcatctaaag tgaggaaagg agttaaacag acacttgacg     840
atgagactga agatgccagc ttggtgggcc atgctattga taatccgaat gttgcaacaa     900
aacaaattta ccccaacaaa agcagcagtc ttctattcca gtgaattcta aagaaatttc     960
ttccagtaaa cgtggtcccc ttgttcaagc aaccatatcg aacttatttt cgaaagcaaa    1020
agcaaaggat gcgggcggaa gcgatgaagt gacacggatc gaaggaagaa agcctgtgat    1080
aggaagcaga acgaagaaaa agcagtctca ggtcgaagat gatgacatag aagagttctc    1140
aaccgaatcg gagttgtttg tgcaggatat tgaggaaagt gatgaagatt gggttgcctg    1200
acacagtatg gtccaatttt gtgttgctgg atatggacag gcaaggactg tgcacgtagt    1260
tagaaagaag acattgctgt gctctttcag aatatgtaat actgtttagc tctgtagaat    1320
taaaaacatg aaatataaga taatttgact ctggttaact ctg                      1363
```

<210> SEQ ID NO 16
<211> LENGTH: 303
<212> TYPE: PRT
<213> ORGANISM: Aquilegia formosa

<400> SEQUENCE: 16

```
Met Val Arg Ala Thr Ser Lys Lys Ile Glu Asn Asp Asp Asp Arg Ser
1               5                   10                  15

Arg Leu Lys Lys Leu Ala Leu Ser Arg Asn Leu Leu Ser Gln Thr Pro
            20                  25                  30

Ser Lys Pro Ser Ser Thr Leu Ser Leu Ser Lys Thr Val Leu Lys His
        35                  40                  45

His Gly Lys Asp Ile Met Lys Lys Ser Gln Arg Lys Asn Arg Phe Leu
    50                  55                  60

Phe Ser Phe Pro Gly Leu Leu Gly Pro Ile Thr Gly Gly Lys Val Gly
65                  70                  75                  80

Glu Leu Lys Asp Leu Gly Thr Met Lys Pro Ile Leu Tyr Leu Asp Phe
                85                  90                  95

Pro Gln Gly Arg Val Lys Met Phe Gly Thr Ile Val Tyr Pro Lys Asn
            100                 105                 110

Arg Tyr Leu Thr Leu His Phe Ser Lys Gly Gly Lys Asn Val Met Cys
        115                 120                 125

Glu Asp His Phe Asp Asn Met Val Val Phe Ser Asp Ala Trp Trp Ile
    130                 135                 140

Gly Thr Lys Asp Glu Asn Pro Glu Glu Val Gln Leu Glu Phe Pro Lys
145                 150                 155                 160
```

-continued

```
Asn Leu Ile Lys Gly Lys His Thr Asp Ala Asp Phe Lys Gly Gly Ala
                165                 170                 175

Gly Ala Gly Ala Thr Ser Glu Gln Lys Pro Gly Pro Asn Lys Pro Arg
            180                 185                 190

Lys Glu Tyr Val Glu Thr Glu Thr Pro Ser Thr Asp Val Glu Asp Val
        195                 200                 205

Ser Glu Asp Phe Asp Ser Leu Asn Glu Lys Asn Lys Asp Leu Met Glu
    210                 215                 220

Val Leu Pro Val Arg Ser Ser Thr Arg Thr Ala Gly Arg Lys Phe Lys
225                 230                 235                 240

Phe Thr Glu Pro Ser Ser Val Asp Asn Ser Thr Glu Ser Asp Ser Asp
                245                 250                 255

Ser Ser Lys Val Arg Lys Gly Val Lys Gln Thr Leu Asp Asp Glu Thr
            260                 265                 270

Glu Asp Ala Ser Leu Val Gly His Ala Ile Asp Asn Pro Asn Val Ala
        275                 280                 285

Thr Lys Gln Ile Tyr Pro Asn Lys Ser Ser Ser Leu Leu Phe Gln
    290                 295                 300
```

<210> SEQ ID NO 17
<211> LENGTH: 1294
<212> TYPE: DNA
<213> ORGANISM: Malus domestica
<220> FEATURE:
<221> NAME/KEY: misc_feature
<222> LOCATION: (1287)..(1287)
<223> OTHER INFORMATION: n is a, c, g, or t

<400> SEQUENCE: 17

```
gcccattccc atttttattt gtacgaaggt attcgaaagc agatcccggg aagtgctaaa     60

agcggggatc tgctggaggg tgggtgaggg gaagaacatc cgagtaagat atgatccatg    120

gttgcctatt ccaagaactt ttatgcctct aggacaatac ttgggtcggg tctgttgggt    180

gcaatagaca ttttagagag agaggtttaa aaccctacag agacaggagg tagggttggt    240

ggtctccggt ccggttgaat caaaatggcg cggacctcgt catcgaagaa gcggaaacac    300

gaagatgatg aaggggcaga ggcagaggca gaacctgagg tcgcgcagcg gaagaggctc    360

aaagccctcg ccttctccaa caaccagctc tcagagatcc ctgcaaagcc ccgcgcgcct    420

ctcacacctt caaacggtgt ccttaagcag catggcaagg acattgtgaa gaaatctcag    480

cggaagaaca agttcctctt ctccttccct ggcctccttg cccccattgg aggtggtaag    540

atcggcgacc tcaaggattt ggacaccaag aaccccgtcc tctacctcca attccctctg    600

ggtcagatga agttgtttgg gactcttgtg ttccccaaga acaggtatct gacaatgcag    660

ttccccaagg gtggaaagag tgtcatgtgc gaggactact tcgataatat gattgtattt    720

tccgatgctt ggtggattgg gacaaaagat gagaatcccg agtaagccca acttgatttt    780

cctaaggaat tgactgaggg acaacactct gagttcgact ttcaaggtgg cgcaggttca    840

acatctgcca aaaagcaaag tgatagtaaa aatgaaacta catatgttga agagtattcg    900

ccccataaca aggttgaaga taatttatca gatgaagaaa acaatgaatt aatgaaggca    960

acaccagttc gacattcagc aagaactgca ggaaaaaaat tcaagtttgg agaagcttct   1020

tctggagatg attctgctga aagtgatacc ccctcagctg aagggagaag ataaaaaagt   1080

tggaagactt gattcttcat ctgggaagca cagtagtgga aagactgaca atctcagctt   1140

tggagatgca gacattgata atgaggatcg tatgaaagga gctcaaactc ccaagcaaaa   1200
```

-continued

```
tgaagattcc tctctgtccg aagctaaatc aaagaaagag tcacattctg cctttgctgg   1260

gactacatct aaagaggact ctcatancaa tcat                               1294


<210> SEQ ID NO 18
<211> LENGTH: 268
<212> TYPE: PRT
<213> ORGANISM: Malus domestica

<400> SEQUENCE: 18

Met Ala Arg Thr Ser Ser Ser Lys Lys Arg Lys His Glu Asp Asp Glu
1               5                   10                  15

Gly Ala Glu Ala Glu Ala Glu Pro Glu Val Ala Gln Arg Lys Arg Leu
            20                  25                  30

Lys Ala Leu Ala Phe Ser Asn Asn Gln Leu Ser Glu Ile Pro Ala Lys
        35                  40                  45

Pro Arg Ala Pro Leu Thr Pro Ser Asn Gly Val Leu Lys Gln His Gly
    50                  55                  60

Lys Asp Ile Val Lys Lys Ser Gln Arg Lys Asn Lys Phe Leu Phe Ser
65                  70                  75                  80

Phe Pro Gly Leu Leu Ala Pro Ile Gly Gly Gly Lys Ile Gly Asp Leu
                85                  90                  95

Lys Asp Leu Asp Thr Lys Asn Pro Val Leu Tyr Leu Gln Phe Pro Leu
            100                 105                 110

Gly Gln Met Lys Leu Phe Gly Thr Leu Val Phe Pro Lys Asn Arg Tyr
        115                 120                 125

Leu Thr Met Gln Phe Pro Lys Gly Gly Lys Ser Val Met Cys Glu Asp
    130                 135                 140

Tyr Phe Asp Asn Met Ile Val Phe Ser Asp Ala Trp Trp Ile Gly Thr
145                 150                 155                 160

Lys Asp Glu Asn Pro Glu Ala Gln Leu Asp Phe Pro Lys Glu Leu Thr
                165                 170                 175

Glu Gly Gln His Ser Glu Phe Asp Phe Gln Gly Gly Ala Gly Ser Thr
            180                 185                 190

Ser Ala Lys Lys Gln Ser Asp Ser Lys Asn Glu Thr Thr Tyr Val Glu
        195                 200                 205

Glu Tyr Ser Pro His Asn Lys Val Glu Asp Asn Leu Ser Asp Glu Glu
    210                 215                 220

Asn Asn Glu Leu Met Lys Ala Thr Pro Val Arg His Ser Ala Arg Thr
225                 230                 235                 240

Ala Gly Lys Lys Phe Lys Phe Gly Glu Ala Ser Ser Gly Asp Asp Ser
                245                 250                 255

Ala Glu Ser Asp Thr Pro Ser Ala Glu Gly Arg Arg
            260                 265


<210> SEQ ID NO 19
<211> LENGTH: 1773
<212> TYPE: DNA
<213> ORGANISM: Physcomitrella patens

<400> SEQUENCE: 19

atggggaaaa agaaagttga ggaggtgagc cagacaaagg aggagaagac attagcgaag     60

gaaagcaaga ggctgcggga gctggctttg acgtccgggt tgctgtcgga gaaaaaagct    120

gtgccggatg cgccaatgca cccgcactct ggtatagtaa gatgtgacgg gaaggacatt    180

tgtaaaaagg ggcataggaa gaacaagtac cttttctctt ttcctggtct cgtagctcct    240
```

```
gtagctgttg gaaaattcgg tgatctgacg caattagaca caaaaaatcc aatattgtac    300

gttgatttcc tacaggcaag tagagctttt gcgcagactg gacgactcaa attattcggc    360

accattgtgt attccaaaaa caagtatatt actttgaact ttgtccgtgg ggcaggaagc    420

atacaatgcg aagatatttt tgagaatctg gtggtatttt cggacgcgtg gtggatcggg    480

acgaaggaag agaatcctga tgaactgcgc cttgaaatgc ctttggattt tcagcaggaa    540

aggcatgctg tgtacgactt cgcaggtgga gctggcaagc ctagaaatat taaagatgat    600

gttgacgtcc aagactcgca attagaacta gtccaggtat cggaattgga atccagtaaa    660

cagtgcacac cgaagggcca actcaaaatg gaccggtggc ttttccaaaa gaaaccttcg    720

gaaaacaaga ccttagagaa atcttttgag agtaatgcga aaacgaagcc aaaaaatgct    780

agtgaatggg agtcagatga agacgaggaa ggttttgtca acctagggga cgcgccaact    840

ccatcccgac aatctgctcg tatagctgag aagaaacact cgtatgcaga gtcttcctcg    900

gaggagaacc agacagacgg cagtgatgaa cacgaccgtg cagatgctga acttagggat    960

cctcgagaca aaactgttaa taaacttttc aatgatgtag aagatggctt cttggctcct   1020

gaatcacaaa tatcacagat ggacttggca gatatggtga cggatagatg tgtatggaat   1080

gtagtttatg atagcatacc cttaagcttt tttccaggtt gctgccgtat tcgaagccct   1140

tgtgtgtttc atgagcgttg tgtgcaattt actaatagct taaagttcac ggctaatttg   1200

gtttacatga agacttacat cgtctgtcat gcagtctcgc cacaaacttc agtaccaaaa   1260

accagtgcaa gtggcatgat actttcaacc tctgtcctag cagatttaac tgccaacaca   1320

ataggagctg ggtcgaagca atcaagtctc tctgcattct ttatgaagtc aagcgaaaag   1380

tcaactttag acaacgatga tgctggtaaa gaagatgaaa acgtaactcc aaaagacgaa   1440

atggaatcgg tattaccctg tacacctcct gatatcaatg attctaaacg caaaagaaaa   1500

tctactccag atggaaagag aaattcgaga gatgatatga atatttcaag agtggataac   1560

ttaccaccgg cattttctga taactgccgt gtaggaactg gaggaaatgg ctaccatatc   1620

gaaggagcag ccgttaatac tggtacaatg ctgaccaaac agagtaatgt tcacaatgtt   1680

gctactttat tttatggacc acagaataag tcttatacat catgtgagaa ctacgccctg   1740

tttttcatgt tttgccatgc ttttggaaaa tga                                1773
```

```
<210> SEQ ID NO 20
<211> LENGTH: 590
<212> TYPE: PRT
<213> ORGANISM: Physcomitrella patens

<400> SEQUENCE: 20

Met Gly Lys Lys Lys Val Glu Glu Val Ser Gln Thr Lys Glu Glu Lys
1               5                   10                  15

Thr Leu Ala Lys Glu Ser Lys Arg Leu Arg Glu Leu Ala Leu Thr Ser
            20                  25                  30

Gly Leu Leu Ser Glu Lys Lys Ala Val Pro Asp Ala Pro Met His Pro
        35                  40                  45

His Ser Gly Ile Val Arg Cys Asp Gly Lys Asp Ile Cys Lys Lys Gly
    50                  55                  60

His Arg Lys Asn Lys Tyr Leu Phe Ser Phe Pro Gly Leu Val Ala Pro
65                  70                  75                  80

Val Ala Val Gly Lys Phe Gly Asp Leu Thr Gln Leu Asp Thr Lys Asn
                85                  90                  95

Pro Ile Leu Tyr Val Asp Phe Leu Gln Ala Ser Arg Ala Phe Ala Gln
```

-continued

```
            100                 105                 110

Thr Gly Arg Leu Lys Leu Phe Gly Thr Ile Val Tyr Ser Lys Asn Lys
        115                 120                 125

Tyr Ile Thr Leu Asn Phe Val Arg Gly Ala Gly Ser Ile Gln Cys Glu
    130                 135                 140

Asp Ile Phe Glu Asn Leu Val Val Phe Ser Asp Ala Trp Trp Ile Gly
145                 150                 155                 160

Thr Lys Glu Glu Asn Pro Asp Glu Leu Arg Leu Glu Met Pro Leu Asp
                165                 170                 175

Phe Gln Gln Glu Arg His Ala Val Tyr Asp Phe Ala Gly Gly Ala Gly
            180                 185                 190

Lys Pro Arg Asn Ile Lys Asp Asp Val Asp Val Gln Asp Ser Gln Leu
        195                 200                 205

Glu Leu Val Gln Val Ser Glu Leu Glu Ser Ser Lys Gln Cys Thr Pro
    210                 215                 220

Lys Gly Gln Leu Lys Met Asp Arg Trp Leu Phe Gln Lys Lys Pro Ser
225                 230                 235                 240

Glu Asn Lys Thr Leu Glu Lys Ser Phe Glu Ser Asn Ala Lys Thr Lys
                245                 250                 255

Pro Lys Asn Ala Ser Glu Trp Glu Ser Asp Glu Asp Glu Glu Gly Phe
            260                 265                 270

Val Asn Leu Gly Asp Ala Pro Thr Pro Ser Arg Gln Ser Ala Arg Ile
        275                 280                 285

Ala Glu Lys Lys His Ser Tyr Ala Glu Ser Ser Ser Glu Glu Asn Gln
    290                 295                 300

Thr Asp Gly Ser Asp Glu His Asp Arg Ala Asp Ala Glu Leu Arg Asp
305                 310                 315                 320

Pro Arg Asp Lys Thr Val Asn Lys Leu Phe Asn Asp Val Glu Asp Gly
                325                 330                 335

Phe Leu Ala Pro Glu Ser Gln Ile Ser Gln Met Asp Leu Ala Asp Met
            340                 345                 350

Val Thr Asp Arg Cys Val Trp Asn Val Val Tyr Asp Ser Ile Pro Leu
        355                 360                 365

Ser Phe Phe Pro Gly Cys Cys Arg Ile Arg Ser Pro Cys Val Phe His
    370                 375                 380

Glu Arg Cys Val Gln Phe Thr Asn Ser Leu Lys Phe Thr Ala Asn Leu
385                 390                 395                 400

Val Tyr Met Lys Thr Tyr Ile Val Cys His Ala Val Ser Pro Gln Thr
                405                 410                 415

Ser Val Pro Lys Thr Ser Ala Ser Gly Met Ile Leu Ser Thr Ser Val
            420                 425                 430

Leu Ala Asp Leu Thr Ala Asn Thr Ile Gly Ala Gly Ser Lys Gln Ser
        435                 440                 445

Ser Leu Ser Ala Phe Phe Met Lys Ser Ser Glu Lys Ser Thr Leu Asp
    450                 455                 460

Asn Asp Asp Ala Gly Lys Glu Asp Glu Asn Val Thr Pro Lys Asp Glu
465                 470                 475                 480

Met Glu Ser Val Leu Pro Cys Thr Pro Pro Asp Ile Asn Asp Ser Lys
                485                 490                 495

Arg Lys Arg Lys Ser Thr Pro Asp Gly Lys Arg Asn Ser Arg Asp Asp
            500                 505                 510

Met Asn Ile Ser Arg Val Asp Asn Leu Pro Pro Ala Phe Ser Asp Asn
        515                 520                 525
```

-continued

```
Cys Arg Val Gly Thr Gly Gly Asn Gly Tyr His Ile Glu Gly Ala Ala
    530                 535                 540

Val Asn Thr Gly Thr Met Leu Thr Lys Gln Ser Asn Val His Asn Val
545                 550                 555                 560

Ala Thr Leu Phe Tyr Gly Pro Gln Asn Lys Ser Tyr Thr Ser Cys Glu
                565                 570                 575

Asn Tyr Ala Leu Phe Phe Met Phe Cys His Ala Phe Gly Lys
            580                 585                 590


<210> SEQ ID NO 21
<211> LENGTH: 2184
<212> TYPE: DNA
<213> ORGANISM: Physcomitrella patens

<400> SEQUENCE: 21

gagaatctca ttacgaagat tgattggatt tttctacgct actgcatttc ccgtcgattg     60

gtaacaaaac gccgtaacta ggagtgcact gggggtatct atctaggagg aagctcttcg    120

ttcatttaga aattcctcat gaaactggct gtctgagctt gggtgaggaa gccgtggtag    180

tcgggatacc gattcctaat ttgtttggcc gtttcatcgt tgaggcgcgg tggttaaatg    240

gtttagcaag catggggaag aagaagcagg tagaagaggt gagtcagacg aaggaggata    300

agtcgctgga gaagcagagt aagaagctgc gggagctagc tcgatcgtgc ggattggtgt    360

cggagaagaa agctttacca gcagaggcgt tgcgtcctaa atggggtatc gtaaaatgcg    420

atggtaaaga tatttgtaaa aaaggacata gaaagaacaa atatctgttt tctttcccgg    480

gtctcgtagc tcctgtttct ggtggtaagt tcggtgaact gacgcaactg gactcgagaa    540

atccaatcct ttatattgat tttccacagg gtcgacttaa attatttgga accatcgtat    600

atcccatcaa caagtacatt acaatgaatt ttgttcgcgg agcaggaagc attctatgcg    660

aagatctctt tgaaagtatg gtggtatttc cggaggcttg gtgggtcggc aaaaaaagaag    720

aaaacccgga tgagctgcgt cttgatatgc ctctggacct tcaacaggaa aaacatcagg    780

tgtacgattt cacaggcgga gctggtgagc caagagattc caggaaatat ggtgatgttc    840

aacccataca atcggaactg gttcaggaaa cacaactaga ttctagcaaa cttagcactc    900

cgaaggctca ggtttctcag agaaaacctt cagagaaaat tccgaagcac aaagttgtaa    960

gtgaatggga gtcagatgat gatgatgatg atcctggttt tgccattgtg ggagctgctc   1020

cgacaccatc acgtcaatcg gctcgcacag ctggaaagaa atactcgtat gcagaatcat   1080

cttcagaaga gaatctatca gacgacgctg atgaaagtga cgatttagat ggcaaacagg   1140

gggaatctag aagcaaggct gccaataagg ctattgaatt tgaggatgcc gacgatactc   1200

tcttggttcc cgaatcacaa gcatctaaga aggacgtgac tgatgcagtg gataaaaatc   1260

cttctacaaa catgactatc acaattgatg aacatgatga cgaagaggct agtgccatcg   1320

accatttagc catgtcacaa accagagctc caagcactgc aggtgacatg cttctttcaa   1380

cttccgttca agcagttgca aatgcaagta ctacaggagc tgggtccagg caatctactc   1440

tgtctacgtt cttcttgaag tcaagcgaga aggaaaaggt taaaaatgtg gagccgcaga   1500

attctgtggt agatataggt ttcacaagga cttatcaaag agaaaaactc acaaagctgc   1560

agtcaacttt tgacaaggga cgcgctgctg aagatgatga aaatgtggca tctaaaaccg   1620

aagtggaatc tgtattacca tttacacctc ctgaaagtaa cggttctaag cgcaaaagaa   1680

aagctccatc agaaagaaaa caaatttcaa aaggagttga aggaaagggt aagactcctg   1740
```

```
taaaaagaag aaagaaaata gctgaagaca aggagcctcg ggcaaaggat cagctgatac   1800

tggtttctga tgacagtgat tcgagttgag cacagagagt tggtcttaga atcctggact   1860

ccacgacttc gcccttgagc acagtttagc cctttcacga agtacgcaat gaaaaactta   1920

tatggtaaag cgttttaatg tacacaataa cgcctgttct gtgacagccg caagattcgg   1980

tttaacgttg atggccttga cagcatatag ttggactagc tgcgagccaa gatacattaa   2040

ctgcattatt gatgtaaagg tcagtgtaca tatgttccaa cacattacat tgattcagct   2100

ggtatccgag acattcagca gattgtttgc gacatgcatt caaactaatg tacatgacaa   2160

aacgccactg gcagtcttca tcca                                          2184


<210> SEQ ID NO 22
<211> LENGTH: 525
<212> TYPE: PRT
<213> ORGANISM: Physcomitrella patens

<400> SEQUENCE: 22

Met Gly Lys Lys Lys Gln Val Glu Glu Val Ser Gln Thr Lys Glu Asp
1               5                   10                  15

Lys Ser Leu Glu Lys Gln Ser Lys Lys Leu Arg Glu Leu Ala Arg Ser
            20                  25                  30

Cys Gly Leu Val Ser Glu Lys Lys Ala Leu Pro Ala Glu Ala Leu Arg
        35                  40                  45

Pro Lys Trp Gly Ile Val Lys Cys Asp Gly Lys Asp Ile Cys Lys Lys
    50                  55                  60

Gly His Arg Lys Asn Lys Tyr Leu Phe Ser Phe Pro Gly Leu Val Ala
65                  70                  75                  80

Pro Val Ser Gly Gly Lys Phe Gly Glu Leu Thr Gln Leu Asp Ser Arg
                85                  90                  95

Asn Pro Ile Leu Tyr Ile Asp Phe Pro Gln Gly Arg Leu Lys Leu Phe
            100                 105                 110

Gly Thr Ile Val Tyr Pro Ile Asn Lys Tyr Ile Thr Met Asn Phe Val
        115                 120                 125

Arg Gly Ala Gly Ser Ile Leu Cys Glu Asp Leu Phe Glu Ser Met Val
    130                 135                 140

Val Phe Pro Glu Ala Trp Trp Val Gly Lys Lys Glu Glu Asn Pro Asp
145                 150                 155                 160

Glu Leu Arg Leu Asp Met Pro Leu Asp Leu Gln Gln Glu Lys His Gln
                165                 170                 175

Val Tyr Asp Phe Thr Gly Gly Ala Gly Glu Pro Arg Asp Ser Arg Lys
            180                 185                 190

Tyr Gly Asp Val Gln Pro Ile Gln Ser Glu Leu Val Gln Glu Thr Gln
        195                 200                 205

Leu Asp Ser Ser Lys Leu Ser Thr Pro Lys Ala Gln Val Ser Gln Arg
    210                 215                 220

Lys Pro Ser Glu Lys Ile Pro Lys His Lys Val Val Ser Glu Trp Glu
225                 230                 235                 240

Ser Asp Asp Asp Asp Asp Asp Pro Gly Phe Ala Ile Val Gly Ala Ala
                245                 250                 255

Pro Thr Pro Ser Arg Gln Ser Ala Arg Thr Ala Gly Lys Lys Tyr Ser
            260                 265                 270

Tyr Ala Glu Ser Ser Ser Glu Glu Asn Leu Ser Asp Asp Ala Asp Glu
        275                 280                 285

Ser Asp Asp Leu Asp Gly Lys Gln Gly Glu Ser Arg Ser Lys Ala Ala
```

-continued

```
    290                 295                 300

Asn Lys Ala Ile Glu Phe Glu Asp Ala Asp Asp Thr Leu Leu Val Pro
305                 310                 315                 320

Glu Ser Gln Ala Ser Lys Lys Asp Val Thr Asp Ala Val Asp Lys Asn
                325                 330                 335

Pro Ser Thr Asn Met Thr Ile Thr Ile Asp Glu His Asp Asp Glu Glu
            340                 345                 350

Ala Ser Ala Ile Asp His Leu Ala Met Ser Gln Thr Arg Ala Pro Ser
        355                 360                 365

Thr Ala Gly Asp Met Leu Leu Ser Thr Ser Val Gln Ala Val Ala Asn
    370                 375                 380

Ala Ser Thr Thr Gly Ala Gly Ser Arg Gln Ser Thr Leu Ser Thr Phe
385                 390                 395                 400

Phe Leu Lys Ser Ser Glu Lys Glu Lys Val Lys Asn Val Glu Pro Gln
                405                 410                 415

Asn Ser Val Val Asp Ile Gly Phe Thr Arg Thr Tyr Gln Arg Glu Lys
            420                 425                 430

Leu Thr Lys Leu Gln Ser Thr Phe Asp Lys Gly Arg Ala Ala Glu Asp
        435                 440                 445

Asp Glu Asn Val Ala Ser Lys Thr Glu Val Glu Ser Val Leu Pro Phe
    450                 455                 460

Thr Pro Pro Glu Ser Asn Gly Ser Lys Arg Lys Arg Lys Ala Pro Ser
465                 470                 475                 480

Glu Arg Lys Gln Ile Ser Lys Gly Val Glu Gly Lys Gly Lys Thr Pro
                485                 490                 495

Val Lys Arg Arg Lys Lys Ile Ala Glu Asp Lys Glu Pro Arg Ala Lys
            500                 505                 510

Asp Gln Leu Ile Leu Val Ser Asp Asp Ser Asp Ser Ser
        515                 520                 525
```

<210> SEQ ID NO 23
<211> LENGTH: 1338
<212> TYPE: DNA
<213> ORGANISM: Solanum tuberosum

<400> SEQUENCE: 23

```
ggtttccagc aactgttccg gcggagttag ggctatggct cgaggaggga agaaggcagc     60

aaatggagaa tccaatccag atatggagga gaagaagagg ttaaagaaac ttgcaatttc    120

gaagcaaatg gtctcagaga atccttcaag ggataataat tctctgaatc catcaaaaac    180

tgtgattaaa catcatggta aagacatttt gcgcaaatct caacggaaga atcgtttcct    240

cttttctctt cccggtttac ttgccccggt ttccgggggt aaaattggtg agctcaaaga    300

ccttggtacc aaaaacccca ttctctacct cgacttccct cagggtcaaa tgaagttgtt    360

tgggacaatt gtatatccaa aaaatggtta tctgactatg cagttctcca gaggtgggaa    420

aaatgtagtg tgcgaagatt accttgacaa tatgattgtg ttttctgatg catggtggat    480

agggaggaaa gatgagaatc ctgaagaagc acgactcgag tttccaaaag agctgaatgt    540

gcagcaagag aaatcggagt gtgattttaa aggtggtgct ggtgctacat gtgttcaaaa    600

acgaagtact agtgaatgtg gggtcaagca tgtggaacaa cagtctcctg aacatgaaca    660

ggaggagtta ttatcagaaa gtcaaaatga ttcaaaagag tttatcgaat taactccatc    720

tcgtcgttca gcaagggcgg caggaaaaaa aatcaatttt gcagaagttt cttccgggga    780

tgaattggtt gacaatgaag tcgaatcttc cgagggggag gagaaaactg gcagtgacat    840
```

```
tctttgtgat gaaactgtag tacaaagtca agttactgga aaaattactg cccttgccga    900

aactgcttcc aagtctaaga aatccgctcg tacaaagcaa agttctctcg ttcaggctac    960

tatttcaaca atgtttaaga aagtggacaa gcttgtcact ccagatagag tttctcaaag   1020

gaaaacaaga aaatcaacaa acaaagggga atccaacaca gaatgtggtt caaccatgcc   1080

tgatcatgtt ggtacttctc agggtgaaga tgacattgaa gagttgtcta gttcatctaa   1140

ggatacagaa gctagtgatg aagattgggc tgcttgagtt ttggatttta tgttttaatc   1200

gatagaatat gaccaccatt tctcatggat ctgcaaatta ctcttggcgg acaatggttg   1260

taatccaatt gaagaagctg ctaatctgga tgcaaaggga gacaccacga agtgaacatc   1320

acatgggctt tgcatgtc                                                 1338
```

<210> SEQ ID NO 24
<211> LENGTH: 380
<212> TYPE: PRT
<213> ORGANISM: Solanum tuberosum

<400> SEQUENCE: 24

```
Met Ala Arg Gly Gly Lys Lys Ala Ala Asn Gly Glu Ser Asn Pro Asp
1               5                   10                  15

Met Glu Glu Lys Lys Arg Leu Lys Lys Leu Ala Ile Ser Lys Gln Met
            20                  25                  30

Val Ser Glu Asn Pro Ser Arg Asp Asn Asn Ser Leu Asn Pro Ser Lys
        35                  40                  45

Thr Val Ile Lys His His Gly Lys Asp Ile Leu Arg Lys Ser Gln Arg
    50                  55                  60

Lys Asn Arg Phe Leu Phe Ser Leu Pro Gly Leu Leu Ala Pro Val Ser
65                  70                  75                  80

Gly Gly Lys Ile Gly Glu Leu Lys Asp Leu Gly Thr Lys Asn Pro Ile
                85                  90                  95

Leu Tyr Leu Asp Phe Pro Gln Gly Gln Met Lys Leu Phe Gly Thr Ile
            100                 105                 110

Val Tyr Pro Lys Asn Gly Tyr Leu Thr Met Gln Phe Ser Arg Gly Gly
        115                 120                 125

Lys Asn Val Val Cys Glu Asp Tyr Leu Asp Asn Met Ile Val Phe Ser
    130                 135                 140

Asp Ala Trp Trp Ile Gly Arg Lys Asp Glu Asn Pro Glu Glu Ala Arg
145                 150                 155                 160

Leu Glu Phe Pro Lys Glu Leu Asn Val Gln Gln Glu Lys Ser Glu Cys
                165                 170                 175

Asp Phe Lys Gly Gly Ala Gly Ala Thr Cys Val Gln Lys Arg Ser Thr
            180                 185                 190

Ser Glu Cys Gly Val Lys His Val Glu Gln Gln Ser Pro Glu His Glu
        195                 200                 205

Gln Glu Glu Leu Leu Ser Glu Ser Gln Asn Asp Ser Lys Glu Phe Ile
    210                 215                 220

Glu Leu Thr Pro Ser Arg Arg Ser Ala Arg Ala Ala Gly Lys Lys Ile
225                 230                 235                 240

Asn Phe Ala Glu Val Ser Ser Gly Asp Glu Leu Val Asp Asn Glu Val
                245                 250                 255

Glu Ser Ser Glu Gly Glu Glu Lys Thr Gly Ser Asp Ile Leu Cys Asp
            260                 265                 270

Glu Thr Val Val Gln Ser Gln Val Thr Gly Lys Ile Thr Ala Leu Ala
```

-continued

```
        275                 280                 285

Glu Thr Ala Ser Lys Ser Lys Lys Ser Ala Arg Thr Lys Gln Ser Ser
    290                 295                 300

Leu Val Gln Ala Thr Ile Ser Thr Met Phe Lys Lys Val Asp Lys Leu
305                 310                 315                 320

Val Thr Pro Asp Arg Val Ser Gln Arg Lys Thr Arg Lys Ser Thr Asn
                325                 330                 335

Lys Gly Glu Ser Asn Thr Glu Cys Gly Ser Thr Met Pro Asp His Val
            340                 345                 350

Gly Thr Ser Gln Gly Glu Asp Asp Ile Glu Glu Leu Ser Ser Ser Ser
        355                 360                 365

Lys Asp Thr Glu Ala Ser Asp Glu Asp Trp Ala Ala
    370                 375                 380


<210> SEQ ID NO 25
<211> LENGTH: 1083
<212> TYPE: DNA
<213> ORGANISM: Vitis shuttleworthii

<400> SEQUENCE: 25

ctacaaattt gggatgaatc aacttgttga agctgcagcc ttaatttcat ccacaaacca      60

tcatccttgc tctaattgac tgtttgaagc ttagaaagtt gtcacactgg ttttctggga     120

tatgattatc agtaactctt aataactatt ctccaagaga agtagggcag gcagaatggt     180

acgagtttca aagaagaatg aaaatggtgg agtatctgaa ctgaatccag aagctgaaga     240

gcgtaaaaga cgaaaaaaat tggcgttctc caagaactta ctgtcagata ctccttcaaa     300

agcgttttca gctctgagcc cttcaaaaac agtgatcaaa caccatggaa aagatattct     360

gaagaaatct cagaggaaga atcggttcct cttctcattc ccaggtcttc ttgctcctat     420

cgctggcggc aagatcggtg aactcaagga tttgggaacc aagaatccta tactctacct     480

tgatttccct cagggtcaaa tgaagttgtt tgggactata gtttacccga agaacaggta     540

tttgactctg catttctcta gaggcggaaa aaatgtaatg tgtgaggatt actttgataa     600

tatgattgta ttttctgatg catggtggat tgggagaaag gaggagaatc cagaagaagc     660

ccgactcgag tttcctaaag aactgagtga aggacaaagt gttgaatacg attttaaagg     720

gggtgcaggc atggcatctg acagtaagca aggtgttaat aaacctgaaa tgaaatatgt     780

agaaccgcag tcacctaaac ctgagctaga agatgatttg tctggtgaag acagtttgaa     840

agatgtggtt gaaatgacac cgaaagatgt tgaagtgaca ccagttcgac attcacagag     900

aactgcagga aaaacattca attttgcaga agcttcttct ggagatgatt ctgttgaaaa     960

tgatggcaac atatctgatg gacaagaaaa ttctggctct gcaacacctg aaagtggcaa    1020

tgaagatgct gaagcaagga ctcgagcaac cacacaaatt caagagtctg ctggggcagc    1080

tac                                                                  1083


<210> SEQ ID NO 26
<211> LENGTH: 303
<212> TYPE: PRT
<213> ORGANISM: Vitis shuttleworthii

<400> SEQUENCE: 26

Met Val Arg Val Ser Lys Lys Asn Glu Asn Gly Gly Val Ser Glu Leu
1               5                   10                  15

Asn Pro Glu Ala Glu Glu Arg Lys Arg Arg Lys Lys Leu Ala Phe Ser
            20                  25                  30
```

```
Lys Asn Leu Leu Ser Asp Thr Pro Ser Lys Ala Phe Ser Ala Leu Ser
        35                  40                  45

Pro Ser Lys Thr Val Ile Lys His His Gly Lys Asp Ile Leu Lys Lys
    50                  55                  60

Ser Gln Arg Lys Asn Arg Phe Leu Phe Ser Phe Pro Gly Leu Leu Ala
65                  70                  75                  80

Pro Ile Ala Gly Gly Lys Ile Gly Glu Leu Lys Asp Leu Gly Thr Lys
                85                  90                  95

Asn Pro Ile Leu Tyr Leu Asp Phe Pro Gln Gly Gln Met Lys Leu Phe
            100                 105                 110

Gly Thr Ile Val Tyr Pro Lys Asn Arg Tyr Leu Thr Leu His Phe Ser
        115                 120                 125

Arg Gly Gly Lys Asn Val Met Cys Glu Asp Tyr Phe Asp Asn Met Ile
    130                 135                 140

Val Phe Ser Asp Ala Trp Trp Ile Gly Arg Lys Glu Glu Asn Pro Glu
145                 150                 155                 160

Glu Ala Arg Leu Glu Phe Pro Lys Glu Leu Ser Glu Gly Gln Ser Val
                165                 170                 175

Glu Tyr Asp Phe Lys Gly Gly Ala Gly Met Ala Ser Asp Ser Lys Gln
            180                 185                 190

Gly Val Asn Lys Pro Glu Met Lys Tyr Val Glu Pro Gln Ser Pro Lys
        195                 200                 205

Pro Glu Leu Glu Asp Asp Leu Ser Gly Glu Asp Ser Leu Lys Asp Val
    210                 215                 220

Val Glu Met Thr Pro Lys Asp Val Glu Val Thr Pro Val Arg His Ser
225                 230                 235                 240

Gln Arg Thr Ala Gly Lys Thr Phe Asn Phe Ala Glu Ala Ser Ser Gly
                245                 250                 255

Asp Asp Ser Val Glu Asn Asp Gly Asn Ile Ser Asp Gly Gln Glu Asn
            260                 265                 270

Ser Gly Ser Ala Thr Pro Glu Ser Gly Asn Glu Asp Ala Glu Ala Arg
        275                 280                 285

Thr Arg Ala Thr Thr Gln Ile Gln Glu Ser Ala Gly Ala Ala Thr
    290                 295                 300


<210> SEQ ID NO 27
<211> LENGTH: 1350
<212> TYPE: DNA
<213> ORGANISM: Vitis vinifera

<400> SEQUENCE: 27

atggtacgag tttcaaagaa gaatgaaaat ggtggagtat ctgaactgaa tccagaagct      60

gaagagcgta aaagacgaaa aaaattggcg ttctccaaga acttactgtc agatactcct     120

tcaaaagcgt tttcagctct gagcccttca aaaacagtga tcaaacacca tggaaaagat     180

attctgaaga aatctcagag gaagaatcgg ttcctcttct cattcccagg tcttcttgct     240

cctattgctg gtggcaagat tggtgaactc aaggatttgg gaaccaagaa tcctatactc     300

taccttgatt tccctcaggg tcaaatgaag ttgtttggga ctatagttta cccgaagaac     360

aggtatttga ctctgcattt ctctagaggc ggaaaaaatg taatgtgtga ggattacttt     420

gataatatga ttgtattttc tgatgcatgg tggattggga gaaaggagga gaatccagaa     480

gaagcccgac tcgagtttcc taaagaactg agtgaaggac aaagtgttga atacgacttt     540

aaagggggtg caggcatggc atctgacagt aagcaaggtg ttaataaacc tgaaatgaaa     600
```

```
tatgtagaac cgcagtcacc taaacctgag ctagaagatg atttgtctgg tgaagacagt    660

ttgaaagatg tggttgaaat gacaccgaaa gatgttgaag tgacaccagt tcgacattca    720

cagagaactg caggaaaaac attcaatttt gcagaagctt cttctggaga tgattctgtt    780

gaaaatgatg gcaacatatc tgatggacaa gaaaattctg gctctgcaac acctgaaagt    840

ggcaatgaag atgctgaagc aaggactgga gcaaccacac aaattcaaga gtctgctggg    900

gcagctacca agtcaaggaa acgactatct caagctacta tatccacatt gtttaagaaa    960

gtggaggaac agaaaacatc cagaactcca aggaaatcct catcagccaa agcttctgct   1020

cagaagactg attccaggaa agctccggaa cacgggaaaa aaagaaaagt aattgaggaa   1080

acaaaatctg agatagacat ctcaacagaa agtgaacaat ctgatgagga aaagaaaaca   1140

tctagaaccc caaggaaatc gtcatcaacc aaagtttctg cccggaagac tgatgccagg   1200

aaagcccagg gacccaggaa aaggagaaaa gtaatcgagg aaacaaaatc tgagatagac   1260

atctcaacag aaggcgagca atctgataat ccgacctctg atgcttctgt tagagtgtac   1320

aagagaaaga tgaaaagccc tgcagcttaa                                    1350
```

<210> SEQ ID NO 28
<211> LENGTH: 449
<212> TYPE: PRT
<213> ORGANISM: Vitis vinifera

<400> SEQUENCE: 28

```
Met Val Arg Val Ser Lys Lys Asn Glu Asn Gly Gly Val Ser Glu Leu
1               5                   10                  15

Asn Pro Glu Ala Glu Glu Arg Lys Arg Arg Lys Lys Leu Ala Phe Ser
            20                  25                  30

Lys Asn Leu Leu Ser Asp Thr Pro Ser Lys Ala Phe Ser Ala Leu Ser
        35                  40                  45

Pro Ser Lys Thr Val Ile Lys His His Gly Lys Asp Ile Leu Lys Lys
    50                  55                  60

Ser Gln Arg Lys Asn Arg Phe Leu Phe Ser Phe Pro Gly Leu Leu Ala
65                  70                  75                  80

Pro Ile Ala Gly Gly Lys Ile Gly Glu Leu Lys Asp Leu Gly Thr Lys
                85                  90                  95

Asn Pro Ile Leu Tyr Leu Asp Phe Pro Gln Gly Gln Met Lys Leu Phe
            100                 105                 110

Gly Thr Ile Val Tyr Pro Lys Asn Arg Tyr Leu Thr Leu His Phe Ser
        115                 120                 125

Arg Gly Gly Lys Asn Val Met Cys Glu Asp Tyr Phe Asp Asn Met Ile
    130                 135                 140

Val Phe Ser Asp Ala Trp Trp Ile Gly Arg Lys Glu Glu Asn Pro Glu
145                 150                 155                 160

Glu Ala Arg Leu Glu Phe Pro Lys Glu Leu Ser Glu Gly Gln Ser Val
                165                 170                 175

Glu Tyr Asp Phe Lys Gly Gly Ala Gly Met Ala Ser Asp Ser Lys Gln
            180                 185                 190

Gly Val Asn Lys Pro Glu Met Lys Tyr Val Glu Pro Gln Ser Pro Lys
        195                 200                 205

Pro Glu Leu Glu Asp Asp Leu Ser Gly Glu Asp Ser Leu Lys Asp Val
    210                 215                 220

Val Glu Met Thr Pro Lys Asp Val Glu Val Thr Pro Val Arg His Ser
225                 230                 235                 240
```

```
Gln Arg Thr Ala Gly Lys Thr Phe Asn Phe Ala Glu Ala Ser Ser Gly
                245                 250                 255

Asp Asp Ser Val Glu Asn Asp Gly Asn Ile Ser Asp Gly Gln Glu Asn
            260                 265                 270

Ser Gly Ser Ala Thr Pro Glu Ser Gly Asn Glu Asp Ala Glu Ala Arg
        275                 280                 285

Thr Gly Ala Thr Thr Gln Ile Gln Glu Ser Ala Gly Ala Ala Thr Lys
    290                 295                 300

Ser Arg Lys Arg Leu Ser Gln Ala Thr Ile Ser Thr Leu Phe Lys Lys
305                 310                 315                 320

Val Glu Glu Gln Lys Thr Ser Arg Thr Pro Arg Lys Ser Ser Ser Ala
                325                 330                 335

Lys Ala Ser Ala Gln Lys Thr Asp Ser Arg Lys Ala Pro Glu His Gly
            340                 345                 350

Lys Lys Arg Lys Val Ile Glu Glu Thr Lys Ser Glu Ile Asp Ile Ser
        355                 360                 365

Thr Glu Ser Glu Gln Ser Asp Glu Glu Lys Lys Thr Ser Arg Thr Pro
    370                 375                 380

Arg Lys Ser Ser Ser Thr Lys Val Ser Ala Arg Lys Thr Asp Ala Arg
385                 390                 395                 400

Lys Ala Gln Gly Pro Arg Lys Arg Arg Lys Val Ile Glu Glu Thr Lys
                405                 410                 415

Ser Glu Ile Asp Ile Ser Thr Glu Gly Glu Gln Ser Asp Asn Pro Thr
            420                 425                 430

Ser Asp Ala Ser Val Arg Val Tyr Lys Arg Lys Met Lys Ser Pro Ala
        435                 440                 445

Ala


<210> SEQ ID NO 29
<211> LENGTH: 21
<212> TYPE: PRT
<213> ORGANISM: Artificial sequence
<220> FEATURE:
<223> OTHER INFORMATION: motif 1
<220> FEATURE:
<221> NAME/KEY: VARIANT
<222> LOCATION: (1)..(1)
<223> OTHER INFORMATION: / replace = “Val”
<220> FEATURE:
<221> NAME/KEY: VARIANT
<222> LOCATION: (3)..(3)
<223> OTHER INFORMATION: / replace = “Lys”
<220> FEATURE:
<221> NAME/KEY: VARIANT
<222> LOCATION: (4)..(4)
<223> OTHER INFORMATION: / replace = “Gly”
<220> FEATURE:
<221> NAME/KEY: VARIANT
<222> LOCATION: (5)..(5)
<223> OTHER INFORMATION: / replace = “Gly”
<220> FEATURE:
<221> NAME/KEY: VARIANT
<222> LOCATION: (9)..(9)
<223> OTHER INFORMATION: / replace = “Ser”
<220> FEATURE:
<221> NAME/KEY: VARIANT
<222> LOCATION: (10)..(10)
<223> OTHER INFORMATION: / replace = “Lys”
<220> FEATURE:
<221> NAME/KEY: VARIANT
<222> LOCATION: (11)..(11)
<223> OTHER INFORMATION: / replace = “Tyr”

<400> SEQUENCE: 29
```

```
Ile Arg Arg Lys Ser Gln Arg Lys Asn Arg Phe Leu Phe Ser Phe Pro
1               5                   10                  15

Gly Leu Leu Ala Pro
            20


<210> SEQ ID NO 30
<211> LENGTH: 29
<212> TYPE: PRT
<213> ORGANISM: Artificial sequence
<220> FEATURE:
<223> OTHER INFORMATION: motif 2
<220> FEATURE:
<221> NAME/KEY: VARIANT
<222> LOCATION: (4)..(4)
<223> OTHER INFORMATION: / replace = "Arg"
<220> FEATURE:
<221> NAME/KEY: VARIANT
<222> LOCATION: (5)..(5)
<223> OTHER INFORMATION: / replace = "Val"
<220> FEATURE:
<221> NAME/KEY: VARIANT
<222> LOCATION: (7)..(7)
<223> OTHER INFORMATION: / replace = "Asp"
<220> FEATURE:
<221> NAME/KEY: VARIANT
<222> LOCATION: (9)..(9)
<223> OTHER INFORMATION: / replace = "Ala"
<220> FEATURE:
<221> NAME/KEY: VARIANT
<222> LOCATION: (12)..(12)
<223> OTHER INFORMATION: / replace = "Asp"
<220> FEATURE:
<221> NAME/KEY: VARIANT
<222> LOCATION: (17)..(17)
<223> OTHER INFORMATION: / replace = "Leu" / replace = "Val"
<220> FEATURE:
<221> NAME/KEY: VARIANT
<222> LOCATION: (26)..(26)
<223> OTHER INFORMATION: / replace = "Gln"

<400> SEQUENCE: 30

Ser Gly Gly Lys Ile Gly Glu Leu Lys Asp Leu Gly Thr Lys Asn Pro
1               5                   10                  15

Ile Leu Tyr Leu Asp Phe Pro Gln Gly Arg Met Lys Leu
            20                  25


<210> SEQ ID NO 31
<211> LENGTH: 21
<212> TYPE: PRT
<213> ORGANISM: Artificial sequence
<220> FEATURE:
<223> OTHER INFORMATION: motif 3
<220> FEATURE:
<221> NAME/KEY: VARIANT
<222> LOCATION: (3)..(3)
<223> OTHER INFORMATION: / replace = "Ser"
<220> FEATURE:
<221> NAME/KEY: VARIANT
<222> LOCATION: (14)..(14)
<223> OTHER INFORMATION: / replace = "Leu"
<220> FEATURE:
<221> NAME/KEY: VARIANT
<222> LOCATION: (15)..(15)
<223> OTHER INFORMATION: / replace = "Asn"
<220> FEATURE:
<221> NAME/KEY: VARIANT
<222> LOCATION: (16)..(16)
<223> OTHER INFORMATION: / replace = "Tyr"
<220> FEATURE:
<221> NAME/KEY: VARIANT
<222> LOCATION: (17)..(17)
<223> OTHER INFORMATION: / replace = "Thr"
<220> FEATURE:
```

-continued

<221> NAME/KEY: misc_feature
<222> LOCATION: (19)..(19)
<223> OTHER INFORMATION: Xaa can be any naturally occurring amino acid

<400> SEQUENCE: 31

Thr Pro Val Arg Gln Ser Ala Arg Thr Ala Gly Lys Lys Phe Lys Phe
1 5 10 15

Ala Glu Xaa Ser Ser
20

<210> SEQ ID NO 32
<211> LENGTH: 21
<212> TYPE: PRT
<213> ORGANISM: Artificial sequence
<220> FEATURE:
<223> OTHER INFORMATION: motif 4
<220> FEATURE:
<221> NAME/KEY: VARIANT
<222> LOCATION: (4)..(4)
<223> OTHER INFORMATION: / replace = "Asp"
<220> FEATURE:
<221> NAME/KEY: VARIANT
<222> LOCATION: (10)..(10)
<223> OTHER INFORMATION: / replace = "Ala"
<220> FEATURE:
<221> NAME/KEY: VARIANT
<222> LOCATION: (11)..(11)
<223> OTHER INFORMATION: / replace = "Lys"
<220> FEATURE:
<221> NAME/KEY: VARIANT
<222> LOCATION: (13)..(13)
<223> OTHER INFORMATION: / replace = "Glu"
<220> FEATURE:
<221> NAME/KEY: VARIANT
<222> LOCATION: (18)..(18)
<223> OTHER INFORMATION: / replace = "Phe"
<220> FEATURE:
<221> NAME/KEY: VARIANT
<222> LOCATION: (20)..(20)
<223> OTHER INFORMATION: / replace = "Asn" / replace = "Gln"
<220> FEATURE:
<221> NAME/KEY: VARIANT
<222> LOCATION: (21)..(21)
<223> OTHER INFORMATION: / replace = "Asp"

<400> SEQUENCE: 32

Gly Thr Lys Glu Glu Asn Pro Glu Glu Leu Arg Leu Asp Phe Pro Lys
1 5 10 15

Glu Leu Gln Glu Gly
20

<210> SEQ ID NO 33
<211> LENGTH: 29
<212> TYPE: PRT
<213> ORGANISM: Artificial sequence
<220> FEATURE:
<223> OTHER INFORMATION: motif 5
<220> FEATURE:
<221> NAME/KEY: VARIANT
<222> LOCATION: (1)..(1)
<223> OTHER INFORMATION: / replace = "Asn"
<220> FEATURE:
<221> NAME/KEY: VARIANT
<222> LOCATION: (2)..(2)
<223> OTHER INFORMATION: / replace = "Asn"
<220> FEATURE:
<221> NAME/KEY: VARIANT
<222> LOCATION: (3)..(3)
<223> OTHER INFORMATION: / replace = "Leu"
<220> FEATURE:
<221> NAME/KEY: VARIANT
<222> LOCATION: (5)..(5)
<223> OTHER INFORMATION: / replace = "Gln" / replace = "Val"

<220> FEATURE:
<221> NAME/KEY: VARIANT
<222> LOCATION: (6)..(6)
<223> OTHER INFORMATION: / replace = “Arg”
<220> FEATURE:
<221> NAME/KEY: VARIANT
<222> LOCATION: (7)..(7)
<223> OTHER INFORMATION: / replace = “Asp” / replace = “Gly”
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: VARIANT
<222> LOCATION: (10)..(10)
<223> OTHER INFORMATION: / replace = “Ser”
<220> FEATURE:
<221> NAME/KEY: VARIANT
<222> LOCATION: (11)..(11)
<223> OTHER INFORMATION: / replace = “Ala”
<220> FEATURE:
<221> NAME/KEY: VARIANT
<222> LOCATION: (14)..(14)
<223> OTHER INFORMATION: / replace = “Ala”
<220> FEATURE:
<221> NAME/KEY: VARIANT
<222> LOCATION: (15)..(15)
<223> OTHER INFORMATION: / replace = “Pro” / replace = “Ser”
<220> FEATURE:
<221> NAME/KEY: VARIANT
<222> LOCATION: (21)..(21)
<223> OTHER INFORMATION: / replace = “Ala” / replace = “Gly”
<220> FEATURE:
<221> NAME/KEY: VARIANT
<222> LOCATION: (24)..(24)
<223> OTHER INFORMATION: / replace = “Arg”
<220> FEATURE:
<221> NAME/KEY: VARIANT
<222> LOCATION: (25)..(25)
<223> OTHER INFORMATION: / replace = “Leu”
<220> FEATURE:
<221> NAME/KEY: VARIANT
<222> LOCATION: (26)..(26)
<223> OTHER INFORMATION: / replace = “Gln”
<220> FEATURE:
<221> NAME/KEY: VARIANT
<222> LOCATION: (28)..(28)
<223> OTHER INFORMATION: / replace = “Arg”

<400> SEQUENCE: 33

```
Ser Gly Asn Leu Leu Ser Glu Xaa Pro Ala Lys Pro Arg Ser Ala Leu
1               5                   10                  15

Ala Pro Ser Lys Thr Val Leu Lys His His Gly Lys Asp
            20                  25
```

<210> SEQ ID NO 34
<211> LENGTH: 18
<212> TYPE: PRT
<213> ORGANISM: Artificial sequence
<220> FEATURE:
<223> OTHER INFORMATION: motif 6
<220> FEATURE:
<221> NAME/KEY: VARIANT
<222> LOCATION: (3)..(3)
<223> OTHER INFORMATION: / replace = “Asp”
<220> FEATURE:
<221> NAME/KEY: VARIANT
<222> LOCATION: (4)..(4)
<223> OTHER INFORMATION: / replace = “Tyr”
<220> FEATURE:
<221> NAME/KEY: VARIANT
<222> LOCATION: (14)..(14)
<223> OTHER INFORMATION: / replace = “Ser”
<220> FEATURE:
<221> NAME/KEY: VARIANT
<222> LOCATION: (16)..(16)

<223> OTHER INFORMATION: / replace = “Ser”
<220> FEATURE:
<221> NAME/KEY: VARIANT
<222> LOCATION: (17)..(17)
<223> OTHER INFORMATION: / replace = “Ala”

<400> SEQUENCE: 34

His Ala Glu Cys Asp Phe Lys Gly Gly Ala Gly Ala Ala Cys Asp Glu
1 5 10 15

Lys Gln

<210> SEQ ID NO 35
<211> LENGTH: 29
<212> TYPE: PRT
<213> ORGANISM: Artificial sequence
<220> FEATURE:
<223> OTHER INFORMATION: motif 7
<220> FEATURE:
<221> NAME/KEY: VARIANT
<222> LOCATION: (1)..(1)
<223> OTHER INFORMATION: / replace = “Ser” / replace = “Asn”
<220> FEATURE:
<221> NAME/KEY: VARIANT
<222> LOCATION: (2)..(2)
<223> OTHER INFORMATION: / replace = “Glu” / replace = “Pro”
<220> FEATURE:
<221> NAME/KEY: VARIANT
<222> LOCATION: (4)..(4)
<223> OTHER INFORMATION: / replace = “Glu” / replace = “Lys”
<220> FEATURE:
<221> NAME/KEY: VARIANT
<222> LOCATION: (5)..(5)
<223> OTHER INFORMATION: / replace = “Lys” / replace = “Thr”
<220> FEATURE:
<221> NAME/KEY: VARIANT
<222> LOCATION: (6)..(6)
<223> OTHER INFORMATION: / replace = “Thr” / replace = “Glu”
<220> FEATURE:
<221> NAME/KEY: VARIANT
<222> LOCATION: (7)..(7)
<223> OTHER INFORMATION: / replace = “Thr”
<220> FEATURE:
<221> NAME/KEY: VARIANT
<222> LOCATION: (8)..(8)
<223> OTHER INFORMATION: / replace = “Thr”
<220> FEATURE:
<221> NAME/KEY: VARIANT
<222> LOCATION: (9)..(9)
<223> OTHER INFORMATION: / replace = “Gly”
<220> FEATURE:
<221> NAME/KEY: VARIANT
<222> LOCATION: (11)..(11)
<223> OTHER INFORMATION: / replace = “Leu” / replace = “Gln”
<220> FEATURE:
<221> NAME/KEY: VARIANT
<222> LOCATION: (14)..(14)
<223> OTHER INFORMATION: / replace = “Glu”
<220> FEATURE:
<221> NAME/KEY: VARIANT
<222> LOCATION: (15)..(15)
<223> OTHER INFORMATION: / replace = “Thr”
<220> FEATURE:
<221> NAME/KEY: VARIANT
<222> LOCATION: (16)..(16)
<223> OTHER INFORMATION: / replace = “Glu”
<220> FEATURE:
<221> NAME/KEY: VARIANT
<222> LOCATION: (17)..(17)
<223> OTHER INFORMATION: / replace = “Leu” / replace = “Val”
<220> FEATURE:
<221> NAME/KEY: VARIANT
<222> LOCATION: (18)..(18)
<223> OTHER INFORMATION: / replace = “Asp”
<220> FEATURE:
<221> NAME/KEY: VARIANT
<222> LOCATION: (19)..(19)

<223> OTHER INFORMATION: / replace = “Ile”
<220> FEATURE:
<221> NAME/KEY: VARIANT
<222> LOCATION: (20)..(20)
<223> OTHER INFORMATION: / replace = “Val”
<220> FEATURE:
<221> NAME/KEY: VARIANT
<222> LOCATION: (21)..(21)
<223> OTHER INFORMATION: / replace = “Ser”
<220> FEATURE:
<221> NAME/KEY: VARIANT
<222> LOCATION: (23)..(23)
<223> OTHER INFORMATION: / replace = “Asp”
<220> FEATURE:
<221> NAME/KEY: VARIANT
<222> LOCATION: (24)..(24)
<223> OTHER INFORMATION: / replace = “Glu”
<220> FEATURE:
<221> NAME/KEY: VARIANT
<222> LOCATION: (25)..(25)
<223> OTHER INFORMATION: / replace = “Asp”
<220> FEATURE:
<221> NAME/KEY: VARIANT
<222> LOCATION: (26)..(26)
<223> OTHER INFORMATION: / replace = “Asp” / replace = “Ser”
<220> FEATURE:
<221> NAME/KEY: VARIANT
<222> LOCATION: (27)..(27)
<223> OTHER INFORMATION: / replace = “Asp”
<220> FEATURE:
<221> NAME/KEY: VARIANT
<222> LOCATION: (29)..(29)
<223> OTHER INFORMATION: / replace = “Lys”

<400> SEQUENCE: 35

```
Lys Lys Pro Gly Glu Lys Tyr Val Glu Glu Glu Ser Pro Lys Ile Glu
1               5                   10                  15

Ser Glu Asp Asp Leu Ser Glu Asp Ser Asn Leu Lys Asp
            20                  25
```

<210> SEQ ID NO 36
<211> LENGTH: 21
<212> TYPE: PRT
<213> ORGANISM: Artificial sequence
<220> FEATURE:
<223> OTHER INFORMATION: motif 8
<220> FEATURE:
<221> NAME/KEY: VARIANT
<222> LOCATION: (3)..(3)
<223> OTHER INFORMATION: / replace = “Ala”
<220> FEATURE:
<221> NAME/KEY: VARIANT
<222> LOCATION: (13)..(13)
<223> OTHER INFORMATION: / replace = “Met”
<220> FEATURE:
<221> NAME/KEY: VARIANT
<222> LOCATION: (14)..(14)
<223> OTHER INFORMATION: / replace = “Ala”
<220> FEATURE:
<221> NAME/KEY: VARIANT
<222> LOCATION: (16)..(16)
<223> OTHER INFORMATION: / replace = “Gln”
<220> FEATURE:
<221> NAME/KEY: VARIANT
<222> LOCATION: (18)..(18)
<223> OTHER INFORMATION: / replace = “Ala”
<220> FEATURE:
<221> NAME/KEY: VARIANT
<222> LOCATION: (20)..(20)
<223> OTHER INFORMATION: / replace = “Ile”

<400> SEQUENCE: 36

```
Lys Gly Pro Ala Ala Lys Lys Gln Arg Ala Ser Pro Glu Glu Lys His
1               5                   10                  15
```

```
Pro Thr Gly Lys Lys
            20


<210> SEQ ID NO 37
<211> LENGTH: 29
<212> TYPE: PRT
<213> ORGANISM: Artificial sequence
<220> FEATURE:
<223> OTHER INFORMATION: motif 9
<220> FEATURE:
<221> NAME/KEY: VARIANT
<222> LOCATION: (1)..(1)
<223> OTHER INFORMATION: / replace = "Asn"
<220> FEATURE:
<221> NAME/KEY: VARIANT
<222> LOCATION: (5)..(5)
<223> OTHER INFORMATION: / replace = "Asp"
<220> FEATURE:
<221> NAME/KEY: VARIANT
<222> LOCATION: (7)..(7)
<223> OTHER INFORMATION: / replace = "Val"
<220> FEATURE:
<221> NAME/KEY: VARIANT
<222> LOCATION: (9)..(9)
<223> OTHER INFORMATION: / replace = "Glu"
<220> FEATURE:
<221> NAME/KEY: VARIANT
<222> LOCATION: (10)..(10)
<223> OTHER INFORMATION: / replace = "Ser"
<220> FEATURE:
<221> NAME/KEY: VARIANT
<222> LOCATION: (11)..(11)
<223> OTHER INFORMATION: / replace = "Leu"
<220> FEATURE:
<221> NAME/KEY: VARIANT
<222> LOCATION: (12)..(12)
<223> OTHER INFORMATION: / replace = "Val"
<220> FEATURE:
<221> NAME/KEY: VARIANT
<222> LOCATION: (16)..(16)
<223> OTHER INFORMATION: / replace = "Glu"
<220> FEATURE:
<221> NAME/KEY: VARIANT
<222> LOCATION: (22)..(22)
<223> OTHER INFORMATION: / replace = "Arg"
<220> FEATURE:
<221> NAME/KEY: VARIANT
<222> LOCATION: (24)..(24)
<223> OTHER INFORMATION: / replace = "Asp"

<400> SEQUENCE: 37

Ser Val Met Cys Glu Asp Tyr Phe Asp Asn Met Ile Val Phe Ser Asp
1               5                   10                  15

Ala Trp Trp Ile Gly Thr Lys Glu Glu Asn Pro Glu Glu
            20                  25


<210> SEQ ID NO 38
<211> LENGTH: 29
<212> TYPE: PRT
<213> ORGANISM: Artificial sequence
<220> FEATURE:
<223> OTHER INFORMATION: motif 10
<220> FEATURE:
<221> NAME/KEY: VARIANT
<222> LOCATION: (2)..(2)
<223> OTHER INFORMATION: / replace = "Ile" / replace = "Leu" /
      replace = "Val"
<220> FEATURE:
<221> NAME/KEY: VARIANT
<222> LOCATION: (4)..(4)
<223> OTHER INFORMATION: / replace = "Ala"
<220> FEATURE:
<221> NAME/KEY: VARIANT
<222> LOCATION: (5)..(5)
<223> OTHER INFORMATION: / replace = "Val" / replace = "Ala"
```

-continued

<220> FEATURE:
<221> NAME/KEY: VARIANT
<222> LOCATION: (6)..(6)
<223> OTHER INFORMATION: / replace = "Ala"
<220> FEATURE:
<221> NAME/KEY: VARIANT
<222> LOCATION: (9)..(9)
<223> OTHER INFORMATION: / replace = "Arg"
<220> FEATURE:
<221> NAME/KEY: VARIANT
<222> LOCATION: (10)..(10)
<223> OTHER INFORMATION: / replace = "Val" / replace = "Phe"
<220> FEATURE:
<221> NAME/KEY: VARIANT
<222> LOCATION: (12)..(12)
<223> OTHER INFORMATION: / replace = "Asp"
<220> FEATURE:
<221> NAME/KEY: VARIANT
<222> LOCATION: (14)..(14)
<223> OTHER INFORMATION: / replace = "Ala"
<220> FEATURE:
<221> NAME/KEY: VARIANT
<222> LOCATION: (17)..(17)
<223> OTHER INFORMATION: / replace = "Asp" / replace = "Ser"
<220> FEATURE:
<221> NAME/KEY: VARIANT
<222> LOCATION: (18)..(18)
<223> OTHER INFORMATION: / replace = "Ser"
<220> FEATURE:
<221> NAME/KEY: VARIANT
<222> LOCATION: (22)..(22)
<223> OTHER INFORMATION: / replace = "Val" / replace = "Leu"

<400> SEQUENCE: 38

```
Leu Ala Ala Pro Ile Ser Gly Gly Lys Ile Gly Glu Leu Lys Asp Leu
1               5                   10                  15

Gly Thr Lys Asn Pro Ile Leu Tyr Leu Asp Phe Pro Gln
            20                  25
```

<210> SEQ ID NO 39
<211> LENGTH: 21
<212> TYPE: PRT
<213> ORGANISM: Artificial sequence
<220> FEATURE:
<223> OTHER INFORMATION: motif 11
<220> FEATURE:
<221> NAME/KEY: VARIANT
<222> LOCATION: (2)..(2)
<223> OTHER INFORMATION: / replace = "Gln"
<220> FEATURE:
<221> NAME/KEY: VARIANT
<222> LOCATION: (3)..(3)
<223> OTHER INFORMATION: / replace = "Leu"
<220> FEATURE:
<221> NAME/KEY: VARIANT
<222> LOCATION: (9)..(9)
<223> OTHER INFORMATION: / replace = "Leu"
<220> FEATURE:
<221> NAME/KEY: VARIANT
<222> LOCATION: (14)..(14)
<223> OTHER INFORMATION: / replace = "Lys"
<220> FEATURE:
<221> NAME/KEY: VARIANT
<222> LOCATION: (16)..(16)
<223> OTHER INFORMATION: / replace = "Ile"

<400> SEQUENCE: 39

```
Gly Arg Met Lys Leu Phe Gly Thr Ile Val Tyr Pro Lys Asn Arg Tyr
1               5                   10                  15

Leu Thr Leu Gln Phe
            20
```

<210> SEQ ID NO 40

<211> LENGTH: 55
<212> TYPE: DNA
<213> ORGANISM: Artificial sequence
<220> FEATURE:
<223> OTHER INFORMATION: primer 1

<400> SEQUENCE: 40
ggggacaagt ttgtacaaaa aagcaggctt aaacaatggt acgagcttca tcgtc 55

<210> SEQ ID NO 41
<211> LENGTH: 52
<212> TYPE: DNA
<213> ORGANISM: Artificial sequence
<220> FEATURE:
<223> OTHER INFORMATION: primer 2

<400> SEQUENCE: 41
ggggaccact ttgtacaaga aagctgggtt tctggaaaag atttctttaa gc 52

<210> SEQ ID NO 42
<211> LENGTH: 2194
<212> TYPE: DNA
<213> ORGANISM: Oryza sativa

<400> SEQUENCE: 42
aatccgaaaa gtttctgcac cgttttcacc ccctaactaa caatataggg aacgtgtgct 60
aaatataaaa tgagacctta tatatgtagc gctgataact agaactatgc aagaaaaact 120
catccaccta ctttagtggc aatcgggcta aataaaaaag agtcgctaca ctagtttcgt 180
tttccttagt aattaagtgg gaaaatgaaa tcattattgc ttagaatata cgttcacatc 240
tctgtcatga agttaaatta ttcgaggtag ccataattgt catcaaactc ttcttgaata 300
aaaaaatctt tctagctgaa ctcaatgggt aaagagagag atttttttta aaaaaataga 360
atgaagatat tctgaacgta ttggcaaaga tttaaacata taattatata attttatagt 420
ttgtgcattc gtcatatcgc acatcattaa ggacatgtct tactccatcc caatttttat 480
ttagtaatta aagacaattg acttattttt attatttatc ttttttcgat tagatgcaag 540
gtacttacgc acacactttg tgctcatgtg catgtgtgag tgcacctcct caatacacgt 600
tcaactagca acacatctct aatatcactc gcctatttaa tacatttagg tagcaatatc 660
tgaattcaag cactccacca tcaccagacc acttttaata atatctaaaa tacaaaaaat 720
aattttacag aatagcatga aaagtatgaa acgaactatt taggtttttc acatacaaaa 780
aaaaaaagaa ttttgctcgt gcgcgagcgc caatctccca tattgggcac acaggcaaca 840
acagagtggc tgcccacaga acaacccaca aaaaacgatg atctaacgga ggacagcaag 900
tccgcaacaa ccttttaaca gcaggctttg cggccaggag agaggaggag aggcaaagaa 960
aaccaagcat cctccttctc ccatctataa attcctcccc ccttttcccc tctctatata 1020
ggaggcatcc aagccaagaa gagggagagc accaaggaca cgcgactagc agaagccgag 1080
cgaccgcctt ctcgatccat atcttccggt cgagttcttg gtcgatctct tccctcctcc 1140
acctcctcct cacagggtat gtgcctccct tcggttgttc ttggatttat tgttctaggt 1200
tgtgtagtac gggcgttgat gttaggaaag gggatctgta tctgtgatga ttcctgttct 1260
tggatttggg atagaggggt tcttgatgtt gcatgttatc ggttcggttt gattagtagt 1320
atggttttca atcgtctgga gagctctatg gaaatgaaat ggtttaggga tcggaatctt 1380
gcgattttgt gagtaccttt tgtttgaggt aaaatcagag caccggtgat tttgcttggt 1440
gtaataaagt acggttgttt ggtcctcgat tctggtagtg atgcttctcg atttgacgaa 1500

-continued

```
gctatccttt gtttattccc tattgaacaa aaataatcca actttgaaga cggtcccgtt   1560

gatgagattg aatgattgat tcttaagcct gtccaaaatt tcgcagctgg cttgtttaga   1620

tacagtagtc cccatcacga aattcatgga aacagttata atcctcagga acaggggatt   1680

ccctgttctt ccgatttgct ttagtcccag aatttttttt cccaaatatc ttaaaaagtc   1740

actttctggt tcagttcaat gaattgattg ctacaaataa tgcttttata gcgttatcct   1800

agctgtagtt cagttaatag gtaatacccc tatagtttag tcaggagaag aacttatccg   1860

atttctgatc tccattttta attatatgaa atgaactgta gcataagcag tattcatttg   1920

gattattttt tttattagct ctcacccctt cattattctg agctgaaagt ctggcatgaa   1980

ctgtcctcaa ttttgtttc aaattcacat cgattatcta tgcattatcc tcttgtatct    2040

acctgtagaa gtttcttttt ggttattcct tgactgcttg attacagaaa gaaatttatg   2100

aagctgtaat cgggatagtt atactgcttg ttcttatgat tcatttcctt tgtgcagttc   2160

ttggtgtagc ttgccacttt caccagcaaa gttc                               2194
```

<210> SEQ ID NO 43
<211> LENGTH: 1264
<212> TYPE: DNA
<213> ORGANISM: Oryza sativa

<400> SEQUENCE: 43

```
tcgacgctac tcaagtggtg ggaggccacc gcatgttcca acgaagcgcc aaagaaagcc     60

ttgcagactc taatgctatt agtcgcctag gatatttgga atgaaaggaa ccgcagagtt    120

tttcagcacc aagagcttcc ggtggctagt ctgatagcca aaattaagga ggatgccaaa    180

acatgggtct tggcgggcgc gaaacacctt gataggtggc ttacctttta acatgttcgg    240

gccaaaggcc ttgagacggt aaagttttct atttgcgctt gcgcatgtac aattttattc    300

ctctattcaa tgaaattggt ggctcactgg ttcattaaaa aaaaaagaat ctagcctgtt    360

cgggaagaag aggattttgt tcgtgagaga gagagagaga gagagagaga gagagagaga    420

gaaggaggag gaggatttc aggcttcgca ttgcccaacc tctgcttctg ttggcccaag     480

aagaatccca ggcgcccatg ggctggcagt ttaccacgga cctacctagc ctaccttagc    540

tatctaagcg ggccgaccta gtagccacgt gcctagtgta gattaaagtt gccgggccag    600

caggaagcca cgctgcaatg gcatcttccc ctgtccttcg cgtacgtgaa aacaaaccca    660

ggtaagctta gaatcttctt gcccgttgga ctgggacacc caccaatccc accatgcccc    720

gatattcctc cggtctcggt tcatgtgatg tcctctcttg tgtgatcacg gagcaagcat    780

tcttaaacgg caaaagaaaa tcaccaactt gctcacgcag tcacgctgca ccgcgcgaag    840

cgacgcccga taggccaaga tcgcgagata aaataacaac caatgatcat aaggaaacaa    900

gcccgcgatg tgtcgtgtgc agcaatcttg gtcatttgcg ggatcgagtg cttcacagct    960

aaccaaatat tcggccgatg atttaacaca ttatcagcgt agatgtacgt acgatttgtt   1020

aattaatcta cgagccttgc tagggcaggt gttctgccag ccaatccaga tcgccctcgt   1080

atgcacgctc acatgatggc agggcagggt tcacatgagc tctaacggtc gattaattaa   1140

tcccggggct cgactataaa tacctcccta atcccatgat caaaaccatc tcaagcagcc   1200

taatcatctc cagctgatca agagctctta attagctagc tagtgattag ctgcgcttgt   1260

gatc                                                                1264
```

<210> SEQ ID NO 44

<211> LENGTH: 1221
<212> TYPE: DNA
<213> ORGANISM: Oryza sativa

<400> SEQUENCE: 44

```
atggcatacc atggacagct ggatggacgc caagcttcag gtttgatgcg tgatggcgcc     60
ttccctgcag ccagcctttc tggccgccaa cctttggatc gcgctgccac cgctctggag    120
atcttggaaa agaaacttgc tgagcagacc gccgaggcag aaaagcttat cagagagaat    180
cagcgattgg catctagcca tgtcgtcttg aggcaggata ttgttgatac tgagaaagaa    240
atgcaaatga tccgtgctca cctaggtgat gttcagacag agactgatat gcatatgaga    300
gatttgatgg agagaatgag attgatggaa gcagatatac aagctggtga tgcagtgaag    360
aaggaacttc atcaagtgca tatggaggca aagagactta ttgctgagag gcagatgctc    420
actgttgaga tggataaagt aactaaagag ctacataagt tctctggtga cagtaagaaa    480
cttcctgaat tactgactga gctagatggg ctccgaaaag agcatcagag tctaagatct    540
gcttttgaat atgagaaaaa cacaaacatc aagcaagttg agcagatgcg gacgatggag    600
atgaatttaa tgactatgac caaagaggct gacaagttgc gtgctgatgt ggcaaatgct    660
gaaaaacgag ctcaagtggc agcggctcaa gcagtagcag cacaggcggg ggtggcacat    720
gtgactgctt cacaaccagg ggcagcacaa gctgtggcag tgccagctgc ctcaaaccca    780
tattcaagtg catttaccgg tcatccctct gcatatcacc aaggagccac ccaagctggg    840
gtttatcagc aagggaccac ccaagttggg gcatatcagc aaggatctac ccaagctggg    900
gcatatgctt acccaactta tgatgccgct actgcttacc agatgcatgc tgcgcaagca    960
aatgcatacg cgggctatcc tggttatcca gttgcagggt acacacaggc cgctttgccc   1020
ggttatccta gtgcgtatgc tgcaccgcag caaccaataa gcagtggtgt agctacagat   1080
gttgcaagca tgtatggcgc gatcagtagt gctggatatc ctgctggagt tgttcagtca   1140
agcagtggag ctgccaatgc aggacaagca ccagctactt atcctgtcgc atacgaccca   1200
accagagcag gccagaggtg a                                              1221
```

<210> SEQ ID NO 45
<211> LENGTH: 406
<212> TYPE: PRT
<213> ORGANISM: Oryza sativa

<400> SEQUENCE: 45

```
Met Ala Tyr His Gly Gln Leu Asp Gly Arg Gln Ala Ser Gly Leu Met
1               5                   10                  15

Arg Asp Gly Ala Phe Pro Ala Ala Ser Leu Ser Gly Arg Gln Pro Leu
            20                  25                  30

Asp Arg Ala Ala Thr Ala Leu Glu Ile Leu Glu Lys Lys Leu Ala Glu
        35                  40                  45

Gln Thr Ala Glu Ala Glu Lys Leu Ile Arg Glu Asn Gln Arg Leu Ala
    50                  55                  60

Ser Ser His Val Val Leu Arg Gln Asp Ile Val Asp Thr Glu Lys Glu
65                  70                  75                  80

Met Gln Met Ile Arg Ala His Leu Gly Asp Val Gln Thr Glu Thr Asp
                85                  90                  95

Met His Met Arg Asp Leu Met Glu Arg Met Arg Leu Met Glu Ala Asp
            100                 105                 110

Ile Gln Ala Gly Asp Ala Val Lys Lys Glu Leu His Gln Val His Met
        115                 120                 125
```

-continued

```
Glu Ala Lys Arg Leu Ile Ala Glu Arg Gln Met Leu Thr Val Glu Met
    130                 135                 140

Asp Lys Val Thr Lys Glu Leu His Lys Phe Ser Gly Asp Ser Lys Lys
145                 150                 155                 160

Leu Pro Glu Leu Leu Thr Glu Leu Asp Gly Leu Arg Lys Glu His Gln
                165                 170                 175

Ser Leu Arg Ser Ala Phe Glu Tyr Glu Lys Asn Thr Asn Ile Lys Gln
            180                 185                 190

Val Glu Gln Met Arg Thr Met Glu Met Asn Leu Met Thr Met Thr Lys
        195                 200                 205

Glu Ala Asp Lys Leu Arg Ala Asp Val Ala Asn Ala Glu Lys Arg Ala
    210                 215                 220

Gln Val Ala Ala Ala Gln Ala Val Ala Ala Gln Ala Gly Val Ala His
225                 230                 235                 240

Val Thr Ala Ser Gln Pro Gly Ala Ala Gln Ala Val Ala Val Pro Ala
                245                 250                 255

Ala Ser Asn Pro Tyr Ser Ser Ala Phe Thr Gly His Pro Ser Ala Tyr
            260                 265                 270

His Gln Gly Ala Thr Gln Ala Gly Val Tyr Gln Gln Gly Thr Thr Gln
        275                 280                 285

Val Gly Ala Tyr Gln Gln Gly Ser Thr Gln Ala Gly Ala Tyr Ala Tyr
    290                 295                 300

Pro Thr Tyr Asp Ala Ala Thr Ala Tyr Gln Met His Ala Ala Gln Ala
305                 310                 315                 320

Asn Ala Tyr Ala Gly Tyr Pro Gly Tyr Pro Val Ala Gly Tyr Thr Gln
                325                 330                 335

Ala Ala Leu Pro Gly Tyr Pro Ser Ala Tyr Ala Ala Pro Gln Gln Pro
            340                 345                 350

Ile Ser Ser Gly Val Ala Thr Asp Val Ala Ser Met Tyr Gly Ala Ile
        355                 360                 365

Ser Ser Ala Gly Tyr Pro Ala Gly Val Val Gln Ser Ser Ser Gly Ala
    370                 375                 380

Ala Asn Ala Gly Gln Ala Pro Ala Thr Tyr Pro Val Ala Tyr Asp Pro
385                 390                 395                 400

Thr Arg Ala Gly Gln Arg
                405
```

<210> SEQ ID NO 46
<211> LENGTH: 1080
<212> TYPE: DNA
<213> ORGANISM: Arabidopsis thaliana

<400> SEQUENCE: 46

```
atggaaagca aaggaagaat ccatccatct catcatcata tgaggcgtcc tcttccaggt      60

cccggtggct gtatagcgca tccggagact ttcggtaatc acggtgctat accaccttct     120

gctgctcaag gtgtgtatcc ttccttcaac atgttacctc cacctgaagt tatggagcaa     180

aagtttgtgg cacaacacgg ggaattacag agacttgcta tagagaatca gagacttggt     240

ggaactcatg gtagtttaag acaagagtta gcagcagcac agcatgaaat acagatgttg     300

cacgcgcaaa ttgggtcgat gaagtccgag agagagcaac ggatgatggg tcttgctgag     360

aaagttgcta aaatggagac tgagcttcag aaatctgagg ctgttaagtt ggagatgcaa     420

caagcacgtg ctgaggcacg gagtcttgtt gtggctaggg aggagcttat gtctaaagtg     480
```

-continued

```
catcagttga ctcaggaact tcaaaaatct cgttctgatg tgcagcaaat acctgctctg    540

atgtctgaac ttgagaatct aagacaggag taccagcagt gcagggcaac atatgactat    600

gagaagaagt tttataatga ccatctcgag tcacttcagg caatggagaa gaactacatg    660

actatggcta gggaagttga aaaacttcaa gcacagttga tgaacaatgc aaattcagat    720

agaagagcag gtggccctta tggtaacaac ataaatgctg aaattgacgc ttctggacat    780

cagagtggaa acggttatta tgaagatgct tttggtcctc agggatatat tcctcaacca    840

gtagctggta acgcaactgg accaaattca gttgttggcg cagctcaata cccttatcaa    900

ggagtaactc agccaggata cttccctcaa agacccggtt acaactttcc aagaggccct    960

cctggttcat atgacccaac aacaaggtta ccaacaggac cttacggcgc tccattccca   1020

cctggaccat ctaacaatac tccttacgcc ggtacacacg gaaaccctag tcgcagatga   1080


<210> SEQ ID NO 47
<211> LENGTH: 359
<212> TYPE: PRT
<213> ORGANISM: Arabidopsis thaliana

<400> SEQUENCE: 47

Met Glu Ser Lys Gly Arg Ile His Pro Ser His His His Met Arg Arg
1               5                   10                  15

Pro Leu Pro Gly Pro Gly Gly Cys Ile Ala His Pro Glu Thr Phe Gly
            20                  25                  30

Asn His Gly Ala Ile Pro Pro Ser Ala Ala Gln Gly Val Tyr Pro Ser
        35                  40                  45

Phe Asn Met Leu Pro Pro Pro Glu Val Met Glu Gln Lys Phe Val Ala
    50                  55                  60

Gln His Gly Glu Leu Gln Arg Leu Ala Ile Glu Asn Gln Arg Leu Gly
65                  70                  75                  80

Gly Thr His Gly Ser Leu Arg Gln Glu Leu Ala Ala Ala Gln His Glu
                85                  90                  95

Ile Gln Met Leu His Ala Gln Ile Gly Ser Met Lys Ser Glu Arg Glu
            100                 105                 110

Gln Arg Met Met Gly Leu Ala Glu Lys Val Ala Lys Met Glu Thr Glu
        115                 120                 125

Leu Gln Lys Ser Glu Ala Val Lys Leu Glu Met Gln Gln Ala Arg Ala
    130                 135                 140

Glu Ala Arg Ser Leu Val Val Ala Arg Glu Glu Leu Met Ser Lys Val
145                 150                 155                 160

His Gln Leu Thr Gln Glu Leu Gln Lys Ser Arg Ser Asp Val Gln Gln
                165                 170                 175

Ile Pro Ala Leu Met Ser Glu Leu Glu Asn Leu Arg Gln Glu Tyr Gln
            180                 185                 190

Gln Cys Arg Ala Thr Tyr Asp Tyr Glu Lys Lys Phe Tyr Asn Asp His
        195                 200                 205

Leu Glu Ser Leu Gln Ala Met Glu Lys Asn Tyr Met Thr Met Ala Arg
    210                 215                 220

Glu Val Glu Lys Leu Gln Ala Gln Leu Met Asn Asn Ala Asn Ser Asp
225                 230                 235                 240

Arg Arg Ala Gly Gly Pro Tyr Gly Asn Asn Ile Asn Ala Glu Ile Asp
                245                 250                 255

Ala Ser Gly His Gln Ser Gly Asn Gly Tyr Tyr Glu Asp Ala Phe Gly
            260                 265                 270
```

-continued

```
Pro Gln Gly Tyr Ile Pro Gln Pro Val Ala Gly Asn Ala Thr Gly Pro
        275                 280                 285

Asn Ser Val Val Gly Ala Ala Gln Tyr Pro Tyr Gln Gly Val Thr Gln
    290                 295                 300

Pro Gly Tyr Phe Pro Gln Arg Pro Gly Tyr Asn Phe Pro Arg Gly Pro
305                 310                 315                 320

Pro Gly Ser Tyr Asp Pro Thr Thr Arg Leu Pro Thr Gly Pro Tyr Gly
                325                 330                 335

Ala Pro Phe Pro Pro Gly Pro Ser Asn Asn Thr Pro Tyr Ala Gly Thr
            340                 345                 350

His Gly Asn Pro Ser Arg Arg
        355
```

<210> SEQ ID NO 48
<211> LENGTH: 1368
<212> TYPE: DNA
<213> ORGANISM: Hordeum vulgare

<400> SEQUENCE: 48

```
atggggagca agggtcggat gcctccttct taccaccacc ggccgctccc aggttccggc     60

tctggcccgc cgcatggcat gatgcaccgt gatccgtacg gcccgggcat gcacccaccg    120

ccagggccgg ggccataccc ctacgatatg ttgccgccgc ctgagatcct ggagcagaag    180

ctggcggtgc agtgtggaga gatacagaag ctggcggtgg agaacgaacg gctcgccacg    240

agccacgtgt ctctgaggaa agagctggct gccgcgcagc aggagctgca gaggctgcag    300

gcgcagggtg aggcggcgaa ggccgccgag gagcaggaga tgagggggct ccttgacaag    360

gctgccaaga tggaggccga tctgaagtcg tacgagtctg tcaaggcgga cctgcagcag    420

gcgcacaccg aggcgcagaa cctggcggca gcaaggcagc atttgtcggc ggaggtgcag    480

aagctgaaca aagacctgca gaggaacttt ggggaggcac aacagctgcc agcactcatg    540

gctgatcttg atgctgctag acaggaatat cagcacctaa gggctgcata tgagtatgaa    600

aggaaactga agatggacca ctcggagtcg ctgcaggtaa ccaagacaaa ttatgactcc    660

atggttacag agttagagaa gcttcgtgct gagttgacaa actcaactaa tattgacaga    720

agtggtactt tgtacaatcc taatttggct cagaaggatg gtggtacatc tggtcggcat    780

tctgcttatg atggtggcta tgggggtgca caggctagga cgccccctgg tatgccagac    840

cctctaagcg gaagcccagc tggaactgct cctctttctg gatatgatcc atcaagaggg    900

aatgcatatg agacttctcg tcttgctaga gtccatgatg catcaagggg tgctactggt    960

tacgactctc taaaagttgc tggatatgat acttctagaa tgcccgcact tggagctcag   1020

acagcggctc caactgctca tgggagtagt gctggttact atggatctgc acaggtgcca   1080

ccatcatatg cttctgggcc agtctcgtct tcatcatacg gcgcaacaac agcgcgacct   1140

catggctcag ctcagggact atcatcatat ggacaaacac aggctccatc ttcttatgca   1200

cacacacaga taccaccatc ctatggacta gcacaggcat catcacactt tggcccaact   1260

caggggggggt caccgtatgg gttgtctgca cggccccagg cctatggatc cgcgcaagca   1320

gcacctaaca ctggtggtgc ttatcaaact ccacatggac gtagataa                  1368
```

<210> SEQ ID NO 49
<211> LENGTH: 455
<212> TYPE: PRT
<213> ORGANISM: Hordeum vulgare

<400> SEQUENCE: 49

```
Met Gly Ser Lys Gly Arg Met Pro Pro Ser Tyr His His Arg Pro Leu
1               5                   10                  15

Pro Gly Ser Gly Ser Gly Pro Pro His Gly Met Met His Arg Asp Pro
            20                  25                  30

Tyr Gly Pro Gly Met His Pro Pro Pro Gly Pro Gly Pro Tyr Pro Tyr
        35                  40                  45

Asp Met Leu Pro Pro Pro Glu Ile Leu Glu Gln Lys Leu Ala Val Gln
    50                  55                  60

Cys Gly Glu Ile Gln Lys Leu Ala Val Glu Asn Glu Arg Leu Ala Thr
65                  70                  75                  80

Ser His Val Ser Leu Arg Lys Glu Leu Ala Ala Ala Gln Gln Glu Leu
                85                  90                  95

Gln Arg Leu Gln Ala Gln Gly Glu Ala Ala Lys Ala Ala Glu Glu Gln
            100                 105                 110

Glu Met Arg Gly Leu Leu Asp Lys Ala Ala Lys Met Glu Ala Asp Leu
        115                 120                 125

Lys Ser Tyr Glu Ser Val Lys Ala Asp Leu Gln Gln Ala His Thr Glu
    130                 135                 140

Ala Gln Asn Leu Ala Ala Ala Arg Gln His Leu Ser Ala Glu Val Gln
145                 150                 155                 160

Lys Leu Asn Lys Asp Leu Gln Arg Asn Phe Gly Glu Ala Gln Gln Leu
                165                 170                 175

Pro Ala Leu Met Ala Asp Leu Asp Ala Ala Arg Gln Glu Tyr Gln His
            180                 185                 190

Leu Arg Ala Ala Tyr Glu Tyr Glu Arg Lys Leu Lys Met Asp His Ser
        195                 200                 205

Glu Ser Leu Gln Val Thr Lys Thr Asn Tyr Asp Ser Met Val Thr Glu
    210                 215                 220

Leu Glu Lys Leu Arg Ala Glu Leu Thr Asn Ser Thr Asn Ile Asp Arg
225                 230                 235                 240

Ser Gly Thr Leu Tyr Asn Pro Asn Leu Ala Gln Lys Asp Gly Gly Thr
                245                 250                 255

Ser Gly Arg His Ser Ala Tyr Asp Gly Gly Tyr Gly Gly Ala Gln Ala
            260                 265                 270

Arg Thr Pro Pro Gly Met Pro Asp Pro Leu Ser Gly Ser Pro Ala Gly
        275                 280                 285

Thr Ala Pro Leu Ser Gly Tyr Asp Pro Ser Arg Gly Asn Ala Tyr Glu
    290                 295                 300

Thr Ser Arg Leu Ala Arg Val His Asp Ala Ser Arg Gly Ala Thr Gly
305                 310                 315                 320

Tyr Asp Ser Leu Lys Val Ala Gly Tyr Asp Thr Ser Arg Met Pro Ala
                325                 330                 335

Leu Gly Ala Gln Thr Ala Ala Pro Thr Ala His Gly Ser Ser Ala Gly
            340                 345                 350

Tyr Tyr Gly Ser Ala Gln Val Pro Pro Ser Tyr Ala Ser Gly Pro Val
        355                 360                 365

Ser Ser Ser Ser Tyr Gly Ala Thr Thr Ala Arg Pro His Gly Ser Ala
    370                 375                 380

Gln Gly Leu Ser Ser Tyr Gly Gln Thr Gln Ala Pro Ser Ser Tyr Ala
385                 390                 395                 400

His Thr Gln Ile Pro Pro Ser Tyr Gly Leu Ala Gln Ala Ser Ser His
                405                 410                 415
```

-continued

Phe Gly Pro Thr Gln Gly Gly Ser Pro Tyr Gly Leu Ser Ala Arg Pro
420 425 430

Gln Ala Tyr Gly Ser Ala Gln Ala Ala Pro Asn Thr Gly Gly Ala Tyr
435 440 445

Gln Thr Pro His Gly Arg Arg
450 455

<210> SEQ ID NO 50
<211> LENGTH: 1329
<212> TYPE: DNA
<213> ORGANISM: Lycopersicon esculentum

<400> SEQUENCE: 50
atgggaagca aaggtcgagg gccacctccc aacattaggc gtccgcctcc aggacccggc 60
atgatgtatc ctgattcttt tggtcctcct acgcataacc ctccaccagt tgatttcccc 120
ccttttgaca ggctacctcc tccagagatt ttggaacaga agattggtgc acaacatctt 180
gagatgcaaa aacttactac agaaaatcag aggcttgctg ccacccatgt aactttgagg 240
cgagatttag ctgctgcaca acatgagcta caaatgttgc atgttcagat agaaacagtc 300
aaggccaaca gggaacaaga gactaaaggc ctcagtgata aaatttctag gatagaggct 360
gaacttcaag ctgctgaatc tatcaaaaaa gaattgccgc aagcacaagg ggaagctcgc 420
actttgtttg cagcaaggca agaacttgtt actaaaatac aaatgctgac tcaggatctt 480
caaagggctc acgctgatgt gctacatatt cctcgtttgc tggctgagtt ggagagccta 540
aaaaaggagt atcagcagtg ccggactacc tatgagtgcg agaggaagtt atacagtgat 600
catcttgaat ctcttcaagt gatggagaag aactacatga ctatgtccag agaggtggaa 660
aagcttaggg cagagttagc gaacacttct aactctgaca gacaaacagg tggaccttat 720
ggtggttcaa ctggatacaa tgaaaatgat gccactaata attatgctac tgggcaaaac 780
atctatgcag acggctatgg agtttatcag ggtagaggct ccgtaccaac agggactaat 840
gctggaggag ttcctgctgt tgactcacca caagttggag ctcagtctgt gcctccgtca 900
aacaggcctc cttatgatac atcaaatatg tctggttatg atgcacaaag gggaattaga 960
ggccctgttg gacatggtta tgaagcacaa atgggatcaa gtggtcctgg ctatgatgcg 1020
caaagaggat ctggtttagc agcttatgaa gctcagaggg ggcatgggta tgatagggga 1080
cctgggtatg atgctcagag ggcagcgggt tatgaagctt acagaggacc tggctatgat 1140
gcatatgggg cccctgttta tgatcctagc aaggcctcta actatgacgc atcttccaaa 1200
ggcggtgttg caactcaagg acaggtagca cctataggaa atgctcctcc tggggcagct 1260
ccctcaccgg gtcatattgg tcctggatat gatgcatcag cacaaggtgg aaatccagca 1320
cgtagatga 1329

<210> SEQ ID NO 51
<211> LENGTH: 442
<212> TYPE: PRT
<213> ORGANISM: Lycopersicon esculentum

<400> SEQUENCE: 51

Met Gly Ser Lys Gly Arg Gly Pro Pro Pro Asn Ile Arg Arg Pro Pro
1 5 10 15

Pro Gly Pro Gly Met Met Tyr Pro Asp Ser Phe Gly Pro Pro Thr His
20 25 30

Asn Pro Pro Pro Val Asp Phe Pro Pro Phe Asp Arg Leu Pro Pro Pro
35 40 45

```
Glu Ile Leu Glu Gln Lys Ile Gly Ala Gln His Leu Glu Met Gln Lys
    50                  55                  60

Leu Thr Thr Glu Asn Gln Arg Leu Ala Ala Thr His Val Thr Leu Arg
65                  70                  75                  80

Arg Asp Leu Ala Ala Ala Gln His Glu Leu Gln Met Leu His Val Gln
                85                  90                  95

Ile Glu Thr Val Lys Ala Asn Arg Glu Gln Glu Thr Lys Gly Leu Ser
            100                 105                 110

Asp Lys Ile Ser Arg Ile Glu Ala Glu Leu Gln Ala Ala Glu Ser Ile
        115                 120                 125

Lys Lys Glu Leu Pro Gln Ala Gln Gly Glu Ala Arg Thr Leu Phe Ala
    130                 135                 140

Ala Arg Gln Glu Leu Val Thr Lys Ile Gln Met Leu Thr Gln Asp Leu
145                 150                 155                 160

Gln Arg Ala His Ala Asp Val Leu His Ile Pro Arg Leu Leu Ala Glu
                165                 170                 175

Leu Glu Ser Leu Lys Lys Glu Tyr Gln Gln Cys Arg Thr Thr Tyr Glu
            180                 185                 190

Cys Glu Arg Lys Leu Tyr Ser Asp His Leu Glu Ser Leu Gln Val Met
        195                 200                 205

Glu Lys Asn Tyr Met Thr Met Ser Arg Glu Val Glu Lys Leu Arg Ala
    210                 215                 220

Glu Leu Ala Asn Thr Ser Asn Ser Asp Arg Gln Thr Gly Gly Pro Tyr
225                 230                 235                 240

Gly Gly Ser Thr Gly Tyr Asn Glu Asn Asp Ala Thr Asn Asn Tyr Ala
                245                 250                 255

Thr Gly Gln Asn Ile Tyr Ala Asp Gly Tyr Gly Val Tyr Gln Gly Arg
            260                 265                 270

Gly Ser Val Pro Thr Gly Thr Asn Ala Gly Gly Val Pro Ala Val Asp
        275                 280                 285

Ser Pro Gln Val Gly Ala Gln Ser Val Pro Pro Ser Asn Arg Pro Pro
    290                 295                 300

Tyr Asp Thr Ser Asn Met Ser Gly Tyr Asp Ala Gln Arg Gly Ile Arg
305                 310                 315                 320

Gly Pro Val Gly His Gly Tyr Glu Ala Gln Met Gly Ser Ser Gly Pro
                325                 330                 335

Gly Tyr Asp Ala Gln Arg Gly Ser Gly Leu Ala Ala Tyr Glu Ala Gln
            340                 345                 350

Arg Gly His Gly Tyr Asp Arg Gly Pro Gly Tyr Asp Ala Gln Arg Ala
        355                 360                 365

Ala Gly Tyr Glu Ala Tyr Arg Gly Pro Gly Tyr Asp Ala Tyr Gly Ala
    370                 375                 380

Pro Val Tyr Asp Pro Ser Lys Ala Ser Asn Tyr Asp Ala Ser Ser Lys
385                 390                 395                 400

Gly Gly Val Ala Thr Gln Gly Gln Val Ala Pro Ile Gly Asn Ala Pro
                405                 410                 415

Pro Gly Ala Ala Pro Ser Pro Gly His Ile Gly Pro Gly Tyr Asp Ala
            420                 425                 430

Ser Ala Gln Gly Gly Asn Pro Ala Arg Arg
        435                 440
```

<210> SEQ ID NO 52
<211> LENGTH: 1530

-continued

<212> TYPE: DNA
<213> ORGANISM: Oryza sativa

<400> SEQUENCE: 52
atggggagca aggggagggc gccgccgcct taccaccacc ggggggcgca caagatgatg 60
caccgggacc cgtacggggg ggcaccgggg atgccggggc cgttcccgta cgacatgctg 120
gcggcggcgg cgccgccgcc ggagatcctg gagcagaagc tgatggcgca gcggggggag 180
ctgcagaagc tggcggtgga gaacgaccgg ctggcgatga gccacgactc gctgcggaag 240
gagctcgccg cggcgcagca ggaggcgcag aggctgcagg cgcaggggca ggcggcgatg 300
gcggccgagg agcaggaggc gagggggatc ctcgacaagg tcgccaagat ggaggccgac 360
ctcaaggccc gcgaccccgt caaggccgag ctgcagcagg cgcacgccga ggcgcagggc 420
ctcgtcgtcg cgaggcagca gctggccgcc gacacgcaga agctgagcaa ggacctgcag 480
aggaacctcg gcgaggcgca gcagctcccc gcgctcgtgg ccgagcgcga cgccgctagg 540
caggagtatc agcacctcag ggctacgtat gagtacgaaa ggaaactcag gatggatcac 600
tccgagtcgc tgcaggtgat gaagaggaat tatgacacca tggtcgctga gctagacaag 660
cttcgtgctg agctgatgaa cacggctaat attgacagag gaggcatgcc gtttatctgt 720
tgttccattt tttttaccac aatttttggt agcatatata gaaaccacac catgagacat 780
tttctatgtg taggtatgct atacaatact aatactgctc aaaaggatga tggcgcgcct 840
agtcttcctg ttggacaaat tgcttatgat agcggttatg gagctgcgca gggaaggaca 900
ccacctgctg gactgggaga ctctttaagc ggaaacccag ctggcacagc tcctcggact 960
ggatttgatc catcaagagg caatatgtat gacgcttctc gtattgctag cttcagttct 1020
tcaaaagctg gaggacatga tgcatcaagg ggtgccgcag gctacaattc tttgaaaggt 1080
gctggatatg atccttctaa agcacctgca cttggaggac aggcaacagc tgcagctgct 1140
catgggagta gtgctgatta ctatggatca aatcaggcaa caccaccttc atatgcttgg 1200
ggacaagctg catccgctta tggatctgca caagtgccac agtcacatgc atctggacct 1260
cctgttcaat caacatccta cagtgcaaca acagcacgta actttggctc tgcccaggct 1320
ttaccatcat atgcacatgc acaggagcaa ccttcatatg gacacgcaca gctaccatcc 1380
tcatatggat tagcgcaagc atcatttcca tttgccccag cgcaaggggt gtcaccctat 1440
gggtcaggtg cacagcctcc gcagtatgga gctgggcaag cagcaactaa tcctggcagt 1500
gcttaccaag cacctcatgg acgtaaataa 1530

<210> SEQ ID NO 53
<211> LENGTH: 509
<212> TYPE: PRT
<213> ORGANISM: Oryza sativa

<400> SEQUENCE: 53

Met Gly Ser Lys Gly Arg Ala Pro Pro Pro Tyr His His Arg Gly Ala
1 5 10 15

His Lys Met Met His Arg Asp Pro Tyr Gly Gly Ala Pro Gly Met Pro
20 25 30

Gly Pro Phe Pro Tyr Asp Met Leu Ala Ala Ala Ala Pro Pro Pro Glu
35 40 45

Ile Leu Glu Gln Lys Leu Met Ala Gln Arg Gly Glu Leu Gln Lys Leu
50 55 60

Ala Val Glu Asn Asp Arg Leu Ala Met Ser His Asp Ser Leu Arg Lys
65 70 75 80

```
Glu Leu Ala Ala Ala Gln Gln Glu Ala Gln Arg Leu Gln Ala Gln Gly
                85                  90                  95

Gln Ala Ala Met Ala Ala Glu Glu Gln Glu Ala Arg Gly Ile Leu Asp
            100                 105                 110

Lys Val Ala Lys Met Glu Ala Asp Leu Lys Ala Arg Asp Pro Val Lys
        115                 120                 125

Ala Glu Leu Gln Gln Ala His Ala Glu Ala Gln Gly Leu Val Val Ala
    130                 135                 140

Arg Gln Gln Leu Ala Ala Asp Thr Gln Lys Leu Ser Lys Asp Leu Gln
145                 150                 155                 160

Arg Asn Leu Gly Glu Ala Gln Gln Leu Pro Ala Leu Val Ala Glu Arg
                165                 170                 175

Asp Ala Ala Arg Gln Glu Tyr Gln His Leu Arg Ala Thr Tyr Glu Tyr
            180                 185                 190

Glu Arg Lys Leu Arg Met Asp His Ser Glu Ser Leu Gln Val Met Lys
        195                 200                 205

Arg Asn Tyr Asp Thr Met Val Ala Glu Leu Asp Lys Leu Arg Ala Glu
    210                 215                 220

Leu Met Asn Thr Ala Asn Ile Asp Arg Gly Gly Met Pro Phe Ile Cys
225                 230                 235                 240

Cys Ser Ile Phe Phe Thr Thr Ile Phe Gly Ser Ile Tyr Arg Asn His
                245                 250                 255

Thr Met Arg His Phe Leu Cys Val Gly Met Leu Tyr Asn Thr Asn Thr
            260                 265                 270

Ala Gln Lys Asp Asp Gly Ala Pro Ser Leu Pro Val Gly Gln Ile Ala
        275                 280                 285

Tyr Asp Ser Gly Tyr Gly Ala Ala Gln Gly Arg Thr Pro Pro Ala Gly
    290                 295                 300

Leu Gly Asp Ser Leu Ser Gly Asn Pro Ala Gly Thr Ala Pro Arg Thr
305                 310                 315                 320

Gly Phe Asp Pro Ser Arg Gly Asn Met Tyr Asp Ala Ser Arg Ile Ala
                325                 330                 335

Ser Phe Ser Ser Ser Lys Ala Gly Gly His Asp Ala Ser Arg Gly Ala
            340                 345                 350

Ala Gly Tyr Asn Ser Leu Lys Gly Ala Gly Tyr Asp Pro Ser Lys Ala
        355                 360                 365

Pro Ala Leu Gly Gly Gln Ala Thr Ala Ala Ala Ala His Gly Ser Ser
    370                 375                 380

Ala Asp Tyr Tyr Gly Ser Asn Gln Ala Thr Pro Pro Ser Tyr Ala Trp
385                 390                 395                 400

Gly Gln Ala Ala Ser Ala Tyr Gly Ser Ala Gln Val Pro Gln Ser His
                405                 410                 415

Ala Ser Gly Pro Pro Val Gln Ser Thr Ser Tyr Ser Ala Thr Thr Ala
            420                 425                 430

Arg Asn Phe Gly Ser Ala Gln Ala Leu Pro Ser Tyr Ala His Ala Gln
        435                 440                 445

Glu Gln Pro Ser Tyr Gly His Ala Gln Leu Pro Ser Ser Tyr Gly Leu
    450                 455                 460

Ala Gln Ala Ser Phe Pro Phe Ala Pro Ala Gln Gly Val Ser Pro Tyr
465                 470                 475                 480

Gly Ser Gly Ala Gln Pro Pro Gln Tyr Gly Ala Gly Gln Ala Ala Thr
                485                 490                 495
```

```
Asn Pro Gly Ser Ala Tyr Gln Ala Pro His Gly Arg Lys
            500                 505


<210> SEQ ID NO 54
<211> LENGTH: 930
<212> TYPE: DNA
<213> ORGANISM: Picea sitchensis

<400> SEQUENCE: 54

atggctggaa gaaatcgcct acctgcacac cctcttaagg gcggtccacg gggaatgcct      60

ccaatgcgag agggccctta tgccaggggt ccagggcctt tgccacctca tcctggcctt     120

gttgaagaga ttcgtgatgg cccctttgga agaggcccag gtcctctgcc cccacaccct     180

gcattgatcg aggagaagct tgcagctcag catcaagaga ttcagggact acttgtggag     240

aatcagcggc ttgctgccac tcatgtagct ttacgacagg aacttgcatc agcgcagcag     300

gagctgcaac acatgaatca tatggctgct aatatgcagg ctgacaaaga gcaccatctc     360

agggagttgt atgacaaatc tatgaagcta gaagcagatt tgcgtgcaaa tgagccaatg     420

aaagctgaac ttatgcagct gcgtgcagat aatcagaaga tgggtgctat caggcaagaa     480

atgacagctc aggtgcaagc acttacacaa gatttggtga gagctcgagc agatatgcag     540

caggtgggtg ccatgagggc agagatagaa agcatgcacc aggagctgca acgagcaaga     600

actgccattg aatatgagaa gaaggcacgt gctgaccagc tggagcaggg tcaggcaatg     660

gagaaaaact tgatctcaat ggctcgtgaa gttgagaaac ttcgagctga gcttgcaaat     720

gctgacaaga gagggcgtgt tgctgcaaac cctggtggag catatgctgg gaactatggt     780

ggtgcagaaa tgggctactc gggtggtgct tatggtgatg gttatggcgt gcacccggcc     840

caagggggtg cagaaagtgg tggtcagtat ggggctggag ctgctccatg gggagcatat     900

gaaatgcagc gttcccatgt acgtagataa                                     930


<210> SEQ ID NO 55
<211> LENGTH: 309
<212> TYPE: PRT
<213> ORGANISM: Picea sitchensis

<400> SEQUENCE: 55

Met Ala Gly Arg Asn Arg Leu Pro Ala His Pro Leu Lys Gly Gly Pro
1               5                   10                  15

Arg Gly Met Pro Pro Met Arg Glu Gly Pro Tyr Ala Arg Gly Pro Gly
            20                  25                  30

Pro Leu Pro Pro His Pro Gly Leu Val Glu Glu Ile Arg Asp Gly Pro
        35                  40                  45

Phe Gly Arg Gly Pro Gly Pro Leu Pro Pro His Pro Ala Leu Ile Glu
    50                  55                  60

Glu Lys Leu Ala Ala Gln His Gln Glu Ile Gln Gly Leu Leu Val Glu
65                  70                  75                  80

Asn Gln Arg Leu Ala Ala Thr His Val Ala Leu Arg Gln Glu Leu Ala
                85                  90                  95

Ser Ala Gln Gln Glu Leu Gln His Met Asn His Met Ala Ala Asn Met
            100                 105                 110

Gln Ala Asp Lys Glu His His Leu Arg Glu Leu Tyr Asp Lys Ser Met
        115                 120                 125

Lys Leu Glu Ala Asp Leu Arg Ala Asn Glu Pro Met Lys Ala Glu Leu
    130                 135                 140

Met Gln Leu Arg Ala Asp Asn Gln Lys Met Gly Ala Ile Arg Gln Glu
```

-continued

```
145                 150                 155                 160

Met Thr Ala Gln Val Gln Ala Leu Thr Gln Asp Leu Val Arg Ala Arg
                165                 170                 175

Ala Asp Met Gln Gln Val Gly Ala Met Arg Ala Glu Ile Glu Ser Met
            180                 185                 190

His Gln Glu Leu Gln Arg Ala Arg Thr Ala Ile Glu Tyr Glu Lys Lys
        195                 200                 205

Ala Arg Ala Asp Gln Leu Glu Gln Gly Gln Ala Met Glu Lys Asn Leu
    210                 215                 220

Ile Ser Met Ala Arg Glu Val Glu Lys Leu Arg Ala Glu Leu Ala Asn
225                 230                 235                 240

Ala Asp Lys Arg Gly Arg Val Ala Ala Asn Pro Gly Gly Ala Tyr Ala
                245                 250                 255

Gly Asn Tyr Gly Gly Ala Glu Met Gly Tyr Ser Gly Gly Ala Tyr Gly
            260                 265                 270

Asp Gly Tyr Gly Val His Pro Ala Gln Gly Gly Ala Glu Ser Gly Gly
        275                 280                 285

Gln Tyr Gly Ala Gly Ala Ala Pro Trp Gly Ala Tyr Glu Met Gln Arg
    290                 295                 300

Ser His Val Arg Arg
305
```

<210> SEQ ID NO 56
<211> LENGTH: 894
<212> TYPE: DNA
<213> ORGANISM: Populus tremuloides

<400> SEQUENCE: 56

```
atgtctgcaa gaaggcatat tcgaccaact ttagaagggc gtgttatcca agcacctggg      60

atgatgcgtc atggtccatt tcctgctggc caccatacat cagaaccact ctctcgttct     120

gatcttctag agcataggtt tgctgctcag gctgcggaca ttgaacaact tgcaggggat     180

aataatagac tggttactag tcacatggcc ttgagggagg accttgctgc tgctcagcag     240

gaagtgcaaa gactcaaggc acatattaga agcatccaga ctgaaagtga tatccagatc     300

agggttttgc tggataaaat tgcaaaaatg gaaaaagaca tcagggctgg tgagaacgtg     360

aaaaaggacc tcaaacaggc acatgtggag gcacagaact tggtcaaaga aagacaagag     420

cttgctacac aaatccaaca ggcttcacac gagttgcaga aaatccacac tgatgtaaag     480

agtataccag atctgcatgc tgagcttgag aattcaaggc atgaactcaa gaggttaaga     540

gctacattcg agtacgaaaa aggattaaat atagagaagg tggagcaaat gcgagcaatg     600

gaacagaatc tcataggtat ggcaagagaa atggaaaatt tgcgcgttga tgtcttgaat     660

gctgagacca gagcacgtgc tccaaaccaa tatattggtg gctacgcaaa tcctgatgga     720

tatgggaggc cttttgttca catgggtgtt ggaccagcag gggaagggat aattccttac     780

aacagtagca acagtgtagt gtccaatgtt gggtttggtg gtgcagcaat gtctactact     840

ggtggtgtcg ctcaatgggt agggcctttt gatccgtcac atgctcgggg gtga           894
```

<210> SEQ ID NO 57
<211> LENGTH: 297
<212> TYPE: PRT
<213> ORGANISM: Populus tremuloides

<400> SEQUENCE: 57

```
Met Ser Ala Arg Arg His Ile Arg Pro Thr Leu Glu Gly Arg Val Ile
```

-continued

```
1               5                   10                  15

Gln Ala Pro Gly Met Met Arg His Gly Pro Phe Pro Ala Gly His His
            20                  25                  30

Thr Ser Glu Pro Leu Ser Arg Ser Asp Leu Leu Glu His Arg Phe Ala
        35                  40                  45

Ala Gln Ala Ala Asp Ile Glu Gln Leu Ala Gly Asp Asn Asn Arg Leu
    50                  55                  60

Val Thr Ser His Met Ala Leu Arg Glu Asp Leu Ala Ala Ala Gln Gln
65                  70                  75                  80

Glu Val Gln Arg Leu Lys Ala His Ile Arg Ser Ile Gln Thr Glu Ser
                85                  90                  95

Asp Ile Gln Ile Arg Val Leu Leu Asp Lys Ile Ala Lys Met Glu Lys
            100                 105                 110

Asp Ile Arg Ala Gly Glu Asn Val Lys Lys Asp Leu Lys Gln Ala His
        115                 120                 125

Val Glu Ala Gln Asn Leu Val Lys Glu Arg Gln Glu Leu Ala Thr Gln
    130                 135                 140

Ile Gln Gln Ala Ser His Glu Leu Gln Lys Ile His Thr Asp Val Lys
145                 150                 155                 160

Ser Ile Pro Asp Leu His Ala Glu Leu Glu Asn Ser Arg His Glu Leu
                165                 170                 175

Lys Arg Leu Arg Ala Thr Phe Glu Tyr Glu Lys Gly Leu Asn Ile Glu
            180                 185                 190

Lys Val Glu Gln Met Arg Ala Met Glu Gln Asn Leu Ile Gly Met Ala
        195                 200                 205

Arg Glu Met Glu Asn Leu Arg Val Asp Val Leu Asn Ala Glu Thr Arg
    210                 215                 220

Ala Arg Ala Pro Asn Gln Tyr Ile Gly Gly Tyr Ala Asn Pro Asp Gly
225                 230                 235                 240

Tyr Gly Arg Pro Phe Val His Met Gly Val Gly Pro Ala Gly Glu Gly
                245                 250                 255

Ile Ile Pro Tyr Asn Ser Ser Asn Ser Val Val Ser Asn Val Gly Phe
            260                 265                 270

Gly Gly Ala Ala Met Ser Thr Thr Gly Gly Val Ala Gln Trp Val Gly
        275                 280                 285

Pro Phe Asp Pro Ser His Ala Arg Gly
    290                 295
```

<210> SEQ ID NO 58
<211> LENGTH: 1272
<212> TYPE: DNA
<213> ORGANISM: Saccharum officinarum
<220> FEATURE:
<221> NAME/KEY: misc_feature
<222> LOCATION: (1219)..(1219)
<223> OTHER INFORMATION: n is a, c, g, or t

<400> SEQUENCE: 58

```
atggctcgcc gtggacacct agatggactg actgcccaag ctccagctct gatgcgccat      60

ggttccttcg ctgcaggcag cctgtctagc cactcacctt tgcagtcttc atccacactg     120

gagatgctgg agagcaagct tgccatgcaa actgcagaag tggaaaagct tatcatggag     180

aatcagcggt tagcatcaag ccatgtggtc ctgaggcagg acatcgttga tacggagaaa     240

gagatgcaaa tgatccgcac ccacctaagt gaagttcaga cagagactga tctgcagatt     300

agagatttgt tggagagaat cagattaatg gaggcagaca tacatagtgg tgatgcagtg     360
```

```
aagaaagagc ttcaccaagt gcatatggag gcaaagagac ttattactga aaggcagatg    420

ctaacccttg agatagataa tgtgactaaa gaattacata aaatctctgc ccctggtgac    480

gggaaaagcc ttcctgaatt gcttgctgag ctagatgggc tacggaaaga gcatcataat    540

ttacgatctc aatttgaata tgagaaaaat acaaacatca agcaagttga gcagatgcgg    600

acaatggaaa tgaacctgat aaccatgact aaacaagctg agaagttacg tggtgatgtg    660

gcaaatgctg aaagacgggc acaggcagct gcggctcaag cagcggcaca tgcagctggt    720

gcacaggtga cagcttcaca gcctgggaca gctcaagcta cagcggtttc agcagcagct    780

acagacccat atgctggtgc atatgccagt tacccctcgg catatcagca gggagcccag    840

gctggggcat atcagcaggg agcccaggct ggggcatatc agcagggaac ccaagctggg    900

gcatatcagc ttggggcata tcaacaggga acccaagctg gggcatatca aaaaggaaac    960

caagctggaa catacaccta tgcttatgat gctgccaccg cttacacata tgcgggttac   1020

tccggttatc caattgcagg ctatgcgcaa aaggcagtgc ccaattattc ctatgccgta   1080

cctccgcagc caagcagcgg tgcagctaca gacgccgcaa gcctgtatgg cgcagctggt   1140

agtgctggat atcctactgg gcaagttcag ccgagcagtg tcactgcaaa tgcagcgcaa   1200

ccaccttctt caccactgnc gactgcacca tatcctagca catatgacca aaccagagga   1260

gcccagagat ga                                                        1272


<210> SEQ ID NO 59
<211> LENGTH: 423
<212> TYPE: PRT
<213> ORGANISM: Saccharum officinarum
<220> FEATURE:
<221> NAME/KEY: misc_feature
<222> LOCATION: (407)..(407)
<223> OTHER INFORMATION: Xaa can be any naturally occurring amino acid

<400> SEQUENCE: 59

Met Ala Arg Arg Gly His Leu Asp Gly Leu Thr Ala Gln Ala Pro Ala
1               5                   10                  15

Leu Met Arg His Gly Ser Phe Ala Ala Gly Ser Leu Ser Ser His Ser
            20                  25                  30

Pro Leu Gln Ser Ser Ser Thr Leu Glu Met Leu Glu Ser Lys Leu Ala
        35                  40                  45

Met Gln Thr Ala Glu Val Glu Lys Leu Ile Met Glu Asn Gln Arg Leu
    50                  55                  60

Ala Ser Ser His Val Val Leu Arg Gln Asp Ile Val Asp Thr Glu Lys
65                  70                  75                  80

Glu Met Gln Met Ile Arg Thr His Leu Ser Glu Val Gln Thr Glu Thr
                85                  90                  95

Asp Leu Gln Ile Arg Asp Leu Leu Glu Arg Ile Arg Leu Met Glu Ala
            100                 105                 110

Asp Ile His Ser Gly Asp Ala Val Lys Lys Glu Leu His Gln Val His
        115                 120                 125

Met Glu Ala Lys Arg Leu Ile Thr Glu Arg Gln Met Leu Thr Leu Glu
    130                 135                 140

Ile Asp Asn Val Thr Lys Glu Leu His Lys Ile Ser Ala Pro Gly Asp
145                 150                 155                 160

Gly Lys Ser Leu Pro Glu Leu Leu Ala Glu Leu Asp Gly Leu Arg Lys
                165                 170                 175

Glu His His Asn Leu Arg Ser Gln Phe Glu Tyr Glu Lys Asn Thr Asn
```

```
            180                 185                 190

Ile Lys Gln Val Glu Gln Met Arg Thr Met Glu Met Asn Leu Ile Thr
        195                 200                 205

Met Thr Lys Gln Ala Glu Lys Leu Arg Gly Asp Val Ala Asn Ala Glu
    210                 215                 220

Arg Arg Ala Gln Ala Ala Ala Ala Gln Ala Ala Ala His Ala Ala Gly
225                 230                 235                 240

Ala Gln Val Thr Ala Ser Gln Pro Gly Thr Ala Gln Ala Thr Ala Val
                245                 250                 255

Ser Ala Ala Ala Thr Asp Pro Tyr Ala Gly Ala Tyr Ala Ser Tyr Pro
            260                 265                 270

Ser Ala Tyr Gln Gln Gly Ala Gln Ala Gly Ala Tyr Gln Gln Gly Ala
        275                 280                 285

Gln Ala Gly Ala Tyr Gln Gln Gly Thr Gln Ala Gly Ala Tyr Gln Leu
    290                 295                 300

Gly Ala Tyr Gln Gln Gly Thr Gln Ala Gly Ala Tyr Gln Lys Gly Asn
305                 310                 315                 320

Gln Ala Gly Thr Tyr Thr Tyr Ala Tyr Asp Ala Ala Thr Ala Tyr Thr
                325                 330                 335

Tyr Ala Gly Tyr Ser Gly Tyr Pro Ile Ala Gly Tyr Ala Gln Lys Ala
            340                 345                 350

Val Pro Asn Tyr Ser Tyr Ala Val Pro Pro Gln Pro Ser Ser Gly Ala
        355                 360                 365

Ala Thr Asp Ala Ala Ser Leu Tyr Gly Ala Ala Gly Ser Ala Gly Tyr
    370                 375                 380

Pro Thr Gly Gln Val Gln Pro Ser Ser Val Thr Ala Asn Ala Ala Gln
385                 390                 395                 400

Pro Pro Ser Ser Pro Leu Xaa Thr Ala Pro Tyr Pro Ser Thr Tyr Asp
                405                 410                 415

Gln Thr Arg Gly Ala Gln Arg
            420
```

<210> SEQ ID NO 60
<211> LENGTH: 1344
<212> TYPE: DNA
<213> ORGANISM: Sorghum bicolor

<400> SEQUENCE: 60

```
atgttcagga taatggctca tcgtggtcac ctagatggac tgactgccca agctccagct      60

ctgatgcacc atggttcctt cgctgctggc aaactctcta gccactcacc tttgcagtct     120

tcatccacac tggagatgct ggagaacaag cttgccatgc aaactgcaga agtagaaaag     180

cttatcatgg agaatcagcg gttagcatca agccatgtgg tcttgaggca ggacattgtt     240

gatacggaga aagagatgca aatgatccgc acccacctag gtgaagttca gacagagact     300

gatttgcaga ttagagattt gttggagaga atcagattaa tggaggcaga catacatagt     360

ggtgatgcag tgaagaagga gcttcaccaa gtgcatatgg aggcaaagag acttattact     420

gaaaggcaga tgctaaccct tgacatagag aatgtgatta aagaattaca gaaactctct     480

gcctctggtg acggtaaaag ccttcctgaa ttgcttgctg agctagatgg gctacggaaa     540

gagcatcata atttacgatc tcaatttgaa tttgagaaaa atacaaacat caagcaagtt     600

gagcagatgc ggacaatgga aatgaacctg ataaccatga ctaaacaagc cgagaagtta     660

cgtggtgatg tagcaaatgc tgaaagacgg gcacaggcag ctgcggctca agcagcggca     720
```

-continued

```
catgcagctg gtgcgcaggt gacagcttca cagcctggga cagctcaagc tacagcggtt    780

tcagcagcag ctacagaccc atatgcaggt gcatatgcca gttacccctc ggcatatcag    840

cagggagccc aggctgcagc atatcagcag ggagcccagg ctgcggcata tcagcaggga    900

gcccaggctg ggcatatca gcagggagcc caggctgggg catatcagca gggagcccag    960

gctggggcat atcagcaggg agcccaggtt ggggcatatc agcacggaac ccaagctggg   1020

gcatatcagc aaggaaacca ggctggagca tacacctatg cttatgatgc tgccacggct   1080

tacgcatatg caggttactc tggctatcca ggctatgcgc aaagtgcagt gcccaattat   1140

tcctatgccg tacctccgca gccaagcagc ggtgcaacta cagaggccgc aagcatgtat   1200

ggcgcagctg gtagtgctgg atatcctact gcgcaagttc agccgagcag tgccactgca   1260

aatgcagcgc aaccacctcc tccaccaccg cctgcagcac catatcctag cacatatgac   1320

caaaccagag gagcccagag gtga                                          1344
```

```
<210> SEQ ID NO 61
<211> LENGTH: 443
<212> TYPE: PRT
<213> ORGANISM: Sorghum bicolor

<400> SEQUENCE: 61

Met Ala His Arg Gly His Leu Asp Gly Leu Thr Ala Gln Ala Pro Ala
1               5                   10                  15

Leu Met His His Gly Ser Phe Ala Ala Gly Lys Leu Ser Ser His Ser
            20                  25                  30

Pro Leu Gln Ser Ser Ser Thr Leu Glu Met Leu Glu Asn Lys Leu Ala
        35                  40                  45

Met Gln Thr Ala Glu Val Glu Lys Leu Ile Met Glu Asn Gln Arg Leu
    50                  55                  60

Ala Ser Ser His Val Val Leu Arg Gln Asp Ile Val Asp Thr Glu Lys
65                  70                  75                  80

Glu Met Gln Met Ile Arg Thr His Leu Gly Glu Val Gln Thr Glu Thr
                85                  90                  95

Asp Leu Gln Ile Arg Asp Leu Leu Glu Arg Ile Arg Leu Met Glu Ala
            100                 105                 110

Asp Ile His Ser Gly Asp Ala Val Lys Lys Glu Leu His Gln Val His
        115                 120                 125

Met Glu Ala Lys Arg Leu Ile Thr Glu Arg Gln Met Leu Thr Leu Asp
    130                 135                 140

Ile Glu Asn Val Ile Lys Glu Leu Gln Lys Leu Ser Ala Ser Gly Asp
145                 150                 155                 160

Gly Lys Ser Leu Pro Glu Leu Leu Ala Glu Leu Asp Gly Leu Arg Lys
                165                 170                 175

Glu His His Asn Leu Arg Ser Gln Phe Glu Phe Glu Lys Asn Thr Asn
            180                 185                 190

Ile Lys Gln Val Glu Gln Met Arg Thr Met Glu Met Asn Leu Ile Thr
        195                 200                 205

Met Thr Lys Gln Ala Glu Lys Leu Arg Gly Asp Val Ala Asn Ala Glu
    210                 215                 220

Arg Arg Ala Gln Ala Ala Ala Ala Gln Ala Ala Ala His Ala Ala Gly
225                 230                 235                 240

Ala Gln Val Thr Ala Ser Gln Pro Gly Thr Ala Gln Ala Thr Ala Val
                245                 250                 255

Ser Ala Ala Ala Thr Asp Pro Tyr Ala Gly Ala Tyr Ala Ser Tyr Pro
```

```
            260                 265                 270

Ser Ala Tyr Gln Gln Gly Ala Gln Ala Ala Ala Tyr Gln Gln Gly Ala
        275                 280                 285

Gln Ala Ala Ala Tyr Gln Gln Gly Ala Gln Ala Gly Ala Tyr Gln Gln
    290                 295                 300

Gly Ala Gln Ala Gly Ala Tyr Gln Gln Gly Ala Gln Ala Gly Ala Tyr
305                 310                 315                 320

Gln Gln Gly Ala Gln Val Gly Ala Tyr Gln His Gly Thr Gln Ala Gly
                325                 330                 335

Ala Tyr Gln Gln Gly Asn Gln Ala Gly Ala Tyr Thr Tyr Ala Tyr Asp
            340                 345                 350

Ala Ala Thr Ala Tyr Ala Tyr Ala Gly Tyr Ser Gly Tyr Pro Gly Tyr
        355                 360                 365

Ala Gln Ser Ala Val Pro Asn Tyr Ser Tyr Ala Val Pro Pro Gln Pro
    370                 375                 380

Ser Ser Gly Ala Thr Thr Glu Ala Ala Ser Met Tyr Gly Ala Ala Gly
385                 390                 395                 400

Ser Ala Gly Tyr Pro Thr Ala Gln Val Gln Pro Ser Ser Ala Thr Ala
                405                 410                 415

Asn Ala Ala Gln Pro Pro Pro Pro Pro Pro Pro Ala Ala Pro Tyr Pro
            420                 425                 430

Ser Thr Tyr Asp Gln Thr Arg Gly Ala Gln Arg
        435                 440
```

```
<210> SEQ ID NO 62
<211> LENGTH: 1512
<212> TYPE: DNA
<213> ORGANISM: Zea mays

<400> SEQUENCE: 62

atggctcacc gtggacacct agatggactg actgcccaag ctccagcact gatgcgccat      60

ggttccttcg ctgcaggcag cctttctagc cactcacctt tggagtcttc atctacactg     120

gagatgctgg agaacaagct tgccatgcag actgcagaag tggaaaagct tatcatggag     180

aatcagcggt tagcatcaag ccatgtggtc ttgaggcagg acattgttga tacagagaaa     240

gagatgcaaa taatccgcac ccacctaggt gaagttcaga cagagactga tttgcatatt     300

agagatttat tggagagaat tagattaatg gaggcagaca tacatagtgg tgatgcggtg     360

aagaaggagc ttcatcaagt gcatatggag gcaaagagac ttattactga aaggcagatg     420

ctgacccttg agacagagga tgtgaataaa gaattacaga aactctctgc ctctggtgac     480

agtaaaagcc ttcctgaatt gctagctgag ctagatgggc taaggaaaga gcatcttaat     540

ttacgatctc aatttgaatt tgagaaaaat acaaacatca agcaagttga gcagatgcgg     600

acaatggaaa tgaacttgat gaccatgact aaacaagctg agaagttacg aggtgatgtg     660

gcaaatgctg aaagacgggc acaggcagct gtggctaaag caacagggca tgcagctggt     720

gcacaggtga cagcttcaca gcctgggaca gctcaagcta cagcggttcc agcagcagct     780

acagacccat atgcaggtgc atatgccagt tacccccctg catatcagca gggagcccag     840

gctggggcat atcagcaggg agcccaggct ggggcatatc agcagggagc ccaggctggg     900

gcatatcagc aggggggcca ggatggggca tatcagcagg gggctcaggc tggggcatat     960

cagcagggag cccaggctgg ggcatatcag cagggagccc aggctggggc atatcagcag    1020

ggtgctcagg ctggggcata tcagcaggga gcccaggctg ggcatatca gcagggggcc     1080
```

```
cagtctgggg catatcagca gggggcccag gctggggcat atcagcaggg agcccaggat   1140

ggggcatatc agcagggagc ccaggatggg gcatatcagc agggtgctca ggctggagca   1200

tacaactatg cttatgatgc tggcacggct tatgcatatg caggttactc tggctatcca   1260

gttgcaggct acgcgcaaag tgcagtgccc aactattctt atgctgcacc tccgcagcca   1320

acaagcagcg gtgcagctac gaacgccgca ggaggccagt atggggcagt tggtagtgct   1380

ggatatccta ctgggcaagt tcagccgagc agtggcactg caaatgcagc gcaagcacct   1440

cctcctccac caccaccggc agcaccatat ccccccagca catatgacca aaccagagga   1500

gcccagagat aa                                                       1512


<210> SEQ ID NO 63
<211> LENGTH: 503
<212> TYPE: PRT
<213> ORGANISM: Zea mays

<400> SEQUENCE: 63

Met Ala His Arg Gly His Leu Asp Gly Leu Thr Ala Gln Ala Pro Ala
1               5                   10                  15

Leu Met Arg His Gly Ser Phe Ala Ala Gly Ser Leu Ser Ser His Ser
            20                  25                  30

Pro Leu Glu Ser Ser Ser Thr Leu Glu Met Leu Glu Asn Lys Leu Ala
        35                  40                  45

Met Gln Thr Ala Glu Val Glu Lys Leu Ile Met Glu Asn Gln Arg Leu
    50                  55                  60

Ala Ser Ser His Val Val Leu Arg Gln Asp Ile Val Asp Thr Glu Lys
65                  70                  75                  80

Glu Met Gln Ile Ile Arg Thr His Leu Gly Glu Val Gln Thr Glu Thr
                85                  90                  95

Asp Leu His Ile Arg Asp Leu Leu Glu Arg Ile Arg Leu Met Glu Ala
            100                 105                 110

Asp Ile His Ser Gly Asp Ala Val Lys Lys Glu Leu His Gln Val His
        115                 120                 125

Met Glu Ala Lys Arg Leu Ile Thr Glu Arg Gln Met Leu Thr Leu Glu
    130                 135                 140

Thr Glu Asp Val Asn Lys Glu Leu Gln Lys Leu Ser Ala Ser Gly Asp
145                 150                 155                 160

Ser Lys Ser Leu Pro Glu Leu Leu Ala Glu Leu Asp Gly Leu Arg Lys
                165                 170                 175

Glu His Leu Asn Leu Arg Ser Gln Phe Glu Phe Glu Lys Asn Thr Asn
            180                 185                 190

Ile Lys Gln Val Glu Gln Met Arg Thr Met Glu Met Asn Leu Met Thr
        195                 200                 205

Met Thr Lys Gln Ala Glu Lys Leu Arg Gly Asp Val Ala Asn Ala Glu
    210                 215                 220

Arg Arg Ala Gln Ala Ala Val Ala Lys Ala Thr Gly His Ala Ala Gly
225                 230                 235                 240

Ala Gln Val Thr Ala Ser Gln Pro Gly Thr Ala Gln Ala Thr Ala Val
                245                 250                 255

Pro Ala Ala Ala Thr Asp Pro Tyr Ala Gly Ala Tyr Ala Ser Tyr Pro
            260                 265                 270

Pro Ala Tyr Gln Gln Gly Ala Gln Ala Gly Ala Tyr Gln Gln Gly Ala
        275                 280                 285

Gln Ala Gly Ala Tyr Gln Gln Gly Ala Gln Ala Gly Ala Tyr Gln Gln
```

```
    290                 295                 300

Gly Gly Gln Asp Gly Ala Tyr Gln Gln Gly Ala Gln Ala Gly Ala Tyr
305                 310                 315                 320

Gln Gln Gly Ala Gln Ala Gly Ala Tyr Gln Gln Gly Ala Gln Ala Gly
                325                 330                 335

Ala Tyr Gln Gln Gly Ala Gln Ala Gly Ala Tyr Gln Gln Gly Ala Gln
            340                 345                 350

Ala Gly Ala Tyr Gln Gln Gly Ala Gln Ser Gly Ala Tyr Gln Gln Gly
        355                 360                 365

Ala Gln Ala Gly Ala Tyr Gln Gln Gly Ala Gln Asp Gly Ala Tyr Gln
    370                 375                 380

Gln Gly Ala Gln Asp Gly Ala Tyr Gln Gln Gly Ala Gln Ala Gly Ala
385                 390                 395                 400

Tyr Asn Tyr Ala Tyr Asp Ala Gly Thr Ala Tyr Ala Tyr Ala Gly Tyr
                405                 410                 415

Ser Gly Tyr Pro Val Ala Gly Tyr Ala Gln Ser Ala Val Pro Asn Tyr
            420                 425                 430

Ser Tyr Ala Ala Pro Pro Gln Pro Thr Ser Ser Gly Ala Ala Thr Asn
        435                 440                 445

Ala Ala Gly Gly Gln Tyr Gly Ala Val Gly Ser Ala Gly Tyr Pro Thr
    450                 455                 460

Gly Gln Val Gln Pro Ser Ser Gly Thr Ala Asn Ala Ala Gln Ala Pro
465                 470                 475                 480

Pro Pro Pro Pro Pro Pro Ala Ala Pro Tyr Pro Pro Ser Thr Tyr Asp
                485                 490                 495

Gln Thr Arg Gly Ala Gln Arg
            500


<210> SEQ ID NO 64
<211> LENGTH: 1605
<212> TYPE: DNA
<213> ORGANISM: Zea mays

<400> SEQUENCE: 64

atggctcatc gtggacatct agatggactg actggccaag ctcctgctct tatgcgccat      60

ggttccttcg ctgcaggcag cctctctagc cgctcacctt tgcagtcttc atccacactg     120

gagatgctgg agaacaagct tgccatgcaa actacagaag tggaaaagct tatcacggag     180

aatcagcggt tagcatcaag ccatgtggtc ttgaggcagg acattgttga tacggagaaa     240

gagatgcaaa tgatccgcac ccacctaggt gaagttcaga cagagactga tttgcagatt     300

agagatttgt tggagagaat cagattaatg gaggtagata tacatagtgg taatgtagtg     360

aacaaggagc ttcaccaaat gcatatggag gcaaagagac ttattactga aaggcagatg     420

ctaacccttg agatagagga tgtgactaaa gaattacaga aactctctgc ctctggggac     480

aataaaagcc ttcctgaatt gctttctgag ctagataggc tacggaaaga gcatcataat     540

ttacgatctc agtttgaatt tgagaaaaat acaaacgtca agcaagttga gcagatgcgg     600

acaatggaaa tgaacttgat aaccatgacc aaacaagctg agaagttacg tgttgatgtg     660

gcaaatgctg aaagacgggc acaagcagct gcggctcaag cagcagcaca tgcagctggt     720

gcacaggtga cagcttcgca gcctggacag ctcaagctac cacggtttca gcagcagcag     780

ccacagactc atatgcaggt gcatatacca gctacccccc tgcatatcag cagggagccc     840

aggctggggc atatcagcag ggtgctcagg ctggggtata tcagcaggga gcccaggctg     900
```

-continued

```
gggcatatca gcagggagcc caggctgggg catatcagca ggggggccag gatggggcat    960

atcagcaggg ggctcaggct ggggcatatc agcagggagc ccaggctggg gcatatcagc   1020

agggagccca ggctggggca tatcagcagg gtgctcaggc tggggcatat cagcagggag   1080

cccaggctgg ggcatatcag cagggggccc agtctggggc atatcagcag gggggcccagg   1140

ctggggcata tcagcaggga gcccaggatg gggcatatca gcagggagcc caggatgggg   1200

catatcagca gggtgctcag gctggagcat acaactatgc ttatgatgct ggcacggctt   1260

atgcatatgc aggttactct ggctatccag ttgcaggcta cgcgcaaagt gcagtgccca   1320

actattccta tgctgcacct ccgcagccaa caagcagcgg tgcagctacg aacgccgcag   1380

gaggccagta tggggcagtt ggtagtgctg gatatcctac tgggcaagtt cagccgagca   1440

gtggcactgc aaatgcagcg caagcacctc ctcctccacc accaccggca gcaccatatc   1500

cccccagcac atatgaccaa accagaggag cccagagata aaatctggga tgtaaaccag   1560

atggatgttt gccatgcaca tttgttgagc agacaaatat ggtga                   1605
```

<210> SEQ ID NO 65
<211> LENGTH: 469
<212> TYPE: PRT
<213> ORGANISM: Zea mays

<400> SEQUENCE: 65

```
Met Ala His Arg Gly His Leu Asp Gly Leu Thr Ala Gln Ala Pro Ala
1               5                   10                  15

Leu Met Arg His Gly Ser Phe Ala Ala Gly Ser Leu Ser Ser His Ser
            20                  25                  30

Pro Leu Glu Ser Ser Ser Thr Leu Glu Met Leu Glu Asn Lys Leu Ala
        35                  40                  45

Met Gln Thr Ala Glu Val Glu Lys Leu Ile Met Glu Asn Gln Arg Leu
    50                  55                  60

Ala Ser Ser His Val Val Leu Arg Gln Asp Ile Val Asp Thr Glu Lys
65                  70                  75                  80

Glu Met Gln Ile Ile Arg Thr His Leu Gly Glu Val Gln Thr Glu Thr
                85                  90                  95

Asp Leu His Ile Arg Asp Leu Leu Glu Arg Ile Arg Leu Met Glu Ala
            100                 105                 110

Asp Ile His Ser Gly Asp Ala Val Lys Lys Glu Leu His Gln Val His
        115                 120                 125

Met Glu Ala Lys Arg Leu Ile Thr Glu Arg Gln Met Leu Thr Leu Glu
    130                 135                 140

Thr Glu Asp Val Thr Lys Glu Leu Gln Lys Leu Ser Ala Ser Gly Asp
145                 150                 155                 160

Ser Lys Ser Leu Pro Glu Leu Leu Ala Glu Leu Asp Gly Leu Arg Lys
                165                 170                 175

Glu His Leu Asn Leu Arg Ser Gln Phe Glu Phe Glu Lys Asn Thr Asn
            180                 185                 190

Ile Lys Gln Val Glu Gln Met Arg Thr Met Glu Met Asn Leu Met Thr
        195                 200                 205

Met Thr Lys Gln Ala Glu Lys Leu Arg Gly Asp Val Ala Asn Ala Glu
    210                 215                 220

Arg Arg Ala Gln Ala Ala Val Ala Lys Ala Thr Gly His Ala Ala Gly
225                 230                 235                 240

Ala Gln Val Thr Ala Ser Gln Pro Gly Thr Ala Gln Ala Thr Ala Val
                245                 250                 255
```

```
Pro Ala Ala Ala Thr Asp Pro Tyr Ala Gly Ala Tyr Ala Ser Tyr Pro
            260                 265                 270

Pro Ala Tyr Gln Gln Gly Ala Gln Ala Gly Ala Tyr Gln Gln Gly Ala
        275                 280                 285

Gln Ala Gly Thr Tyr Gln Gln Gly Ala Gly Thr Gln Ala Gly Ala Tyr
    290                 295                 300

Gln Gln Gly Ala Gln Ala Gly Ala Tyr Gln Gln Gly Ala Gln Ala Gly
305                 310                 315                 320

Ala Tyr Gln Gln Gly Ala Gln Ser Gly Ala Tyr Gln Gln Gly Ala Gln
                325                 330                 335

Ala Gly Ala Tyr Gln Gln Gly Ala Gln Asp Gly Ala Tyr Gln Gln Gly
            340                 345                 350

Ala Gln Asp Gly Ala Tyr Gln Gln Gly Ala Gln Ala Gly Ala Tyr Asn
        355                 360                 365

Tyr Ala Tyr Asp Ala Gly Thr Ala Tyr Ala Tyr Ala Gly Tyr Ser Gly
    370                 375                 380

Tyr Pro Val Ala Gly Tyr Ala Gln Ser Ala Val Pro Asn Tyr Ser Tyr
385                 390                 395                 400

Ala Ala Pro Pro Gln Pro Thr Ser Ser Gly Ala Ala Thr Asn Ala Ala
                405                 410                 415

Gly Gly Gln Tyr Gly Ala Val Gly Ser Ala Gly Tyr Pro Thr Gly Gln
            420                 425                 430

Val Gln Pro Ser Ser Gly Thr Ala Asn Ala Ala Gln Ala Pro Pro Pro
        435                 440                 445

Pro Pro Pro Pro Ala Ala Pro Tyr Pro Pro Ser Thr Tyr Asp Gln Thr
    450                 455                 460

Arg Gly Ala Gln Arg
465
```

<210> SEQ ID NO 66
<211> LENGTH: 1605
<212> TYPE: DNA
<213> ORGANISM: Zea mays

<400> SEQUENCE: 66

```
atggctcatc gtggacatct agatggactg actggccaag ctcctgctct tatgcgccat      60

ggttccttcg ctgcaggcag cctctctagc cgctcacctt tgcagtcttc atccacactg     120

gagatgctgg agaacaagct tgccatgcaa actacagaag tggaaaagct tatcacggag     180

aatcagcggt tagcatcaag ccatgtggtc ttgaggcagg acattgttga tacggagaaa     240

gagatgcaaa tgatccgcac ccacctaggt gaagttcaga cagagactga tttgcagatt     300

agagatttgt tggagagaat cagattaatg gaggtagata tacatagtgg taatgtagtg     360

aacaaggagc ttcaccaaat gcatatggag gcaaagagac ttattactga aaggcagatg     420

ctaacccttg agatagagga tgtgactaaa gaattacaga aactctctgc ctctggggac     480

aataaaagcc ttcctgaatt gctttctgag ctagataggc tacggaaaga gcatcataat     540

ttacgatctc agtttgaatt tgagaaaaat acaaacgtca agcaagttga gcagatgcgg     600

acaatggaaa tgaacttgat aaccatgacc aaacaagctg agaagttacg tgttgatgtg     660

gcaaatgctg aaagacgggc acaagcagct gcggctcaag cagcagcaca tgcagctggt     720

gcacaggtga cagcttcgca gcctggacag ctcaagctac cacggtttca gcagcagcag     780

ccacagactc atatgcaggt gcatatacca gctacccccc tgcatatcag cagggagccc     840
```

-continued

```
aggctggggc atatcagcag ggtgctcagg ctggggtata tcagcaggga gcccaggctg     900

gggcatatca gcagggagcc caggctgggg catatcagca ggggggccag gatggggcat     960

atcagcaggg ggctcaggct ggggcatatc agcagggagc ccaggctggg gcatatcagc    1020

agggagccca ggctggggca tatcagcagg gtgctcaggc tggggcatat cagcagggag    1080

cccaggctgg ggcatatcag caggggggccc agtctggggc atatcagcag ggggcccagg   1140

ctggggcata tcagcaggga gcccaggatg gggcatatca gcagggagcc caggatgggg    1200

catatcagca gggtgctcag gctggagcat acaactatgc ttatgatgct ggcacggctt    1260

atgcatatgc aggttactct ggctatccag ttgcaggcta cgcgcaaagt gcagtgccca    1320

actattccta tgctgcacct ccgcagccaa caagcagcgg tgcagctacg aacgccgcag    1380

gaggccagta tggggcagtt ggtagtgctg gatatcctac tgggcaagtt cagccgagca    1440

gtggcactgc aaatgcagcg caagcacctc ctcctccacc accaccggca gcaccatatc    1500

cccccagcac atatgaccaa accagaggag cccagagata aaatctggga tgtaaaccag    1560

atggatgttt gccatgcaca tttgttgagc agacaaatat ggtga                    1605
```

```
<210> SEQ ID NO 67
<211> LENGTH: 534
<212> TYPE: PRT
<213> ORGANISM: Zea mays

<400> SEQUENCE: 67

Met Ala His Arg Gly His Leu Asp Gly Leu Thr Gly Gln Ala Pro Ala
1               5                   10                  15

Leu Met Arg His Gly Ser Phe Ala Ala Gly Ser Leu Ser Ser Arg Ser
            20                  25                  30

Pro Leu Gln Ser Ser Ser Thr Leu Glu Met Leu Glu Asn Lys Leu Ala
        35                  40                  45

Met Gln Thr Thr Glu Val Glu Lys Leu Ile Thr Glu Asn Gln Arg Leu
    50                  55                  60

Ala Ser Ser His Val Val Leu Arg Gln Asp Ile Val Asp Thr Glu Lys
65                  70                  75                  80

Glu Met Gln Met Ile Arg Thr His Leu Gly Glu Val Gln Thr Glu Thr
                85                  90                  95

Asp Leu Gln Ile Arg Asp Leu Leu Glu Arg Ile Arg Leu Met Glu Val
            100                 105                 110

Asp Ile His Ser Gly Asn Val Val Asn Lys Glu Leu His Gln Met His
        115                 120                 125

Met Glu Ala Lys Arg Leu Ile Thr Glu Arg Gln Met Leu Thr Leu Glu
    130                 135                 140

Ile Glu Asp Val Thr Lys Glu Leu Gln Lys Leu Ser Ala Ser Gly Asp
145                 150                 155                 160

Asn Lys Ser Leu Pro Glu Leu Leu Ser Glu Leu Asp Arg Leu Arg Lys
                165                 170                 175

Glu His His Asn Leu Arg Ser Gln Phe Glu Phe Glu Lys Asn Thr Asn
            180                 185                 190

Val Lys Gln Val Glu Gln Met Arg Thr Met Glu Met Asn Leu Ile Thr
        195                 200                 205

Met Thr Lys Gln Ala Glu Lys Leu Arg Val Asp Val Ala Asn Ala Glu
    210                 215                 220

Arg Arg Ala Gln Ala Ala Ala Ala Gln Ala Ala Ala His Ala Ala Gly
225                 230                 235                 240
```

```
Ala Gln Val Thr Ala Ser Gln Pro Gly Gln Leu Lys Leu Pro Arg Phe
                245                 250                 255

Gln Gln Gln Gln Pro Gln Thr His Met Gln Val His Ile Pro Ala Thr
            260                 265                 270

Pro Leu His Ile Ser Arg Glu Pro Arg Leu Gly His Ile Ser Arg Val
        275                 280                 285

Leu Arg Leu Gly Tyr Ile Ser Arg Glu Pro Arg Leu Gly His Ile Ser
    290                 295                 300

Arg Glu Pro Arg Leu Gly His Ile Ser Arg Gly Ala Arg Met Gly His
305                 310                 315                 320

Ile Ser Arg Gly Leu Arg Leu Gly His Ile Ser Arg Glu Pro Arg Leu
                325                 330                 335

Gly His Ile Ser Arg Glu Pro Arg Leu Gly His Ile Ser Arg Val Leu
            340                 345                 350

Arg Leu Gly His Ile Ser Arg Glu Pro Arg Leu Gly His Ile Ser Arg
        355                 360                 365

Gly Pro Ser Leu Gly His Ile Ser Arg Gly Pro Arg Leu Gly His Ile
    370                 375                 380

Ser Arg Glu Pro Arg Met Gly His Ile Ser Arg Glu Pro Arg Met Gly
385                 390                 395                 400

His Ile Ser Arg Val Leu Arg Leu Glu His Thr Thr Met Leu Met Met
                 405                 410                 415

Leu Ala Arg Leu Met His Met Gln Val Thr Leu Ala Ile Gln Leu Gln
            420                 425                 430

Ala Thr Arg Lys Val Gln Cys Pro Thr Ile Pro Met Leu His Leu Arg
        435                 440                 445

Ser Gln Gln Ala Ala Val Gln Leu Arg Thr Pro Gln Glu Ala Ser Met
    450                 455                 460

Gly Gln Leu Val Val Leu Asp Ile Leu Leu Gly Lys Phe Ser Arg Ala
465                 470                 475                 480

Val Ala Leu Gln Met Gln Arg Lys His Leu Leu Leu His His His Arg
                485                 490                 495

Gln His His Ile Pro Pro Ala His Met Thr Lys Pro Glu Glu Pro Arg
            500                 505                 510

Asp Lys Ile Trp Asp Val Asn Gln Met Asp Val Cys His Ala His Leu
        515                 520                 525

Leu Ser Arg Gln Ile Trp
    530
```

<210> SEQ ID NO 68
<211> LENGTH: 1767
<212> TYPE: DNA
<213> ORGANISM: Zea mays

<400> SEQUENCE: 68

```
atggctcatc gtggacatct agatggactg actggccaag ctcctgctct tatgcgccat      60

ggttccttcg ctgcaggcag cctctctagc cgctcacctt tgcagtcttc atccacactg     120

gagatgctgg agaacaagct tgccatgcaa actacagaag tggaaaagct tatcacggag     180

aatcagcggt tagcatcaag ccatgtggtc ttgaggcagg acattgttga tacggagaaa     240

gagatgcaaa tgatccgcac ccacctaggt gaagttcaga cagagactga tttgcagatt     300

agagatttgt tggagagaat cagattaatg gaggtagata tacatagtgg taatgtagtg     360

aacaaggagc ttcaccaaat gcatatggag gcaaagagac ttattactga aaggcagatg     420
```

```
ctaacccttg agatagagga tgtgactaaa gaattacaga aactctctgc ctctggggac    480

aataaaagcc ttcctgaatt gctttctgag ctagataggc tacggaaaga gcatcataat    540

ttacgatctc agtttgaatt tgagaaaaat acaaacgtca agcaagttga gcagatgcgg    600

acaatggaaa tgaacttgat aaccatgacc aaacaagctg agaagttacg tgttgatgtg    660

gcaaatgctg aaagacgggc acaagcagct gcggctcaag cagcagcaca tgcagctggt    720

gcacaggtga cagcttcgca gcctggacag ctcaagctac cacggtttca gcagcagcag    780

ccacagactc atatgcaggt gcatatacca gctacccccc tgcatatcag cagggagccc    840

aggctggggc atatcagcag ggtgctcagg ctggggtata tcagcaggga gcccaggctg    900

gggcatatca gcagggagcc caggctgggg catatcagca ggggggccag gatggggcat    960

atcagcaggg ggctcaggct ggggcatatc agcagggagc ccaggctggg gcatatcagc   1020

agggagccca ggctggggca tatcagcagg gtgctcaggc tggggcatat cagcagggtg   1080

ctcaggctgg ggtatatcag cagggaaccc aggctggggc atatcagcag ggagcccagg   1140

ctggggcata tcagcagggg ggccaggatg gggcatatca gcagggggct caggctgggg   1200

catatcagca gggagcccag gctggggcat atcagcaggg agcccaggct ggggcatatc   1260

agcagggggc ccagtctggg gcatatcagc agggggccca ggctggggca tatcagcagg   1320

gagcccagga tggggcatat cagcagggag cccaggatgg ggcatatcag cagggtgctc   1380

aggctggagc atacaactat gcttatgatg ctggcacggc ttatgcatat gcaggttact   1440

ctggctatcc agttgcaggc tacgcgcaaa gtgcagtgcc caactattcc tatgctgcac   1500

ctccgcagcc aacaagcagc ggtgcagcta cgaacgccgc aggaggccag tatggggcag   1560

ttggtagtgc tggatatcct actgggcaag ttcagccgag cagtggcact gcaaatgcag   1620

cgcaagcacc tcctcctcca ccaccaccgg cagcaccata tcccccccagc acatatgacc   1680

aaaccagagg agcccagaga taaaatctgg gatgtaaacc agatggatgt ttgccatgca   1740

catttgttga gcagacaaat atggtga                                       1767
```

<210> SEQ ID NO 69
<211> LENGTH: 588
<212> TYPE: PRT
<213> ORGANISM: Zea mays

<400> SEQUENCE: 69

```
Met Ala His Arg Gly His Leu Asp Gly Leu Thr Gly Gln Ala Pro Ala
1               5                   10                  15

Leu Met Arg His Gly Ser Phe Ala Ala Gly Ser Leu Ser Ser Arg Ser
            20                  25                  30

Pro Leu Gln Ser Ser Ser Thr Leu Glu Met Leu Glu Asn Lys Leu Ala
        35                  40                  45

Met Gln Thr Thr Glu Val Glu Lys Leu Ile Thr Glu Asn Gln Arg Leu
    50                  55                  60

Ala Ser Ser His Val Val Leu Arg Gln Asp Ile Val Asp Thr Glu Lys
65                  70                  75                  80

Glu Met Gln Met Ile Arg Thr His Leu Gly Glu Val Gln Thr Glu Thr
                85                  90                  95

Asp Leu Gln Ile Arg Asp Leu Leu Glu Arg Ile Arg Leu Met Glu Val
            100                 105                 110

Asp Ile His Ser Gly Asn Val Val Asn Lys Glu Leu His Gln Met His
        115                 120                 125

Met Glu Ala Lys Arg Leu Ile Thr Glu Arg Gln Met Leu Thr Leu Glu
```

-continued

```
    130                 135                 140

Ile Glu Asp Val Thr Lys Glu Leu Gln Lys Leu Ser Ala Ser Gly Asp
145                 150                 155                 160

Asn Lys Ser Leu Pro Glu Leu Leu Ser Glu Leu Asp Arg Leu Arg Lys
                165                 170                 175

Glu His His Asn Leu Arg Ser Gln Phe Glu Phe Glu Lys Asn Thr Asn
            180                 185                 190

Val Lys Gln Val Glu Gln Met Arg Thr Met Glu Met Asn Leu Ile Thr
        195                 200                 205

Met Thr Lys Gln Ala Glu Lys Leu Arg Val Asp Val Ala Asn Ala Glu
    210                 215                 220

Arg Arg Ala Gln Ala Ala Ala Ala Gln Ala Ala Ala His Ala Ala Gly
225                 230                 235                 240

Ala Gln Val Thr Ala Ser Gln Pro Gly Gln Leu Lys Leu Pro Arg Phe
                245                 250                 255

Gln Gln Gln Gln Pro Gln Thr His Met Gln Val His Ile Pro Ala Thr
            260                 265                 270

Pro Leu His Ile Ser Arg Glu Pro Arg Leu Gly His Ile Ser Arg Val
        275                 280                 285

Leu Arg Leu Gly Tyr Ile Ser Arg Glu Pro Arg Leu Gly His Ile Ser
    290                 295                 300

Arg Glu Pro Arg Leu Gly His Ile Ser Arg Gly Ala Arg Met Gly His
305                 310                 315                 320

Ile Ser Arg Gly Leu Arg Leu Gly His Ile Ser Arg Glu Pro Arg Leu
                325                 330                 335

Gly His Ile Ser Arg Glu Pro Arg Leu Gly His Ile Ser Arg Val Leu
            340                 345                 350

Arg Leu Gly His Ile Ser Arg Val Leu Arg Leu Gly Tyr Ile Ser Arg
        355                 360                 365

Glu Pro Arg Leu Gly His Ile Ser Arg Glu Pro Arg Leu Gly His Ile
    370                 375                 380

Ser Arg Gly Ala Arg Met Gly His Ile Ser Arg Gly Leu Arg Leu Gly
385                 390                 395                 400

His Ile Ser Arg Glu Pro Arg Leu Gly His Ile Ser Arg Glu Pro Arg
                405                 410                 415

Leu Gly His Ile Ser Arg Gly Pro Ser Leu Gly His Ile Ser Arg Gly
            420                 425                 430

Pro Arg Leu Gly His Ile Ser Arg Glu Pro Arg Met Gly His Ile Ser
        435                 440                 445

Arg Glu Pro Arg Met Gly His Ile Ser Arg Val Leu Arg Leu Glu His
    450                 455                 460

Thr Thr Met Leu Met Met Leu Ala Arg Leu Met His Met Gln Val Thr
465                 470                 475                 480

Leu Ala Ile Gln Leu Gln Ala Thr Arg Lys Val Gln Cys Pro Thr Ile
                485                 490                 495

Pro Met Leu His Leu Arg Ser Gln Gln Ala Ala Val Gln Leu Arg Thr
            500                 505                 510

Pro Gln Glu Ala Ser Met Gly Gln Leu Val Val Leu Asp Ile Leu Leu
        515                 520                 525

Gly Lys Phe Ser Arg Ala Val Ala Leu Gln Met Gln Arg Lys His Leu
    530                 535                 540

Leu Leu His His His Arg Gln His His Ile Pro Pro Ala His Met Thr
545                 550                 555                 560
```

```
Lys Pro Glu Glu Pro Arg Asp Lys Ile Trp Asp Val Asn Gln Met Asp
                565                 570                 575

Val Cys His Ala His Leu Leu Ser Arg Gln Ile Trp
            580                 585


<210> SEQ ID NO 70
<211> LENGTH: 214
<212> TYPE: PRT
<213> ORGANISM: Artificial sequence
<220> FEATURE:
<223> OTHER INFORMATION: Coiled coil domain comprised in SEQ ID NO:2

<400> SEQUENCE: 70

Arg Gln Pro Leu Asp Arg Ala Ala Thr Ala Leu Glu Ile Leu Glu Lys
1               5                   10                  15

Lys Leu Ala Glu Gln Thr Ala Glu Ala Glu Lys Leu Ile Arg Glu Asn
            20                  25                  30

Gln Arg Leu Ala Ser Ser His Val Val Leu Arg Gln Asp Ile Val Asp
        35                  40                  45

Thr Glu Lys Glu Met Gln Met Ile Arg Ala His Leu Gly Asp Val Gln
    50                  55                  60

Thr Glu Thr Asp Met His Met Arg Asp Leu Met Glu Arg Met Arg Leu
65                  70                  75                  80

Met Glu Ala Asp Ile Gln Ala Gly Asp Ala Val Lys Lys Glu Leu His
                85                  90                  95

Gln Val His Met Glu Ala Lys Arg Leu Ile Ala Glu Arg Gln Met Leu
            100                 105                 110

Thr Val Glu Met Asp Lys Val Thr Lys Glu Leu His Lys Phe Ser Gly
        115                 120                 125

Asp Ser Lys Lys Leu Pro Glu Leu Leu Thr Glu Leu Asp Gly Leu Arg
    130                 135                 140

Lys Glu His Gln Ser Leu Arg Ser Ala Phe Glu Tyr Glu Lys Asn Thr
145                 150                 155                 160

Asn Ile Lys Gln Val Glu Gln Met Arg Thr Met Glu Met Asn Leu Met
                165                 170                 175

Thr Met Thr Lys Glu Ala Asp Lys Leu Arg Ala Asp Val Ala Asn Ala
            180                 185                 190

Glu Lys Arg Ala Gln Val Ala Ala Ala Gln Ala Val Ala Ala Gln Ala
        195                 200                 205

Gly Val Ala His Val Thr
    210


<210> SEQ ID NO 71
<211> LENGTH: 2194
<212> TYPE: DNA
<213> ORGANISM: Oryza sativa

<400> SEQUENCE: 71

aatccgaaaa gtttctgcac cgttttcacc ccctaactaa caatataggg aacgtgtgct      60

aaatataaaa tgagacctta tatatgtagc gctgataact agaactatgc aagaaaaact     120

catccaccta ctttagtggc aatcgggcta aataaaaaag agtcgctaca ctagtttcgt     180

tttccttagt aattaagtgg gaaaatgaaa tcattattgc ttagaatata cgttcacatc     240

tctgtcatga agttaaatta ttcgaggtag ccataattgt catcaaactc ttcttgaata     300

aaaaaatctt tctagctgaa ctcaatgggt aaagagagag atttttttta aaaaaataga     360
```

atgaagatat tctgaacgta ttggcaaaga tttaaacata taattatata attttatagt 420
ttgtgcattc gtcatatcgc acatcattaa ggacatgtct tactccatcc caatttttat 480
ttagtaatta aagacaattg acttattttt attatttatc ttttttcgat tagatgcaag 540
gtacttacgc acacactttg tgctcatgtg catgtgtgag tgcacctcct caatacacgt 600
tcaactagca acacatctct aatatcactc gcctatttaa tacatttagg tagcaatatc 660
tgaattcaag cactccacca tcaccagacc acttttaata atatctaaaa tacaaaaaat 720
aattttacag aatagcatga aaagtatgaa acgaactatt taggtttttc acatacaaaa 780
aaaaaaagaa ttttgctcgt gcgcgagcgc caatctccca tattgggcac acaggcaaca 840
acagagtggc tgcccacaga acaacccaca aaaaacgatg atctaacgga ggacagcaag 900
tccgcaacaa ccttttaaca gcaggctttg cggccaggag agaggaggag aggcaaagaa 960
aaccaagcat cctccttctc ccatctataa attcctcccc ccttttcccc tctctatata 1020
ggaggcatcc aagccaagaa gagggagagc accaaggaca cgcgactagc agaagccgag 1080
cgaccgcctt ctcgatccat atcttccggt cgagttcttg gtcgatctct tccctcctcc 1140
acctcctcct cacagggtat gtgcctccct tcggttgttc ttggatttat tgttctaggt 1200
tgtgtagtac gggcgttgat gttaggaaag gggatctgta tctgtgatga ttcctgttct 1260
tggatttggg atagaggggt tcttgatgtt gcatgttatc ggttcggttt gattagtagt 1320
atggttttca atcgtctgga gagctctatg gaaatgaaat ggtttaggga tcggaatctt 1380
gcgattttgt gagtaccttt tgtttgaggt aaaatcagag caccggtgat tttgcttggt 1440
gtaataaagt acggttgttt ggtcctcgat tctggtagtg atgcttctcg atttgacgaa 1500
gctatccttt gtttattccc tattgaacaa aaataatcca actttgaaga cggtcccgtt 1560
gatgagattg aatgattgat tcttaagcct gtccaaaatt tcgcagctgg cttgtttaga 1620
tacagtagtc cccatcacga aattcatgga aacagttata atcctcagga acaggggatt 1680
ccctgttctt ccgatttgct ttagtcccag aatttttttt cccaaatatc ttaaaaagtc 1740
actttctggt tcagttcaat gaattgattg ctacaaataa tgcttttata gcgttatcct 1800
agctgtagtt cagttaatag gtaatacccc tatagtttag tcaggagaag aacttatccg 1860
atttctgatc tccattttta attatatgaa atgaactgta gcataagcag tattcatttg 1920
gattattttt tttattagct ctcacccctt cattattctg agctgaaagt ctggcatgaa 1980
ctgtcctcaa ttttgttttc aaattcacat cgattatcta tgcattatcc tcttgtatct 2040
acctgtagaa gtttcttttt ggttattcct tgactgcttg attacagaaa gaaatttatg 2100
aagctgtaat cgggatagtt atactgcttg ttcttatgat tcatttcctt tgtgcagttc 2160
ttggtgtagc ttgccacttt caccagcaaa gttc 2194

<210> SEQ ID NO 72
<211> LENGTH: 1008
<212> TYPE: DNA
<213> ORGANISM: Oryza sativa

<400> SEQUENCE: 72
gccccccgcc ggacctcccg tggccccgtg gcgcctggag ggaggagagg ggagagatgg 60
tgagagagga ggaagaagag gaggggtgac aatgatatgt ggggccatgt gggccccacc 120
attttttaat tcattctttt gttgaaactg acatgtgggt cccatgagat ttattatttt 180
tcggatcgaa ttgccacgta agcgctacgt caatgctacg tcagatgaag accgagtcaa 240
attagccacg taagcgccac gtcagccaaa accaccatcc aaaccgccga gggacctcat 300

```
ctgcactggt tttgatagtt gagggacccg ttgtatctgg tttttcgatt gaaggacgag    360

aatcaaattt gttgacaagt taagggacct taaatgaact tattccattt caaaatattc    420

tgtgagccat atataccgtg ggcttccaat cctcctcaaa ttaaagggcc tttttaaaat    480

agataattgc cttctttcag tcacccataa aagtacaaaa ctactaccaa caagcaacat    540

gcgcagttac acacattttc tgcacatttc caccacgtca caaagagcta agagttatcc    600

ctaggacaat ctcattagtg tagatacatc cattaatctt ttatcagagg caaacgtaaa    660

gccgctcttt atgacaaaaa taggtgacac aaaagtgtta tctgccacat acataacttc    720

agaaattacc caacaccaag agaaaaataa aaaaaaatct ttttgcaagc tccaaatctt    780

ggaaaccttt ttcactcttt gcagcattgt actcttgctc tttttccaac cgatccatgt    840

caccctcaag cttctacttg atctacacga agctcaccgt gcacacaacc atggccacaa    900

aaaccctata aaaccccatc cgatcgccat catctcatca tcagttcatc accaacaaac    960

aaaagaggaa aaaaaacata tacacttcta gtgattgtct gattgatc                1008


<210> SEQ ID NO 73
<211> LENGTH: 52
<212> TYPE: DNA
<213> ORGANISM: Artificial sequence
<220> FEATURE:
<223> OTHER INFORMATION: primer: prm02265

<400> SEQUENCE: 73

ggggacaagt ttgtacaaaa aagcaggctt cacaatggca taccatggac ag             52


<210> SEQ ID NO 74
<211> LENGTH: 46
<212> TYPE: DNA
<213> ORGANISM: Artificial sequence
<220> FEATURE:
<223> OTHER INFORMATION: primer: prm02266

<400> SEQUENCE: 74

ggggaccact ttgtacaaga aagctgggta tttcacctct ggcctg                    46


<210> SEQ ID NO 75
<211> LENGTH: 321
<212> TYPE: DNA
<213> ORGANISM: Arabidopsis thaliana

<400> SEQUENCE: 75

atggataaca ctgaccgtcg tcgccgtcgt aagcaacaca aaatcgccct ccatgactct     60

gaagaagtga gcagtatcga attggagttt atcaacatga ctgaacaaga agaagatctc    120

atctttcgaa tgtacagact tgtcggtgat aggtgggatt tgatagcagg aagagttcct    180

ggaagacaac cagaggagat agagagatat tggataatga gaaacagtga aggctttgct    240

gataaacgac gccagcttca ctcatcttcc cacaaacata ccaagcctca ccgtcctcgc    300

ttttctatct atccttccta g                                              321


<210> SEQ ID NO 76
<211> LENGTH: 106
<212> TYPE: PRT
<213> ORGANISM: Arabidopsis thaliana

<400> SEQUENCE: 76

Met Asp Asn Thr Asp Arg Arg Arg Arg Arg Lys Gln His Lys Ile Ala
1               5                   10                  15
```

```
Leu His Asp Ser Glu Glu Val Ser Ser Ile Glu Trp Glu Phe Ile Asn
            20                  25                  30

Met Thr Glu Gln Glu Glu Asp Leu Ile Phe Arg Met Tyr Arg Leu Val
        35                  40                  45

Gly Asp Arg Trp Asp Leu Ile Ala Gly Arg Val Pro Gly Arg Gln Pro
    50                  55                  60

Glu Glu Ile Glu Arg Tyr Trp Ile Met Arg Asn Ser Glu Gly Phe Ala
65                  70                  75                  80

Asp Lys Arg Arg Gln Leu His Ser Ser Ser His Lys His Thr Lys Pro
                85                  90                  95

His Arg Pro Arg Phe Ser Ile Tyr Pro Ser
            100                 105


<210> SEQ ID NO 77
<211> LENGTH: 231
<212> TYPE: DNA
<213> ORGANISM: Agrostis capillaris

<400> SEQUENCE: 77

atgagcagtg gaagcttggt gaagaactcc aagacaatgg gtgtccatga agcgaaagaa      60

gttaatggca cttcacagca tttcgttgat ttcacagaag cagaggagaa tctcgttttc     120

agaatgcaca ggcttgtcgg gaccaggtgg gagcttatag ctggagaaat ccccggaaga     180

acggcaaaag aagtagagat gttttgggca aaaaagcccc gggagcaatg a              231


<210> SEQ ID NO 78
<211> LENGTH: 76
<212> TYPE: PRT
<213> ORGANISM: Agrostis capillaris

<400> SEQUENCE: 78

Met Ser Ser Gly Ser Leu Val Lys Asn Ser Lys Thr Met Gly Val His
1               5                   10                  15

Glu Ala Lys Glu Val Asn Gly Thr Ser Gln His Phe Val Asp Phe Thr
            20                  25                  30

Glu Ala Glu Glu Asn Leu Val Phe Arg Met His Arg Leu Val Gly Thr
        35                  40                  45

Arg Trp Glu Leu Ile Ala Gly Glu Ile Pro Gly Arg Thr Ala Lys Glu
    50                  55                  60

Val Glu Met Phe Trp Ala Lys Lys Pro Arg Glu Gln
65                  70                  75


<210> SEQ ID NO 79
<211> LENGTH: 231
<212> TYPE: DNA
<213> ORGANISM: Agrostis capillaris

<400> SEQUENCE: 79

atgagcagtg aaagcttggc gaagaactcc aagatcatgg ctatccatga aacgaaagga      60

aataatacca ctgcacagca tttcgttgat ttcacagaag cagaggaaga tctcgttttc     120

agaatgcaca ggcttgtcgg gaacaggtgg gagcttatag ctggaagaat ccccggaaga     180

acggcaaaag aagtagagat gttttgggca aaaaagcacc aggagcaatg a              231


<210> SEQ ID NO 80
<211> LENGTH: 76
<212> TYPE: PRT
<213> ORGANISM: Agrostis capillaris
```

<400> SEQUENCE: 80

```
Met Ser Ser Glu Ser Leu Ala Lys Asn Ser Lys Ile Met Ala Ile His
1               5                   10                  15

Glu Thr Lys Gly Asn Asn Thr Thr Ala Gln His Phe Val Asp Phe Thr
            20                  25                  30

Glu Ala Glu Glu Asp Leu Val Phe Arg Met His Arg Leu Val Gly Asn
        35                  40                  45

Arg Trp Glu Leu Ile Ala Gly Arg Ile Pro Gly Arg Thr Ala Lys Glu
    50                  55                  60

Val Glu Met Phe Trp Ala Lys Lys His Gln Glu Gln
65                  70                  75
```

<210> SEQ ID NO 81
<211> LENGTH: 198
<212> TYPE: DNA
<213> ORGANISM: Arachis hypogaea

<400> SEQUENCE: 81

```
atgagacaag aggaggagcc tactatgttg gaattctccg aagatgagga agatcttgtt      60

gccaggatgt ttagattggt tgggaagagg tggtctctta tcgctgggag aatccctgga     120

agaacagcac aagagattga aaagtattgg agttcaaagt gcgcatttcc cagtgaccaa     180

tgctcttcct ctgcataa                                                   198
```

<210> SEQ ID NO 82
<211> LENGTH: 65
<212> TYPE: PRT
<213> ORGANISM: Arachis hypogaea

<400> SEQUENCE: 82

```
Met Arg Gln Glu Glu Glu Pro Thr Met Leu Glu Phe Ser Glu Asp Glu
1               5                   10                  15

Glu Asp Leu Val Ala Arg Met Phe Arg Leu Val Gly Lys Arg Trp Ser
            20                  25                  30

Leu Ile Ala Gly Arg Ile Pro Gly Arg Thr Ala Gln Glu Ile Glu Lys
        35                  40                  45

Tyr Trp Ser Ser Lys Cys Ala Phe Pro Ser Asp Gln Cys Ser Ser Ser
    50                  55                  60

Ala
65
```

<210> SEQ ID NO 83
<211> LENGTH: 231
<212> TYPE: DNA
<213> ORGANISM: Avena sativa

<400> SEQUENCE: 83

```
atgagcagta aaagcttggc gaagaacttc aagaccatgg gtgtccatga agcgaaagaa      60

gttaatagca ctgcacagca tttcgttgat ttcacagaag cagaggaaga tcttgttttc     120

agaatgcaca ggcttgttgg gaacaggtgg gaacttatag ctggaagaat ccccggaaga     180

acagcaaaag aagtagagat gttttgggca aaaaagcaca gggaacaatg a              231
```

<210> SEQ ID NO 84
<211> LENGTH: 76
<212> TYPE: PRT
<213> ORGANISM: Avena sativa

<400> SEQUENCE: 84

Met Ser Ser Lys Ser Leu Ala Lys Asn Phe Lys Thr Met Gly Val His
1 5 10 15

Glu Ala Lys Glu Val Asn Ser Thr Ala Gln His Phe Val Asp Phe Thr
20 25 30

Glu Ala Glu Glu Asp Leu Val Phe Arg Met His Arg Leu Val Gly Asn
35 40 45

Arg Trp Glu Leu Ile Ala Gly Arg Ile Pro Gly Arg Thr Ala Lys Glu
50 55 60

Val Glu Met Phe Trp Ala Lys Lys His Arg Glu Gln
65 70 75

<210> SEQ ID NO 85
<211> LENGTH: 252
<212> TYPE: DNA
<213> ORGANISM: Arabidopsis thaliana

<400> SEQUENCE: 85
atgaatacgc agcgtaagtc gaagcatctt aagaccaatc caaccattgt tgcctcttct 60
tctgaagaag tgagcagtct tgagtgggaa gaaatagcaa tggctcagga agaagaggat 120
ttgatttgca ggatgtataa gcttgtcggt gaaaggtggg atttaatagc tgggaggatt 180
ccaggaagaa cagcagaaga gattgagagg ttttgggtga tgaagaatca tcgaagatct 240
caattacgtt ga 252

<210> SEQ ID NO 86
<211> LENGTH: 83
<212> TYPE: PRT
<213> ORGANISM: Arabidopsis thaliana

<400> SEQUENCE: 86

Met Asn Thr Gln Arg Lys Ser Lys His Leu Lys Thr Asn Pro Thr Ile
1 5 10 15

Val Ala Ser Ser Ser Glu Glu Val Ser Ser Leu Glu Trp Glu Glu Ile
20 25 30

Ala Met Ala Gln Glu Glu Glu Asp Leu Ile Cys Arg Met Tyr Lys Leu
35 40 45

Val Gly Glu Arg Trp Asp Leu Ile Ala Gly Arg Ile Pro Gly Arg Thr
50 55 60

Ala Glu Glu Ile Glu Arg Phe Trp Val Met Lys Asn His Arg Arg Ser
65 70 75 80

Gln Leu Arg

<210> SEQ ID NO 87
<211> LENGTH: 1833
<212> TYPE: DNA
<213> ORGANISM: Arabidopsis thaliana

<400> SEQUENCE: 87
atggttgcta ataataatac tagtagcaat cgcaggaaga gaatcattac tgaaggcgac 60
atcgccactc ttttgctgag atatgatatg gagacgatac tgagaatgct acaggagata 120
tcttattgtt ccgaaaccaa gatggactgg aatgcgttgg tgaagaagac cactaccgga 180
attactaatg ctagagagta ccagttgcta tggcgtcatc tttcttatcg gcatcctctc 240
ctccctgtgg aagatgatgc tctacctctg gacgacgata gtgacatgga gtgcgaattg 300
gaagcttctc ctgcagtcag ccatgaagca tcagtggagg ctattgcaca tgtcaaagtg 360

```
atggctgctt catatgttct aagtgagtct gatatactcg acgattcaac agttgaggct    420
cccttgacta taaacatacc ttatgctttg cctgagggtt ctcaggaacc atcagagtct    480
ccttggtcgt caagagggat gaatatcaac tttccggtct gtcttcagaa agttacatct    540
accgagggga tgaatggaaa tggttcagct ggtattagca tggcttttcg gaggaaaagg    600
aaaagatggt ctgctgagga ggatgaggag ctgttcgccg ctgtaaagcg atgtggtgaa    660
gggaactggg ctcatattgt taagggagac tttagaggag agagaaccgc ctcccaactc    720
tcgcagaggt gggcgcttat aagaaaaagg tgtcacactt cgacctctgt tagccaatgt    780
ggcctacaag gaactgaagc gaaactagca gttaaccatg cattatcttt agctctggga    840
aatcggcccc cttcaaataa gcttgcaata ggtcttatgc caacgacgtc atcttgtacc    900
atcacagaaa cggaagcgaa tgggggaagt tcttctcaag gtcaacaaca gtccaaacca    960
attgttcaag cattgcctcg ggcaggaaca tcacttccgg ctgcaaagtc tcgagttgtt   1020
aaaaaaacaa cagcaagctc cacttccaga tcggatctta tggtaacagc taattcagta   1080
gctgcagctg catgcatggg tgatgtattg actgctgcat caggacgaaa ggtcgaacct   1140
ggaaaaactg atgctccacg agtgccaaag actaaacctg taaaacatgc ttctacagtc   1200
tgcatgcctc agccctcagg tagcctctcc atgccaaagg ttgaaccagg aacgagtgtt   1260
gccgcctcta tacggtctct agctaatgga aaattgaaac ctgttatggc ttcatcatct   1320
tccaacaaac ctcctctcat agctcctcgt tcagaaggat cttcaatgct ttctgcttcc   1380
gccccccttgg cttctctatc aaggattgtc tccaatcaga gagtttttgc aggctctgtc   1440
ccagctactg agattgtcac ttgcaaacca gatggtggac agaaagggca agctcgtgga   1500
aatgaagcaa gctcatcggc tgcaatccag ccacatcaaa taacctcaag aaacttggag   1560
attagccagg gaaagcaggc tacacaggct cagtccccta atctcttgcc taggaaagtt   1620
ccagtagttc ggactgcagt tcattgtgcc actaaccaaa agttgatgga taaaccatct   1680
gatcaaactg tagtacctat cagaggagct ggttcgcaat ctaaagccaa aggtgaagta   1740
aacagtaagg ttggtccggt gatcaaagtg agtagtgttt gcggaaaacc ccttgaggtt   1800
gcaactgtgg cagggaccgg acagggtgtt tag                               1833
```

<210> SEQ ID NO 88
<211> LENGTH: 610
<212> TYPE: PRT
<213> ORGANISM: Arabidopsis thaliana

<400> SEQUENCE: 88

```
Met Val Ala Asn Asn Asn Thr Ser Ser Asn Arg Arg Lys Arg Ile Ile
1               5                   10                  15

Thr Glu Gly Asp Ile Ala Thr Leu Leu Leu Arg Tyr Asp Met Glu Thr
            20                  25                  30

Ile Leu Arg Met Leu Gln Glu Ile Ser Tyr Cys Ser Glu Thr Lys Met
        35                  40                  45

Asp Trp Asn Ala Leu Val Lys Lys Thr Thr Thr Gly Ile Thr Asn Ala
    50                  55                  60

Arg Glu Tyr Gln Leu Leu Trp Arg His Leu Ser Tyr Arg His Pro Leu
65                  70                  75                  80

Leu Pro Val Glu Asp Asp Ala Leu Pro Leu Asp Asp Asp Ser Asp Met
                85                  90                  95

Glu Cys Glu Leu Glu Ala Ser Pro Ala Val Ser His Glu Ala Ser Val
            100                 105                 110
```

```
Glu Ala Ile Ala His Val Lys Val Met Ala Ala Ser Tyr Val Leu Ser
        115                 120                 125

Glu Ser Asp Ile Leu Asp Asp Ser Thr Val Glu Ala Pro Leu Thr Ile
    130                 135                 140

Asn Ile Pro Tyr Ala Leu Pro Glu Gly Ser Gln Glu Pro Ser Glu Ser
145                 150                 155                 160

Pro Trp Ser Ser Arg Gly Met Asn Ile Asn Phe Pro Val Cys Leu Gln
                165                 170                 175

Lys Val Thr Ser Thr Glu Gly Met Asn Gly Asn Gly Ser Ala Gly Ile
            180                 185                 190

Ser Met Ala Phe Arg Arg Lys Arg Lys Arg Trp Ser Ala Glu Glu Asp
        195                 200                 205

Glu Glu Leu Phe Ala Ala Val Lys Arg Cys Gly Glu Gly Asn Trp Ala
    210                 215                 220

His Ile Val Lys Gly Asp Phe Arg Gly Glu Arg Thr Ala Ser Gln Leu
225                 230                 235                 240

Ser Gln Arg Trp Ala Leu Ile Arg Lys Arg Cys His Thr Ser Thr Ser
                245                 250                 255

Val Ser Gln Cys Gly Leu Gln Gly Thr Glu Ala Lys Leu Ala Val Asn
            260                 265                 270

His Ala Leu Ser Leu Ala Leu Gly Asn Arg Pro Pro Ser Asn Lys Leu
        275                 280                 285

Ala Ile Gly Leu Met Pro Thr Thr Ser Ser Cys Thr Ile Thr Glu Thr
    290                 295                 300

Glu Ala Asn Gly Gly Ser Ser Ser Gln Gly Gln Gln Gln Ser Lys Pro
305                 310                 315                 320

Ile Val Gln Ala Leu Pro Arg Ala Gly Thr Ser Leu Pro Ala Ala Lys
                325                 330                 335

Ser Arg Val Val Lys Lys Thr Thr Ala Ser Ser Thr Ser Arg Ser Asp
            340                 345                 350

Leu Met Val Thr Ala Asn Ser Val Ala Ala Ala Ala Cys Met Gly Asp
        355                 360                 365

Val Leu Thr Ala Ala Ser Gly Arg Lys Val Glu Pro Gly Lys Thr Asp
    370                 375                 380

Ala Pro Arg Val Pro Lys Thr Lys Pro Val Lys His Ala Ser Thr Val
385                 390                 395                 400

Cys Met Pro Gln Pro Ser Gly Ser Leu Ser Met Pro Lys Val Glu Pro
                405                 410                 415

Gly Thr Ser Val Ala Ala Ser Ile Arg Ser Leu Ala Asn Gly Lys Leu
            420                 425                 430

Lys Pro Val Met Ala Ser Ser Ser Ser Asn Lys Pro Pro Leu Ile Ala
        435                 440                 445

Pro Arg Ser Glu Gly Ser Ser Met Leu Ser Ala Ser Ala Pro Leu Ala
    450                 455                 460

Ser Leu Ser Arg Ile Val Ser Asn Gln Arg Val Phe Ala Gly Ser Val
465                 470                 475                 480

Pro Ala Thr Glu Ile Val Thr Cys Lys Pro Asp Gly Gly Gln Lys Gly
                485                 490                 495

Gln Ala Arg Gly Asn Glu Ala Ser Ser Ser Ala Ala Ile Gln Pro His
            500                 505                 510

Gln Ile Thr Ser Arg Asn Leu Glu Ile Ser Gln Gly Lys Gln Ala Thr
        515                 520                 525
```

```
Gln Ala Gln Ser Pro Asn Leu Leu Pro Arg Lys Val Pro Val Val Arg
    530                 535                 540

Thr Ala Val His Cys Ala Thr Asn Gln Lys Leu Met Asp Lys Pro Ser
545                 550                 555                 560

Asp Gln Thr Val Val Pro Ile Arg Gly Ala Gly Ser Gln Ser Lys Ala
                565                 570                 575

Lys Gly Glu Val Asn Ser Lys Val Gly Pro Val Ile Lys Val Ser Ser
            580                 585                 590

Val Cys Gly Lys Pro Leu Glu Val Ala Thr Val Ala Gly Thr Gly Gln
        595                 600                 605

Gly Val
    610


<210> SEQ ID NO 89
<211> LENGTH: 924
<212> TYPE: DNA
<213> ORGANISM: Arabidopsis thaliana

<400> SEQUENCE: 89

atggtgagat cttgttcttc aaaatcaaag aatccttgga caaacgaaga agacacaacc     60

caaaagtttg tgtttgcgtc tgcgtccaaa aacggatgtg cagctcctaa gaaaatagga    120

cttaggagat gtggaaagag ttgcagagtg agaaagactg atcattcagg aaccaaacat    180

gagagcttca cttctgaaga cgaagatctg atcatcaaga tgcacgcagc aatgggaagc    240

agatggcaac ttattgcaca acatttacca ggaaagacag aagaagaagt gaagatgttt    300

tggaacacaa aactgaagaa gaaactgtcg gaaatgggga tagatcatgt cactcaccgt    360

ccctttctc acgtacttgc tgaatacggc aacatcaatg gtggtggaaa cctaaaccct    420

aatccctcga accaagccgg atctcttgga cgcaatcact cgctcaatga tgatggtcat    480

caacaacaac ctaatgattc aggagatctc atgtttcatt tacaagcaat caagcttatg    540

acagattcat cgaaccaagt caagcctgag tctacgtttg tgtacgcctc ttcgtcttct    600

tctaactcgt ctcctccatt gttctcttca acttgttcta ccatagctca ggagaattca    660

gaggttaact tcacttggtc tgacttcctt cttgaccaag aaaccttcca tgaaaaccaa    720

cagaatcatc ctcaagaact agacagcttg tttgggaacg acttctccga ggtaacagca    780

gctacaatgg ctaacacatc aaccgtacca tctcagatcg aagaagaatc tttgagcaat    840

gggttcgttg aatcgattat cgctaaagaa aaggagtttt tcttgggatt tccgagctat    900

ctggaacaac ctttccactt ttag                                           924


<210> SEQ ID NO 90
<211> LENGTH: 307
<212> TYPE: PRT
<213> ORGANISM: Arabidopsis thaliana

<400> SEQUENCE: 90

Met Val Arg Ser Cys Ser Ser Lys Ser Lys Asn Pro Trp Thr Asn Glu
1               5                   10                  15

Glu Asp Thr Thr Gln Lys Phe Val Phe Ala Ser Ala Ser Lys Asn Gly
            20                  25                  30

Cys Ala Ala Pro Lys Lys Ile Gly Leu Arg Arg Cys Gly Lys Ser Cys
        35                  40                  45

Arg Val Arg Lys Thr Asp His Ser Gly Thr Lys His Glu Ser Phe Thr
    50                  55                  60

Ser Glu Asp Glu Asp Leu Ile Ile Lys Met His Ala Ala Met Gly Ser
```

-continued

```
65                  70                  75                  80

Arg Trp Gln Leu Ile Ala Gln His Leu Pro Gly Lys Thr Glu Glu Glu
                85                  90                  95

Val Lys Met Phe Trp Asn Thr Lys Leu Lys Lys Lys Leu Ser Glu Met
            100                 105                 110

Gly Ile Asp His Val Thr His Arg Pro Phe Ser His Val Leu Ala Glu
        115                 120                 125

Tyr Gly Asn Ile Asn Gly Gly Gly Asn Leu Asn Pro Asn Pro Ser Asn
    130                 135                 140

Gln Ala Gly Ser Leu Gly Arg Asn His Ser Leu Asn Asp Asp Gly His
145                 150                 155                 160

Gln Gln Gln Pro Asn Asp Ser Gly Asp Leu Met Phe His Leu Gln Ala
                165                 170                 175

Ile Lys Leu Met Thr Asp Ser Ser Asn Gln Val Lys Pro Glu Ser Thr
            180                 185                 190

Phe Val Tyr Ala Ser Ser Ser Ser Ser Asn Ser Ser Pro Pro Leu Phe
        195                 200                 205

Ser Ser Thr Cys Ser Thr Ile Ala Gln Glu Asn Ser Glu Val Asn Phe
    210                 215                 220

Thr Trp Ser Asp Phe Leu Leu Asp Gln Glu Thr Phe His Glu Asn Gln
225                 230                 235                 240

Gln Asn His Pro Gln Glu Leu Asp Ser Leu Phe Gly Asn Asp Phe Ser
                245                 250                 255

Glu Val Thr Ala Ala Thr Met Ala Asn Thr Ser Thr Val Pro Ser Gln
            260                 265                 270

Ile Glu Glu Glu Ser Leu Ser Asn Gly Phe Val Glu Ser Ile Ile Ala
        275                 280                 285

Lys Glu Lys Glu Phe Phe Leu Gly Phe Pro Ser Tyr Leu Glu Gln Pro
    290                 295                 300

Phe His Phe
305
```

<210> SEQ ID NO 91
<211> LENGTH: 2505
<212> TYPE: DNA
<213> ORGANISM: Arabidopsis thaliana

<400> SEQUENCE: 91

```
atggttgata acagtaacaa taagaagagg aaagagttca tcagtgaagc agacatcgcc     60

actcttttgc agagatatga tactgtgacg atactgaagt tgctacaaga aatggcgtat    120

tatgctgaag caaagatgaa ttggaatgag ttagtgaaga agacaagtac tggaattact    180

agtgctagag aatatcagtt gctttggcgg catcttgctt atagagattc tctcgtccct    240

gtgggaaata atgctcgagt tctggatgat gatagtgata tggagtgtga attggaagca    300

tcccctggag ttagtgttga tgtagtaacg gaagctgttg cgcatgtgaa agtgatggct    360

gcttcctatg tgccaagtga gtccgatatt cccgaagact caacggttga ggctcccttg    420

accattaaca taccttacag cctgcatagg gggcctcagg aaccatcaga ctcatattgg    480

tcatcaagag ggatgaatat cacctttcct gtttttcttc cgaaagcagc tgaaggacat    540

aatgggaatg ggttagccag tagcttggct cctcggaaga gaagaaaaaa atggtcagct    600

gaggaggatg aggagctgat tgctgctgtt aagcgacatg gtgaaggcag ctgggccctt    660

atctctaagg aagaatttga aggagagcga acagcctcac aactctcaca gcggtggggg    720
```

-continued

```
gctataagga gaaggactga tacttcaaac acttctaccc aaactggcct acagcgaaca    780

gaagcacaaa tggcagctaa tcgtgcatta tctttagcgg tgggaaatcg gttaccctca    840

aaaaaacttg cagtaggtat gactccaatg ctgtcatccg gtaccatcaa gggagcacaa    900

gccaatggtg ccagcagtgg tagtacattg caaggtcaac aacagcctca gccacaaatt    960

caagcattat cacgggcaac aacatcagtg ccagttgcaa aatctcgagt tcctgtaaag   1020

aaaacaacag ggaactccac ttcgagagca gacctaatgg taactgctaa ttcagtagct   1080

gctgcagcct gtatgtctgg cctggcaacc gctgtaacag tgcctaagat tgaaccagga   1140

aagaatgctg tttctgcgtt ggtgccgaag actgaacccg taaaaaccgc ttccacagtt   1200

tctatgcctc gtccttcagg tatatcatca gcactgaata ctgagcctgt aaaaaccgct   1260

gtggcagcct ctttgcctcg ttcatcaggt attatttcag caccaaaggt tgagcctgta   1320

aaaaccgctg cttcagcagc ctctttgcct cgtccatcag gaatgatatc agcaccaaag   1380

gttgagcctg tgaaaaccac cgcctctgta gcctctttgc ctcgtccatc aggtattatt   1440

tcagctccaa aggctgagcc tgtaaaaacc gctgcttctg cagcctcttc gcctcgtcca   1500

tcaggaatga tatcagcacc aaaggttgag tctgtgaaaa ccaccgcctc tatgcctcgt   1560

ccatcaggta ttatatccgc accaaaggct gagcttgtaa aatccgccgc ttctgcagcc   1620

tctttgcctt gtacatcagg tattatatct tcaccaaagg ctgagcttgt aaaatccgcc   1680

gcttctgcag cctcttttcc tcgcccatca agtatgctat cagcaccaaa ggctgaccca   1740

gtaaagattg ttcctgctgc tgccactaac actaaatcgg ttggaccttt gaatttaagg   1800

catgcagtca atggaagccc aaaccacacg ataccttcat caccctttac taagccttta   1860

catatggctc ctctctccaa aggatctaca atccagagta attcagttcc tcctagtttt   1920

gcatcgtcaa ggttggtccc cacacagaga gctcctgcgg ctactgttgt cacgccacaa   1980

aagccaagtg tggtagcggc agctactgtt gtcacgccac aaaagccaag tgtgggagca   2040

gcagctactg ttgtaacgcc acaaaagcca agtgtgggag cagcagctaa tgttgtaacg   2100

ccacaaaagc caagtgtggg atcagcagct actgttgtaa cgccacaaaa gccaagtgtg   2160

ggagcagcag ttaccgtcac ttccaagccg gttggtgtac agaaagagca aactcaggga   2220

aacagagcaa gccccttggt tacagcaaca cttccgccaa ataaaaccat cccagcaaat   2280

tcagtgattg gcacagcaaa agcggtggct gcgaaagtgg agactcctcc tagccttatg   2340

cctaagaaaa atgaagtagt tggcagttgc accgataaaa gttcattgga taaaccacct   2400

gagaaagaaa gtactaccac ggtgtcacct ctagctgtag ctgcgactaa atcaaaaccc   2460

aaagatgaag caaccgtgac agggaccgga ctgaaggagt tgtag                    2505
```

<210> SEQ ID NO 92
<211> LENGTH: 834
<212> TYPE: PRT
<213> ORGANISM: Arabidopsis thaliana

<400> SEQUENCE: 92

```
Met Val Asp Asn Ser Asn Asn Lys Lys Arg Lys Glu Phe Ile Ser Glu
1               5                   10                  15

Ala Asp Ile Ala Thr Leu Leu Gln Arg Tyr Asp Thr Val Thr Ile Leu
            20                  25                  30

Lys Leu Leu Gln Glu Met Ala Tyr Tyr Ala Glu Ala Lys Met Asn Trp
        35                  40                  45

Asn Glu Leu Val Lys Lys Thr Ser Thr Gly Ile Thr Ser Ala Arg Glu
    50                  55                  60
```

```
Tyr Gln Leu Leu Trp Arg His Leu Ala Tyr Arg Asp Ser Leu Val Pro
65                  70                  75                  80

Val Gly Asn Asn Ala Arg Val Leu Asp Asp Asp Ser Asp Met Glu Cys
                85                  90                  95

Glu Leu Glu Ala Ser Pro Gly Val Ser Val Asp Val Val Thr Glu Ala
            100                 105                 110

Val Ala His Val Lys Val Met Ala Ala Ser Tyr Val Pro Ser Glu Ser
        115                 120                 125

Asp Ile Pro Glu Asp Ser Thr Val Glu Ala Pro Leu Thr Ile Asn Ile
    130                 135                 140

Pro Tyr Ser Leu His Arg Gly Pro Gln Glu Pro Ser Asp Ser Tyr Trp
145                 150                 155                 160

Ser Ser Arg Gly Met Asn Ile Thr Phe Pro Val Phe Leu Pro Lys Ala
                165                 170                 175

Ala Glu Gly His Asn Gly Asn Gly Leu Ala Ser Ser Leu Ala Pro Arg
            180                 185                 190

Lys Arg Arg Lys Lys Trp Ser Ala Glu Glu Asp Glu Glu Leu Ile Ala
        195                 200                 205

Ala Val Lys Arg His Gly Glu Gly Ser Trp Ala Leu Ile Ser Lys Glu
    210                 215                 220

Glu Phe Glu Gly Glu Arg Thr Ala Ser Gln Leu Ser Gln Arg Trp Gly
225                 230                 235                 240

Ala Ile Arg Arg Arg Thr Asp Thr Ser Asn Thr Ser Thr Gln Thr Gly
                245                 250                 255

Leu Gln Arg Thr Glu Ala Gln Met Ala Ala Asn Arg Ala Leu Ser Leu
            260                 265                 270

Ala Val Gly Asn Arg Leu Pro Ser Lys Lys Leu Ala Val Gly Met Thr
        275                 280                 285

Pro Met Leu Ser Ser Gly Thr Ile Lys Gly Ala Gln Ala Asn Gly Ala
    290                 295                 300

Ser Ser Gly Ser Thr Leu Gln Gly Gln Gln Gln Pro Gln Pro Gln Ile
305                 310                 315                 320

Gln Ala Leu Ser Arg Ala Thr Thr Ser Val Pro Val Ala Lys Ser Arg
                325                 330                 335

Val Pro Val Lys Lys Thr Thr Gly Asn Ser Thr Ser Arg Ala Asp Leu
            340                 345                 350

Met Val Thr Ala Asn Ser Val Ala Ala Ala Ala Cys Met Ser Gly Leu
        355                 360                 365

Ala Thr Ala Val Thr Val Pro Lys Ile Glu Pro Gly Lys Asn Ala Val
    370                 375                 380

Ser Ala Leu Val Pro Lys Thr Glu Pro Val Lys Thr Ala Ser Thr Val
385                 390                 395                 400

Ser Met Pro Arg Pro Ser Gly Ile Ser Ser Ala Leu Asn Thr Glu Pro
                405                 410                 415

Val Lys Thr Ala Val Ala Ala Ser Leu Pro Arg Ser Ser Gly Ile Ile
            420                 425                 430

Ser Ala Pro Lys Val Glu Pro Val Lys Thr Ala Ala Ser Ala Ala Ser
        435                 440                 445

Leu Pro Arg Pro Ser Gly Met Ile Ser Ala Pro Lys Val Glu Pro Val
    450                 455                 460

Lys Thr Thr Ala Ser Val Ala Ser Leu Pro Arg Pro Ser Gly Ile Ile
465                 470                 475                 480
```

-continued

```
Ser Ala Pro Lys Ala Glu Pro Val Lys Thr Ala Ala Ser Ala Ala Ser
                485                 490                 495

Ser Pro Arg Pro Ser Gly Met Ile Ser Ala Pro Lys Val Glu Ser Val
            500                 505                 510

Lys Thr Thr Ala Ser Met Pro Arg Pro Ser Gly Ile Ile Ser Ala Pro
        515                 520                 525

Lys Ala Glu Leu Val Lys Ser Ala Ala Ser Ala Ala Ser Leu Pro Cys
    530                 535                 540

Thr Ser Gly Ile Ile Ser Ser Pro Lys Ala Glu Leu Val Lys Ser Ala
545                 550                 555                 560

Ala Ser Ala Ala Ser Phe Pro Arg Pro Ser Ser Met Leu Ser Ala Pro
                565                 570                 575

Lys Ala Asp Pro Val Lys Ile Val Pro Ala Ala Ala Thr Asn Thr Lys
            580                 585                 590

Ser Val Gly Pro Leu Asn Leu Arg His Ala Val Asn Gly Ser Pro Asn
        595                 600                 605

His Thr Ile Pro Ser Ser Pro Phe Thr Lys Pro Leu His Met Ala Pro
    610                 615                 620

Leu Ser Lys Gly Ser Thr Ile Gln Ser Asn Ser Val Pro Pro Ser Phe
625                 630                 635                 640

Ala Ser Ser Arg Leu Val Pro Thr Gln Arg Ala Pro Ala Ala Thr Val
                645                 650                 655

Val Thr Pro Gln Lys Pro Ser Val Val Ala Ala Ala Thr Val Val Thr
            660                 665                 670

Pro Gln Lys Pro Ser Val Gly Ala Ala Ala Thr Val Val Thr Pro Gln
        675                 680                 685

Lys Pro Ser Val Gly Ala Ala Ala Asn Val Val Thr Pro Gln Lys Pro
    690                 695                 700

Ser Val Gly Ser Ala Ala Thr Val Val Thr Pro Gln Lys Pro Ser Val
705                 710                 715                 720

Gly Ala Ala Val Thr Val Thr Ser Lys Pro Val Gly Val Gln Lys Glu
                725                 730                 735

Gln Thr Gln Gly Asn Arg Ala Ser Pro Leu Val Thr Ala Thr Leu Pro
            740                 745                 750

Pro Asn Lys Thr Ile Pro Ala Asn Ser Val Ile Gly Thr Ala Lys Ala
        755                 760                 765

Val Ala Ala Lys Val Glu Thr Pro Pro Ser Leu Met Pro Lys Lys Asn
    770                 775                 780

Glu Val Val Gly Ser Cys Thr Asp Lys Ser Ser Leu Asp Lys Pro Pro
785                 790                 795                 800

Glu Lys Glu Ser Thr Thr Thr Val Ser Pro Leu Ala Val Ala Ala Thr
                805                 810                 815

Lys Ser Lys Pro Lys Asp Glu Ala Thr Val Thr Gly Thr Gly Leu Lys
            820                 825                 830

Glu Leu
```

<210> SEQ ID NO 93
<211> LENGTH: 588
<212> TYPE: DNA
<213> ORGANISM: Arabidopsis thaliana

<400> SEQUENCE: 93

```
atgaacaaaa cccgccttcg tgctctctcc ccaccttccg gtatgcaaca ccgtaagaga      60

tgtcgattga gaggtcgaaa ctacgtaagg ccagaagtta aacaacgcaa cttctcaaaa     120
```

```
gatgaagacg atctcatcct caagcttcat gcacttcttg gcaatagatg gtcattgata    180

gcgggaagat tgccaggacg aaccgacaac gaagttagga tccattggga aacttaccta    240

aaaaggaagc tcgtaaaaat gggaatcgac ccaaccaatc atcgtctcca ccatcacacc    300

aactacattt ctagacgtca cctccattct tcacataagg aacatgaaac caagattatt    360

agtgatcaat cttcttcggt atccgaatca tgtggtgtaa caattttgcc cattccaagt    420

accaattgct cggaggatag tactagtacc ggacgaagtc atttgcctga cctaaacatt    480

ggtctcatcc cggccgtgac ttctttgcca gctctttgcc ttcaggactc tagcgaatcc    540

tctaccaatg gttcaacagg tcaagaaacg cttcttctat tccgatga                 588
```

<210> SEQ ID NO 94
<211> LENGTH: 195
<212> TYPE: PRT
<213> ORGANISM: Arabidopsis thaliana

<400> SEQUENCE: 94

```
Met Asn Lys Thr Arg Leu Arg Ala Leu Ser Pro Pro Ser Gly Met Gln
1               5                   10                  15

His Arg Lys Arg Cys Arg Leu Arg Gly Arg Asn Tyr Val Arg Pro Glu
            20                  25                  30

Val Lys Gln Arg Asn Phe Ser Lys Asp Glu Asp Asp Leu Ile Leu Lys
        35                  40                  45

Leu His Ala Leu Leu Gly Asn Arg Trp Ser Leu Ile Ala Gly Arg Leu
    50                  55                  60

Pro Gly Arg Thr Asp Asn Glu Val Arg Ile His Trp Glu Thr Tyr Leu
65                  70                  75                  80

Lys Arg Lys Leu Val Lys Met Gly Ile Asp Pro Thr Asn His Arg Leu
                85                  90                  95

His His His Thr Asn Tyr Ile Ser Arg Arg His Leu His Ser Ser His
            100                 105                 110

Lys Glu His Glu Thr Lys Ile Ile Ser Asp Gln Ser Ser Ser Val Ser
        115                 120                 125

Glu Ser Cys Gly Val Thr Ile Leu Pro Ile Pro Ser Thr Asn Cys Ser
    130                 135                 140

Glu Asp Ser Thr Ser Thr Gly Arg Ser His Leu Pro Asp Leu Asn Ile
145                 150                 155                 160

Gly Leu Ile Pro Ala Val Thr Ser Leu Pro Ala Leu Cys Leu Gln Asp
                165                 170                 175

Ser Ser Glu Ser Ser Thr Asn Gly Ser Thr Gly Gln Glu Thr Leu Leu
            180                 185                 190

Leu Phe Arg
        195
```

<210> SEQ ID NO 95
<211> LENGTH: 339
<212> TYPE: DNA
<213> ORGANISM: Arabidopsis thaliana

<400> SEQUENCE: 95

```
atggataata ccaaccgtct tcgtcttcgt cgcggtccca gtcttaggca aactaagttc     60

actcgatccc gatatgactc tgaagaagtg agtagcatcg aatgggagtt tatcagtatg    120

accgaacaag aagaagatct catctctcga atgtacagac ttgtcggtaa taggtgggat    180

ttaatagcag gaagagtcgt aggaagaaag gcaaatgaga ttgagagata ctggattatg    240
```

agaaactctg actatttttc tcacaaacga cgacgtctta ataattctcc cttttttct 300 acttctcctc ttaatctcca agaaaatcta aaattgtaa 339

<210> SEQ ID NO 96
<211> LENGTH: 112
<212> TYPE: PRT
<213> ORGANISM: Arabidopsis thaliana

<400> SEQUENCE: 96

Met Asp Asn Thr Asn Arg Leu Arg Leu Arg Arg Gly Pro Ser Leu Arg
1 5 10 15

Gln Thr Lys Phe Thr Arg Ser Arg Tyr Asp Ser Glu Glu Val Ser Ser
20 25 30

Ile Glu Trp Glu Phe Ile Ser Met Thr Glu Gln Glu Glu Asp Leu Ile
35 40 45

Ser Arg Met Tyr Arg Leu Val Gly Asn Arg Trp Asp Leu Ile Ala Gly
50 55 60

Arg Val Val Gly Arg Lys Ala Asn Glu Ile Glu Arg Tyr Trp Ile Met
65 70 75 80

Arg Asn Ser Asp Tyr Phe Ser His Lys Arg Arg Arg Leu Asn Asn Ser
85 90 95

Pro Phe Phe Ser Thr Ser Pro Leu Asn Leu Gln Glu Asn Leu Lys Leu
100 105 110

<210> SEQ ID NO 97
<211> LENGTH: 285
<212> TYPE: DNA
<213> ORGANISM: Arabidopsis thaliana

<400> SEQUENCE: 97
atgtttcgtt cagacaaggc ggaaaaaatg gataaacgac gacggagaca gagcaaagcc 60
aaggcttctt gttccgaaga ggtgagtagt atcgaatggg aagctgtgaa gatgtcagaa 120
gaagaagaag atctcatttc tcggatgtat aaactcgttg gcgacaggtg ggagttgatc 180
gccggaagga tcccgggacg gacgccggag gagatagaga gatattggct tatgaaacac 240
ggcgtcgttt ttgccaacag acgaagagac ttttttagga aatga 285

<210> SEQ ID NO 98
<211> LENGTH: 94
<212> TYPE: PRT
<213> ORGANISM: Arabidopsis thaliana

<400> SEQUENCE: 98

Met Phe Arg Ser Asp Lys Ala Glu Lys Met Asp Lys Arg Arg Arg Arg
1 5 10 15

Gln Ser Lys Ala Lys Ala Ser Cys Ser Glu Glu Val Ser Ser Ile Glu
20 25 30

Trp Glu Ala Val Lys Met Ser Glu Glu Glu Glu Asp Leu Ile Ser Arg
35 40 45

Met Tyr Lys Leu Val Gly Asp Arg Trp Glu Leu Ile Ala Gly Arg Ile
50 55 60

Pro Gly Arg Thr Pro Glu Glu Ile Glu Arg Tyr Trp Leu Met Lys His
65 70 75 80

Gly Val Val Phe Ala Asn Arg Arg Arg Asp Phe Phe Arg Lys
85 90

-continued

```
<210> SEQ ID NO 99
<211> LENGTH: 234
<212> TYPE: DNA
<213> ORGANISM: Arabidopsis thaliana

<400> SEQUENCE: 99

atggataacc atcgcaggac taagcaaccc aagaccaact ccatcgttac ttcttcttct      60

gaaggaacag aagtgagtag tcttgagtgg gaagttgtga acatgagtca agaagaagaa     120

gatttggtct ctcgaatgca taagcttgtc ggtgacaggt gggaactgat agctgggagg     180

atcccaggaa gaaccgctgg agaaattgag aggttttggg tcatgaaaaa ttga           234


<210> SEQ ID NO 100
<211> LENGTH: 77
<212> TYPE: PRT
<213> ORGANISM: Arabidopsis thaliana

<400> SEQUENCE: 100

Met Asp Asn His Arg Arg Thr Lys Gln Pro Lys Thr Asn Ser Ile Val
1               5                   10                  15

Thr Ser Ser Ser Glu Gly Thr Glu Val Ser Ser Leu Glu Trp Glu Val
            20                  25                  30

Val Asn Met Ser Gln Glu Glu Glu Asp Leu Val Ser Arg Met His Lys
        35                  40                  45

Leu Val Gly Asp Arg Trp Glu Leu Ile Ala Gly Arg Ile Pro Gly Arg
    50                  55                  60

Thr Ala Gly Glu Ile Glu Arg Phe Trp Val Met Lys Asn
65                  70                  75


<210> SEQ ID NO 101
<211> LENGTH: 225
<212> TYPE: DNA
<213> ORGANISM: Bruguiera gymnorrhiza

<400> SEQUENCE: 101

atggctgacg tggataactc atccgttgat gaattctctg ttgattctag agaggaatcc      60

agccaggatt ctaagcttga gttctcagag gatgaggaga cccttattac taggatgtac     120

aatctggttg gtgagaggtg gcctttgatt gctgggagga ttcctggaag gacagcagag     180

gagattgaga agtactggac ttcaagatac tctacaagcc aatga                     225


<210> SEQ ID NO 102
<211> LENGTH: 74
<212> TYPE: PRT
<213> ORGANISM: Bruguiera gymnorrhiza

<400> SEQUENCE: 102

Met Ala Asp Val Asp Asn Ser Ser Val Asp Glu Phe Ser Val Asp Ser
1               5                   10                  15

Arg Glu Glu Ser Ser Gln Asp Ser Lys Leu Glu Phe Ser Glu Asp Glu
            20                  25                  30

Glu Thr Leu Ile Thr Arg Met Tyr Asn Leu Val Gly Glu Arg Trp Pro
        35                  40                  45

Leu Ile Ala Gly Arg Ile Pro Gly Arg Thr Ala Glu Glu Ile Glu Lys
    50                  55                  60

Tyr Trp Thr Ser Arg Tyr Ser Thr Ser Gln
65                  70


<210> SEQ ID NO 103
```

```
<211> LENGTH: 309
<212> TYPE: DNA
<213> ORGANISM: Brassica napus

<400> SEQUENCE: 103

atggattcaa cgtatcgacg tcagcgtcac aactctgaag aagtgtgtag cgtaaagtgg      60

gatttcatca aaatgagcca acaggaggaa gatctcatct taagaatgta cagactcgta     120

ggcgataggt gggaaataat agcaggaaga gtaccggcga agaaaagctg tggagataga     180

gagatattgg atcatgagaa acaacacaca tgtccgccct ccatcttcca aattttaacc     240

tccttcttgt gctgtgcctc ccatgtttgt tttaagtgtt atattttcat ttccaaaact     300

aaaaactag                                                             309


<210> SEQ ID NO 104
<211> LENGTH: 102
<212> TYPE: PRT
<213> ORGANISM: Brassica napus

<400> SEQUENCE: 104

Met Asp Ser Thr Tyr Arg Arg Gln Arg His Asn Ser Glu Glu Val Cys
1               5                   10                  15

Ser Val Lys Trp Asp Phe Ile Lys Met Ser Gln Gln Glu Glu Asp Leu
            20                  25                  30

Ile Leu Arg Met Tyr Arg Leu Val Gly Asp Arg Trp Glu Ile Ile Ala
        35                  40                  45

Gly Arg Val Pro Ala Lys Lys Ser Cys Gly Asp Arg Glu Ile Leu Asp
    50                  55                  60

His Glu Lys Gln His Thr Cys Pro Pro Ser Ile Phe Gln Ile Leu Thr
65                  70                  75                  80

Ser Phe Leu Cys Cys Ala Ser His Val Cys Phe Lys Cys Tyr Ile Phe
                85                  90                  95

Ile Ser Lys Thr Lys Asn
            100


<210> SEQ ID NO 105
<211> LENGTH: 324
<212> TYPE: DNA
<213> ORGANISM: Brassica napus

<400> SEQUENCE: 105

atggataaca ctgaccgtcg tcgccgtcgt aagcaacaca aagtcactct ccatgactct      60

gaagaagtga gcagtattga atgggagttt atcaatatga cagaacaaga agaagatctc     120

atctttcgaa tgcatagact tgtcggtgat aggtgggatt taatagcagg acgagtgcca     180

ggaagacaac cagaagagat agagagatac tggataatga gaaacagtga tggctttgct     240

gagaaacgac gccaacttca tcactcctct tctcacaaaa gtaccaaacc tcatcgtcca     300

cgtttttcta tttatccttc ttag                                            324


<210> SEQ ID NO 106
<211> LENGTH: 107
<212> TYPE: PRT
<213> ORGANISM: Brassica napus

<400> SEQUENCE: 106

Met Asp Asn Thr Asp Arg Arg Arg Arg Arg Lys Gln His Lys Val Thr
1               5                   10                  15

Leu His Asp Ser Glu Glu Val Ser Ser Ile Glu Trp Glu Phe Ile Asn
```

```
            20                  25                  30

Met Thr Glu Gln Glu Glu Asp Leu Ile Phe Arg Met His Arg Leu Val
        35                  40                  45

Gly Asp Arg Trp Asp Leu Ile Ala Gly Arg Val Pro Gly Arg Gln Pro
    50                  55                  60

Glu Glu Ile Glu Arg Tyr Trp Ile Met Arg Asn Ser Asp Gly Phe Ala
65                  70                  75                  80

Glu Lys Arg Arg Gln Leu His His Ser Ser Ser His Lys Ser Thr Lys
                85                  90                  95

Pro His Arg Pro Arg Phe Ser Ile Tyr Pro Ser
            100                 105


<210> SEQ ID NO 107
<211> LENGTH: 249
<212> TYPE: DNA
<213> ORGANISM: Brassica napus

<400> SEQUENCE: 107

atggataagc agcgtaagtc gaagcatccc aagaccaatg cttatgccac cattgtttcc      60

tcttcttcgg aagaagtgag cagtcttgag tgggaagaaa tagcaatgac acaagaagaa     120

gaggatttga tctgcaggat gtataagctt gtcggcgaaa ggtgggattt aataactggg     180

aggattccag gaagaacggc acaagtgatc gagaggtttt gggtcatgaa gaatcatcga     240

agagcttga                                                             249


<210> SEQ ID NO 108
<211> LENGTH: 82
<212> TYPE: PRT
<213> ORGANISM: Brassica napus

<400> SEQUENCE: 108

Met Asp Lys Gln Arg Lys Ser Lys His Pro Lys Thr Asn Ala Tyr Ala
1               5                   10                  15

Thr Ile Val Ser Ser Ser Ser Glu Glu Val Ser Ser Leu Glu Trp Glu
            20                  25                  30

Glu Ile Ala Met Thr Gln Glu Glu Glu Asp Leu Ile Cys Arg Met Tyr
        35                  40                  45

Lys Leu Val Gly Glu Arg Trp Asp Leu Ile Thr Gly Arg Ile Pro Gly
    50                  55                  60

Arg Thr Ala Gln Val Ile Glu Arg Phe Trp Val Met Lys Asn His Arg
65                  70                  75                  80

Arg Ala


<210> SEQ ID NO 109
<211> LENGTH: 258
<212> TYPE: DNA
<213> ORGANISM: Brassica napus

<400> SEQUENCE: 109

atggatagac gacgtcgtag acagagcaag gccaaagcgt cgtgttccga agaagtgagt      60

agcatagaat gggaagctgt gaagatgacg gaggaagaag aagatctcat ttctcggatg     120

tataaactcg tcggagacag gtgggaattg atagccggaa ggattccagg acggacgccg     180

gaggagatag aaagatattg gcttatgaaa cacggtgtcg tttttgccaa ccgaccaaga     240

gattttgtta ggagatga                                                   258
```

```
<210> SEQ ID NO 110
<211> LENGTH: 85
<212> TYPE: PRT
<213> ORGANISM: Brassica napus

<400> SEQUENCE: 110

Met Asp Arg Arg Arg Arg Arg Gln Ser Lys Ala Lys Ala Ser Cys Ser
1               5                   10                  15

Glu Glu Val Ser Ser Ile Glu Trp Glu Ala Val Lys Met Thr Glu Glu
            20                  25                  30

Glu Glu Asp Leu Ile Ser Arg Met Tyr Lys Leu Val Gly Asp Arg Trp
        35                  40                  45

Glu Leu Ile Ala Gly Arg Ile Pro Gly Arg Thr Pro Glu Glu Ile Glu
    50                  55                  60

Arg Tyr Trp Leu Met Lys His Gly Val Val Phe Ala Asn Arg Pro Arg
65                  70                  75                  80

Asp Phe Val Arg Arg
                85


<210> SEQ ID NO 111
<211> LENGTH: 237
<212> TYPE: DNA
<213> ORGANISM: Brassica napus

<400> SEQUENCE: 111

atggattcaa cgtatcgacg tcagcgtcac aactctgaag aagtgtgtag cgtaaagtgg      60

gatttcatca aaatgagcca acaggaggaa gatctcatct taagaatgta cagactcgta     120

ggcgataggt gggaaataat agcaggaaga gtaccgggaa gaaaagctgt ggagatagag     180

agatactgga tcatgagaaa caacacacat ttcttgcctc catcttccaa attttaa        237


<210> SEQ ID NO 112
<211> LENGTH: 78
<212> TYPE: PRT
<213> ORGANISM: Brassica napus

<400> SEQUENCE: 112

Met Asp Ser Thr Tyr Arg Arg Gln Arg His Asn Ser Glu Glu Val Cys
1               5                   10                  15

Ser Val Lys Trp Asp Phe Ile Lys Met Ser Gln Gln Glu Glu Asp Leu
            20                  25                  30

Ile Leu Arg Met Tyr Arg Leu Val Gly Asp Arg Trp Glu Ile Ile Ala
        35                  40                  45

Gly Arg Val Pro Gly Arg Lys Ala Val Glu Ile Glu Arg Tyr Trp Ile
    50                  55                  60

Met Arg Asn Asn Thr His Phe Leu Pro Pro Ser Ser Lys Phe
65                  70                  75


<210> SEQ ID NO 113
<211> LENGTH: 228
<212> TYPE: DNA
<213> ORGANISM: Coffea canephora

<400> SEQUENCE: 113

atggctgact cggatcaatc cacaactttg aatgaaaaat ctgtcggctc tcaagaggat      60

aaaagtcaag actctgagct tcatttctct gaagatgagg aaattctcat cattaggatg     120

ttcaacttgg ttggtaaaag gtggtcttta attgctggaa gaatccctgg aagaactgca     180

aaggaaattg aggagtattg gaatacaaga tctgcaacca gtccatga                  228
```

<210> SEQ ID NO 114
<211> LENGTH: 75
<212> TYPE: PRT
<213> ORGANISM: Coffea canephora

<400> SEQUENCE: 114

```
Met Ala Asp Ser Asp Gln Ser Thr Thr Leu Asn Glu Lys Ser Val Gly
1               5                   10                  15

Ser Gln Glu Asp Lys Ser Gln Asp Ser Glu Leu His Phe Ser Glu Asp
            20                  25                  30

Glu Glu Ile Leu Ile Ile Arg Met Phe Asn Leu Val Gly Lys Arg Trp
        35                  40                  45

Ser Leu Ile Ala Gly Arg Ile Pro Gly Arg Thr Ala Lys Glu Ile Glu
    50                  55                  60

Glu Tyr Trp Asn Thr Arg Ser Ala Thr Ser Pro
65                  70                  75
```

<210> SEQ ID NO 115
<211> LENGTH: 261
<212> TYPE: DNA
<213> ORGANISM: Curcuma longa

<400> SEQUENCE: 115

```
atggagcgcc gtcgcaagaa gcagcgcagg tcgtccgacg actccgaaga agaggtgaac      60

agtgtggagt ggcagtccat cagcatgacc gagcaggagg aagacctcat ctgcagaatg     120

tatcgcctcg tcggcgacag gtgggatttg atagcagggc gagttccggg tcgaaaacct     180

gaagaaatag agaggttctg gatcatgaga catcgtcaag attcaagaag gcgttcctct     240

ttcgccagtc atgcaaaata a                                               261
```

<210> SEQ ID NO 116
<211> LENGTH: 86
<212> TYPE: PRT
<213> ORGANISM: Curcuma longa

<400> SEQUENCE: 116

```
Met Glu Arg Arg Arg Lys Lys Gln Arg Arg Ser Ser Asp Asp Ser Glu
1               5                   10                  15

Glu Glu Val Asn Ser Val Glu Trp Gln Ser Ile Ser Met Thr Glu Gln
            20                  25                  30

Glu Glu Asp Leu Ile Cys Arg Met Tyr Arg Leu Val Gly Asp Arg Trp
        35                  40                  45

Asp Leu Ile Ala Gly Arg Val Pro Gly Arg Lys Pro Glu Glu Ile Glu
    50                  55                  60

Arg Phe Trp Ile Met Arg His Arg Gln Asp Ser Arg Arg Arg Ser Ser
65                  70                  75                  80

Phe Ala Ser His Ala Lys
                85
```

<210> SEQ ID NO 117
<211> LENGTH: 213
<212> TYPE: DNA
<213> ORGANISM: Cyamopsis tetragonoloba

<400> SEQUENCE: 117

```
atggatcgct cttctgatga tgtttctgca gattcttcag agcaacgcag tcagggttcc      60

aaggttgaat tttccgaaga tgaggaaact cttataatca gaatgtataa actggttggg     120
```

aagaggtggc ctttgattgc aggaagaatt cccggaagaa cggcagaaga aatagaaaaa 180
ttttggaatt caagattctc caatagcaaa tga 213

<210> SEQ ID NO 118
<211> LENGTH: 70
<212> TYPE: PRT
<213> ORGANISM: Cyamopsis tetragonoloba

<400> SEQUENCE: 118

Met Asp Arg Ser Ser Asp Asp Val Ser Ala Asp Ser Ser Glu Gln Arg
1 5 10 15

Ser Gln Gly Ser Lys Val Glu Phe Ser Glu Asp Glu Glu Thr Leu Ile
20 25 30

Ile Arg Met Tyr Lys Leu Val Gly Lys Arg Trp Pro Leu Ile Ala Gly
35 40 45

Arg Ile Pro Gly Arg Thr Ala Glu Glu Ile Glu Lys Phe Trp Asn Ser
50 55 60

Arg Phe Ser Asn Ser Lys
65 70

<210> SEQ ID NO 119
<211> LENGTH: 231
<212> TYPE: DNA
<213> ORGANISM: Euphorbia esula

<400> SEQUENCE: 119
atggctgatt ctgaacattc ttctacttct gatgagatct atttggacta tcaagatgaa 60
cagagtcatg agtactcaaa gcaagaattc tctgaagatg aggaagaact tgtaattagg 120
atgtacaatt tggttggaga aaggtggcat ctaattgctg ggaggattcc aggaagaaca 180
gcagatgaga ttgagaagta ttggaattct agatattcaa ctagtgctta g 231

<210> SEQ ID NO 120
<211> LENGTH: 76
<212> TYPE: PRT
<213> ORGANISM: Euphorbia esula

<400> SEQUENCE: 120

Met Ala Asp Ser Glu His Ser Ser Thr Ser Asp Glu Ile Tyr Leu Asp
1 5 10 15

Tyr Gln Asp Glu Gln Ser His Glu Tyr Ser Lys Gln Glu Phe Ser Glu
20 25 30

Asp Glu Glu Glu Leu Val Ile Arg Met Tyr Asn Leu Val Gly Glu Arg
35 40 45

Trp His Leu Ile Ala Gly Arg Ile Pro Gly Arg Thr Ala Asp Glu Ile
50 55 60

Glu Lys Tyr Trp Asn Ser Arg Tyr Ser Thr Ser Ala
65 70 75

<210> SEQ ID NO 121
<211> LENGTH: 267
<212> TYPE: DNA
<213> ORGANISM: Gossypium hirsutum

<400> SEQUENCE: 121
atggctgact ctcaacattc ctcttctggt aaaacttatg tcaactctca agactttagt 60
tcagaggagg aaacaaatga agaatcaaag cttaaattct ctgaagatga ggaaacactt 120

```
ataattagga tgtttaatct ggttggagag aggtgggctt taattgctgg aagaatcccc    180

ggtagaacag ctgaagaaat tgaagagtat tggaatacca ggtattcaac aaggaaggac    240

atttttaaag aaaggggcca aatttga                                        267
```

<210> SEQ ID NO 122
<211> LENGTH: 88
<212> TYPE: PRT
<213> ORGANISM: Gossypium hirsutum

<400> SEQUENCE: 122

```
Met Ala Asp Ser Gln His Ser Ser Ser Gly Lys Thr Tyr Val Asn Ser
1               5                   10                  15

Gln Asp Phe Ser Ser Glu Glu Glu Thr Asn Glu Glu Ser Lys Leu Lys
            20                  25                  30

Phe Ser Glu Asp Glu Glu Thr Leu Ile Ile Arg Met Phe Asn Leu Val
        35                  40                  45

Gly Glu Arg Trp Ala Leu Ile Ala Gly Arg Ile Pro Gly Arg Thr Ala
    50                  55                  60

Glu Glu Ile Glu Glu Tyr Trp Asn Thr Arg Tyr Ser Thr Arg Lys Asp
65                  70                  75                  80

Ile Phe Lys Glu Arg Gly Gln Ile
                85
```

<210> SEQ ID NO 123
<211> LENGTH: 270
<212> TYPE: DNA
<213> ORGANISM: Gossypium hirsutum

<400> SEQUENCE: 123

```
cttttaatcg aataaaactg caactacctt cttccatttc ccatctcgac aaaaagacct     60

tgtgccatac atcaacaaac ggcatgcact gcaatttgca acccttacag ggaaggaaac    120

agagcaccaa acacagacac agatcataaa caacattaga cccaaaaaaa aacataacat    180

tgttccatcg ctaatataaa agaaatgaat gccgttattt tcaaacagaa ccgtgtctca    240

tcttcagctc ccttcgcctc tttgcaaata                                     270
```

<210> SEQ ID NO 124
<211> LENGTH: 89
<212> TYPE: PRT
<213> ORGANISM: Gossypium hirsutum

<400> SEQUENCE: 124

```
Met Asp Lys Arg Asp Arg Lys Gln Ala Lys Thr Gly Ser Cys Cys Ser
1               5                   10                  15

Glu Glu Val Ser Ser Thr Glu Trp Glu Phe Ile Asn Met Ser Glu Gln
            20                  25                  30

Glu Glu Asp Leu Ile Tyr Arg Met Tyr Lys Leu Val Gly Asp Arg Trp
        35                  40                  45

Gly Leu Ile Ala Gly Arg Ile Pro Gly Gln Lys Ala Glu Glu Ile Glu
    50                  55                  60

Arg Phe Trp Ile Met Arg His Gly Glu Leu Phe Ala Lys Arg Arg Arg
65                  70                  75                  80

Glu Leu Lys Met Arg His Gly Ser Val
                85
```

<210> SEQ ID NO 125
<211> LENGTH: 234

```
<212> TYPE: DNA
<213> ORGANISM: Gossypium hirsutum

<400> SEQUENCE: 125

ataaaaacta gagggaaata aaattggaat agaagggatg tataggatac gagaaacgca      60

tccaacttac atctacattc aacattccta tgttacaaca ataacatcat aattaatcat     120

gctgtctacc atcaaagttg agcaaaattc ccagaatgtt ttttcactgg cttgttgagt     180

atcttgtgtt ccaatatttc tcaatctcct cggctgttct tccagggatt ctcc           234


<210> SEQ ID NO 126
<211> LENGTH: 77
<212> TYPE: PRT
<213> ORGANISM: Gossypium hirsutum

<400> SEQUENCE: 126

Met Ala Glu Ser Glu Tyr Ser Ser Ser Glu Asn Ala Ser Thr Asp Ser
1               5                   10                  15

Asn Ser Ile Ala Glu Gln Ser Lys Gln Asp Leu Glu Leu Gln Phe Ser
            20                  25                  30

Glu Asp Glu Glu Thr Leu Val Ile Arg Met Phe Asn Leu Val Gly Glu
        35                  40                  45

Arg Trp Gly Leu Ile Ala Gly Arg Ile Pro Gly Arg Thr Ala Glu Glu
    50                  55                  60

Ile Glu Lys Tyr Trp Asn Thr Arg Tyr Ser Thr Ser Gln
65                  70                  75


<210> SEQ ID NO 127
<211> LENGTH: 228
<212> TYPE: DNA
<213> ORGANISM: Gossypium hirsutum

<400> SEQUENCE: 127

atggctgaca tggatggttc ttctgttgat tctaaagagg aatccagtga agattccaag      60

cttgacttct cagaagatga ggaaaccctc attattagaa tgttcaattt ggttggagaa     120

aggtggtctt tgatagcagg gagaatccct ggaagaacag ctgaggagat tcagaagtat     180

tgggcttcta gattctctta caataatcca atgcccaatc tgagttag                  228


<210> SEQ ID NO 128
<211> LENGTH: 75
<212> TYPE: PRT
<213> ORGANISM: Gossypium hirsutum

<400> SEQUENCE: 128

Met Ala Asp Met Asp Gly Ser Ser Val Asp Ser Lys Glu Glu Ser Ser
1               5                   10                  15

Glu Asp Ser Lys Leu Asp Phe Ser Glu Asp Glu Glu Thr Leu Ile Ile
            20                  25                  30

Arg Met Phe Asn Leu Val Gly Glu Arg Trp Ser Leu Ile Ala Gly Arg
        35                  40                  45

Ile Pro Gly Arg Thr Ala Glu Glu Ile Gln Lys Tyr Trp Ala Ser Arg
    50                  55                  60

Phe Ser Tyr Asn Asn Pro Met Pro Asn Leu Ser
65                  70                  75


<210> SEQ ID NO 129
<211> LENGTH: 240
<212> TYPE: DNA
```

<213> ORGANISM: Glycine max

<400> SEQUENCE: 129
atgtccacca ccgcaactac aacctctgaa gttagcagca atgagtggaa agtcatacac 60
atgagcgagc aagaggagga tctcattcgc aggatgtaca agctagtcgg ggacaagtgg 120
aatttgatag ccggtcgcat tcccagtcgt aaagcagaag aaatagagag attctggatt 180
atgagacacg gtgatgcttt ctctgttaaa agacacagaa gtaaagccca agactcatga 240

<210> SEQ ID NO 130
<211> LENGTH: 79
<212> TYPE: PRT
<213> ORGANISM: Glycine max

<400> SEQUENCE: 130

Met Ser Thr Thr Ala Thr Thr Thr Ser Glu Val Ser Ser Asn Glu Trp
1 5 10 15

Lys Val Ile His Met Ser Glu Gln Glu Glu Asp Leu Ile Arg Arg Met
20 25 30

Tyr Lys Leu Val Gly Asp Lys Trp Asn Leu Ile Ala Gly Arg Ile Pro
35 40 45

Ser Arg Lys Ala Glu Glu Ile Glu Arg Phe Trp Ile Met Arg His Gly
50 55 60

Asp Ala Phe Ser Val Lys Arg His Arg Ser Lys Ala Gln Asp Ser
65 70 75

<210> SEQ ID NO 131
<211> LENGTH: 228
<212> TYPE: DNA
<213> ORGANISM: Glycine max

<400> SEQUENCE: 131
atggctgact cggatctctc ttcaagtcaa atttctacac attctactga ttcaggaaat 60
cgagggtctt ccaaagttga attttctgaa gatgaggaaa ccctcatcat caggatgtat 120
aaactggtag gggagaggtg gtctataatt gctggaagga ttcctggaag aacagcagag 180
gaaatagaga agtattggac ttcaagattc tcgggctcta gtgaatga 228

<210> SEQ ID NO 132
<211> LENGTH: 75
<212> TYPE: PRT
<213> ORGANISM: Glycine max

<400> SEQUENCE: 132

Met Ala Asp Ser Asp Leu Ser Ser Ser Gln Ile Ser Thr His Ser Thr
1 5 10 15

Asp Ser Gly Asn Arg Gly Ser Ser Lys Val Glu Phe Ser Glu Asp Glu
20 25 30

Glu Thr Leu Ile Ile Arg Met Tyr Lys Leu Val Gly Glu Arg Trp Ser
35 40 45

Ile Ile Ala Gly Arg Ile Pro Gly Arg Thr Ala Glu Glu Ile Glu Lys
50 55 60

Tyr Trp Thr Ser Arg Phe Ser Gly Ser Ser Glu
65 70 75

<210> SEQ ID NO 133
<211> LENGTH: 225
<212> TYPE: DNA
<213> ORGANISM: Glycine max

<400> SEQUENCE: 133

```
atggctgaca tagatcgctc ctttgataat aatgtttctg ctgtttctac tgagaaatca     60

agccaagttt cagatgttga attttctgaa gctgaggaaa tccttattgc catggtgtat    120

aatctggttg gggagaggtg gtctttgatt gctggaagaa ttcctggaag aactgcagaa    180

gagatagaga aatattggac ttcaagattt tcgactagcc aatga                    225
```

<210> SEQ ID NO 134
<211> LENGTH: 74
<212> TYPE: PRT
<213> ORGANISM: Glycine max

<400> SEQUENCE: 134

```
Met Ala Asp Ile Asp Arg Ser Phe Asp Asn Asn Val Ser Ala Val Ser
1               5                   10                  15

Thr Glu Lys Ser Ser Gln Val Ser Asp Val Glu Phe Ser Glu Ala Glu
            20                  25                  30

Glu Ile Leu Ile Ala Met Val Tyr Asn Leu Val Gly Glu Arg Trp Ser
        35                  40                  45

Leu Ile Ala Gly Arg Ile Pro Gly Arg Thr Ala Glu Glu Ile Glu Lys
    50                  55                  60

Tyr Trp Thr Ser Arg Phe Ser Thr Ser Gln
65                  70
```

<210> SEQ ID NO 135
<211> LENGTH: 222
<212> TYPE: DNA
<213> ORGANISM: Glycine soja

<400> SEQUENCE: 135

```
atgactgaca tagatcgctc ctctgataat gtttcttctg attctattga gaaatcaagc     60

caagtttctg atgttgaatt ttctgaagct gaggaaatcc ttattgccat ggtgtataat    120

ctggttggag aaaggtggtc tttgattgct ggaagaattc ctggaagaac tgcagaagaa    180

atagagaaat attggacttc aagattttcg actagccaat ga                       222
```

<210> SEQ ID NO 136
<211> LENGTH: 73
<212> TYPE: PRT
<213> ORGANISM: Glycine soja

<400> SEQUENCE: 136

```
Met Thr Asp Ile Asp Arg Ser Ser Asp Asn Val Ser Ser Asp Ser Ile
1               5                   10                  15

Glu Lys Ser Ser Gln Val Ser Asp Val Glu Phe Ser Glu Ala Glu Glu
            20                  25                  30

Ile Leu Ile Ala Met Val Tyr Asn Leu Val Gly Glu Arg Trp Ser Leu
        35                  40                  45

Ile Ala Gly Arg Ile Pro Gly Arg Thr Ala Glu Glu Ile Glu Lys Tyr
    50                  55                  60

Trp Thr Ser Arg Phe Ser Thr Ser Gln
65                  70
```

<210> SEQ ID NO 137
<211> LENGTH: 231
<212> TYPE: DNA
<213> ORGANISM: Hordeum vulgare

<400> SEQUENCE: 137
tccaggatct tcttgctcgt gctgctctta ctgatgagca cattgttgag actcctatgg 60
agctcaatgt tcacctttct gctactgatg gtgatcccct gcctgacccg acgcgttatc 120
gtcatcttgt tggcagtttt gtttatctcg ctgtcactcg tctggatatc tcttatccgg 180
ttcatattct gagtcagttc gtctctgctc ccacatcggt tcactatagt c 231

<210> SEQ ID NO 138
<211> LENGTH: 76
<212> TYPE: PRT
<213> ORGANISM: Hordeum vulgare

<400> SEQUENCE: 138

Met Ser Ser Lys Ser Leu Gly Lys Asn Ser Lys Ile Met Ser Gly Arg
1 5 10 15

Glu Arg Lys Glu Val Asn Ser Asn Ala Lys His Phe Val Asp Phe Thr
20 25 30

Glu Ala Glu Glu Asp Leu Val Phe Arg Met His Arg Leu Val Gly Asn
35 40 45

Arg Trp Glu Leu Ile Ala Gly Arg Ile Pro Gly Arg Thr Ala Glu Glu
50 55 60

Val Glu Met Phe Trp Ala Lys Lys His Gln Asp Gln
65 70 75

<210> SEQ ID NO 139
<211> LENGTH: 246
<212> TYPE: DNA
<213> ORGANISM: Ipomoea nil

<400> SEQUENCE: 139
atggcagatt tggataattc cagtacctgt ggagaagcag aagcttgtgt ggaaattaca 60
gaagtggagg tcactagcca agattcaaat aagctagttt tctcggtgga tgaggaagct 120
ctggtagtca gaatgtataa cttggtggga gagaggtggt cactaattgc tgggagaatc 180
ccaggaagaa gtgcggagga aattgagaag tactggaact caacacactc aactagtcat 240
caatga 246

<210> SEQ ID NO 140
<211> LENGTH: 81
<212> TYPE: PRT
<213> ORGANISM: Ipomoea nil

<400> SEQUENCE: 140

Met Ala Asp Leu Asp Asn Ser Ser Thr Cys Gly Glu Ala Glu Ala Cys
1 5 10 15

Val Glu Ile Thr Glu Val Glu Val Thr Ser Gln Asp Ser Asn Lys Leu
20 25 30

Val Phe Ser Val Asp Glu Glu Ala Leu Val Val Arg Met Tyr Asn Leu
35 40 45

Val Gly Glu Arg Trp Ser Leu Ile Ala Gly Arg Ile Pro Gly Arg Ser
50 55 60

Ala Glu Glu Ile Glu Lys Tyr Trp Asn Ser Thr His Ser Thr Ser His
65 70 75 80

Gln

<210> SEQ ID NO 141
<211> LENGTH: 267

<212> TYPE: DNA
<213> ORGANISM: Juglans hindsii x regia

<400> SEQUENCE: 141
atggataaac gtccgcggaa acaagcaaag agtacaaaga gctccacatc agaagaagtg 60
agcagtattg agtgggagtt cataaagatg actgaacaag aagaggatct catcttccgg 120
atgtacaaac ttgttgggga caggtgggat ttgatagcag gtcgtgttcc agggcgaaaa 180
ccagaagaaa tagagaggtt ttggattatg agacacggtg aggtatttgc ccagaaaaga 240
gacgcagctg ccaagaatta ttcgtga 267

<210> SEQ ID NO 142
<211> LENGTH: 88
<212> TYPE: PRT
<213> ORGANISM: Juglans hindsii x regia

<400> SEQUENCE: 142

Met Asp Lys Arg Pro Arg Lys Gln Ala Lys Ser Thr Lys Ser Ser Thr
1 5 10 15

Ser Glu Glu Val Ser Ser Ile Glu Trp Glu Phe Ile Lys Met Thr Glu
20 25 30

Gln Glu Glu Asp Leu Ile Phe Arg Met Tyr Lys Leu Val Gly Asp Arg
35 40 45

Trp Asp Leu Ile Ala Gly Arg Val Pro Gly Arg Lys Pro Glu Glu Ile
50 55 60

Glu Arg Phe Trp Ile Met Arg His Gly Glu Val Phe Ala Gln Lys Arg
65 70 75 80

Asp Ala Ala Ala Lys Asn Tyr Ser
85

<210> SEQ ID NO 143
<211> LENGTH: 261
<212> TYPE: DNA
<213> ORGANISM: Juglans hindsii x regia

<400> SEQUENCE: 143
atggctgact ctcaaaactc ttcttccaat ggggttagga atgaaacccc ttccaatgat 60
actttcgccg actctagatc agaggaaaca agtgaagcat ccaagctaga gttctccgaa 120
gacgaagaaa tgcttatcat aaggatgttc aatctggttg gagaaaggtg gtctctgatt 180
gccggaagga tcccaggaag aacagctgag gaaattgaga agtactggac ttctagatat 240
tcaacaagcg aaatgaaata a 261

<210> SEQ ID NO 144
<211> LENGTH: 86
<212> TYPE: PRT
<213> ORGANISM: Juglans hindsii x regia

<400> SEQUENCE: 144

Met Ala Asp Ser Gln Asn Ser Ser Ser Asn Gly Val Arg Asn Glu Thr
1 5 10 15

Pro Ser Asn Asp Thr Phe Ala Asp Ser Arg Ser Glu Glu Thr Ser Glu
20 25 30

Ala Ser Lys Leu Glu Phe Ser Glu Asp Glu Glu Met Leu Ile Ile Arg
35 40 45

Met Phe Asn Leu Val Gly Glu Arg Trp Ser Leu Ile Ala Gly Arg Ile
50 55 60

-continued

```
Pro Gly Arg Thr Ala Glu Glu Ile Glu Lys Tyr Trp Thr Ser Arg Tyr
65                  70                  75                  80

Ser Thr Ser Glu Met Lys
                85


<210> SEQ ID NO 145
<211> LENGTH: 222
<212> TYPE: DNA
<213> ORGANISM: Lotus japonicus

<400> SEQUENCE: 145

atggctgaca gagaacactc ctctgataat gtttctgcag attctacaga gaaatccagt      60

caagcttcaa atgtggaatt ctctgaagat gaggaaatcc ttattaccat ggtttataat     120

ctggttgggg aaaggtggtc tttgattgct ggaagaattc ctggaagaac agcagaagaa     180

atagagaagt actggacttc aagatactcc actagtgaat ga                        222


<210> SEQ ID NO 146
<211> LENGTH: 73
<212> TYPE: PRT
<213> ORGANISM: Lotus japonicus

<400> SEQUENCE: 146

Met Ala Asp Arg Glu His Ser Ser Asp Asn Val Ser Ala Asp Ser Thr
1               5                   10                  15

Glu Lys Ser Ser Gln Ala Ser Asn Val Glu Phe Ser Glu Asp Glu Glu
            20                  25                  30

Ile Leu Ile Thr Met Val Tyr Asn Leu Val Gly Glu Arg Trp Ser Leu
        35                  40                  45

Ile Ala Gly Arg Ile Pro Gly Arg Thr Ala Glu Glu Ile Glu Lys Tyr
    50                  55                  60

Trp Thr Ser Arg Tyr Ser Thr Ser Glu
65                  70


<210> SEQ ID NO 147
<211> LENGTH: 252
<212> TYPE: DNA
<213> ORGANISM: Lolium multiflorum

<400> SEQUENCE: 147

atgttgtctt ctcggaagga tatgagcagt aaaagcttgg cgaagaactc caagacgatg      60

ggtgtccatg aagcgaaaga agttactagc accacacagc atttcgttga tttcacagaa     120

gcagaggaag atctcgtatt cagaatgcac aggcttgtcg ggaacaggtg ggaacttata     180

gctggaagga tccccggaag aacagcagga gaagtagaga tgttttgggc gaaaaagcaa     240

aaggaacaat ga                                                         252


<210> SEQ ID NO 148
<211> LENGTH: 83
<212> TYPE: PRT
<213> ORGANISM: Lolium multiflorum

<400> SEQUENCE: 148

Met Leu Ser Ser Arg Lys Asp Met Ser Ser Lys Ser Leu Ala Lys Asn
1               5                   10                  15

Ser Lys Thr Met Gly Val His Glu Ala Lys Glu Val Thr Ser Thr Thr
            20                  25                  30

Gln His Phe Val Asp Phe Thr Glu Ala Glu Glu Asp Leu Val Phe Arg
        35                  40                  45
```

```
Met His Arg Leu Val Gly Asn Arg Trp Glu Leu Ile Ala Gly Arg Ile
    50                  55                  60

Pro Gly Arg Thr Ala Gly Glu Val Glu Met Phe Trp Ala Lys Lys Gln
65                  70                  75                  80

Lys Glu Gln


<210> SEQ ID NO 149
<211> LENGTH: 237
<212> TYPE: DNA
<213> ORGANISM: Lactuca saligna

<400> SEQUENCE: 149

atggctaact tggataagta ctctacttcc aatgatactt ccactcatac tagagggcca      60

tcaaatcaag aatctcgggt tcatttctct gaagacgaaa aaactctcat cactaggatg     120

tataagcttg tcggagaaag atggtctttg attgctggaa ggattcctgg aagatctgca     180

gaggaaattg agaagtactg gacttccaaa tattcaagaa ctaatgatca gatgtag        237


<210> SEQ ID NO 150
<211> LENGTH: 78
<212> TYPE: PRT
<213> ORGANISM: Lactuca saligna

<400> SEQUENCE: 150

Met Ala Asn Leu Asp Lys Tyr Ser Thr Ser Asn Asp Thr Ser Thr His
1               5                   10                  15

Thr Arg Gly Pro Ser Asn Gln Glu Ser Arg Val His Phe Ser Glu Asp
            20                  25                  30

Glu Lys Thr Leu Ile Thr Arg Met Tyr Lys Leu Val Gly Glu Arg Trp
        35                  40                  45

Ser Leu Ile Ala Gly Arg Ile Pro Gly Arg Ser Ala Glu Glu Ile Glu
    50                  55                  60

Lys Tyr Trp Thr Ser Lys Tyr Ser Arg Thr Asn Asp Gln Met
65                  70                  75


<210> SEQ ID NO 151
<211> LENGTH: 228
<212> TYPE: DNA
<213> ORGANISM: Lactuca serriola

<400> SEQUENCE: 151

atgaagcaca attctgagtt tgaagaggtg agcagtagaa aatgggagtt cattaatatg      60

agcgaacaag aagaagatat catttataga atgcacaaac ttgctggtaa caggtgggat     120

ttaatagctg gtaggatttc gggacggaat ccggaagaaa tagagagatt ttggttaatg     180

agacatagtg aagcgtatga ggatttaagg aaaagagtca aatcttga                  228


<210> SEQ ID NO 152
<211> LENGTH: 75
<212> TYPE: PRT
<213> ORGANISM: Lactuca serriola

<400> SEQUENCE: 152

Met Lys His Asn Ser Glu Phe Glu Glu Val Ser Ser Arg Lys Trp Glu
1               5                   10                  15

Phe Ile Asn Met Ser Glu Gln Glu Glu Asp Ile Ile Tyr Arg Met His
            20                  25                  30

Lys Leu Ala Gly Asn Arg Trp Asp Leu Ile Ala Gly Arg Ile Ser Gly
```

```
        35                  40                  45

Arg Asn Pro Glu Glu Ile Glu Arg Phe Trp Leu Met Arg His Ser Glu
    50                  55                  60

Ala Tyr Glu Asp Leu Arg Lys Arg Val Lys Ser
65                  70                  75


<210> SEQ ID NO 153
<211> LENGTH: 219
<212> TYPE: DNA
<213> ORGANISM: Liriodendron tulipifera

<400> SEQUENCE: 153

atggctgact tagatcattc atctgaggat gtttctgatg attctcaagg aaccagtcaa      60

gattctaagc tggagtttac ggaggatgag cagactctca ttgaaaggat gtttaatctt     120

cttggagaga ggtggtctct gattgctggg agaatcccag gaagaacagc agaagagatt     180

gagaagtact ggacttcaag gtactcttca agtgaatga                            219


<210> SEQ ID NO 154
<211> LENGTH: 72
<212> TYPE: PRT
<213> ORGANISM: Liriodendron tulipifera

<400> SEQUENCE: 154

Met Ala Asp Leu Asp His Ser Ser Glu Asp Val Ser Asp Asp Ser Gln
1               5                   10                  15

Gly Thr Ser Gln Asp Ser Lys Leu Glu Phe Thr Glu Asp Glu Gln Thr
            20                  25                  30

Leu Ile Glu Arg Met Phe Asn Leu Leu Gly Glu Arg Trp Ser Leu Ile
        35                  40                  45

Ala Gly Arg Ile Pro Gly Arg Thr Ala Glu Glu Ile Glu Lys Tyr Trp
    50                  55                  60

Thr Ser Arg Tyr Ser Ser Ser Glu
65                  70


<210> SEQ ID NO 155
<211> LENGTH: 225
<212> TYPE: DNA
<213> ORGANISM: Malus domestica

<400> SEQUENCE: 155

atggcggact ccgagcactc ttcttccgat gacactttct cggactctcg agagaagagc      60

acagaaaaat ctgagcttca attctccgag gatgaggaag cacttatcat aagaatgtac     120

aatctagtag gggagaggtg ggctttgatt gccgggagga ttccggggag aacagcagaa     180

gaaattgaga agtattggac ttctacacac tcaactagtc aataa                     225


<210> SEQ ID NO 156
<211> LENGTH: 74
<212> TYPE: PRT
<213> ORGANISM: Malus domestica

<400> SEQUENCE: 156

Met Ala Asp Ser Glu His Ser Ser Ser Asp Asp Thr Phe Ser Asp Ser
1               5                   10                  15

Arg Glu Lys Ser Thr Glu Lys Ser Glu Leu Gln Phe Ser Glu Asp Glu
            20                  25                  30

Glu Ala Leu Ile Ile Arg Met Tyr Asn Leu Val Gly Glu Arg Trp Ala
        35                  40                  45
```

```
Leu Ile Ala Gly Arg Ile Pro Gly Arg Thr Ala Glu Glu Ile Glu Lys
    50                  55                  60

Tyr Trp Thr Ser Thr His Ser Thr Ser Gln
65                  70


<210> SEQ ID NO 157
<211> LENGTH: 264
<212> TYPE: DNA
<213> ORGANISM: Manihot esculenta

<400> SEQUENCE: 157

atggatagac gccgcaagaa gcaatccaag gcagcaactc cgcgctctga agaggtaagc      60

agtattgaat gggagttcat aaacatgtcc gaacaagaag aagatcttat ttatagaatg     120

tataagcttg tcggagacag gtgggctttg attgctggtc ggattccagg tcggaaagct     180

gaagaaatag aaaggttttg gataatgagg catggtgaag ggtttgccgg tcgacgaaaa     240

gagctcaaga agtccaaatg ttaa                                            264


<210> SEQ ID NO 158
<211> LENGTH: 87
<212> TYPE: PRT
<213> ORGANISM: Manihot esculenta

<400> SEQUENCE: 158

Met Asp Arg Arg Arg Lys Lys Gln Ser Lys Ala Ala Thr Pro Arg Ser
1               5                   10                  15

Glu Glu Val Ser Ser Ile Glu Trp Glu Phe Ile Asn Met Ser Glu Gln
            20                  25                  30

Glu Glu Asp Leu Ile Tyr Arg Met Tyr Lys Leu Val Gly Asp Arg Trp
        35                  40                  45

Ala Leu Ile Ala Gly Arg Ile Pro Gly Arg Lys Ala Glu Glu Ile Glu
    50                  55                  60

Arg Phe Trp Ile Met Arg His Gly Glu Gly Phe Ala Gly Arg Arg Lys
65                  70                  75                  80

Glu Leu Lys Lys Ser Lys Cys
                85


<210> SEQ ID NO 159
<211> LENGTH: 225
<212> TYPE: DNA
<213> ORGANISM: Manihot esculenta

<400> SEQUENCE: 159

atggctgact tggatcattc ttctagtgat gatgtttctg ttgattctag agaggaatca      60

agccaagaat ctaagcttga attcacagag gatgaagaaa cccttattac taggatgtat     120

aatcttgttg gagagaggtg gcctctaatt gctgggagaa ttccaggaag aacagcggag     180

gaaattgaga agtactggaa ttccagattc tcttcaagtc aataa                     225


<210> SEQ ID NO 160
<211> LENGTH: 74
<212> TYPE: PRT
<213> ORGANISM: Manihot esculenta

<400> SEQUENCE: 160

Met Ala Asp Leu Asp His Ser Ser Ser Asp Asp Val Ser Val Asp Ser
1               5                   10                  15

Arg Glu Glu Ser Ser Gln Glu Ser Lys Leu Glu Phe Thr Glu Asp Glu
```

```
            20                  25                  30

Glu Thr Leu Ile Thr Arg Met Tyr Asn Leu Val Gly Glu Arg Trp Pro
        35                  40                  45

Leu Ile Ala Gly Arg Ile Pro Gly Arg Thr Ala Glu Glu Ile Glu Lys
    50                  55                  60

Tyr Trp Asn Ser Arg Phe Ser Ser Ser Gln
65                  70


<210> SEQ ID NO 161
<211> LENGTH: 276
<212> TYPE: DNA
<213> ORGANISM: Medicago truncatula

<400> SEQUENCE: 161

atggaagaaa aacgacgttc ccattcccaa aataaggcaa atatctcccc aaacacaagt      60

caaacctctg aagctggtgg agaagtgagc agcactgagt gggagttcat agagatgagc     120

gagcaagagg aggatctcat tcgcaggatg tacgacctag ttggagatag gtggaatttg     180

atagcaggtc gcattccagg tcgtaaagca gaagaaatag agagattctg gattatgaga     240

cacactgatg ctttttctgc caaaagaaag aagtga                               276


<210> SEQ ID NO 162
<211> LENGTH: 91
<212> TYPE: PRT
<213> ORGANISM: Medicago truncatula

<400> SEQUENCE: 162

Met Glu Glu Lys Arg Arg Ser His Ser Gln Asn Lys Ala Asn Ile Ser
1               5                   10                  15

Pro Asn Thr Ser Gln Thr Ser Glu Ala Gly Gly Glu Val Ser Ser Thr
            20                  25                  30

Glu Trp Glu Phe Ile Glu Met Ser Glu Gln Glu Glu Asp Leu Ile Arg
        35                  40                  45

Arg Met Tyr Asp Leu Val Gly Asp Arg Trp Asn Leu Ile Ala Gly Arg
    50                  55                  60

Ile Pro Gly Arg Lys Ala Glu Glu Ile Glu Arg Phe Trp Ile Met Arg
65                  70                  75                  80

His Thr Asp Ala Phe Ser Ala Lys Arg Lys Lys
                85                  90


<210> SEQ ID NO 163
<211> LENGTH: 237
<212> TYPE: DNA
<213> ORGANISM: Oryza minuta

<400> SEQUENCE: 163

atggatagca gcagtggtag ccagggaaag aattccaaaa ccagtgatgg ttgtgaaaca      60

aaagaagtta atagcactgc actgaatttt attcatttca cggaagaaga ggaagatctc     120

gttttcagaa tgcacaggct tgttgggaac aggtgggaac ttatagctgg aagaatccct     180

ggaaggacag caaaagaagt agaaatgttc tgggcaataa agcaccagga cacataa        237


<210> SEQ ID NO 164
<211> LENGTH: 78
<212> TYPE: PRT
<213> ORGANISM: Oryza minuta

<400> SEQUENCE: 164
```

-continued

```
Met Asp Ser Ser Ser Gly Ser Gln Gly Lys Asn Ser Lys Thr Ser Asp
1               5                   10                  15

Gly Cys Glu Thr Lys Glu Val Asn Ser Thr Ala Leu Asn Phe Ile His
            20                  25                  30

Phe Thr Glu Glu Glu Glu Asp Leu Val Phe Arg Met His Arg Leu Val
        35                  40                  45

Gly Asn Arg Trp Glu Leu Ile Ala Gly Arg Ile Pro Gly Arg Thr Ala
    50                  55                  60

Lys Glu Val Glu Met Phe Trp Ala Ile Lys His Gln Asp Thr
65                  70                  75


<210> SEQ ID NO 165
<211> LENGTH: 237
<212> TYPE: DNA
<213> ORGANISM: Oryza sativa

<400> SEQUENCE: 165

atggatagca gcagtggtag ccagggaaag aattccaaaa ccagtgatgg ttgtgaaaca      60

aaagaagtta ataacactgc acagaatttt gttcatttca cggaagaaga ggaagatctc     120

gttttcagaa tgcacaggct tgttgggaac aggtgggaac ttatagctgg aagaatccct     180

ggaagaacag caaaagaagt agaaatgttc tgggcagtaa agcaccagaa tacataa        237


<210> SEQ ID NO 166
<211> LENGTH: 78
<212> TYPE: PRT
<213> ORGANISM: Oryza sativa

<400> SEQUENCE: 166

Met Asp Ser Ser Ser Gly Ser Gln Gly Lys Asn Ser Lys Thr Ser Asp
1               5                   10                  15

Gly Cys Glu Thr Lys Glu Val Asn Asn Thr Ala Gln Asn Phe Val His
            20                  25                  30

Phe Thr Glu Glu Glu Glu Asp Leu Val Phe Arg Met His Arg Leu Val
        35                  40                  45

Gly Asn Arg Trp Glu Leu Ile Ala Gly Arg Ile Pro Gly Arg Thr Ala
    50                  55                  60

Lys Glu Val Glu Met Phe Trp Ala Val Lys His Gln Asn Thr
65                  70                  75


<210> SEQ ID NO 167
<211> LENGTH: 162
<212> TYPE: DNA
<213> ORGANISM: Phalaenopsis equestris

<400> SEQUENCE: 167

atgtccaaac ctaacttcac agaggaagaa gacgacctca ttgccagaat gtataagctc      60

gttggagaca gatggtctct gattgctgga aggatcccag gaagaacaag cgaggagatt     120

gagaattact ggaagtcaaa aaattctacc tcgtctacat aa                        162


<210> SEQ ID NO 168
<211> LENGTH: 53
<212> TYPE: PRT
<213> ORGANISM: Phalaenopsis equestris

<400> SEQUENCE: 168

Met Ser Lys Pro Asn Phe Thr Glu Glu Glu Asp Asp Leu Ile Ala Arg
1               5                   10                  15
```

```
Met Tyr Lys Leu Val Gly Asp Arg Trp Ser Leu Ile Ala Gly Arg Ile
            20                  25                  30

Pro Gly Arg Thr Ser Glu Glu Ile Glu Asn Tyr Trp Lys Ser Lys Asn
        35                  40                  45

Ser Thr Ser Ser Thr
    50


<210> SEQ ID NO 169
<211> LENGTH: 324
<212> TYPE: DNA
<213> ORGANISM: Picea glauca

<400> SEQUENCE: 169

cattatatgg gtaacttcag tactttaaat cttgtccata cattgtattt ctctctgttg      60

ccaggactga aatattttga acgtgacaag cacatgataa aggtcagccg ttccattaat     120

atgattggtt tcaattaagg atatctgaat tgatctacat aacttgggac ctacattcaa     180

aattgatccg ctacgaaatt tcctatacca tcagaccaaa tacaaagagc aaaacctcta     240

tactttttct ctgattagag aaaacactgc aattaaggaa acctcgacta actttctctg     300

attaaagaaa atacaatgaa gaaa                                            324


<210> SEQ ID NO 170
<211> LENGTH: 107
<212> TYPE: PRT
<213> ORGANISM: Picea glauca

<400> SEQUENCE: 170

Met Glu Lys Asn Val Tyr Cys Ser Ser Ala Ile Leu Glu Tyr Asp Thr
1               5                   10                  15

Glu Glu Gly Ser Ser Leu Asp Trp Glu Cys Asp Met Ser Glu Glu Glu
            20                  25                  30

Glu Asp Leu Ile Leu Arg Met Tyr Lys Leu Val Gly Asn Lys Trp Ser
        35                  40                  45

Leu Ile Ala Gly Arg Ile Pro Gly Arg Lys Ala Glu Glu Ile Glu Arg
    50                  55                  60

Tyr Trp Ala Met Arg Thr Gln Gln Leu Cys Gly Gly His Gly Ala Ile
65                  70                  75                  80

Phe Thr Asn Lys Lys Gln Thr Ala Asn Met Ile Ser Ile Gln Tyr Arg
                85                  90                  95

Ile Asn Gly Cys Asn Asp Val Glu Val Asn Ser
            100                 105


<210> SEQ ID NO 171
<211> LENGTH: 258
<212> TYPE: DNA
<213> ORGANISM: Petunia hybrida

<400> SEQUENCE: 171

atggcagata aaggacaaag ttcttcatct gtaaatactc cggctgattc tcaagatggg      60

gtggctcctc ggatgttagt ttcaggaaag acatcaaaag tagctgaaat aaaattctct     120

gaagaagaag aagacttgat cattaggatg tataatttgg ttggcgagag atggtctctt     180

atagctggaa gaatcccagg aagaagtgca gaagagattg agaaatattg gaatactcga     240

tcttcaacca gccaataa                                                   258


<210> SEQ ID NO 172
<211> LENGTH: 85
```

<212> TYPE: PRT
<213> ORGANISM: Petunia hybrida

<400> SEQUENCE: 172

```
Met Ala Asp Lys Gly Gln Ser Ser Ser Ser Val Asn Thr Pro Ala Asp
1               5                   10                  15

Ser Gln Asp Gly Val Ala Pro Arg Met Leu Val Ser Gly Lys Thr Ser
            20                  25                  30

Lys Val Ala Glu Ile Lys Phe Ser Glu Glu Glu Glu Asp Leu Ile Ile
        35                  40                  45

Arg Met Tyr Asn Leu Val Gly Glu Arg Trp Ser Leu Ile Ala Gly Arg
    50                  55                  60

Ile Pro Gly Arg Ser Ala Glu Glu Ile Glu Lys Tyr Trp Asn Thr Arg
65                  70                  75                  80

Ser Ser Thr Ser Gln
                85
```

<210> SEQ ID NO 173
<211> LENGTH: 327
<212> TYPE: DNA
<213> ORGANISM: Pseudotsuga menziesii

<400> SEQUENCE: 173

```
atggagaaga atgtgtactg tagcacttct attctggagt atgacaccga ggaagggagt      60

agcttagatt gggaatgcga catgtccgag gaagaagaag atcttattct cagaatgtac     120

aaacttatcg ggaacaagtg gtcgctgatt gccggacgta ttcctggaag aaaagcagag     180

gagattgaga ggtactgggc gatgagaacc caacaatttt gcggcagcca tggcgccacc     240

attttcgcca gcaataagca gatgggcaat atgatctcga ttccatacca cattaatgga     300

tgcaatgacg ttgaagtaca ttcgtag                                         327
```

<210> SEQ ID NO 174
<211> LENGTH: 108
<212> TYPE: PRT
<213> ORGANISM: Pseudotsuga menziesii

<400> SEQUENCE: 174

```
Met Glu Lys Asn Val Tyr Cys Ser Thr Ser Ile Leu Glu Tyr Asp Thr
1               5                   10                  15

Glu Glu Gly Ser Ser Leu Asp Trp Glu Cys Asp Met Ser Glu Glu Glu
            20                  25                  30

Glu Asp Leu Ile Leu Arg Met Tyr Lys Leu Ile Gly Asn Lys Trp Ser
        35                  40                  45

Leu Ile Ala Gly Arg Ile Pro Gly Arg Lys Ala Glu Glu Ile Glu Arg
    50                  55                  60

Tyr Trp Ala Met Arg Thr Gln Gln Phe Cys Gly Ser His Gly Ala Thr
65                  70                  75                  80

Ile Phe Ala Ser Asn Lys Gln Met Gly Asn Met Ile Ser Ile Pro Tyr
                85                  90                  95

His Ile Asn Gly Cys Asn Asp Val Glu Val His Ser
            100                 105
```

<210> SEQ ID NO 175
<211> LENGTH: 225
<212> TYPE: DNA
<213> ORGANISM: Prunus persica

<400> SEQUENCE: 175
atggctgact tggatcactc cacctctgat gacaattctg tggattctag agaggaaagt 60
agtcaagact ctaagcttca cttctcagaa gatgaggaaa ctctaatcac taggatgttt 120
aacctggttg gtgagaggtg gtctctgatt gctggtagaa ttcctggaag atcagcagag 180
gagattgaaa agtactggac ttcaagatac tcaacaagtg aatga 225

<210> SEQ ID NO 176
<211> LENGTH: 74
<212> TYPE: PRT
<213> ORGANISM: Prunus persica

<400> SEQUENCE: 176

Met Ala Asp Leu Asp His Ser Thr Ser Asp Asp Asn Ser Val Asp Ser
1 5 10 15

Arg Glu Glu Ser Ser Gln Asp Ser Lys Leu His Phe Ser Glu Asp Glu
20 25 30

Glu Thr Leu Ile Thr Arg Met Phe Asn Leu Val Gly Glu Arg Trp Ser
35 40 45

Leu Ile Ala Gly Arg Ile Pro Gly Arg Ser Ala Glu Glu Ile Glu Lys
50 55 60

Tyr Trp Thr Ser Arg Tyr Ser Thr Ser Glu
65 70

<210> SEQ ID NO 177
<211> LENGTH: 252
<212> TYPE: DNA
<213> ORGANISM: Pinus pinaster

<400> SEQUENCE: 177
atggatcgtg cagacacaga tgaagaccga ctctcctctt cacataaaga agtagaagaa 60
gcagggaaag agagaacaag cagtacaaat ataaacgagg acgaagaaga tctcatcatt 120
aggctgcaca aattggtggg agataggtgg tcgctgattg ctggcagaat acctggacga 180
accccagagg agattgagaa gtactggaag tcgagaaagc aggaaaattc caaacgcaaa 240
agaggcaaat ga 252

<210> SEQ ID NO 178
<211> LENGTH: 83
<212> TYPE: PRT
<213> ORGANISM: Pinus pinaster

<400> SEQUENCE: 178

Met Asp Arg Ala Asp Thr Asp Glu Asp Arg Leu Ser Ser Ser His Lys
1 5 10 15

Glu Val Glu Glu Ala Gly Lys Glu Arg Thr Ser Ser Thr Asn Ile Asn
20 25 30

Glu Asp Glu Glu Asp Leu Ile Ile Arg Leu His Lys Leu Val Gly Asp
35 40 45

Arg Trp Ser Leu Ile Ala Gly Arg Ile Pro Gly Arg Thr Pro Glu Glu
50 55 60

Ile Glu Lys Tyr Trp Lys Ser Arg Lys Gln Glu Asn Ser Lys Arg Lys
65 70 75 80

Arg Gly Lys

<210> SEQ ID NO 179
<211> LENGTH: 348
<212> TYPE: DNA

<213> ORGANISM: Pinus pinaster

<400> SEQUENCE: 179
atggctcgtt cctcctccct cagtatggag aagaatatgt actgtagttc tactcttctg 60
gagtatgata ctgaggaagg gagtagttta gattgggaat gcgacatgtc cgaggaagaa 120
gaagatctta tactcagaat gtacaaactt atcggcaaca agtggtcgct gattgccggg 180
cgcattcctg gaagaaaagc agaggagatt gagaggtact gggccatgag aacccaacaa 240
ttgtgtggcg gccatgatgc tattttgacg aagaaacagc agaaaaccaa tatgatatcg 300
attcagtacc gcattaatgg acccaatgat gttgaagtaa attcgtag 348

<210> SEQ ID NO 180
<211> LENGTH: 115
<212> TYPE: PRT
<213> ORGANISM: Pinus pinaster

<400> SEQUENCE: 180

Met Ala Arg Ser Ser Ser Leu Ser Met Glu Lys Asn Met Tyr Cys Ser
1 5 10 15

Ser Thr Leu Leu Glu Tyr Asp Thr Glu Glu Gly Ser Ser Leu Asp Trp
20 25 30

Glu Cys Asp Met Ser Glu Glu Glu Glu Asp Leu Ile Leu Arg Met Tyr
35 40 45

Lys Leu Ile Gly Asn Lys Trp Ser Leu Ile Ala Gly Arg Ile Pro Gly
50 55 60

Arg Lys Ala Glu Glu Ile Glu Arg Tyr Trp Ala Met Arg Thr Gln Gln
65 70 75 80

Leu Cys Gly Gly His Asp Ala Ile Leu Thr Lys Lys Gln Gln Lys Thr
85 90 95

Asn Met Ile Ser Ile Gln Tyr Arg Ile Asn Gly Pro Asn Asp Val Glu
100 105 110

Val Asn Ser
115

<210> SEQ ID NO 181
<211> LENGTH: 246
<212> TYPE: DNA
<213> ORGANISM: Picea sitchensis

<400> SEQUENCE: 181
atggacgtgc aagaccttca acagcagtcc tctgaaggag agagtgactc tcagggtgga 60
aggagccggc aagggttatg tgattctgat atctctgctg acgaagaaga tttgattatc 120
agactccaca agcttcttgg tgacaggtgg gcgttgattg ccgggcgcct cccatggcga 180
acgactgagg aaattgagaa atactggaaa atgagaagtc aggagatcga tcagagcagc 240
gattaa 246

<210> SEQ ID NO 182
<211> LENGTH: 81
<212> TYPE: PRT
<213> ORGANISM: Picea sitchensis

<400> SEQUENCE: 182

Met Asp Val Gln Asp Leu Gln Gln Gln Ser Ser Glu Gly Glu Ser Asp
1 5 10 15

Ser Gln Gly Gly Arg Ser Arg Gln Gly Leu Cys Asp Ser Asp Ile Ser
20 25 30

```
Ala Asp Glu Glu Asp Leu Ile Ile Arg Leu His Lys Leu Leu Gly Asp
        35                  40                  45

Arg Trp Ala Leu Ile Ala Gly Arg Leu Pro Trp Arg Thr Thr Glu Glu
    50                  55                  60

Ile Glu Lys Tyr Trp Lys Met Arg Ser Gln Glu Ile Asp Gln Ser Ser
65                  70                  75                  80

Asp


<210> SEQ ID NO 183
<211> LENGTH: 324
<212> TYPE: DNA
<213> ORGANISM: Picea sitchensis

<400> SEQUENCE: 183

ttattggttt caattaagga tatctgaatt gagctacata acttgggacc tacattcaaa      60

attgatccgc tacgaaattc cctataccat cagaccaaat acaaagagca aaacctctat     120

actttttctc tgattagaga aaacactgca attaaggaaa cctcgacgaa ctttctctga     180

ttaaagaaaa tacaatgaag aaaatctccc tgaatttgct ctaattggag aaaatacaca     240

gagcaaaatc tctacgaatt tacttcgacg tcattgcatc cattaatgcg gtattgaatc     300

gagatcatat tggccgtctg cttc                                            324


<210> SEQ ID NO 184
<211> LENGTH: 107
<212> TYPE: PRT
<213> ORGANISM: Picea sitchensis

<400> SEQUENCE: 184

Met Glu Lys Asn Val Tyr Cys Ser Ser Ala Ile Leu Glu Tyr Asp Thr
1               5                   10                  15

Glu Glu Gly Ser Ser Leu Asp Trp Glu Cys Asp Met Ser Glu Glu Glu
            20                  25                  30

Glu Asp Leu Ile Leu Arg Met Tyr Lys Leu Val Gly Asn Lys Trp Ser
        35                  40                  45

Leu Ile Ala Gly Arg Ile Pro Gly Arg Lys Ala Glu Glu Ile Glu Arg
    50                  55                  60

Tyr Trp Ala Met Arg Thr Gln Gln Leu Cys Gly Gly His Gly Ala Ile
65                  70                  75                  80

Phe Thr Asn Lys Lys Gln Thr Ala Asn Met Ile Ser Ile Gln Tyr Arg
                85                  90                  95

Ile Asn Gly Cys Asn Asp Val Glu Val Asn Ser
            100                 105


<210> SEQ ID NO 185
<211> LENGTH: 255
<212> TYPE: DNA
<213> ORGANISM: Pinus taeda

<400> SEQUENCE: 185

atggatcgtg cagacacaga tgaagaccga ctctcgtctt cacataaaga agtagaagaa      60

gcaggggaag agaggagaac aaggagtaca aatatgaacg aggacgaaga agatctcatc     120

attaggctgc acaaattgtt gggagagagg tggtcgctga ttgctggcag aatacctgga     180

cgaaccccag aggagattga gaagtactgg aagtcgagaa agcaggaaaa ttccaaacgc     240

aaaagaggca aatga                                                      255
```

<210> SEQ ID NO 186
<211> LENGTH: 84
<212> TYPE: PRT
<213> ORGANISM: Pinus taeda

<400> SEQUENCE: 186

```
Met Asp Arg Ala Asp Thr Asp Glu Asp Arg Leu Ser Ser Ser His Lys
1               5                   10                  15

Glu Val Glu Glu Ala Gly Glu Glu Arg Arg Thr Arg Ser Thr Asn Met
            20                  25                  30

Asn Glu Asp Glu Glu Asp Leu Ile Ile Arg Leu His Lys Leu Leu Gly
        35                  40                  45

Glu Arg Trp Ser Leu Ile Ala Gly Arg Ile Pro Gly Arg Thr Pro Glu
    50                  55                  60

Glu Ile Glu Lys Tyr Trp Lys Ser Arg Lys Gln Glu Asn Ser Lys Arg
65                  70                  75                  80

Lys Arg Gly Lys
```

<210> SEQ ID NO 187
<211> LENGTH: 237
<212> TYPE: DNA
<213> ORGANISM: Populus tremula

<400> SEQUENCE: 187

```
atggctgact ctgaacattc ttcttctgat gaaacttttg cgtattcgag agaggaaaca      60

agtcaggaaa caagtcagga atcaaggctt gaattctctg aggatgagga gacacttata     120

attaggatgt ttaatctagt tggagagagg tggtctctga ttgctggaag gattcctgga     180

agaacagctg aggaaataga gaagtactgg aacactagat actctacaag tgaatga       237
```

<210> SEQ ID NO 188
<211> LENGTH: 78
<212> TYPE: PRT
<213> ORGANISM: Populus tremula

<400> SEQUENCE: 188

```
Met Ala Asp Ser Glu His Ser Ser Ser Asp Glu Thr Phe Ala Tyr Ser
1               5                   10                  15

Arg Glu Glu Thr Ser Gln Glu Thr Ser Gln Glu Ser Arg Leu Glu Phe
            20                  25                  30

Ser Glu Asp Glu Glu Thr Leu Ile Ile Arg Met Phe Asn Leu Val Gly
        35                  40                  45

Glu Arg Trp Ser Leu Ile Ala Gly Arg Ile Pro Gly Arg Thr Ala Glu
    50                  55                  60

Glu Ile Glu Lys Tyr Trp Asn Thr Arg Tyr Ser Thr Ser Glu
65                  70                  75
```

<210> SEQ ID NO 189
<211> LENGTH: 288
<212> TYPE: DNA
<213> ORGANISM: Populus tremula

<400> SEQUENCE: 189

```
atggaaagta tggaccgccg ccggcgccgg aaacaaccta aaattaacag ttctgagtct      60

gaagaggtca gtagtattga atgggagttt ataaacatga gcgagcaaga ggaagacctc     120

atttacagaa tgcataaact tgttggtgaa aggtgggatt tgatagctgg aaggattcct     180

ggccgaaaag cagaagaaat agagaggttt tggataatga aacaccgcga agggtttgct     240
```

ggaaacggaa aattgtataa cgaagtgaag tctaggactt ctagttga 288

<210> SEQ ID NO 190
<211> LENGTH: 95
<212> TYPE: PRT
<213> ORGANISM: Populus tremula

<400> SEQUENCE: 190

Met Glu Ser Met Asp Arg Arg Arg Arg Arg Lys Gln Pro Lys Ile Asn
1 5 10 15

Ser Ser Glu Ser Glu Glu Val Ser Ser Ile Glu Trp Glu Phe Ile Asn
20 25 30

Met Ser Glu Gln Glu Glu Asp Leu Ile Tyr Arg Met His Lys Leu Val
35 40 45

Gly Glu Arg Trp Asp Leu Ile Ala Gly Arg Ile Pro Gly Arg Lys Ala
50 55 60

Glu Glu Ile Glu Arg Phe Trp Ile Met Lys His Arg Glu Gly Phe Ala
65 70 75 80

Gly Asn Gly Lys Leu Tyr Asn Glu Val Lys Ser Arg Thr Ser Ser
85 90 95

<210> SEQ ID NO 191
<211> LENGTH: 225
<212> TYPE: DNA
<213> ORGANISM: Populus tremula

<400> SEQUENCE: 191
atggctgact tggatcactc ctctagtgat gacaactctg ttgattctag agaggaaacc 60
agccaagatt ccaagcttga attctcagaa gatgaggaaa ctcttatcac caggatgtac 120
aatctggctg gtgagaggtg gccattaatt gctgggagga ttccaggaag aacagcagaa 180
gaaattgaga agtactggac ttcaagatac tctacgagtc agtaa 225

<210> SEQ ID NO 192
<211> LENGTH: 74
<212> TYPE: PRT
<213> ORGANISM: Populus tremula

<400> SEQUENCE: 192

Met Ala Asp Leu Asp His Ser Ser Ser Asp Asp Asn Ser Val Asp Ser
1 5 10 15

Arg Glu Glu Thr Ser Gln Asp Ser Lys Leu Glu Phe Ser Glu Asp Glu
20 25 30

Glu Thr Leu Ile Thr Arg Met Tyr Asn Leu Ala Gly Glu Arg Trp Pro
35 40 45

Leu Ile Ala Gly Arg Ile Pro Gly Arg Thr Ala Glu Glu Ile Glu Lys
50 55 60

Tyr Trp Thr Ser Arg Tyr Ser Thr Ser Gln
65 70

<210> SEQ ID NO 193
<211> LENGTH: 234
<212> TYPE: DNA
<213> ORGANISM: Populus tremula

<400> SEQUENCE: 193
atggctggct cgggtcacac ctcaaataac acaaatcaag ataccaaggc tgcaaagagt 60
aatcaagact ccaacctgca ggatttctct gaagatgaag agaatctcat tgctagaatg 120

```
tttggcttgg ttgggaagag atggtcacta attgctggga gaataccagg aagaacagca    180

gaggagattg agaagtattg gacttcaaag cagaggtcat caaaggaaag atga          234


<210> SEQ ID NO 194
<211> LENGTH: 77
<212> TYPE: PRT
<213> ORGANISM: Populus tremula

<400> SEQUENCE: 194

Met Ala Gly Ser Gly His Thr Ser Asn Asn Thr Asn Gln Asp Thr Lys
1               5                   10                  15

Ala Ala Lys Ser Asn Gln Asp Ser Asn Leu Gln Asp Phe Ser Glu Asp
            20                  25                  30

Glu Glu Asn Leu Ile Ala Arg Met Phe Gly Leu Val Gly Lys Arg Trp
        35                  40                  45

Ser Leu Ile Ala Gly Arg Ile Pro Gly Arg Thr Ala Glu Glu Ile Glu
    50                  55                  60

Lys Tyr Trp Thr Ser Lys Gln Arg Ser Ser Lys Glu Arg
65                  70                  75


<210> SEQ ID NO 195
<211> LENGTH: 222
<212> TYPE: DNA
<213> ORGANISM: Populus trichocarpa

<400> SEQUENCE: 195

atggctgact cggatcactc ctctagtgat gatctctctg ttgattctag agatacaagc     60

caagattcca agcttgaatt ctcagaagac gaggaaactc ttattactag gatgtacaat    120

ctggttggtg agaggtggac tttaattgct gggaggattc ctggaagaac agcagaggaa    180

attgagaagt actggacttc aagatactct acaagtcagt aa                       222


<210> SEQ ID NO 196
<211> LENGTH: 73
<212> TYPE: PRT
<213> ORGANISM: Populus trichocarpa

<400> SEQUENCE: 196

Met Ala Asp Ser Asp His Ser Ser Ser Asp Asp Leu Ser Val Asp Ser
1               5                   10                  15

Arg Asp Thr Ser Gln Asp Ser Lys Leu Glu Phe Ser Glu Asp Glu Glu
            20                  25                  30

Thr Leu Ile Thr Arg Met Tyr Asn Leu Val Gly Glu Arg Trp Thr Leu
        35                  40                  45

Ile Ala Gly Arg Ile Pro Gly Arg Thr Ala Glu Glu Ile Glu Lys Tyr
    50                  55                  60

Trp Thr Ser Arg Tyr Ser Thr Ser Gln
65                  70


<210> SEQ ID NO 197
<211> LENGTH: 225
<212> TYPE: DNA
<213> ORGANISM: Populus trichocarpa

<400> SEQUENCE: 197

atggctgact ctgaacattc ttcttctgat gaaacttttg tgtattcgag agaggaaaca     60

agtaaggaat caaagcttga attctctgag gatgaggaga cacttataat taggatgttt    120
```

aatctagttg gagagaggtg gtctttgatt gctggaagga ttcctggaag aacagctgag 180
gaaatagaga agtactggaa cactagatac tctacaagtg aatga 225

<210> SEQ ID NO 198
<211> LENGTH: 74
<212> TYPE: PRT
<213> ORGANISM: Populus trichocarpa

<400> SEQUENCE: 198

Met Ala Asp Ser Glu His Ser Ser Ser Asp Glu Thr Phe Val Tyr Ser
1 5 10 15

Arg Glu Glu Thr Ser Lys Glu Ser Lys Leu Glu Phe Ser Glu Asp Glu
20 25 30

Glu Thr Leu Ile Ile Arg Met Phe Asn Leu Val Gly Glu Arg Trp Ser
35 40 45

Leu Ile Ala Gly Arg Ile Pro Gly Arg Thr Ala Glu Glu Ile Glu Lys
50 55 60

Tyr Trp Asn Thr Arg Tyr Ser Thr Ser Glu
65 70

<210> SEQ ID NO 199
<211> LENGTH: 225
<212> TYPE: DNA
<213> ORGANISM: Populus trichocarpa

<400> SEQUENCE: 199
atggctgact tggatcactc ctctagtgat gacaactctg ttgattctag agaggaaacc 60
agccaagatt cgaagcttga attctcagaa gatgaggaaa ctcttatcac caggatgtac 120
aatctggttg gtgagaggtg gcccttaatt gctgggagga ttccaggaag aacagcagaa 180
gaaattgaga agtactggac ttcaagatac tctacaagtc agtaa 225

<210> SEQ ID NO 200
<211> LENGTH: 74
<212> TYPE: PRT
<213> ORGANISM: Populus trichocarpa

<400> SEQUENCE: 200

Met Ala Asp Leu Asp His Ser Ser Ser Asp Asp Asn Ser Val Asp Ser
1 5 10 15

Arg Glu Glu Thr Ser Gln Asp Ser Lys Leu Glu Phe Ser Glu Asp Glu
20 25 30

Glu Thr Leu Ile Thr Arg Met Tyr Asn Leu Val Gly Glu Arg Trp Pro
35 40 45

Leu Ile Ala Gly Arg Ile Pro Gly Arg Thr Ala Glu Glu Ile Glu Lys
50 55 60

Tyr Trp Thr Ser Arg Tyr Ser Thr Ser Gln
65 70

<210> SEQ ID NO 201
<211> LENGTH: 294
<212> TYPE: DNA
<213> ORGANISM: Populus trichocarpa

<400> SEQUENCE: 201
atggaaagta tggaccgccg ccgccgccga cgccgcaaac aagctaaaat taacaattct 60
gggtctgaag aggtcagtag tattgaatgg gagtttatag acatgagtga acaagaggaa 120
gacctcattt acagaatgta taggcttgtt ggagaaaggt gggatttggt agctggaagg 180
attccaggcc ggaaagcaga agaaatagag aggttttgga taatgaaaca ccgtgaaggg 240
tttgctgaga aacgaaggtt gcatagcaaa gcgaagtcta agacttatcg ttag 294

<210> SEQ ID NO 202
<211> LENGTH: 97
<212> TYPE: PRT
<213> ORGANISM: Populus trichocarpa

<400> SEQUENCE: 202

Met Glu Ser Met Asp Arg Arg Arg Arg Arg Arg Arg Lys Gln Ala Lys
1 5 10 15

Ile Asn Asn Ser Gly Ser Glu Glu Val Ser Ser Ile Glu Trp Glu Phe
20 25 30

Ile Asp Met Ser Glu Gln Glu Glu Asp Leu Ile Tyr Arg Met Tyr Arg
35 40 45

Leu Val Gly Glu Arg Trp Asp Leu Val Ala Gly Arg Ile Pro Gly Arg
50 55 60

Lys Ala Glu Glu Ile Glu Arg Phe Trp Ile Met Lys His Arg Glu Gly
65 70 75 80

Phe Ala Glu Lys Arg Arg Leu His Ser Lys Ala Lys Ser Lys Thr Tyr
85 90 95

Arg

<210> SEQ ID NO 203
<211> LENGTH: 267
<212> TYPE: DNA
<213> ORGANISM: Populus trichocarpa

<400> SEQUENCE: 203
atggatagac gtcgcaagaa gcaagccaag actacatctt gttgttctga acaagaggtg 60
agcagcattg agtgggagtt cattaacatg tcagaacaag aagaagatct catttacaga 120
atgcataatc tggtggggga caggtgggct ttgatcgctg gtcgaattcc aggacgcaaa 180
gctgaagaaa tagagagatt ttggctaatg agacacggtg aagggtttgc cagtcgacga 240
agagagcaaa agagatgtca ttcctaa 267

<210> SEQ ID NO 204
<211> LENGTH: 88
<212> TYPE: PRT
<213> ORGANISM: Populus trichocarpa

<400> SEQUENCE: 204

Met Asp Arg Arg Arg Lys Lys Gln Ala Lys Thr Thr Ser Cys Cys Ser
1 5 10 15

Glu Gln Glu Val Ser Ser Ile Glu Trp Glu Phe Ile Asn Met Ser Glu
20 25 30

Gln Glu Glu Asp Leu Ile Tyr Arg Met His Asn Leu Val Gly Asp Arg
35 40 45

Trp Ala Leu Ile Ala Gly Arg Ile Pro Gly Arg Lys Ala Glu Glu Ile
50 55 60

Glu Arg Phe Trp Leu Met Arg His Gly Glu Gly Phe Ala Ser Arg Arg
65 70 75 80

Arg Glu Gln Lys Arg Cys His Ser
85

<210> SEQ ID NO 205

<211> LENGTH: 228
<212> TYPE: DNA
<213> ORGANISM: Phaseolus vulgaris

<400> SEQUENCE: 205
atggctgact ccaatacctc ttccactcaa acttcttcac attcttctga ttcagggaag 60
cgtggaactt ccaaggttga gttttctgaa gacgaggaaa ctcttattac caggatgtat 120
aaactggttg ggaaaaggtg gtctttaatt gctggaagaa ttcctggaag aacagcagag 180
gaaatagaga agtattggac ttcgaaactc tcgagttcta gtaaatga 228

<210> SEQ ID NO 206
<211> LENGTH: 75
<212> TYPE: PRT
<213> ORGANISM: Phaseolus vulgaris

<400> SEQUENCE: 206

Met Ala Asp Ser Asn Thr Ser Ser Thr Gln Thr Ser Ser His Ser Ser
1 5 10 15

Asp Ser Gly Lys Arg Gly Thr Ser Lys Val Glu Phe Ser Glu Asp Glu
20 25 30

Glu Thr Leu Ile Thr Arg Met Tyr Lys Leu Val Gly Lys Arg Trp Ser
35 40 45

Leu Ile Ala Gly Arg Ile Pro Gly Arg Thr Ala Glu Glu Ile Glu Lys
50 55 60

Tyr Trp Thr Ser Lys Leu Ser Ser Ser Ser Lys
65 70 75

<210> SEQ ID NO 207
<211> LENGTH: 237
<212> TYPE: DNA
<213> ORGANISM: Sorghum bicolor

<400> SEQUENCE: 207
atggatagca gcagcggcag ccaggacaag aaatccaaag gcaatgatcg ccgtgaagca 60
aaagaagcta atggcactgc acagcatttt gttgatttca cggaagcaga ggaagatctt 120
gtttccagaa tgcacaggct tgtggggaac aggtgggaga ttatagcagg gagaatccca 180
ggaaggacag cagaagaggt agagatgttc tggtccaaaa aacaccagga aagatga 237

<210> SEQ ID NO 208
<211> LENGTH: 78
<212> TYPE: PRT
<213> ORGANISM: Sorghum bicolor

<400> SEQUENCE: 208

Met Asp Ser Ser Ser Gly Ser Gln Asp Lys Lys Ser Lys Gly Asn Asp
1 5 10 15

Arg Arg Glu Ala Lys Glu Ala Asn Gly Thr Ala Gln His Phe Val Asp
20 25 30

Phe Thr Glu Ala Glu Glu Asp Leu Val Ser Arg Met His Arg Leu Val
35 40 45

Gly Asn Arg Trp Glu Ile Ile Ala Gly Arg Ile Pro Gly Arg Thr Ala
50 55 60

Glu Glu Val Glu Met Phe Trp Ser Lys Lys His Gln Glu Arg
65 70 75

<210> SEQ ID NO 209
<211> LENGTH: 270

<212> TYPE: DNA
<213> ORGANISM: Salvia miltiorrhiza

<400> SEQUENCE: 209
atggataagt gtcggcagaa gcagatcaag attcggaaat accctctgtg tgaagaggtg 60
agcagtattg aatgggagtt tgtgaacatg actgatcaag aagaagacat catcaacaga 120
atgcacaagc ttgttgggga caggtggggt ttgatagctg ggagacttcc tgggaggaaa 180
gctgaggaga ttgagagatt ttggttgatg agaaatagtg acaattttac agataaaaga 240
aaggaatatc ataggagaca aaagtcttga 270

<210> SEQ ID NO 210
<211> LENGTH: 89
<212> TYPE: PRT
<213> ORGANISM: Salvia miltiorrhiza

<400> SEQUENCE: 210

Met Asp Lys Cys Arg Gln Lys Gln Ile Lys Ile Arg Lys Tyr Pro Leu
1 5 10 15

Cys Glu Glu Val Ser Ser Ile Glu Trp Glu Phe Val Asn Met Thr Asp
20 25 30

Gln Glu Glu Asp Ile Ile Asn Arg Met His Lys Leu Val Gly Asp Arg
35 40 45

Trp Gly Leu Ile Ala Gly Arg Leu Pro Gly Arg Lys Ala Glu Glu Ile
50 55 60

Glu Arg Phe Trp Leu Met Arg Asn Ser Asp Asn Phe Thr Asp Lys Arg
65 70 75 80

Lys Glu Tyr His Arg Arg Gln Lys Ser
85

<210> SEQ ID NO 211
<211> LENGTH: 285
<212> TYPE: DNA
<213> ORGANISM: Salvia miltiorrhiza

<400> SEQUENCE: 211
atggataagt gtagtagcac tcagaagcat cccaagattc agaatgaggc aagctctctt 60
gaatgggaat tcataaagat gacagagcaa gaagaagata tcatatgtag aatgcacaag 120
cttgtgggag acaagtggga gttaatagca ggaagaattc caggcagaag tgcagaagag 180
attgaaagat tttggttgat gagaaatggc gatgagagga agaggaaagc aaataatatt 240
gagcgggccc caccgctaca tgttcgagtt tcatcggccg actag 285

<210> SEQ ID NO 212
<211> LENGTH: 94
<212> TYPE: PRT
<213> ORGANISM: Salvia miltiorrhiza

<400> SEQUENCE: 212

Met Asp Lys Cys Ser Ser Thr Gln Lys His Pro Lys Ile Gln Asn Glu
1 5 10 15

Ala Ser Ser Leu Glu Trp Glu Phe Ile Lys Met Thr Glu Gln Glu Glu
20 25 30

Asp Ile Ile Cys Arg Met His Lys Leu Val Gly Asp Lys Trp Glu Leu
35 40 45

Ile Ala Gly Arg Ile Pro Gly Arg Ser Ala Glu Glu Ile Glu Arg Phe
50 55 60

```
Trp Leu Met Arg Asn Gly Asp Glu Arg Lys Arg Lys Ala Asn Asn Ile
65                  70                  75                  80

Glu Arg Ala Pro Pro Leu His Val Arg Val Ser Ser Ala Asp
                85                  90


<210> SEQ ID NO 213
<211> LENGTH: 231
<212> TYPE: DNA
<213> ORGANISM: Solanum tuberosum

<400> SEQUENCE: 213

atgggcgctc ttcaaggctt acttggtatc gggaatggaa tagataaagc atttgaggcc      60

aaaaaggaag agagctcgaa gcttgaattt tcccaagatg aggaaatcct tattactaaa     120

atgttcaact tggttggtga gaggtggtca ttaattgctg gaagaattcc agggagaact     180

gcagaagaaa ttgagaagta ttggaactca agaaattcca ccagccaata a              231


<210> SEQ ID NO 214
<211> LENGTH: 76
<212> TYPE: PRT
<213> ORGANISM: Solanum tuberosum

<400> SEQUENCE: 214

Met Gly Ala Leu Gln Gly Leu Leu Gly Ile Gly Asn Gly Ile Asp Lys
1               5                   10                  15

Ala Phe Glu Ala Lys Lys Glu Glu Ser Ser Lys Leu Glu Phe Ser Gln
            20                  25                  30

Asp Glu Glu Ile Leu Ile Thr Lys Met Phe Asn Leu Val Gly Glu Arg
        35                  40                  45

Trp Ser Leu Ile Ala Gly Arg Ile Pro Gly Arg Thr Ala Glu Glu Ile
    50                  55                  60

Glu Lys Tyr Trp Asn Ser Arg Asn Ser Thr Ser Gln
65                  70                  75


<210> SEQ ID NO 215
<211> LENGTH: 231
<212> TYPE: DNA
<213> ORGANISM: Triticum aestivum

<400> SEQUENCE: 215

atgagcagcg aaagcttggg caagaactcc aagatcatgg gtggccgtga aagaaaagaa      60

gttaatagca ccgcaaagca ttttgttgat ttcacagaag cagaggaaga tcttgttttc     120

agaatgcaca ggcttgtcgg gaacaggtgg gaacttatag ctggaagaat ccccggaaga     180

acagcagaag aagtagagat gttctgggca aaaaggcacc aggaccaatg a              231


<210> SEQ ID NO 216
<211> LENGTH: 76
<212> TYPE: PRT
<213> ORGANISM: Triticum aestivum

<400> SEQUENCE: 216

Met Ser Ser Glu Ser Leu Gly Lys Asn Ser Lys Ile Met Gly Gly Arg
1               5                   10                  15

Glu Arg Lys Glu Val Asn Ser Thr Ala Lys His Phe Val Asp Phe Thr
            20                  25                  30

Glu Ala Glu Glu Asp Leu Val Phe Arg Met His Arg Leu Val Gly Asn
        35                  40                  45

Arg Trp Glu Leu Ile Ala Gly Arg Ile Pro Gly Arg Thr Ala Glu Glu
```

```
    50                  55                  60

Val Glu Met Phe Trp Ala Lys Arg His Gln Asp Gln
65                  70                  75


<210> SEQ ID NO 217
<211> LENGTH: 198
<212> TYPE: DNA
<213> ORGANISM: Tamarix androssowii

<400> SEQUENCE: 217

aaagtacaac aaatgtcatg catgcaccga cgctgatctc cttcctaaaa acgactgaag      60

aggtctggac tcgagtctag tctaatctag tctagcagta tgataacgcc gctaatttcc     120

aaaacaaaga gaaagcactt aaaaatatac atagggagga tagaagagga gcacaaccgc     180

tacaactttt catacaac                                                   198


<210> SEQ ID NO 218
<211> LENGTH: 65
<212> TYPE: PRT
<213> ORGANISM: Tamarix androssowii

<400> SEQUENCE: 218

Met Lys Ile Arg Ser Ile Pro Gln Ser Thr Ala Thr Lys Ser Leu Ser
1               5                   10                  15

Arg Asn Phe Ser Glu Asp Glu Glu Thr Leu Ile Thr Arg Met Phe Asn
            20                  25                  30

Leu Val Gly Glu Arg Trp Ser Leu Ile Ala Gly Arg Ile Pro Gly Arg
        35                  40                  45

Thr Ala Glu Glu Ile Glu Lys Tyr Trp Thr Ser Arg Tyr Tyr Thr Ser
    50                  55                  60

Arg
65


<210> SEQ ID NO 219
<211> LENGTH: 309
<212> TYPE: DNA
<213> ORGANISM: Triphysaria sp

<400> SEQUENCE: 219

atggctgatg atcaattgca gaaacctagt gctactaatg ataatgcaat agacggcaat      60

aaagatgata aggtagtagc tgagagtcca agtatcgtcg atgattcgaa gcagcttgag     120

attacagaag atgaagaaac cctaattaat aggatgtaca atttggttgg agaaagatgg     180

tcattgattg ctggaagaat accggggaga agtgccgagg aaattgagaa gtattggaat     240

tttagaccac aatctacact aaaacagtta ctcgataatg caatcttggt tgtggataat     300

caaccatag                                                             309


<210> SEQ ID NO 220
<211> LENGTH: 102
<212> TYPE: PRT
<213> ORGANISM: Triphysaria sp

<400> SEQUENCE: 220

Met Ala Asp Asp Gln Leu Gln Lys Pro Ser Ala Thr Asn Asp Asn Ala
1               5                   10                  15

Ile Asp Gly Asn Lys Asp Asp Lys Val Val Ala Glu Ser Pro Ser Ile
            20                  25                  30

Val Asp Asp Ser Lys Gln Leu Glu Ile Thr Glu Asp Glu Glu Thr Leu
```

```
        35                  40                  45

Ile Asn Arg Met Tyr Asn Leu Val Gly Glu Arg Trp Ser Leu Ile Ala
    50                  55                  60

Gly Arg Ile Pro Gly Arg Ser Ala Glu Glu Ile Glu Lys Tyr Trp Asn
65                  70                  75                  80

Phe Arg Pro Gln Ser Thr Leu Lys Gln Leu Leu Asp Asn Ala Ile Leu
                85                  90                  95

Val Val Asp Asn Gln Pro
            100


<210> SEQ ID NO 221
<211> LENGTH: 228
<212> TYPE: DNA
<213> ORGANISM: Vitis vinifera

<400> SEQUENCE: 221

atggctgact cagaatactc tacttctaat gacacttctt gtgttgattc tcaagagcaa      60

agcagccaag aagctaagct tgaattctct gaagacgagg aaacactgat cattaggatg     120

tttaatctgg ttggagagag gtgggctcta attgctggga ggatccctgg gagaacagca     180

gaggacattg agaagtactg gaattcaaga tactcaacca gtgagtga                  228


<210> SEQ ID NO 222
<211> LENGTH: 75
<212> TYPE: PRT
<213> ORGANISM: Vitis vinifera

<400> SEQUENCE: 222

Met Ala Asp Ser Glu Tyr Ser Thr Ser Asn Asp Thr Ser Cys Val Asp
1               5                   10                  15

Ser Gln Glu Gln Ser Ser Gln Glu Ala Lys Leu Glu Phe Ser Glu Asp
            20                  25                  30

Glu Glu Thr Leu Ile Ile Arg Met Phe Asn Leu Val Gly Glu Arg Trp
        35                  40                  45

Ala Leu Ile Ala Gly Arg Ile Pro Gly Arg Thr Ala Glu Asp Ile Glu
    50                  55                  60

Lys Tyr Trp Asn Ser Arg Tyr Ser Thr Ser Glu
65                  70                  75


<210> SEQ ID NO 223
<211> LENGTH: 279
<212> TYPE: DNA
<213> ORGANISM: Vitis vinifera

<400> SEQUENCE: 223

atgtcaccac tagtgaggac accaaaggta cccacacaac acccttctct gtcttcatct      60

tgttcactga tctgggtttg ttctggttca gaggaaacag caaaggattc caaggtggag     120

ttctctgaag atgaggagac actcatagct agaatgttta gattggtggg agacagatgg     180

aatttgattg cgggaaggat cccgggaaga tctgcagaag agatcaagaa gtattggact     240

tccaagtctg tctcatcgtc gactaaacaa catgattga                             279


<210> SEQ ID NO 224
<211> LENGTH: 92
<212> TYPE: PRT
<213> ORGANISM: Vitis vinifera

<400> SEQUENCE: 224
```

Met Ser Pro Leu Val Arg Thr Pro Lys Val Pro Thr Gln His Pro Ser
1 5 10 15

Leu Ser Ser Ser Cys Ser Leu Ile Trp Val Cys Ser Gly Ser Glu Glu
20 25 30

Thr Ala Lys Asp Ser Lys Val Glu Phe Ser Glu Asp Glu Glu Thr Leu
35 40 45

Ile Ala Arg Met Phe Arg Leu Val Gly Asp Arg Trp Asn Leu Ile Ala
50 55 60

Gly Arg Ile Pro Gly Arg Ser Ala Glu Glu Ile Lys Lys Tyr Trp Thr
65 70 75 80

Ser Lys Ser Val Ser Ser Ser Thr Lys Gln His Asp
85 90

<210> SEQ ID NO 225
<211> LENGTH: 222
<212> TYPE: DNA
<213> ORGANISM: Vitis vinifera

<400> SEQUENCE: 225
atggctgact tggatcactc ctctgatggc agctctctgg attctagaga gggaagcagt 60
caagattcca agcttgaatt ctctgaagat gaggaaaccc tgatcactag gatgttcaat 120
ctggttggag agaggtggtc tctgattgct gggagaattc ctggaagaac ggcagaggaa 180
attgagaagt actggacttc aagatattca tcaagtgaat ga 222

<210> SEQ ID NO 226
<211> LENGTH: 73
<212> TYPE: PRT
<213> ORGANISM: Vitis vinifera

<400> SEQUENCE: 226

Met Ala Asp Leu Asp His Ser Ser Asp Gly Ser Ser Leu Asp Ser Arg
1 5 10 15

Glu Gly Ser Ser Gln Asp Ser Lys Leu Glu Phe Ser Glu Asp Glu Glu
20 25 30

Thr Leu Ile Thr Arg Met Phe Asn Leu Val Gly Glu Arg Trp Ser Leu
35 40 45

Ile Ala Gly Arg Ile Pro Gly Arg Thr Ala Glu Glu Ile Glu Lys Tyr
50 55 60

Trp Thr Ser Arg Tyr Ser Ser Ser Glu
65 70

<210> SEQ ID NO 227
<211> LENGTH: 237
<212> TYPE: DNA
<213> ORGANISM: Zea mays

<400> SEQUENCE: 227
atggatagca gcagtggtag ccaggacaag aaattcagag acaatgatcg ccctgaagca 60
aaagaagcta atagcaccgc ccagcatctt gttgacttca cggaagcaga ggaagatctt 120
gtttccagaa tgcacaggct tgtggggaac aggtgggaga ttatagcagg aagaatccca 180
ggaaggacag cagaagaggt agagatgttc tggtccaaaa aataccagga aagatga 237

<210> SEQ ID NO 228
<211> LENGTH: 78
<212> TYPE: PRT
<213> ORGANISM: Zea mays

<400> SEQUENCE: 228

Met Asp Ser Ser Ser Gly Ser Gln Asp Lys Lys Phe Arg Asp Asn Asp
1 5 10 15

Arg Pro Glu Ala Lys Glu Ala Asn Ser Thr Ala Gln His Leu Val Asp
20 25 30

Phe Thr Glu Ala Glu Glu Asp Leu Val Ser Arg Met His Arg Leu Val
35 40 45

Gly Asn Arg Trp Glu Ile Ile Ala Gly Arg Ile Pro Gly Arg Thr Ala
50 55 60

Glu Glu Val Glu Met Phe Trp Ser Lys Lys Tyr Gln Glu Arg
65 70 75

<210> SEQ ID NO 229
<211> LENGTH: 27
<212> TYPE: PRT
<213> ORGANISM: Artificial sequence
<220> FEATURE:
<223> OTHER INFORMATION: motif 12
<220> FEATURE:
<221> NAME/KEY: VARIANT
<222> LOCATION: (1)..(1)
<223> OTHER INFORMATION: / replace = “Met”
<220> FEATURE:
<221> NAME/KEY: VARIANT
<222> LOCATION: (2)..(2)
<223> OTHER INFORMATION: / replace = “Thr”
<220> FEATURE:
<221> NAME/KEY: VARIANT
<222> LOCATION: (4)..(4)
<223> OTHER INFORMATION: / replace = “Gln”
<220> FEATURE:
<221> NAME/KEY: VARIANT
<222> LOCATION: (7)..(7)
<223> OTHER INFORMATION: / replace = “Thr”
<220> FEATURE:
<221> NAME/KEY: VARIANT
<222> LOCATION: (13)..(13)
<223> OTHER INFORMATION: / replace = “His” / replace = “Phe”
<220> FEATURE:
<221> NAME/KEY: VARIANT
<222> LOCATION: (14)..(14)
<223> OTHER INFORMATION: / replace = “Lys” / replace = “Arg”
<220> FEATURE:
<221> NAME/KEY: VARIANT
<222> LOCATION: (18)..(18)
<223> OTHER INFORMATION: / replace = “Asp” / replace = “Asn”
<220> FEATURE:
<221> NAME/KEY: VARIANT
<222> LOCATION: (21)..(21)
<223> OTHER INFORMATION: / replace = “Glu”

<400> SEQUENCE: 229

Phe Ser Glu Asp Glu Glu Asp Leu Ile Ile Arg Met Tyr Asn Leu Val
1 5 10 15

Gly Glu Arg Trp Ser Leu Ile Ala Gly Arg Ile
20 25

<210> SEQ ID NO 230
<211> LENGTH: 15
<212> TYPE: PRT
<213> ORGANISM: Artificial sequence
<220> FEATURE:
<223> OTHER INFORMATION: motif 13
<220> FEATURE:
<221> NAME/KEY: VARIANT
<222> LOCATION: (4)..(4)
<223> OTHER INFORMATION: / replace = “Lys”
<220> FEATURE:
<221> NAME/KEY: VARIANT
<222> LOCATION: (10)..(10)

<223> OTHER INFORMATION: / replace = “Arg”
<220> FEATURE:
<221> NAME/KEY: VARIANT
<222> LOCATION: (11)..(11)
<223> OTHER INFORMATION: / replace = “Phe”
<220> FEATURE:
<221> NAME/KEY: VARIANT
<222> LOCATION: (14)..(14)
<223> OTHER INFORMATION: / replace = “Leu”
<220> FEATURE:
<221> NAME/KEY: VARIANT
<222> LOCATION: (15)..(15)
<223> OTHER INFORMATION: / replace = “Lys”

<400> SEQUENCE: 230

Pro Gly Arg Thr Ala Glu Glu Ile Glu Lys Tyr Trp Thr Ser Arg
1 5 10 15

<210> SEQ ID NO 231
<211> LENGTH: 11
<212> TYPE: PRT
<213> ORGANISM: Artificial sequence
<220> FEATURE:
<223> OTHER INFORMATION: motif 14
<220> FEATURE:
<221> NAME/KEY: VARIANT
<222> LOCATION: (6)..(6)
<223> OTHER INFORMATION: / replace = “Thr”
<220> FEATURE:
<221> NAME/KEY: VARIANT
<222> LOCATION: (7)..(7)
<223> OTHER INFORMATION: / replace = “Asp”
<220> FEATURE:
<221> NAME/KEY: VARIANT
<222> LOCATION: (8)..(8)
<223> OTHER INFORMATION: / replace = “Trp”
<220> FEATURE:
<221> NAME/KEY: VARIANT
<222> LOCATION: (9)..(9)
<223> OTHER INFORMATION: / replace = “Lys”
<220> FEATURE:
<221> NAME/KEY: VARIANT
<222> LOCATION: (10)..(10)
<223> OTHER INFORMATION: / replace = “Leu”
<220> FEATURE:
<221> NAME/KEY: VARIANT
<222> LOCATION: (11)..(11)
<223> OTHER INFORMATION: / replace = “Glu”

<400> SEQUENCE: 231

Glu Glu Val Ser Ser Gln Glu Ser Glu Phe Ile
1 5 10

<210> SEQ ID NO 232
<211> LENGTH: 31
<212> TYPE: PRT
<213> ORGANISM: Artificial sequence
<220> FEATURE:
<223> OTHER INFORMATION: motif 15
<220> FEATURE:
<221> NAME/KEY: VARIANT
<222> LOCATION: (2)..(2)
<223> OTHER INFORMATION: / replace = “Asp”
<220> FEATURE:
<221> NAME/KEY: VARIANT
<222> LOCATION: (3)..(3)
<223> OTHER INFORMATION: / replace = “Glu” / replace = “Thr”
<220> FEATURE:
<221> NAME/KEY: VARIANT
<222> LOCATION: (4)..(4)
<223> OTHER INFORMATION: / replace = “Ile”
<220> FEATURE:
<221> NAME/KEY: VARIANT
<222> LOCATION: (5)..(5)
<223> OTHER INFORMATION: / replace = “Val”

<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: VARIANT
<222> LOCATION: (7)..(7)
<223> OTHER INFORMATION: / replace = "Lys"
<220> FEATURE:
<221> NAME/KEY: VARIANT
<222> LOCATION: (8)..(8)
<223> OTHER INFORMATION: / replace = "Phe" / replace = "Met"
<220> FEATURE:
<221> NAME/KEY: VARIANT
<222> LOCATION: (9)..(9)
<223> OTHER INFORMATION: / replace = "Tyr"
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: VARIANT
<222> LOCATION: (12)..(12)
<223> OTHER INFORMATION: / replace = "Phe" / replace = "Val"
<220> FEATURE:
<221> NAME/KEY: VARIANT
<222> LOCATION: (14)..(14)
<223> OTHER INFORMATION: / replace = "Glu" / replace = "Asp"
<220> FEATURE:
<221> NAME/KEY: VARIANT
<222> LOCATION: (15)..(15)
<223> OTHER INFORMATION: / replace = "Lys"
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: VARIANT
<222> LOCATION: (18)..(18)
<223> OTHER INFORMATION: / replace = "Ile"
<220> FEATURE:
<221> NAME/KEY: VARIANT
<222> LOCATION: (21)..(21)
<223> OTHER INFORMATION: / replace = "Arg" / replace = "Lys"
<220> FEATURE:
<221> NAME/KEY: VARIANT
<222> LOCATION: (23)..(23)
<223> OTHER INFORMATION: / replace = "Ile" / replace = "Val"
<220> FEATURE:
<221> NAME/KEY: VARIANT
<222> LOCATION: (24)..(24)
<223> OTHER INFORMATION: / replace = "Val"
<220> FEATURE:
<221> NAME/KEY: VARIANT
<222> LOCATION: (27)..(27)
<223> OTHER INFORMATION: / replace = "Lys" / replace = "Glu" /
      replace = "Gln"
<220> FEATURE:
<221> NAME/KEY: VARIANT
<222> LOCATION: (28)..(28)
<223> OTHER INFORMATION: / replace = "Ala" / replace = "Pro"
<220> FEATURE:
<221> NAME/KEY: VARIANT
<222> LOCATION: (29)..(29)
<223> OTHER INFORMATION: / replace = "Glu" / replace = "Lys" /
      replace = "Gly"
<220> FEATURE:
<221> NAME/KEY: VARIANT
<222> LOCATION: (30)..(30)
<223> OTHER INFORMATION: / replace = "Gln"
<220> FEATURE:
<221> NAME/KEY: VARIANT
<222> LOCATION: (31)..(31)
<223> OTHER INFORMATION: / replace = "Val" / replace = "Gln"

<400> SEQUENCE: 232

Glu Glu Asp Leu Ile Xaa Arg Leu His Xaa Leu Leu Gly Asn Arg Trp
1               5                   10                  15

```
Xaa Leu Ile Ala Gly Arg Leu Pro Gly Arg Thr Asp Asn Glu Ile
            20                  25                  30


<210> SEQ ID NO 233
<211> LENGTH: 56
<212> TYPE: DNA
<213> ORGANISM: Artificial sequence
<220> FEATURE:
<223> OTHER INFORMATION: primer: prm09014

<400> SEQUENCE: 233

ggggacaagt ttgtacaaaa aagcaggctt aaacaatgga taacactgac cgtcgt         56


<210> SEQ ID NO 234
<211> LENGTH: 50
<212> TYPE: DNA
<213> ORGANISM: Artificial sequence
<220> FEATURE:
<223> OTHER INFORMATION: primer: prm09015

<400> SEQUENCE: 234

ggggaccact ttgtacaaga aagctgggtt ttttcgttgg cttaaaaaca                50


<210> SEQ ID NO 235
<211> LENGTH: 1264
<212> TYPE: DNA
<213> ORGANISM: Oryza sativa

<400> SEQUENCE: 235

tcgacgctac tcaagtggtg ggaggccacc gcatgttcca acgaagcgcc aaagaaagcc     60

ttgcagactc taatgctatt agtcgcctag gatatttgga atgaaaggaa ccgcagagtt    120

tttcagcacc aagagcttcc ggtggctagt ctgatagcca aaattaagga ggatgccaaa    180

acatgggtct tggcgggcgc gaaacacctt gataggtggc ttacctttta acatgttcgg    240

gccaaaggcc ttgagacggt aaagttttct atttgcgctt gcgcatgtac aattttattc    300

ctctattcaa tgaaattggt ggctcactgg ttcattaaaa aaaaaagaat ctagcctgtt    360

cgggaagaag aggattttgt tcgtgagaga gagagagaga gagagagaga gagagagaga    420

gaaggaggag gaggattttc aggcttcgca ttgcccaacc tctgcttctg ttggcccaag    480

aagaatccca ggcgcccatg ggctggcagt ttaccacgga cctacctagc ctaccttagc    540

tatctaagcg ggccgaccta gtagccacgt gcctagtgta gattaaagtt gccgggccag    600

caggaagcca cgctgcaatg gcatcttccc ctgtccttcg cgtacgtgaa aacaaaccca    660

ggtaagctta gaatcttctt gcccgttgga ctgggacacc caccaatccc accatgcccc    720

gatattcctc cggtctcggt tcatgtgatg tcctctcttg tgtgatcacg gagcaagcat    780

tcttaaacgg caaaagaaaa tcaccaactt gctcacgcag tcacgctgca ccgcgcgaag    840

cgacgcccga taggccaaga tcgcgagata aaataacaac caatgatcat aaggaaacaa    900

gcccgcgatg tgtcgtgtgc agcaatcttg gtcatttgcg ggatcgagtg cttcacagct    960

aaccaaatat tcggccgatg atttaacaca ttatcagcgt agatgtacgt acgatttgtt   1020

aattaatcta cgagccttgc tagggcaggt gttctgccag ccaatccaga tcgccctcgt   1080

atgcacgctc acatgatggc agggcagggt tcacatgagc tctaacggtc gattaattaa   1140

tcccggggct cgactataaa tacctcccta atcccatgat caaaaccatc tcaagcagcc   1200

taatcatctc cagctgatca agagctctta attagctagc tagtgattag ctgcgcttgt   1260

gatc                                                                1264
```

<210> SEQ ID NO 236
<211> LENGTH: 1640
<212> TYPE: DNA
<213> ORGANISM: Artificial sequence
<220> FEATURE:
<223> OTHER INFORMATION: expression cassette with RCc3 promoter

<400> SEQUENCE: 236

```
tcgacgctac tcaagtggtg ggaggccacc gcatgttcca acgaagcgcc aaagaaagcc     60
ttgcagactc taatgctatt agtcgcctag gatatttgga atgaaaggaa ccgcagagtt    120
tttcagcacc aagagcttcc ggtggctagt ctgatagcca aaattaagga ggatgccaaa    180
acatgggtct tggcgggcgc gaaacacctt gataggtggc ttacctttta acatgttcgg    240
gccaaaggcc ttgagacggt aaagttttct atttgcgctt gcgcatgtac aattttattc    300
ctctattcaa tgaaattggt ggctcactgg ttcattaaaa aaaaaagaat ctagcctgtt    360
cgggaagaag aggattttgt tcgtgagaga gagagagaga gagagagaga gagagagaga    420
gaaggaggag gaggattttc aggcttcgca ttgcccaacc tctgcttctg ttggcccaag    480
aagaatccca ggcgcccatg ggctggcagt ttaccacgga cctacctagc ctaccttagc    540
tatctaagcg ggccgaccta gtagccacgt gcctagtgta gattaaagtt gccgggccag    600
caggaagcca cgctgcaatg gcatcttccc ctgtccttcg cgtacgtgaa aacaaaccca    660
ggtaagctta gaatcttctt gcccgttgga ctgggacacc caccaatccc accatgcccc    720
gatattcctc cggtctcggt tcatgtgatg tcctctcttg tgtgatcacg gagcaagcat    780
tcttaaacgg caaaagaaaa tcaccaactt gctcacgcag tcacgctgca ccgcgcgaag    840
cgacgcccga taggccaaga tcgcgagata aaataacaac caatgatcat aaggaaacaa    900
gcccgcgatg tgtcgtgtgc agcaatcttg gtcatttgcg ggatcgagtg cttcacagct    960
aaccaaatat tcggccgatg atttaacaca ttatcagcgt agatgtacgt acgatttgtt   1020
aattaatcta cgagccttgc tagggcaggt gttctgccag ccaatccaga tcgccctcgt   1080
atgcacgctc acatgatggc agggcagggt tcacatgagc tctaacggtc gattaattaa   1140
tcccggggct cgactataaa tacctcccta atcccatgat caaaaccatc tcaagcagcc   1200
taatcatctc cagctgatca agagctctta attagctagc tagtgattag ctgcgcttgt   1260
gatcatttaa atcaactagg gatatcacaa gtttgtacaa aaaagcaggc ttaaacaatg   1320
gataacactg accgtcgtcg ccgtcgtaag caacacaaaa tcgccctcca tgactctgaa   1380
gaagtgagca gtatcgaatt ggagtttatc aacatgactg aacaagaaga agatctcatc   1440
tttcgaatgt acagacttgt cggtgatagg tgggatttga tagcaggaag agttcctgga   1500
agacaaccag aggagataga gagatattgg ataatgagaa acagtgaagg ctttgctgat   1560
aaacgacgcc agcttcactc atcttcccac aaacatacca agcctcaccg tcctcgcttt   1620
tctatctatc cttcctagtg                                               1640
```

<210> SEQ ID NO 237
<211> LENGTH: 2194
<212> TYPE: DNA
<213> ORGANISM: Oryza sativa

<400> SEQUENCE: 237

```
aatccgaaaa gtttctgcac cgttttcacc ccctaactaa caatataggg aacgtgtgct     60
aaatataaaa tgagacctta tatatgtagc gctgataact agaactatgc aagaaaaact    120
```

-continued

```
catccaccta ctttagtggc aatcgggcta aataaaaaag agtcgctaca ctagtttcgt    180
tttccttagt aattaagtgg gaaaatgaaa tcattattgc ttagaatata cgttcacatc    240
tctgtcatga agttaaatta ttcgaggtag ccataattgt catcaaactc ttcttgaata    300
aaaaaatctt tctagctgaa ctcaatgggt aaagagagag attttttta aaaaaataga    360
atgaagatat tctgaacgta ttggcaaaga tttaaacata taattatata atttatagt    420
ttgtgcattc gtcatatcgc acatcattaa ggacatgtct tactccatcc caatttttat    480
ttagtaatta aagacaattg acttattttt attatttatc tttttcgat tagatgcaag    540
gtacttacgc acacactttg tgctcatgtg catgtgtgag tgcacctcct caatacacgt    600
tcaactagca acacatctct aatatcactc gcctatttaa tacatttagg tagcaatatc    660
tgaattcaag cactccacca tcaccagacc acttttaata atatctaaaa tacaaaaaat    720
aattttacag aatagcatga aaagtatgaa acgaactatt taggtttttc acatacaaaa    780
aaaaaaagaa ttttgctcgt gcgcgagcgc caatctccca tattgggcac acaggcaaca    840
acagagtggc tgcccacaga acaacccaca aaaaacgatg atctaacgga ggacagcaag    900
tccgcaacaa ccttttaaca gcaggctttg cggccaggag agaggaggag aggcaaagaa    960
aaccaagcat cctccttctc ccatctataa attcctcccc ccttttcccc tctctatata   1020
ggaggcatcc aagccaagaa gagggagagc accaaggaca cgcgactagc agaagccgag   1080
cgaccgcctt ctcgatccat atcttccggt cgagttcttg gtcgatctct tccctcctcc   1140
acctcctcct cacagggtat gtgcctccct tcggttgttc ttggatttat tgttctaggt   1200
tgtgtagtac gggcgttgat gttaggaaag gggatctgta tctgtgatga ttcctgttct   1260
tggatttggg atagaggggt tcttgatgtt gcatgttatc ggttcggttt gattagtagt   1320
atggttttca atcgtctgga gagctctatg gaaatgaaat ggtttaggga tcggaatctt   1380
gcgattttgt gagtaccttt tgtttgaggt aaaatcagag caccggtgat tttgcttggt   1440
gtaataaagt acggttgttt ggtcctcgat tctggtagtg atgcttctcg atttgacgaa   1500
gctatccttt gtttattccc tattgaacaa aaataatcca actttgaaga cggtcccgtt   1560
gatgagattg aatgattgat tcttaagcct gtccaaaatt tcgcagctgg cttgtttaga   1620
tacagtagtc cccatcacga aattcatgga aacagttata atcctcagga acaggggatt   1680
ccctgttctt ccgatttgct ttagtcccag aattttttt cccaaatatc ttaaaaagtc   1740
actttctggt tcagttcaat gaattgattg ctacaaataa tgcttttata gcgttatcct   1800
agctgtagtt cagttaatag gtaatacccc tatagtttag tcaggagaag aacttatccg   1860
atttctgatc tccattttta attatatgaa atgaactgta gcataagcag tattcatttg   1920
gattattttt tttattagct ctcacccctt cattattctg agctgaaagt ctggcatgaa   1980
ctgtcctcaa ttttgtttc aaattcacat cgattatcta tgcattatcc tcttgtatct   2040
acctgtagaa gtttcttttt ggttattcct tgactgcttg attacagaaa gaaatttatg   2100
aagctgtaat cgggatagtt atactgcttg ttcttatgat tcatttcctt tgtgcagttc   2160
ttggtgtagc ttgccacttt caccagcaaa gttc                               2194
```

<210> SEQ ID NO 238
<211> LENGTH: 831
<212> TYPE: DNA
<213> ORGANISM: Arabidopsis thaliana

<400> SEQUENCE: 238

```
atgacggcat caggaggagg atcaacggcg gcgacgggga ggatgccgac gtggaaggaa     60
```

```
agagagaaca acaagaagag agaaagaaga agaagagcaa tagcagctaa aatcttcacc    120

ggacttagat ctcaaggcaa ttataaactt cctaaacact gtgacaacaa tgaagtcctc    180

aaagctcttt gtcttgaagc tggttggatc gttcatgaag atggcaccac ttatcgaaag    240

ggttctcgac caacagaaac aacagtgccg tgttcgtcaa tccaacttag tccacaatca    300

tcggcctttc aaagcccaat tccttcgtat caagctagcc cttcatcgtc atcttaccca    360

agtccgaccc ggtttgaccc gaatcaatcc tcgacttatc tcattcccta tctccaaaac    420

ctagcttcgt ctggaaacct cgctcctcta cgaatttcca atagtgcccc tgttacaccg    480

ccgatttctt cacctagaag atcaaatccg agacttccga gatggcaaag cagtaatttc    540

ccagtctcag ctccgtcaag cccaacacgg cgtctccatc actacacatc gattccagaa    600

tgcgatgaat cggatgtttc gacggttgat tcttgtcgat ggggaaattt ccaatcggtt    660

aacgtttctc agacatgtcc tccgtcgccg acatttaacc tggtcggaaa aagcgttagc    720

tccgtcggag tagatgtgtc ggtgaagccg tgggaaggtg agaagattca cgatgttggt    780

atcgatgact tggagctgac gctaggtcac aacaccaaag gacgcggcta g             831
```

<210> SEQ ID NO 239
<211> LENGTH: 276
<212> TYPE: PRT
<213> ORGANISM: Arabidopsis thaliana

<400> SEQUENCE: 239

```
Met Thr Ala Ser Gly Gly Gly Ser Thr Ala Ala Thr Gly Arg Met Pro
1               5                   10                  15

Thr Trp Lys Glu Arg Glu Asn Asn Lys Lys Arg Glu Arg Arg Arg Arg
            20                  25                  30

Ala Ile Ala Ala Lys Ile Phe Thr Gly Leu Arg Ser Gln Gly Asn Tyr
        35                  40                  45

Lys Leu Pro Lys His Cys Asp Asn Asn Glu Val Leu Lys Ala Leu Cys
    50                  55                  60

Leu Glu Ala Gly Trp Ile Val His Glu Asp Gly Thr Thr Tyr Arg Lys
65                  70                  75                  80

Gly Ser Arg Pro Thr Glu Thr Thr Val Pro Cys Ser Ser Ile Gln Leu
                85                  90                  95

Ser Pro Gln Ser Ser Ala Phe Gln Ser Pro Ile Pro Ser Tyr Gln Ala
            100                 105                 110

Ser Pro Ser Ser Ser Ser Tyr Pro Ser Pro Thr Arg Phe Asp Pro Asn
        115                 120                 125

Gln Ser Ser Thr Tyr Leu Ile Pro Tyr Leu Gln Asn Leu Ala Ser Ser
    130                 135                 140

Gly Asn Leu Ala Pro Leu Arg Ile Ser Asn Ser Ala Pro Val Thr Pro
145                 150                 155                 160

Pro Ile Ser Ser Pro Arg Arg Ser Asn Pro Arg Leu Pro Arg Trp Gln
                165                 170                 175

Ser Ser Asn Phe Pro Val Ser Ala Pro Ser Ser Pro Thr Arg Arg Leu
            180                 185                 190

His His Tyr Thr Ser Ile Pro Glu Cys Asp Glu Ser Asp Val Ser Thr
        195                 200                 205

Val Asp Ser Cys Arg Trp Gly Asn Phe Gln Ser Val Asn Val Ser Gln
    210                 215                 220

Thr Cys Pro Pro Ser Pro Thr Phe Asn Leu Val Gly Lys Ser Val Ser
225                 230                 235                 240
```

```
Ser Val Gly Val Asp Val Ser Val Lys Pro Trp Glu Gly Glu Lys Ile
                245                 250                 255

His Asp Val Gly Ile Asp Asp Leu Glu Leu Thr Leu Gly His Asn Thr
            260                 265                 270

Lys Gly Arg Gly
        275


<210> SEQ ID NO 240
<211> LENGTH: 1008
<212> TYPE: DNA
<213> ORGANISM: Arabidopsis thaliana

<400> SEQUENCE: 240

atgacgtctg acggagcaac gtcgacgtca gctgcagctg cagcagcagc gatggcgacg      60

aggaggaaac cgtcgtggag agagagggag aacaatcgga gaagagagcg gcggagaaga     120

gctgttgcgg cgaagattta tactggtctt agagctcaag gtaactacaa tcttccaaaa     180

cattgtgaca acaatgaggt tcttaaggct ctttgttctg aagctggttg ggttgttgaa     240

gaagacggaa ctacttatcg caagggacac aagcctctac ctggtgacat ggctggatca     300

tcttctcgag caactcctta ctcttcccat aaccaaagtc ctctttcttc cacttttgat     360

agccccatct tatcttacca agtcagtcct tcctcttctt cattcccgag tccttctcga     420

gttggtgatc cacacaatat ctccacaatc ttccctttcc tcaggaatgg tggtattcct     480

tcatcgcttc ctccacttag aatctcaaac agtgctcctg tcactccacc agtgtcatcc     540

ccaacttcta gaaaccccaa accattgcct acttgggaat cttttaccaa acaatccatg     600

tccatggctg ctaaacagtc aatgacttct ttgaactacc cgttttatgc ggtgtctgca     660

cctgccagtc ctactcatca tcgccagttc catgctccgg ctactatacc tgaatgtgat     720

gagtctgact cttccactgt tgattctggt cattggataa gctttcaaaa gtttgcacaa     780

caacagccat tctctgcctc tatggtgcca acctcgccta ccttcaatct cgtgaaacct     840

gcaccacagc aattgtctcc aaacacagca gcaatccaag agattggtca aagctccgag     900

tttaagtttg agaacagcca agttaagcca tgggaagggg agaggatcca tgatgtggct     960

atggaggatc tagagctcac gcttggaaat ggtaaagctc atagttga                 1008


<210> SEQ ID NO 241
<211> LENGTH: 335
<212> TYPE: PRT
<213> ORGANISM: Arabidopsis thaliana

<400> SEQUENCE: 241

Met Thr Ser Asp Gly Ala Thr Ser Thr Ser Ala Ala Ala Ala Ala Ala
1               5                   10                  15

Ala Met Ala Thr Arg Arg Lys Pro Ser Trp Arg Glu Arg Glu Asn Asn
            20                  25                  30

Arg Arg Arg Glu Arg Arg Arg Arg Ala Val Ala Ala Lys Ile Tyr Thr
        35                  40                  45

Gly Leu Arg Ala Gln Gly Asn Tyr Asn Leu Pro Lys His Cys Asp Asn
    50                  55                  60

Asn Glu Val Leu Lys Ala Leu Cys Ser Glu Ala Gly Trp Val Val Glu
65                  70                  75                  80

Glu Asp Gly Thr Thr Tyr Arg Lys Gly His Lys Pro Leu Pro Gly Asp
                85                  90                  95

Met Ala Gly Ser Ser Ser Arg Ala Thr Pro Tyr Ser Ser His Asn Gln
```

```
            100                 105                 110

Ser Pro Leu Ser Ser Thr Phe Asp Ser Pro Ile Leu Ser Tyr Gln Val
        115                 120                 125

Ser Pro Ser Ser Ser Ser Phe Pro Ser Pro Ser Arg Val Gly Asp Pro
    130                 135                 140

His Asn Ile Ser Thr Ile Phe Pro Phe Leu Arg Asn Gly Gly Ile Pro
145                 150                 155                 160

Ser Ser Leu Pro Pro Leu Arg Ile Ser Asn Ser Ala Pro Val Thr Pro
                165                 170                 175

Pro Val Ser Ser Pro Thr Ser Arg Asn Pro Lys Pro Leu Pro Thr Trp
            180                 185                 190

Glu Ser Phe Thr Lys Gln Ser Met Ser Met Ala Ala Lys Gln Ser Met
        195                 200                 205

Thr Ser Leu Asn Tyr Pro Phe Tyr Ala Val Ser Ala Pro Ala Ser Pro
    210                 215                 220

Thr His His Arg Gln Phe His Ala Pro Ala Thr Ile Pro Glu Cys Asp
225                 230                 235                 240

Glu Ser Asp Ser Ser Thr Val Asp Ser Gly His Trp Ile Ser Phe Gln
                245                 250                 255

Lys Phe Ala Gln Gln Gln Pro Phe Ser Ala Ser Met Val Pro Thr Ser
            260                 265                 270

Pro Thr Phe Asn Leu Val Lys Pro Ala Pro Gln Gln Leu Ser Pro Asn
        275                 280                 285

Thr Ala Ala Ile Gln Glu Ile Gly Gln Ser Ser Glu Phe Lys Phe Glu
    290                 295                 300

Asn Ser Gln Val Lys Pro Trp Glu Gly Glu Arg Ile His Asp Val Ala
305                 310                 315                 320

Met Glu Asp Leu Glu Leu Thr Leu Gly Asn Gly Lys Ala His Ser
                325                 330                 335
```

<210> SEQ ID NO 242
<211> LENGTH: 1011
<212> TYPE: DNA
<213> ORGANISM: Arabidopsis thaliana

<400> SEQUENCE: 242

```
atgacttcgg atggagctac gtcgacatca gcagctgcag ctgcggcggc ggcagcagcg      60

gcgaggagga agccgtcgtg gagagaaagg gagaataatc ggaggagaga aagacggaga     120

agagctgtag ctgcgaagat atacactggg cttagagctc aaggtgatta taatttgcct     180

aaacattgtg ataataatga agtccttaaa gctctttgtg ttgaagctgg ttgggttgtt     240

gaagaagatg gtactactta tcgcaaggga tgcaagcctt tacctggtga gatagctggg     300

acttcatctc gagtaactcc atattcatca cagaaccaga gccctctttc atcagccttt     360

caaagtccca tcccatctta ccaagttagc ccgtcttctt catcattccc gagtccttct     420

cgcggtgaac caaataacaa catgtcctct acattcttcc ctttcctcag aaatggtggc     480

attccttctt ctcttccttc cctcagaatc tcaaacagtt gtccagttac cccaccggtc     540

tcatcgccga cttctaagaa cccgaaaccg ttgcctaact gggaatctat cgctaagcaa     600

tccatggcca ttgctaaaca atcaatggcg tcttttaatt atcctttcta tgcggtttct     660

gcacctgcta gtccgacaca tcgccaccag tttcataccc cggctactat acctgaatgt     720

gatgagtctg actcttccac tgttgattct ggtcattgga taagctttca gaagtttgca     780

caacaacagc cattctctgc ctctatggtg ccaacctctc ctaccttcaa tcttgtgaaa     840
```

```
cctgcgcctc agcagatgtc tccaaatact gctgccttcc aagagattgg tcaaagctct     900

gagtttaaat ttgagaatag ccaagttaaa ccctgggaag gagagaggat acatgatgtg     960

ggtatggagg atcttgagct tacacttgga aatgggaagg ctcgtggttg a             1011


<210> SEQ ID NO 243
<211> LENGTH: 336
<212> TYPE: PRT
<213> ORGANISM: Arabidopsis thaliana

<400> SEQUENCE: 243

Met Thr Ser Asp Gly Ala Thr Ser Thr Ser Ala Ala Ala Ala Ala Ala
1               5                   10                  15

Ala Ala Ala Ala Ala Arg Arg Lys Pro Ser Trp Arg Glu Arg Glu Asn
            20                  25                  30

Asn Arg Arg Arg Glu Arg Arg Arg Arg Ala Val Ala Ala Lys Ile Tyr
        35                  40                  45

Thr Gly Leu Arg Ala Gln Gly Asp Tyr Asn Leu Pro Lys His Cys Asp
    50                  55                  60

Asn Asn Glu Val Leu Lys Ala Leu Cys Val Glu Ala Gly Trp Val Val
65                  70                  75                  80

Glu Glu Asp Gly Thr Thr Tyr Arg Lys Gly Cys Lys Pro Leu Pro Gly
                85                  90                  95

Glu Ile Ala Gly Thr Ser Ser Arg Val Thr Pro Tyr Ser Ser Gln Asn
            100                 105                 110

Gln Ser Pro Leu Ser Ser Ala Phe Gln Ser Pro Ile Pro Ser Tyr Gln
        115                 120                 125

Val Ser Pro Ser Ser Ser Ser Phe Pro Ser Pro Ser Arg Gly Glu Pro
    130                 135                 140

Asn Asn Asn Met Ser Ser Thr Phe Phe Pro Phe Leu Arg Asn Gly Gly
145                 150                 155                 160

Ile Pro Ser Ser Leu Pro Ser Leu Arg Ile Ser Asn Ser Cys Pro Val
                165                 170                 175

Thr Pro Pro Val Ser Ser Pro Thr Ser Lys Asn Pro Lys Pro Leu Pro
            180                 185                 190

Asn Trp Glu Ser Ile Ala Lys Gln Ser Met Ala Ile Ala Lys Gln Ser
        195                 200                 205

Met Ala Ser Phe Asn Tyr Pro Phe Tyr Ala Val Ser Ala Pro Ala Ser
    210                 215                 220

Pro Thr His Arg His Gln Phe His Thr Pro Ala Thr Ile Pro Glu Cys
225                 230                 235                 240

Asp Glu Ser Asp Ser Ser Thr Val Asp Ser Gly His Trp Ile Ser Phe
                245                 250                 255

Gln Lys Phe Ala Gln Gln Gln Pro Phe Ser Ala Ser Met Val Pro Thr
            260                 265                 270

Ser Pro Thr Phe Asn Leu Val Lys Pro Ala Pro Gln Gln Met Ser Pro
        275                 280                 285

Asn Thr Ala Ala Phe Gln Glu Ile Gly Gln Ser Ser Glu Phe Lys Phe
    290                 295                 300

Glu Asn Ser Gln Val Lys Pro Trp Glu Gly Glu Arg Ile His Asp Val
305                 310                 315                 320

Gly Met Glu Asp Leu Glu Leu Thr Leu Gly Asn Gly Lys Ala Arg Gly
                325                 330                 335
```

<210> SEQ ID NO 244
<211> LENGTH: 978
<212> TYPE: DNA
<213> ORGANISM: Arabidopsis thaliana

<400> SEQUENCE: 244
atgacatcag ggacgagaat gccgacatgg agggaaagag agaacaacaa gagaagagaa 60
agacgacgga gagcaatcgc agctaagatc ttcaccggat taagaatgta cggtaattac 120
gagcttccga agcattgcga caacaacgaa gtgcttaaag cactctgtaa cgaagctggt 180
tggatcgtcg aacctgatgg aactacttac cgcaagggat gtagtagacc tgtagagcgt 240
atggagatag gtggtggttc agcaaccgct agtccttgct cttcctatca gccaagtccc 300
tgtgcttctt ataatcctag tccaggctcc tccaacttca tgagtcctgc ttcatcctca 360
tttgctaatc ttacctctgg tgatggccaa tctctcatcc catggctaaa acacctctca 420
acaacatcat cctcatcagc ttcttcatca tcaagactcc ctaattacct ctatatccct 480
ggaggctcca taagcgctcc tgtaactcct cctttaagct ctccaacagc tcgtaccccg 540
agaatgaaca ctgattggca gcaactcaac aactccttct ttgtctcctc aacaccgcca 600
agtcccacgc gtcagatcat ccctgactct gaatggttct cagggattca actagcacaa 660
agtgttccag cttcaccaac gtttagcctc gtctcacaaa acccatttgg attcaaagaa 720
gaagcagcct ctgctgctgg aggcggagga gggtcaagga tgtggacacc aggtcaaagc 780
ggaacctgct cccctgctat tcctcctggt gctgaccaga cagcagatgt tccaatgtct 840
gaagccgtgg ctcctccaga gtttgctttt gggagtaata caaacgggct agtgaaagca 900
tgggaaggag agaggataca cgaggagagt ggttcagatg atcttgaact cactcttgga 960
aactcaagca ccaggtaa 978

<210> SEQ ID NO 245
<211> LENGTH: 325
<212> TYPE: PRT
<213> ORGANISM: Arabidopsis thaliana

<400> SEQUENCE: 245

Met Thr Ser Gly Thr Arg Met Pro Thr Trp Arg Glu Arg Glu Asn Asn
1 5 10 15

Lys Arg Arg Glu Arg Arg Arg Arg Ala Ile Ala Ala Lys Ile Phe Thr
20 25 30

Gly Leu Arg Met Tyr Gly Asn Tyr Glu Leu Pro Lys His Cys Asp Asn
35 40 45

Asn Glu Val Leu Lys Ala Leu Cys Asn Glu Ala Gly Trp Ile Val Glu
50 55 60

Pro Asp Gly Thr Thr Tyr Arg Lys Gly Cys Ser Arg Pro Val Glu Arg
65 70 75 80

Met Glu Ile Gly Gly Gly Ser Ala Thr Ala Ser Pro Cys Ser Ser Tyr
85 90 95

Gln Pro Ser Pro Cys Ala Ser Tyr Asn Pro Ser Pro Gly Ser Ser Asn
100 105 110

Phe Met Ser Pro Ala Ser Ser Ser Phe Ala Asn Leu Thr Ser Gly Asp
115 120 125

Gly Gln Ser Leu Ile Pro Trp Leu Lys His Leu Ser Thr Thr Ser Ser
130 135 140

Ser Ser Ala Ser Ser Ser Ser Arg Leu Pro Asn Tyr Leu Tyr Ile Pro
145 150 155 160

```
Gly Gly Ser Ile Ser Ala Pro Val Thr Pro Pro Leu Ser Ser Pro Thr
                165                 170                 175

Ala Arg Thr Pro Arg Met Asn Thr Asp Trp Gln Gln Leu Asn Asn Ser
            180                 185                 190

Phe Phe Val Ser Ser Thr Pro Pro Ser Pro Thr Arg Gln Ile Ile Pro
        195                 200                 205

Asp Ser Glu Trp Phe Ser Gly Ile Gln Leu Ala Gln Ser Val Pro Ala
    210                 215                 220

Ser Pro Thr Phe Ser Leu Val Ser Gln Asn Pro Phe Gly Phe Lys Glu
225                 230                 235                 240

Glu Ala Ala Ser Ala Ala Gly Gly Gly Gly Gly Ser Arg Met Trp Thr
                245                 250                 255

Pro Gly Gln Ser Gly Thr Cys Ser Pro Ala Ile Pro Pro Gly Ala Asp
            260                 265                 270

Gln Thr Ala Asp Val Pro Met Ser Glu Ala Val Ala Pro Pro Glu Phe
        275                 280                 285

Ala Phe Gly Ser Asn Thr Asn Gly Leu Val Lys Ala Trp Glu Gly Glu
    290                 295                 300

Arg Ile His Glu Glu Ser Gly Ser Asp Asp Leu Glu Leu Thr Leu Gly
305                 310                 315                 320

Asn Ser Ser Thr Arg
                325


<210> SEQ ID NO 246
<211> LENGTH: 855
<212> TYPE: DNA
<213> ORGANISM: Arabidopsis thaliana

<400> SEQUENCE: 246

atgacgtcgg ggactagaac gccgacttgg aaagagagag agaacaacaa acggcgagag      60

cggcgaagac gagcgattgc ggctaagatc ttcgcaggac taaggattca tggaaacttc     120

aagctcccta aacactgcga caacaatgaa gtcctcaaag ctttatgcaa tgaagctggt     180

tggactgtag aagacgacgg aactacttac cgcaagggat gcaaaccaat ggatcgaatg     240

gacctcatga atggttctac ttcagctagt ccatgctcat cgtatcaaca tagccctcgt     300

gcttcctaca atccaagccc ttcgtcttca tcattcccga gtcctacaaa cccatttggt     360

gatgctaact cactaatccc atggctcaag aacctctctt caaactcacc ttccaagctt     420

cccttcttcc atggaaattc aataagcgct cccgtgactc cgccattggc tcgaagccct     480

actcgtgatc aagtaaccat ccctgactct ggatggctct caggaatgca aactccgcag     540

agcggaccgt cttctcctac tttcagttta gtttcaagaa acccgttttt cgacaaagag     600

gcttttaaaa tgggagattg taattcacca atgtggactc ctggacaaag tggaaactgc     660

tctccagcta ttcctgctgg tgttgatcag aactctgatg tgccaatggc tgatggaatg     720

acggctgagt ttgcgtttgg ttgtaacgca atggctgcga atggaatggt gaagccttgg     780

gaaggagaaa ggatacatgg agaatgtgtt tcagatgatt tagaacttac acttggaaac     840

tcaagaacca gatga                                                      855


<210> SEQ ID NO 247
<211> LENGTH: 284
<212> TYPE: PRT
<213> ORGANISM: Arabidopsis thaliana

<400> SEQUENCE: 247
```

-continued

```
Met Thr Ser Gly Thr Arg Thr Pro Thr Trp Lys Glu Arg Glu Asn Asn
1               5                   10                  15

Lys Arg Arg Glu Arg Arg Arg Arg Ala Ile Ala Ala Lys Ile Phe Ala
            20                  25                  30

Gly Leu Arg Ile His Gly Asn Phe Lys Leu Pro Lys His Cys Asp Asn
        35                  40                  45

Asn Glu Val Leu Lys Ala Leu Cys Asn Glu Ala Gly Trp Thr Val Glu
    50                  55                  60

Asp Asp Gly Thr Thr Tyr Arg Lys Gly Cys Lys Pro Met Asp Arg Met
65                  70                  75                  80

Asp Leu Met Asn Gly Ser Thr Ser Ala Ser Pro Cys Ser Ser Tyr Gln
                85                  90                  95

His Ser Pro Arg Ala Ser Tyr Asn Pro Ser Pro Ser Ser Ser Ser Phe
            100                 105                 110

Pro Ser Pro Thr Asn Pro Phe Gly Asp Ala Asn Ser Leu Ile Pro Trp
        115                 120                 125

Leu Lys Asn Leu Ser Ser Asn Ser Pro Ser Lys Leu Pro Phe Phe His
    130                 135                 140

Gly Asn Ser Ile Ser Ala Pro Val Thr Pro Pro Leu Ala Arg Ser Pro
145                 150                 155                 160

Thr Arg Asp Gln Val Thr Ile Pro Asp Ser Gly Trp Leu Ser Gly Met
                165                 170                 175

Gln Thr Pro Gln Ser Gly Pro Ser Ser Pro Thr Phe Ser Leu Val Ser
            180                 185                 190

Arg Asn Pro Phe Phe Asp Lys Glu Ala Phe Lys Met Gly Asp Cys Asn
        195                 200                 205

Ser Pro Met Trp Thr Pro Gly Gln Ser Gly Asn Cys Ser Pro Ala Ile
    210                 215                 220

Pro Ala Gly Val Asp Gln Asn Ser Asp Val Pro Met Ala Asp Gly Met
225                 230                 235                 240

Thr Ala Glu Phe Ala Phe Gly Cys Asn Ala Met Ala Ala Asn Gly Met
                245                 250                 255

Val Lys Pro Trp Glu Gly Glu Arg Ile His Gly Glu Cys Val Ser Asp
            260                 265                 270

Asp Leu Glu Leu Thr Leu Gly Asn Ser Arg Thr Arg
        275                 280
```

<210> SEQ ID NO 248
<211> LENGTH: 510
<212> TYPE: DNA
<213> ORGANISM: Arabidopsis thaliana

<400> SEQUENCE: 248

```
atggccgccg gaggaggagg aggaggagga ggatcatcgt cgggacgtac tccgacgtgg      60

aaagagagag agaacaataa gaagagagaa agaagaagaa gagccatcac tgctaagatt     120

tactctggtc ttagagctca aggtaactat aagcttccta agcactgcga taacaacgag     180

gttcttaaag ctctctgtct cgaagctggt tggatcgtcg aagacgatgg caccacttat     240

cgcaaggggt ttagccacca gcatcagata tttcaggaac tcctacaaac ttcagcacaa     300

attcatcaat ccaaccaagt ccacaatcat cagcttttcc aagtcctgca ccttcgtacc     360

acggaagtcc agtctcatca tccttcccga gtccatctcg ctatgacgga aacccttctt     420

cataccttct tcttccgttc ctacacaaca tcgcttcttc gattcctgct aaccttccac     480

ctcttagaat atccaacagt gcgcctgtga                                      510
```

<210> SEQ ID NO 249
<211> LENGTH: 169
<212> TYPE: PRT
<213> ORGANISM: Arabidopsis thaliana

<400> SEQUENCE: 249

```
Met Ala Ala Gly Gly Gly Gly Gly Gly Gly Gly Ser Ser Ser Gly Arg
1               5                   10                  15

Thr Pro Thr Trp Lys Glu Arg Glu Asn Asn Lys Lys Arg Glu Arg Arg
            20                  25                  30

Arg Arg Ala Ile Thr Ala Lys Ile Tyr Ser Gly Leu Arg Ala Gln Gly
        35                  40                  45

Asn Tyr Lys Leu Pro Lys His Cys Asp Asn Asn Glu Val Leu Lys Ala
    50                  55                  60

Leu Cys Leu Glu Ala Gly Trp Ile Val Glu Asp Asp Gly Thr Thr Tyr
65                  70                  75                  80

Arg Lys Gly Phe Ser His Gln His Gln Ile Phe Gln Glu Leu Leu Gln
                85                  90                  95

Thr Ser Ala Gln Ile His Gln Ser Asn Gln Val His Asn His Gln Leu
            100                 105                 110

Phe Gln Val Leu His Leu Arg Thr Thr Glu Val Gln Ser His His Pro
        115                 120                 125

Ser Arg Val His Leu Ala Met Thr Glu Thr Leu Leu His Thr Phe Phe
    130                 135                 140

Phe Arg Ser Tyr Thr Thr Ser Leu Leu Arg Phe Leu Leu Thr Phe His
145                 150                 155                 160

Leu Leu Glu Tyr Pro Thr Val Arg Leu
                165
```

<210> SEQ ID NO 250
<211> LENGTH: 936
<212> TYPE: DNA
<213> ORGANISM: Glycine max

<400> SEQUENCE: 250

```
atggccgacg acggagcaac ctcggcggcg acgagccgga gaaagccgtc gtggagagaa     60
agagaaaaca acaggagaag agaaagaagg agaagagcaa tagctgcgaa aatatactct    120
ggacttcgag ctcaggggaa cttcaacttg ccaaagcact gcgacaacaa cgaagttctg    180
aaagctctct gcgcagaagc tggttggtgc gtggaagaag acggaaccac ttatcgcaag    240
ggttgcaagc cacctctggc caatggtgca gggagctcca tgagaaacat taccttttct    300
tcttctcaaa atccaagtcc tctgtcttcg tcatttccca gcccaattcc ttcataccaa    360
gtgagccctt cctcctcctc tttcccgagc ccgtttcgtt tagatgtgga taaggacaat    420
gtatcaaacc tcattccata cattcgcaat gcgtccttgt ctcttcctcc tctcaggata    480
tcaaacagtg cccctgtgac accacctctt tcatcaccaa catcaagaaa tccaaaacca    540
attcctactt gggagtctat tgccaaagaa tccatggcct ccttcagtta ccctttcttt    600
gcagcttctg cccctgctag ccccacacac cgtcaccttt acactccgcc cactattcca    660
gaatgcgatg aatccgatac ttccaccggc gagtctggcc agtgggtgaa attccaagca    720
tttgctcctt cttcatctgt gttgccaatt tctccaacct ttaatcttgt taaacctgtg    780
attccgcaca ggatgcctga taactcaatc caagtgatga ggacgagttc agaagagttt    840
ggggtacagg taaagccttg ggttggggaa aaaattcatg aagtggcatt ggatgattta    900
```

gagctcacac ttggaagtgg gaaggtgcgg agttag 936

<210> SEQ ID NO 251
<211> LENGTH: 311
<212> TYPE: PRT
<213> ORGANISM: Glycine max

<400> SEQUENCE: 251

Met Ala Asp Asp Gly Ala Thr Ser Ala Ala Thr Ser Arg Arg Lys Pro
1 5 10 15

Ser Trp Arg Glu Arg Glu Asn Asn Arg Arg Arg Glu Arg Arg Arg Arg
20 25 30

Ala Ile Ala Ala Lys Ile Tyr Ser Gly Leu Arg Ala Gln Gly Asn Phe
35 40 45

Asn Leu Pro Lys His Cys Asp Asn Asn Glu Val Leu Lys Ala Leu Cys
50 55 60

Ala Glu Ala Gly Trp Cys Val Glu Glu Asp Gly Thr Thr Tyr Arg Lys
65 70 75 80

Gly Cys Lys Pro Pro Leu Ala Asn Gly Ala Gly Ser Ser Met Arg Asn
85 90 95

Ile Thr Phe Ser Ser Ser Gln Asn Pro Ser Pro Leu Ser Ser Ser Phe
100 105 110

Pro Ser Pro Ile Pro Ser Tyr Gln Val Ser Pro Ser Ser Ser Ser Phe
115 120 125

Pro Ser Pro Phe Arg Leu Asp Val Asp Lys Asp Asn Val Ser Asn Leu
130 135 140

Ile Pro Tyr Ile Arg Asn Ala Ser Leu Ser Leu Pro Pro Leu Arg Ile
145 150 155 160

Ser Asn Ser Ala Pro Val Thr Pro Pro Leu Ser Ser Pro Thr Ser Arg
165 170 175

Asn Pro Lys Pro Ile Pro Thr Trp Glu Ser Ile Ala Lys Glu Ser Met
180 185 190

Ala Ser Phe Ser Tyr Pro Phe Phe Ala Ala Ser Ala Pro Ala Ser Pro
195 200 205

Thr His Arg His Leu Tyr Thr Pro Pro Thr Ile Pro Glu Cys Asp Glu
210 215 220

Ser Asp Thr Ser Thr Gly Glu Ser Gly Gln Trp Val Lys Phe Gln Ala
225 230 235 240

Phe Ala Pro Ser Ser Ser Val Leu Pro Ile Ser Pro Thr Phe Asn Leu
245 250 255

Val Lys Pro Val Ile Pro His Arg Met Pro Asp Asn Ser Ile Gln Val
260 265 270

Met Arg Thr Ser Ser Glu Glu Phe Gly Val Gln Val Lys Pro Trp Val
275 280 285

Gly Glu Lys Ile His Glu Val Ala Leu Asp Asp Leu Glu Leu Thr Leu
290 295 300

Gly Ser Gly Lys Val Arg Ser
305 310

<210> SEQ ID NO 252
<211> LENGTH: 1005
<212> TYPE: DNA
<213> ORGANISM: Glycine max

<400> SEQUENCE: 252
atgacgtccg tcgcgaggca gccaacgtgg aaggagcggg agaacaacaa gaggcgagag 60
aggaggagga gagccatcgc ggcgaagatc ttctccggcc tgcgaatgta cggcaactac 120
aagctcccca aacactgcga caacaacgaa gttctcaagg ctctctgcaa cgaagccggc 180
tggaccgtag aagccgatgg caccacctat cgcaagggat gcaagcctcc tgttgaacgc 240
atggacatag taggtggttc tgcagcagca agcccatgct catcttacca tccaagtccc 300
tgtgcttcct acaaccctag tccaggctct tcttgcttac cgagccctcg cgcatccccc 360
tttcctccaa acccaaatgc tgatggcaat tctctcattc catggctcaa aaacctttca 420
tcaggatcat catcggcatc ctcttccaag cttccgcagc tgtacattcc gaatggctcc 480
atcagtgctc cagtcactcc tccaatcagc tctccatcat cccgaaagcc ccgaatcaaa 540
gctgactggg aggatctgtc cactcgtccg gcagcgtggg gcggacctgc atacaccttc 600
ctgccctctt caactcctcc tagccccggt cgccaggttg ctgaaacaga ttggttttcc 660
aagatcagga ttcctcaggt aggactaaca ccaacttctc caaccttcag cctggtctct 720
tccaacccat ttggcttcaa ggaagatgct atgggtggca gcggttcccg catgtggacg 780
acaccagggg caagtggaac atgttctcca gccgtagctg caggctctga aaacacttct 840
gacattccaa tggctgaagc agtttcagat gaatttgcct ttggaagcag ctcatcaggt 900
ttagtgaatg cctggaaagg agagaggatc catgaagctt cttttggaac agatgatctt 960
gagctcactc ttgggagctc caagaccagg ttgctccata agtga 1005

<210> SEQ ID NO 253
<211> LENGTH: 334
<212> TYPE: PRT
<213> ORGANISM: Glycine max

<400> SEQUENCE: 253

Met Thr Ser Val Ala Arg Gln Pro Thr Trp Lys Glu Arg Glu Asn Asn
1               5                   10                  15

Lys Arg Arg Glu Arg Arg Arg Arg Ala Ile Ala Ala Lys Ile Phe Ser
            20                  25                  30

Gly Leu Arg Met Tyr Gly Asn Tyr Lys Leu Pro Lys His Cys Asp Asn
        35                  40                  45

Asn Glu Val Leu Lys Ala Leu Cys Asn Glu Ala Gly Trp Thr Val Glu
    50                  55                  60

Ala Asp Gly Thr Thr Tyr Arg Lys Gly Cys Lys Pro Pro Val Glu Arg
65                  70                  75                  80

Met Asp Ile Val Gly Gly Ser Ala Ala Ala Ser Pro Cys Ser Ser Tyr
                85                  90                  95

His Pro Ser Pro Cys Ala Ser Tyr Asn Pro Ser Pro Gly Ser Ser Cys
            100                 105                 110

Leu Pro Ser Pro Arg Ala Ser Pro Phe Pro Pro Asn Pro Asn Ala Asp
        115                 120                 125

Gly Asn Ser Leu Ile Pro Trp Leu Lys Asn Leu Ser Ser Gly Ser Ser
    130                 135                 140

Ser Ala Ser Ser Ser Lys Leu Pro Gln Leu Tyr Ile Pro Asn Gly Ser
145                 150                 155                 160

Ile Ser Ala Pro Val Thr Pro Pro Ile Ser Ser Pro Ser Ser Arg Lys
                165                 170                 175

Pro Arg Ile Lys Ala Asp Trp Glu Asp Leu Ser Thr Arg Pro Ala Ala
            180                 185                 190

Trp Gly Gly Pro Ala Tyr Thr Phe Leu Pro Ser Ser Thr Pro Pro Ser

```
        195                 200                 205

Pro Gly Arg Gln Val Ala Glu Thr Asp Trp Phe Ser Lys Ile Arg Ile
    210                 215                 220

Pro Gln Val Gly Leu Thr Pro Thr Ser Pro Thr Phe Ser Leu Val Ser
225                 230                 235                 240

Ser Asn Pro Phe Gly Phe Lys Glu Asp Ala Met Gly Gly Ser Gly Ser
                245                 250                 255

Arg Met Trp Thr Thr Pro Gly Ala Ser Gly Thr Cys Ser Pro Ala Val
            260                 265                 270

Ala Ala Gly Ser Glu Asn Thr Ser Asp Ile Pro Met Ala Glu Ala Val
        275                 280                 285

Ser Asp Glu Phe Ala Phe Gly Ser Ser Ser Ser Gly Leu Val Asn Ala
    290                 295                 300

Trp Lys Gly Glu Arg Ile His Glu Ala Ser Phe Gly Thr Asp Asp Leu
305                 310                 315                 320

Glu Leu Thr Leu Gly Ser Ser Lys Thr Arg Leu Leu His Lys
                325                 330


<210> SEQ ID NO 254
<211> LENGTH: 933
<212> TYPE: DNA
<213> ORGANISM: Glycine max

<400> SEQUENCE: 254

atgaccggcg gcggatcgac ggggaggttg ccaacatgga aggagagaga aaacaacaag      60

aggagagaga ggagacgaag agcgatcgcc gctaagatct acaccggtct tcgagctcag     120

gggaactaca agcttccgaa gcactgtgac aacaacgagg tcctgaaagc tctatgcgcc     180

gaagctggtt ggatcgtgga agaggatggc accacttatc gaaagggatg caagagaccc     240

agcgcgagtg agattggagg aacagtggca aacataagcg cgtgttcttc gattcagcca     300

agtccacaat cctcgtcata cccgagtcct gtaccatcct accacgctag cccaacctct     360

tcctcgttcc caagccccac gcgcattgac ggaaaccacc cttcttcctt tctcatccca     420

ttcatccgca acataacttc catccccgcc aacctccctc ctctcaggat atccaacagc     480

gcccccgtca ccccacctct ctcctctcct cgtagctcta agcgcaaggc tgatttcgac     540

tccctccata acgcctccct ccgccaccct ctttttgaca cctccgcccc ttccagcccc     600

tctcgccgcc accacctcgc cacctccacc atcccggagt gcgatgagtc cgacgcctcc     660

accgttgact ccgcctctgg gcgctgggtt agttttcagg ttcagacgac gatggcggcc     720

gctcctcctt ctcccacctt taacctcatg aaacccgcca tgcagcagat cgctgcccag     780

gaaggcatgc tgtggggttc tgttgcggag cgagtcagag gaggctccga ttttgacttc     840

gagaatggca gagtcaaacc ctgggagggt gagagaatac acgaggttgg aatggatgat     900

ttggagctta ctctaggagt tggaaaggct tga                                  933


<210> SEQ ID NO 255
<211> LENGTH: 310
<212> TYPE: PRT
<213> ORGANISM: Glycine max

<400> SEQUENCE: 255

Met Thr Gly Gly Gly Ser Thr Gly Arg Leu Pro Thr Trp Lys Glu Arg
1               5                   10                  15

Glu Asn Asn Lys Arg Arg Glu Arg Arg Arg Arg Ala Ile Ala Ala Lys
            20                  25                  30
```

```
Ile Tyr Thr Gly Leu Arg Ala Gln Gly Asn Tyr Lys Leu Pro Lys His
        35                  40                  45

Cys Asp Asn Asn Glu Val Leu Lys Ala Leu Cys Ala Glu Ala Gly Trp
    50                  55                  60

Ile Val Glu Glu Asp Gly Thr Thr Tyr Arg Lys Gly Cys Lys Arg Pro
65                  70                  75                  80

Ser Ala Ser Glu Ile Gly Gly Thr Val Ala Asn Ile Ser Ala Cys Ser
                85                  90                  95

Ser Ile Gln Pro Ser Pro Gln Ser Ser Ser Tyr Pro Ser Pro Val Pro
            100                 105                 110

Ser Tyr His Ala Ser Pro Thr Ser Ser Ser Phe Pro Ser Pro Thr Arg
        115                 120                 125

Ile Asp Gly Asn His Pro Ser Ser Phe Leu Ile Pro Phe Ile Arg Asn
    130                 135                 140

Ile Thr Ser Ile Pro Ala Asn Leu Pro Pro Leu Arg Ile Ser Asn Ser
145                 150                 155                 160

Ala Pro Val Thr Pro Pro Leu Ser Ser Pro Arg Ser Ser Lys Arg Lys
                165                 170                 175

Ala Asp Phe Asp Ser Leu His Asn Ala Ser Leu Arg His Pro Leu Phe
            180                 185                 190

Asp Thr Ser Ala Pro Ser Ser Pro Ser Arg Arg His His Leu Ala Thr
        195                 200                 205

Ser Thr Ile Pro Glu Cys Asp Glu Ser Asp Ala Ser Thr Val Asp Ser
    210                 215                 220

Ala Ser Gly Arg Trp Val Ser Phe Gln Val Gln Thr Thr Met Ala Ala
225                 230                 235                 240

Ala Pro Pro Ser Pro Thr Phe Asn Leu Met Lys Pro Ala Met Gln Gln
                245                 250                 255

Ile Ala Ala Gln Glu Gly Met Leu Trp Gly Ser Val Ala Glu Arg Val
            260                 265                 270

Arg Gly Gly Ser Asp Phe Asp Phe Glu Asn Gly Arg Val Lys Pro Trp
        275                 280                 285

Glu Gly Glu Arg Ile His Glu Val Gly Met Asp Asp Leu Glu Leu Thr
    290                 295                 300

Leu Gly Val Gly Lys Ala
305                 310
```

<210> SEQ ID NO 256
<211> LENGTH: 927
<212> TYPE: DNA
<213> ORGANISM: Glycine max

<400> SEQUENCE: 256

```
atgaccggcg gcggatccac ggggaggttg ccgacgtgga aggagagaga gaacaacaag     60

aggagagaga gaagacgaag agcgattgca gctaagatct acactggcct tcgagcccag    120

gggaactaca agcttccaaa gcactgcgac aacaacgagg tcctgaaagc tctctgcgcc    180

gaagctggct ggatcgtgga agaagatggc acaacttatc gaaagggatg taagagaccc    240

acgagtgaga ttggaggaac accactgaac ttaagcgcgt gttcttccat tcaggcaagt    300

ccacaatcct cgtcataccc gagtcctgta ccatcctacc atgctagccc aacctcttcc    360

tcgttcccaa gccccacgcg cattgacgga aaccaccctt cttcctttct catcccattc    420

atccgcaaca taacttccat ccccgccaac ctccctcctc tcaggatatc caacagcgcc    480
```

```
cccgtcaccc cacctctttc ttctccccga agctcaaagc gcaaggcgga tttcgactcc    540

ctccgccacc ctctttttgc cacctccgcc ccgtccagcc ccacgcgccg ccaccacgtt    600

gccacctcca ccatcccgga gtgcgacgag tccgacgcct ccaccgtgga ctccgcctcg    660

ggccgctggg ttagtttcca ggttcagacg acgatggtgg ctgcggcggc ggctgctcct    720

ccttcgccta cctttaacct catgaagccc gcgatgcagc agatcgctgc ccaggaaggc    780

atgcagtggg gttctgttgc cgagagaggc agaggaggct ccgattttga cttcgagaat    840

ggcagagtga aaccctggga gggtgagaga atacacgagg ttggaatgga tgatttggag    900

cttactctag gagttggaaa ggcttga                                        927


<210> SEQ ID NO 257
<211> LENGTH: 308
<212> TYPE: PRT
<213> ORGANISM: Glycine max

<400> SEQUENCE: 257

Met Thr Gly Gly Gly Ser Thr Gly Arg Leu Pro Thr Trp Lys Glu Arg
1               5                   10                  15

Glu Asn Asn Lys Arg Arg Glu Arg Arg Arg Arg Ala Ile Ala Ala Lys
            20                  25                  30

Ile Tyr Thr Gly Leu Arg Ala Gln Gly Asn Tyr Lys Leu Pro Lys His
        35                  40                  45

Cys Asp Asn Asn Glu Val Leu Lys Ala Leu Cys Ala Glu Ala Gly Trp
    50                  55                  60

Ile Val Glu Glu Asp Gly Thr Thr Tyr Arg Lys Gly Cys Lys Arg Pro
65                  70                  75                  80

Thr Ser Glu Ile Gly Gly Thr Pro Leu Asn Leu Ser Ala Cys Ser Ser
                85                  90                  95

Ile Gln Ala Ser Pro Gln Ser Ser Ser Tyr Pro Ser Pro Val Pro Ser
            100                 105                 110

Tyr His Ala Ser Pro Thr Ser Ser Ser Phe Pro Ser Pro Thr Arg Ile
        115                 120                 125

Asp Gly Asn His Pro Ser Ser Phe Leu Ile Pro Phe Ile Arg Asn Ile
    130                 135                 140

Thr Ser Ile Pro Ala Asn Leu Pro Pro Leu Arg Ile Ser Asn Ser Ala
145                 150                 155                 160

Pro Val Thr Pro Pro Leu Ser Ser Pro Arg Ser Ser Lys Arg Lys Ala
                165                 170                 175

Asp Phe Asp Ser Leu Arg His Pro Leu Phe Ala Thr Ser Ala Pro Ser
            180                 185                 190

Ser Pro Thr Arg Arg His His Val Ala Thr Ser Thr Ile Pro Glu Cys
        195                 200                 205

Asp Glu Ser Asp Ala Ser Thr Val Asp Ser Ala Ser Gly Arg Trp Val
    210                 215                 220

Ser Phe Gln Val Gln Thr Thr Met Val Ala Ala Ala Ala Ala Ala Pro
225                 230                 235                 240

Pro Ser Pro Thr Phe Asn Leu Met Lys Pro Ala Met Gln Gln Ile Ala
                245                 250                 255

Ala Gln Glu Gly Met Gln Trp Gly Ser Val Ala Glu Arg Gly Arg Gly
            260                 265                 270

Gly Ser Asp Phe Asp Phe Glu Asn Gly Arg Val Lys Pro Trp Glu Gly
        275                 280                 285

Glu Arg Ile His Glu Val Gly Met Asp Asp Leu Glu Leu Thr Leu Gly
```

290 295 300

Val Gly Lys Ala
305

<210> SEQ ID NO 258
<211> LENGTH: 1053
<212> TYPE: DNA
<213> ORGANISM: Hordeum vulgare

<400> SEQUENCE: 258
atggcgacgg ggggtggagg aggagcggac ttcggggcgg cggggggagc gggcggcagg 60
atgccgacgt ggagggagcg ggagaacaac aagcggaggg agcggcggcg gcgggcgatc 120
gccgccaaga tattctccgg cctgcgggcg cacggcgggt acaagctccc caagcactgc 180
gacaacaacg aggtcctcaa ggccctctgc aacgaggccg gctgggtcgt cgagcccgac 240
ggcaccacct accgcaaggg atgcagacct gcagagcgca tggatgggat tgggtgctcc 300
gtgtcgccaa gcccatgttc ctcatatcag ccaagcccgc gggcatcata caacgcgagc 360
cctacctcct cttcattccc cagcggcgca tcgtcgccct tcctcccaca ttctaacaac 420
atggtaaatg gcgtcgatgc aactcccatc ctaccatggc tgcaaacgtt ctccaattcg 480
aataagcggc cgcatcttcc cccgctgctg attcacggcg gctccattag cgccccggtg 540
actcctccac tgagctcacc gactgcccgc acccctcgca tgaagacgga ctgggacgag 600
tcggtgatcc agccaccatg gcacggttca aacagtccct gcgtggtgaa ctccaccccg 660
ccgagccccg ggcgtcaaat ggttcctgac ccagcatggc tggccggcat ccagatctcg 720
tcaacgagcc cttcatcgcc cacgtttagt ctcatgtcct ccaacccatt cagcgtcttc 780
aaagaagcga tcccgggcgg cggttcgtcc aggatgtgca cgccggggca gagcggcacg 840
tgctcgccgg tgatccccgg catggcgcgg cacccggacg ttcacatgat ggacgtggtt 900
tctgacgagt ttgcatttgg aagcagcacc aacggtgttg ctcagcaggc caccgccgga 960
ttggtgaggg cgtgggaggg cgagaggatc cacgaggact ctgggtcgga cgagctggag 1020
ctcactctcg ggagcaccag gacgaggagc tga 1053

<210> SEQ ID NO 259
<211> LENGTH: 350
<212> TYPE: PRT
<213> ORGANISM: Hordeum vulgare

<400> SEQUENCE: 259

Met Ala Thr Gly Gly Gly Gly Gly Ala Asp Phe Gly Ala Ala Gly Gly
1 5 10 15

Ala Gly Gly Arg Met Pro Thr Trp Arg Glu Arg Glu Asn Asn Lys Arg
20 25 30

Arg Glu Arg Arg Arg Arg Ala Ile Ala Ala Lys Ile Phe Ser Gly Leu
35 40 45

Arg Ala His Gly Gly Tyr Lys Leu Pro Lys His Cys Asp Asn Asn Glu
50 55 60

Val Leu Lys Ala Leu Cys Asn Glu Ala Gly Trp Val Val Glu Pro Asp
65 70 75 80

Gly Thr Thr Tyr Arg Lys Gly Cys Arg Pro Ala Glu Arg Met Asp Gly
85 90 95

Ile Gly Cys Ser Val Ser Pro Ser Pro Cys Ser Ser Tyr Gln Pro Ser
100 105 110

Pro Arg Ala Ser Tyr Asn Ala Ser Pro Thr Ser Ser Ser Phe Pro Ser

```
        115                 120                 125

Gly Ala Ser Ser Pro Phe Leu Pro His Ser Asn Asn Met Val Asn Gly
    130                 135                 140

Val Asp Ala Thr Pro Ile Leu Pro Trp Leu Gln Thr Phe Ser Asn Ser
145                 150                 155                 160

Asn Lys Arg Pro His Leu Pro Pro Leu Leu Ile His Gly Gly Ser Ile
                165                 170                 175

Ser Ala Pro Val Thr Pro Pro Leu Ser Ser Pro Thr Ala Arg Thr Pro
            180                 185                 190

Arg Met Lys Thr Asp Trp Asp Glu Ser Val Ile Gln Pro Pro Trp His
        195                 200                 205

Gly Ser Asn Ser Pro Cys Val Val Asn Ser Thr Pro Pro Ser Pro Gly
    210                 215                 220

Arg Gln Met Val Pro Asp Pro Ala Trp Leu Ala Gly Ile Gln Ile Ser
225                 230                 235                 240

Ser Thr Ser Pro Ser Ser Pro Thr Phe Ser Leu Met Ser Ser Asn Pro
                245                 250                 255

Phe Ser Val Phe Lys Glu Ala Ile Pro Gly Gly Gly Ser Ser Arg Met
            260                 265                 270

Cys Thr Pro Gly Gln Ser Gly Thr Cys Ser Pro Val Ile Pro Gly Met
        275                 280                 285

Ala Arg His Pro Asp Val His Met Met Asp Val Val Ser Asp Glu Phe
    290                 295                 300

Ala Phe Gly Ser Ser Thr Asn Gly Val Ala Gln Gln Ala Thr Ala Gly
305                 310                 315                 320

Leu Val Arg Ala Trp Glu Gly Glu Arg Ile His Glu Asp Ser Gly Ser
                325                 330                 335

Asp Glu Leu Glu Leu Thr Leu Gly Ser Thr Arg Thr Arg Ser
            340                 345                 350


<210> SEQ ID NO 260
<211> LENGTH: 1002
<212> TYPE: DNA
<213> ORGANISM: Lycopersicon esculentum

<400> SEQUENCE: 260

atgatgtggg aagctggaga atcaccagca tcttcttcgg ccggtgccgg agctggtgga      60

agtggaggtg ccggagttgg tttaccggaa agtggtggtg gtggtggtgg tgggagaagg     120

aaaccatcat ggagagaaag agagaataac aggagaagag agaggaggag gagagctgta     180

gctgctaaga tttatactgg tttaagagct caaggaaact ataatcttcc gaagcactgt     240

gataacaatg aagttcttaa agctctttgt actgaagctg gttggatcgt tgaacctgat     300

ggtaccactt atcgcaaggg atgcaagcca accccgatgg agattggagg cacttcaaca     360

aacatcacgc caagttcttc acggcatcca agtcccccat catcatactt tgctagccca     420

attccatctt atcagccaag tccaacttcc tcttctttcc ccagtccatc tcgtgctgat     480

gccaacatgt tatcacatcc atattctttt ctccaaaatg tcgttccttc atcccttcct     540

ccattacgaa tatcaaacag tgcccctgta actccacctc tttcatcacc aactaggcat     600

cctaagcaaa ctttcaattt agaaactttg gccaaagaat caatgtttgc tttaaacatc     660

cctttctttg ctgcttcagc cccagcaagc ccaactaggg ttcagcgttt tactcctcca     720

actatacccg agtgtgatga atctgactca tctaccattg attcaggcca gtggatcaac     780

tttcaaaagt atgcgtcaaa tgttccacct tctccaacat ttaatcttgt aaaacctgtg     840
```

```
cctcagccgc ttcgtcctaa tgatatgatc acagacaagg gtaagagcat agacttcgac    900

tttgaaaatg tatcagtcaa ggcatgggaa ggtgaaagga ttcacgatgt aggattcgat    960

gatctggaac tcacacttgg aagtggcaat gctcgcatat ga                      1002


<210> SEQ ID NO 261
<211> LENGTH: 333
<212> TYPE: PRT
<213> ORGANISM: Lycopersicon esculentum

<400> SEQUENCE: 261

Met Met Trp Glu Ala Gly Glu Ser Pro Ala Ser Ser Ser Ala Gly Ala
1               5                   10                  15

Gly Ala Gly Gly Ser Gly Gly Ala Gly Val Gly Leu Pro Glu Ser Gly
            20                  25                  30

Gly Gly Gly Gly Gly Gly Arg Arg Lys Pro Ser Trp Arg Glu Arg Glu
        35                  40                  45

Asn Asn Arg Arg Arg Glu Arg Arg Arg Arg Ala Val Ala Ala Lys Ile
    50                  55                  60

Tyr Thr Gly Leu Arg Ala Gln Gly Asn Tyr Asn Leu Pro Lys His Cys
65                  70                  75                  80

Asp Asn Asn Glu Val Leu Lys Ala Leu Cys Thr Glu Ala Gly Trp Ile
                85                  90                  95

Val Glu Pro Asp Gly Thr Thr Tyr Arg Lys Gly Cys Lys Pro Thr Pro
            100                 105                 110

Met Glu Ile Gly Gly Thr Ser Thr Asn Ile Thr Pro Ser Ser Ser Arg
        115                 120                 125

His Pro Ser Pro Pro Ser Ser Tyr Phe Ala Ser Pro Ile Pro Ser Tyr
    130                 135                 140

Gln Pro Ser Pro Thr Ser Ser Ser Phe Pro Ser Pro Ser Arg Ala Asp
145                 150                 155                 160

Ala Asn Met Leu Ser His Pro Tyr Ser Phe Leu Gln Asn Val Val Pro
                165                 170                 175

Ser Ser Leu Pro Pro Leu Arg Ile Ser Asn Ser Ala Pro Val Thr Pro
            180                 185                 190

Pro Leu Ser Ser Pro Thr Arg His Pro Lys Gln Thr Phe Asn Leu Glu
        195                 200                 205

Thr Leu Ala Lys Glu Ser Met Phe Ala Leu Asn Ile Pro Phe Phe Ala
    210                 215                 220

Ala Ser Ala Pro Ala Ser Pro Thr Arg Val Gln Arg Phe Thr Pro Pro
225                 230                 235                 240

Thr Ile Pro Glu Cys Asp Glu Ser Asp Ser Ser Thr Ile Asp Ser Gly
                245                 250                 255

Gln Trp Ile Asn Phe Gln Lys Tyr Ala Ser Asn Val Pro Pro Ser Pro
            260                 265                 270

Thr Phe Asn Leu Val Lys Pro Val Pro Gln Pro Leu Arg Pro Asn Asp
        275                 280                 285

Met Ile Thr Asp Lys Gly Lys Ser Ile Asp Phe Asp Phe Glu Asn Val
    290                 295                 300

Ser Val Lys Ala Trp Glu Gly Glu Arg Ile His Asp Val Gly Phe Asp
305                 310                 315                 320

Asp Leu Glu Leu Thr Leu Gly Ser Gly Asn Ala Arg Ile
                325                 330
```

<210> SEQ ID NO 262
<211> LENGTH: 687
<212> TYPE: DNA
<213> ORGANISM: Lycopersicon esculentum
<220> FEATURE:
<221> NAME/KEY: misc_feature
<222> LOCATION: (481)..(481)
<223> OTHER INFORMATION: n is a, c, g, or t
<220> FEATURE:
<221> NAME/KEY: misc_feature
<222> LOCATION: (562)..(562)
<223> OTHER INFORMATION: n is a, c, g, or t
<220> FEATURE:
<221> NAME/KEY: misc_feature
<222> LOCATION: (573)..(573)
<223> OTHER INFORMATION: n is a, c, g, or t
<220> FEATURE:
<221> NAME/KEY: misc_feature
<222> LOCATION: (632)..(632)
<223> OTHER INFORMATION: n is a, c, g, or t
<220> FEATURE:
<221> NAME/KEY: misc_feature
<222> LOCATION: (634)..(635)
<223> OTHER INFORMATION: n is a, c, g, or t
<220> FEATURE:
<221> NAME/KEY: misc_feature
<222> LOCATION: (639)..(640)
<223> OTHER INFORMATION: n is a, c, g, or t
<220> FEATURE:
<221> NAME/KEY: misc_feature
<222> LOCATION: (656)..(657)
<223> OTHER INFORMATION: n is a, c, g, or t
<220> FEATURE:
<221> NAME/KEY: misc_feature
<222> LOCATION: (660)..(660)
<223> OTHER INFORMATION: n is a, c, g, or t
<220> FEATURE:
<221> NAME/KEY: misc_feature
<222> LOCATION: (662)..(662)
<223> OTHER INFORMATION: n is a, c, g, or t
<220> FEATURE:
<221> NAME/KEY: misc_feature
<222> LOCATION: (674)..(674)
<223> OTHER INFORMATION: n is a, c, g, or t
<220> FEATURE:
<221> NAME/KEY: misc_feature
<222> LOCATION: (680)..(680)
<223> OTHER INFORMATION: n is a, c, g, or t
<220> FEATURE:
<221> NAME/KEY: misc_feature
<222> LOCATION: (683)..(683)
<223> OTHER INFORMATION: n is a, c, g, or t

<400> SEQUENCE: 262
atgacggccg gcaccggcgg tggaggatcg tcgggaaggt tgccgacgtg gaaggagagg 60
gaaaacaata agagaagaga gaggagaaga agagctattg ccgccaaaat atttactggc 120
ttacgaactc aaggtaactt caagcttcca aaacactgtg ataataacga ggtcttgaaa 180
gctctatgta ttgaagctgg ttggatcgtt gaagatgatg gcaccactta tcgcaaggga 240
cacaggcctc caccaattga aaatggatgt gtctctatga atatcagtgc atcttcatcg 300
attcagccta gcccaatgtc atcctctttc cccagtcctg taccttctta ccatgccagc 360
ccaacatcat cctcatttcc tagtccctcc cgttgtgacg ggaacccctc atcatacatc 420
cttccctttc tccataactt agcttccatt ccctctactc tgccacctct tcgtatatct 480
natagtgccc ctgttacccc tcctctttct tctcctaccc gacgttcaaa gccccccaaa 540
cctttatggg aatccctctc cngggttcca ttnaattctt tccagcaccc actttttgct 600
gcttctgcac catcaagtcc cactcgacgc cnannctcnn gcctgctaca attccnnaan 660
gngatgagtc tgangccgcn canttga 687

```
<210> SEQ ID NO 263
<211> LENGTH: 228
<212> TYPE: PRT
<213> ORGANISM: Lycopersicon esculentum
<220> FEATURE:
<221> NAME/KEY: misc_feature
<222> LOCATION: (161)..(161)
<223> OTHER INFORMATION: Xaa can be any naturally occurring amino acid
<220> FEATURE:
<221> NAME/KEY: misc_feature
<222> LOCATION: (188)..(188)
<223> OTHER INFORMATION: Xaa can be any naturally occurring amino acid
<220> FEATURE:
<221> NAME/KEY: misc_feature
<222> LOCATION: (191)..(191)
<223> OTHER INFORMATION: Xaa can be any naturally occurring amino acid
<220> FEATURE:
<221> NAME/KEY: misc_feature
<222> LOCATION: (211)..(212)
<223> OTHER INFORMATION: Xaa can be any naturally occurring amino acid
<220> FEATURE:
<221> NAME/KEY: misc_feature
<222> LOCATION: (214)..(214)
<223> OTHER INFORMATION: Xaa can be any naturally occurring amino acid
<220> FEATURE:
<221> NAME/KEY: misc_feature
<222> LOCATION: (219)..(221)
<223> OTHER INFORMATION: Xaa can be any naturally occurring amino acid
<220> FEATURE:
<221> NAME/KEY: misc_feature
<222> LOCATION: (225)..(225)
<223> OTHER INFORMATION: Xaa can be any naturally occurring amino acid
<220> FEATURE:
<221> NAME/KEY: misc_feature
<222> LOCATION: (227)..(228)
<223> OTHER INFORMATION: Xaa can be any naturally occurring amino acid

<400> SEQUENCE: 263

Met Thr Ala Gly Thr Gly Gly Gly Gly Ser Ser Gly Arg Leu Pro Thr
1               5                   10                  15

Trp Lys Glu Arg Glu Asn Asn Lys Arg Arg Glu Arg Arg Arg Arg Ala
            20                  25                  30

Ile Ala Ala Lys Ile Phe Thr Gly Leu Arg Thr Gln Gly Asn Phe Lys
        35                  40                  45

Leu Pro Lys His Cys Asp Asn Asn Glu Val Leu Lys Ala Leu Cys Ile
    50                  55                  60

Glu Ala Gly Trp Ile Val Glu Asp Asp Gly Thr Thr Tyr Arg Lys Gly
65                  70                  75                  80

His Arg Pro Pro Pro Ile Glu Asn Gly Cys Val Ser Met Asn Ile Ser
                85                  90                  95

Ala Ser Ser Ser Ile Gln Pro Ser Pro Met Ser Ser Ser Phe Pro Ser
            100                 105                 110

Pro Val Pro Ser Tyr His Ala Ser Pro Thr Ser Ser Ser Phe Pro Ser
        115                 120                 125

Pro Ser Arg Cys Asp Gly Asn Pro Ser Ser Tyr Ile Leu Pro Phe Leu
    130                 135                 140

His Asn Leu Ala Ser Ile Pro Ser Thr Leu Pro Pro Leu Arg Ile Ser
145                 150                 155                 160

Xaa Ser Ala Pro Val Thr Pro Pro Leu Ser Ser Pro Thr Arg Arg Ser
                165                 170                 175

Lys Pro Pro Lys Pro Leu Trp Glu Ser Leu Ser Xaa Val Pro Xaa Asn
            180                 185                 190

Ser Phe Gln His Pro Leu Phe Ala Ala Ser Ala Pro Ser Ser Pro Thr
        195                 200                 205
```

```
Arg Arg Xaa Xaa Ser Xaa Leu Leu Gln Phe Xaa Xaa Xaa Met Ser Leu
    210                 215                 220

Xaa Pro Xaa Xaa
225


<210> SEQ ID NO 264
<211> LENGTH: 960
<212> TYPE: DNA
<213> ORGANISM: Lycopersicon esculentum

<400> SEQUENCE: 264

atgacggccg gcaccggcgg tggaggatcg tcgggaaggt tgccgacgtg gaaggagagg      60

gaaaacaata agagaagaga gaggagaaga agagctattg ccgccaaaat atttactggc     120

ttacgaactc aaggtaactt caagcttcca aaacactgtg ataataacga ggtcttgaaa     180

gctctatgta ttgaagctgg ttggatcgtt gaagatgatg gcaccactta tcgcaaggga     240

cacaggcctc caccaattga aaatggatgt gtctctatga atatcagtgc atcttcatcg     300

attcagccta gcccaatgtc atcctctttc cccagtcctg taccttctta ccatgccagc     360

ccaacatcat cctcatttcc tagtccctcc cgttgtgacg ggaacccctc atcatacatc     420

cttccctttc tccataactt agcttccatt ccctctactc tgccacctct tcgtatatct     480

aatagtgccc ctgttacccc tcctctttct tctcctaccc gacgttcaaa gccccccaaa     540

cctttatggg aatccctctc cagggttcca ttgaattctt tccagcaccc actttttgct     600

gcttctgcac catcaagtcc cactcgacgc cgatactcta agcctgctac aattccagaa     660

tgtgatgagt ctgatgccgc ctcagttgaa tctgcacgct gggtcagctt ccagacggtg     720

gcagctccaa cttcgcctac ttttaacctt gtaaaacctc ttcctcagca gaacattctc     780

ttagatgcct taagtggaca tggaatggtt ggctggggcg aaacagcagc tcaaaaggga     840

catggcgctg aatttgattt tgagagctgt aaagtgaagg catgggaagg tgagagaata     900

catgaagttg ctgtggatga tctagagctc actcttggta gtgcaaaagc acgtgcttaa     960


<210> SEQ ID NO 265
<211> LENGTH: 319
<212> TYPE: PRT
<213> ORGANISM: Lycopersicon esculentum

<400> SEQUENCE: 265

Met Thr Ala Gly Thr Gly Gly Gly Gly Ser Ser Gly Arg Leu Pro Thr
1               5                   10                  15

Trp Lys Glu Arg Glu Asn Asn Lys Arg Arg Glu Arg Arg Arg Arg Ala
            20                  25                  30

Ile Ala Ala Lys Ile Phe Thr Gly Leu Arg Thr Gln Gly Asn Phe Lys
        35                  40                  45

Leu Pro Lys His Cys Asp Asn Asn Glu Val Leu Lys Ala Leu Cys Ile
    50                  55                  60

Glu Ala Gly Trp Ile Val Glu Asp Asp Gly Thr Thr Tyr Arg Lys Gly
65                  70                  75                  80

His Arg Pro Pro Pro Ile Glu Asn Gly Cys Val Ser Met Asn Ile Ser
                85                  90                  95

Ala Ser Ser Ser Ile Gln Pro Ser Pro Met Ser Ser Ser Phe Pro Ser
            100                 105                 110

Pro Val Pro Ser Tyr His Ala Ser Pro Thr Ser Ser Ser Phe Pro Ser
        115                 120                 125

Pro Ser Arg Cys Asp Gly Asn Pro Ser Ser Tyr Ile Leu Pro Phe Leu
```

```
    130                 135                 140

His Asn Leu Ala Ser Ile Pro Ser Thr Leu Pro Pro Leu Arg Ile Ser
145                 150                 155                 160

Asn Ser Ala Pro Val Thr Pro Pro Leu Ser Ser Pro Thr Arg Arg Ser
                165                 170                 175

Lys Pro Pro Lys Pro Leu Trp Glu Ser Leu Ser Arg Val Pro Leu Asn
            180                 185                 190

Ser Phe Gln His Pro Leu Phe Ala Ala Ser Ala Pro Ser Ser Pro Thr
        195                 200                 205

Arg Arg Arg Tyr Ser Lys Pro Ala Thr Ile Pro Glu Cys Asp Glu Ser
    210                 215                 220

Asp Ala Ala Ser Val Glu Ser Ala Arg Trp Val Ser Phe Gln Thr Val
225                 230                 235                 240

Ala Ala Pro Thr Ser Pro Thr Phe Asn Leu Val Lys Pro Leu Pro Gln
                245                 250                 255

Gln Asn Ile Leu Leu Asp Ala Leu Ser Gly His Gly Met Val Gly Trp
            260                 265                 270

Gly Glu Thr Ala Ala Gln Lys Gly His Gly Ala Glu Phe Asp Phe Glu
        275                 280                 285

Ser Cys Lys Val Lys Ala Trp Glu Gly Glu Arg Ile His Glu Val Ala
    290                 295                 300

Val Asp Asp Leu Glu Leu Thr Leu Gly Ser Ala Lys Ala Arg Ala
305                 310                 315


<210> SEQ ID NO 266
<211> LENGTH: 999
<212> TYPE: DNA
<213> ORGANISM: Lycopersicon esculentum

<400> SEQUENCE: 266

atgtgggaag ctggagaatc accagcatct tcttcggccg gtgccggagc tggtggaagt      60

ggaggtgccg gagttggttt accggaaagt ggtggtggtg gtggtggtgg gagaaggaaa     120

ccatcatgga gagaaagaga gaataacagg agaagagaga ggaggaggag agctgtagct     180

gctaagattt atactggttt aagagctcaa ggaaactata atcttccgaa gcactgtgat     240

aacaatgaag ttcttaaagc tctttgtact gaagctggtt ggatcgttga acctgatggt     300

accacttatc gcaagggatg caagccaacc ccgatggaga ttggaggcac ttcaacaaac     360

atcacgccaa gttcttcacg gcatccaagt cccccatcat catactttgc tagcccaatt     420

ccatcttatc agccaagtcc aacttcctct tctttcccca gtccatctcg tgctgatgcc     480

aacatgtcat cacatccata ttcttttctc caaaatgtcg ttccttcatc ccttccccca     540

ttacgaatat caaacagtgc ccctgtaact ccacctcttt catcaccaac taggcatcct     600

aagcaaactt tcaatttaga aactttggcc aaagaaacaa tgtttgcttt aaacatcccc     660

ttccttgctg cttcagcccc agcaagccca actaggggtc agcgttttac tcctccaact     720

atacccgagt gtgatgaatc tgactcatct accattgatt caggccagtg gatcaacttt     780

caaaagtatg cgtcaaatgt tccaccttct ccaacattta atcttgtaaa acctgtgcct     840

cagccgcttc gtcctaatga tatgatcaca gacaagggta agagcataga cttcgacttt     900

gaaaatgtat cagtcaaggc atgggaaggt gaaaggattc acgatgtagg attcgatgat     960

ctggaactca cacttggaag tggcaatgct cgcatatga                            999


<210> SEQ ID NO 267
```

<211> LENGTH: 332
<212> TYPE: PRT
<213> ORGANISM: Lycopersicon esculentum

<400> SEQUENCE: 267

```
Met Trp Glu Ala Gly Glu Ser Pro Ala Ser Ser Ser Ala Gly Ala Gly
1               5                   10                  15

Ala Gly Gly Ser Gly Gly Ala Gly Val Gly Leu Pro Glu Ser Gly Gly
            20                  25                  30

Gly Gly Gly Gly Gly Arg Arg Lys Pro Ser Trp Arg Glu Arg Glu Asn
        35                  40                  45

Asn Arg Arg Arg Glu Arg Arg Arg Arg Ala Val Ala Ala Lys Ile Tyr
    50                  55                  60

Thr Gly Leu Arg Ala Gln Gly Asn Tyr Asn Leu Pro Lys His Cys Asp
65                  70                  75                  80

Asn Asn Glu Val Leu Lys Ala Leu Cys Thr Glu Ala Gly Trp Ile Val
                85                  90                  95

Glu Pro Asp Gly Thr Thr Tyr Arg Lys Gly Cys Lys Pro Thr Pro Met
            100                 105                 110

Glu Ile Gly Gly Thr Ser Thr Asn Ile Thr Pro Ser Ser Ser Arg His
        115                 120                 125

Pro Ser Pro Pro Ser Ser Tyr Phe Ala Ser Pro Ile Pro Ser Tyr Gln
    130                 135                 140

Pro Ser Pro Thr Ser Ser Ser Phe Pro Ser Pro Ser Arg Ala Asp Ala
145                 150                 155                 160

Asn Met Ser Ser His Pro Tyr Ser Phe Leu Gln Asn Val Val Pro Ser
                165                 170                 175

Ser Leu Pro Pro Leu Arg Ile Ser Asn Ser Ala Pro Val Thr Pro Pro
            180                 185                 190

Leu Ser Ser Pro Thr Arg His Pro Lys Gln Thr Phe Asn Leu Glu Thr
        195                 200                 205

Leu Ala Lys Glu Thr Met Phe Ala Leu Asn Ile Pro Phe Leu Ala Ala
    210                 215                 220

Ser Ala Pro Ala Ser Pro Thr Arg Gly Gln Arg Phe Thr Pro Pro Thr
225                 230                 235                 240

Ile Pro Glu Cys Asp Glu Ser Asp Ser Ser Thr Ile Asp Ser Gly Gln
                245                 250                 255

Trp Ile Asn Phe Gln Lys Tyr Ala Ser Asn Val Pro Pro Ser Pro Thr
            260                 265                 270

Phe Asn Leu Val Lys Pro Val Pro Gln Pro Leu Arg Pro Asn Asp Met
        275                 280                 285

Ile Thr Asp Lys Gly Lys Ser Ile Asp Phe Asp Phe Glu Asn Val Ser
    290                 295                 300

Val Lys Ala Trp Glu Gly Glu Arg Ile His Asp Val Gly Phe Asp Asp
305                 310                 315                 320

Leu Glu Leu Thr Leu Gly Ser Gly Asn Ala Arg Ile
                325                 330
```

<210> SEQ ID NO 268
<211> LENGTH: 498
<212> TYPE: DNA
<213> ORGANISM: Medicago truncatula

<400> SEQUENCE: 268

```
atgacatcag gtacaagact accaacatgg aaggagagag agaacaacaa gaggagagag     60
```

```
agaagaagaa gagctatagc tgctaagatc ttctctggtt tgagaatgta tggtaacttt    120

agattaccta aacattgtga taacaatgaa gttcttaaag ctccttgtaa tgaagctggt    180

tggactgttg aacctgatgg aaccacttat cgtaagggat gcaagccttt agagaacatg    240

gatatggttg gtggatcatc agctgcaagc ccttgttcat cttaccatcc aagccccggc    300

tcgtcttcct tcccgagtcc atcttcatcc ccttacgctg caaatcgtaa cgctgatggt    360

aattccctca ttccatggct caaaaacctc tccacagctt catcttcagg atcatctccg    420

aaacttcctc atccctactt tcatagtggc tccatcagtg ctcctgtcac acctcccctg    480

agctctccga cttcctaa                                                  498
```

<210> SEQ ID NO 269
<211> LENGTH: 165
<212> TYPE: PRT
<213> ORGANISM: Medicago truncatula

<400> SEQUENCE: 269

```
Met Thr Ser Gly Thr Arg Leu Pro Thr Trp Lys Glu Arg Glu Asn Asn
1               5                   10                  15

Lys Arg Arg Glu Arg Arg Arg Arg Ala Ile Ala Ala Lys Ile Phe Ser
            20                  25                  30

Gly Leu Arg Met Tyr Gly Asn Phe Arg Leu Pro Lys His Cys Asp Asn
        35                  40                  45

Asn Glu Val Leu Lys Ala Pro Cys Asn Glu Ala Gly Trp Thr Val Glu
    50                  55                  60

Pro Asp Gly Thr Thr Tyr Arg Lys Gly Cys Lys Pro Leu Glu Asn Met
65                  70                  75                  80

Asp Met Val Gly Gly Ser Ser Ala Ala Ser Pro Cys Ser Ser Tyr His
                85                  90                  95

Pro Ser Pro Gly Ser Ser Ser Phe Pro Ser Pro Ser Ser Ser Pro Tyr
            100                 105                 110

Ala Ala Asn Arg Asn Ala Asp Gly Asn Ser Leu Ile Pro Trp Leu Lys
        115                 120                 125

Asn Leu Ser Thr Ala Ser Ser Ser Gly Ser Ser Pro Lys Leu Pro His
    130                 135                 140

Pro Tyr Phe His Ser Gly Ser Ile Ser Ala Pro Val Thr Pro Pro Leu
145                 150                 155                 160

Ser Ser Pro Thr Ser
                165
```

<210> SEQ ID NO 270
<211> LENGTH: 972
<212> TYPE: DNA
<213> ORGANISM: Medicago truncatula

<400> SEQUENCE: 270

```
atgaccggcg gtggatcctc cgggagatta ccaacatgga aggagagaga aaacaacaaa     60

agaagagaga gaagaagaag agctattgct gctaagatct attcaggttt acgagctcaa    120

ggtaatttta agcttcctaa acactgtgat aataatgaag tcttgaaagc tctttgttct    180

gaagctggtt ggatcgttga agaagatggt actacttatc gaaagggaag taagagacca    240

ttaccaaatg agatgggagg aactcctaca aatatgagtg cttgttcttc aatgcaacca    300

agtccacaat cttcttcgtt cccaagtcca caatcttctt cgttcccaag tccaatacca    360

tcatacccta cgagtccaac tcgcatggat ggaattacaa acccctcttc ctttctccta    420
```

-continued

```
ccattcatcc gcaacataac ttcaatccca acaaatcttc caccccttag gatttccaac    480

agtgctcctg ttacgccacc tctttcttct ccaagaagtt caaagcgaaa agcagatttt    540

gaatcccttt gtaatggttc ctttaactcc tcgtttcgcc acccccttt cgctacctct    600

gcaccatcaa gcccctcgcg acgtaaccac ttaccccctt ccaccattcc agaatgtgat    660

gagtcagatg cttctacagt ggactctggt cggtgggtta gttttcagac aacaactgcc    720

catggtgcag ctcctccttc ccctactttt aatcttatga aaccagcaat gcagatcact    780

ccccagagtt cgatggatat gaaacatatg aatgaagcca tgcaatggag tgcaggttca    840

gctactgaga gaggtagagg ctcagatttt gactttgaga atggcagagt tgtgaagccg    900

tgggaaggtg agagaattca tgaggtagga atggaagagt tggagcttac tctagggttt    960

ggtaaggcct ga                                                        972
```

<210> SEQ ID NO 271
<211> LENGTH: 323
<212> TYPE: PRT
<213> ORGANISM: Medicago truncatula

<400> SEQUENCE: 271

```
Met Thr Gly Gly Gly Ser Ser Gly Arg Leu Pro Thr Trp Lys Glu Arg
1               5                   10                  15

Glu Asn Asn Lys Arg Arg Glu Arg Arg Arg Arg Ala Ile Ala Ala Lys
            20                  25                  30

Ile Tyr Ser Gly Leu Arg Ala Gln Gly Asn Phe Lys Leu Pro Lys His
        35                  40                  45

Cys Asp Asn Asn Glu Val Leu Lys Ala Leu Cys Ser Glu Ala Gly Trp
    50                  55                  60

Ile Val Glu Glu Asp Gly Thr Thr Tyr Arg Lys Gly Ser Lys Arg Pro
65                  70                  75                  80

Leu Pro Asn Glu Met Gly Gly Thr Pro Thr Asn Met Ser Ala Cys Ser
                85                  90                  95

Ser Met Gln Pro Ser Pro Gln Ser Ser Ser Phe Pro Ser Pro Gln Ser
            100                 105                 110

Ser Ser Phe Pro Ser Pro Ile Pro Ser Tyr Pro Thr Ser Pro Thr Arg
        115                 120                 125

Met Asp Gly Ile Thr Asn Pro Ser Ser Phe Leu Leu Pro Phe Ile Arg
    130                 135                 140

Asn Ile Thr Ser Ile Pro Thr Asn Leu Pro Pro Leu Arg Ile Ser Asn
145                 150                 155                 160

Ser Ala Pro Val Thr Pro Pro Leu Ser Ser Pro Arg Ser Ser Lys Arg
                165                 170                 175

Lys Ala Asp Phe Glu Ser Leu Cys Asn Gly Ser Phe Asn Ser Ser Phe
            180                 185                 190

Arg His Pro Leu Phe Ala Thr Ser Ala Pro Ser Ser Pro Ser Arg Arg
        195                 200                 205

Asn His Leu Pro Pro Ser Thr Ile Pro Glu Cys Asp Glu Ser Asp Ala
    210                 215                 220

Ser Thr Val Asp Ser Gly Arg Trp Val Ser Phe Gln Thr Thr Thr Ala
225                 230                 235                 240

His Gly Ala Ala Pro Pro Ser Pro Thr Phe Asn Leu Met Lys Pro Ala
                245                 250                 255

Met Gln Ile Thr Pro Gln Ser Ser Met Asp Met Lys His Met Asn Glu
            260                 265                 270
```

```
Ala Met Gln Trp Ser Ala Gly Ser Ala Thr Glu Arg Gly Arg Gly Ser
        275                 280                 285

Asp Phe Asp Phe Glu Asn Gly Arg Val Val Lys Pro Trp Glu Gly Glu
    290                 295                 300

Arg Ile His Glu Val Gly Met Glu Glu Leu Glu Leu Thr Leu Gly Phe
305                 310                 315                 320

Gly Lys Ala
```

<210> SEQ ID NO 272
<211> LENGTH: 522
<212> TYPE: DNA
<213> ORGANISM: Medicago truncatula

<400> SEQUENCE: 272

```
atggcttctg acggagcaac ttcggcggcg aattcaagtc gtcggaagcc gtcgtggagg      60

gagagagaga acaacaggag gagagagaga cggaggagag ctatagcggc aaagatttac     120

gcgggattaa ggtctcaggg gaattataat ttaccaaaac actgtgataa caatgaggtc     180

ttgaaagctc tttgtgctga agctggttgg actgttgaag aagatggcac cacttatcgc     240

aggggatcaa gggcagaaac accaggcgat ggtgcaggaa atttcaacag aaacaaccca     300

ttttcatctc aaaatctaag tcctctttca tcatcatttc caagtccaat cccttcctac     360

caagttagcc cctcttcctc ttcattcccg agcccgtctc gtatggatgc aaacaacaat     420

gcatcaaatt acattccata tgctcgcacc atgttcccca acatgtctct cccacctttg     480

agaatatcaa acagcgcgcc cgtgactcca cctgtctcat aa                        522
```

<210> SEQ ID NO 273
<211> LENGTH: 173
<212> TYPE: PRT
<213> ORGANISM: Medicago truncatula

<400> SEQUENCE: 273

```
Met Ala Ser Asp Gly Ala Thr Ser Ala Ala Asn Ser Ser Arg Arg Lys
1               5                   10                  15

Pro Ser Trp Arg Glu Arg Glu Asn Asn Arg Arg Arg Glu Arg Arg Arg
            20                  25                  30

Arg Ala Ile Ala Ala Lys Ile Tyr Ala Gly Leu Arg Ser Gln Gly Asn
        35                  40                  45

Tyr Asn Leu Pro Lys His Cys Asp Asn Asn Glu Val Leu Lys Ala Leu
    50                  55                  60

Cys Ala Glu Ala Gly Trp Thr Val Glu Glu Asp Gly Thr Thr Tyr Arg
65                  70                  75                  80

Arg Gly Ser Arg Ala Glu Thr Pro Gly Asp Gly Ala Gly Asn Phe Asn
                85                  90                  95

Arg Asn Asn Pro Phe Ser Ser Gln Asn Leu Ser Pro Leu Ser Ser Ser
            100                 105                 110

Phe Pro Ser Pro Ile Pro Ser Tyr Gln Val Ser Pro Ser Ser Ser Ser
        115                 120                 125

Phe Pro Ser Pro Ser Arg Met Asp Ala Asn Asn Asn Ala Ser Asn Tyr
    130                 135                 140

Ile Pro Tyr Ala Arg Thr Met Phe Pro Asn Met Ser Leu Pro Pro Leu
145                 150                 155                 160

Arg Ile Ser Asn Ser Ala Pro Val Thr Pro Pro Val Ser
                165                 170
```

<210> SEQ ID NO 274
<211> LENGTH: 1095
<212> TYPE: DNA
<213> ORGANISM: Oryza sativa

<400> SEQUENCE: 274

```
atggcgacgg gaggaggagg aggaggggga gggatggggg gaggaggtgt cggaggagga     60
gcgggggcgg cgggggtggg ggtgggaggg aggatgccga cgtggaggga gcgggagaac    120
aacaagcgga gggagcggcg gcgtcgcgcg atcgccgcca agatcttcgc cggcctccgc    180
gcccacggcg gctacaagct ccccaagcac tgcgacaaca acgaggtcct caaggccctc    240
tgcaacgagg ccggctgggt cgtcgagccc gacggcacca cctaccgcaa gggatacaag    300
cctcctgaac gcatggaagt gattgggtgc tccgtatcac caagcccgtg ttcctcgtat    360
caaccaagcc cgcgggcatc atacaatgcg agtcctactt cctcctcatt ccctagcggc    420
gcatcctccc ccttccttcc tcaccctaac aacatggcca atggtgttga tggtaatcct    480
atcctcccat ggcttaaaac actgtccaat tctccatcat caaagaaaca tccacagctt    540
cccccactat tgattcacgg tggttccatt agtgcccctg taactcctcc attgagttca    600
ccaactgctc gcactcctcg catgaagaca gattgggatg aatcaaatgt ccagcctacg    660
tggactggtt cgaacagtcc ctgcgtggtg aactccacgc cgcccagccc cggacgcaca    720
atgcttccgg acccagcatg gttagctggt atccaaatat catcaacaag tccatcatca    780
ccgacattta gtcttgtgtc atcaaatcca tttagtgtct ttaaagacgc gattctggtg    840
ggcaacaatt catcgaggat gtgcacgcca gggcaaagcg gcacatgctc ccctgcgatt    900
cctggcatgg caccacaccc agatattcat atgatggatg cggtttctga tgagtttgca    960
tttggaagca gcacaaacgg tggccatcag gcggctggtc tggtgagggc gtgggaaggc   1020
gagaggatcc acgaggactc gggatcggac gacctagagc tgactcttgg aagctctagg   1080
acaagagctg ctgct                                                    1095
```

<210> SEQ ID NO 275
<211> LENGTH: 365
<212> TYPE: PRT
<213> ORGANISM: Oryza sativa

<400> SEQUENCE: 275

```
Met Ala Thr Gly Gly Gly Gly Gly Gly Gly Gly Met Gly Gly Gly Gly
1               5                   10                  15

Val Gly Gly Gly Ala Gly Ala Ala Gly Val Gly Val Gly Gly Arg Met
            20                  25                  30

Pro Thr Trp Arg Glu Arg Glu Asn Asn Lys Arg Arg Glu Arg Arg Arg
        35                  40                  45

Arg Ala Ile Ala Ala Lys Ile Phe Ala Gly Leu Arg Ala His Gly Gly
    50                  55                  60

Tyr Lys Leu Pro Lys His Cys Asp Asn Asn Glu Val Leu Lys Ala Leu
65                  70                  75                  80

Cys Asn Glu Ala Gly Trp Val Val Glu Pro Asp Gly Thr Thr Tyr Arg
                85                  90                  95

Lys Gly Tyr Lys Pro Pro Glu Arg Met Glu Val Ile Gly Cys Ser Val
            100                 105                 110

Ser Pro Ser Pro Cys Ser Ser Tyr Gln Pro Ser Pro Arg Ala Ser Tyr
        115                 120                 125

Asn Ala Ser Pro Thr Ser Ser Ser Phe Pro Ser Gly Ala Ser Ser Pro
    130                 135                 140
```

```
Phe Leu Pro His Pro Asn Asn Met Ala Asn Gly Val Asp Gly Asn Pro
145                 150                 155                 160

Ile Leu Pro Trp Leu Lys Thr Leu Ser Asn Ser Pro Ser Ser Lys Lys
                165                 170                 175

His Pro Gln Leu Pro Pro Leu Leu Ile His Gly Gly Ser Ile Ser Ala
            180                 185                 190

Pro Val Thr Pro Pro Leu Ser Ser Pro Thr Ala Arg Thr Pro Arg Met
        195                 200                 205

Lys Thr Asp Trp Asp Glu Ser Asn Val Gln Pro Thr Trp Thr Gly Ser
    210                 215                 220

Asn Ser Pro Cys Val Val Asn Ser Thr Pro Pro Ser Pro Gly Arg Thr
225                 230                 235                 240

Met Leu Pro Asp Pro Ala Trp Leu Ala Gly Ile Gln Ile Ser Ser Thr
                245                 250                 255

Ser Pro Ser Ser Pro Thr Phe Ser Leu Val Ser Ser Asn Pro Phe Ser
            260                 265                 270

Val Phe Lys Asp Ala Ile Leu Val Gly Asn Asn Ser Ser Arg Met Cys
        275                 280                 285

Thr Pro Gly Gln Ser Gly Thr Cys Ser Pro Ala Ile Pro Gly Met Ala
    290                 295                 300

Pro His Pro Asp Ile His Met Met Asp Ala Val Ser Asp Glu Phe Ala
305                 310                 315                 320

Phe Gly Ser Ser Thr Asn Gly Gly His Gln Ala Ala Gly Leu Val Arg
                325                 330                 335

Ala Trp Glu Gly Glu Arg Ile His Glu Asp Ser Gly Ser Asp Asp Leu
            340                 345                 350

Glu Leu Thr Leu Gly Ser Ser Arg Thr Arg Ala Ala Ala
        355                 360                 365
```

<210> SEQ ID NO 276
<211> LENGTH: 1179
<212> TYPE: DNA
<213> ORGANISM: Oryza sativa

<400> SEQUENCE: 276

```
atgagcctga agcacccgca ctctccggtg ctggacgggg acccgccgcc gcaccgccgc      60

ccgcggggcc tcgtctccac cccaccccca cccgccgtcg cggccgacac ctccccctcc     120

ccctccccct cccccgcggc gcctccgcct cggcggcgcg gcggcggcgg agggggaggc     180

gagagggaga gggagaggga gaaggagcgg acgaagctga gggagcggca ccgccgggcc     240

atcaccagcc gcatgctgtc cgggctgcgg cagcacggca acttcccgct ccccgcccgc     300

gccgacatga acgacgtcct cgccgccctc gcgcgcgccg cagggtggac cgtgcatccc     360

gacggcacca ccttccgcgc ctcgtcgcaa cccctccacc ctcccacccc ccaatcgcca     420

gggatttttc atgttaattc tgttgaaacc ccatctttta ctagtgttct caacagctac     480

gccatcggga caccattaga ctcgcaggct tctatgctac aaacagatga tagtttatcg     540

ccatcatcgt tggactctgt tgtggtggca gaccaaagca taaaaaatga gaaatatggg     600

aattcagatt ctgtcagctc tctgaattgt ttggaaaatc accagctgac gagagcatca     660

gcagcgctgg caggtgatta caccagaact ccatatatac cagtctatgc ttctctgcct     720

atgggcatta tcaatagcca ttgccaattg attgatccag agggcatacg tgcagaactg     780

atgcatctga agtctttgaa tgttgatgga gttatcgttg actgttggtg ggggatagtg     840
```

-continued

```
gaagcctgga ttcctcacaa atacgagtgg tctggttaca gggacctttt cggtatcatt    900

aaagagttca agctaaaagt tcaggctgta ttgtcattcc atgggtctgg ggagactgga    960

tctggtggtg tgtctctccc aaagtgggtc atggaaattg cacaagagaa ccaggatgta   1020

tttttactg atcgtgaagg taggagaaat atggaatgtc tttcctgggg aattgacaaa   1080

gagcgagtcc ttcgcgggag aactggcatc gaggtattgg gtcatccttg gcgtattttg   1140

atttcatgag gagctttcat atggaattca gaaacctga                          1179
```

<210> SEQ ID NO 277
<211> LENGTH: 391
<212> TYPE: PRT
<213> ORGANISM: Oryza sativa

<400> SEQUENCE: 277

```
Met Ser Leu Lys His Pro His Ser Pro Val Leu Asp Gly Asp Pro Pro
1               5                   10                  15

Pro His Arg Arg Pro Arg Gly Leu Val Ser Thr Pro Pro Pro Pro Ala
            20                  25                  30

Val Ala Ala Asp Thr Ser Pro Ser Pro Ser Pro Ser Pro Ala Ala Pro
        35                  40                  45

Pro Pro Arg Arg Arg Gly Gly Gly Gly Gly Gly Gly Glu Arg Glu Arg
    50                  55                  60

Glu Arg Glu Lys Glu Arg Thr Lys Leu Arg Glu Arg His Arg Arg Ala
65                  70                  75                  80

Ile Thr Ser Arg Met Leu Ser Gly Leu Arg Gln His Gly Asn Phe Pro
                85                  90                  95

Leu Pro Ala Arg Ala Asp Met Asn Asp Val Leu Ala Ala Leu Ala Arg
            100                 105                 110

Ala Ala Gly Trp Thr Val His Pro Asp Gly Thr Thr Phe Arg Ala Ser
        115                 120                 125

Ser Gln Pro Leu His Pro Pro Thr Pro Gln Ser Pro Gly Ile Phe His
    130                 135                 140

Val Asn Ser Val Glu Thr Pro Ser Phe Thr Ser Val Leu Asn Ser Tyr
145                 150                 155                 160

Ala Ile Gly Thr Pro Leu Asp Ser Gln Ala Ser Met Leu Gln Thr Asp
                165                 170                 175

Asp Ser Leu Ser Pro Ser Ser Leu Asp Ser Val Val Val Ala Asp Gln
            180                 185                 190

Ser Ile Lys Asn Glu Lys Tyr Gly Asn Ser Asp Ser Val Ser Ser Leu
        195                 200                 205

Asn Cys Leu Glu Asn His Gln Leu Thr Arg Ala Ser Ala Ala Leu Ala
    210                 215                 220

Gly Asp Tyr Thr Arg Thr Pro Tyr Ile Pro Val Tyr Ala Ser Leu Pro
225                 230                 235                 240

Met Gly Ile Ile Asn Ser His Cys Gln Leu Ile Asp Pro Glu Gly Ile
                245                 250                 255

Arg Ala Glu Leu Met His Leu Lys Ser Leu Asn Val Asp Gly Val Ile
            260                 265                 270

Val Asp Cys Trp Trp Gly Ile Val Glu Ala Trp Ile Pro His Lys Tyr
        275                 280                 285

Glu Trp Ser Gly Tyr Arg Asp Leu Phe Gly Ile Ile Lys Glu Phe Lys
    290                 295                 300

Leu Lys Val Gln Ala Val Leu Ser Phe His Gly Ser Gly Glu Thr Gly
305                 310                 315                 320
```

```
Ser Gly Gly Val Ser Leu Pro Lys Trp Val Met Glu Ile Ala Gln Glu
                325                 330                 335

Asn Gln Asp Val Phe Phe Thr Asp Arg Glu Gly Arg Arg Asn Met Glu
            340                 345                 350

Cys Leu Ser Trp Gly Ile Asp Lys Glu Arg Val Leu Arg Gly Arg Thr
        355                 360                 365

Gly Ile Glu Val Leu Gly His Pro Trp Arg Ile Leu Ile Ser Gly Ala
    370                 375                 380

Phe Ile Trp Asn Ser Glu Thr
385                 390
```

```
<210> SEQ ID NO 278
<211> LENGTH: 1068
<212> TYPE: DNA
<213> ORGANISM: Oryza sativa

<400> SEQUENCE: 278

atgacgaacg gggcgggggg aggaggagga ggagggggat tggggggcac gagggtgccg      60

acgtggaggg agcgggagaa caaccggcgg agggagcggc ggcggcgggc gatcgcggcc     120

aagatctacg ccgggctgcg cgcctacggc aactacaacc tccccaagca ctgcgacaac     180

aacgaggtgc tcaaggcgct ctgcaacgag gccggctgga ccgtcgagcc cgacggcacc     240

acctaccgca agggatgtaa acctcctcaa gcagagcgtc ctgatccaat tggaagatcg     300

gcttcgccaa gcccttgctc ttcatatcaa ccaagtccgc gggcttcata caacccaagt     360

cctgcatcgt cctcctttcc aagctctgga tcctcctcgc atatcactat tggtggaaac     420

agcttgattg gtggtgtcga gggaagctcc ctcattccat ggctgaagac acttccgttg     480

agttcatcat atgcctcctc ctccaagttc ccacagcttc accatttata tttcaatgga     540

ggttccatta gtgcaccagt gactcctcca tccagctccc ctactcgcac acctcgctta     600

aggactgatt gggagaacgc aagtgttcag ccaccatggg ctagtgcaaa ttatacatct     660

cttcccaact ctacaccacc gagcccaggc cacaagattg caccagaccc agcatggctc     720

tcaggatttc aaatatcatc tgctggtccc tcatcgccaa catacaatct tgtttcgccg     780

aatccatttg ggattttcaa agaagctatt gccagcactt ccagggtgtg cacccctggt     840

cagagcggaa catgttcccc ggtaatgggt ggcatgccgg ctcatcatga tgttcagatg     900

gttgatggtg cgccggatga ttttgccttt gggagcagca gcaatggcaa caatgaatca     960

cctggactgg tgaaggcatg ggagggggag cggatacatg aagaatgcgc ctccgatgag    1020

ctggagctca ctcttgggag ctcaaagact cgtgcggatc cctcctga                 1068
```

```
<210> SEQ ID NO 279
<211> LENGTH: 355
<212> TYPE: PRT
<213> ORGANISM: Oryza sativa

<400> SEQUENCE: 279

Met Thr Asn Gly Ala Gly Gly Gly Gly Gly Gly Gly Gly Leu Gly Gly
1               5                   10                  15

Thr Arg Val Pro Thr Trp Arg Glu Arg Glu Asn Asn Arg Arg Arg Glu
            20                  25                  30

Arg Arg Arg Arg Ala Ile Ala Ala Lys Ile Tyr Ala Gly Leu Arg Ala
        35                  40                  45

Tyr Gly Asn Tyr Asn Leu Pro Lys His Cys Asp Asn Asn Glu Val Leu
    50                  55                  60
```

Lys Ala Leu Cys Asn Glu Ala Gly Trp Thr Val Glu Pro Asp Gly Thr
65 70 75 80

Thr Tyr Arg Lys Gly Cys Lys Pro Pro Gln Ala Glu Arg Pro Asp Pro
85 90 95

Ile Gly Arg Ser Ala Ser Pro Ser Pro Cys Ser Ser Tyr Gln Pro Ser
100 105 110

Pro Arg Ala Ser Tyr Asn Pro Ser Pro Ala Ser Ser Ser Phe Pro Ser
115 120 125

Ser Gly Ser Ser Ser His Ile Thr Ile Gly Gly Asn Ser Leu Ile Gly
130 135 140

Gly Val Glu Gly Ser Ser Leu Ile Pro Trp Leu Lys Thr Leu Pro Leu
145 150 155 160

Ser Ser Ser Tyr Ala Ser Ser Ser Lys Phe Pro Gln Leu His His Leu
165 170 175

Tyr Phe Asn Gly Gly Ser Ile Ser Ala Pro Val Thr Pro Pro Ser Ser
180 185 190

Ser Pro Thr Arg Thr Pro Arg Leu Arg Thr Asp Trp Glu Asn Ala Ser
195 200 205

Val Gln Pro Pro Trp Ala Ser Ala Asn Tyr Thr Ser Leu Pro Asn Ser
210 215 220

Thr Pro Pro Ser Pro Gly His Lys Ile Ala Pro Asp Pro Ala Trp Leu
225 230 235 240

Ser Gly Phe Gln Ile Ser Ser Ala Gly Pro Ser Ser Pro Thr Tyr Asn
245 250 255

Leu Val Ser Pro Asn Pro Phe Gly Ile Phe Lys Glu Ala Ile Ala Ser
260 265 270

Thr Ser Arg Val Cys Thr Pro Gly Gln Ser Gly Thr Cys Ser Pro Val
275 280 285

Met Gly Gly Met Pro Ala His His Asp Val Gln Met Val Asp Gly Ala
290 295 300

Pro Asp Asp Phe Ala Phe Gly Ser Ser Ser Asn Gly Asn Asn Glu Ser
305 310 315 320

Pro Gly Leu Val Lys Ala Trp Glu Gly Glu Arg Ile His Glu Glu Cys
325 330 335

Ala Ser Asp Glu Leu Glu Leu Thr Leu Gly Ser Ser Lys Thr Arg Ala
340 345 350

Asp Pro Ser
355

<210> SEQ ID NO 280
<211> LENGTH: 897
<212> TYPE: DNA
<213> ORGANISM: Oryza sativa

<400> SEQUENCE: 280
atgacgtccg gggcggcggc ggcggggagg acgccgacgt ggaaggagag ggagaacaac 60
aagaggcggg agcggcggcg gcgtgccatc gccgccaaga tcttcacggg gctccgggcg 120
ctcgggaact acaacctccc caagcactgc gacaacaacg aggtgctcaa ggcgctctgc 180
cgcgaggccg gctgggttgt cgaggacgac ggcaccacct accgcaaggg atgtaagccg 240
ccgccatcgt cggctggggg agcgtcggtg gggatgagcc cctgctcgtc aacgcagctg 300
ctgagcgcgc cgtcgtcgtc gttcccgagc ccggtgccgt cgtaccacgc gagcccggcg 360
tcgtcgagct tcccgagccc cagccggatc gacaacccga gcgcctcctg cctcctcccg 420
ttcctccggg ggctccccaa cctcccgccg ctccgcgtct ccagcagcgc gcccgtcacg 480
ccgccgctct cgtcgccgac ggcgtcgcgg ccgcccaaga tcaggaagcc ggactgggac 540
gtcgacccgt tccggcaccc cttcttcgcg gtctccgcgc cggcgagccc cacccgcggc 600
cgccgcctcg agcacccgga cacgataccg gagtgcgacg agtccgacgt ctccacggtg 660
gactccggcc ggtggatcag cttccagatg gccacgacgg cgccgacgtc gcccacctac 720
aacctcgtca acccgggcgc ctccacctcc aactccatgg agatagaagg gacggccggc 780
cgaggcggcg cggagttcga gttcgacaag gggagggtga cgccatggga gggcgagagg 840
atccacgagg tcgccgccga ggagctcgag ctcacgctcg gcgtcggcgc gaaatga 897

<210> SEQ ID NO 281
<211> LENGTH: 298
<212> TYPE: PRT
<213> ORGANISM: Oryza sativa

<400> SEQUENCE: 281

Met Thr Ser Gly Ala Ala Ala Ala Gly Arg Thr Pro Thr Trp Lys Glu
1 5 10 15

Arg Glu Asn Asn Lys Arg Arg Glu Arg Arg Arg Arg Ala Ile Ala Ala
20 25 30

Lys Ile Phe Thr Gly Leu Arg Ala Leu Gly Asn Tyr Asn Leu Pro Lys
35 40 45

His Cys Asp Asn Asn Glu Val Leu Lys Ala Leu Cys Arg Glu Ala Gly
50 55 60

Trp Val Val Glu Asp Asp Gly Thr Thr Tyr Arg Lys Gly Cys Lys Pro
65 70 75 80

Pro Pro Ser Ser Ala Gly Gly Ala Ser Val Gly Met Ser Pro Cys Ser
85 90 95

Ser Thr Gln Leu Leu Ser Ala Pro Ser Ser Ser Phe Pro Ser Pro Val
100 105 110

Pro Ser Tyr His Ala Ser Pro Ala Ser Ser Ser Phe Pro Ser Pro Ser
115 120 125

Arg Ile Asp Asn Pro Ser Ala Ser Cys Leu Leu Pro Phe Leu Arg Gly
130 135 140

Leu Pro Asn Leu Pro Pro Leu Arg Val Ser Ser Ser Ala Pro Val Thr
145 150 155 160

Pro Pro Leu Ser Ser Pro Thr Ala Ser Arg Pro Pro Lys Ile Arg Lys
165 170 175

Pro Asp Trp Asp Val Asp Pro Phe Arg His Pro Phe Phe Ala Val Ser
180 185 190

Ala Pro Ala Ser Pro Thr Arg Gly Arg Arg Leu Glu His Pro Asp Thr
195 200 205

Ile Pro Glu Cys Asp Glu Ser Asp Val Ser Thr Val Asp Ser Gly Arg
210 215 220

Trp Ile Ser Phe Gln Met Ala Thr Thr Ala Pro Thr Ser Pro Thr Tyr
225 230 235 240

Asn Leu Val Asn Pro Gly Ala Ser Thr Ser Asn Ser Met Glu Ile Glu
245 250 255

Gly Thr Ala Gly Arg Gly Gly Ala Glu Phe Glu Phe Asp Lys Gly Arg
260 265 270

Val Thr Pro Trp Glu Gly Glu Arg Ile His Glu Val Ala Ala Glu Glu
275 280 285

```
Leu Glu Leu Thr Leu Gly Val Gly Ala Lys
    290                 295


<210> SEQ ID NO 282
<211> LENGTH: 1071
<212> TYPE: DNA
<213> ORGANISM: Physcomitrella patens

<400> SEQUENCE: 282

atgacgtccg ggacgcgcct gcccacatgg aaggagcgag agaacaacaa gaggagagag      60

cggcgccggc gcgccattgc ggccaagatc ttcgccggcc tgcgccttta tggcaactac     120

aagctgccga agcactgcga caacaatgaa gttctcaaag cgttgtgcgt ggaggcgggc     180

tggacggtgg aagaggacgg caccacgtac cgcaagggct cgaagccacc ggcgcagccc     240

atggaggtct gcacctcccc atctgaggtg agccctacga actcctaccc gggtgccacc     300

gatggcactt ccctgattcc atggctgaag gggctgtctt ccaatggagg cagtggggca     360

gccaccccga gcagcagcgc gggtcttccg cccttgcacg taatgcatgg aggctcctct     420

agcgcacccg tcacgccacc actgagctct cccactcacc gtggtcctcc agtcaaacca     480

gattgggatc acatcaagga gactgatcac catccccacg ggtttcctcc aaccggcacg     540

cccacatgga accatcaccc tttcctggcc gcggctgccg ccgcagctca agctgctgct     600

tcaaatcagt cccatctccg ccctggctac tgcgacactc cggacggcgc tcgcactccc     660

attgaagagg gagattctga aatctctcca gaggcggctc ttgaatttgc taccgtctgt     720

ggctccaact ccagcaagtg ggccaacggg gttagggtgc ggacgagctc ggaagggcgg     780

ctgctgagcg ggatggcggg tctggggcct ttcccatcag caaatagcga ttccccccttg    840

gaaactttct cccatccctg gcggaatccg atgcagaagt ccatcagtat gcctgtttct     900

cccgtttctt ctcggatgaa gggctcattt ggggataggc tcgggaggtg tccatccgag     960

ctggagttcc ccggcgctgt gcagggattg ggtcgctgt gggatggcct ggctcctgag     1020

gttgggggga agatgaaact gccggcggac gatttggagc tgaagctttg a             1071


<210> SEQ ID NO 283
<211> LENGTH: 356
<212> TYPE: PRT
<213> ORGANISM: Physcomitrella patens

<400> SEQUENCE: 283

Met Thr Ser Gly Thr Arg Leu Pro Thr Trp Lys Glu Arg Glu Asn Asn
1               5                   10                  15

Lys Arg Arg Glu Arg Arg Arg Arg Ala Ile Ala Ala Lys Ile Phe Ala
            20                  25                  30

Gly Leu Arg Leu Tyr Gly Asn Tyr Lys Leu Pro Lys His Cys Asp Asn
        35                  40                  45

Asn Glu Val Leu Lys Ala Leu Cys Val Glu Ala Gly Trp Thr Val Glu
    50                  55                  60

Glu Asp Gly Thr Thr Tyr Arg Lys Gly Ser Lys Pro Pro Ala Gln Pro
65                  70                  75                  80

Met Glu Val Cys Thr Ser Pro Ser Glu Val Ser Pro Thr Asn Ser Tyr
                85                  90                  95

Pro Gly Ala Thr Asp Gly Thr Ser Leu Ile Pro Trp Leu Lys Gly Leu
            100                 105                 110

Ser Ser Asn Gly Gly Ser Gly Ala Ala Thr Pro Ser Ser Ser Ala Gly
        115                 120                 125
```

```
Leu Pro Pro Leu His Val Met His Gly Gly Ser Ser Ser Ala Pro Val
    130                 135                 140

Thr Pro Pro Leu Ser Ser Pro Thr His Arg Gly Pro Pro Val Lys Pro
145                 150                 155                 160

Asp Trp Asp His Ile Lys Glu Thr Asp His His Pro His Gly Phe Pro
                165                 170                 175

Pro Thr Gly Thr Pro Thr Trp Asn His His Pro Phe Leu Ala Ala Ala
            180                 185                 190

Ala Ala Ala Ala Gln Ala Ala Ala Ser Asn Gln Ser His Leu Arg Pro
        195                 200                 205

Gly Tyr Cys Asp Thr Pro Asp Gly Ala Arg Thr Pro Ile Glu Glu Gly
    210                 215                 220

Asp Ser Glu Ile Ser Pro Glu Ala Ala Leu Glu Phe Ala Thr Val Cys
225                 230                 235                 240

Gly Ser Asn Ser Ser Lys Trp Ala Asn Gly Val Arg Val Arg Thr Ser
                245                 250                 255

Ser Glu Gly Arg Leu Leu Ser Gly Met Ala Gly Leu Gly Pro Phe Pro
            260                 265                 270

Ser Ala Asn Ser Asp Ser Pro Leu Glu Thr Phe Ser His Pro Trp Arg
        275                 280                 285

Asn Pro Met Gln Lys Ser Ile Ser Met Pro Val Ser Pro Val Ser Ser
    290                 295                 300

Arg Met Lys Gly Ser Phe Gly Asp Arg Leu Gly Arg Cys Pro Ser Glu
305                 310                 315                 320

Leu Glu Phe Pro Gly Ala Val Gln Gly Leu Gly Ser Leu Trp Asp Gly
                325                 330                 335

Leu Ala Pro Glu Val Gly Gly Lys Met Lys Leu Pro Ala Asp Asp Leu
            340                 345                 350

Glu Leu Lys Leu
        355


<210> SEQ ID NO 284
<211> LENGTH: 1902
<212> TYPE: DNA
<213> ORGANISM: Physcomitrella patens

<400> SEQUENCE: 284

atggcacagg catgtgcaag ccacacccca cacattccgc atgtttccag aatgctcaga      60

atttcaagcc gatttttgca acaattccag agaggaagaa acagaagaaa aagaacagga     120

aataaaaata acaggagggt aactgcgacg acttcgtcta ctgctccttc tgcttcgtcg     180

gcttcttgtg ctgtttctgc tactgctgct ggttctggtt cttctggttc ttcttcttct     240

tcttcgcctg caacctgcag tttcgggtgt gcgtgtcgtc aatttgccgg tcaagactgt     300

ttcaaaggcg ctgctttggt gatgatggtg gagttcctcc gggagggttg ggtagatttg     360

acttgtgtca gaacgcgaaa gagagcagca ggggttttga gcgagggagg gtctggttcc     420

ttccgagtcg ctagcccgca cgcgcgagca acacctttat ttggagggtg cttcgttgtc     480

cctgagcctg tgctgtatcg cccctcttgt cttggttcga agatcggcga tatgacgtcc     540

gggacgcgct tgcccacctg gaaggaacga gagaacaaca agaggagaga gcgccgccgg     600

cgcgccattg cagctaagat cttcgccggc ctgcgtctct atggaaacta caagctgccc     660

aagcactgcg acaacaatga agtcctcaag gcgctctgcg tggaggctgg ctggactgtg     720

gaagaagacg gcaccactta ccgtaaggga tcgaagccgc ccgcgcagcc catggaagtg     780
```

```
tgcacatcac cttctgaggc gagccccact agttcctacc ccggcgcagc tgaaggcact    840

tctctgattc cgtggcttaa ggggctatct tcaaatggtg gcagtggcac cgctaccccg    900

agcagcagcg cgggcctgcc acccttgcac gtcatgcacg gtggctcctc cagcgcgccg    960

gtcacgccac ctctttcgtc ccccactcac cgcggtcctc cggtcaagcc cgactgggac   1020

cacatcaagg acgccgatca ccattcccac ggattccccc catccggccc tcccacatgg   1080

aaccatcacc ctttcttagc tgccgctgcg gctgcagctc aagctgccgc ttccaatcag   1140

tcccatctcc ggcctggcta ctgcgatacg cccgacggtg ctcgtacccc catcgaagag   1200

gccgagtccg aaatctcgcc tgggaccgct ttggagtttg ccaccgtctg tggctcgaac   1260

tccagcaaat gggctaacgg ggttagggtg cgaactagct caggggggcg gcttctcggg   1320

ggaatggcag gccttggtcc atttccttcg gctaataatg actcccccctt ggagacattc  1380

tcccatgcat ggcgaaatcc tatgcagaaa tcgattagta tgcctgtttc gcctgtttcc   1440

tcgcgaatga aggggtcatt cggagataga cttggtaggt gtccgtcaga gctggagctc   1500

tccggcgctg ttcaggggtt agggtcgctg tgggagctgg acggggtggt acctgaagtt   1560

ggtgcgaaga ggaaattgcc agccgacgat ttagagctga agctaattgc tggtggtctg   1620

gtgccgatcg ccactgaagt tgttcaggtt aaactttggg tcttccaagc ggtgcactta   1680

aaggatgtgg ggttagtgag cgttgtgtac ttcgtcggtt tacacttgct ggagccgctt   1740

catgagggcg cactctattc ctctacaacc ttaatactgc agtttaatgc ggtgaagtct   1800

gcactgtttg tttctgagag tggctccgcc tcctctaccc caaaaaatcg tgctgaagtc   1860

ttcccagtca ccagtgcgac ggagttatca aggcaactat aa                      1902


<210> SEQ ID NO 285
<211> LENGTH: 633
<212> TYPE: PRT
<213> ORGANISM: Physcomitrella patens

<400> SEQUENCE: 285

Met Ala Gln Ala Cys Ala Ser His Thr Pro His Ile Pro His Val Ser
1               5                   10                  15

Arg Met Leu Arg Ile Ser Ser Arg Phe Leu Gln Gln Phe Gln Arg Gly
            20                  25                  30

Arg Asn Arg Arg Lys Arg Thr Gly Asn Lys Asn Asn Arg Arg Val Thr
        35                  40                  45

Ala Thr Thr Ser Ser Thr Ala Pro Ser Ala Ser Ser Ala Ser Cys Ala
    50                  55                  60

Val Ser Ala Thr Ala Ala Gly Ser Gly Ser Ser Gly Ser Ser Ser Ser
65                  70                  75                  80

Ser Ser Pro Ala Thr Cys Ser Phe Gly Cys Ala Cys Arg Gln Phe Ala
                85                  90                  95

Gly Gln Asp Cys Phe Lys Gly Ala Ala Leu Val Met Met Val Glu Phe
            100                 105                 110

Leu Arg Glu Gly Trp Val Asp Leu Thr Cys Val Arg Thr Arg Lys Arg
        115                 120                 125

Ala Ala Gly Val Leu Ser Glu Gly Gly Ser Gly Ser Phe Arg Val Ala
    130                 135                 140

Ser Pro His Ala Arg Ala Thr Pro Leu Phe Gly Gly Cys Phe Val Val
145                 150                 155                 160

Pro Glu Pro Val Leu Tyr Arg Pro Ser Cys Leu Gly Ser Lys Ile Gly
                165                 170                 175
```

-continued

```
Asp Met Thr Ser Gly Thr Arg Leu Pro Thr Trp Lys Glu Arg Glu Asn
            180                 185                 190

Asn Lys Arg Arg Glu Arg Arg Arg Arg Ala Ile Ala Ala Lys Ile Phe
        195                 200                 205

Ala Gly Leu Arg Leu Tyr Gly Asn Tyr Lys Leu Pro Lys His Cys Asp
    210                 215                 220

Asn Asn Glu Val Leu Lys Ala Leu Cys Val Glu Ala Gly Trp Thr Val
225                 230                 235                 240

Glu Glu Asp Gly Thr Thr Tyr Arg Lys Gly Ser Lys Pro Pro Ala Gln
                245                 250                 255

Pro Met Glu Val Cys Thr Ser Pro Ser Glu Ala Ser Pro Thr Ser Ser
            260                 265                 270

Tyr Pro Gly Ala Ala Glu Gly Thr Ser Leu Ile Pro Trp Leu Lys Gly
        275                 280                 285

Leu Ser Ser Asn Gly Gly Ser Gly Thr Ala Thr Pro Ser Ser Ser Ala
    290                 295                 300

Gly Leu Pro Pro Leu His Val Met His Gly Gly Ser Ser Ser Ala Pro
305                 310                 315                 320

Val Thr Pro Pro Leu Ser Ser Pro Thr His Arg Gly Pro Pro Val Lys
                325                 330                 335

Pro Asp Trp Asp His Ile Lys Asp Ala Asp His His Ser His Gly Phe
            340                 345                 350

Pro Pro Ser Gly Pro Pro Thr Trp Asn His His Pro Phe Leu Ala Ala
        355                 360                 365

Ala Ala Ala Ala Ala Gln Ala Ala Ala Ser Asn Gln Ser His Leu Arg
    370                 375                 380

Pro Gly Tyr Cys Asp Thr Pro Asp Gly Ala Arg Thr Pro Ile Glu Glu
385                 390                 395                 400

Ala Glu Ser Glu Ile Ser Pro Gly Thr Ala Leu Glu Phe Ala Thr Val
                405                 410                 415

Cys Gly Ser Asn Ser Ser Lys Trp Ala Asn Gly Val Arg Val Arg Thr
            420                 425                 430

Ser Ser Gly Gly Arg Leu Leu Gly Gly Met Ala Gly Leu Gly Pro Phe
        435                 440                 445

Pro Ser Ala Asn Asn Asp Ser Pro Leu Glu Thr Phe Ser His Ala Trp
    450                 455                 460

Arg Asn Pro Met Gln Lys Ser Ile Ser Met Pro Val Ser Pro Val Ser
465                 470                 475                 480

Ser Arg Met Lys Gly Ser Phe Gly Asp Arg Leu Gly Arg Cys Pro Ser
                485                 490                 495

Glu Leu Glu Leu Ser Gly Ala Val Gln Gly Leu Gly Ser Leu Trp Glu
            500                 505                 510

Leu Asp Gly Val Val Pro Glu Val Gly Ala Lys Arg Lys Leu Pro Ala
        515                 520                 525

Asp Asp Leu Glu Leu Lys Leu Ile Ala Gly Gly Leu Val Pro Ile Ala
    530                 535                 540

Thr Glu Val Val Gln Val Lys Leu Trp Val Phe Gln Ala Val His Leu
545                 550                 555                 560

Lys Asp Val Gly Leu Val Ser Val Val Tyr Phe Val Gly Leu His Leu
                565                 570                 575

Leu Glu Pro Leu His Glu Gly Ala Leu Tyr Ser Ser Thr Thr Leu Ile
            580                 585                 590

Leu Gln Phe Asn Ala Val Lys Ser Ala Leu Phe Val Ser Glu Ser Gly
```

-continued 595 600 605

Ser Ala Ser Ser Thr Pro Lys Asn Arg Ala Glu Val Phe Pro Val Thr
610 615 620

Ser Ala Thr Glu Leu Ser Arg Gln Leu
625 630

<210> SEQ ID NO 286
<211> LENGTH: 1671
<212> TYPE: DNA
<213> ORGANISM: Physcomitrella patens

<400> SEQUENCE: 286
atgcaggtcg gcgatcggag ttttgaacaa ggtgaaagca gtgaggttcg caaatgcacc 60
gtccgaggct gcataaagtc aacctccgga ccgtggatag tacgccgtcc tccaggcaaa 120
ggtcaatcaa ctgccccagc tgtacttagg atgccctcgg cacgagagcg cgagaacaat 180
aagaggaggg agaggcggcg acgagctata gctgctaaaa tatttgctgg gttgcgcgcc 240
catgggaact attgtcttcc caaacacgcc gatcataatg aggtactcaa agccttgtgt 300
caggaggccg gctggcaagt ggaggaggat ggcaccatct tcagaaagaa cagttttcga 360
gcagtacatc ctgttattca aagaattgta gaagctaaac cgatccgtac cgttcagttg 420
atcagcctac aaatgcagca tagcatagtt cgccaattca ttaggaatca acagcaagga 480
tcgcagccac cttcaaggga agtaactaca gcgcacaata ctcctgaagg cacgccatca 540
tacgagagat ccttcaagtc agataccagt ccctcaacct cctgcagcca agctgggcaa 600
accagtgatg aacccacgtg cactgctagg agcggcggcg ccgaagtcag gcaccttggc 660
agaataagtg ttgattctca gtttgaagat aaaagacagc gctgtgaccc gctctccaac 720
ttcaaaacag tggtagcatt tccttccgct gtgcaagcaa ggaacccgaa tcctaattcc 780
agagatccga agaatagggc aggacctaaa tctgtggcag ggtttctgct tccagagcaa 840
acggtgaggt tgcaccatgt tggcaacttg aacgatccgc cagtacctgg cgcagaggat 900
attgccgaag tctgcactgc actggcggtg aagaacgaat gggaaaccac gcagggtact 960
gcaggtgtgc tgtattcagg aggacaaact gttggacaga cctatattgt gtcgtgtgca 1020
tcggaaaagg acacctctga ttgctttgag cgtgtatctg tgacggcagg acacgacagg 1080
ttttcccatg accccttgt tgcggacatg atggattgtg tggaccttgg tcaacaactc 1140
gaatgtggta gacgaaaaag gttccttgaa caccagtcca agcagctgga atacgaccag 1200
ctcaatccct acctcaacgt gcatatgaac ggagactcgt ctgtggtatc ccaagttcaa 1260
aggcaaaccc aagacccaga tccggggaag cactacacgt tattccccga agcggccgac 1320
ttgctcaacc aatcgcaacg agaacaaggg gatcaatact catgcatcac tcacgaaatg 1380
gtggatgtca ctggtcaagc atacaagtcc ctcaaggatg gtctctgctt gtggtccgga 1440
agagatggag cttccgtcag cacaggttca actcgtttga gcttgcaccc agcagcagca 1500
gcagcatcta ctacagcgag taaccgcggt ggagcttcaa tcatctctct tcaacacaaa 1560
aaggtcgacg cagacgagga tattgttaag gacatcgctg atgacctcac gctcactctg 1620
tgcacttcgg tgagacatac ccacactcca gagtccagcc gtgtggtcta a 1671

<210> SEQ ID NO 287
<211> LENGTH: 556
<212> TYPE: PRT
<213> ORGANISM: Physcomitrella patens

<400> SEQUENCE: 287

-continued

```
Met Gln Val Gly Asp Arg Ser Phe Glu Gln Gly Glu Ser Ser Glu Val
1               5                   10                  15

Arg Lys Cys Thr Val Arg Gly Cys Ile Lys Ser Thr Ser Gly Pro Trp
            20                  25                  30

Ile Val Arg Arg Pro Pro Gly Lys Gly Gln Ser Thr Ala Pro Ala Val
        35                  40                  45

Leu Arg Met Pro Ser Ala Arg Glu Arg Glu Asn Asn Lys Arg Arg Glu
    50                  55                  60

Arg Arg Arg Arg Ala Ile Ala Ala Lys Ile Phe Ala Gly Leu Arg Ala
65                  70                  75                  80

His Gly Asn Tyr Cys Leu Pro Lys His Ala Asp His Asn Glu Val Leu
                85                  90                  95

Lys Ala Leu Cys Gln Glu Ala Gly Trp Gln Val Glu Glu Asp Gly Thr
            100                 105                 110

Ile Phe Arg Lys Asn Ser Phe Arg Ala Val His Pro Val Ile Gln Arg
        115                 120                 125

Ile Val Glu Ala Lys Pro Ile Arg Thr Val Gln Leu Ile Ser Leu Gln
    130                 135                 140

Met Gln His Ser Ile Val Arg Gln Phe Ile Arg Asn Gln Gln Gln Gly
145                 150                 155                 160

Ser Gln Pro Pro Ser Arg Glu Val Thr Thr Ala His Asn Thr Pro Glu
                165                 170                 175

Gly Thr Pro Ser Tyr Glu Arg Ser Phe Lys Ser Asp Thr Ser Pro Ser
            180                 185                 190

Thr Ser Cys Ser Gln Ala Gly Gln Thr Ser Asp Glu Pro Thr Cys Thr
        195                 200                 205

Ala Arg Ser Gly Gly Ala Glu Val Arg His Leu Gly Arg Ile Ser Val
    210                 215                 220

Asp Ser Gln Phe Glu Asp Lys Arg Gln Arg Cys Asp Pro Leu Ser Asn
225                 230                 235                 240

Phe Lys Thr Val Val Ala Phe Pro Ser Ala Val Gln Ala Arg Asn Pro
                245                 250                 255

Asn Pro Asn Ser Arg Asp Pro Lys Asn Arg Ala Gly Pro Lys Ser Val
            260                 265                 270

Ala Gly Phe Leu Leu Pro Glu Gln Thr Val Arg Leu His His Val Gly
        275                 280                 285

Asn Leu Asn Asp Pro Pro Val Pro Gly Ala Glu Asp Ile Ala Glu Val
    290                 295                 300

Cys Thr Ala Leu Ala Val Lys Asn Glu Trp Glu Thr Thr Gln Gly Thr
305                 310                 315                 320

Ala Gly Val Leu Tyr Ser Gly Gly Gln Thr Val Gly Gln Thr Tyr Ile
                325                 330                 335

Val Ser Cys Ala Ser Glu Lys Asp Thr Ser Asp Cys Phe Glu Arg Val
            340                 345                 350

Ser Val Thr Ala Gly His Asp Arg Phe Ser His Asp Pro Leu Val Ala
        355                 360                 365

Asp Met Met Asp Cys Val Asp Leu Gly Gln Gln Leu Glu Cys Gly Arg
    370                 375                 380

Arg Lys Arg Phe Leu Glu His Gln Ser Lys Gln Leu Glu Tyr Asp Gln
385                 390                 395                 400

Leu Asn Pro Tyr Leu Asn Val His Met Asn Gly Asp Ser Ser Val Val
                405                 410                 415
```

```
Ser Gln Val Gln Arg Gln Thr Gln Asp Pro Asp Pro Gly Lys His Tyr
            420                 425                 430

Thr Leu Phe Pro Glu Ala Ala Asp Leu Leu Asn Gln Ser Gln Arg Glu
        435                 440                 445

Gln Gly Asp Gln Tyr Ser Cys Ile Thr His Glu Met Val Asp Val Thr
    450                 455                 460

Gly Gln Ala Tyr Lys Ser Leu Lys Asp Gly Leu Cys Leu Trp Ser Gly
465                 470                 475                 480

Arg Asp Gly Ala Ser Val Ser Thr Gly Ser Thr Arg Leu Ser Leu His
                485                 490                 495

Pro Ala Ala Ala Ala Ala Ser Thr Thr Ala Ser Asn Arg Gly Gly Ala
            500                 505                 510

Ser Ile Ile Ser Leu Gln His Lys Lys Val Asp Ala Asp Glu Asp Ile
        515                 520                 525

Val Lys Asp Ile Ala Asp Asp Leu Thr Leu Thr Leu Cys Thr Ser Val
    530                 535                 540

Arg His Thr His Thr Pro Glu Ser Ser Arg Val Val
545                 550                 555
```

<210> SEQ ID NO 288
<211> LENGTH: 1104
<212> TYPE: DNA
<213> ORGANISM: Picea sitchensis

<400> SEQUENCE: 288

```
atgacgtctg gttcgaggct gccgacctgg aaagaacggg agaataacaa gaagagagag      60

cggcgaaggc gagcgatcgc ggctaagatc tatgccgggc ttcggatgta tggaaactac     120

aagctgccga agcattgcga taacaacgag gttctcaagg ccctgtgtgc agaagccggc     180

tggatggtcg aggaagatgg aacaacttac cgcaagggat gcaagccgac ggagcgcata     240

gaggtcgcgg gatcgagttc cgttagcccg gcgtcttctt atcatccgag cccggcgcct     300

tcctaccagc ccagccctgc gtcgtcgtcg ttcgcgagcc cggcttcgtc atcgttcgag     360

cccgcgggaa ccggggcggc gaattctttg atcccgtggc tcaagaacct ctcgtcgtcg     420

tcgtcggcgt cttcttcggg ccggctgatt cacggcgggg gctcgatcag cgcgccggtg     480

actccgcctc tgagctcccc aacaggccgc ggcgcgcggg cgaagctgga ctgggacgcc     540

atggttaaag ccgttgccaa tgagagcaat gattgtccta attcggggtt ctctaccccc     600

gtgagcccct ggtcgaatta ccccttcgtg gcgtcctcca ccccggcgag cccggggcgt     660

cacgccgaga tggccacgca gttgagcaac gccgtggtgg acaaggggcg ctggatgggc     720

gggatccgga tgatggcgtt cccctcggcg gggccttcgt cgcccacgtt caatctgctg     780

accccggccg cgcagcttca gcacggcctt gcaacggagg gcggcaggct gtggacgccg     840

gggcagagtg gcgtctcgtc tccttgtaac aaccgggcag gtgaggagga gaggttattg     900

ccgccgtttc aagaaggtat ggatgcttca gacgagtttg ctttcggcag cgttgcggtc     960

aagccgtggc aaggcgagag gattcatgag gagtgcgggg gagagatagg atccgacgac    1020

ctagagctta cgctaggatc tttctcgtca tcttcttcaa agttaagatc tgaccgagaa    1080

cccttgtttt ctgttaaaga gtag                                           1104
```

<210> SEQ ID NO 289
<211> LENGTH: 367
<212> TYPE: PRT
<213> ORGANISM: Picea sitchensis

<400> SEQUENCE: 289

```
Met Thr Ser Gly Ser Arg Leu Pro Thr Trp Lys Glu Arg Glu Asn Asn
1               5                   10                  15

Lys Lys Arg Glu Arg Arg Arg Arg Ala Ile Ala Ala Lys Ile Tyr Ala
            20                  25                  30

Gly Leu Arg Met Tyr Gly Asn Tyr Lys Leu Pro Lys His Cys Asp Asn
        35                  40                  45

Asn Glu Val Leu Lys Ala Leu Cys Ala Glu Ala Gly Trp Met Val Glu
    50                  55                  60

Glu Asp Gly Thr Thr Tyr Arg Lys Gly Cys Lys Pro Thr Glu Arg Ile
65                  70                  75                  80

Glu Val Ala Gly Ser Ser Ser Val Ser Pro Ala Ser Ser Tyr His Pro
                85                  90                  95

Ser Pro Ala Pro Ser Tyr Gln Pro Ser Pro Ala Ser Ser Ser Phe Ala
            100                 105                 110

Ser Pro Ala Ser Ser Ser Phe Glu Pro Ala Gly Thr Gly Ala Ala Asn
        115                 120                 125

Ser Leu Ile Pro Trp Leu Lys Asn Leu Ser Ser Ser Ser Ser Ala Ser
    130                 135                 140

Ser Ser Gly Arg Leu Ile His Gly Gly Gly Ser Ile Ser Ala Pro Val
145                 150                 155                 160

Thr Pro Pro Leu Ser Ser Pro Thr Gly Arg Gly Ala Arg Ala Lys Leu
                165                 170                 175

Asp Trp Asp Ala Met Val Lys Ala Val Ala Asn Glu Ser Asn Asp Cys
            180                 185                 190

Pro Asn Ser Gly Phe Ser Thr Pro Val Ser Pro Trp Ser Asn Tyr Pro
        195                 200                 205

Phe Val Ala Ser Ser Thr Pro Ala Ser Pro Gly Arg His Ala Glu Met
    210                 215                 220

Ala Thr Gln Leu Ser Asn Ala Val Val Asp Lys Gly Arg Trp Met Gly
225                 230                 235                 240

Gly Ile Arg Met Met Ala Phe Pro Ser Ala Gly Pro Ser Ser Pro Thr
                245                 250                 255

Phe Asn Leu Leu Thr Pro Ala Ala Gln Leu Gln His Gly Leu Ala Thr
            260                 265                 270

Glu Gly Gly Arg Leu Trp Thr Pro Gly Gln Ser Gly Val Ser Ser Pro
        275                 280                 285

Cys Asn Asn Arg Ala Gly Glu Glu Glu Arg Leu Leu Pro Pro Phe Gln
    290                 295                 300

Glu Gly Met Asp Ala Ser Asp Glu Phe Ala Phe Gly Ser Val Ala Val
305                 310                 315                 320

Lys Pro Trp Gln Gly Glu Arg Ile His Glu Glu Cys Gly Gly Glu Ile
                325                 330                 335

Gly Ser Asp Asp Leu Glu Leu Thr Leu Gly Ser Phe Ser Ser Ser Ser
            340                 345                 350

Ser Lys Leu Arg Ser Asp Arg Glu Pro Leu Phe Ser Val Lys Glu
        355                 360                 365
```

<210> SEQ ID NO 290
<211> LENGTH: 987
<212> TYPE: DNA
<213> ORGANISM: Populus trichocarpa

<400> SEQUENCE: 290

```
atgacttcag gtacgagact accaacatgg aaagaaagag agaacaacaa gagaagagaa     60

aggagaagaa gagccattgc agcaaagata ttttctgggc taagaatgta tggcaactac    120

aagcttccaa aacattgtga caataatgaa gtccttaaag ccctctgcaa tgaggctggc    180

tggaccgtcg agcccgatgg cactactttc cgtaagggat gcaaacctgt agaacgcatg    240

gacattcttg gtgtttctgc aacaacaagt ccatgctcct cgtaccaccc tagcccttgt    300

gcttcctaca acccaagtcc tggatcctct tcctttccca gtccagcttc atcctcatac    360

gctgctaatg ccaatatgga ttgcaattcc ctcataccat ggctcaaaaa cctctcatca    420

gcatcttcat cagcttcctc ctctaagttt cctcatctct acatccatgg tggctccata    480

agtgctcctg ttactcctcc tttgagctct ccaacagctc gaaccgctcg aataaaagct    540

gactgggaag accaatctat ccgcccaggc tggggtgggc agcactactc cttcttgcca    600

tcttcaactc caccgagtcc tggccgccaa attgttcccg atccagaatg gtttaggggg    660

attcgaatac cacaaggcgg tccaacgtct cccacattca gcctagttgc ctccaaccca    720

tttggcttca aggaagaggc ttttggtggt ggtggatcca atggtggatc ccgcatgtgg    780

actccaggtc aaagtggtac atgttcacct gccattgcag ctggctctga tcatacagct    840

gatattccca tggccgagat ttcagatgag tttgcatttc gatgtaatgc aactggtcta    900

gtgaagccat gggaaggaga gaggatccat gaagaatgtg gatcagacga tctagagctt    960

acgcttggga actcaagaac caggtga                                        987
```

<210> SEQ ID NO 291
<211> LENGTH: 328
<212> TYPE: PRT
<213> ORGANISM: Populus trichocarpa

<400> SEQUENCE: 291

```
Met Thr Ser Gly Thr Arg Leu Pro Thr Trp Lys Glu Arg Glu Asn Asn
1               5                   10                  15

Lys Arg Arg Glu Arg Arg Arg Arg Ala Ile Ala Ala Lys Ile Phe Ser
            20                  25                  30

Gly Leu Arg Met Tyr Gly Asn Tyr Lys Leu Pro Lys His Cys Asp Asn
        35                  40                  45

Asn Glu Val Leu Lys Ala Leu Cys Asn Glu Ala Gly Trp Thr Val Glu
    50                  55                  60

Pro Asp Gly Thr Thr Phe Arg Lys Gly Cys Lys Pro Val Glu Arg Met
65                  70                  75                  80

Asp Ile Leu Gly Val Ser Ala Thr Thr Ser Pro Cys Ser Ser Tyr His
                85                  90                  95

Pro Ser Pro Cys Ala Ser Tyr Asn Pro Ser Pro Gly Ser Ser Ser Phe
            100                 105                 110

Pro Ser Pro Ala Ser Ser Ser Tyr Ala Ala Asn Ala Asn Met Asp Cys
        115                 120                 125

Asn Ser Leu Ile Pro Trp Leu Lys Asn Leu Ser Ser Ala Ser Ser Ser
    130                 135                 140

Ala Ser Ser Ser Lys Phe Pro His Leu Tyr Ile His Gly Gly Ser Ile
145                 150                 155                 160

Ser Ala Pro Val Thr Pro Pro Leu Ser Ser Pro Thr Ala Arg Thr Ala
                165                 170                 175

Arg Ile Lys Ala Asp Trp Glu Asp Gln Ser Ile Arg Pro Gly Trp Gly
            180                 185                 190

Gly Gln His Tyr Ser Phe Leu Pro Ser Ser Thr Pro Pro Ser Pro Gly
```

```
        195                 200                 205

Arg Gln Ile Val Pro Asp Pro Glu Trp Phe Arg Gly Ile Arg Ile Pro
    210                 215                 220

Gln Gly Gly Pro Thr Ser Pro Thr Phe Ser Leu Val Ala Ser Asn Pro
225                 230                 235                 240

Phe Gly Phe Lys Glu Glu Ala Phe Gly Gly Gly Gly Ser Asn Gly Gly
                245                 250                 255

Ser Arg Met Trp Thr Pro Gly Gln Ser Gly Thr Cys Ser Pro Ala Ile
            260                 265                 270

Ala Ala Gly Ser Asp His Thr Ala Asp Ile Pro Met Ala Glu Ile Ser
        275                 280                 285

Asp Glu Phe Ala Phe Arg Cys Asn Ala Thr Gly Leu Val Lys Pro Trp
    290                 295                 300

Glu Gly Glu Arg Ile His Glu Glu Cys Gly Ser Asp Asp Leu Glu Leu
305                 310                 315                 320

Thr Leu Gly Asn Ser Arg Thr Arg
                325


<210> SEQ ID NO 292
<211> LENGTH: 1017
<212> TYPE: DNA
<213> ORGANISM: Populus trichocarpa

<400> SEQUENCE: 292

atgacttcag gtacgagact accaacatgg aaagaaagag agaacaacaa gagaagagaa      60

aggagaagaa gagccattgc agcaaagata ttttctgggc taagaatgta tggcaactac     120

aagcttccaa aacattgtga caataatgaa gtccttaaag ccctctgcaa tgaggctggc     180

tggaccgtcg agcccgatgg cactactttc cgtaagggat gcaaacctgt agaacgcatg     240

gacattcttg gtgtttctgc aacaacaagt ccatgctcct cgtaccaccc tagcccttgt     300

gcttcctaca acccaagtcc tggatcctct tcctttccca gtccagcttc atcctcatac     360

gctgctaatg ccaatatgga ttgcaattcc ctcataccat ggctcaaaaa cctctcatca     420

gcatcttcat cagcttcctc ctctaagttt cctcatctct acatccatgg tggctccata     480

agtgctcctg ttactcctcc tttgagctct ccaacagctc gaaccgctcg aataaaagct     540

gactgggaag accaatctat ccgcccaggc tggggtgggc agcactactc cttcttgcca     600

tcttcaactc caccgagtcc tggccgccaa attgttcccg atccagaatg gtttaggggg     660

gttcgaatgc cacaaggcgg tccaacgtct cccacattta gcctagttgc ctccaaccca     720

tttggcttca aggaagaggc ttttggtggt ggtggatcca atggtggatc ccgcatgtgg     780

actccaggtc aaagtggtac atgttcacct gccattgcag ctggctctga tcatacagct     840

gatattccca tggccgagat ttcagatgag tttgcatttc gatgtaatgc tactggtcta     900

gtgaagccat gggaaggaga gaggatccat gaagaatgtg gatcagacga tctagagcta     960

acgcttggga actcaagaac cagataaaca attgcaaaaa tgaaaattcc cgagtga       1017


<210> SEQ ID NO 293
<211> LENGTH: 328
<212> TYPE: PRT
<213> ORGANISM: Populus trichocarpa

<400> SEQUENCE: 293

Met Thr Ser Gly Thr Arg Leu Pro Thr Trp Lys Glu Arg Glu Asn Asn
1               5                   10                  15
```

```
Lys Arg Arg Glu Arg Arg Arg Arg Ala Ile Ala Ala Lys Ile Phe Ser
            20                  25                  30

Gly Leu Arg Met Tyr Gly Asn Tyr Lys Leu Pro Lys His Cys Asp Asn
        35                  40                  45

Asn Glu Val Leu Lys Ala Leu Cys Asn Glu Ala Gly Trp Thr Val Glu
    50                  55                  60

Pro Asp Gly Thr Thr Phe Arg Lys Gly Cys Lys Pro Val Glu Arg Met
65                  70                  75                  80

Asp Ile Leu Gly Val Ser Ala Thr Thr Ser Pro Cys Ser Ser Tyr His
                85                  90                  95

Pro Ser Pro Cys Ala Ser Tyr Asn Pro Ser Pro Gly Ser Ser Ser Phe
            100                 105                 110

Pro Ser Pro Ala Ser Ser Ser Tyr Ala Ala Asn Ala Asn Met Asp Cys
        115                 120                 125

Asn Ser Leu Ile Pro Trp Leu Lys Asn Leu Ser Ser Ala Ser Ser Ser
    130                 135                 140

Ala Ser Ser Ser Lys Phe Pro His Leu Tyr Ile His Gly Gly Ser Ile
145                 150                 155                 160

Ser Ala Pro Val Thr Pro Pro Leu Ser Ser Pro Thr Ala Arg Thr Ala
                165                 170                 175

Arg Ile Lys Ala Asp Trp Glu Asp Gln Ser Ile Arg Pro Gly Trp Gly
            180                 185                 190

Gly Gln His Tyr Ser Phe Leu Pro Ser Ser Thr Pro Pro Ser Pro Gly
        195                 200                 205

Arg Gln Ile Val Pro Asp Pro Glu Trp Phe Arg Gly Val Arg Met Pro
    210                 215                 220

Gln Gly Gly Pro Thr Ser Pro Thr Phe Ser Leu Val Ala Ser Asn Pro
225                 230                 235                 240

Phe Gly Phe Lys Glu Glu Ala Phe Gly Gly Gly Gly Ser Asn Gly Gly
                245                 250                 255

Ser Arg Met Trp Thr Pro Gly Gln Ser Gly Thr Cys Ser Pro Ala Ile
            260                 265                 270

Ala Ala Gly Ser Asp His Thr Ala Asp Ile Pro Met Ala Glu Ile Ser
        275                 280                 285

Asp Glu Phe Ala Phe Arg Cys Asn Ala Thr Gly Leu Val Lys Pro Trp
    290                 295                 300

Glu Gly Glu Arg Ile His Glu Glu Cys Gly Ser Asp Asp Leu Glu Leu
305                 310                 315                 320

Thr Leu Gly Asn Ser Arg Thr Arg
                325
```

<210> SEQ ID NO 294
<211> LENGTH: 954
<212> TYPE: DNA
<213> ORGANISM: Populus trichocarpa

<400> SEQUENCE: 294

```
atgacgtcag atggggcaac ctcgacgtca gctgcaatgg cggcagctac aaggaggaag      60

ccatcgtgga gggagaggga gaataatagg aggagagaga ggaggaggag agctatagct     120

gcaaaaatat ttactgggtt aagggctcaa gggaattata atttgcctaa atattgtgac     180

aataatgagg tattgaaagc tctctgtgct gaggctggtt gggttgttga agaagatgga     240

actacttatc gcaagggaca caggccacct cctattgaga tagtaggtac ttcgacgagg     300

gtaaccccat actcatccca aaatcctagt ccactatctt cgttgtttcc cagtccaatt     360
```

ccttcctatc aagccagtcc ctcctcctcc tcgtttccta gccctactcg tggcgataac 420
aatgcctctt ctaatctcct tccattcctt cgaagtgcca ttccattgtc tcttcctcct 480
cttcgaatct caaacagtgc gcctgtaacc ccacctctct cgtccccgac ctcaagaaac 540
cccaagccaa ttcccaactg ggattttatt gccaaacaat ccatggcctc ctttagttac 600
ccattcaatg cagtgtctgc tccggctagc ccaactcatc gtcaatttca tgctccagcc 660
actatacctg aatgtgatga gtctgataca tccactgtgg agtctggtca gtggataagc 720
tttcaaaagt ttgcgccttc tgtggctgca gcaatgccaa cctctcctac ctataatctt 780
gtgatacccg tggctcagca aatttcgtct agcaatttgg tcaaagagag tgcagtgccc 840
atggattttg agtttggtag tgaacaggtg aaaccatggg aaggagagag gattcatgaa 900
gtaggattag atgatctaga gctcacactt ggaagtggca aggctcagag ttag 954

<210> SEQ ID NO 295
<211> LENGTH: 317
<212> TYPE: PRT
<213> ORGANISM: Populus trichocarpa

<400> SEQUENCE: 295

Met Thr Ser Asp Gly Ala Thr Ser Thr Ser Ala Ala Met Ala Ala Ala
1 5 10 15

Thr Arg Arg Lys Pro Ser Trp Arg Glu Arg Glu Asn Asn Arg Arg Arg
20 25 30

Glu Arg Arg Arg Arg Ala Ile Ala Ala Lys Ile Phe Thr Gly Leu Arg
35 40 45

Ala Gln Gly Asn Tyr Asn Leu Pro Lys Tyr Cys Asp Asn Asn Glu Val
50 55 60

Leu Lys Ala Leu Cys Ala Glu Ala Gly Trp Val Val Glu Glu Asp Gly
65 70 75 80

Thr Thr Tyr Arg Lys Gly His Arg Pro Pro Pro Ile Glu Ile Val Gly
85 90 95

Thr Ser Thr Arg Val Thr Pro Tyr Ser Ser Gln Asn Pro Ser Pro Leu
100 105 110

Ser Ser Leu Phe Pro Ser Pro Ile Pro Ser Tyr Gln Ala Ser Pro Ser
115 120 125

Ser Ser Ser Phe Pro Ser Pro Thr Arg Gly Asp Asn Asn Ala Ser Ser
130 135 140

Asn Leu Leu Pro Phe Leu Arg Ser Ala Ile Pro Leu Ser Leu Pro Pro
145 150 155 160

Leu Arg Ile Ser Asn Ser Ala Pro Val Thr Pro Pro Leu Ser Ser Pro
165 170 175

Thr Ser Arg Asn Pro Lys Pro Ile Pro Asn Trp Asp Phe Ile Ala Lys
180 185 190

Gln Ser Met Ala Ser Phe Ser Tyr Pro Phe Asn Ala Val Ser Ala Pro
195 200 205

Ala Ser Pro Thr His Arg Gln Phe His Ala Pro Ala Thr Ile Pro Glu
210 215 220

Cys Asp Glu Ser Asp Thr Ser Thr Val Glu Ser Gly Gln Trp Ile Ser
225 230 235 240

Phe Gln Lys Phe Ala Pro Ser Val Ala Ala Ala Met Pro Thr Ser Pro
245 250 255

Thr Tyr Asn Leu Val Ile Pro Val Ala Gln Gln Ile Ser Ser Ser Asn
260 265 270

```
Leu Val Lys Glu Ser Ala Val Pro Met Asp Phe Glu Phe Gly Ser Glu
        275                 280                 285

Gln Val Lys Pro Trp Glu Gly Glu Arg Ile His Glu Val Gly Leu Asp
    290                 295                 300

Asp Leu Glu Leu Thr Leu Gly Ser Gly Lys Ala Gln Ser
305                 310                 315


<210> SEQ ID NO 296
<211> LENGTH: 996
<212> TYPE: DNA
<213> ORGANISM: Populus trichocarpa

<400> SEQUENCE: 296

atgacagccg gtggatcctc agcgaggtta ccaacgtgga aagaaagaga gaataacatg      60

agaagagaaa gaaggagaag agctatagct gccaagatct atacaggact taggactcaa     120

ggaaattata agttaccaaa acattgtgat aataatgaag tcttgaaagc tctttgtgct     180

gaagctggtt ggattgtcga agaagacggt accacttatc gcaagggctg caagccacct     240

ccatctgaga ttgctggcat gccagcaaac atcagtgcat gctcctcaat tcaaccaagc     300

ccgcaatcct caaattttgc aagccctgtg ccttcctacc atgctagtcc ctcatcctcc     360

tcattcccaa gtcctacttg tttcgatgga aactcctcca cgtacctcct ccctttcctc     420

cgaaacatag cttccatccc cacaaacctc ccgcctctta gaatatccaa tagtgctcct     480

gtaaccccac cacgttcttc ccctacatgt agaagttcaa agcggaaagt tgactgggaa     540

tccctctcaa atggctccct aaactcgttt cgccatcccc tttttgcagc ttctgctcct     600

tcaagtccta cacggcgccc ccatctaaca cctgccacaa ttccagaatg tgacgagtct     660

gatgcctcta ccgtggactc tggccgctgg ttgagttttc aggcagtggc accccaagta     720

gcccctcctt caccaacatt taatcttgtt aaaccagtgg atcaacagtg tgcttttcag     780

attggagttg ataggcatga aggtttgagc tggggagtag cagcagaaag gggagaggt      840

gctgagtttg agtttgagaa ttgtagggtg aagccatggg agggtgagag gattcatgag     900

attggggtgg atgatcttga gctcacactt ggaagtggaa aggtccatgg tcaagcctcc     960

attgatgatc tagcctggga acgtagcaac aagtag                               996


<210> SEQ ID NO 297
<211> LENGTH: 331
<212> TYPE: PRT
<213> ORGANISM: Populus trichocarpa

<400> SEQUENCE: 297

Met Thr Ala Gly Gly Ser Ser Ala Arg Leu Pro Thr Trp Lys Glu Arg
1               5                   10                  15

Glu Asn Asn Met Arg Arg Glu Arg Arg Arg Arg Ala Ile Ala Ala Lys
            20                  25                  30

Ile Tyr Thr Gly Leu Arg Thr Gln Gly Asn Tyr Lys Leu Pro Lys His
        35                  40                  45

Cys Asp Asn Asn Glu Val Leu Lys Ala Leu Cys Ala Glu Ala Gly Trp
    50                  55                  60

Ile Val Glu Glu Asp Gly Thr Thr Tyr Arg Lys Gly Cys Lys Pro Pro
65                  70                  75                  80

Pro Ser Glu Ile Ala Gly Met Pro Ala Asn Ile Ser Ala Cys Ser Ser
                85                  90                  95

Ile Gln Pro Ser Pro Gln Ser Ser Asn Phe Ala Ser Pro Val Pro Ser
```

```
            100                 105                 110

Tyr His Ala Ser Pro Ser Ser Ser Ser Phe Pro Ser Pro Thr Cys Phe
        115                 120                 125

Asp Gly Asn Ser Ser Thr Tyr Leu Leu Pro Phe Leu Arg Asn Ile Ala
    130                 135                 140

Ser Ile Pro Thr Asn Leu Pro Pro Leu Arg Ile Ser Asn Ser Ala Pro
145                 150                 155                 160

Val Thr Pro Pro Arg Ser Ser Pro Thr Cys Arg Ser Ser Lys Arg Lys
                165                 170                 175

Val Asp Trp Glu Ser Leu Ser Asn Gly Ser Leu Asn Ser Phe Arg His
            180                 185                 190

Pro Leu Phe Ala Ala Ser Ala Pro Ser Ser Pro Thr Arg Arg Pro His
        195                 200                 205

Leu Thr Pro Ala Thr Ile Pro Glu Cys Asp Glu Ser Asp Ala Ser Thr
    210                 215                 220

Val Asp Ser Gly Arg Trp Leu Ser Phe Gln Ala Val Ala Pro Gln Val
225                 230                 235                 240

Ala Pro Pro Ser Pro Thr Phe Asn Leu Val Lys Pro Val Asp Gln Gln
                245                 250                 255

Cys Ala Phe Gln Ile Gly Val Asp Arg His Glu Gly Leu Ser Trp Gly
            260                 265                 270

Val Ala Ala Glu Arg Gly Arg Gly Ala Glu Phe Glu Phe Glu Asn Cys
        275                 280                 285

Arg Val Lys Pro Trp Glu Gly Glu Arg Ile His Glu Ile Gly Val Asp
    290                 295                 300

Asp Leu Glu Leu Thr Leu Gly Ser Gly Lys Val His Gly Gln Ala Ser
305                 310                 315                 320

Ile Asp Asp Leu Ala Trp Glu Arg Ser Asn Lys
                325                 330
```

<210> SEQ ID NO 298
<211> LENGTH: 954
<212> TYPE: DNA
<213> ORGANISM: Populus trichocarpa

<400> SEQUENCE: 298

```
atgacgtcag atggggccac ttctacatca gctgcagcgg cggcaactac gaggaggaag      60

ccgtcgtgga gggagagaga gaataatagg aggagagaga ggaggagaag agccatagct     120

gcaaaaatat ttactgggtt aagggctcaa gggaattata atttgcccaa atattgtgac     180

aataatgagg tgttaaaagc tctctgtgct gaggctggtt gggttgttga agaggacggg     240

actacttatc gcaagggaca caggccacct ccaatagaga tagtaggttc atcaatgaga     300

gtaaccccat actcatccca aaatccgagc ccgctatctt catcgtttcc cagcccgatt     360

ccttcctatc aagtcagtcc ctcctcctcg tcatttccta gccccactcg tggtgataac     420

aatgtctctt ctaatctcct tccattcctt caaagtgcca ttccgttgtc tcttcctcct     480

ctccgaatct caaacagtgc acctgtaacc ccacctctct cgtccccgac ctcaagaaat     540

cccaagccaa tacctaactg ggattttatt gctaaacaat ccatggcatc cttcagttac     600

cctttcaatg cagtgtctgc cccagctagc ccaactcacc gtcagtttca tgctccagcc     660

actatacctg aatgtgacga gtctgattca tccactgttg agtctggtca gtggataagc     720

tttcaaaagt ttgctccttc tgtggctgca gcaatgccca cctctcctac ctataatctt     780

gtgaaacctg tggctcggca aattttgtcc aacaatctgg tcaaagataa tggaatgtca     840
```

```
atggattttg agtttggtag cgaacaggtg aaaccatggg aaggagagag gattcatgaa    900

gtaggattag atgatctaga gctcacactt ggaggtggca aggctcggag ttag          954


<210> SEQ ID NO 299
<211> LENGTH: 317
<212> TYPE: PRT
<213> ORGANISM: Populus trichocarpa

<400> SEQUENCE: 299

Met Thr Ser Asp Gly Ala Thr Ser Thr Ser Ala Ala Ala Ala Ala Thr
1               5                   10                  15

Thr Arg Arg Lys Pro Ser Trp Arg Glu Arg Glu Asn Asn Arg Arg Arg
            20                  25                  30

Glu Arg Arg Arg Arg Ala Ile Ala Ala Lys Ile Phe Thr Gly Leu Arg
        35                  40                  45

Ala Gln Gly Asn Tyr Asn Leu Pro Lys Tyr Cys Asp Asn Asn Glu Val
    50                  55                  60

Leu Lys Ala Leu Cys Ala Glu Ala Gly Trp Val Val Glu Glu Asp Gly
65                  70                  75                  80

Thr Thr Tyr Arg Lys Gly His Arg Pro Pro Pro Ile Glu Ile Val Gly
                85                  90                  95

Ser Ser Met Arg Val Thr Pro Tyr Ser Ser Gln Asn Pro Ser Pro Leu
            100                 105                 110

Ser Ser Ser Phe Pro Ser Pro Ile Pro Ser Tyr Gln Val Ser Pro Ser
        115                 120                 125

Ser Ser Ser Phe Pro Ser Pro Thr Arg Gly Asp Asn Asn Val Ser Ser
    130                 135                 140

Asn Leu Leu Pro Phe Leu Gln Ser Ala Ile Pro Leu Ser Leu Pro Pro
145                 150                 155                 160

Leu Arg Ile Ser Asn Ser Ala Pro Val Thr Pro Pro Leu Ser Ser Pro
                165                 170                 175

Thr Ser Arg Asn Pro Lys Pro Ile Pro Asn Trp Asp Phe Ile Ala Lys
            180                 185                 190

Gln Ser Met Ala Ser Phe Ser Tyr Pro Phe Asn Ala Val Ser Ala Pro
        195                 200                 205

Ala Ser Pro Thr His Arg Gln Phe His Ala Pro Ala Thr Ile Pro Glu
    210                 215                 220

Cys Asp Glu Ser Asp Ser Ser Thr Val Glu Ser Gly Gln Trp Ile Ser
225                 230                 235                 240

Phe Gln Lys Phe Ala Pro Ser Val Ala Ala Ala Met Pro Thr Ser Pro
                245                 250                 255

Thr Tyr Asn Leu Val Lys Pro Val Ala Arg Gln Ile Leu Ser Asn Asn
            260                 265                 270

Leu Val Lys Asp Asn Gly Met Ser Met Asp Phe Glu Phe Gly Ser Glu
        275                 280                 285

Gln Val Lys Pro Trp Glu Gly Glu Arg Ile His Glu Val Gly Leu Asp
    290                 295                 300

Asp Leu Glu Leu Thr Leu Gly Gly Gly Lys Ala Arg Ser
305                 310                 315


<210> SEQ ID NO 300
<211> LENGTH: 996
<212> TYPE: DNA
<213> ORGANISM: Populus trichocarpa
```

<400> SEQUENCE: 300

```
atgacgtcgg ggacgagaat gccgacgtgg aaggagcgag agaacaataa gagaagagaa     60
aggagaagga gagcgatcgc agcgaagatc tattcaggac ttagaatgta cgggaattat    120
aagctaccaa aacactgtga caataatgaa gtgcttaaag ctctctgtaa agaagctggt    180
tggactgttg aagaggatgg cactacttat cgaaagggat gcaaacctgt ggaacgcatg    240
gatattatgg gaggttctgc atcagctagt ccatgttcat cataccatcg aagtccatgt    300
gcatcctata atccaagccc tgcctcatct tcttttccaa gtcctgtttc atcccattat    360
gctgccaacg ctaatggtaa tgctgatccc aattccctca tcccatggct caaaaacctc    420
tcctctggct catcatcagc ctctcccaag catcctcacc atctcttcat tcacactggt    480
tccataagcg ctcctgttac ccctccattg agctccccaa ctgcacgaac cccacgtacc    540
aagaatgact gggatgacgc agctgctggc caatcttgga tgggacagaa ctactcattt    600
atgccctcat ctatgccctc gtctacccca cctagtcctg gccgtcacgt cctaccagat    660
tcaggttggc tagctggtat ccaaattccc caaagtggac cctcatcacc aacatttagt    720
cttgtatcac ggaatccatt tggctttaga gaggaggctt tatcaggtgc aggatcacga    780
atgtggactc ctggacaaag tgggacatgc tctccagcaa ttccggcagg cattgatcag    840
acagctgatg tgccaatgtc ggacagtatg gcagccgagt ttgcatttgg aagcaatgca    900
gcaggattgg tgaaaccttg ggaaggagag aggatccatg aggaatgtgt ttctgatgat    960
cttgagctta cactaggaaa ctcaaatacc agatag                              996
```

<210> SEQ ID NO 301
<211> LENGTH: 331
<212> TYPE: PRT
<213> ORGANISM: Populus trichocarpa

<400> SEQUENCE: 301

```
Met Thr Ser Gly Thr Arg Met Pro Thr Trp Lys Glu Arg Glu Asn Asn
1               5                   10                  15

Lys Arg Arg Glu Arg Arg Arg Arg Ala Ile Ala Ala Lys Ile Tyr Ser
            20                  25                  30

Gly Leu Arg Met Tyr Gly Asn Tyr Lys Leu Pro Lys His Cys Asp Asn
        35                  40                  45

Asn Glu Val Leu Lys Ala Leu Cys Lys Glu Ala Gly Trp Thr Val Glu
    50                  55                  60

Glu Asp Gly Thr Thr Tyr Arg Lys Gly Cys Lys Pro Val Glu Arg Met
65                  70                  75                  80

Asp Ile Met Gly Gly Ser Ala Ser Ala Ser Pro Cys Ser Ser Tyr His
                85                  90                  95

Arg Ser Pro Cys Ala Ser Tyr Asn Pro Ser Pro Ala Ser Ser Ser Phe
            100                 105                 110

Pro Ser Pro Val Ser Ser His Tyr Ala Ala Asn Ala Asn Gly Asn Ala
        115                 120                 125

Asp Pro Asn Ser Leu Ile Pro Trp Leu Lys Asn Leu Ser Ser Gly Ser
    130                 135                 140

Ser Ser Ala Ser Pro Lys His Pro His His Leu Phe Ile His Thr Gly
145                 150                 155                 160

Ser Ile Ser Ala Pro Val Thr Pro Pro Leu Ser Ser Pro Thr Ala Arg
                165                 170                 175

Thr Pro Arg Thr Lys Asn Asp Trp Asp Asp Ala Ala Ala Gly Gln Ser
            180                 185                 190
```

Trp Met Gly Gln Asn Tyr Ser Phe Met Pro Ser Ser Met Pro Ser Ser
195 200 205

Thr Pro Pro Ser Pro Gly Arg His Val Leu Pro Asp Ser Gly Trp Leu
210 215 220

Ala Gly Ile Gln Ile Pro Gln Ser Gly Pro Ser Ser Pro Thr Phe Ser
225 230 235 240

Leu Val Ser Arg Asn Pro Phe Gly Phe Arg Glu Glu Ala Leu Ser Gly
245 250 255

Ala Gly Ser Arg Met Trp Thr Pro Gly Gln Ser Gly Thr Cys Ser Pro
260 265 270

Ala Ile Pro Ala Gly Ile Asp Gln Thr Ala Asp Val Pro Met Ser Asp
275 280 285

Ser Met Ala Ala Glu Phe Ala Phe Gly Ser Asn Ala Ala Gly Leu Val
290 295 300

Lys Pro Trp Glu Gly Glu Arg Ile His Glu Glu Cys Val Ser Asp Asp
305 310 315 320

Leu Glu Leu Thr Leu Gly Asn Ser Asn Thr Arg
325 330

<210> SEQ ID NO 302
<211> LENGTH: 954
<212> TYPE: DNA
<213> ORGANISM: Populus trichocarpa

<400> SEQUENCE: 302
atgacagccg gtggatcctc agggaggtta ccaacatgga aggaaagaga gaataacaag 60
agaagagaaa gaaggagaag agctatagct gctaagatat atacaggtct tagaactcaa 120
gggaatttta agttaccaaa acactgtgat aataatgaag tcttgaaagc actttgtgct 180
gaagctggtt ggattgttga agaagatggt accacttatc gcaagggctg caagccgcct 240
ccaactgaga ttgcaggcac tccaacaaat atcagtgcat gttcctcaat tcaaccaagt 300
ccacaatcct ccaattttcc aagccctgta gcttcctacc atgctagtcc aacatcctcc 360
tcattcccaa gcccctctcg tttcgatgga aacccctcca cttacctcct cccattcctc 420
cgaaacatag cttccatccc cacaaacctc cctcctctta gaatatccaa tagtgctcct 480
gtaaccccac cactttcttc ccctacatct agaggttcga aacggaaagc tgactgggaa 540
tccctctcaa atggcaccct taactcgctt caccatcccc ttttggcagc ttctgcccca 600
tcaagtccta cacggcgcca ccatctaacg cctgccacaa taccagaatg tgacgagtct 660
gatgcttcca ctgtggactc tggccgctgg gtgagttttc tggcaggggc accccatgta 720
gctcctccct cgccaacttt taatcttgtt aaaccagtgg cacaacagag tggttttcag 780
gatggagttg ataggcatgg tggtttaagc tgggggggcag cagcagagag ggggagaggt 840
gcggagtttg agtttgagaa ttgtagggtg aagccatggg agggcgagag gattcatgag 900
attggggtag atgatcttga gctcacactt ggaggtggaa aagctcgtgg ttaa 954

<210> SEQ ID NO 303
<211> LENGTH: 317
<212> TYPE: PRT
<213> ORGANISM: Populus trichocarpa

<400> SEQUENCE: 303

Met Thr Ala Gly Gly Ser Ser Gly Arg Leu Pro Thr Trp Lys Glu Arg
1 5 10 15

Glu Asn Asn Lys Arg Arg Glu Arg Arg Arg Arg Ala Ile Ala Ala Lys
            20                  25                  30

Ile Tyr Thr Gly Leu Arg Thr Gln Gly Asn Phe Lys Leu Pro Lys His
        35                  40                  45

Cys Asp Asn Asn Glu Val Leu Lys Ala Leu Cys Ala Glu Ala Gly Trp
    50                  55                  60

Ile Val Glu Glu Asp Gly Thr Thr Tyr Arg Lys Gly Cys Lys Pro Pro
65                  70                  75                  80

Pro Thr Glu Ile Ala Gly Thr Pro Thr Asn Ile Ser Ala Cys Ser Ser
                85                  90                  95

Ile Gln Pro Ser Pro Gln Ser Ser Asn Phe Pro Ser Pro Val Ala Ser
            100                 105                 110

Tyr His Ala Ser Pro Thr Ser Ser Ser Phe Pro Ser Pro Ser Arg Phe
        115                 120                 125

Asp Gly Asn Pro Ser Thr Tyr Leu Leu Pro Phe Leu Arg Asn Ile Ala
    130                 135                 140

Ser Ile Pro Thr Asn Leu Pro Pro Leu Arg Ile Ser Asn Ser Ala Pro
145                 150                 155                 160

Val Thr Pro Pro Leu Ser Ser Pro Thr Ser Arg Gly Ser Lys Arg Lys
                165                 170                 175

Ala Asp Trp Glu Ser Leu Ser Asn Gly Thr Leu Asn Ser Leu His His
            180                 185                 190

Pro Leu Leu Ala Ala Ser Ala Pro Ser Ser Pro Thr Arg Arg His His
        195                 200                 205

Leu Thr Pro Ala Thr Ile Pro Glu Cys Asp Glu Ser Asp Ala Ser Thr
    210                 215                 220

Val Asp Ser Gly Arg Trp Val Ser Phe Leu Ala Gly Ala Pro His Val
225                 230                 235                 240

Ala Pro Pro Ser Pro Thr Phe Asn Leu Val Lys Pro Val Ala Gln Gln
                245                 250                 255

Ser Gly Phe Gln Asp Gly Val Asp Arg His Gly Gly Leu Ser Trp Gly
            260                 265                 270

Ala Ala Ala Glu Arg Gly Arg Gly Ala Glu Phe Glu Phe Glu Asn Cys
        275                 280                 285

Arg Val Lys Pro Trp Glu Gly Glu Arg Ile His Glu Ile Gly Val Asp
    290                 295                 300

Asp Leu Glu Leu Thr Leu Gly Gly Gly Lys Ala Arg Gly
305                 310                 315

<210> SEQ ID NO 304
<211> LENGTH: 1002
<212> TYPE: DNA
<213> ORGANISM: Populus trichocarpa

<400> SEQUENCE: 304
atgacgtcgg ggacgagaat gccgacgtgg aaggagcgag agaacaacaa aagaagagaa 60
aggagaagga gagcgattgc agcgaagatc tatgcaggac ttagaatgta cgggagttat 120
aagctaccaa aacactgtga caataatgaa gtgcttaaag ctctctgcaa cgaagctggt 180
tggactgttg aagaagacgg cactacttat cgaaagggat gcaaacctgt ggaacgcatg 240
gatattatag gtgggtctgc atcagctagt ccatgttcat cttaccatca gagtccatgt 300
gcatcctata atccaagtcc tgcctcatct tcgtttccta gtcctgtttc atcccgttat 360
gctgccaatg gtaatggtaa tgttgatgct gatgccaatt ccctcatccc atggcttaga 420

```
aacctctctt ccggctcatc ctcagcctca cccaagcatc caaaccatct attcattcac    480

actggttcca taagtgctcc cgtcacccct ccattgagct cccctactgc acgaactccc    540

cgtacaagaa atgactggga cgacccagct gctgggcaat cttggatggg gcagaactac    600

tcatttctgc cctcatctat gccctcgtct acaccaccta gccctggccg tcaggttcta    660

ccagattccg gctggctagc tggtattcaa atccccccaaa gcggaccctc atcaccaaca    720

tttagtcttg tatcccggaa tccatttggc tttaaagagg aggctttatc aggtgcaggg    780

tcgcgaatgt ggactcctgg acaaagcggg acatgctctc ctgcagttcc ggcaggcatt    840

gatcagacag ctgatgtgcc aatggcagac agtatggcag ctgagtttgc atttggaagt    900

aacacagcag ggttggtgaa accatgggaa ggagagagga tccatgagga atgtgtttct    960

gatgatcttg agcttacact tggaaactct agtaccaggt aa                      1002


<210> SEQ ID NO 305
<211> LENGTH: 333
<212> TYPE: PRT
<213> ORGANISM: Populus trichocarpa

<400> SEQUENCE: 305

Met Thr Ser Gly Thr Arg Met Pro Thr Trp Lys Glu Arg Glu Asn Asn
1               5                   10                  15

Lys Arg Arg Glu Arg Arg Arg Arg Ala Ile Ala Ala Lys Ile Tyr Ala
            20                  25                  30

Gly Leu Arg Met Tyr Gly Ser Tyr Lys Leu Pro Lys His Cys Asp Asn
        35                  40                  45

Asn Glu Val Leu Lys Ala Leu Cys Asn Glu Ala Gly Trp Thr Val Glu
    50                  55                  60

Glu Asp Gly Thr Thr Tyr Arg Lys Gly Cys Lys Pro Val Glu Arg Met
65                  70                  75                  80

Asp Ile Ile Gly Gly Ser Ala Ser Ala Ser Pro Cys Ser Ser Tyr His
                85                  90                  95

Gln Ser Pro Cys Ala Ser Tyr Asn Pro Ser Pro Ala Ser Ser Ser Phe
            100                 105                 110

Pro Ser Pro Val Ser Ser Arg Tyr Ala Ala Asn Gly Asn Gly Asn Val
        115                 120                 125

Asp Ala Asp Ala Asn Ser Leu Ile Pro Trp Leu Arg Asn Leu Ser Ser
    130                 135                 140

Gly Ser Ser Ser Ala Ser Pro Lys His Pro Asn His Leu Phe Ile His
145                 150                 155                 160

Thr Gly Ser Ile Ser Ala Pro Val Thr Pro Pro Leu Ser Ser Pro Thr
                165                 170                 175

Ala Arg Thr Pro Arg Thr Arg Asn Asp Trp Asp Asp Pro Ala Ala Gly
            180                 185                 190

Gln Ser Trp Met Gly Gln Asn Tyr Ser Phe Leu Pro Ser Ser Met Pro
        195                 200                 205

Ser Ser Thr Pro Pro Ser Pro Gly Arg Gln Val Leu Pro Asp Ser Gly
    210                 215                 220

Trp Leu Ala Gly Ile Gln Ile Pro Gln Ser Gly Pro Ser Ser Pro Thr
225                 230                 235                 240

Phe Ser Leu Val Ser Arg Asn Pro Phe Gly Phe Lys Glu Glu Ala Leu
                245                 250                 255

Ser Gly Ala Gly Ser Arg Met Trp Thr Pro Gly Gln Ser Gly Thr Cys
            260                 265                 270
```

-continued

```
Ser Pro Ala Val Pro Ala Gly Ile Asp Gln Thr Ala Asp Val Pro Met
        275                 280                 285

Ala Asp Ser Met Ala Ala Glu Phe Ala Phe Gly Ser Asn Thr Ala Gly
    290                 295                 300

Leu Val Lys Pro Trp Glu Gly Glu Arg Ile His Glu Glu Cys Val Ser
305                 310                 315                 320

Asp Asp Leu Glu Leu Thr Leu Gly Asn Ser Ser Thr Arg
                325                 330


<210> SEQ ID NO 306
<211> LENGTH: 960
<212> TYPE: DNA
<213> ORGANISM: Populus trichocarpa

<400> SEQUENCE: 306

atgacttcag gtacgagact accaacatgg aaagaaagag agaacaacaa gagaagagaa      60

aggagaagaa gagccattgc agcaaagatc ttttctgggc tacgaatgta tggcaacttc     120

aagcttccaa agcactgtga caataatgaa gtccttaaag ccctctgcaa tgaggctggt     180

tgggccgtcg agcccgatgg caccacttac cgcaagggat gcaaacctgc ggagcacatg     240

gacattattg gtggttctgc tacagcaagc ccatgctcct catacctccc tagcccctgt     300

gcttcctata acccaagtcc tggatcctct tcctttccca gtccagtttc atcctcctat     360

gctgctaatg ccaatttgga tgacaattcc ctcctcccgt ggctcaaaaa cctctcatcg     420

gcttcctctt ctaagcttcc ccatctatac atccatggtg gctctataag tgctcctgtt     480

actcctccct tgagctcgcc aactgctaga accccccgaa taaaaactgg ctgggaagac     540

caaccaatcc acccaggctg gtgtgggcag cactacttgc catcttcaac tccaccaagc     600

cctggccgtc aaattgttcc tgatccagga tggtttgctg ggattcgatt gccacaaggt     660

ggtccaactt ctcccacatt cagcctggtt gcctccaacc cgtttggctt caaggaagag     720

gctttagctg gtggtgggtc ccgcatgtgg actcctggtc aaagtggtac gtgttcacct     780

gccattgcag ctggctctga ccagacagct gatattccca tggcagaggt gatctcggac     840

gagtttgcat tccgatgcaa tgcaactggg ctagtgaagc catgggaagg ggagaggatc     900

catgaagagt gtggatcaga tgatctagag cttacacttg ggaactcaag aaccaggtga     960


<210> SEQ ID NO 307
<211> LENGTH: 319
<212> TYPE: PRT
<213> ORGANISM: Populus trichocarpa

<400> SEQUENCE: 307

Met Thr Ser Gly Thr Arg Leu Pro Thr Trp Lys Glu Arg Glu Asn Asn
1               5                   10                  15

Lys Arg Arg Glu Arg Arg Arg Arg Ala Ile Ala Ala Lys Ile Phe Ser
            20                  25                  30

Gly Leu Arg Met Tyr Gly Asn Phe Lys Leu Pro Lys His Cys Asp Asn
        35                  40                  45

Asn Glu Val Leu Lys Ala Leu Cys Asn Glu Ala Gly Trp Ala Val Glu
    50                  55                  60

Pro Asp Gly Thr Thr Tyr Arg Lys Gly Cys Lys Pro Ala Glu His Met
65                  70                  75                  80

Asp Ile Ile Gly Gly Ser Ala Thr Ala Ser Pro Cys Ser Ser Tyr Leu
                85                  90                  95

Pro Ser Pro Cys Ala Ser Tyr Asn Pro Ser Pro Gly Ser Ser Ser Phe
```

-continued

```
            100                 105                 110

Pro Ser Pro Val Ser Ser Ser Tyr Ala Ala Asn Ala Asn Leu Asp Asp
        115                 120                 125

Asn Ser Leu Leu Pro Trp Leu Lys Asn Leu Ser Ser Ala Ser Ser Ser
    130                 135                 140

Lys Leu Pro His Leu Tyr Ile His Gly Gly Ser Ile Ser Ala Pro Val
145                 150                 155                 160

Thr Pro Pro Leu Ser Ser Pro Thr Ala Arg Thr Pro Arg Ile Lys Thr
                165                 170                 175

Gly Trp Glu Asp Gln Pro Ile His Pro Gly Trp Cys Gly Gln His Tyr
            180                 185                 190

Leu Pro Ser Ser Thr Pro Pro Ser Pro Gly Arg Gln Ile Val Pro Asp
        195                 200                 205

Pro Gly Trp Phe Ala Gly Ile Arg Leu Pro Gln Gly Gly Pro Thr Ser
    210                 215                 220

Pro Thr Phe Ser Leu Val Ala Ser Asn Pro Phe Gly Phe Lys Glu Glu
225                 230                 235                 240

Ala Leu Ala Gly Gly Gly Ser Arg Met Trp Thr Pro Gly Gln Ser Gly
                245                 250                 255

Thr Cys Ser Pro Ala Ile Ala Ala Gly Ser Asp Gln Thr Ala Asp Ile
            260                 265                 270

Pro Met Ala Glu Val Ile Ser Asp Glu Phe Ala Phe Arg Cys Asn Ala
        275                 280                 285

Thr Gly Leu Val Lys Pro Trp Glu Gly Glu Arg Ile His Glu Glu Cys
    290                 295                 300

Gly Ser Asp Asp Leu Glu Leu Thr Leu Gly Asn Ser Arg Thr Arg
305                 310                 315
```

<210> SEQ ID NO 308
<211> LENGTH: 1023
<212> TYPE: DNA
<213> ORGANISM: Solanum lycopersicum

<400> SEQUENCE: 308

```
atgacgtcgg gaacaaggat gccgacgtgg aaggagcggg agaataataa gaggagagaa      60

cgacggcgaa aagccattgc agctaaaata ttcgccggat taagaatgta cggtaactat     120

caacttccta aacactgcga taataatgaa gtactaaaag ccctctgcaa tgaagccgga     180

tggacagttg agcccgatgg caccacctac cgcaagggct gcaaaccaat ggagagattg     240

gactttttag gtggttcaac atcattaagt ccatgttcat cttaccagcc aagccccttc     300

acttccaaca acccaagccc tgcttcctct tcctttccta gtccagcttc gtcctcatac     360

gcagcaaacc tgaacatgga cggaaaatcc ctcatcccgt ggcttaaaaa cctctcctct     420

ggatcatcgt ccgcttcctc ctccaaactt cctaactttc acatccatac tggctccatc     480

agtgctccag tgactcctcc tttcagctca ccaactgccc ggacccctcg gattaaaaca     540

gatgctggct gggctggatt tcgttaccct taccttccat catccacacc agctagccct     600

ggtcgtcaga atttcattaa tgcagaatgt tttgctggaa taagtggacc tccttctcca     660

acatatagtc ttgtttcgcc aaatccgttt gggttcaaaa tggatggtct atcgcgtggt     720

ggatctcgaa tgtgcactcc tggacagagt ggtgcatgtt cacctgctat tgctgcagga     780

ttagatcata atgccgatgt tcccatggct gaagtgatga tctctgatga gtttgcattc     840

ggaagcaacg tggcagggat ggtgaagccg tgggaaggag agaggatcca tgaggactgt     900
```

gttccagatg atcttgagct tactcttggg agttcaaaga caagataaaa cttggaagtg 960
tgcaagcaag cagaattggc tcttattgat gtcaaggtgc gacagtcgac ggggttgtgt 1020
taa 1023

<210> SEQ ID NO 309
<211> LENGTH: 339
<212> TYPE: PRT
<213> ORGANISM: Solanum lycopersicum

<400> SEQUENCE: 309

```
Met Thr Ser Gly Thr Arg Met Pro Thr Trp Lys Glu Arg Glu Asn Asn
1               5                   10                  15

Lys Arg Arg Glu Arg Arg Arg Lys Ala Ile Ala Ala Lys Ile Phe Ala
            20                  25                  30

Gly Leu Arg Met Tyr Gly Asn Tyr Gln Leu Pro Lys His Cys Asp Asn
        35                  40                  45

Asn Glu Val Leu Lys Ala Leu Cys Asn Glu Ala Gly Trp Thr Val Glu
    50                  55                  60

Pro Asp Gly Thr Thr Tyr Arg Lys Gly Cys Lys Pro Met Glu Arg Leu
65                  70                  75                  80

Asp Phe Leu Gly Gly Ser Thr Ser Leu Ser Pro Cys Ser Ser Tyr Gln
                85                  90                  95

Pro Ser Pro Phe Thr Ser Asn Asn Pro Ser Pro Ala Ser Ser Ser Phe
            100                 105                 110

Pro Ser Pro Ala Ser Ser Ser Tyr Ala Ala Asn Leu Asn Met Asp Gly
        115                 120                 125

Lys Ser Leu Ile Pro Trp Leu Lys Asn Leu Ser Ser Gly Ser Ser Ser
    130                 135                 140

Ala Ser Ser Ser Lys Leu Pro Asn Phe His Ile His Thr Gly Ser Ile
145                 150                 155                 160

Ser Ala Pro Val Thr Pro Pro Phe Ser Ser Pro Thr Ala Arg Thr Pro
                165                 170                 175

Arg Ile Lys Thr Asp Ala Gly Trp Ala Gly Phe Arg Tyr Pro Tyr Leu
            180                 185                 190

Pro Ser Ser Thr Pro Ala Ser Pro Gly Arg Gln Asn Phe Ile Asn Ala
        195                 200                 205

Glu Cys Phe Ala Gly Ile Ser Gly Pro Pro Ser Pro Thr Tyr Ser Leu
    210                 215                 220

Val Ser Pro Asn Pro Phe Gly Phe Lys Met Asp Gly Leu Ser Arg Gly
225                 230                 235                 240

Gly Ser Arg Met Cys Thr Pro Gly Gln Ser Gly Ala Cys Ser Pro Ala
                245                 250                 255

Ile Ala Ala Gly Leu Asp His Asn Ala Asp Val Pro Met Ala Glu Val
            260                 265                 270

Met Ile Ser Asp Glu Phe Ala Phe Gly Ser Asn Val Ala Gly Met Val
        275                 280                 285

Lys Pro Trp Glu Gly Glu Arg Ile His Glu Asp Cys Val Pro Asp Asp
    290                 295                 300

Leu Glu Leu Thr Leu Gly Ser Ser Lys Thr Arg Asn Leu Glu Val Cys
305                 310                 315                 320

Lys Gln Ala Glu Leu Ala Leu Ile Asp Val Lys Val Arg Gln Ser Thr
                325                 330                 335

Gly Leu Cys
```

<210> SEQ ID NO 310
<211> LENGTH: 924
<212> TYPE: DNA
<213> ORGANISM: Vitis vinifera

<400> SEQUENCE: 310
atgacgtcag agaggacgcc gacgaggagg aaggcgtcgt ggaaggagag ggagaacaac 60
atgaggagag agaggaggag gagagccata gcggcaaaga tatatgcggg cctcagggct 120
cagggcaact atcgtcttcc aaaacactgc gataacaacg aggtcctcaa ggctctctgc 180
tccgaagctg gttggaccgt tgaagatgac ggcaccacct atcgcaaggg atgcaagcct 240 ccccccctcaa ctgagattgc aggaacttcc acaaacaaca ctccctgctc ttcccagaaa 300
ccaagcccac catcttcctc ctttccaagc gcattcgctt cctaccaacc cagtccctca 360
tcctcaaacc tgtctttcat ggatgccaat gcctctctca atctccttcc atttctctac 420
aagtctatcc cttcatctct gcctcctctc cgaatatcaa acagtgctcc tgtaacacca 480
cctatttcgt ccccaacctc cagagttccc atgcctaaac ccaactggga gtcccttgcc 540
aaagaatcca tggcctctat ccatcaccat taccccatct ttgctgcttc tgccccagca 600
agcccttctc gctgtcagta tattgctcct gccactatac ctgaatatga ggagtctgac 660
acctcaactg ttgagtcagg ccagtgggtg agtttccaga cgtttgcacg ccatcttgct 720
ccattgcccc caaccttcaa tcttatgaaa cctgtggctc agaaaatttc accagatgga 780
gcaaccaaag agaaggggat aactcccgag ttggaaattg gaagtgcaca ggtgaagccc 840
tgggaagggg agaggattca tgagataggt ttggatgatc tggagcttac actaggaagt 900
ggaaagagta ggagtaaagg ctaa 924

<210> SEQ ID NO 311
<211> LENGTH: 307
<212> TYPE: PRT
<213> ORGANISM: Vitis vinifera

<400> SEQUENCE: 311

Met Thr Ser Glu Arg Thr Pro Thr Arg Arg Lys Ala Ser Trp Lys Glu
1 5 10 15

Arg Glu Asn Asn Met Arg Arg Glu Arg Arg Arg Arg Ala Ile Ala Ala
20 25 30

Lys Ile Tyr Ala Gly Leu Arg Ala Gln Gly Asn Tyr Arg Leu Pro Lys
35 40 45

His Cys Asp Asn Asn Glu Val Leu Lys Ala Leu Cys Ser Glu Ala Gly
50 55 60

Trp Thr Val Glu Asp Asp Gly Thr Thr Tyr Arg Lys Gly Cys Lys Pro
65 70 75 80

Pro Pro Ser Thr Glu Ile Ala Gly Thr Ser Thr Asn Asn Thr Pro Cys
85 90 95

Ser Ser Gln Lys Pro Ser Pro Pro Ser Ser Ser Phe Pro Ser Ala Phe
100 105 110

Ala Ser Tyr Gln Pro Ser Pro Ser Ser Ser Asn Leu Ser Phe Met Asp
115 120 125

Ala Asn Ala Ser Leu Asn Leu Leu Pro Phe Leu Tyr Lys Ser Ile Pro
130 135 140

Ser Ser Leu Pro Pro Leu Arg Ile Ser Asn Ser Ala Pro Val Thr Pro
145 150 155 160

Pro Ile Ser Ser Pro Thr Ser Arg Val Pro Met Pro Lys Pro Asn Trp

```
                165                 170                 175

Glu Ser Leu Ala Lys Glu Ser Met Ala Ser Ile His His His Tyr Pro
            180                 185                 190

Ile Phe Ala Ala Ser Ala Pro Ala Ser Pro Ser Arg Cys Gln Tyr Ile
        195                 200                 205

Ala Pro Ala Thr Ile Pro Glu Tyr Glu Glu Ser Asp Thr Ser Thr Val
    210                 215                 220

Glu Ser Gly Gln Trp Val Ser Phe Gln Thr Phe Ala Arg His Leu Ala
225                 230                 235                 240

Pro Leu Pro Pro Thr Phe Asn Leu Met Lys Pro Val Ala Gln Lys Ile
                245                 250                 255

Ser Pro Asp Gly Ala Thr Lys Glu Lys Gly Ile Thr Pro Glu Leu Glu
            260                 265                 270

Ile Gly Ser Ala Gln Val Lys Pro Trp Glu Gly Glu Arg Ile His Glu
        275                 280                 285

Ile Gly Leu Asp Asp Leu Glu Leu Thr Leu Gly Ser Gly Lys Ser Arg
    290                 295                 300

Ser Lys Gly
305


<210> SEQ ID NO 312
<211> LENGTH: 414
<212> TYPE: DNA
<213> ORGANISM: Zea mays
<220> FEATURE:
<221> NAME/KEY: misc_feature
<222> LOCATION: (18)..(18)
<223> OTHER INFORMATION: n is a, c, g, or t

<400> SEQUENCE: 312

atgacgtcgg ggtccgcngc ggcggcggcg gtgggaggcc tcgggcggac gccgacatgg      60

aaggagcggg agaacaacaa gcgcccggag cgcccggcgga gggccatcgc cgccaagatc    120

ttcacgggcc tccgcgcgct cggcaactac aagctgccca agcactgcga caacaacgag    180

gtgctcaagg cgctgtgccg cgaggcgggg tgggtcgtcg aggacgacgg caccacctac    240

cgaaagggat gcaagccgcc gccagggatg atgagcccgt gctcgtcctc gcagctgctg    300

agcgcgccgt cctcgagctt cccgagcccg gtgccgtcct accacgccag cccggcgtcg    360

tcgagcttcc cgagcccgac gcgcctcgac cacggcagcg gcagcaacac atga           414


<210> SEQ ID NO 313
<211> LENGTH: 137
<212> TYPE: PRT
<213> ORGANISM: Zea mays

<400> SEQUENCE: 313

Met Thr Ser Gly Ser Ala Ala Ala Ala Ala Val Gly Gly Leu Gly Arg
1               5                   10                  15

Thr Pro Thr Trp Lys Glu Arg Glu Asn Asn Lys Arg Arg Glu Arg Arg
            20                  25                  30

Arg Arg Ala Ile Ala Ala Lys Ile Phe Thr Gly Leu Arg Ala Leu Gly
        35                  40                  45

Asn Tyr Lys Leu Pro Lys His Cys Asp Asn Asn Glu Val Leu Lys Ala
    50                  55                  60

Leu Cys Arg Glu Ala Gly Trp Val Val Glu Asp Asp Gly Thr Thr Tyr
65                  70                  75                  80

Arg Lys Gly Cys Lys Pro Pro Pro Gly Met Met Ser Pro Cys Ser Ser
```

```
                85                  90                  95

Ser Gln Leu Leu Ser Ala Pro Ser Ser Ser Phe Pro Ser Pro Val Pro
            100                 105                 110

Ser Tyr His Ala Ser Pro Ala Ser Ser Ser Phe Pro Ser Pro Thr Arg
        115                 120                 125

Leu Asp His Gly Ser Gly Ser Asn Thr
    130                 135


<210> SEQ ID NO 314
<211> LENGTH: 699
<212> TYPE: DNA
<213> ORGANISM: Zea mays

<400> SEQUENCE: 314

atgcagcagg cggggctggc cgatgacgac gacgaggaga tatgggtaaa ggaggaggat      60

gacgaggagg aggaggacgg gtactatatg gacccccgga gcccggccgt gtggacgccc     120

ggcggcaggg cgggagggac ctcaaaccgg cggcgcgcgc gcgaggagaa ggagcggacc     180

aagatgcggg agcggcagcg gcgcgcgatc acggggcgga tcctggcggg cctgcgccag     240

cacggcaact acaggctgcg ggcgcgcgcc gacatcaacg aggtgatcgc cgcgctcgca     300

agggaggccg gctgggttgt cctccccgac ggcaccactt tcccctcttc atcctccttc     360

gccgccgtgg ctgcacagcc gccccgcccc gtgatggtcg ccgccgcgtc gccctccgcc     420

accccgctcg cgctcccggc ctcctcggcg ctccccctcc gcggcatcgc gcccgtcgcc     480

gcgcgcccta tctcccaccg ccccgcgccc gcgttcgctc tcctgttgcc cccgcgggcc     540

gccgcggcct cgcgatcccc ggccgacgac gttcccgacg ggaattcctc gcacctcctc     600

gccgtccccg tccctgtccc catggacccc gccgccgctg aagacgtccc cgttgccaag     660

cagctgcagg tgcccgatgt gtcgccgcgc ccgccctga                             699


<210> SEQ ID NO 315
<211> LENGTH: 232
<212> TYPE: PRT
<213> ORGANISM: Zea mays

<400> SEQUENCE: 315

Met Gln Gln Ala Gly Leu Ala Asp Asp Asp Asp Glu Glu Ile Trp Val
1               5                   10                  15

Lys Glu Glu Asp Asp Glu Glu Glu Glu Asp Gly Tyr Tyr Met Asp Pro
            20                  25                  30

Arg Ser Pro Ala Val Trp Thr Pro Gly Gly Arg Ala Gly Gly Thr Ser
        35                  40                  45

Asn Arg Arg Arg Ala Arg Glu Glu Lys Glu Arg Thr Lys Met Arg Glu
    50                  55                  60

Arg Gln Arg Arg Ala Ile Thr Gly Arg Ile Leu Ala Gly Leu Arg Gln
65                  70                  75                  80

His Gly Asn Tyr Arg Leu Arg Ala Arg Ala Asp Ile Asn Glu Val Ile
                85                  90                  95

Ala Ala Leu Ala Arg Glu Ala Gly Trp Val Val Leu Pro Asp Gly Thr
            100                 105                 110

Thr Phe Pro Ser Ser Ser Ser Phe Ala Ala Val Ala Ala Gln Pro Pro
        115                 120                 125

Arg Pro Val Met Val Ala Ala Ala Ser Pro Ser Ala Thr Pro Leu Ala
    130                 135                 140

Leu Pro Ala Ser Ser Ala Leu Pro Leu Arg Gly Ile Ala Pro Val Ala
```

```
145                 150                 155                 160

Ala Arg Pro Ile Ser His Arg Pro Ala Pro Ala Phe Ala Leu Leu Leu
                165                 170                 175

Pro Pro Arg Ala Ala Ala Ala Ser Arg Ser Pro Ala Asp Asp Val Pro
            180                 185                 190

Asp Gly Asn Ser Ser His Leu Leu Ala Val Pro Val Pro Val Pro Met
        195                 200                 205

Asp Pro Ala Ala Ala Glu Asp Val Pro Val Ala Lys Gln Leu Gln Val
    210                 215                 220

Pro Asp Val Ser Pro Arg Pro Pro
225                 230
```

<210> SEQ ID NO 316
<211> LENGTH: 1068
<212> TYPE: DNA
<213> ORGANISM: Zea mays

<400> SEQUENCE: 316

```
atgacgagcg gcgccggggg agccgcggcc gggatcgggg gcaccagggt gcccacgtgg     60

agggagcgcg agaacaaccg ccgcagggag cgccggcgcc gcgcgatcgc cgccaagatc    120

ttcgccggcc tcagggccta cggcaactac aacctgccca agcactgcga caacaacgag    180

gtgctcaagg cgctctgcaa cgaggccggc tggaccgtcg agcccgacgg caccacctac    240

cgcaagggat gtaaacctct ggcaacagag cgtccagatc caattgggag gtctgcatca    300

ccaagcccct gctcttcata tcaaccaagt ccgcgagcct catacaaccc aagcgcggca    360

tcctcctcgt tcccaagctc tggtcctcc tcccacatta ctcttggcgg gagcaacttc    420

atgggaggcg tcgagggcag ctcccttatc ccgtggctaa agaacctctc gtcgagctcc    480

tcgttcgcct cctcctccaa gttcccgcag cttcaccacc tctacttcaa cggcggttcc    540

atcagcgcgc cggtgacgcc tccatccagc tctccaaccc gcacgcctcg catcaagact    600

gactgggaga acccgagtgt tcagccaccg tgggctgggg cgaactacgc gtctcttccc    660

aactcccagc cgccgagccc tgggcaccag gttgctccgg acccggcgtg gctagccggg    720

ttccagattt cgtctgctgg cccttcgtct ccaacttaca gccttgtggc tccgaatccg    780

tttggtatct tcaaggagac catcgtcagc acctcaagaa tgtgcacccc tgggcagagt    840

ggaacgtgct ctcctgtaat gggcggtgcg ccgatccatc acgatgtcca gatggctgat    900

ggtgccccag atgacttcgc cttcgggagc agcagcaacg gcaacaacga gtcgcctggt    960

ctcgtgaagg catgggaggg ggaacggata cacgaggagt gcgcctcgga cgagcatgag   1020

ctggagctca cccttgggag ctcaaagact cgtgcagatc cttcctga                1068
```

<210> SEQ ID NO 317
<211> LENGTH: 355
<212> TYPE: PRT
<213> ORGANISM: Zea mays

<400> SEQUENCE: 317

```
Met Thr Ser Gly Ala Gly Gly Ala Ala Ala Gly Ile Gly Gly Thr Arg
1               5                   10                  15

Val Pro Thr Trp Arg Glu Arg Glu Asn Asn Arg Arg Arg Glu Arg Arg
            20                  25                  30

Arg Arg Ala Ile Ala Ala Lys Ile Phe Ala Gly Leu Arg Ala Tyr Gly
        35                  40                  45

Asn Tyr Asn Leu Pro Lys His Cys Asp Asn Asn Glu Val Leu Lys Ala
```

-continued 50 55 60

Leu Cys Asn Glu Ala Gly Trp Thr Val Glu Pro Asp Gly Thr Thr Tyr
65 70 75 80

Arg Lys Gly Cys Lys Pro Leu Ala Thr Glu Arg Pro Asp Pro Ile Gly
85 90 95

Arg Ser Ala Ser Pro Ser Pro Cys Ser Ser Tyr Gln Pro Ser Pro Arg
100 105 110

Ala Ser Tyr Asn Pro Ser Ala Ala Ser Ser Ser Phe Pro Ser Ser Gly
115 120 125

Ser Ser Ser His Ile Thr Leu Gly Gly Ser Asn Phe Met Gly Gly Val
130 135 140

Glu Gly Ser Ser Leu Ile Pro Trp Leu Lys Asn Leu Ser Ser Ser Ser
145 150 155 160

Ser Phe Ala Ser Ser Ser Lys Phe Pro Gln Leu His His Leu Tyr Phe
165 170 175

Asn Gly Gly Ser Ile Ser Ala Pro Val Thr Pro Pro Ser Ser Ser Pro
180 185 190

Thr Arg Thr Pro Arg Ile Lys Thr Asp Trp Glu Asn Pro Ser Val Gln
195 200 205

Pro Pro Trp Ala Gly Ala Asn Tyr Ala Ser Leu Pro Asn Ser Gln Pro
210 215 220

Pro Ser Pro Gly His Gln Val Ala Pro Asp Pro Ala Trp Leu Ala Gly
225 230 235 240

Phe Gln Ile Ser Ser Ala Gly Pro Ser Ser Pro Thr Tyr Ser Leu Val
245 250 255

Ala Pro Asn Pro Phe Gly Ile Phe Lys Glu Thr Ile Val Ser Thr Ser
260 265 270

Arg Met Cys Thr Pro Gly Gln Ser Gly Thr Cys Ser Pro Val Met Gly
275 280 285

Gly Ala Pro Ile His His Asp Val Gln Met Ala Asp Gly Ala Pro Asp
290 295 300

Asp Phe Ala Phe Gly Ser Ser Ser Asn Gly Asn Asn Glu Ser Pro Gly
305 310 315 320

Leu Val Lys Ala Trp Glu Gly Glu Arg Ile His Glu Glu Cys Ala Ser
325 330 335

Asp Glu His Glu Leu Glu Leu Thr Leu Gly Ser Ser Lys Thr Arg Ala
340 345 350

Asp Pro Ser
355

<210> SEQ ID NO 318
<211> LENGTH: 1038
<212> TYPE: DNA
<213> ORGANISM: Zea mays

<400> SEQUENCE: 318
atggcgagcg gcggcggcgg gggcctgggt gcggctggcg cgggaggccg gatgcccacg 60
tggagggagc gcgagaacaa caagcgccgg gagcgccgcc gccgcgcgat cgccgccaag 120
atcttcgccg gcctccgcgc gcacggcggc tacaagctgc ccaagcactg cgacaacaac 180
gaggtgctca aggcgctctg caacgaggcc ggctgggtcg tcgagcccga cggcaccacc 240
taccgccagg gaagcaagcc catggaacgc atggatccca tcggttgctc cgtgtcacca 300
agcccatgtt cctcgtacca accaagtccg cgggcgtcat acaatgcaag ccctacctcg 360

```
tcctcattcc ccagcggcgc atcctccccc ttcctccctc ccaacgaaat gcccaacggt    420

atcgacggca atccaatcct accatggctc aagacattct ccaacggcac tccatcaaag    480

aaacacccgc tcctcccacc gctgctgatc cacggcggct caatcagcgc tccggtaacc    540

cctcctctaa gctcgccgtc tgcccggacg ccccggatga agacggactg ggacgaagcg    600

gccgtccagc ctccatggca cggtgcaagc agccccacaa tagtgaactc cacgccgccc    660

agccccggcc ggcccatcgc gcctgacccg gcatggcttg ccggcatcca gatctcgtcc    720

accagtccaa actccccgac cttcagcctc gtctccacca acccgttcgg cgtcttcaag    780

gagtccatcc cggtcggcgg cggcgactcg tcgatgagga tgtgcacgcc ggggcagagc    840

ggcgcctgct cccccgcgat cccgggcatg ccacggcact cggacgtcca catgatggat    900

gtggtctcgg acgagttcgc gttcgggagc agcaccaacg gcgcgcagca ggccgccggg    960

ctggtgaggg cctgggaggg cgagcggatc cacgaggact ctgggtccga cgacctggag   1020

ctgaccctga agctctag                                                 1038
```

<210> SEQ ID NO 319
<211> LENGTH: 345
<212> TYPE: PRT
<213> ORGANISM: Zea mays

<400> SEQUENCE: 319

```
Met Ala Ser Gly Gly Gly Gly Gly Leu Gly Ala Ala Gly Ala Gly Gly
1               5                   10                  15

Arg Met Pro Thr Trp Arg Glu Arg Glu Asn Asn Lys Arg Arg Glu Arg
            20                  25                  30

Arg Arg Arg Ala Ile Ala Ala Lys Ile Phe Ala Gly Leu Arg Ala His
        35                  40                  45

Gly Gly Tyr Lys Leu Pro Lys His Cys Asp Asn Asn Glu Val Leu Lys
    50                  55                  60

Ala Leu Cys Asn Glu Ala Gly Trp Val Val Glu Pro Asp Gly Thr Thr
65                  70                  75                  80

Tyr Arg Gln Gly Ser Lys Pro Met Glu Arg Met Asp Pro Ile Gly Cys
                85                  90                  95

Ser Val Ser Pro Ser Pro Cys Ser Ser Tyr Gln Pro Ser Pro Arg Ala
            100                 105                 110

Ser Tyr Asn Ala Ser Pro Thr Ser Ser Ser Phe Pro Ser Gly Ala Ser
        115                 120                 125

Ser Pro Phe Leu Pro Pro Asn Glu Met Pro Asn Gly Ile Asp Gly Asn
    130                 135                 140

Pro Ile Leu Pro Trp Leu Lys Thr Phe Ser Asn Gly Thr Pro Ser Lys
145                 150                 155                 160

Lys His Pro Leu Leu Pro Pro Leu Leu Ile His Gly Gly Ser Ile Ser
                165                 170                 175

Ala Pro Val Thr Pro Pro Leu Ser Ser Pro Ser Ala Arg Thr Pro Arg
            180                 185                 190

Met Lys Thr Asp Trp Asp Glu Ala Ala Val Gln Pro Pro Trp His Gly
        195                 200                 205

Ala Ser Ser Pro Thr Ile Val Asn Ser Thr Pro Pro Ser Pro Gly Arg
    210                 215                 220

Pro Ile Ala Pro Asp Pro Ala Trp Leu Ala Gly Ile Gln Ile Ser Ser
225                 230                 235                 240

Thr Ser Pro Asn Ser Pro Thr Phe Ser Leu Val Ser Thr Asn Pro Phe
                245                 250                 255
```

```
Gly Val Phe Lys Glu Ser Ile Pro Val Gly Gly Gly Asp Ser Ser Met
            260                 265                 270

Arg Met Cys Thr Pro Gly Gln Ser Gly Ala Cys Ser Pro Ala Ile Pro
        275                 280                 285

Gly Met Pro Arg His Ser Asp Val His Met Met Asp Val Val Ser Asp
    290                 295                 300

Glu Phe Ala Phe Gly Ser Ser Thr Asn Gly Ala Gln Gln Ala Ala Gly
305                 310                 315                 320

Leu Val Arg Ala Trp Glu Gly Glu Arg Ile His Glu Asp Ser Gly Ser
                325                 330                 335

Asp Asp Leu Glu Leu Thr Leu Lys Leu
            340                 345


<210> SEQ ID NO 320
<211> LENGTH: 53
<212> TYPE: DNA
<213> ORGANISM: Artificial sequence
<220> FEATURE:
<223> OTHER INFORMATION: primer 1

<400> SEQUENCE: 320

ggggacaagt ttgtacaaaa aagcaggctt aaacaatgac ggcatcagga gga           53


<210> SEQ ID NO 321
<211> LENGTH: 50
<212> TYPE: DNA
<213> ORGANISM: Artificial sequence
<220> FEATURE:
<223> OTHER INFORMATION: primer 2

<400> SEQUENCE: 321

ggggaccact ttgtacaaga aagctgggta ccacgatatt aacctagccg                50


<210> SEQ ID NO 322
<211> LENGTH: 2194
<212> TYPE: DNA
<213> ORGANISM: Oryza sativa

<400> SEQUENCE: 322

aatccgaaaa gtttctgcac cgttttcacc ccctaactaa caatataggg aacgtgtgct     60

aaatataaaa tgagacctta tatatgtagc gctgataact agaactatgc aagaaaaact    120

catccaccta ctttagtggc aatcgggcta aataaaaaag agtcgctaca ctagtttcgt    180

tttccttagt aattaagtgg gaaaatgaaa tcattattgc ttagaatata cgttcacatc    240

tctgtcatga agttaaatta ttcgaggtag ccataattgt catcaaactc ttcttgaata    300

aaaaaatctt tctagctgaa ctcaatgggt aaagagagag attttttta aaaaaataga    360

atgaagatat tctgaacgta ttggcaaaga tttaaacata taattatata attttatagt    420

ttgtgcattc gtcatatcgc acatcattaa ggacatgtct tactccatcc caatttttat    480

ttagtaatta aagacaattg acttattttt attatttatc ttttttcgat tagatgcaag    540

gtacttacgc acacactttg tgctcatgtg catgtgtgag tgcacctcct caatacacgt    600

tcaactagca acacatctct aatatcactc gcctatttaa tacatttagg tagcaatatc    660

tgaattcaag cactccacca tcaccagacc acttttaata atatctaaaa tacaaaaaat    720

aattttacag aatagcatga aaagtatgaa acgaactatt taggtttttc acatacaaaa    780

aaaaaaagaa ttttgctcgt gcgcgagcgc caatctccca tattgggcac acaggcaaca    840
```

```
acagagtggc tgcccacaga acaacccaca aaaaacgatg atctaacgga ggacagcaag    900

tccgcaacaa ccttttaaca gcaggctttg cggccaggag agaggaggag aggcaaagaa    960

aaccaagcat cctccttctc ccatctataa attcctcccc ccttttcccc tctctatata   1020

ggaggcatcc aagccaagaa gagggagagc accaaggaca cgcgactagc agaagccgag   1080

cgaccgcctt ctcgatccat atcttccggt cgagttcttg gtcgatctct tccctcctcc   1140

acctcctcct cacagggtat gtgcctccct tcggttgttc ttggatttat tgttctaggt   1200

tgtgtagtac gggcgttgat gttaggaaag gggatctgta tctgtgatga ttcctgttct   1260

tggatttggg atagaggggt tcttgatgtt gcatgttatc ggttcggttt gattagtagt   1320

atggttttca atcgtctgga gagctctatg gaaatgaaat ggtttaggga tcggaatctt   1380

gcgattttgt gagtaccttt tgtttgaggt aaaatcagag caccggtgat tttgcttggt   1440

gtaataaagt acggttgttt ggtcctcgat tctggtagtg atgcttctcg atttgacgaa   1500

gctatccttt gtttattccc tattgaacaa aaataatcca actttgaaga cggtcccgtt   1560

gatgagattg aatgattgat tcttaagcct gtccaaaatt tcgcagctgg cttgtttaga   1620

tacagtagtc cccatcacga aattcatgga aacagttata atcctcagga acaggggatt   1680

ccctgttctt ccgatttgct ttagtcccag aatttttttt cccaaatatc ttaaaaagtc   1740

actttctggt tcagttcaat gaattgattg ctacaaataa tgcttttata gcgttatcct   1800

agctgtagtt cagttaatag gtaatacccc tatagtttag tcaggagaag aacttatccg   1860

atttctgatc tccattttta attatatgaa atgaactgta gcataagcag tattcatttg   1920

gattattttt tttattagct ctcacccctt cattattctg agctgaaagt ctggcatgaa   1980

ctgtcctcaa ttttgttttc aaattcacat cgattatcta tgcattatcc tcttgtatct   2040

acctgtagaa gtttcttttt ggttattcct tgactgcttg attacagaaa gaaatttatg   2100

aagctgtaat cgggatagtt atactgcttg ttcttatgat tcatttcctt tgtgcagttc   2160

ttggtgtagc ttgccacttt caccagcaaa gttc                               2194
```

<210> SEQ ID NO 323
<211> LENGTH: 11
<212> TYPE: PRT
<213> ORGANISM: Artificial sequence
<220> FEATURE:
<223> OTHER INFORMATION: motif 16

<400> SEQUENCE: 323

```
Ser Ala Pro Val Thr Pro Pro Leu Ser Ser Pro
1               5                   10
```

<210> SEQ ID NO 324
<211> LENGTH: 11
<212> TYPE: PRT
<213> ORGANISM: Artificial sequence
<220> FEATURE:
<223> OTHER INFORMATION: motif 17

<400> SEQUENCE: 324

```
Val Lys Pro Trp Glu Gly Glu Arg Ile His Glu
1               5                   10
```

<210> SEQ ID NO 325
<211> LENGTH: 7
<212> TYPE: PRT
<213> ORGANISM: Artificial sequence
<220> FEATURE:
<223> OTHER INFORMATION: motif 18

-continued

```
<400> SEQUENCE: 325

Asp Leu Glu Leu Thr Leu Gly
1               5


<210> SEQ ID NO 326
<211> LENGTH: 50
<212> TYPE: PRT
<213> ORGANISM: Artificial sequence
<220> FEATURE:
<223> OTHER INFORMATION: BHLH-like domain

<400> SEQUENCE: 326

Arg Glu Arg Arg Arg Arg Ala Ile Ala Ala Lys Ile Phe Thr Gly Leu
1               5                   10                  15

Arg Ser Gln Gly Asn Tyr Lys Leu Pro Lys His Cys Asp Asn Asn Glu
            20                  25                  30

Val Leu Lys Ala Leu Cys Leu Glu Ala Gly Trp Ile Val His Glu Asp
        35                  40                  45

Gly Thr
    50


<210> SEQ ID NO 327
<211> LENGTH: 8
<212> TYPE: PRT
<213> ORGANISM: Artificial sequence
<220> FEATURE:
<223> OTHER INFORMATION: DNA binding element BRRE
<220> FEATURE:
<221> NAME/KEY: VARIANT
<222> LOCATION: (7)..(7)
<223> OTHER INFORMATION: /replace = "Cys"

<400> SEQUENCE: 327

Cys Gly Thr Gly Cys Thr Thr Gly
1               5


<210> SEQ ID NO 328
<211> LENGTH: 6
<212> TYPE: PRT
<213> ORGANISM: Artificial sequence
<220> FEATURE:
<223> OTHER INFORMATION: E-box

<400> SEQUENCE: 328

Cys Ala Asn Asn Thr Cys
1               5
```

PLANTS HAVING ENHANCED YIELD-RELATED TRAITS AND A METHOD FOR MAKING THE SAME

RELATED APPLICATIONS

This application is a national stage application (under 35 U.S.C. §371) of PCT/EP2009/057722, filed Jun. 22, 2009, which claims benefit of European application 08159089.5, filed Jun. 26, 2008; U.S. Provisional Application 61/075,909, filed Jun. 26, 2008; European Application 08159099.4, filed Jun. 26, 2008; European Application 08159093.7, filed Jun. 26, 2008; U.S. Provisional Application 61/076,178, filed Jun. 27, 2008; U.S. Provisional Application 61/076,158, filed Jun. 27, 2008; European Application 08159746.0, filed Jul. 4, 2008 and U.S. Provisional Application 61/078,471 filed on Jul. 7, 2008.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing__13987__00135. The size of the text file is 458 KB, and the text file was created on Dec. 17, 2010.

The present invention relates generally to the field of molecular biology and concerns a method for enhancing various plant yield-related traits by modulating expression in a plant of a nucleic acid encoding a RHL1 (Root Hairless 1). The present invention also concerns plants having modulated expression of a nucleic acid encoding a RHL1, which plants have enhanced various plant yield-related relative to corresponding wild type plants or other control plants. The invention also provides constructs useful in the methods of the invention.

The present invention relates generally to the field of molecular biology and concerns a method for increasing various plant seed yield-related traits by increasing expression in a plant of a nucleic acid sequence encoding a transglutaminase (TGase) polypeptide. The present invention also concerns plants having increased expression of a nucleic acid sequence encoding a TGase polypeptide, which plants have increased seed yield-related traits relative to control plants. The invention additionally relates to nucleic acid sequences, nucleic acid constructs, vectors and plants containing said nucleic acid sequences.

The present invention relates generally to the field of molecular biology and concerns a method for improving various plant growth characteristics by modulating expression in a plant of a nucleic acid encoding a TRY-like (Tryptichon) polypeptide. The present invention also concerns plants having modulated expression of a nucleic acid encoding a TRY-like polypeptide, which plants have improved growth characteristics relative to corresponding wild type plants or other control plants. The invention also provides constructs useful in the methods of the invention.

The present invention relates generally to the field of molecular biology and concerns a method for increasing seed yield in plants. More specifically, the present invention concerns a method for increasing seed yield in plants by modulating expression in a plant of a nucleic acid encoding a BZR (BRASSINAZOLE-RESISTANT) polypeptide. The present invention also concerns plants having modulated expression of a nucleic acid encoding a BZR polypeptide, which plants have increased seed yield relative to control plants. The invention also provides hitherto unknown BZR-encoding nucleic acids, and constructs comprising the same, useful in performing the methods of the invention.

The ever-increasing world population and the dwindling supply of arable land available for agriculture fuels research towards increasing the efficiency of agriculture. Conventional means for crop and horticultural improvements utilise selective breeding techniques to identify plants having desirable characteristics. However, such selective breeding techniques have several drawbacks, namely that these techniques are typically labour intensive and result in plants that often contain heterogeneous genetic components that may not always result in the desirable trait being passed on from parent plants. Advances in molecular biology have allowed mankind to modify the germplasm of animals and plants. Genetic engineering of plants entails the isolation and manipulation of genetic material (typically in the form of DNA or RNA) and the subsequent introduction of that genetic material into a plant. Such technology has the capacity to deliver crops or plants having various improved economic, agronomic or horticultural traits.

A trait of particular economic interest is increased yield. Yield is normally defined as the measurable produce of economic value from a crop. This may be defined in terms of quantity and/or quality. Yield is directly dependent on several factors, for example, the number and size of the organs, plant architecture (for example, the number of branches), seed production, leaf senescence and more. Root development, nutrient uptake, stress tolerance and early vigour may also be important factors in determining yield. Optimizing the above-mentioned factors may therefore contribute to increasing crop yield.

Seed yield is a particularly important trait, since the seeds of many plants are important for human and animal nutrition. Crops such as corn, rice, wheat, canola and soybean account for over half the total human caloric intake, whether through direct consumption of the seeds themselves or through consumption of meat products raised on processed seeds. They are also a source of sugars, oils and many kinds of metabolites used in industrial processes. Seeds contain an embryo (the source of new shoots and roots) and an endosperm (the source of nutrients for embryo growth during germination and during early growth of seedlings). The development of a seed involves many genes, and requires the transfer of metabolites from the roots, leaves and stems into the growing seed. The endosperm, in particular, assimilates the metabolic precursors of carbohydrates, oils and proteins and synthesizes them into storage macromolecules to fill out the grain.

Plant biomass is yield for forage crops like alfalfa, silage corn and hay. Many proxies for yield have been used in grain crops. Chief amongst these are estimates of plant size. Plant size can be measured in many ways depending on species and developmental stage, but include total plant dry weight, above-ground dry weight, above-ground fresh weight, leaf area, stem volume, plant height, rosette diameter, leaf length, root length, root mass, tiller number and leaf number. Many species maintain a conservative ratio between the size of different parts of the plant at a given developmental stage. These allometric relationships are used to extrapolate from one of these measures of size to another (e.g. Tittonell et al 2005 Agric Ecosys & Environ 105: 213). Plant size at an early developmental stage will typically correlate with plant size later in development. A larger plant with a greater leaf area can typically absorb more light and carbon dioxide than a smaller plant and therefore will likely gain a greater weight during the same period (Fasoula & Tollenaar 2005 Maydica 50:39). This is in addition to the potential continuation of the micro-environmental or genetic advantage that the plant had to achieve the larger size initially. There is a strong genetic component to plant size and growth rate (e.g. ter Steege et al 2005 Plant Physiology 139:1078), and so for a range of diverse genotypes plant size under one environmental condition is likely to correlate with size under another (Hittalmani et al 2003 Theoretical Applied Genetics 107:679). In this way a standard environment is used as a proxy for the diverse and dynamic environments encountered at different locations and times by crops in the field.

Another important trait for many crops is early vigour. Improving early vigour is an important objective of modern rice breeding programs in both temperate and tropical rice cultivars. Long roots are important for proper soil anchorage in water-seeded rice. Where rice is sown directly into flooded fields, and where plants must emerge rapidly through water, longer shoots are associated with vigour. Where drill-seeding is practiced, longer mesocotyls and coleoptiles are important for good seedling emergence. The ability to engineer early vigour into plants would be of great importance in agriculture. For example, poor early vigour has been a limitation to the introduction of maize (*Zea mays* L.) hybrids based on Corn Belt germplasm in the European Atlantic.

Harvest index, the ratio of seed yield to aboveground dry weight, is relatively stable under many environmental conditions and so a robust correlation between plant size and grain yield can often be obtained (e.g. Rebetzke et al 2002 Crop Science 42:739). These processes are intrinsically linked because the majority of grain biomass is dependent on current or stored photosynthetic productivity by the leaves and stem of the plant (Gardener et al 1985 Physiology of Crop Plants. Iowa State University Press, pp 68-73). Therefore, selecting for plant size, even at early stages of development, has been used as an indicator for future potential yield (e.g. Tittonell et al 2005 Agric Ecosys & Environ 105: 213). When testing for the impact of genetic differences on stress tolerance, the ability to standardize soil properties, temperature, water and nutrient availability and light intensity is an intrinsic advantage of greenhouse or plant growth chamber environments compared to the field. However, artificial limitations on yield due to poor pollination due to the absence of wind or insects, or insufficient space for mature root or canopy growth, can restrict the use of these controlled environments for testing yield differences. Therefore, measurements of plant size in early development, under standardized conditions in a growth chamber or greenhouse, are standard practices to provide indication of potential genetic yield advantages.

A further important trait is that of improved abiotic stress tolerance. Abiotic stress is a primary cause of crop loss worldwide, reducing average yields for most major crop plants by more than 50% (Wang et al., Planta (2003) 218: 1-14). Abiotic stresses may be caused by drought, salinity, extremes of temperature, chemical toxicity and oxidative stress. The ability to improve plant tolerance to abiotic stress would be of great economic advantage to farmers worldwide and would allow for the cultivation of crops during adverse conditions and in territories where cultivation of crops may not otherwise be possible.

Crop yield may therefore be increased by optimising one of the above-mentioned factors.

Depending on the end use, the modification of certain yield traits may be favoured over others. For example for applications such as forage or wood production, or bio-fuel resource, an increase in the vegetative parts of a plant may be desirable, and for applications such as flour, starch or oil production, an increase in seed parameters may be particularly desirable. Even amongst the seed parameters, some may be favoured over others, depending on the application. Various mechanisms may contribute to increasing seed yield, whether that is in the form of increased seed size or increased seed number.

One approach to increasing yield (seed yield and/or biomass) in plants may be through modification of the inherent growth mechanisms of a plant, such as the cell cycle or various signalling pathways involved in plant growth or in defense mechanisms.

Concerning BZR, depending on the end use, the modification of certain yield traits may be favoured over others. For example for applications such as forage or wood production, or bio-fuel resource, an increase in the vegetative parts of a plant may be desirable, and for applications such as flour, starch or oil production, an increase in seed parameters may be particularly desirable. Even amongst the seed parameters, some may be favoured over others, depending on the application. Various mechanisms may contribute to increasing seed yield, whether that is in the form of increased seed size or increased seed number or increase number of inflorescences.

It has now been found that various plant yield-related may be improved in plants by modulating expression in a plant of a nucleic acid encoding a RHL1 (Root Hairless 1) in a plant.

Furthermore, it has now been found that various seed yield-related traits may be increased in plants relative to control plants, by increasing expression in a plant of a nucleic acid sequence encoding a transglutaminase (TGase) polypeptide. The increased seed yield-related traits comprise one or more of: increased total seed yield per plant, increased number of filled seeds, and increased harvest index.

Even furthermore, it has now been found that various growth characteristics may be improved in plants by modulating expression in a plant of a nucleic acid encoding a TRY-like (Tryptichon) in a plant.

Yet furthermore, It has now been found that seed yield may be improved in plants by modulating expression in a plant of a nucleic acid encoding a BZR (BRASSINAZOLE-RESISTANT) polypeptide in a plant.

BACKGROUND

1. Root Hairless 1 (RHL1)

An RHL1 polypeptide was first described in 1998 by Schneider at al. (Genes Dev. 12, 2013-2021) as a nuclear targeted protein required for root hair initiation in *Arabidopsis thaliana*. RHL1 polypeptides are ubiquitous to the viridiplantae kingdom. Sequence comparison of RHL1 originating from different organism reveals that RHL1 polypeptides share an overall sequence similarity around 30-80% identity. RHL1 polypeptides comprise a number of putative nuclear localization signals as well as phosphorylation sites and a PEST sequence which is a putative proteasome-dependent proteins degradation motif. The presence of such motifs may reportedly confer some regulatory roles by modulating subcellular localization of topos and for their interaction with other proteins. The C-terminus of RHL1 proteins has weak but significant sequence similarity to the C-terminal of mammalian Topo II-alpha protein (Sugimoto-Shirasu et al. 2005 PNAS 102, 18736-17741). Eukaryotic topo II proteins belong to the subclass of the type II topo (typeIIA) that is required to unwind replicating double-stranded DNA. Physical Interaction between an RHL1 polypeptide and a plant topo VI protein, At TOP6B, has been reported (Sugimoto-Shirasu et al. 2005). It has been suggested that RHL1 polypeptides function in a plant topo VI complex active during the mitotic cell cycle and endocycle of plant cells. *Arabidopsis thaliana* plants, hyp7, carrying mutations in an RHL1 gene exhibit an extreme drawf phenotype and defects in endoreduplication (Sugimoto-Shirasu et al. 2005).

2. Transglutaminases (TGases)

Transglutaminases (TGases, EC 2.3.2.13; protein-glutamine-gamma-glutamyltransferase) are a family of enzymes that have a range of calcium (Ca)-dependent catalytic activities, most of which concern the post-translational modification of proteins. They catalyze the covalent attachment to proteins and polypeptides of a series of substances containing primary amine groups, i.e., they promote the formation of amide linkages, generally in a Ca-dependent fashion, between the primary amine of an amine donor substrate and the y-carboxamide group of peptide-bound endo-glutamine residues in proteins or polypeptides that are the amine acceptors:

protein glutamine+alkylamine=protein N5-alkyl-glutamine+NH3.

Polyamines have been shown to serve as physiological substrates of TGases. Polyamines appear to play an essential role in growth and cell division process in animals, microorganisms, and plants. One of the roles of polyamines is their regulatory action by a TGase-mediated process of post-translational modification (addition of polyamine moieties) of enzymes and structural proteins.

TGases enzymes are found intracellularly and extracellularly, and are widely distributed in bacteria, animals and plants. In plants, the TGase activity is found in chloroplasts. Rubisco and apoproteins of the antenna complex have been shown to be substrates of TGase activity, thereby suggesting a role of these enzymes in photosynthesis related processes, such as protection of photosystem antenna proteins (Villalobos et al. (2004) Gene 336: 93-104).

Transgenic rice plants (Claparols et al. (2004) Transgenic Research 13: 195-199) expressing a gene encoding rat prostate calcium-dependent transglutaminase polypeptide under the control of maize constitutive promoter accumulated the recombinant enzyme in an inactive form.

International patent application WO 2003/102128 describes a nucleic acid sequence encoding a corn TGase polypeptide, vectors, micro-organisms and plants comprising such nucleic acid sequences, and the use of polypeptides with such TGase activity in food manipulation, processing and transformation.

Surprisingly, it has now been found that increasing expression in a plant of a nucleic acid sequence encoding a TGase polypeptide as defined herein, gives plants having increased seed yield-related traits relative to control plants.

According to one embodiment, there is provided a method for increasing seed yield-related traits in plants relative to control plants, comprising increasing expression in a plant of a nucleic acid sequence encoding a TGase polypeptide as defined herein. The increased seed yield-related traits comprise one or more of: increased total seed yield per plant, increased number of filled seeds, and increased harvest index.

3. Tryptichon (TRY-Like)

The *Arabidopsis* gene Tryptichon encodes a protein that reportedly negatively regulates trychome development and positively regulates root hair development. Trichome patterning in *Arabidopsis* is a model for the generation of a spacing pattern from initially equivalent cells. Schellmann et al. (EMBO J. 21, 5036-5046, 2002) show that the Tryptichon gene that functions in lateral inhibition encodes a single-repeat MYB-related transcription factor that lacks a recognizable activation domain. It has high sequence similarity to the root hair patterning gene Caprice. Both genes are expressed in trichomes and act together during lateral inhibition. They further show that Tryptichon and Caprice act redundantly in the position-dependent cell fate determination in the root epidermis. Thus, the same lateral inhibition mechanism seems to be involved in both de novo patterning and position-dependent cell determination (Schellmann et al., 2002).

4. Brassinazole Resistant1 (BZR1)

The regulation of gene expression is key to the viability of any cell. Several hundreds of proteins are involved in the regulation of gene transcription. In particular transcription factors play a central role and act directly on gene promoters. Plant genomes devote approximately 7% of their coding sequence to transcription factors (TFs; Rushton et al. 2008 Plant Physiology 147:280-295 (2008).

Plants encode a particular class of transcription factors, the BES or BZR proteins, which modulate gene response to fluctuations in plant steroid hormones such as brassinosteroids (BRs). BZR transcription factors (BZR TFs) are characterized by the presence of a conserved BZR1 repressor domain typically found at the N-terminus of the protein and involved in binding to the targeted gene promoter. Plant typically encode a small number of BZR TFs. For example the *Arabidopsis* genome contains only 6 genes encoding BZR TFs, while tobacco, a plant in which this family of TFs is expanded encodes 19 BZR TFs. All TFs comprised a conserved BZR1 repressor domain and are predicted to function in the modulation of BR signalling.

In *Arabidopsis thaliana*, the cascade of events in BR signalling are triggered upon binding of BRs to the BRASSINOSTEROID INSENSITIVE1 (BRI1)/BKI1 receptor complex at the plasma membrane, causing the release of BKI1. The subsequent dimerization of BRI1 and BRI1 ASSOCIATED RECEPTOR KINASE1 (BAK1) activates a downstream signal transductionpathway that leads to BRI1 EMS SUPPRESSOR1 (BES1) and BRASSINAZOLE RESISTANT1 (BZR1). The phosphorylation of BES1 and BZR1 by the kinase BIN2 appears to control their signalling activity by acting on the subcelullar localization and stability of the protein. Dephosphorilated BZR1 accumulates in the nuclei which is the site at which the transcriptional function is performed (Wang et al., 2006 Cell Res. 16: 427-434). Mechanistically, transcription factors of the BZR1 family directly bind to the promoter of the targeted gene and may act to activate or repress expression.

Methods for modulating the Brassinosteroid response pathway to modify a number of traits in plants have been disclosed (U.S. Pat. No. 6,921,848). The traits as defined in U.S. Pat. No. 6,921,848 comprised increased growth and cell elongation in various organs and tissues. However those effects did not result in an increase in the number of organs such as the number of seeds produced and/or in an increase in the seed yield of the plant.

SUMMARY

1. Root Hairless 1 (RHL1)

Surprisingly, it has now been found that modulating expression of a nucleic acid encoding a RHL1 polypeptide gives plants having enhanced yield-related traits relative to control plants.

According one embodiment, there is provided a method for enhancing yield related traits of a plant relative to control plants, comprising modulating expression of a nucleic acid encoding a RHL1 polypeptide in a plant. The enhanced yield related traits comprised increased early vigour, seed yield, number of seed and harvest index of a plant.

2. Tryptichon (TRY-Like)

Surprisingly, it has now been found that modulating expression of a nucleic acid encoding a TRY-like polypeptide gives plants having enhanced yield-related traits in particular increased emergence vigour and/or increased yield relative to control plants.

According one embodiment, there is provided a method for improving yield related traits of a plant relative to control plants, comprising modulating expression of a nucleic acid encoding a TRY-like polypeptide in a plant. The improved yield related traits comprised increased seed yield, including total weight of seeds.

3. Brassinazole Resistant1 (BZR1)

Surprisingly, it has now been found that modulating expression of a nucleic acid encoding a BZR polypeptide gives plants having increased seed yield relative to control plants.

According to one embodiment of the invention there is provided a method for increasing plant seed yield relative to control plants, comprising modulating expression of a nucleic acid encoding a BZR polypeptide in a plant.

DEFINITIONS

Polypeptide(s)/Protein(s)

The terms "polypeptide" and "protein" are used interchangeably herein and refer to amino acids in a polymeric form of any length, linked together by peptide bonds.

Polynucleotide(s)/Nucleic Acid(s)/Nucleic Acid Sequence(s)/Nucleotide Sequence(s)

The terms "polynucleotide(s)", "nucleic acid sequence(s)", "nucleotide sequence(s)", "nucleic acid(s)", "nucleic acid molecule" are used interchangeably herein and refer to nucleotides, either ribonucleotides or deoxyribonucleotides or a combination of both, in a polymeric unbranched form of any length.

Control Plant(s)

The choice of suitable control plants is a routine part of an experimental setup and may include corresponding wild type plants or corresponding plants without the gene of interest. The control plant is typically of the same plant species or even of the same variety as the plant to be assessed. The control plant may also be a nullizygote of the plant to be assessed. Nullizygotes are individuals missing the transgene by segregation. A "control plant" as used herein refers not only to whole plants, but also to plant parts, including seeds and seed parts.

Homologue(s)

"Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived.

A deletion refers to removal of one or more amino acids from a protein.

An insertion refers to one or more amino acid residues being introduced into a predetermined site in a protein. Insertions may comprise N-terminal and/or C-terminal fusions as well as intra-sequence insertions of single or multiple amino acids. Generally, insertions within the amino acid sequence will be smaller than N- or C-terminal fusions, of the order of about 1 to 10 residues. Examples of N- or C-terminal fusion proteins or peptides include the binding domain or activation domain of a transcriptional activator as used in the yeast two-hybrid system, phage coat proteins, (histidine)-6-tag, glutathione S-transferase-tag, protein A, maltose-binding protein, dihydrofolate reductase, Tag•100 epitope, c-myc epitope, FLAG®-epitope, lacZ, CMP (calmodulin-binding peptide), HA epitope, protein C epitope and VSV epitope.

A substitution refers to replacement of amino acids of the protein with other amino acids having similar properties (such as similar hydrophobicity, hydrophilicity, antigenicity, propensity to form or break α-helical structures or β-sheet structures). Amino acid substitutions are typically of single residues, but may be clustered depending upon functional constraints placed upon the polypeptide; insertions will usually be of the order of about 1 to 10 amino acid residues. The amino acid substitutions are preferably conservative amino acid substitutions. Conservative substitution tables are well known in the art (see for example Creighton (1984) Proteins. W.H. Freeman and Company (Eds) and Table 1 below).

TABLE 1

Examples of conserved amino acid substitutions

| Residue | Conservative Substitutions |
|---|---|
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

Amino acid substitutions, deletions and/or insertions may readily be made using peptide synthetic techniques well known in the art, such as solid phase peptide synthesis and the like, or by recombinant DNA manipulation. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

Derivatives

"Derivatives" include peptides, oligopeptides, polypeptides which may, compared to the amino acid sequence of the naturally-occurring form of the protein, such as the protein of interest, comprise substitutions of amino acids with non-naturally occurring amino acid residues, or additions of non-naturally occurring amino acid residues. "Derivatives" of a protein also encompass peptides, oligopeptides, polypeptides which comprise naturally occurring altered (glycosylated, acylated, prenylated, phosphorylated, myristoylated, sulphated etc.) or non-naturally altered amino acid residues compared to the amino acid sequence of a naturally-occurring form of the polypeptide. A derivative may also comprise one or more non-amino acid substituents or additions compared to the amino acid sequence from which it is derived, for example a reporter molecule or other ligand, covalently or non-covalently bound to the amino acid sequence, such as a reporter molecule which is bound to facilitate its detection, and non-naturally occurring amino acid residues relative to the amino acid sequence of a naturally-occurring protein. Furthermore, "derivatives" also include fusions of the naturally-occurring form of the protein with tagging peptides such as FLAG, HIS6 or thioredoxin (for a review of tagging peptides, see Terpe, Appl. Microbiol. Biotechnol. 60, 523-533, 2003).

Orthologue(s)/Paralogue(s)

Orthologues and paralogues encompass evolutionary concepts used to describe the ancestral relationships of genes. Paralogues are genes within the same species that have originated through duplication of an ancestral gene; orthologues are genes from different organisms that have originated through speciation, and are also derived from a common ancestral gene.

Domain

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein. Identified by their high degree of conservation in aligned sequences of a family of protein homologues, they can be used as identifiers to determine if any polypeptide in question belongs to a previously identified polypeptide family.

Motif/Consensus Sequence/Signature

The term "motif" or "consensus sequence" or "signature" refers to a short conserved region in the sequence of evolutionarily related proteins. Motifs are frequently highly conserved parts of domains, but may also include only part of the domain, or be located outside of conserved domain (if all of the amino acids of the motif fall outside of a defined domain).

Hybridisation

The term "hybridisation" as defined herein is a process wherein substantially homologous complementary nucleotide sequences anneal to each other. The hybridisation process can occur entirely in solution, i.e. both complementary nucleic acids are in solution. The hybridisation process can also occur with one of the complementary nucleic acids immobilised to a matrix such as magnetic beads, Sepharose beads or any other resin. The hybridisation process can furthermore occur with one of the complementary nucleic acids immobilised to a solid support such as a nitro-cellulose or nylon membrane or immobilised by e.g. photolithography to, for example, a siliceous glass support (the latter known as nucleic acid arrays or microarrays or as nucleic acid chips). In order to allow hybridisation to occur, the nucleic acid molecules are generally thermally or chemically denatured to melt a double strand into two single strands and/or to remove hairpins or other secondary structures from single stranded nucleic acids.

The term "stringency" refers to the conditions under which a hybridisation takes place. The stringency of hybridisation is influenced by conditions such as temperature, salt concentration, ionic strength and hybridisation buffer composition. Generally, low stringency conditions are selected to be about 30° C. lower than the thermal melting point ($T_m$) for the specific sequence at a defined ionic strength and pH. Medium stringency conditions are when the temperature is 20° C. below $T_m$, and high stringency conditions are when the temperature is 10° C. below $T_m$. High stringency hybridisation conditions are typically used for isolating hybridising sequences that have high sequence similarity to the target nucleic acid sequence. However, nucleic acids may deviate in sequence and still encode a substantially identical polypeptide, due to the degeneracy of the genetic code. Therefore medium stringency hybridisation conditions may sometimes be needed to identify such nucleic acid molecules.

The Tm is the temperature under defined ionic strength and pH, at which 50% of the target sequence hybridises to a perfectly matched probe. The $T_m$ is dependent upon the solution conditions and the base composition and length of the probe. For example, longer sequences hybridise specifically at higher temperatures. The maximum rate of hybridisation is obtained from about 16° C. up to 32° C. below $T_m$. The presence of monovalent cations in the hybridisation solution reduce the electrostatic repulsion between the two nucleic acid strands thereby promoting hybrid formation; this effect is visible for sodium concentrations of up to 0.4M (for higher concentrations, this effect may be ignored). Formamide reduces the melting temperature of DNA-DNA and DNA-RNA duplexes with 0.6 to 0.7° C. for each percent formamide, and addition of 50% formamide allows hybridisation to be performed at 30 to 45° C., though the rate of hybridisation will be lowered. Base pair mismatches reduce the hybridisation rate and the thermal stability of the duplexes. On average and for large probes, the Tm decreases about 1° C. per % base mismatch. The Tm may be calculated using the following equations, depending on the types of hybrids:

1) DNA-DNA hybrids (Meinkoth and Wahl, Anal. Biochem., 138: 267-284, 1984):

$$T_m = 81.5°\text{ C.} + 16.6 \times \log_{10}[\text{Na}^+]^a + 0.41 \times \%[G/C^b] - 500 \times [L^c]^{-1} - 0.61 \times \%\text{ formamide}$$

2) DNA-RNA or RNA-RNA hybrids:

$$Tm = 79.8 + 18.5(\log_{10}[\text{Na}^+]^a) + 0.58(\%G/C^b) + 11.8(\%G/C^b)^2 - 820/L^c$$

3) oligo-DNA or oligo-RNA[d] hybrids:

For <20 nucleotides: $T_m = 2(l_n)$

For 20-35 nucleotides: $T_m = 22 + 1.46(l_n)$

[a] or for other monovalent cation, but only accurate in the 0.01-0.4 M range.

[b] only accurate for % GC in the 30% to 75% range.

[c] L=length of duplex in base pairs.

[d] oligo, oligonucleotide; $l_n$, =effective length of primer=2×(no. of G/C)+(no. of A/T).

Non-specific binding may be controlled using any one of a number of known techniques such as, for example, blocking the membrane with protein containing solutions, additions of heterologous RNA, DNA, and SDS to the hybridisation buffer, and treatment with Rnase. For non-homologous probes, a series of hybridizations may be performed by varying one of (i) progressively lowering the annealing temperature (for example from 68° C. to 42° C.) or (ii) progressively lowering the formamide concentration (for example from 50% to 0%). The skilled artisan is aware of various parameters which may be altered during hybridisation and which will either maintain or change the stringency conditions.

Besides the hybridisation conditions, specificity of hybridisation typically also depends on the function of post-hybridisation washes. To remove background resulting from non-specific hybridisation, samples are washed with dilute salt solutions. Critical factors of such washes include the ionic strength and temperature of the final wash solution: the lower the salt concentration and the higher the wash temperature, the higher the stringency of the wash. Wash conditions are typically performed at or below hybridisation stringency.

A positive hybridisation gives a signal that is at least twice of that of the background. Generally, suitable stringent conditions for nucleic acid hybridisation assays or gene amplification detection procedures are as set forth above. More or less stringent conditions may also be selected. The skilled artisan is aware of various parameters which may be altered during washing and which will either maintain or change the stringency conditions.

For example, typical high stringency hybridisation conditions for DNA hybrids longer than 50 nucleotides encompass hybridisation at 65° C. in 1×SSC or at 42° C. in 1×SSC and 50% formamide, followed by washing at 65° C. in 0.3×SSC. Examples of medium stringency hybridisation conditions for DNA hybrids longer than 50 nucleotides encompass hybridisation at 50° C. in 4×SSC or at 40° C. in 6×SSC and 50% formamide, followed by washing at 50° C. in 2×SSC. The length of the hybrid is the anticipated length for the hybridising nucleic acid. When nucleic acids of known sequence are hybridised, the hybrid length may be determined by aligning the sequences and identifying the conserved regions described herein. 1×SSC is 0.15M NaCl and 15 mM sodium citrate; the hybridisation solution and wash solutions may additionally include 5×Denhardt's reagent, 0.5-1.0% SDS, 100 μg/ml denatured, fragmented salmon sperm DNA, 0.5% sodium pyrophosphate.

For the purposes of defining the level of stringency, reference can be made to Sambrook et al. (2001) Molecular Cloning: a laboratory manual, 3rd Edition, Cold Spring Harbor Laboratory Press, CSH, New York or to Current Protocols in Molecular Biology, John Wiley & Sons, N.Y. (1989 and yearly updates).

Splice Variant

The term "splice variant" as used herein encompasses variants of a nucleic acid sequence in which selected introns and/or exons have been excised, replaced, displaced or added, or in which introns have been shortened or lengthened. Such variants will be ones in which the biological activity of the protein is substantially retained; this may be achieved by selectively retaining functional segments of the protein. Such splice variants may be found in nature or may be manmade. Methods for predicting and isolating such splice variants are well known in the art (see for example Foissac and Schiex (2005) BMC Bioinformatics 6: 25).

Allelic Variant

Alleles or allelic variants are alternative forms of a given gene, located at the same chromosomal position. Allelic variants encompass Single Nucleotide Polymorphisms (SNPs), as well as Small Insertion/Deletion Polymorphisms (INDELs). The size of INDELs is usually less than 100 bp. SNPs and INDELs form the largest set of sequence variants in naturally occurring polymorphic strains of most organisms.

Gene Shuffling/Directed Evolution

Gene shuffling or directed evolution consists of iterations of DNA shuffling followed by appropriate screening and/or selection to generate variants of nucleic acids or portions thereof encoding proteins having a modified biological activity (Castle et al., (2004) Science 304(5674): 1151-4; U.S. Pat. Nos. 5,811,238 and 6,395,547).

Regulatory Element/Control Sequence/Promoter

The terms "regulatory element", "control sequence" and "promoter" are all used interchangeably herein and are to be taken in a broad context to refer to regulatory nucleic acid sequences capable of effecting expression of the sequences to which they are ligated. The term "promoter" typically refers to a nucleic acid control sequence located upstream from the transcriptional start of a gene and which is involved in recognising and binding of RNA polymerase and other proteins, thereby directing transcription of an operably linked nucleic acid. Encompassed by the aforementioned terms are transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which alter gene expression in response to developmental and/or external stimuli, or in a tissue-specific manner. Also included within the term is a transcriptional regulatory sequence of a classical prokaryotic gene, in which case it may include a −35 box sequence and/or −10 box transcriptional regulatory sequences. The term "regulatory element" also encompasses a synthetic fusion molecule or derivative that confers, activates or enhances expression of a nucleic acid molecule in a cell, tissue or organ.

A "plant promoter" comprises regulatory elements, which mediate the expression of a coding sequence segment in plant cells. Accordingly, a plant promoter need not be of plant origin, but may originate from viruses or micro-organisms, for example from viruses which attack plant cells. The "plant promoter" can also originate from a plant cell, e.g. from the plant which is transformed with the nucleic acid sequence to be expressed in the inventive process and described herein. This also applies to other "plant" regulatory signals, such as "plant" terminators. The promoters upstream of the nucleotide sequences useful in the methods of the present invention can be modified by one or more nucleotide substitution(s), insertion(s) and/or deletion(s) without interfering with the functionality or activity of either the promoters, the open reading frame (ORF) or the 3'-regulatory region such as terminators or other 3' regulatory regions which are located away from the ORF. It is furthermore possible that the activity of the promoters is increased by modification of their sequence, or that they are replaced completely by more active promoters, even promoters from heterologous organisms. For expression in plants, the nucleic acid molecule must, as described above, be linked operably to or comprise a suitable promoter which expresses the gene at the right point in time and with the required spatial expression pattern.

For the identification of functionally equivalent promoters, the promoter strength and/or expression pattern of a candidate promoter may be analysed for example by operably linking the promoter to a reporter gene and assaying the expression level and pattern of the reporter gene in various tissues of the plant. Suitable well-known reporter genes include for example beta-glucuronidase or beta-galactosidase. The promoter activity is assayed by measuring the enzymatic activity of the beta-glucuronidase or beta-galactosidase. The promoter strength and/or expression pattern may then be compared to that of a reference promoter (such as the one used in the methods of the present invention). Alternatively, promoter strength may be assayed by quantifying mRNA levels or by comparing mRNA levels of the nucleic acid used in the methods of the present invention, with mRNA levels of housekeeping genes such as 18S rRNA, using methods known in the art, such as Northern blotting with densitometric analysis of autoradiograms, quantitative real-time PCR or RT-PCR (Heid et al., 1996 Genome Methods 6: 986-994). Generally by "weak promoter" is intended a promoter that drives expression of a coding sequence at a low level. By "low level" is intended at levels of about 1/10,000 transcripts to about 1/100,000 transcripts, to about 1/500, 0000 transcripts per cell. Conversely, a "strong promoter" drives expression of a coding sequence at high level, or at about 1/10 transcripts to about 1/100 transcripts to about 1/1000 transcripts per cell. Generally, by "medium strength promoter" is intended a promoter that drives expression of a coding sequence at a lower level than a strong promoter, in particular at a level that is in all instances below that obtained when under the control of a 35S CaMV promoter.

Operably Linked

The term "operably linked" as used herein refers to a functional linkage between the promoter sequence and the gene of interest, such that the promoter sequence is able to initiate transcription of the gene of interest.

Constitutive Promoter

A "constitutive promoter" refers to a promoter that is transcriptionally active during most, but not necessarily all, phases of growth and development and under most environmental conditions, in at least one cell, tissue or organ. Table 2a below gives examples of constitutive promoters.

TABLE 2a

Examples of constitutive promoters

| Gene Source | Reference |
|---|---|
| Actin | McElroy et al, Plant Cell, 2: 163-171, 1990 |
| HMGP | WO 2004/070039 |
| CAMV 35S | Odell et al, Nature, 313: 810-812, 1985 |
| CaMV 19S | Nilsson et al., Physiol. Plant. 100: 456-462, 1997 |
| GOS2 | de Pater et al, Plant J Nov; 2(6): 837-44, 1992, WO 2004/065596 |
| Ubiquitin | Christensen et al, Plant Mol. Biol. 18: 675-689, 1992 |
| Rice cyclophilin | Buchholz et al, Plant Mol Biol. 25(5): 837-43, 1994 |
| Maize H3 histone | Lepetit et al, Mol. Gen. Genet. 231: 276-285, 1992 |
| Alfalfa H3 histone | Wu et al. Plant Mol. Biol. 11: 641-649, 1988 |
| Actin 2 | An et al, Plant J. 10(1); 107-121, 1996 |
| 34S FMV | Sanger et al., Plant. Mol. Biol., 14, 1990: 433-443 |
| Rubisco small subunit | U.S. Pat. No. 4,962,028 |
| OCS | Leisner (1988) Proc Natl Acad Sci USA 85(5): 2553 |
| SAD1 | Jain et al., Crop Science, 39 (6), 1999: 1696 |
| SAD2 | Jain et al., Crop Science, 39 (6), 1999: 1696 |

TABLE 2a-continued

Examples of constitutive promoters

| Gene Source | Reference |
|---|---|
| nos | Shaw et al. (1984) Nucleic Acids Res. 12(20): 7831-7846 |
| V-ATPase | WO 01/14572 |
| Super promoter | WO 95/14098 |
| G-box proteins | WO 94/12015 |

Ubiquitous Promoter

A ubiquitous promoter is active in substantially all tissues or cells of an organism.

Developmentally-Regulated Promoter

A developmentally-regulated promoter is active during certain developmental stages or in parts of the plant that undergo developmental changes.

Inducible Promoter

An inducible promoter has induced or increased transcription initiation in response to a chemical (for a review see Gatz 1997, Annu. Rev. Plant Physiol. Plant Mol. Biol., 48:89-108), environmental or physical stimulus, or may be "stress-inducible", i.e. activated when a plant is exposed to various stress conditions, or a "pathogen-inducible" i.e. activated when a plant is exposed to exposure to various pathogens.

Organ-Specific/Tissue-Specific Promoter

An organ-specific or tissue-specific promoter is one that is capable of preferentially initiating transcription in certain organs or tissues, such as the leaves, roots, seed tissue etc. For example, a "root-specific promoter" is a promoter that is transcriptionally active predominantly in plant roots, substantially to the exclusion of any other parts of a plant, whilst still allowing for any leaky expression in these other plant parts. Promoters able to initiate transcription in certain cells only are referred to herein as "cell-specific".

Examples of root-specific promoters are listed in Table 2b below:

TABLE 2b

Examples of root-specific promoters

| Gene Source | Reference |
|---|---|
| RCc3 | Plant Mol Biol. 1995 Jan; 27(2): 237-48 |
| *Arabidopsis* PHT1 | Kovama et al., 2005; Mudge et al. (2002, Plant J. 31: 341) |
| Medicago phosphate transporter | Xiao et al., 2006 |
| *Arabidopsis* Pyk10 | Nitz et al. (2001) Plant Sci 161(2): 337-346 |
| root-expressible genes | Tingey et al., EMBO J. 6: 1, 1987. |
| tobacco auxin-inducible gene | Van der Zaal et al., Plant Mol. Biol. 16, 983, 1991. |
| β-tubulin | Oppenheimer, et al., Gene 63: 87, 1988. |
| tobacco root-specific genes | Conkling, et al., Plant Physiol. 93: 1203, 1990. |
| *B. napus* G1-3b gene | U.S. Pat. No. 5,401,836 |
| SbPRP1 | Suzuki et al., Plant Mol. Biol. 21: 109-119, 1993. |
| LRX1 | Baumberger et al. 2001, Genes & Dev. 15: 1128 |
| BTG-26 *Brassica napus* | US 20050044585 |
| LeAMT1 (tomato) | Lauter et al. (1996, PNAS 3: 8139) |
| The LeNRT1-1 (tomato) | Lauter et al. (1996, PNAS 3: 8139) |
| class I patatin gene (potato) | Liu et al., Plant Mol. Biol. 153: 386-395, 1991. |
| KDC1 (*Daucus carota*) | Downey et al. (2000, J. Biol. Chem. 275: 39420) |
| TobRB7 gene | W Song (1997) PhD Thesis, North Carolina State University, Raleigh, NC USA |
| OsRAB5a (rice) | Wang et al. 2002, Plant Sci. 163: 273 |
| ALF5 (*Arabidopsis*) | Diener et al. (2001, Plant Cell 13: 1625) |
| NRT2; 1Np (*N. plumbaginifolia*) | Quesada et al. (1997, Plant Mol. Biol. 34: 265) |

A seed-specific promoter is transcriptionally active predominantly in seed tissue, but not necessarily exclusively in seed tissue (in cases of leaky expression). The seed-specific promoter may be active during seed development and/or during germination. The seed specific promoter may be endosperm/aleurone/embryo specific. Examples of seed-specific promoters (endosperm/aleurone/embryo specific) are shown in Table 2c to Table 2f below. Further examples of seed-specific promoters are given in Qing Qu and Takaiwa (Plant Biotechnol. J. 2, 113-125, 2004), which disclosure is incorporated by reference herein as if fully set forth.

TABLE 2c

Examples of seed-specific promoters

| Gene source | Reference |
|---|---|
| seed-specific genes | Simon et al., Plant Mol. Biol. 5: 191, 1985; Scofield et al., J. Biol. Chem. 262: 12202, 1987.; Baszczynski et al., Plant Mol. Biol. 14: 633, 1990. |
| Brazil Nut albumin | Pearson et al., Plant Mol. Biol. 18: 235-245, 1992. |
| legumin | Ellis et al., Plant Mol. Biol. 10: 203-214, 1988. |
| glutelin (rice) | Takaiwa et al., Mol. Gen. Genet. 208: 15-22, 1986; Takaiwa et al., FEBS Letts. 221: 43-47, 1987. |
| zein | Matzke et al Plant Mol Biol, 14(3): 323-32 1990 |
| napA | Stalberg et al, Planta 199: 515-519, 1996. |
| wheat LMW and HMW glutenin-1 | Mol Gen Genet 216: 81-90, 1989; NAR 17: 461-2, 1989 |
| wheat SPA | Albani et al, Plant Cell, 9: 171-184, 1997 |
| wheat α,β,γ-gliadins | EMBO J. 3: 1409-15, 1984 |
| barley Itr1 promoter | Diaz et al. (1995) Mol Gen Genet 248(5): 592-8 |
| barley B1, C, D, hordein | Theor Appl Gen 98: 1253-62, 1999; Plant J 4: 343-55, 1993; Mol Gen Genet 250: 750-60, 1996 |
| barley DOF | Mena et al, The Plant Journal, 116(1): 53-62, 1998 |
| blz2 | EP99106056.7 |
| synthetic promoter | Vicente-Carbajosa et al., Plant J. 13: 629-640, 1998. |
| rice prolamin NRP33 | Wu et al, Plant Cell Physiology 39(8) 885-889, 1998 |
| rice a-globulin Glb-1 | Wu et al, Plant Cell Physiology 39(8) 885-889, 1998 |
| rice OSH1 | Sato et al, Proc. Natl. Acad. Sci. USA, 93: 8117-8122, 1996 |
| rice α-globulin REB/OHP-1 | Nakase et al. Plant Mol. Biol. 33: 513-522, 1997 |
| rice ADP-glucose pyrophosphorylase | Trans Res 6: 157-68, 1997 |
| maize ESR gene family | Plant J 12: 235-46, 1997 |
| *sorghum* α-kafirin | DeRose et al., Plant Mol. Biol 32: 1029-35, 1996 |
| KNOX | Postma-Haarsma et al, Plant Mol. Biol. 39: 257-71, 1999 |
| rice oleosin | Wu et al, J. Biochem. 123: 386, 1998 |
| sunflower oleosin | Cummins et al., Plant Mol. Biol. 19: 873-876, 1992 |
| PRO0117, putative rice 40S ribosomal protein | WO 2004/070039 |
| PRO0136, rice alanine aminotransferase | unpublished |
| PRO0147, trypsin inhibitor ITR1 (barley) | unpublished |
| PRO0151, rice WSI18 | WO 2004/070039 |
| PRO0175, rice RAB21 | WO 2004/070039 |
| PRO005 | WO 2004/070039 |
| PRO0095 | WO 2004/070039 |
| α-amylase (Amy32b) | Lanahan et al, Plant Cell 4: 203-211, 1992; Skriver et al, Proc Natl Acad Sci USA 88: 7266-7270, 1991 |
| cathepsin β-like gene | Cejudo et al, Plant Mol Biol 20: 849-856, 1992 |
| Barley Ltp2 | Kalla et al., Plant J. 6: 849-60, 1994 |
| Chi26 | Leah et al., Plant J. 4: 579-89, 1994 |
| Maize B-Peru | Selinger et al., Genetics 149; 1125-38, 1998 |

TABLE 2d examples of endosperm-specific promoters

| Gene source | Reference |
|---|---|
| glutelin (rice) | Takaiwa et al. (1986) Mol Gen Genet 208: 15-22; Takaiwa et al. (1987) FEBS Letts. 221: 43-47 |
| zein | Matzke et al., (1990) Plant Mol Biol 14(3): 323-32 |
| wheat LMW and HMW glutenin-1 | Colot et al. (1989) Mol Gen Genet 216: 81-90, Anderson et al. (1989) NAR 17: 461-2 |
| wheat SPA | Albani et al. (1997) Plant Cell 9: 171-184 |
| wheat gliadins | Rafalski et al. (1984) EMBO 3: 1409-15 |
| barley Itr1 promoter | Diaz et al. (1995) Mol Gen Genet 248(5): 592-8 |
| barley B1, C, D, hordein | Cho et al. (1999) Theor Appl Genet 98: 1253-62; Muller et al. (1993) Plant J 4: 343-55; Sorenson et al. (1996) Mol Gen Genet 250: 750-60 |
| barley DOF | Mena et al, (1998) Plant J 116(1): 53-62 |
| blz2 | Onate et al. (1999) J Biol Chem 274(14): 9175-82 |

TABLE 2d-continued

| examples of endosperm-specific promoters | |
|---|---|
| Gene source | Reference |
| synthetic promoter | Vicente-Carbajosa et al. (1998) Plant J 13: 629-640 |
| rice prolamin NRP33 | Wu et al, (1998) Plant Cell Physiol 39(8) 885-889 |
| rice globulin Glb-1 | Wu et al. (1998) Plant Cell Physiol 39(8) 885-889 |
| rice globulin REB/OHP-1 | Nakase et al. (1997) Plant Molec Biol 33: 513-522 |
| rice ADP-glucose pyrophosphorylase | Russell et al. (1997) Trans Res 6: 157-68 |
| maize ESR gene family | Opsahl-Ferstad et al. (1997) Plant J 12: 235-46 |
| *sorghum* kafirin | DeRose et al. (1996) Plant Mol Biol 32: 1029-35 |

TABLE 2e

| Examples of embryo specific promoters: | |
|---|---|
| Gene source | Reference |
| rice OSH1 | Sato et al, Proc. Natl. Acad. Sci. USA, 93: 8117-8122, 1996 |
| KNOX | Postma-Haarsma et al, Plant Mol. Biol. 39: 257-71, 1999 |
| PRO0151 | WO 2004/070039 |
| PRO0175 | WO 2004/070039 |
| PRO005 | WO 2004/070039 |
| PRO0095 | WO 2004/070039 |

TABLE 2f

| Examples of aleurone-specific promoters: | |
|---|---|
| Gene source | Reference |
| α-amylase (Amy32b) | Lanahan et al, Plant Cell 4: 203-211, 1992; Skriver et al, Proc Natl Acad Sci USA 88: 7266-7270, 1991 |
| cathepsin β-like gene | Cejudo et al, Plant Mol Biol 20: 849-856, 1992 |
| Barley Ltp2 | Kalla et al., Plant J. 6: 849-60, 1994 |
| Chi26 | Leah et al., Plant J. 4: 579-89, 1994 |
| Maize B-Peru | Selinger et al., Genetics 149; 1125-38, 1998 |

A green tissue-specific promoter as defined herein is a promoter that is transcriptionally active predominantly in green tissue, substantially to the exclusion of any other parts of a plant, whilst still allowing for any leaky expression in these other plant parts.

Examples of green tissue-specific promoters which may be used to perform the methods of the invention are shown in Table 2g below.

TABLE 2g

| Examples of green tissue-specific promoters | | |
|---|---|---|
| Gene | Expression | Reference |
| Maize Orthophosphate dikinase | Leaf specific | Fukavama et al., 2001 |
| Maize Phosphoenolpyruvate carboxylase | Leaf specific | Kausch et al., 2001 |
| Rice Phosphoenolpyruvate carboxylase | Leaf specific | Liu et al., 2003 |
| Rice small subunit Rubisco | Leaf specific | Nomura et al., 2000 |
| rice beta expansin EXBP9 | Shoot specific | WO 2004/070039 |
| Pigeonpea small subunit Rubisco | Leaf specific | Panguluri et al., 2005 |
| Pea RBCS3A | Leaf specific | |

Another example of a tissue-specific promoter is a meristem-specific promoter, which is transcriptionally active predominantly in meristematic tissue, substantially to the exclusion of any other parts of a plant, whilst still allowing for any leaky expression in these other plant parts. Examples of green meristem-specific promoters which may be used to perform the methods of the invention are shown in Table 2h below.

TABLE 2h

| Examples of meristem-specific promoters | | |
|---|---|---|
| Gene source | Expression pattern | Reference |
| rice OSH1 | Shoot apical meristem, from embryo globular stage to seedling stage | Sato et al. (1996) Proc. Natl. Acad. Sci. USA, 93: 8117-8122 |
| Rice metallothionein | Meristem specific | BAD87835.1 |
| WAK1 & WAK 2 | Shoot and root apical meristems, and in expanding leaves and sepals | Wagner & Kohorn (2001) Plant Cell 13(2): 303-318 |

Terminator

The term "terminator" encompasses a control sequence which is a DNA sequence at the end of a transcriptional unit which signals 3' processing and polyadenylation of a primary transcript and termination of transcription. The terminator can be derived from the natural gene, from a variety of other plant genes, or from T-DNA. The terminator to be added may be derived from, for example, the nopaline synthase or octopine synthase genes, or alternatively from another plant gene, or less preferably from any other eukaryotic gene.

Modulation

The term "modulation" means in relation to expression or gene expression, a process in which the expression level is changed by said gene expression in comparison to the control plant, the expression level may be increased or decreased. The original, unmodulated expression may be of any kind of expression of a structural RNA (rRNA, tRNA) or mRNA with subsequent translation. The term "modulating the activity" shall mean any change of the expression of the inventive nucleic acid sequences or encoded proteins, which leads to increased yield and/or increased growth of the plants.

Expression

The term "expression" or "gene expression" means the transcription of a specific gene or specific genes or specific genetic construct. The term "expression" or "gene expression" in particular means the transcription of a gene or genes or genetic construct into structural RNA (rRNA, tRNA) or mRNA with or without subsequent translation of the latter into a protein. The process includes transcription of DNA and processing of the resulting mRNA product.

Increased Expression/Overexpression

The term "increased expression" or "overexpression" as used herein means any form of expression that is additional to the original wild-type expression level.

Methods for increasing expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of a nucleic acid encoding the polypeptide of interest. For example, endogenous promoters may be altered in vivo by mutation, deletion, and/or substitution (see, Kmiec, U.S. Pat. No. 5,565,350; Zarling et al., WO9322443), or isolated promoters may be introduced into a plant cell in the proper orientation and distance from a gene of the present invention so as to control the expression of the gene.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added to the 5' untranslated region (UTR) or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg (1988) Mol. Cell biol. 8: 4395-4405; Callis et al. (1987) Genes Dev 1:1183-1200). Such intron enhancement of gene expression is typically greatest when placed near the 5' end of the transcription unit. Use of the maize introns Adh1-S intron 1, 2, and 6, the Bronze-1 intron are known in the art. For general information see: The Maize Handbook, Chapter 116, Freeling and Walbot, Eds., Springer, N.Y. (1994).

Endogenous Gene

Reference herein to an “endogenous” gene not only refers to the gene in question as found in a plant in its natural form (i.e., without there being any human intervention), but also refers to that same gene (or a substantially homologous nucleic acid/gene) in an isolated form subsequently (re)introduced into a plant (a transgene). For example, a transgenic plant containing such a transgene may encounter a substantial reduction of the transgene expression and/or substantial reduction of expression of the endogenous gene. The isolated gene may be isolated from an organism or may be manmade, for example by chemical synthesis.

Decreased Expression

Reference herein to “decreased expression” or “reduction or substantial elimination” of expression is taken to mean a decrease in endogenous gene expression and/or polypeptide levels and/or polypeptide activity relative to control plants. The reduction or substantial elimination is in increasing order of preference at least 10%, 20%, 30%, 40% or 50%, 60%, 70%, 80%, 85%, 90%, or 95%, 96%, 97%, 98%, 99% or more reduced compared to that of control plants. Methods for decreasing expression are known in the art and the skilled person would readily be able to adapt the known methods for silencing so as to achieve reduction of expression of an endogenous gene in a whole plant or in parts thereof through the use of an appropriate promoter, for example.

For the reduction or substantial elimination of expression an endogenous gene in a plant, a sufficient length of substantially contiguous nucleotides of a nucleic acid sequence is required. In order to perform gene silencing, this may be as little as 20, 19, 18, 17, 16, 15, 14, 13, 12, 11, 10 or fewer nucleotides, alternatively this may be as much as the entire gene (including the 5' and/or 3' UTR, either in part or in whole). The stretch of substantially contiguous nucleotides may be derived from the nucleic acid encoding the protein of interest (target gene), or from any nucleic acid capable of encoding an orthologue, paralogue or homologue of the protein of interest. Preferably, the stretch of substantially contiguous nucleotides is capable of forming hydrogen bonds with the target gene (either sense or antisense strand), more preferably, the stretch of substantially contiguous nucleotides has, in increasing order of preference, 50%, 60%, 70%, 80%, 85%, 90%, 95%, 96%, 97%, 98%, 99%, 100% sequence identity to the target gene (either sense or antisense strand). A nucleic acid sequence encoding a (functional) polypeptide is not a requirement for the various methods discussed herein for the reduction or substantial elimination of expression of an endogenous gene.

Examples of various methods for the reduction or substantial elimination of expression in a plant of an endogenous gene, or for lowering levels and/or activity of a protein, are known to the skilled in the art. A skilled person would readily be able to adapt the known methods for silencing, so as to achieve reduction of expression of an endogenous gene in a whole plant or in parts thereof through the use of an appropriate promoter, for example.

This reduction or substantial elimination of expression may be achieved using routine tools and techniques. A preferred method for the reduction or substantial elimination of endogenous gene expression is by introducing and expressing in a plant a genetic construct into which the nucleic acid (in this case a stretch of substantially contiguous nucleotides derived from the gene of interest, or from any nucleic acid capable of encoding an orthologue, paralogue or homologue of any one of the protein of interest) is cloned as an inverted repeat (in part or completely), separated by a spacer (non-coding DNA).

In such a preferred method, expression of the endogenous gene is reduced or substantially eliminated through RNA-mediated silencing using an inverted repeat of a nucleic acid or a part thereof (in this case a stretch of substantially contiguous nucleotides derived from the gene of interest, or from any nucleic acid capable of encoding an orthologue, paralogue or homologue of the protein of interest), preferably capable of forming a hairpin structure. The inverted repeat is cloned in an expression vector comprising control sequences. A non-coding DNA nucleic acid sequence (a spacer, for example a matrix attachment region fragment (MAR), an intron, a polylinker, etc.) is located between the two inverted nucleic acids forming the inverted repeat. After transcription of the inverted repeat, a chimeric RNA with a self-complementary structure is formed (partial or complete). This double-stranded RNA structure is referred to as the hairpin RNA (hpRNA). The hpRNA is processed by the plant into siRNAs that are incorporated into an RNA-induced silencing complex (RISC). The RISC further cleaves the mRNA transcripts, thereby substantially reducing the number of mRNA transcripts to be translated into polypeptides. For further general details see for example, Grierson et al. (1998) WO 98/53083; Waterhouse et al. (1999) WO 99/53050).

Performance of the methods of the invention does not rely on introducing and expressing in a plant a genetic construct into which the nucleic acid is cloned as an inverted repeat, but any one or more of several well-known “gene silencing” methods may be used to achieve the same effects.

One such method for the reduction of endogenous gene expression is RNA-mediated silencing of gene expression (downregulation). Silencing in this case is triggered in a plant by a double stranded RNA sequence (dsRNA) that is substantially similar to the target endogenous gene. This dsRNA is further processed by the plant into about 20 to about 26 nucleotides called short interfering RNAs (siRNAs). The siRNAs are incorporated into an RNA-induced silencing complex (RISC) that cleaves the mRNA transcript of the endogenous target gene, thereby substantially reducing the number of mRNA transcripts to be translated into a polypeptide. Preferably, the double stranded RNA sequence corresponds to a target gene.

Another example of an RNA silencing method involves the introduction of nucleic acid sequences or parts thereof (in this case a stretch of substantially contiguous nucleotides derived from the gene of interest, or from any nucleic acid capable of encoding an orthologue, paralogue or homologue of the protein of interest) in a sense orientation into a plant. "Sense orientation" refers to a DNA sequence that is homologous to an mRNA transcript thereof. Introduced into a plant would therefore be at least one copy of the nucleic acid sequence. The additional nucleic acid sequence will reduce expression of the endogenous gene, giving rise to a phenomenon known as co-suppression. The reduction of gene expression will be more pronounced if several additional copies of a nucleic acid sequence are introduced into the plant, as there is a positive correlation between high transcript levels and the triggering of co-suppression.

Another example of an RNA silencing method involves the use of antisense nucleic acid sequences. An "antisense" nucleic acid sequence comprises a nucleotide sequence that is complementary to a "sense" nucleic acid sequence encoding a protein, i.e. complementary to the coding strand of a double-stranded cDNA molecule or complementary to an mRNA transcript sequence. The antisense nucleic acid sequence is preferably complementary to the endogenous gene to be silenced. The complementarity may be located in the "coding region" and/or in the "non-coding region" of a gene. The term "coding region" refers to a region of the nucleotide sequence comprising codons that are translated into amino acid residues. The term "non-coding region" refers to 5' and 3' sequences that flank the coding region that are transcribed but not translated into amino acids (also referred to as 5' and 3' untranslated regions).

Antisense nucleic acid sequences can be designed according to the rules of Watson and Crick base pairing. The antisense nucleic acid sequence may be complementary to the entire nucleic acid sequence (in this case a stretch of substantially contiguous nucleotides derived from the gene of interest, or from any nucleic acid capable of encoding an orthologue, paralogue or homologue of the protein of interest), but may also be an oligonucleotide that is antisense to only a part of the nucleic acid sequence (including the mRNA 5' and 3' UTR). For example, the antisense oligonucleotide sequence may be complementary to the region surrounding the translation start site of an mRNA transcript encoding a polypeptide. The length of a suitable antisense oligonucleotide sequence is known in the art and may start from about 50, 45, 40, 35, 30, 25, 20, 15 or 10 nucleotides in length or less. An antisense nucleic acid sequence according to the invention may be constructed using chemical synthesis and enzymatic ligation reactions using methods known in the art. For example, an antisense nucleic acid sequence (e.g., an antisense oligonucleotide sequence) may be chemically synthesized using naturally occurring nucleotides or variously modified nucleotides designed to increase the biological stability of the molecules or to increase the physical stability of the duplex formed between the antisense and sense nucleic acid sequences, e.g., phosphorothioate derivatives and acridine substituted nucleotides may be used. Examples of modified nucleotides that may be used to generate the antisense nucleic acid sequences are well known in the art. Known nucleotide modifications include methylation, cyclization and 'caps' and substitution of one or more of the naturally occurring nucleotides with an analogue such as inosine. Other modifications of nucleotides are well known in the art.

The antisense nucleic acid sequence can be produced biologically using an expression vector into which a nucleic acid sequence has been subcloned in an antisense orientation (i.e., RNA transcribed from the inserted nucleic acid will be of an antisense orientation to a target nucleic acid of interest). Preferably, production of antisense nucleic acid sequences in plants occurs by means of a stably integrated nucleic acid construct comprising a promoter, an operably linked antisense oligonucleotide, and a terminator.

The nucleic acid molecules used for silencing in the methods of the invention (whether introduced into a plant or generated in situ) hybridize with or bind to mRNA transcripts and/or genomic DNA encoding a polypeptide to thereby inhibit expression of the protein, e.g., by inhibiting transcription and/or translation. The hybridization can be by conventional nucleotide complementarity to form a stable duplex, or, for example, in the case of an antisense nucleic acid sequence which binds to DNA duplexes, through specific interactions in the major groove of the double helix. Antisense nucleic acid sequences may be introduced into a plant by transformation or direct injection at a specific tissue site. Alternatively, antisense nucleic acid sequences can be modified to target selected cells and then administered systemically. For example, for systemic administration, antisense nucleic acid sequences can be modified such that they specifically bind to receptors or antigens expressed on a selected cell surface, e.g., by linking the antisense nucleic acid sequence to peptides or antibodies which bind to cell surface receptors or antigens. The antisense nucleic acid sequences can also be delivered to cells using the vectors described herein.

According to a further aspect, the antisense nucleic acid sequence is an a-anomeric nucleic acid sequence. An a-anomeric nucleic acid sequence forms specific double-stranded hybrids with complementary RNA in which, contrary to the usual b-units, the strands run parallel to each other (Gaultier et al. (1987) Nucl Ac Res 15: 6625-6641). The antisense nucleic acid sequence may also comprise a 2'-o-methylribonucleotide (Inoue et al. (1987) Nucl Ac Res 15, 6131-6148) or a chimeric RNA-DNA analogue (Inoue et al. (1987) FEBS Lett. 215, 327-330).

The reduction or substantial elimination of endogenous gene expression may also be performed using ribozymes. Ribozymes are catalytic RNA molecules with ribonuclease activity that are capable of cleaving a single-stranded nucleic acid sequence, such as an mRNA, to which they have a complementary region. Thus, ribozymes (e.g., hammerhead ribozymes (described in Haselhoff and Gerlach (1988) Nature 334, 585-591) can be used to catalytically cleave mRNA transcripts encoding a polypeptide, thereby substantially reducing the number of mRNA transcripts to be translated into a polypeptide. A ribozyme having specificity for a nucleic acid sequence can be designed (see for example: Cech et al. U.S. Pat. No. 4,987,071; and Cech et al. U.S. Pat. No. 5,116,742). Alternatively, mRNA transcripts corresponding to a nucleic acid sequence can be used to select a catalytic RNA having a specific ribonuclease activity from a pool of RNA molecules (Bartel and Szostak (1993) Science 261, 1411-1418). The use of ribozymes for gene silencing in plants is known in the art (e.g., Atkins et al. (1994) WO 94/00012;

Lenne et al. (1995) WO 95/03404; Lutziger et al. (2000) WO 00/00619; Prinsen et al. (1997) WO 97/13865 and Scott et al. (1997) WO 97/38116).

Gene silencing may also be achieved by insertion mutagenesis (for example, T-DNA insertion or transposon insertion) or by strategies as described by, among others, Angell and Baulcombe ((1999) Plant J 20(3): 357-62), (Amplicon VIGS WO 98/36083), or Baulcombe (WO 99/15682).

Gene silencing may also occur if there is a mutation on an endogenous gene and/or a mutation on an isolated gene/nucleic acid subsequently introduced into a plant. The reduction or substantial elimination may be caused by a non-functional polypeptide. For example, the polypeptide may bind to various interacting proteins; one or more mutation(s) and/or truncation(s) may therefore provide for a polypeptide that is still able to bind interacting proteins (such as receptor proteins) but that cannot exhibit its normal function (such as signalling ligand).

A further approach to gene silencing is by targeting nucleic acid sequences complementary to the regulatory region of the gene (e.g., the promoter and/or enhancers) to form triple helical structures that prevent transcription of the gene in target cells. See Helene, C., Anticancer Drug Res. 6, 569-84, 1991; Helene et al., Ann. N.Y. Acad. Sci. 660, 27-36 1992; and Maher, L. J. Bioassays 14, 807-15, 1992.

Other methods, such as the use of antibodies directed to an endogenous polypeptide for inhibiting its function in planta, or interference in the signalling pathway in which a polypeptide is involved, will be well known to the skilled man. In particular, it can be envisaged that manmade molecules may be useful for inhibiting the biological function of a target polypeptide, or for interfering with the signalling pathway in which the target polypeptide is involved.

Alternatively, a screening program may be set up to identify in a plant population natural variants of a gene, which variants encode polypeptides with reduced activity. Such natural variants may also be used for example, to perform homologous recombination.

Artificial and/or natural microRNAs (miRNAs) may be used to knock out gene expression and/or mRNA translation. Endogenous miRNAs are single stranded small RNAs of typically 19-24 nucleotides long. They function primarily to regulate gene expression and/or mRNA translation. Most plant microRNAs (miRNAs) have perfect or near-perfect complementarity with their target sequences. However, there are natural targets with up to five mismatches. They are processed from longer non-coding RNAs with characteristic fold-back structures by double-strand specific RNases of the Dicer family. Upon processing, they are incorporated in the RNA-induced silencing complex (RISC) by binding to its main component, an Argonaute protein. mRNAs serve as the specificity components of RISC, since they base-pair to target nucleic acids, mostly mRNAs, in the cytoplasm. Subsequent regulatory events include target mRNA cleavage and destruction and/or translational inhibition. Effects of miRNA overexpression are thus often reflected in decreased mRNA levels of target genes.

Artificial microRNAs (amiRNAs), which are typically 21 nucleotides in length, can be genetically engineered specifically to negatively regulate gene expression of single or multiple genes of interest. Determinants of plant microRNA target selection are well known in the art. Empirical parameters for target recognition have been defined and can be used to aid in the design of specific amiRNAs, (Schwab et al., Dev. Cell 8, 517-527, 2005). Convenient tools for design and generation of amiRNAs and their precursors are also available to the public (Schwab et al., Plant Cell 18, 1121-1133, 2006).

For optimal performance, the gene silencing techniques used for reducing expression in a plant of an endogenous gene requires the use of nucleic acid sequences from monocotyledonous plants for transformation of monocotyledonous plants, and from dicotyledonous plants for transformation of dicotyledonous plants. Preferably, a nucleic acid sequence from any given plant species is introduced into that same species. For example, a nucleic acid sequence from rice is transformed into a rice plant. However, it is not an absolute requirement that the nucleic acid sequence to be introduced originates from the same plant species as the plant in which it will be introduced. It is sufficient that there is substantial homology between the endogenous target gene and the nucleic acid to be introduced.

Described above are examples of various methods for the reduction or substantial elimination of expression in a plant of an endogenous gene. A person skilled in the art would readily be able to adapt the aforementioned methods for silencing so as to achieve reduction of expression of an endogenous gene in a whole plant or in parts thereof through the use of an appropriate promoter, for example.

Selectable Marker (Gene)/Reporter Gene

"Selectable marker", "selectable marker gene" or "reporter gene" includes any gene that confers a phenotype on a cell in which it is expressed to facilitate the identification and/or selection of cells that are transfected or transformed with a nucleic acid construct of the invention. These marker genes enable the identification of a successful transfer of the nucleic acid molecules via a series of different principles. Suitable markers may be selected from markers that confer antibiotic or herbicide resistance, that introduce a new metabolic trait or that allow visual selection. Examples of selectable marker genes include genes conferring resistance to antibiotics (such as nptII that phosphorylates neomycin and kanamycin, or hpt, phosphorylating hygromycin, or genes conferring resistance to, for example, bleomycin, streptomycin, tetracyclin, chloramphenicol, ampicillin, gentamycin, geneticin (G418), spectinomycin or blasticidin), to herbicides (for example bar which provides resistance to Basta®; aroA or gox providing resistance against glyphosate, or the genes conferring resistance to, for example, imidazolinone, phosphinothricin or sulfonylurea), or genes that provide a metabolic trait (such as manA that allows plants to use mannose as sole carbon source or xylose isomerase for the utilisation of xylose, or antinutritive markers such as the resistance to 2-deoxyglucose). Expression of visual marker genes results in the formation of colour (for example β-glucuronidase, GUS or β-galactosidase with its coloured substrates, for example X-Gal), luminescence (such as the luciferin/luceferase system) or fluorescence (Green Fluorescent Protein, GFP, and derivatives thereof). This list represents only a small number of possible markers. The skilled worker is familiar with such markers. Different markers are preferred, depending on the organism and the selection method.

It is known that upon stable or transient integration of nucleic acids into plant cells, only a minority of the cells takes up the foreign DNA and, if desired, integrates it into its genome, depending on the expression vector used and the transfection technique used. To identify and select these integrants, a gene coding for a selectable marker (such as the ones described above) is usually introduced into the host cells together with the gene of interest. These markers can for example be used in mutants in which these genes are not functional by, for example, deletion by conventional methods. Furthermore, nucleic acid molecules encoding a selectable marker can be introduced into a host cell on the same vector that comprises the sequence encoding the polypeptides of the invention or used in the methods of the invention, or else in a separate vector. Cells which have been stably transfected with the introduced nucleic acid can be identified for example by selection (for example, cells which have integrated the selectable marker survive whereas the other cells die). The marker genes may be removed or excised from the transgenic cell once they are no longer needed. Techniques for marker gene removal are known in the art, useful techniques are described above in the definitions section.

Since the marker genes, particularly genes for resistance to antibiotics and herbicides, are no longer required or are undesired in the transgenic host cell once the nucleic acids have been introduced successfully, the process according to the invention for introducing the nucleic acids advantageously employs techniques which enable the removal or excision of these marker genes. One such a method is what is known as co-transformation. The co-transformation method employs two vectors simultaneously for the transformation, one vector bearing the nucleic acid according to the invention and a second bearing the marker gene(s). A large proportion of transformants receives or, in the case of plants, comprises (up to 40% or more of the transformants), both vectors. In case of transformation with *Agrobacteria*, the transformants usually receive only a part of the vector, i.e. the sequence flanked by the T-DNA, which usually represents the expression cassette. The marker genes can subsequently be removed from the transformed plant by performing crosses. In another method, marker genes integrated into a transposon are used for the transformation together with desired nucleic acid (known as the Ac/Ds technology). The transformants can be crossed with a transposase source or the transformants are transformed with a nucleic acid construct conferring expression of a transposase, transiently or stable. In some cases (approx. 10%), the transposon jumps out of the genome of the host cell once transformation has taken place successfully and is lost. In a further number of cases, the transposon jumps to a different location. In these cases the marker gene must be eliminated by performing crosses. In microbiology, techniques were developed which make possible, or facilitate, the detection of such events. A further advantageous method relies on what is known as recombination systems; whose advantage is that elimination by crossing can be dispensed with. The best-known system of this type is what is known as the Cre/lox system. Cre1 is a recombinase that removes the sequences located between the loxP sequences. If the marker gene is integrated between the loxP sequences, it is removed once transformation has taken place successfully, by expression of the recombinase. Further recombination systems are the HIN/HIX, FLP/FRT and REP/STB system (Tribble et al., J. Biol. Chem., 275, 2000: 22255-22267; Velmurugan et al., J. Cell Biol., 149, 2000: 553-566). A site-specific integration into the plant genome of the nucleic acid sequences according to the invention is possible. Naturally, these methods can also be applied to microorganisms such as yeast, fungi or bacteria.

Transgenic/Transgene/Recombinant

For the purposes of the invention, “transgenic”, “transgene” or “recombinant” means with regard to, for example, a nucleic acid sequence, an expression cassette, gene construct or a vector comprising the nucleic acid sequence or an organism transformed with the nucleic acid sequences, expression cassettes or vectors according to the invention, all those constructions brought about by recombinant methods in which either (a) the nucleic acid sequences encoding proteins useful in the methods of the invention, or (b) genetic control sequence(s) which is operably linked with the nucleic acid sequence according to the invention, for example a promoter, or (c) a) and b)

are not located in their natural genetic environment or have been modified by recombinant methods, it being possible for the modification to take the form of, for example, a substitution, addition, deletion, inversion or insertion of one or more nucleotide residues. The natural genetic environment is understood as meaning the natural genomic or chromosomal locus in the original plant or the presence in a genomic library. In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp. A naturally occurring expression cassette—for example the naturally occurring combination of the natural promoter of the nucleic acid sequences with the corresponding nucleic acid sequence encoding a polypeptide useful in the methods of the present invention, as defined above—becomes a transgenic expression cassette when this expression cassette is modified by non-natural, synthetic (“artificial”) methods such as, for example, mutagenic treatment. Suitable methods are described, for example, in U.S. Pat. No. 5,565,350 or WO 00/15815.

A transgenic plant for the purposes of the invention is thus understood as meaning, as above, that the nucleic acids used in the method of the invention are not at their natural locus in the genome of said plant, it being possible for the nucleic acids to be expressed homologously or heterologously. However, as mentioned, transgenic also means that, while the nucleic acids according to the invention or used in the inventive method are at their natural position in the genome of a plant, the sequence has been modified with regard to the natural sequence, and/or that the regulatory sequences of the natural sequences have been modified. Transgenic is preferably understood as meaning the expression of the nucleic acids according to the invention at an unnatural locus in the genome, i.e. homologous or, preferably, heterologous expression of the nucleic acids takes place. Preferred transgenic plants are mentioned herein.

Transformation

The term “introduction” or “transformation” as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

The transfer of foreign genes into the genome of a plant is called transformation. Transformation of plant species is now a fairly routine technique. Advantageously, any of several transformation methods may be used to introduce the gene of interest into a suitable ancestor cell. The methods described for the transformation and regeneration of plants from plant tissues or plant cells may be utilized for transient or for stable transformation. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., (1982) Nature 296, 72-74; Negrutiu I et al. (1987) Plant Mol Biol 8: 363-373); electroporation of protoplasts (Shillito R. D. et al. (1985) Bio/Technol 3, 1099-1102); microinjection into plant material (Crossway A et al., (1986) Mol. Gen Genet 202: 179-185); DNA or RNA-coated particle bombardment (Klein T M et al., (1987) Nature 327: 70) infection with (non-integrative) viruses and the like. Transgenic plants, including transgenic crop plants, are preferably produced via *Agrobacterium*-mediated transformation. An advantageous transformation method is the transformation in planta. To this end, it is possible, for example, to allow the *agrobacteria* to act on plant seeds or to inoculate the plant meristem with *agrobacteria*. It has proved particularly expedient in accordance with the invention to allow a suspension of transformed *agrobacteria* to act on the intact plant or at least on the flower primordia. The plant is subsequently grown on until the seeds of the treated plant are obtained (Clough and Bent, Plant J. (1998) 16, 735-743). Methods for *Agrobacterium*-mediated transformation of rice include well known methods for rice transformation, such as those described in any of the following: European patent application EP 1198985 A1, Aldemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al. (Nat. Biotechnol 14(6): 745-50, 1996) or Frame et al. (Plant Physiol 129(1): 13-22, 2002), which disclosures are incorporated by reference herein as if fully set forth. Said methods are further described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The nucleic acids or the construct to be expressed is preferably cloned into a vector, which is suitable for transforming *Agrobacterium tumefaciens*, for example pBin19 (Bevan et al., Nucl. Acids Res. 12 (1984) 8711). *Agrobacteria* transformed by such a vector can then be used in known manner for the transformation of plants, such as plants used as a model, like *Arabidopsis* (*Arabidopsis thaliana* is within the scope of the present invention not considered as a crop plant), or crop plants such as, by way of example, tobacco plants, for example by immersing bruised leaves or chopped leaves in an agrobacterial solution and then culturing them in suitable media. The transformation of plants by means of *Agrobacterium tumefaciens* is described, for example, by Höfgen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

In addition to the transformation of somatic cells, which then have to be regenerated into intact plants, it is also possible to transform the cells of plant meristems and in particular those cells which develop into gametes. In this case, the transformed gametes follow the natural plant development, giving rise to transgenic plants. Thus, for example, seeds of *Arabidopsis* are treated with *agrobacteria* and seeds are obtained from the developing plants of which a certain proportion is transformed and thus transgenic [Feldman, K A and Marks M D (1987). Mol Gen Genet 208:274-289; Feldmann K (1992). In: C Koncz, N-H Chua and J Shell, eds, Methods in *Arabidopsis* Research. Word Scientific, Singapore, pp. 274-289]. Alternative methods are based on the repeated removal of the inflorescences and incubation of the excision site in the center of the rosette with transformed *agrobacteria*, whereby transformed seeds can likewise be obtained at a later point in time (Chang (1994). Plant J. 5: 551-558; Katavic (1994). Mol Gen Genet, 245: 363-370). However, an especially effective method is the vacuum infiltration method with its modifications such as the "floral dip" method. In the case of vacuum infiltration of *Arabidopsis*, intact plants under reduced pressure are treated with an agrobacterial suspension [Bechthold, N (1993). C R Acad Sci Paris Life Sci, 316: 1194-1199], while in the case of the "floral dip" method the developing floral tissue is incubated briefly with a surfactant-treated agrobacterial suspension [Clough, S J and Bent A F (1998) The Plant J. 16, 735-743]. A certain proportion of transgenic seeds are harvested in both cases, and these seeds can be distinguished from non-transgenic seeds by growing under the above-described selective conditions. In addition the stable transformation of plastids is of advantages because plastids are inherited maternally is most crops reducing or eliminating the risk of transgene flow through pollen. The transformation of the chloroplast genome is generally achieved by a process which has been schematically displayed in Klaus et al., 2004 [Nature Biotechnology 22 (2), 225-229]. Briefly the sequences to be transformed are cloned together with a selectable marker gene between flanking sequences homologous to the chloroplast genome. These homologous flanking sequences direct site specific integration into the plastome. Plastidal transformation has been described for many different plant species and an overview is given in Bock (2001) Transgenic plastids in basic research and plant biotechnology. J Mol Biol. 2001 Sep. 21; 312 (3): 425-38 or Maliga, P (2003) Progress towards commercialization of plastid transformation technology. Trends Biotechnol. 21, 20-28. Further biotechnological progress has recently been reported in form of marker free plastid transformants, which can be produced by a transient co-integrated maker gene (Klaus et al., 2004, Nature Biotechnology 22(2), 225-229).

T-DNA Activation Tagging

T-DNA activation tagging (Hayashi et al. Science (1992) 1350-1353), involves insertion of T-DNA, usually containing a promoter (may also be a translation enhancer or an intron), in the genomic region of the gene of interest or 10 kb up- or downstream of the coding region of a gene in a configuration such that the promoter directs expression of the targeted gene. Typically, regulation of expression of the targeted gene by its natural promoter is disrupted and the gene falls under the control of the newly introduced promoter. The promoter is typically embedded in a T-DNA. This T-DNA is randomly inserted into the plant genome, for example, through *Agrobacterium* infection and leads to modified expression of genes near the inserted T-DNA. The resulting transgenic plants show dominant phenotypes due to modified expression of genes close to the introduced promoter.

TILLING

The term "TILLING" is an abbreviation of "Targeted Induced Local Lesions In Genomes" and refers to a mutagenesis technology useful to generate and/or identify nucleic acids encoding proteins with modified expression and/or activity. TILLING also allows selection of plants carrying such mutant variants. These mutant variants may exhibit modified expression, either in strength or in location or in timing (if the mutations affect the promoter for example). These mutant variants may exhibit higher activity than that exhibited by the gene in its natural form. TILLING combines high-density mutagenesis with high-throughput screening methods. The steps typically followed in TILLING are: (a) EMS mutagenesis (Redei G P and Koncz C (1992) In Methods in *Arabidopsis* Research, Koncz C, Chua N H, Schell J, eds. Singapore, World Scientific Publishing Co, pp. 16-82; Feldmann et al., (1994) In Meyerowitz E M, Somerville C R, eds, *Arabidopsis*. Cold Spring Harbor Laboratory Press, Cold Spring Harbor, N.Y., pp 137-172; Lightner J and Caspar T (1998) In J Martinez-Zapater, J Salinas, eds, Methods on Molecular Biology, Vol. 82. Humana Press, Totowa, N.J., pp 91-104); (b) DNA preparation and pooling of individuals; (c) PCR amplification of a region of interest; (d) denaturation and annealing to allow formation of heteroduplexes; (e) DHPLC, where the presence of a heteroduplex in a pool is detected as an extra peak in the chromatogram; (f) identification of the mutant individual; and (g) sequencing of the mutant PCR product. Methods for TILLING are well known in the art (McCallum et al., (2000) Nat Biotechnol 18: 455-457; reviewed by Stemple (2004) Nat Rev Genet 5(2): 145-50).

Homologous Recombination

Homologous recombination allows introduction in a genome of a selected nucleic acid at a defined selected position. Homologous recombination is a standard technology used routinely in biological sciences for lower organisms such as yeast or the moss *Physcomitrella*. Methods for performing homologous recombination in plants have been described not only for model plants (Offringa et al. (1990) EMBO J 9(10): 3077-84) but also for crop plants, for example rice (Terada et al. (2002) Nat Biotech 20(10): 1030-4; Iida and Terada (2004) Curr Opin Biotech 15(2): 132-8), and approaches exist that are generally applicable regardless of the target organism (Miller et al, Nature Biotechnol. 25, 778-785, 2007).

Yield

The term "yield" in general means a measurable produce of economic value, typically related to a specified crop, to an area, and to a period of time. Individual plant parts directly contribute to yield based on their number, size and/or weight, or the actual yield is the yield per square meter for a crop and year, which is determined by dividing total production (includes both harvested and appraised production) by planted square meters. The term "yield" of a plant may relate to vegetative biomass (root and/or shoot biomass), to reproductive organs, and/or to propagules (such as seeds) of that plant.

Early Vigour

"Early vigour" refers to active healthy well-balanced growth especially during early stages of plant growth, and may result from increased plant fitness due to, for example, the plants being better adapted to their environment (i.e. optimizing the use of energy resources and partitioning between shoot and root). Plants having early vigour also show increased seedling survival and a better establishment of the crop, which often results in highly uniform fields (with the crop growing in uniform manner, i.e. with the majority of plants reaching the various stages of development at substantially the same time), and often better and higher yield. Therefore, early vigour may be determined by measuring various factors, such as thousand kernel weight, percentage germination, percentage emergence, seedling growth, seedling height, root length, root and shoot biomass and many more.

Increase/Improve/Enhance

The terms "increase", "improve" or "enhance" are interchangeable and shall mean in the sense of the application at least a 3%, 4%, 5%, 6%, 7%, 8%, 9% or 10%, preferably at least 15% or 20%, more preferably 25%, 30%, 35% or 40% more yield and/or growth in comparison to control plants as defined herein.

Seed Yield

Increased seed yield may manifest itself as one or more of the following: a) an increase in seed biomass (total seed weight) which may be on an individual seed basis and/or per plant and/or per square meter; b) increased number of flowers per plant; c) increased number of (filled) seeds; d) increased seed filling rate (which is expressed as the ratio between the number of filled seeds divided by the total number of seeds); e) increased harvest index, which is expressed as a ratio of the yield of harvestable parts, such as seeds, divided by the total biomass; and f) increased thousand kernel weight (TKW), and g) increased number of primary panicles, which is extrapolated from the number of filled seeds counted and their total weight. An increased TKW may result from an increased seed size and/or seed weight, and may also result from an increase in embryo and/or endosperm size.

An increase in seed yield may also be manifested as an increase in seed size and/or seed volume. Furthermore, an increase in seed yield may also manifest itself as an increase in seed area and/or seed length and/or seed width and/or seed perimeter. Increased seed yield may also result in modified architecture, or may occur because of modified architecture.

Greenness Index

The "greenness index" as used herein is calculated from digital images of plants. For each pixel belonging to the plant object on the image, the ratio of the green value versus the red value (in the RGB model for encoding color) is calculated. The greenness index is expressed as the percentage of pixels for which the green-to-red ratio exceeds a given threshold. Under normal growth conditions, under salt stress growth conditions, and under reduced nutrient availability growth conditions, the greenness index of plants is measured in the last imaging before flowering. In contrast, under drought stress growth conditions, the greenness index of plants is measured in the first imaging after drought.

Plant

The term "plant" as used herein encompasses whole plants, ancestors and progeny of the plants and plant parts, including seeds, shoots, stems, leaves, roots (including tubers), flowers, and tissues and organs, wherein each of the aforementioned comprise the gene/nucleic acid of interest. The term "plant" also encompasses plant cells, suspension cultures, callus tissue, embryos, meristematic regions, gametophytes, sporophytes, pollen and microspores, again wherein each of the aforementioned comprises the gene/nucleic acid of interest.

Plants that are particularly useful in the methods of the invention include all plants which belong to the superfamily Viridiplantae, in particular monocotyledonous and dicotyledonous plants including fodder or forage legumes, ornamental plants, food crops, trees or shrubs selected from the list comprising *Acer* spp., *Actinidia* spp., *Abelmoschus* spp., *Agave sisalana, Agropyron* spp., *Agrostis stolonifera, Allium* spp., *Amaranthus* spp., *Ammophila arenaria, Ananas comosus, Annona* spp., *Apium graveolens, Arachis* spp, *Artocarpus* spp., *Asparagus officinalis, Avena* spp. (e.g. *Avena sativa, Avena fatua, Avena byzantina, Avena fatua* var. *sativa, Avena hybrida*), *Averrhoa carambola, Bambusa* sp., *Benincasa hispida, Bertholletia excelsea, Beta vulgaris, Brassica* spp. (e.g.

*Brassica napus, Brassica rapa* ssp. [canola, oilseed rape, turnip rape]), *Cadaba farinosa, Camellia sinensis, Canna indica, Cannabis sativa, Capsicum* spp., *Carex elata, Carica papaya, Carissa macrocarpa, Carya* spp., *Carthamus tinctorius, Castanea* spp., *Ceiba pentandra, Cichorium endivia, Cinnamomum* spp., *Citrullus lanatus, Citrus* spp., *Cocos* spp., *Coffea* spp., *Colocasia esculenta, Cola* spp., *Corchorus* sp., *Coriandrum sativum, Corylus* spp., *Crataegus* spp., *Crocus sativus, Cucurbita* spp., *Cucumis* spp., *Cynara* spp., *Daucus carota, Desmodium* spp., *Dimocarpus longan, Dioscorea* spp., *Diospyros* spp., *Echinochloa* spp., *Elaeis* (e.g. *Elaeis guineensis, Elaeis oleifera*), *Eleusine coracana, Eragrostis tef, Erianthus* sp., *Eriobotrya japonica, Eucalyptus* sp., *Eugenia uniflora, Fagopyrum* spp., *Fagus* spp., *Festuca arundinacea, Ficus carica, Fortunella* spp., *Fragaria* spp., *Ginkgo biloba, Glycine* spp. (e.g. *Glycine max, Soja hispida* or *Soja max*), *Gossypium hirsutum, Helianthus* spp. (e.g. *Helianthus annuus*), *Hemerocallis fulva, Hibiscus* spp., *Hordeum* spp. (e.g. *Hordeum vulgare*), *Ipomoea batatas, Juglans* spp., *Lactuca sativa, Lathyrus* spp., *Lens culinaris, Linum usitatissimum, Litchi chinensis, Lotus* spp., *Luffa acutangula, Lupinus* spp., *Luzula sylvatica, Lycopersicon* spp. (e.g. *Lycopersicon esculentum, Lycopersicon lycopersicum, Lycopersicon pyriforme*), *Macrotyloma* spp., *Malus* spp., *Malpighia emarginata, Mammea americana, Mangifera indica, Manihot* spp., *Manilkara zapota, Medicago sativa, Melilotus* spp., *Mentha* spp., *Miscanthus sinensis, Momordica* spp., *Morus nigra, Musa* spp., *Nicotiana* spp., *Olea* spp., *Opuntia* spp., *Ornithopus* spp., *Oryza* spp. (e.g. *Oryza sativa, Oryza latifolia*), *Panicum miliaceum, Panicum virgatum, Passiflora edulis, Pastinaca sativa, Pennisetum* sp., *Persea* spp., *Petroselinum crispum, Phalaris arundinacea, Phaseolus* spp., *Phleum pratense, Phoenix* spp., *Phragmites australis, Physalis* spp., *Pinus* spp., *Pistacia vera, Pisum* spp., *Poa* spp., *Populus* spp., *Prosopis* spp., *Prunus* spp., *Psidium* spp., *Punica granatum, Pyrus communis, Quercus* spp., *Raphanus sativus, Rheum rhabarbarum, Ribes* spp., *Ricinus communis, Rubus* spp., *Saccharum* spp., *Salix* sp., *Sambucus* spp., *Secale cereale, Sesamum* spp., *Sinapis* sp., *Solanum* spp. (e.g. *Solanum tuberosum, Solanum integrifolium* or *Solanum lycopersicum*), *Sorghum bicolor, Spinacia* spp., *Syzygium* spp., *Tagetes* spp., *Tamarindus indica, Theobroma cacao, Trifolium* spp., *Tripsacum dactyloides, Triticale* sp., *Triticosecale rimpaui, Triticum* spp. (e.g. *Triticum aestivum, Triticum durum, Triticum turgidum, Triticum hybernum, Triticum macha, Triticum sativum, Triticum monococcum* or *Triticum vulgare*), *Tropaeolum minus, Tropaeolum majus, Vaccinium* spp., *Vicia* spp., *Vigna* spp., *Viola odorata, Vitis* spp., *Zea mays, Zizania palustris, Ziziphus* spp., amongst others.

DETAILED DESCRIPTION OF THE INVENTION

Surprisingly, it has now been found that modulating expression in a plant of a nucleic acid encoding a RHL1 polypeptide gives plants having enhanced yield-related traits relative to control plants. According to a first embodiment, the present invention provides a method for enhancing yield-related traits in plants relative to control plants, comprising modulating expression in a plant of a nucleic acid encoding a RHL1 polypeptide.

Furthermore, surprisingly, it has now been found that increasing expression in a plant of a nucleic acid sequence encoding a TGase polypeptide as defined herein, gives plants having increased seed yield-related traits relative to control plants. According to a first embodiment, the present invention provides a method for increasing seed yield-related traits in plants relative to control plants, comprising increasing expression in a plant of a nucleic acid sequence encoding a TGase polypeptide.

Furthermore, surprisingly, it has now been found that modulating expression in a plant of a nucleic acid encoding a TRY-like polypeptide gives plants having enhanced yield-related traits relative to control plants. According to a first embodiment, the present invention provides a method for enhancing yield-related traits in plants relative to control plants, comprising modulating expression in a plant of a nucleic acid encoding a TRY-like polypeptide and optionally selecting for plants having enhanced yield-related traits.

Furthermore, surprisingly, it has now been found that modulating expression in a plant of a nucleic acid encoding a BZR polypeptide gives plants having increased seed yield relative to control plants. According to a first embodiment, the present invention provides a method for increasing seed yield in plants relative to control plants, comprising modulating expression in a plant of a nucleic acid encoding a BZR polypeptide.

A preferred method for modulating (preferably, increasing) expression of a nucleic acid sequence encoding a RHL1 polypeptide, or a TGase polypeptide, or a TRY-like polypeptide, or a BZR polypeptide, is by introducing and expressing in a plant a nucleic acid sequence encoding a RHL1 polypeptide, or a TGase polypeptide, or a TRY-like polypeptide, or a BZR polypeptide.

Concerning BZR polypeptides, in a further preferred embodiment the invention provides a method for increasing seed yield in plants relative to control plants, comprising modulating expression in a plant of a nucleic acid encoding a BZR polypeptide wherein said modulation is effected by introducing a nucleic acid encoding a BZR polypeptide under the control of a plant derived promoter.

Concerning RHL1 polypeptides, any reference hereinafter to a "protein useful in the methods of the invention" is taken to mean a RHL1 polypeptide as defined herein. Any reference hereinafter to a "nucleic acid useful in the methods of the invention" is taken to mean a nucleic acid capable of encoding such a RHL1 polypeptide. The nucleic acid to be introduced into a plant (and therefore useful in performing the methods of the invention) is any nucleic acid encoding the type of protein which will now be described, hereafter also named "RHL1 nucleic acid" or "RHL1 gene".

An RHL1 polypeptide" as defined herein refers to any polypeptide comprising a sequence having in increasing order of preference 25%, 30%, 35%, 40%, 45%, 50%, 55%, 60%, 65%, 70%, 75%, 80%, 85%, 90%, 95%, 96%, 97%, 98%, 99% or more sequence identity to the amino acid sequence of any of the polypeptides of Table A1.

A preferred RHL1 polypeptide useful in the methods of the invention comprises a sequence having in increasing order of preference 50%, 55%, 60%, 65%, 70%, 75%, 80%, 85%, 90%, 95%, 96%, 97%, 98%, 99% or more sequence identity to the amino acid sequence of any of the polypeptides of SEQ ID NO: 2 or SEQ ID NO: 10, more preferably comprises SEQ ID NO: 2.

Various conserved protein motifs are found RHL1 polypeptides. Methods to find conserved protein domain in a group of related sequences are well known in the art. Example 4 details the use of one such method, the MEME system, to identify conserved protein motifs in RHL1 polypeptides.

A further preferred RHL1 polypeptide useful in the methods of the invention comprises one or more of the following motifs:

(i) a motif having in increasing order of preference 50%, 55%, 60%, 65%, 70%, 75%, 80%, 85%, 90%, 95%, 96%, 97%, 98%, 99% or more sequence identity to the amino acid sequence of Motif 1: [IV]R[RK][KG][SG]QRK[NS][RK][FY]LFSFPGLLAP (SEQ ID NO: 29);

(ii) a motif having in increasing order of preference 50%, 55%, 60%, 65%, 70%, 75%, 80%, 85%, 90%, 95%, 96%, 97%, 98%, 99% or more sequence identity to the amino acid sequence of Motif 2: SGG[KR][IV]G[ED]L[KA]DL[GD]TKNP [ILV]LYLDFPQG[RQ]MKL] (SEQ ID NO: 30);

(iii) a motif having in increasing order of preference 50%, 55%, 60%, 65%, 70%, 75%, 80%, 85%, 90%, 95%, 96%, 97%, 98%, 99% or more sequence identity to the amino acid sequence of Motif 3: TP[VS]RQSART-AGKK[FL][KN][FY][AT]ExSS (SEQ ID NO: 31);

(iv) a motif having in increasing order of preference 50%, 55%, 60%, 65%, 70%, 75%, 80%, 85%, 90%, 95%, 96%, 97%, 98%, 99% or more sequence identity to the amino acid sequence of Motif 4: GTK[ED]ENPEE[LA][RK]L[DE]FPKE[LF]Q [ENQ][GD] (SEQ ID NO: 32);

(v) a motif having in increasing order of preference 50%, 55%, 60%, 65%, 70%, 75%, 80%, 85%, 90%, 95%, 96%, 97%, 98%, 99% or more sequence identity to the amino acid sequence of Motif 5: [SN][GN][NL]L[LQV][SR][EDG]xP[AS][KA]PR[SA][APS]LAPSK[TAG]VL[KR][HL][HQ]G[KR]D (SEQ ID NO: 33);

(vi) a motif having in increasing order of preference 50%, 55%, 60%, 65%, 70%, 75%, 80%, 85%, 90%, 95%, 96%, 97%, 98%, 99% or more sequence identity to the amino acid sequence of Motif 6: HA[ED][CY]DFKG-GAGAA[CS]D[ES][KA]Q (SEQ ID NO: 34);

(vii) a motif having in increasing order of preference 50%, 55%, 60%, 65%, 70%, 75%, 80%, 85%, 90%, 95%, 96%, 97%, 98%, 99% or more sequence identity to the amino acid sequence of Motif 7: [KSN][KEP]P[GEK][EKT][KTE][YT][VT][EG][EPST][ELQ]SP[KE][IT][ED][SLV][ED][DI][DV][LS]S[ED][DE][SD][NDS][LD]K[DK] (SEQ ID NO: 35);

(viii) a motif having in increasing order of preference 50%, 55%, 60%, 65%, 70%, 75%, 80%, 85%, 90%, 95%, 96%, 97%, 98%, 99% or more sequence identity to the amino acid sequence of Motif 8: KG[PA]AAKKQRASP[EM][EA]K[HQ]P[TA]G[KI]K (SEQ ID NO: 36).

Wherein the amino acids between square brackets are alternatives.

Alternatively a preferred RHL1 polypeptide useful in the methods of the invention comprises:

A. a motif having in increasing order of preference 50%, 55%, 60%, 65%, 70%, 75%, 80%, 85%, 90%, 95%, 96%, 97%, 98%, 99% or more sequence identity to the amino acid sequence of one or more of the following motifs:

```
(i) Motif 9:
                                              (SEQ ID NO: 37)
(SN) VMC (ED) D (YV) F (DE) (NS) (ML) (IV) VFS

(DE) AWWIG (TR) K (ED) ENPEE;

(ii) Motif 10:
                                              (SEQ ID NO: 38)
L (AILV) A (PA) (IVA) (SA) GG (KR) (IVF) G (ED)

L (KA) DL (GDS) (TS) KNP (IVL) LYLDFPQ;

(iii) Motif 11:
                                              (SEQ ID NO: 39)
G (RQ) (ML) KLFGTI (VL) YPKN (RK) Y (LI) TLQF;
```

Wherein the amino acids between brackets (alternative amino acids at that position), are alternatives; or B. any one or more of the following motifs:

```
(i) Motif 9:
                                              (SEQ ID NO: 37)
(SN) VMC (ED) D (YV) F (DE) (NS) (ML) (IV) VFS

(DE) AWWIG (TR) K (ED) ENPEE;

(ii) Motif 10:
                                              (SEQ ID NO: 38)
L (AILV) A (PA) (IVA) (SA) GG (KR) (IVF) G (ED) L

(KA) DL (GDS) (TS) KNP (IVL) LYLDFPQ;

(iii) Motif 11:
                                              (SEQ ID NO: 39)
G (RQ) (ML) KLFGTI (VL) YPKN (RK) Y (LI) TLQF;
```

Wherein the amino acids between brackets are alternatives (alternative amino acids at that position), and wherein in increasing order of preference 0, 1, 2, 3, 4, 5, 6, 7, 8, 9, 10 amino acids are substituted by any other amino acid, preferably by a conservative amino acid.

An even further preferred RHL1 polypeptides useful in the methods of the invention are paralogous or orthologous proteins of any of the polypeptides of Table A.

Alternatively, the homologue of an RHL1 protein has in increasing order of preference at least 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% overall sequence identity to the amino acid represented by SEQ ID NO: 2, provided that the homologous protein comprises one of the conserved motifs as outlined above. The overall sequence identity is determined using a global alignment algorithm, such as the Needleman Wunsch algorithm in the program GAP (GCG Wisconsin Package, Accelrys), preferably with default parameters. Compared to overall sequence identity, the sequence identity will generally be higher when only conserved domains or motifs are considered.

Preferably, the polypeptide sequence which when used in the construction of a phylogenetic tree, such as the one depicted in FIG. 3, clusters with any of the RHL1 polypeptides originating from a dicotyledoneous plant comprising the amino acid sequence represented by SEQ ID NO: 2 rather than with any other group.

Concerning TGase, any reference hereinafter to a "protein useful in the methods of the invention" is taken to mean a TGase polypeptide as defined herein. Any reference hereinafter to a "nucleic acid sequence useful in the methods of the invention" is taken to mean a nucleic acid sequence capable of encoding such a TGase polypeptide. The nucleic acid sequence to be introduced into a plant (and therefore useful in performing the methods of the invention) is any nucleic acid sequence encoding the type of polypeptide, which will now be described, hereafter also named "TGase nucleic acid sequence" or "TGase gene".

A "TGase polypeptide" as defined herein refers to any polypeptide comprising (i) a plastidic transit peptide; (ii) in increasing order of preference at least 50%, 55%, 60%, 65%, 70%, 75%, 80%, 85%, 90%, 95%, 98%, 99% or more amino acid sequence identity to a domain comprising at least one coiled coil as represented by SEQ ID NO: 70; (iii) and an Integrated relational Enzyme database entry EC 2.3.2.13 for protein-glutamine γ-glutamyltransferase.

Alternatively or additionally, a "TGase polypeptide" as defined herein refers to any polypeptide sequence having (i) a plastidic transit peptide; (ii) in increasing order of preference at least 50%, 55%, 60%, 65%, 70%, 75%, 80%, 85%, 90%, 95%, 98%, 99% or more amino acid sequence identity to a polypeptide as represented by SEQ ID NO: 45.

Alternatively or additionally, a "TGase polypeptide" as defined herein refers to any polypeptide having in increasing order of preference at least 50%, 55%, 60%, 65%, 70%, 75%, 80%, 85%, 90%, 95%, 98%, 99% or more amino acid sequence identity to a TGase polypeptide as represented by SEQ ID NO: 45, or to any of the polypeptide sequences given in Table A2 herein.

Alternatively or additionally, a "TGase polypeptide" as defined herein refers to any polypeptide sequence which when used in the construction of a TGase phylogenetic tree, such as the one depicted in FIG. 5, clusters with the clade of TGase polypeptides comprising the polypeptide sequence as represented by SEQ ID NO: 45 (marked by an arrow in FIG. 5; TGases from plants are delimited by a bracket in FIG. 5), rather than with the other clades.

Alternatively or additionally, a "TGase polypeptide" is a polypeptide with enzymatic activity consisting in catalyzing the formation of amide linkages, generally in a Ca-dependent fashion, between the primary amine of an amine donor substrate and the γ-carboxamide group of peptide-bound endoglutamine residues in proteins or polypeptides that are the amine acceptors.

Concerning any reference hereinafter to a "protein useful in the methods of the invention" is taken to mean a TRY-like polypeptide as defined herein. Any reference hereinafter to a "nucleic acid useful in the methods of the invention" is taken to mean a nucleic acid capable of encoding such a TRY-like polypeptide. The nucleic acid to be introduced into a plant (and therefore useful in performing the methods of the invention) is any nucleic acid encoding the type of protein which will now be described, hereafter also named "TRY-like nucleic acid" or "TRY-like gene".

A "TRY-like polypeptide" as defined herein refers to any polypeptide comprising a Myb-like DNA-binding domain (PFam domain PF00249.17, SMART domain SM00717, ProfileScan domain PS50090, Panther PTHR10641:SF26).

Preferably, the TRY-like polypeptide comprises one or more of the following motifs:

```
Motif 12: [FM] [ST] E EE LIIRM [YHF] [NKR] LVG
[EDN] RW [SE] LIAGRI
Motif 13: PGR AEEIE [KR] [YF] WT [SM] [RK]
Motif 14: EEVSS [QT] [ED] [SW] [EK] [FL] [IE]
Motif 15: E [ED] [LI] [IV] X [RK] [LFM] XL [LFV]
G [NED] [RK] WX [LI] I A [GRK] R [LIV] [PV] GR
[NEKG] [EQ] [IVQ]
```

wherein X on position 6 may be any amino acid, but preferably one of I, V, L, Y, S, F, C, or T; and wherein X on position 10 may be any amino acid, but preferably one of R, K, E, S, T, or N; and wherein X on position 17 may be any amino acid, but preferably one of S, D, A, E, P, or T. Preferably Motif 15 is EE[DT][LI][IV]XRM[HY][RKN]LVG[NED]RWX[LI]IA[GR]R[IV][PV]GR[TKEQ][AP][NEKG]E[IVQ]

wherein X on position 6 may be any amino acid, but preferably one of Y, S, F, C, or T; and wherein X on position 17 may be any amino acid, but preferably one of D, A, E, P, or T.

More preferably, the TRY-like polypeptide comprises in increasing order of preference, at least 2, at least 3, or all 4 motifs.

Alternatively, the homologue of a TRY-like protein has in increasing order of preference at least 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% overall sequence identity to the amino acid represented by SEQ ID NO: 76, provided that the homologous protein comprises the conserved motifs as outlined above. The overall sequence identity is determined using a global alignment algorithm, such as the Needleman Wunsch algorithm in the program GAP (GCG Wisconsin Package, Accelrys), preferably with default parameters and preferably with sequences of mature proteins (i.e. without taking into account secretion signals or transit peptides). Compared to overall sequence identity, the sequence identity will generally be higher when only conserved domains or motifs are considered. Preferably the motifs in a TRY-like polypeptide have, in increasing order of preference, at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to the motifs represented by SEQ ID NO: 229 to SEQ ID NO: 232 (Motifs 12 to 15).

Preferably, the polypeptide sequence which when used in the construction of a phylogenetic tree, constructed with the polypeptide sequences of Table A3, clusters with the group of TRY-like polypeptides comprising the amino acid sequence represented by SEQ ID NO: 76 (At5g53200) rather than with any other group.

Concerning BZR polypeptides, any reference hereinafter to a "protein useful in the methods of the invention" is taken to mean a BZR polypeptide as defined herein. Any reference hereinafter to a "nucleic acid useful in the methods of the invention" is taken to mean a nucleic acid capable of encoding such a BZR polypeptide. The nucleic acid to be introduced into a plant (and therefore useful in performing the methods of the invention) is any nucleic acid encoding the type of protein which will now be described, hereafter also named "BZR nucleic acid" or "BZR gene".

A "BZR polypeptide" as defined herein refers to any transcription factor polypeptide comprising a BZR1 transcriptional repressor domain (Interpro accession number: IPR008540). Typically the N-terminus of BZR polypeptides comprises one or more nuclear localization signals and a bHLH-like DNA binding domain (Yin et al. (2008) Plant Physiology 147:280-295.

BZR transcription factors are well known in the art. BZR polypeptides belong to a small family of proteins of plant origin which function as transcriptional modulators involved in controlling the response to Brassinosteroids (BRs).

The BZR polypeptide useful in the methods of the invention comprises a domain having in increasing order of preference at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to the BZR1 transcriptional repressor domain in SEQ ID NO: 238 located at amino acid position (coordinates) 10 to 157 in SEQ ID NO: 238 or to a BZR transcriptional repressor domain comprised in any of the polypeptides of Table A4.

Typically, the BZR polypeptides useful in the methods of the invention have a conserved bHLH-like domain located at the N-terminus of the protein for example such domain corresponds to the sequence RERRRRAIAAKIFTGLR-SQGNYKLPKHCDNNEVLKALCLEAGWIVHEDGT: (SEQ ID NO: 326) located at positions 27 to 76 of SEQ ID NO: 238.

Additionally the BZR polypeptide useful in the methods of the invention may comprise a domain having in increasing order of preference at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to a bHLH-like domain as represented by SEQ ID NO: 326.

Additionally, the BZR polypeptide useful in the methods of the invention may comprise any one or more of the following motifs:

(i) Motif 16: SAPVTPPLSSP (SEQ ID NO: 323), wherein 1, 2, 3 or 4 residues may be substituted by any amino acid.

(ii) Motif 17: VKPWEGERIHE (SEQ ID NO: 324), wherein 1, 2, 3 or 4 residues may be substituted by any amino acid.

(iii) Motif 18: DLELTLG (SEQ ID NO: 325), wherein 1, 2, 3 or 4 residues may be substituted by any amino acid.

Alternatively, the homologue of a BZR protein has in increasing order of preference at least 20%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% overall sequence identity to the amino acid represented by SEQ ID NO: 238, provided that the homologous protein comprises the conserved BZR domain as outlined above. The overall sequence identity is determined using a global alignment algorithm, such as the Needleman Wunsch algorithm in the program GAP (GCG Wisconsin Package, Accelrys), preferably with default parameters and preferably with sequences of mature proteins (i.e. without taking into account secretion signals or transit peptides). Compared to overall sequence identity, the sequence identity will generally be higher when only conserved domains or motifs are considered.

The terms "domain", "signature" and "motif" are defined in the "definitions" section herein. Specialist databases exist for the identification of domains, for example, SMART (Schultz et al. (1998) Proc. Natl. Acad. Sci. USA 95, 5857-5864; Letunic et al. (2002) Nucleic Acids Res 30, 242-244), InterPro (Mulder et al., (2003) Nucl. Acids. Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAI Press, Menlo Park; Hulo et al., Nucl. Acids. Res. 32:D134-D137, (2004)), or Pfam (Bateman et al., Nucleic Acids Research 30(1): 276-280 (2002)). A set of tools for in silico analysis of protein sequences is available on the ExPASy proteomics server (Swiss Institute of Bioinformatics (Gasteiger et al., ExPASy: the proteomics server for in-depth protein knowledge and analysis, Nucleic Acids Res. 31:3784-3788 (2003)). Domains or motifs may also be identified using routine techniques, such as by sequence alignment.

Concerning TGase polypeptides, the term "domain" and "motif" is defined in the "definitions" section herein. Specialist databases exist for the identification of domains, for example, SMART (Schultz et al. (1998) Proc. Natl. Acad. Sci. USA 95, 5857-5864; Letunic et al. (2002) Nucleic Acids Res 30, 242-244), InterPro (Mulder et al., (2003) Nucl. Acids. Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAI Press, Menlo Park; Hulo et al., Nucl. Acids. Res. 32: D134-D137, (2004)), or Pfam (Bateman et al., Nucleic Acids Research 30(1): 276-280 (2002). A set of tools for in silico analysis of protein sequences is available on the ExPASy proteomics server (Swiss Institute of Bioinformatics (Gasteiger et al., ExPASy: the proteomics server for in-depth protein knowledge and analysis, Nucleic Acids Res. 31:3784-3788 (2003)). Domains may also be identified using routine techniques, such as by sequence alignment. An alignment of the polypeptides of Table A2 herein, is shown in FIG. 6. Such alignments are useful for identifying the most conserved domains or motifs between the TGase polypeptides as defined herein. One such domain is a domain comprising at least one coiled coil, marked by X's in FIG. 6, and as represented by SEQ ID NO: 70.

Concerning TGase polypeptides, coiled coils are domains that are important to identify for protein-protein interactions, such as oligomerization, either of identical proteins, of proteins of the same family, or of unrelated proteins. Recently much progress has been made in computational prediction of coiled coils from sequence data. Among algorithms well known to a person skilled in the art are available at the ExPASy Proteomics tools COILS, PAIRCOIL, PAIRCOIL2, MULTICOIL, or MARCOIL, hosted by the Swiss Institute for Bioinformatics. In Example 4 and FIG. 5, are shown respectively the numerical and graphical results of SEQ ID NO: 45 as produced by the COILS algorithm analysis. A domain comprising at one coiled coil is identified in the TGase polypeptide sequence as represented by SEQ ID NO: 45, and is represented as in SEQ ID NO: 70.

Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage. Global percentages of similarity and identity may also be determined using one of the methods available in the MatGAT software package (Campanella et al., BMC Bioinformatics. 2003 Jul. 10; 4:29. MatGAT: an application that generates similarity/identity matrices using protein or DNA sequences). Minor manual editing may be performed to optimise alignment between conserved motifs, as would be apparent to a person skilled in the art. Furthermore, instead of using full-length sequences for the identification of homologues, specific domains may also be used. The sequence identity values may be determined over the entire nucleic acid or amino acid sequence or over selected domains or conserved motif(s), using the programs mentioned above using the default parameters. For local alignments, the Smith-Waterman algorithm is particularly useful (Smith T F, Waterman M S (1981) J. Mol. Biol 147(1); 195-7).

Concerning TGase polypeptides, Example 3 herein describes in Table B2 the percentage identity between the TGase polypeptide as represented by SEQ ID NO: 45 and the TGase polypeptides listed in Table A2, which can be as low as 26% amino acid sequence identity.

The task of protein subcellular localisation prediction is important and well studied. Knowing a protein's localisation helps elucidate its function. Experimental methods for protein localization range from immunolocalization to tagging of proteins using green fluorescent protein (GFP) or beta-glucuronidase (GUS). Such methods are accurate although labor-intensive compared with computational methods. Recently much progress has been made in computational prediction of protein localisation from sequence data. Among algorithms well known to a person skilled in the art are available at the ExPASy Proteomics tools hosted by the Swiss Institute for Bioinformatics, for example, PSort, TargetP, ChloroP, LocTree, Predotar, LipoP, MITOPROT, PATS, PTS1, SignalP, TMHMM, and others. The subcellular localisation of polypeptides useful in performing the methods of the invention was previously described in the literature (Villalobos et al. (2004) Gene 336: 93-104). In particular SEQ ID NO: 45 of the present invention is assigned to the plastidic (chloroplastic) compartment of plant cells.

Methods for targeting to plastids are well known in the art and include the use of transit peptides. Table 3 below shows examples of transit peptides which can be used to target any TGase polypeptide to a plastid, which TGase polypeptide is not, in its natural form, normally targeted to a plastid, or which TGase polypeptide in its natural form is targeted to a plastid by virtue of a different transit peptide (for example, its natural transit peptide). Cloning a nucleic acid sequence encoding a transit peptide upstream and in-frame of a nucleic acid sequence encoding a polypeptide (for example, a TGase polypeptide lacking its own transit peptide), involves standard molecular techniques that are well-known in the art.

TABLE 3

Examples of transit peptide sequences useful in targeting polypeptides to plastids

| NCBI Accession Number/ SEQ ID NO | Source Organism | Protein Function | Transit Peptide Sequence |
|---|---|---|---|
| SEQ ID NO: P07839 | *Chlamydomonas* | Ferredoxin | MAMAMRSTFAARVGAKPAVRGARPASRMSCMA |
| SEQ ID NO: AAR23425 | *Chlamydomonas* | Rubisco activase | MQVTMKSSAVSGQRVGGARVATRSVRRAQLQV |
| SEQ ID NO: CAA56932 | *Arabidopsis thaliana* | Aspartate amino transferase | MASLMLSLGSTSLLPREINKDKLKLGTSASNPFLKAKSFSRVTMTVAVKPSR |
| SEQ ID NO: CAA31991 | *Arabidopsis thaliana* | Acyl carrier protein1 | MATQFSASVSLQTSCLATTRISFQKPALISNHGKTNLSFNLRRSIPSRRLSVSC |
| SEQ ID NO: CAB63798 | *Arabidopsis thaliana* | Acyl carrier protein2 | MASIAASASISLQARPRQLAIAASQVKSFSNGRRSSLSFNLRQLPTRLTVSCAAKPETVDKVCAVVRKQL |
| SEQ ID NO: CAB63799 | *Arabidopsis thaliana* | Acyl carrier protein3 | MASIATSASTSLQARPRQLVIGAKQVKSFSYGSRSNLSFNLRQLPTRLTVYCAAKPETVDKVCAVVRKQLSLKE |

The TGase polypeptide is targeted and active in the chloroplast, i.e., the TGase polypeptide is capable of consisting in catalyzing the formation of amide linkages, generally in a Ca-dependent fashion, between the primary amine of an amine donor substrate and the y-carboxamide group of peptide-bound endo-glutamine residues in proteins or polypeptides that are the amine acceptors (Villalobos et al. (2004) Gene 336: 93-104).

Furthermore, RHL1 polypeptides typically have DNA biding activity. Tools and techniques for measuring DNA biding activity are well known in the art. Further details are provided in the Examples section.

In addition, RHL1 polypeptides, when expressed in rice according to the methods of the present invention as outlined in the Examples section, give plants having increased yield related traits, in particular any one of early vigour, increased total seed weight per plant, increased number of seeds, increased number of filled seeds and increased harvest index.

Furthermore, TRY-like polypeptides (at least in their native form) typically have DNA binding activity. Tools and techniques for measuring DNA binding activity are well known in the art.

In addition, TRY-like polypeptides, when expressed in rice according to the methods of the present invention as outlined in the Examples section, give plants having increased yield related traits, in particular one or more of increased emergence vigour, increased fill rate, increased harvest index, increased total number of seeds, increased thousand kernel weight, increased number of first panicles, increased number of filled seeds and/or increased total weight of seeds.

Furthermore, BZR polypeptides (at least in their native form) typically have DNA-binding activity and optionally protein-binding activity. Tools and techniques for measuring DNA binding activity are well known in the art. For example the EMSA technique which is based is based on the observation that protein:DNA complexes migrate more slowly than free DNA molecules when subjected to non-denaturing polyacrylamide or agarose gel electrophoresis may be used (He et al. Science 307, 134-138 (2005)). Techniques useful to determine interaction between polypeptides are well known in the art and include but are not limited to yeast two hybrid, immunoprecipation, or affinity purification of tagged proteins such as that used in TAP (Tandem Affinity Purification) technology Rigaut et al. Nat Biotechnol. 1999 October; 17(10):1030-2.

Preferably, BZR polypeptides useful in the methods of the invention have DNA binding activity and bind a DNA fragment of preferably and in increasing order of preference at least 20, 30, 40, 50, 75, 100, 150, 200, 250, 300, nucleotides long comprising a BRRE element (Brassinosteroid response element) as represented by SEQ ID NO: 327 element and/or an E-box element as represented by SEQ ID NO: 328. BRRE elements and E-box elements are well known in the art (He et al. 2005; Yin et al 2008). Preferably the BRRE element and the E-box element comprises a sequence having at least 70%, 80%, 85%, 90%, 95% sequence identity to the sequence CGTGC(T/C)G (BRRE element: SEQ ID NO: 90) and CANNTC (E-box: SEQ ID NO: 328) respectively. More preferably the DNA fragment to which the BZR polypeptide binds is selected from the CPD, DWF4, UBC and CNX5 promoter as described by He et al. 2005.

In addition, BZR polypeptides, when expressed in rice according to the methods of the present invention as outlined in the Examples section, give plants having increased seed yield, in particular increased number of filled seeds.

Concerning RHL1 polypeptides, the present invention is illustrated by transforming plants with the nucleic acid sequence represented by SEQ ID NO: 1, encoding the polypeptide sequence of SEQ ID NO: 2. However, performance of the invention is not restricted to these sequences; the methods of the invention may advantageously be performed using any RHL1-encoding nucleic acid or RHL1 polypeptide as defined herein.

Concerning RHL1 polypeptides, examples of nucleic acids encoding RHL1 polypeptides are given in Table A1 of Example 1 herein. Such nucleic acids are useful in performing the methods of the invention. The amino acid sequences given in Table A1 of Example 1 are example sequences of orthologues and paralogues of the RHL1 polypeptide represented by SEQ ID NO: 2, the terms “orthologues” and “paralogues” being as defined herein. Further orthologues and paralogues may readily be identified by performing a so-called reciprocal blast search. Typically, this involves a first BLAST involving BLASTing a query sequence (for example using any of the sequences listed in Table A1 of Example 1) against any sequence database, such as the publicly available NCBI database. BLASTN or TBLASTX (using standard default values) are generally used when starting from a nucleotide sequence, and BLASTP or TBLASTN (using standard default values) when starting from a protein sequence. The BLAST results may optionally be filtered. The full-length sequences of either the filtered results or non-filtered results are then BLASTed back (second BLAST) against sequences from the organism from which the query sequence is derived (where the query sequence is SEQ ID NO: 1 or SEQ ID NO: 2, the second BLAST would therefore be against *Arabidopsis thaliana* sequences). The results of the first and second BLASTs are then compared. A paralogue is identified if a high-ranking hit from the first blast is from the same species as from which the query sequence is derived, a BLAST back then ideally results in the query sequence amongst the highest hits; an orthologue is identified if a high-ranking hit in the first BLAST is not from the same species as from which the query sequence is derived, and preferably results upon BLAST back in the query sequence being among the highest hits.

Concerning TGase polypeptides, the present invention is illustrated by transforming plants with the nucleic acid sequence represented by SEQ ID NO: 44, encoding the TGase polypeptide sequence of SEQ ID NO: 45. However, performance of the invention is not restricted to these sequences; the methods of the invention may advantageously be performed using any nucleic acid sequence encoding a TGase polypeptide as defined herein.

Concerning TGase polypeptides, examples of nucleic acid sequences encoding TGase polypeptides are given in Table A2 of Example 1 herein. Such nucleic acid sequences are useful in performing the methods of the invention. The polypeptide sequences given in Table A2 of Example 1 are example sequences of orthologues and paralogues of the TGase polypeptide represented by SEQ ID NO: 45, the terms “orthologues” and “paralogues” being as defined herein. Further orthologues and paralogues may readily be identified by performing a so-called reciprocal blast search. Typically, this involves a first BLAST involving BLASTing a query sequence (for example using any of the sequences listed in Table A of Example 1) against any sequence database, such as the publicly available NCBI database. BLASTN or TBLASTX (using standard default values) are generally used when starting from a nucleotide sequence, and BLASTP or TBLASTN (using standard default values) when starting from a protein sequence. The BLAST results may optionally be filtered. The full-length sequences of either the filtered results or non-filtered results are then BLASTed back (second BLAST) against sequences from the organism from which the query sequence is derived (where the query sequence is SEQ ID NO: 44 or SEQ ID NO: 45, the second BLAST would therefore be against *Oryza sativa* sequences). The results of the first and second BLASTs are then compared. A paralogue is identified if a high-ranking hit from the first blast is from the same species as from which the query sequence is derived, a BLAST back then ideally results in the query sequence amongst the highest hits; an orthologue is identified if a high-ranking hit in the first BLAST is not from the same species as from which the query sequence is derived, and preferably results upon BLAST back in the query sequence being among the highest hits.

Concerning TRY-like polypeptides, the present invention is illustrated by transforming plants with the nucleic acid sequence represented by SEQ ID NO: 75, encoding the polypeptide sequence of SEQ ID NO: 76. However, performance of the invention is not restricted to these sequences; the methods of the invention may advantageously be performed using any TRY-like-encoding nucleic acid or TRY-like polypeptide as defined herein.

Concerning TRY-like polypeptides, examples of nucleic acids encoding TRY-like polypeptides are given in Table A3 of Example 1 herein. Such nucleic acids are useful in performing the methods of the invention. The amino acid sequences given in Table A3 of Example 1 are example sequences of orthologues and paralogues of the TRY-like polypeptide represented by SEQ ID NO: 76, the terms “orthologues” and “paralogues” being as defined herein. Further orthologues and paralogues may readily be identified by performing a so-called reciprocal blast search. Typically, this involves a first BLAST involving BLASTing a query sequence (for example using any of the sequences listed in Table A3 of Example 1) against any sequence database, such as the publicly available NCBI database. BLASTN or TBLASTX (using standard default values) are generally used when starting from a nucleotide sequence, and BLASTP or TBLASTN (using standard default values) when starting from a protein sequence. The BLAST results may optionally be filtered. The full-length sequences of either the filtered results or non-filtered results are then BLASTed back (second BLAST) against sequences from the organism from which the query sequence is derived (where the query sequence is SEQ ID NO: 75 or SEQ ID NO: 76, the second BLAST would therefore be against *Arabidopsis* sequences). The results of the first and second BLASTs are then compared. A paralogue is identified if a high-ranking hit from the first blast is from the same species as from which the query sequence is derived, a BLAST back then ideally results in the query sequence amongst the highest hits; an orthologue is identified if a high-ranking hit in the first BLAST is not from the same species as from which the query sequence is derived, and preferably results upon BLAST back in the query sequence being among the highest hits.

Concerning BZR polypeptides, the present invention is illustrated by transforming plants with the nucleic acid sequence represented by SEQ ID NO: 238, encoding the polypeptide sequence of SEQ ID NO: 239. However, performance of the invention is not restricted to these sequences; the methods of the invention may advantageously be performed using any BZR-encoding nucleic acid or BZR polypeptide as defined herein.

Concerning BZR polypeptides, examples of nucleic acids encoding BZR polypeptides are given in Table A4 of Example 1 herein. Such nucleic acids are useful in performing the methods of the invention. The amino acid sequences given in Table A4 of Example 1 are example sequences of orthologues and paralogues of the BZR polypeptide represented by SEQ ID NO: 239, the terms "orthologues" and "paralogues" being as defined herein. Further orthologues and paralogues may readily be identified by performing a so-called reciprocal blast search. Typically, this involves a first BLAST involving BLASTing a query sequence (for example using any of the sequences listed in Table A4 of Example 1) against any sequence database, such as the publicly available NCBI database. BLASTN or TBLASTX (using standard default values) are generally used when starting from a nucleotide sequence, and BLASTP or TBLASTN (using standard default values) when starting from a protein sequence. The BLAST results may optionally be filtered. The full-length sequences of either the filtered results or non-filtered results are then BLASTed back (second BLAST) against sequences from the organism from which the query sequence is derived (where the query sequence is SEQ ID NO: 238 or SEQ ID NO: 239, the second BLAST would therefore be against *Arabidopsis thaliana* sequences). The results of the first and second BLASTs are then compared. A paralogue is identified if a high-ranking hit from the first blast is from the same species as from which the query sequence is derived, a BLAST back then ideally results in the query sequence amongst the highest hits; an orthologue is identified if a high-ranking hit in the first BLAST is not from the same species as from which the query sequence is derived, and preferably results upon BLAST back in the query sequence being among the highest hits.

High-ranking hits are those having a low E-value. The lower the E-value, the more significant the score (or in other words the lower the chance that the hit was found by chance). Computation of the E-value is well known in the art. In addition to E-values, comparisons are also scored by percentage identity. Percentage identity refers to the number of identical nucleotides (or amino acids) between the two compared nucleic acid (or polypeptide) sequences over a particular length. In the case of large families, ClustalW may be used, followed by a neighbour joining tree, to help visualize clustering of related genes and to identify orthologues and paralogues.

Concerning BZR polypeptides, preferably, the BZR polynucleotides useful in the methods of the invention encode a polypeptide having in increasing order of preference 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more sequence identity to the amino acid sequence of any of the polypeptides of Table A4.

Nucleic acid variants may also be useful in practising the methods of the invention. Examples of such variants include nucleic acid sequences encoding homologues and derivatives of any one of the amino acid sequences given in Table A1 to A4 of Example 1, the terms "homologue" and "derivative" being as defined herein. Also useful in the methods of the invention are nucleic acid sequences encoding homologues and derivatives of orthologues or paralogues of any one of the amino acid sequences given in Table A1 to A4 of Example 1. Homologues and derivatives useful in the methods of the present invention have substantially the same biological and functional activity as the unmodified protein from which they are derived. Further variants useful in practising the methods of the invention are variants in which codon usage is optimised or in which miRNA target sites are removed.

Further nucleic acid variants useful in practising the methods of the invention include portions of nucleic acid sequences encoding RHL1 polypeptides, or TGase polypeptides, or TRY-like polypeptides, or BZR polypeptides, nucleic acid sequences hybridising to nucleic acid sequences encoding RHL1 polypeptides, or TGase polypeptides, or TRY-like polypeptides, or BZR polypeptides, splice variants of nucleic acid sequences encoding RHL1 polypeptides, or TRY-like polypeptides, or BZR polypeptides, allelic variants of nucleic acids encoding RHL1 polypeptides, or TGase polypeptides, or TRY-like polypeptides, or BZR polypeptides, and variants of nucleic acid sequences encoding RHL1 polypeptides, or TGase polypeptides, or TRY-like polypeptides, or BZR polypeptides, obtained by gene shuffling. The terms hybridising sequence, splice variant, allelic variant and gene shuffling are as described herein.

Nucleic acids encoding RHL1 polypeptides, or TGase polypeptides, or TRY-like polypeptides, or BZR polypeptides, need not be full-length nucleic acids, since performance of the methods of the invention does not rely on the use of full-length nucleic acid sequences. According to the present invention, there is provided a method for enhancing yield-related traits in plants, comprising introducing and expressing in a plant a portion of any one of the nucleic acid sequences given in Table A1 to A4 of Example 1, or a portion of a nucleic acid encoding an orthologue, paralogue or homologue of any of the amino acid sequences given in Table A1 to A4 of Example 1.

A portion of a nucleic acid may be prepared, for example, by making one or more deletions to the nucleic acid. The portions may be used in isolated form or they may be fused to other coding (or non-coding) sequences in order to, for example, produce a protein that combines several activities. When fused to other coding sequences, the resultant polypeptide produced upon translation may be bigger than that predicted for the protein portion.

Concerning RHL1 polypeptides, portions useful in the methods of the invention, encode a RHL1 polypeptide as defined herein, and have substantially the same biological activity as the amino acid sequences given in Table A1 of Example 1. Preferably, the portion is a portion of any one of the nucleic acids given in Table A1 of Example 1, or is a portion of a nucleic acid encoding an orthologue or paralogue of any one of the amino acid sequences given in Table A1 of Example 1. Preferably the portion is at least 500, 550, 600, 650, 700, 750, 800, 850, 900, 950, 1000 consecutive nucleotides in length, the consecutive nucleotides being of any one of the nucleic acid sequences given in Table A1 of Example 1, or of a nucleic acid encoding an orthologue or paralogue of any one of the amino acid sequences given in Table A1 of Example 1. Most preferably the portion is a portion of the nucleic acid of SEQ ID NO: 1. Preferably, the portion encodes a fragment of an amino acid sequence which, when used in the construction of a phylogenetic tree, such as the one depicted in FIG. 3, clusters with any of the RHL1 polypeptides originating from a dicotyledoneous plant comprising the amino acid sequence represented by SEQ ID NO: 2 rather than with any other group.

Concerning TGase polypeptides, portions useful in the methods of the invention, encode a TGase polypeptide as defined herein, and have substantially the same biological activity as the polypeptide sequences given in Table A2 of Example 1. Preferably, the portion is a portion of any one of the nucleic acid sequences given in Table A2 of Example 1, or is a portion of a nucleic acid sequence encoding an orthologue or paralogue of any one of the polypeptide sequences given in Table A2 of Example 1. Preferably the portion is, in increasing order of preference at least 600, 650, 700, 750, 800, 850, 900, 950, 1000, 1050, 1100, 1150, 1200 or more consecutive nucleotides in length, the consecutive nucleotides being of any one of the nucleic acid sequences given in Table A2 of Example 1, or of a nucleic acid sequence encoding an orthologue or paralogue of any one of the polypeptide sequences given in Table A2 of Example 1. Preferably, the portion is a portion of a nucleic sequence encoding a polypeptide sequence having in increasing order of preference at least 50%, 55%, 60%, 65%, 70%, 75%, 80%, 85%, 90%, 95%, 98%, 99% or more amino acid sequence identity to the TGase polypeptide as represented by SEQ ID NO: 45 or to any of the polypeptide sequences given in Table A herein. Most preferably, the portion is a portion of the nucleic acid sequence of SEQ ID NO: 44.

Concerning TRY-like polypeptides, portions useful in the methods of the invention, encode a TRY-like polypeptide as defined herein, and have substantially the same biological activity as the amino acid sequences given in Table A3 of the Example 1. Preferably, the portion is a portion of any one of the nucleic acids given in Table A3 of the Example 1, or is a portion of a nucleic acid encoding an orthologue or paralogue of any one of the amino acid sequences given in Table A3 of the Example 1. Preferably the portion is at least 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500 consecutive nucleotides in length, the consecutive nucleotides being of any one of the nucleic acid sequences given in Table A3 of the Example 1, or of a nucleic acid encoding an orthologue or paralogue of any one of the amino acid sequences given in Table A3 of the Example 1. Most preferably the portion is a portion of the nucleic acid of SEQ ID NO: 75. Preferably, the portion encodes a fragment of an polypeptide comprising a Myb-like DNA-binding domain (PFam domain PF00249.17, SMART domain SM00717, ProfileScan domain PS50090, Panther PTHR10641:SF26).

Concerning BZR polypeptides, portions useful in the methods of the invention, encode a BZR polypeptide as defined herein, and have substantially the same biological activity as the amino acid sequences given in Table A4 of The Example 1. Preferably, the portion is a portion of any one of the nucleic acids given in Table A4 of The Example 1, or is a portion of a nucleic acid encoding an orthologue or paralogue of any one of the amino acid sequences given in Table A4 of The Example 1. Preferably the portion is at least 20, 25, 30, 35, 40, 45, 50, 75, 100, 150, 200, 250, 300, 350, 400, 500, 550, 600, 700, 800, 900 consecutive nucleotides in length, the consecutive nucleotides being of any one of the nucleic acid sequences given in Table A4 of The Example 1, or of a nucleic acid encoding an orthologue or paralogue of any one of the amino acid sequences given Table A4 of The Example 1. Most preferably the portion is a portion of the nucleic acid of SEQ ID NO: 238. Preferably, the portion encodes a fragment of an amino acid sequence comprising a protein domain having in increasing order of preference 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to a bHLH-like domain as represented SEQ ID NO: 326.

Another nucleic acid variant useful in the methods of the invention is a nucleic acid sequence capable of hybridising, under reduced stringency conditions, preferably under stringent conditions, with a nucleic acid encoding a RHL1 polypeptide, or a TGase polypeptide, or a TRY-like polypeptide, or a BZR polypeptide, as defined herein, or with a portion as defined herein.

Concerning RHL1 polypeptides, or TRY-like polypeptides, according to the present invention, there is provided a method for enhancing yield-related traits in plants, comprising introducing and expressing in a plant a nucleic acid capable of hybridizing to any one of the nucleic acids given in Table A1, or Table A3 of Example 1, or comprising introducing and expressing in a plant a nucleic acid capable of hybridising to a nucleic acid encoding an orthologue, paralogue or homologue of any of the nucleic acid sequences given in Table A1, or Table A3 of Example 1.

Concerning TGase polypeptides, according to the present invention, there is provided a method for increasing seed yield-related traits in plants, comprising introducing and expressing in a plant, a nucleic acid sequence capable of hybridizing to any one of the nucleic acid sequences given in Table A2 of Example 1, or comprising introducing and expressing in a plant, a nucleic acid sequence capable of hybridising to a nucleic acid sequence encoding an orthologue, paralogue or homologue of any of the nucleic acid sequences given in Table A2 of Example 1.

Concerning BZR polypeptides, according to the present invention, there is provided a method for increasing seed yield in plants, comprising introducing and expressing in a plant a nucleic acid capable of hybridizing to any one of the nucleic acids given in Table A4 of Example 1, or comprising introducing and expressing in a plant a nucleic acid capable of hybridising to a nucleic acid encoding an orthologue, paralogue or homologue of any of the nucleic acid sequences given in Table A4 of Example 1.

Concerning RHL1 polypeptides, hybridising sequences useful in the methods of the invention encode a RHL1 polypeptide as defined herein, having substantially the same biological activity as the amino acid sequences given in Table A1 of Example 1. Preferably, the hybridising sequence is capable of hybridising to any one of the nucleic acids given in Table A1 of Example 1, or to a portion of any of these sequences, a portion being as defined above, or the hybridising sequence is capable of hybridising to a nucleic acid encoding an orthologue or paralogue of any one of the amino acid sequences given in Table A1 of Example 1. Most preferably, the hybridising sequence is capable of hybridising to a nucleic acid as represented by SEQ ID NO: 1 or to a portion thereof.

Concerning TGase polypeptides, hybridising sequences useful in the methods of the invention encode a TGase polypeptide as defined herein, and have substantially the same biological activity as the polypeptide sequences given in Table A2 of Example 1. Preferably, the hybridising sequence is capable of hybridising to any one of the nucleic acid sequences given in Table A2 of Example 1, or to a complement thereof, or to a portion of any of these sequences, a portion being as defined above, or wherein the hybridising sequence is capable of hybridising to a nucleic acid sequence encoding an orthologue or paralogue of any one of the polypeptide sequences given in Table A2 of Example 1, or to a complement thereof. Preferably, the hybridising sequence is capable of hybridising to a nucleic acid sequence encoding a polypeptide sequence having in increasing order of preference at least 50%, 55%, 60%, 65%, 70%, 75%, 80%, 85%, 90%, 95%, 98%, 99% or more amino acid sequence identity to the TGase polypeptide as represented by SEQ ID NO: 45 or to any of the polypeptide sequences given in Table A herein. Most preferably, the hybridising sequence is capable of hybridising to a nucleic acid sequence as represented by SEQ ID NO: 44 or to a portion thereof.

Concerning TRY-like polypeptides, hybridising sequences useful in the methods of the invention encode a TRY-like polypeptide as defined herein, having substantially the same biological activity as the amino acid sequences given in Table A3 of Example 1. Preferably, the hybridising sequence is capable of hybridising to the complement of any one of the nucleic acids given in Table A3 of Example 1, or to a portion of any of these sequences, a portion being as defined above, or the hybridising sequence is capable of hybridising to the complement of a nucleic acid encoding an orthologue or paralogue of any one of the amino acid sequences given in Table A3 of Example 1. Most preferably, the hybridising sequence is capable of hybridising to the complement of a nucleic acid as represented by SEQ ID NO: 75 or to a portion thereof.

Concerning BZR polypeptides, hybridising sequences useful in the methods of the invention encode a BZR polypeptide as defined herein, having substantially the same biological activity as the amino acid sequences given in Table A4 of Example 1. Preferably, the hybridising sequence is capable of hybridising to the complement of any one of the nucleic acids given in Table A4 of Example 1, or to a portion of any of these sequences, a portion being as defined above, or the hybridising sequence is capable of hybridising to the complement of a nucleic acid encoding an orthologue or paralogue of any one of the amino acid sequences given in Table A4 of Example 1. Most preferably, the hybridising sequence is capable of hybridising to the complement of a nucleic acid as represented by SEQ ID NO: 238 or to a portion thereof.

Concerning RHL1 polypeptides, preferably, the hybridising sequence encodes a polypeptide with an amino acid sequence which, when full-length and used in the construction of a phylogenetic tree, such as the one depicted in FIG. 3, clusters with any of the RHL1 polypeptides originating from a dicotyledoneous plant comprising the amino acid sequence represented by SEQ ID NO: 2 rather than with any other group.

Concerning TRY-like polypeptides, preferably, the hybridising sequence encodes a polypeptide comprising a Myb-like DNA-binding domain (PFam domain PF00249.17, SMART domain SM00717, ProfileScan domain PS50090, Panther PTHR10641:SF26).

Concerning BZR polypeptides, preferably, the hybridising sequence comprises a protein domain or encodes a polypeptide with an amino acid sequence which, when full-length comprises a protein domain having in increasing order of preference 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to a bHLH-like domain as represented SEQ ID NO: 326.

Another nucleic acid sequence variant useful in the methods of the invention is a splice variant encoding a RHL1 polypeptide, or a TGase polypeptide, or a TRY-like polypeptide, or a BZR polypeptide, as defined hereinabove, a splice variant being as defined herein.

Concerning RHL1 polypeptides, or TRY-like polypeptides, according to the present invention, there is provided a method for enhancing yield-related traits in plants, comprising introducing and expressing in a plant a splice variant of any one of the nucleic acid sequences given in Table A1, or Table A3 of Example 1, or a splice variant of a nucleic acid encoding an orthologue, paralogue or homologue of any of the amino acid sequences given in Table A1, or Table A3 of Example 1.

Concerning TGase polypeptides, according to the present invention, there is provided a method for increasing seed yield-related traits, comprising introducing and expressing in a plant, a splice variant of any one of the nucleic acid sequences given in Table A2 of Example 1, or a splice variant of a nucleic acid sequence encoding an orthologue, paralogue or homologue of any of the polypeptide sequences given in Table A2 of Example 1, having substantially the same biological activity as the polypeptide sequence as represented by SEQ ID NO: 45 and any of the polypeptide sequences depicted in Table A2 of Example 1.

Concerning BZR polypeptides, according to the present invention, there is provided a method for increasing seed yield in plants, comprising introducing and expressing in a plant a splice variant of any one of the nucleic acid sequences given in Table A4 of Example 1, or a splice variant of a nucleic acid encoding an orthologue, paralogue or homologue of any of the amino acid sequences given in Table A4 of Example 1.

Concerning RHL1 polypeptides, preferred splice variants are splice variants of a nucleic acid represented by SEQ ID NO: 1, or a splice variant of a nucleic acid encoding an orthologue or paralogue of SEQ ID NO: 2. Preferably, the amino acid sequence encoded by the splice variant, when used in the construction of a phylogenetic tree, such as the one depicted in FIG. 3, clusters with any of the RHL1 polypeptides originating from a dicotyledoneous plant comprising the amino acid sequence represented by SEQ ID NO: 2 rather than with any other group.

Concerning TGase polypeptides, preferred splice variants are splice variants of a nucleic acid sequence represented by SEQ ID NO: 44, or a splice variant of a nucleic acid sequence encoding an orthologue or paralogue of SEQ ID NO: 45. Preferably, the splice variant is a splice variant of a nucleic acid sequence encoding a polypeptide sequence having in increasing order of preference at least 50%, 55%, 60%, 65%, 70%, 75%, 80%, 85%, 90%, 95%, 98%, 99% or more amino acid sequence identity to the TGase polypeptide as represented by SEQ ID NO: 45 or to any of the polypeptide sequences given in Table A2 herein.

Concerning TRY-like polypeptides, preferred splice variants are splice variants of a nucleic acid represented by SEQ ID NO: 75, or a splice variant of a nucleic acid encoding an orthologue or paralogue of SEQ ID NO: 76. Preferably, the amino acid sequence encoded by the splice variant comprises a Myb-like DNA-binding domain (PFam domain PF00249.17, SMART domain SM00717, ProfileScan domain PS50090, Panther PTHR10641:SF26).

Concerning BZR polypeptides, preferred splice variants are splice variants of a nucleic acid represented by SEQ ID NO: 238, or a splice variant of a nucleic acid encoding an orthologue or paralogue of SEQ ID NO: 239. Preferably, the amino acid sequence encoded by the splice variant comprises a protein domain having in increasing order of preference 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to a bHLH-like domain as represented SEQ ID NO: 326.

Another nucleic acid sequence variant useful in performing the methods of the invention is an allelic variant of a nucleic acid encoding a RHL1 polypeptide, or a TGase polypeptide, or TRY-like polypeptide, or a BZR polypeptide, as defined hereinabove, an allelic variant being as defined herein.

Concerning RHL1 polypeptides, or TRY-like polypeptides, according to the present invention, there is provided a method for enhancing yield-related traits in plants, comprising introducing and expressing in a plant an allelic variant of any one of the nucleic acids given in Table A1, or Table A3 of Example 1, or comprising introducing and expressing in a plant an allelic variant of a nucleic acid encoding an orthologue, paralogue or homologue of any of the amino acid sequences given in Table A1, or Table A3 of Example 1.

Concerning TGase polypeptides, according to the present invention, there is provided a method for increasing seed yield-related traits, comprising introducing and expressing in a plant, an allelic variant of any one of the nucleic acid sequences given in Table A2 of Example 1, or comprising introducing and expressing in a plant, an allelic variant of a nucleic acid sequence encoding an orthologue, paralogue or homologue of any of the polypeptide sequences given in Table A2 of Example 1.

Concerning BZR polypeptides, according to the present invention, there is provided a method for increasing seed yield in plants, comprising introducing and expressing in a plant an allelic variant of any one of the nucleic acids given in Table A4 of Example 1, or comprising introducing and expressing in a plant an allelic variant of a nucleic acid encoding an orthologue, paralogue or homologue of any of the amino acid sequences given in Table A4 of Example 1.

Concerning RHL1 polypeptides, the polypeptides encoded by allelic variants useful in the methods of the present invention have substantially the same biological activity as the RHL1 polypeptide of SEQ ID NO: 2 and any of the amino acids depicted in Table A1 of Example 1. Allelic variants exist in nature, and encompassed within the methods of the present invention is the use of these natural alleles. Preferably, the allelic variant is an allelic variant of SEQ ID NO: 1 or an allelic variant of a nucleic acid encoding an orthologue or paralogue of SEQ ID NO: 2. Preferably, the amino acid sequence encoded by the allelic variant, when used in the construction of a phylogenetic tree, such as the one depicted in FIG. 3, clusters with any of the RHL1 polypeptides originating from a dicotyledoneous plant comprising the amino acid sequence represented by SEQ ID NO: 2 rather than with any other group.

Concerning TGase polypeptides, the allelic variants useful in the methods of the present invention have substantially the same biological activity as the TGase polypeptide of SEQ ID NO: 45 and any of the polypeptide sequences depicted in Table A2 of Example 1. Allelic variants exist in nature, and encompassed within the methods of the present invention is the use of these natural alleles. Preferably, the allelic variant is an allelic variant of SEQ ID NO: 44 or an allelic variant of a nucleic acid sequence encoding an orthologue or paralogue of SEQ ID NO: 45. Preferably, the allelic variant is an allelic variant of a polypeptide sequence having in increasing order of preference at least 50%, 55%, 60%, 65%, 70%, 75%, 80%, 85%, 90%, 95%, 98%, 99% or more amino acid sequence identity to the TGase polypeptide as represented by SEQ ID NO: 45 or to any of the polypeptide sequences given in Table A2 herein.

Concerning TRY-like polypeptides, the polypeptides encoded by allelic variants useful in the methods of the present invention have substantially the same biological activity as the TRY-like polypeptide of SEQ ID NO: 76 and any of the amino acids depicted in Table A3 of Example 1. Allelic variants exist in nature, and encompassed within the methods of the present invention is the use of these natural alleles. Allelic variants of SEQ ID NO: 76 are for example described in Schellmann et al. (2002). Preferably, the allelic variant is an allelic variant of SEQ ID NO: 75 or an allelic variant of a nucleic acid encoding an orthologue or paralogue of SEQ ID NO: 76. Preferably, the amino acid sequence encoded by the allelic variant, polypeptide comprises a Myb-like DNA-binding domain (PFam domain PF00249.17, SMART domain SM00717, ProfileScan domain PS50090, Panther PTHR10641:SF26).

Concerning BZR polypeptides, the polypeptides encoded by allelic variants useful in the methods of the present invention have substantially the same biological activity as the BZR polypeptide of SEQ ID NO: 239 and any of the amino acids depicted in Table A4 of Example 1. Allelic variants exist in nature, and encompassed within the methods of the present invention is the use of these natural alleles. Preferably, the allelic variant is an allelic variant of SEQ ID NO: 238 or an allelic variant of a nucleic acid encoding an orthologue or paralogue of SEQ ID NO: 239. Preferably, the amino acid sequence encoded by the allelic comprises a protein domain having in increasing order of preference 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to a bHLH-like domain as represented SEQ ID NO: 326.

Gene shuffling or directed evolution may also be used to generate variants of nucleic acid sequences encoding RHL1 polypeptides, or TGase polypeptides, or TRY-like polypeptides, or BZR polypeptides, as defined above; the term "gene shuffling" being as defined herein.

Concerning RHL1 polypeptides, or TRY-like polypeptides, according to the present invention, there is provided a method for enhancing yield-related traits in plants, comprising introducing and expressing in a plant a variant of any one of the nucleic acid sequences given in Table A1, or Table A3 of Example 1, or comprising introducing and expressing in a plant a variant of a nucleic acid encoding an orthologue, paralogue or homologue of any of the amino acid sequences given in Table A1, or Table A3 of Example 1, which variant nucleic acid is obtained by gene shuffling.

Concerning TGase polypeptides, according to the present invention, there is provided a method for increasing seed yield-related traits, comprising introducing and expressing in a plant, a variant of any one of the nucleic acid sequences given in Table A2 of Example 1, or comprising introducing and expressing in a plant a variant of a nucleic acid sequence encoding an orthologue, paralogue or homologue of any of the polypeptide sequences given in Table A2 of Example 1, which variant nucleic acid sequence is obtained by gene shuffling.

Concerning BZR polypeptides, according to the present invention, there is provided a method for increasing seed yield in plants, comprising introducing and expressing in a plant a variant of any one of the nucleic acid sequences given in Table A4 of Example 1, or comprising introducing and expressing in a plant a variant of a nucleic acid encoding an orthologue, paralogue or homologue of any of the amino acid sequences given in Table A4 of Example 1, which variant nucleic acid is obtained by gene shuffling.

Concerning RHL1 polypeptides, preferably, the amino acid sequence encoded by the variant nucleic acid obtained by gene shuffling, when used in the construction of a phylogenetic tree such as the one depicted in FIG. 3, clusters with any of the RHL1 polypeptides originating from a dicotyledoneous plant comprising the amino acid sequence represented by SEQ ID NO: 2 rather than with any other group.

Concerning TGase polypeptides, preferably, the variant nucleic acid sequence obtained by gene shuffling encodes a polypeptide sequence having in increasing order of preference at least 50%, 55%, 60%, 65%, 70%, 75%, 80%, 85%, 90%, 95%, 98%, 99%, or more amino acid sequence identity to the TGase polypeptide as represented by SEQ ID NO: 45 or to any of the polypeptide sequences given in Table A2 herein.

Concerning TRY-like polypeptides, preferably, the amino acid sequence encoded by the variant nucleic acid obtained by gene shuffling, comprises a Myb-like DNA-binding domain (PFam domain PF00249.17, SMART domain SM00717, ProfileScan domain PS50090, Panther PTHR10641:SF26).

Concerning BZR polypeptides, preferably, the amino acid sequence encoded by the variant nucleic acid obtained by gene shuffling comprises a protein domain having in increasing order of preference 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to a bHLH-like domain as represented SEQ ID NO: 326.

Furthermore, nucleic acid variants may also be obtained by site-directed mutagenesis. Several methods are available to achieve site-directed mutagenesis, the most common being PCR based methods (Current Protocols in Molecular Biology. Wiley Eds.).

Nucleic acids encoding RHL1 polypeptides may be derived from any natural or artificial source. The nucleic acid may be modified from its native form in composition and/or genomic environment through deliberate human manipulation. Preferably the RHL1 polypeptide-encoding nucleic acid is from a plant, further preferably from a dicocotyledonous plant, more preferably from the family Breassicaceae, most preferably the nucleic acid is from *Arabidopsis thaliana.*

Nucleic acid sequences encoding TGase polypeptides may be derived from any natural or artificial source. The nucleic acid sequence may be modified from its native form in composition and/or genomic environment through deliberate human manipulation. The nucleic acid sequence encoding a TGase polypeptide is from a plant, further preferably from a dicotyledonous plant, more preferably from the family Poaceae, most preferably the nucleic acid sequence is from *Oryza sativa.*

Nucleic acids encoding TRY-like polypeptides may be derived from any natural or artificial source. The nucleic acid may be modified from its native form in composition and/or genomic environment through deliberate human manipulation. Preferably the TRY-like polypeptide-encoding nucleic acid is from a plant, further preferably from a dicotyledonous plant, more preferably from the family Brassicaceae, most preferably the nucleic acid is from *Arabidopsis thaliana.*

Nucleic acids encoding BZR polypeptides may be derived from any natural or artificial source. The nucleic acid may be modified from its native form in composition and/or genomic environment through deliberate human manipulation. Preferably the BZR polypeptide-encoding nucleic acid is from a plant, further preferably from a heterologous plant, more preferably from a dicotyledonous plant, even more preferably from the family Brassicaceae, most preferably the nucleic acid is from *Arabidopsis thaliana.*

Advantageously, the present invention provides hitherto unknown BZR nucleic acid and polypeptide sequences.

According to a further embodiment of the present invention, there is provided an isolated nucleic acid molecule comprising:

(i) a nucleic acid represented by any one of SEQ ID NO: 13, 15, 17, 19;

(ii) a nucleic acid or fragment thereof that is complementary to any one of SEQ ID NO: 13, 15, 17, 19;

(iii) a nucleic acid encoding an BZR polypeptide having, in increasing order of preference, at least 80%, 81%, 82%, 83%, 84%, 85%, 86%, 87%, 88%, 89%, 90%, 91%, 92%, 93%, 94%, 95%, 96%, 97%, 98%, or 99% or more sequence identity to one of SEQ ID NO: 14, 16, 18, 20;

(iv) a nucleic acid capable of hybridizing under stringent conditions to any one of the nucleic acids given in (i), (ii) or (iii) above.

According to a further embodiment of the present invention, there is therefore provided an isolated polypeptide comprising:

(i) an amino acid sequence having, in increasing order of preference, at least at least 80%, 81%, 82%, 83%, 84%, 85%, 86%, 87%, 88%, 89%, 90%, 91%, 92%, 93%, 94%, 95%, 96%, 97%, 98%, or 99% or more sequence identity to one of SEQ ID NO: 14, 16, 18, 20;

(ii) derivatives of any of the amino acid sequences given in (i).

Concerning RHL1 polypeptides, performance of the methods of the invention gives plants having enhanced yield-related traits. In particular performance of the methods of the invention gives plants having increased yield, especially increased seed yield relative to control plants. The terms "yield" and "seed yield" are described in more detail in the "definitions" section herein.

Concerning TGase polypeptides, performance of the methods of the invention gives plants having increased seed yield-related traits relative to control plants. The terms "yield" and "seed yield" are described in more detail in the "definitions" section herein.

Concerning TRY-like polypeptides, performance of the methods of the invention gives plants having enhanced yield-related traits. In particular performance of the methods of the invention gives plants having increased early vigour (emergence vigour) and increased yield, especially increased seed yield relative to control plants. The terms "early vigour", "yield" and "seed yield" are described in more detail in the "definitions" section herein.

Concerning BZR polypeptides, performance of the methods of the invention gives plants having increased seed yield Concerning RHL1 polypeptides, reference herein to enhanced yield-related traits is taken to mean an increase in biomass (weight) of one or more parts of a plant, which may include aboveground (harvestable) parts and/or (harvestable) parts below ground. In particular, such harvestable parts are seeds, and performance of the methods of the invention results in plants having increased seed yield relative to the seed yield of control plants.

Concerning TRY-like polypeptides, reference herein to enhanced yield-related traits is taken to mean an increase in early vigour and/or an increase in biomass (weight) of one or more parts of a plant, which may include aboveground (harvestable) parts and/or (harvestable) parts below ground. In particular, such harvestable parts are seeds, and performance of the methods of the invention results in plants having increased seed yield relative to the seed yield of control plants.

Concerning BZR polypeptides, reference herein to increase seed yield is taken to mean any one or more of the following seed parameters: an increase in the seed weight, the total number of seed, the number of filled seeds, the seed filing rate, the proportion of filled seeds, the size of the seed, the volume of the seed harvested. The skill in art will recognized that the abovementioned seed yield parameters may be expressed in different units including but not limited to per panicle and/or per plant and/or per harvest. Performance of the methods of the invention results in plants having increased seed yield relative to the seed yield of control plants.

Taking corn as an example, a yield increase may be manifested as one or more of the following: increase in the number of plants established per square meter, an increase in the number of ears per plant, an increase in the number of rows, number of kernels per row, kernel weight, thousand kernel weight, ear length/diameter, increase in the seed filling rate (which is the number of filled seeds divided by the total number of seeds and multiplied by 100), among others. Taking rice as an example, a yield increase may manifest itself as an increase in one or more of the following: number of plants per square meter, number of panicles per plant, number of spikelets per panicle, number of flowers (florets) per panicle (which is expressed as a ratio of the number of filled seeds over the number of primary panicles), increase in the seed filling rate (which is the number of filled seeds divided by the total number of seeds and multiplied by 100), increase in thousand kernel weight, among others.

The present invention provides a method for increasing yield, especially seed yield of plants, relative to control plants, which method comprises modulating expression in a plant of a nucleic acid encoding a RHL1 polypeptide, or a TRY-like polypeptide, as defined herein.

The present invention also provides a method for increasing seed yield-related traits of plants relative to control plants, which method comprises increasing expression in a plant of a nucleic acid sequence encoding a TGase polypeptide as defined herein.

The present invention furthermore provides a method for increasing seed yield of plants, relative to control plants, which method comprises modulating expression in a plant of a nucleic acid encoding a BZR polypeptide as defined herein.

Since the transgenic plants according to the present invention have increased yield and/or increased seed yield-related traits and/or yield, it is likely that these plants exhibit an increased growth rate (during at least part of their life cycle), relative to the growth rate of control plants at a corresponding stage in their life cycle.

The increased growth rate may be specific to one or more parts of a plant (including seeds), or may be throughout substantially the whole plant. Plants having an increased growth rate may have a shorter life cycle. The life cycle of a plant may be taken to mean the time needed to grow from a dry mature seed up to the stage where the plant has produced dry mature seeds, similar to the starting material. This life cycle may be influenced by factors such as early vigour, growth rate, greenness index, flowering time and speed of seed maturation. The increase in growth rate may take place at one or more stages in the life cycle of a plant or during substantially the whole plant life cycle. Increased growth rate during the early stages in the life cycle of a plant may reflect enhanced vigour. The increase in growth rate may alter the harvest cycle of a plant allowing plants to be sown later and/or harvested sooner than would otherwise be possible (a similar effect may be obtained with earlier flowering time). If the growth rate is sufficiently increased, it may allow for the further sowing of seeds of the same plant species (for example sowing and harvesting of rice plants followed by sowing and harvesting of further rice plants all within one conventional growing period). Similarly, if the growth rate is sufficiently increased, it may allow for the further sowing of seeds of different plants species (for example the sowing and harvesting of corn plants followed by, for example, the sowing and optional harvesting of soybean, potato or any other suitable plant). Harvesting additional times from the same rootstock in the case of some crop plants may also be possible. Altering the harvest cycle of a plant may lead to an increase in annual biomass production per square meter (due to an increase in the number of times (say in a year) that any particular plant may be grown and harvested). An increase in growth rate may also allow for the cultivation of transgenic plants in a wider geographical area than their wild-type counterparts, since the territorial limitations for growing a crop are often determined by adverse environmental conditions either at the time of planting (early season) or at the time of harvesting (late season). Such adverse conditions may be avoided if the harvest cycle is shortened. The growth rate may be determined by deriving various parameters from growth curves, such parameters may be: T-Mid (the time taken for plants to reach 50% of their maximal size) and T-90 (time taken for plants to reach 90% of their maximal size), amongst others.

According to a preferred feature of the present invention, performance of the methods of the invention gives plants having an increased growth rate relative to control plants. Therefore, according to the present invention, there is provided a method for increasing the growth rate of plants, which method comprises modulating expression in a plant of a nucleic acid sequence encoding a RHL1 polypeptide, or a TGase polypeptide, or TRY-like polypeptide, a BZR polypeptide, as defined herein.

Increased seed yield-related traits occur whether the plant is under non-stress conditions or whether the plant is exposed to various stresses compared to control plants grown under comparable conditions. Plants typically respond to exposure to stress by growing more slowly. In conditions of severe stress, the plant may even stop growing altogether. Mild stress on the other hand is defined herein as being any stress to which a plant is exposed which does not result in the plant ceasing to grow altogether without the capacity to resume growth. Mild stress in the sense of the invention leads to a reduction in the growth of the stressed plants of less than 40%, 35% or 30%, preferably less than 25%, 20% or 15%, more preferably less than 14%, 13%, 12%, 11% or 10% or less in comparison to the control plant under non-stress conditions. Due to advances in agricultural practices (irrigation, fertilization, pesticide treatments) severe stresses are not often encountered in cultivated crop plants. As a consequence, the compromised growth induced by mild stress is often an undesirable feature for agriculture. Mild stresses are the everyday biotic and/or abiotic (environmental) stresses to which a plant is exposed. Abiotic stresses may be due to drought or excess water, anaerobic stress, salt stress, chemical toxicity, oxidative stress and hot, cold or freezing temperatures. The abiotic stress may be an osmotic stress caused by a water stress (particularly due to drought), salt stress, oxidative stress or an ionic stress. Biotic stresses are typically those stresses caused by pathogens, such as bacteria, viruses, fungi, nematodes, and insects. The term "non-stress" conditions as used herein are those environmental conditions that allow optimal growth of plants. Persons skilled in the art are aware of normal soil conditions and climatic conditions for a given location.

In particular, the methods of the present invention may be performed under non-stress conditions or under conditions of mild drought to give plants having increased yield relative to control plants. As reported in Wang et al. (Planta (2003) 218: 1-14), abiotic stress leads to a series of morphological, physiological, biochemical and molecular changes that adversely affect plant growth and productivity. Drought, salinity, extreme temperatures and oxidative stress are known to be interconnected and may induce growth and cellular damage through similar mechanisms. Rabbani et al. (Plant Physiol (2003) 133: 1755-1767) describes a particularly high degree of "cross talk" between drought stress and high-salinity stress. For example, drought and/or salinisation are manifested primarily as osmotic stress, resulting in the disruption of homeostasis and ion distribution in the cell. Oxidative stress, which frequently accompanies high or low temperature, salinity or drought stress, may cause denaturing of functional and structural proteins. As a consequence, these diverse environmental stresses often activate similar cell signalling pathways and cellular responses, such as the production of stress proteins, up-regulation of anti-oxidants, accumulation of compatible solutes and growth arrest. The term "non-stress" conditions as used herein are those environmental conditions that allow optimal growth of plants. Persons skilled in the art are aware of normal soil conditions and climatic conditions for a given location. Plants with optimal growth conditions, (grown under non-stress conditions) typically yield in increasing order of preference at least 97%, 95%, 92%, 90%, 87%, 85%, 83%, 80%, 77% or 75% A of the average production of such plant in a given environment. Average production may be calculated on harvest and/or season basis. Persons skilled in the art are aware of average yield productions of a crop.

The term "abiotic stress" as defined herein is taken to mean any one or more of: water stress (due to drought or excess water), anaerobic stress, salt stress, temperature stress (due to hot, cold or freezing temperatures), chemical toxicity stress and oxidative stress. According to one aspect of the invention, the abiotic stress is an osmotic stress, selected from water stress, salt stress, oxidative stress and ionic stress. Preferably, the water stress is drought stress. The term salt stress is not restricted to common salt (NaCl), but may be any stress caused by one or more of: NaCl, KCl, LiCl, $MgCl_2$, $CaCl_2$, amongst others.

Performance of the methods of the invention gives plants having increased seed yield-related traits, under abiotic stress conditions relative to control plants grown in comparable stress conditions. Therefore, according to the present invention, there is provided a method for increasing seed yield-related traits, in plants grown under abiotic stress conditions, which method comprises increasing expression in a plant of a nucleic acid sequence encoding a TGase polypeptide. According to one aspect of the invention, the abiotic stress is an osmotic stress, selected from one or more of the following: water stress, salt stress, oxidative stress and ionic stress.

Another example of abiotic environmental stress is the reduced availability of one or more nutrients that need to be assimilated by the plants for growth and development. Because of the strong influence of nutrition utilization efficiency on plant yield and product quality, a huge amount of fertilizer is poured onto fields to optimize plant growth and quality. Productivity of plants ordinarily is limited by three primary nutrients, phosphorous, potassium and nitrogen, which is usually the rate-limiting element in plant growth of these three. Therefore the major nutritional element required for plant growth is nitrogen (N). It is a constituent of numerous important compounds found in living cells, including amino acids, proteins (enzymes), nucleic acids, and chlorophyll. 1.5% to 2% of plant dry matter is nitrogen and approximately 16% of total plant protein. Thus, nitrogen availability is a major limiting factor for crop plant growth and production (Frink et al. (1999) Proc Natl Acad Sci USA 96(4): 1175-1180), and has as well a major impact on protein accumulation and amino acid composition. Therefore, of great interest are crop plants with increased seed yield-related traits, when grown under nitrogen-limiting conditions.

Performance of the methods of the invention gives plants grown under conditions of reduced nutrient availability, particularly under conditions of reduced nitrogen availablity, having increased seed yield-related traits relative to control plants grown under comparable conditions. Therefore, according to the present invention, there is provided a method for increasing seed yield-related traits in plants grown under conditions of reduced nutrient availablity, preferably reduced nitrogen availability, which method comprises increasing expression in a plant of a nucleic acid sequence encoding a TGase polypeptide. Reduced nutrient availability may result from a deficiency or excess of nutrients such as nitrogen, phosphates and other phosphorous-containing compounds, potassium, calcium, cadmium, magnesium, manganese, iron and boron, amongst others. Preferably, reduced nutrient availablity is reduced nitrogen availability.

Concerning RHL1 polypeptides, performance of the methods of the invention gives plants grown under non-stress conditions or under mild drought conditions increased yield relative to control plants grown under comparable conditions. Therefore, according to the present invention, there is provided a method for increasing yield in plants grown under non-stress conditions or under mild drought conditions, which method comprises modulating expression in a plant of a nucleic acid sequence encoding a RHL1 polypeptide.

Concerning TGase polypeptides, performance of the methods of the invention gives plants grown under non-stress conditions or under mild stress conditions having increased seed yield-related traits, relative to control plants grown under comparable conditions. Therefore, according to the present invention, there is provided a method for increasing seed yield-related traits in plants grown under non-stress conditions or under mild stress conditions, which method comprises increasing expression in a plant of a nucleic acid sequence encoding a TGase polypeptide.

Concerning TRY-like polypeptides, performance of the methods of the invention gives plants grown under non-stress conditions or under mild drought conditions increased yield relative to control plants grown under comparable conditions. Therefore, according to one embodiment of the present invention, there is provided a method for increasing yield in plants grown under non-stress conditions or under mild drought conditions, which method comprises modulating expression in a plant of a nucleic acid encoding a TRY-like polypeptide.

Concerning BZR polypeptides, performance of the methods of the invention gives plants grown under non-stress conditions or under mild drought conditions increased seed yield relative to control plants grown under comparable conditions. Therefore, according to the present invention, there is provided a method for increasing seed yield in plants grown under non-stress conditions or under mild drought conditions, which method comprises modulating expression in a plant of a nucleic acid encoding a BZR polypeptide.

Concerning RHL1 polypeptides, performance of the methods of the invention gives plants grown under conditions of nutrient deficiency, particularly under conditions of nitrogen deficiency, increased yield relative to control plants grown under comparable conditions. Therefore, according to the present invention, there is provided a method for increasing yield in plants grown under conditions of nutrient deficiency, which method comprises modulating expression in a plant of a nucleic acid encoding a RHL1 polypeptide. Nutrient deficiency may result from a lack of nutrients such as nitrogen, phosphates and other phosphorous-containing compounds, potassium, calcium, cadmium, magnesium, manganese, iron and boron, amongst others.

Concerning TRY-like polypeptides, performance of the methods of the invention gives plants grown under conditions of nutrient deficiency, particularly under conditions of nitrogen deficiency, increased yield relative to control plants grown under comparable conditions. Therefore, according to the present invention, there is provided a method for increasing yield in plants grown under conditions of nutrient deficiency, which method comprises modulating expression in a plant of a nucleic acid encoding a TRY-like polypeptide. Nutrient deficiency may result from a lack of nutrients such as nitrogen, phosphates and other phosphorous-containing compounds, potassium, calcium, magnesium, manganese, iron and boron, amongst others. In another embodiment of the invention, the improved yield related traits are obtained under conditions of nitrogen deficiency.

Concerning BZR polypeptides, performance of the methods of the invention gives plants grown under conditions of nutrient deficiency, particularly under conditions of nitrogen deficiency, increased seed yield relative to control plants grown under comparable conditions. Therefore, according to the present invention, there is provided a method for increasing seed yield in plants grown under conditions of nutrient deficiency, which method comprises modulating expression in a plant of a nucleic acid encoding a BZR polypeptide. Nutrient deficiency may result from a lack of nutrients such as nitrogen, phosphates and other phosphorous-containing compounds, potassium, calcium, cadmium, magnesium, manganese, iron and boron, amongst others.

Concerning TRY-like polypeptides, performance of the methods of the invention gives plants grown under conditions of salt stress, increased yield relative to control plants grown under comparable conditions. Therefore, according to the present invention, there is provided a method for increasing yield in plants grown under conditions of salt stress, which method comprises modulating expression in a plant of a nucleic acid encoding a TRY-like polypeptide. The term salt stress is not restricted to common salt (NaCl), but may be any one or more of: NaCl, KCl, LiCl, $MgCl_2$, $CaCl_2$, amongst others.

Concerning BZR polypeptides, performance of the methods of the invention gives plants grown under conditions of salt stress, increased seed yield relative to control plants grown under comparable conditions. Therefore, according to the present invention, there is provided a method for increasing seed yield in plants grown under conditions of salt stress, which method comprises modulating expression in a plant of a nucleic acid encoding a BZR polypeptide. The term salt stress is not restricted to common salt (NaCl), but may be any one or more of: NaCl, KCl, LiCl, $MgCl_2$, $CaCl_2$, amongst others.

The present invention encompasses plants or parts thereof (including seeds) or cells thereof obtainable by the methods according to the present invention. The plants or parts thereof comprise a nucleic acid transgene encoding a RHL1 polypeptide, or a TGase polypeptide, or a TRY-like polypeptide, or a BZR polypeptide, as defined above, operably linked to a promoter functioning in plants.

The invention also provides genetic constructs and vectors to facilitate introduction and/or expression in plants of nucleic acids sequences encoding RHL1 polypeptides, or TGase polypeptides, or TRY-like polypeptides, or BZR polypeptides. The gene constructs may be inserted into vectors, which may be commercially available, suitable for transforming into plants and suitable for expression of the gene of interest in the transformed cells. The invention also provides use of a gene construct as defined herein in the methods of the invention.

More specifically, the present invention provides a construct comprising:
  (a) a nucleic acid encoding a RHL1 polypeptide, or a TGase polypeptide, or a TRY-like polypeptide, or a BZR polypeptide, as defined above;
  (b) one or more control sequences capable of driving, or increasing expression of the nucleic acid sequence of (a); and optionally
  (c) a transcription termination sequence.

Preferably, the nucleic acid sequence encoding a RHL1 polypeptide, or a TGase polypeptide, or a TRY-like polypeptide, or a BZR polypeptide, is as defined above. The term "control sequence" and "termination sequence" are as defined herein.

Concerning TGase polypeptides, preferably, one of the control sequences of a construct is a seed-specific promoter isolated from a plant genome. An example of a seed-specific promoter is an alpha-globulin promoter, preferably a rice alpha-globulin promoter, more preferably an alpha-globulin promoter as represented by SEQ ID NO: 72. Alternatively, a control sequence is a constitutive promoter, for example a GOS2 promoter, preferably a GOS2 promoter from rice, most preferably a GOS2 sequence as represented by SEQ ID NO: 71.

Plants are transformed with a vector comprising any of the nucleic acids described above. The skilled artisan is well aware of the genetic elements that must be present on the vector in order to successfully transform, select and propagate host cells containing the sequence of interest. The sequence of interest is operably linked to one or more control sequences (at least to a promoter).

Concerning RHL1 polypeptides, advantageously, any type of promoter, whether natural or synthetic, may be used to drive expression of the nucleic acid sequence, but preferably the promoter is of plant origin. A constitutive promoter is particularly useful in the methods. Preferably the constitutive promoter is also a ubiquitous promoter. See the "Definitions" section herein for definitions of the various promoter types. Also useful in the methods of the invention is a root-specific promoter.

Concerning TGase polypeptides, advantageously, any type of promoter, whether natural or synthetic, may be used to increase expression of the nucleic acid sequence. A constitutive promoter is particularly useful in the methods, preferably a constitutive promoter isolated from a plant genome. The plant constitutive promoter drives expression of a coding sequence at a level that is in all instances below that obtained under the control of a 35S CaMV viral promoter. An example of such a promoter is a GOS2 promoter as represented by SEQ ID NO: 71. Organ-specific promoters, for example for preferred expression in leaves, stems, tubers, meristems, are useful in performing the methods of the invention. Developmentally-regulated and inducible promoters are also useful in performing the methods of the invention. Preferably, seed-specific promoters are particularly useful in the methods of the invention. See the "Definitions" section herein for definitions of the various promoter types.

Concerning TRY-like polypeptides, advantageously, any type of promoter, whether natural or synthetic, may be used to drive expression of the nucleic acid sequence, but preferably the promoter is of plant origin. A constitutive promoter is particularly useful in the methods. Preferably the constitutive promoter is a ubiquitous constitutive promoter of medium strength. See the "Definitions" section herein for definitions of the various promoter types. Also useful in the methods of the invention is a root-specific promoter.

Concerning BZR polypeptides, advantageously, any type of promoter, whether natural or synthetic, may be used to drive expression of the nucleic acid sequence, but preferably the promoter is of plant origin. A constitutive promoter is particularly useful in the methods. Preferably the constitutive promoter is also a ubiquitous promoter of medium strength. See the "Definitions" section herein for definitions of the various promoter types.

Concerning RHL1 polypeptides, it should be clear that the applicability of the present invention is not restricted to the RHL1 polypeptide-encoding nucleic acid represented by SEQ ID NO: 1, nor is the applicability of the invention restricted to expression of a RHL1 polypeptide-encoding nucleic acid when driven by a constitutive promoter, or when driven by a root-specific promoter.

The constitutive promoter is preferably a medium strength promoter, such as a GOS2 promoter, preferably the promoter is a GOS2 promoter from rice. Further preferably the constitutive promoter is represented by a nucleic acid sequence substantially similar to SEQ ID NO: 39, most preferably the constitutive promoter is as represented by SEQ ID NO: 39. See Table 2 in the "Definitions" section herein for further examples of constitutive promoters.

According to another preferred feature of the invention, the nucleic acid encoding an polypeptide is operably linked to a root-specific promoter. The root-specific promoter is preferably an RCc3 promoter (Plant Mol Biol. 1995 January; 27(2): 237-48), more preferably the RCc3 promoter is from rice, further preferably the RCc3 promoter is represented by a nucleic acid sequence substantially similar to SEQ ID NO: 43, most preferably the promoter is as represented by SEQ ID NO: 43. Examples of other root-specific promoters which may also be used to perform the methods of the invention are shown in Table 3 in the "Definitions" section above.

Concerning TGase polypeptides, it should be clear that the applicability of the present invention is not restricted to a nucleic acid sequence encoding the TGase polypeptide, as represented by SEQ ID NO: 45, nor is the applicability of the invention restricted to expression of a TGase polypeptide-encoding nucleic acid sequence when driven by a seed-specific promoter.

Concerning TRY-like polypeptides, it should be clear that the applicability of the present invention is not restricted to the TRY-like polypeptide-encoding nucleic acid represented by SEQ ID NO: 75, nor is the applicability of the invention restricted to expression of a TRY-like polypeptide-encoding nucleic acid when driven by a constitutive promoter, or when driven by a root-specific promoter.

The constitutive promoter is preferably a medium strength promoter, more preferably selected from a plant, such as a GOS2 promoter, more preferably is the promoter GOS2 promoter from rice. Further preferably the constitutive promoter is represented by a nucleic acid sequence substantially similar to SEQ ID NO: 237, most preferably the constitutive promoter is as represented by SEQ ID NO: 237. See the "Definitions" section herein for further examples of constitutive promoters.

According to another preferred feature of the invention, the nucleic acid encoding a TRY-like polypeptide is operably linked to a root-specific promoter. The root-specific promoter is preferably an RCc3 promoter (Plant Mol Biol. 1995 January; 27(2):237-48), more preferably the RCc3 promoter is from rice, further preferably the RCc3 promoter is represented by a nucleic acid sequence substantially similar to SEQ ID NO: 235, most preferably the promoter is as represented by SEQ ID NO: 235. Examples of other root-specific promoters which may also be used to perform the methods of the invention are shown in Table 2 in the "Definitions" section above.

Concerning TRY-like polypeptides, optionally, one or more terminator sequences may be used in the construct introduced into a plant. Preferably, the construct comprises an expression cassette essentially similar or identical to SEQ ID NO 236, comprising the RCc3 promoter and the nucleic acid encoding the TRY-like polypeptide, or an expression cassette wherein the nucleic acid encoding the TRY-like polypeptide is operably linked to a rice GOS2 promoter that is substantially similar to SEQ ID NO: 237.

Concerning BZR polypeptides, it should be clear that the applicability of the present invention is not restricted to the BZR polypeptide-encoding nucleic acid represented by SEQ ID NO: 238, nor is the applicability of the invention restricted to expression of a BZR polypeptide-encoding nucleic acid when driven by a constitutive promoter.

The constitutive promoter is preferably a medium strength promoter, more preferably selected from a plant derived promoter, such as a GOS2 promoter, more preferably is the promoter GOS2 promoter from rice. Further preferably the constitutive promoter is represented by a nucleic acid sequence substantially similar to SEQ ID NO: 322, most preferably the constitutive promoter is as represented by SEQ ID NO: 322. See the "Definitions" section herein for further examples of plant derived and constitutive promoters. A plant derived promoter is preferably of plant origin. The plant derived promoter can be isolated by any of the well known techniques in the art from a plant or may be obtained via others methods such as chemical synthesis using any of the well-known suitable techniques in the art. The plant derived promoter preferably has substantially the same expression pattern and strength as that of a plant promoter of plant origin. Sequence and element structure of the plant derived promoter are similar to that of a promoter of plant origin. Preferably the plant derived promoter comprises a sequence having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to a promoter of plant origin.

Optionally, one or more terminator sequences may be used in the construct introduced into a plant. Additional regulatory elements may include transcriptional as well as translational enhancers. Those skilled in the art will be aware of terminator and enhancer sequences that may be suitable for use in performing the invention. An intron sequence may also be added to the 5' untranslated region (UTR) or in the coding sequence to increase the amount of the mature message that accumulates in the cytosol, as described in the definitions section.

Other control sequences (besides promoter, enhancer, silencer, intron sequences, 3'UTR and/or 5'UTR regions) may be protein and/or RNA stabilizing elements. Such sequences would be known or may readily be obtained by a person skilled in the art.

The genetic constructs of the invention may further include an origin of replication sequence that is required for maintenance and/or replication in a specific cell type. One example is when a genetic construct is required to be maintained in a bacterial cell as an episomal genetic element (e.g. plasmid or cosmid molecule). Preferred origins of replication include, but are not limited to, the f1-ori and colE1.

For the detection of the successful transfer of the nucleic acid sequences as used in the methods of the invention and/or selection of transgenic plants comprising these nucleic acids, it is advantageous to use marker genes (or reporter genes). Therefore, the genetic construct may optionally comprise a selectable marker gene. Selectable markers are described in more detail in the "definitions" section herein. The marker genes may be removed or excised from the transgenic cell once they are no longer needed. Techniques for marker removal are known in the art, useful techniques are described above in the definitions section.

For the detection of the successful transfer of the nucleic acid sequences as used in the methods of the invention and/or selection of transgenic plants comprising these nucleic acids, it is advantageous to use marker genes (or reporter genes). Therefore, the genetic construct may optionally comprise a selectable marker gene. Selectable markers are described in more detail in the "definitions" section herein. The marker genes may be removed or excised from the transgenic cell once they are no longer needed. Techniques for marker removal are known in the art, useful techniques are described above in the definitions section.

It is known that upon stable or transient integration of nucleic acid sequences into plant cells, only a minority of the cells takes up the foreign DNA and, if desired, integrates it into its genome, depending on the expression vector used and the transfection technique used. To identify and select these integrants, a gene coding for a selectable marker (such as the ones described above) is usually introduced into the host cells together with the gene of interest. These markers can for example be used in mutants in which these genes are not functional by, for example, deletion by conventional methods. Furthermore, nucleic acid sequence molecules encoding a selectable marker can be introduced into a host cell on the same vector that comprises the sequence encoding the polypeptides of the invention or used in the methods of the invention, or else in a separate vector. Cells which have been stably transfected with the introduced nucleic acid sequence can be identified for example by selection (for example, cells which have integrated the selectable marker survive whereas the other cells die). The marker genes may be removed or excised from the transgenic cell once they are no longer needed. Techniques for marker gene removal are known in the art, useful techniques are described above in the definitions section.

Concerning RHL1 polypeptides, or TRY-like polypeptides, the invention also provides a method for the production of transgenic plants having enhanced yield-related traits relative to control plants, comprising introduction and expression in a plant of any nucleic acid encoding a RHL1 polypeptide, or a TRY-like polypeptide, as defined hereinabove.

Concerning TGase polypeptides, the invention also provides a method for the production of transgenic plants having increased seed yield-related traits relative to control plants, comprising introduction and expression in a plant of any nucleic acid sequence encoding a TGase polypeptide as defined hereinabove.

Concerning BZR polypeptides, the invention also provides a method for the production of transgenic plants having increased seed yield relative to control plants, comprising introduction and expression in a plant of any nucleic acid encoding a BZR polypeptide as defined hereinabove.

Concerning RHL1 polypeptides, more specifically, the present invention provides a method for the production of transgenic plants having increased enhanced yield-related traits, particularly increased (seed) yield, which method comprises:

(i) introducing and expressing in a plant or plant cell a RHL1 polypeptide-encoding nucleic acid; and
(ii) cultivating the plant cell under conditions promoting plant growth and development.

The nucleic acid of (i) may be any of the nucleic acids capable of encoding a RHL1 polypeptide as defined herein.

Concerning TGase polypeptides, more specifically, the present invention provides a method for the production of transgenic plants having increased seed yield-related traits relative to control plants, which method comprises:

(i) introducing and expressing in a plant, plant part, or plant cell a nucleic acid sequence encoding a TGase polypeptide; and
(ii) cultivating the plant cell, plant part or plant under conditions promoting plant growth and development.

The nucleic acid sequence of (i) may be any of the nucleic acid sequences capable of encoding a TGase polypeptide as defined herein.

Concerning TRY-like polypeptides, more specifically, the present invention provides a method for the production of transgenic plants having enhanced yield-related traits, particularly increased early vigour and/or increased seed yield, which method comprises:

(i) introducing and expressing in a plant or plant cell a TRY-like polypeptide-encoding nucleic acid; and
(ii) cultivating the plant cell under conditions promoting plant growth and development.

The nucleic acid of (i) may be any of the nucleic acids capable of encoding a TRY-like polypeptide as defined herein.

Concerning BZR polypeptides, more specifically, the present invention provides a method for the production of transgenic plants having increased seed yield, which method comprises:

(i) introducing and expressing in a plant or plant cell a BZR polypeptide-encoding nucleic acid; and
(ii) cultivating the plant cell under conditions promoting plant growth and development.

The nucleic acid of (i) may be any of the nucleic acids capable of encoding a BZR polypeptide as defined herein.

The nucleic acid sequence may be introduced directly into a plant cell or into the plant itself (including introduction into a tissue, organ or any other part of a plant). According to a preferred feature of the present invention, the nucleic acid is preferably introduced into a plant by transformation. The term "transformation" is described in more detail in the "definitions" section herein.

The genetically modified plant cells can be regenerated via all methods with which the skilled worker is familiar. Suitable methods can be found in the abovementioned publications by S. D. Kung and R. Wu, Potrykus or Höfgen and Willmitzer.

Generally after transformation, plant cells or cell groupings are selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above.

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The present invention clearly extends to any plant cell or plant produced by any of the methods described herein, and to all plant parts and propagules thereof. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced by the parent in the methods according to the invention.

The invention also includes host cells containing an isolated nucleic acid sequence encoding a TGase polypeptide as defined hereinabove. Preferred host cells according to the invention are plant cells. Host plants for the nucleic acid sequences or the vector used in the method according to the invention, the expression cassette or construct or vector are, in principle, advantageously all plants, which are capable of synthesizing the polypeptides used in the inventive method.

The methods of the invention are advantageously applicable to any plant. Plants that are particularly useful in the methods of the invention include all plants which belong to the superfamily Viridiplantae, in particular monocotyledonous and dicotyledonous plants including fodder or forage legumes, ornamental plants, food crops, trees or shrubs. According to a preferred embodiment of the present invention, the plant is a crop plant. Examples of crop plants include soybean, sunflower, canola, alfalfa, rapeseed, linseed, cotton, tomato, potato and tobacco. Further preferably, the plant is a monocotyledonous plant. Examples of monocotyledonous plants include sugarcane. More preferably the plant is a cereal. Examples of cereals include rice, maize, wheat, barley, millet, rye, triticale, sorghum, emmer, spelt, secale, einkorn, teff, milo and oats.

The invention also extends to harvestable parts of a plant such as, but not limited to seeds, leaves, fruits, flowers, stems, roots, rhizomes, tubers and bulbs, which harvestable parts comprise a recombinant nucleic acid encoding a BZR polypeptide. The invention furthermore relates to products derived, preferably directly derived, from a harvestable part of such a plant, such as dry pellets or powders, oil, fat and fatty acids, starch or proteins.

According to a preferred feature of the invention, the modulated expression is increased expression. Methods for increasing expression of nucleic acids or genes, or gene products, are well documented in the art and examples are provided in the definitions section.

Concerning RHL1 polypeptides, or TRY-like polypeptides, as mentioned above, a preferred method for modulating expression of a nucleic acid sequence encoding a RHL1 polypeptide is by introducing and expressing in a plant a nucleic acid sequence encoding a RHL1 polypeptide, or a TRY-like polypeptide; however the effects of performing the method, i.e. enhancing yield-related traits may also be achieved using other well known techniques, including but not limited to T-DNA activation tagging, TILLING, homologous recombination. A description of these techniques is provided in the definitions section.

Concerning TGase polypeptides, as mentioned above, a preferred method for increasing expression of a nucleic acid sequence encoding a TGase polypeptide is by introducing and expressing in a plant a nucleic acid sequence encoding a TGase polypeptide; however the effects of performing the method, i.e. increasing seed yield-related traits, may also be achieved using other well known techniques, including but not limited to T-DNA activation tagging, TILLING, homologous recombination. A description of these techniques is provided in the definitions section.

Concerning BZR polypeptides, as mentioned above, a preferred method for modulating expression of a nucleic acid sequence encoding a BZR polypeptide is by introducing and expressing in a plant a nucleic acid sequence encoding a BZR polypeptide; however the effects of performing the method, i.e. increasing seed yield may also be achieved using other well known techniques, including but not limited to T-DNA activation tagging, TILLING, homologous recombination. A description of these techniques is provided in the definitions section.

The present invention also encompasses use of nucleic acid sequences encoding RHL1 polypeptides as described herein and use of these RHL1 polypeptides in enhancing any of the aforementioned yield-related traits in plants.

Furthermore, the present invention also encompasses use of nucleic acid sequences encoding TGase polypeptides as described herein and use of these TGase polypeptides in increasing any of the aforementioned seed yield-related traits in plants, under normal growth conditions, under abiotic stress growth (preferably osmotic stress growth conditions) conditions, and under growth conditions of reduced nutrient availability, preferably under conditions of reduced nitrogen availability.

Even furthermore, the present invention also encompasses use of nucleic acids encoding TRY-like polypeptides as described herein and use of these TRY-like polypeptides in enhancing any of the aforementioned yield-related traits in plants.

Furthermore, the present invention also encompasses use of nucleic acids encoding BZR polypeptides as described herein and use of these BZR polypeptides in increasing any of the aforementioned seed yield parameters in plants.

Concerning RHL1 polypeptides, nucleic acid sequences encoding RHL1 polypeptide described herein, or the RHL1 polypeptides themselves, may find use in breeding programmes in which a DNA marker is identified which may be genetically linked to a RHL1 polypeptide-encoding gene. The nucleic acid sequences/genes, or the RHL1 polypeptides themselves may be used to define a molecular marker. This DNA or protein marker may then be used in breeding programmes to select plants having enhanced yield-related traits as defined hereinabove in the methods of the invention.

Concerning TGase polypeptides, nucleic acid sequences encoding TGase polypeptides described herein, or the TGase polypeptides themselves, may find use in breeding programmes in which a DNA marker is identified that may be genetically linked to a TGase polypeptide-encoding gene. The genes/nucleic acid sequences, or the TGase polypeptides themselves may be used to define a molecular marker. This DNA or protein marker may then be used in breeding programmes to select plants having increased seed yield-related traits, as defined hereinabove in the methods of the invention.

Concerning TRY-like polypeptides, nucleic acid sequences encoding TRY-like polypeptide described herein, or the TRY-like polypeptides themselves, may find use in breeding programmes in which a DNA marker is identified which may be genetically linked to a TRY-like polypeptide-encoding gene. The nucleic acid sequences/genes, or the TRY-like polypeptides themselves may be used to define a molecular marker. This DNA or protein marker may then be used in breeding programmes to select plants having enhanced yield-related traits as defined hereinabove in the methods of the invention.

Concerning BZR polypeptides, nucleic acid sequences encoding BZR polypeptide described herein, or the BZR polypeptides themselves, may find use in breeding programmes in which a DNA marker is identified which may be genetically linked to a BZR polypeptide-encoding gene. The nucleic acid sequences/genes, or the BZR polypeptides themselves may be used to define a molecular marker. This DNA or protein marker may then be used in breeding programmes to select plants having increased seed yield as defined hereinabove in the methods of the invention.

Allelic variants of a nucleic acid/gene encoding a RHL1 polypeptide, or a TGase polypeptide, or a TRY-like polypeptide, or a BZR polypeptide, may also find use in marker-assisted breeding programmes. Such breeding programmes sometimes require introduction of allelic variation by mutagenic treatment of the plants, using for example EMS mutagenesis; alternatively, the programme may start with a collection of allelic variants of so called “natural” origin caused unintentionally. Identification of allelic variants then takes place, for example, by PCR. This is followed by a step for selection of superior allelic variants of the sequence in question and which give increased yield. Selection is typically carried out by monitoring growth performance of plants containing different allelic variants of the sequence in question. Growth performance may be monitored in a greenhouse or in the field. Further optional steps include crossing plants in which the superior allelic variant was identified with another plant. This could be used, for example, to make a combination of interesting phenotypic features.

Nucleic acid sequences encoding RHL1 polypeptides, or TGase polypeptides, or TRY-like polypeptides, or BZR polypeptides, may also be used as probes for genetically and physically mapping the genes that they are a part of, and as markers for traits linked to those genes. Such information may be useful in plant breeding in order to develop lines with desired phenotypes. Such use of nucleic acid sequences encoding a RHL1 polypeptide, or a TGase polypeptide, or a TRY-like polypeptide, or a BZR polypeptide, requires only a nucleic acid sequence of at least 15 nucleotides in length. The nucleic acid sequences encoding a RHL1 polypeptide, or a TGase polypeptide, or a TRY-like polypeptide, or a BZR polypeptide, may be used as restriction fragment length polymorphism (RFLP) markers. Southern blots (Sambrook J, Fritsch E F and Maniatis T (1989) Molecular Cloning, A Laboratory Manual) of restriction-digested plant genomic DNA may be probed with the nucleic acid sequences encoding a RHL1 polypeptide, or a TGase polypeptide, or a TRY-like polypeptide, or a BZR polypeptide. The resulting banding patterns may then be subjected to genetic analyses using computer programs such as MapMaker (Lander et al. (1987) Genomics 1: 174-181) in order to construct a genetic map. In addition, the nucleic acid sequences may be used to probe Southern blots containing restriction endonuclease-treated genomic DNAs of a set of individuals representing parent and progeny of a defined genetic cross. Segregation of the DNA polymorphisms is noted and used to calculate the position of the nucleic acid sequence encoding a RHL1 polypeptide, or a TGase polypeptide, or a TRY-like polypeptide, or a BZR polypeptide, in the genetic map previously obtained using this population (Botstein et al. (1980) Am. J. Hum. Genet. 32: 314-331).

The production and use of plant gene-derived probes for use in genetic mapping is described in Bernatzky and Tanksley (1986) Plant Mol. Biol. Reporter 4: 37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

The nucleic acid sequence probes may also be used for physical mapping (i.e., placement of sequences on physical maps; see Hoheisel et al. In: Non-mammalian Genomic Analysis: A Practical Guide, Academic press 1996, pp. 319-346, and references cited therein).

In another embodiment, the nucleic acid sequence probes may be used in direct fluorescence in situ hybridisation (FISH) mapping (Trask (1991) Trends Genet. 7:149-154). Although current methods of FISH mapping favour use of large clones (several kb to several hundred kb; see Laan et al. (1995) Genome Res. 5:13-20), improvements in sensitivity may allow performance of FISH mapping using shorter probes.

A variety of nucleic acid sequence amplification-based methods for genetic and physical mapping may be carried out using the nucleic acid sequences. Examples include allele-specific amplification (Kazazian (1989) J. Lab. Clin. Med 11:95-96), polymorphism of PCR-amplified fragments (CAPS; Sheffield et al. (1993) Genomics 16:325-332), allele-specific ligation (Landegren et al. (1988) Science 241:1077-1080), nucleotide extension reactions (Sokolov (1990) Nucleic acid sequence Res. 18:3671), Radiation Hybrid Mapping (Walter et al. (1997) Nat. Genet. 7:22-28) and Happy Mapping (Dear and Cook (1989) Nucleic acid sequence Res. 17:6795-6807). For these methods, the sequence of a nucleic acid sequence is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence.

This, however, is generally not necessary for mapping methods.

The methods according to the present invention result in plants having enhanced yield-related traits, as described hereinbefore. These traits may also be combined with other economically advantageous traits, such as further yield-enhancing traits, tolerance to other abiotic and biotic stresses, traits modifying various architectural features and/or biochemical and/or physiological features.

Furthermore, the methods according to the present invention also result in plants having increased seed yield-related traits, as described hereinbefore. These traits may also be combined with other economically advantageous traits, such as further yield-increasing traits, tolerance to abiotic and biotic stresses, tolerance to herbicides, insectides, traits modifying various architectural features and/or biochemical and/or physiological features.

Even furthermore, the methods according to the present invention also result in plants having increased seed yield, as described hereinbefore. These traits may also be combined with other economically advantageous traits, such as further yield-enhancing traits, tolerance to other abiotic and biotic stresses, traits modifying various architectural features and/or biochemical and/or physiological features.

Items

1. A method for enhancing yield-related traits in plants relative to control plants, comprising modulating expression in a plant of a nucleic acid encoding a Root Hairless polypeptide and optionally selecting for plants having enhanced yield-related traits.
2. Method according to item 1, wherein said Root Hairless polypeptide comprises any one or more of the following motifs:

```
(i) Motif 9:
                                        (SEQ ID NO: 37)
(SN) VMC (ED) D (YV) F (DE) (NS) (ML) (IV) VFS

(DE) AWWIG (TR) K (ED) ENPEE;

(ii) Motif 10:
                                        (SEQ ID NO: 38)
L (AILV) A (PA) (IVA) (SA) GG (KR) (IVF) G (ED)

L (KA) DL (GDS) (TS) KNP (IVL) LYLDFPQ;

(iii) Motif 11:
                                        (SEQ ID NO: 39)
G (RQ) (ML) KLFGTI (VL) YPKN (RK) Y (LI) TLQF;
```

Wherein the amino acids between brackets are alternative amino acids at that position, and wherein in increasing order of preference 0, 1, 2, 3, 4, 5, 6, 7, 8, 9, 10 amino acids are substituted by any other amino acid, preferably by a conservative amino acid
3. Method according to item 1 or 2 wherein said modulated expression is effected by introducing and expressing in a plant a nucleic acid encoding an Root Hairless polypeptide.
4. Method according to any preceding item, wherein said nucleic acid encoding an Root Hairless polypeptide encodes any one of the proteins listed in Table A1 or is a portion of such a nucleic acid, or a nucleic acid capable of hybridising with such a nucleic acid or the complement thereof.
5. Method according to any preceding item, wherein said nucleic acid sequence encodes an orthologue or paralogue of any of the proteins given in Table A1.
6. Method according to any preceding item, wherein said enhanced yield-related traits comprise increased seed yield relative to control plants.
7. Method according to any preceding item wherein said enhanced yield-related traits are obtained under cultivation conditions of nitrogen deficiency.
8. Method according to any one of items 3 to 7, wherein said nucleic acid is operably linked to a constitutive promoter, preferably to a GOS2 promoter, most preferably to a GOS2 promoter from rice.
9. Method according to any preceding item, wherein said nucleic acid encoding an Root Hairless polypeptide is of plant origin, preferably from a dicotyledonous plant, further preferably from the family Brassicaceae, most preferably from *Arabidopsis thaliana.*
10. Plant or part thereof, including seeds, obtainable by a method according to any preceeding item, wherein said plant or part thereof comprises a recombinant nucleic acid encoding an Root Hairless polypeptide.
11. Construct comprising:
    (i) nucleic acid encoding a Root Hairless polypeptide as defined in items 1, 2 or 3;
    (ii) one or more control sequences capable of driving expression of the nucleic acid sequence of (a); and optionally
    (iii) a transcription termination sequence.
12. Construct according to item 11, wherein one of said control sequences is a constitutive promoter, preferably a GOS2 promoter, most preferably a GOS2 promoter from rice.
13. Use of a construct according to item 11 or 12 in a method for making plants having increased yield, particularly increased seed yield relative to control plants.
14. Plant, plant part or plant cell transformed with a construct according to item 11 or 12.
15. Method for the production of a transgenic plant having increased yield, preferably increased seed yield relative to control plants, comprising:
    (a) introducing and expressing in a plant a nucleic acid encoding an Root Hairless polypeptide as defined in item 1 or 2; and
    (b) cultivating the plant cell under conditions promoting plant growth and development; and optionally
    (c) selecting for plants having enhanced yield-related traits
16. Transgenic plant having increased yield, particularly increased biomass, relative to control plants, resulting from modulated expression of a nucleic acid encoding an Root Hairless polypeptide as defined in item 1 or 2 or a transgenic plant cell derived from said transgenic plant.
17. Transgenic plant according to item 10, 14 or 16, or a transgenic plant cell derived thereof, wherein said plant is a crop plant or a monocot or a cereal, such as rice, maize, wheat, barley, millet, rye, triticale, sorghum and oats.
18. Harvestable parts of a plant according to item 17, wherein said harvestable parts are preferably shoot biomass and/or seeds.
19. Products derived from a plant according to item 17 and/or from harvestable parts of a plant according to item 18.
20. Use of a nucleic acid encoding a Root Hairless polypeptide in increasing yield, particularly in increasing shoot and/or biomass in plants, relative to control plants.
21. A method for increasing seed yield-related traits in plants relative to control plants, comprising increasing expression in a plant of a nucleic acid sequence encoding a transglutaminase (TGase) polypeptide, which TGase polypeptide comprises (i) a plastidic transit peptide; (ii) in increasing order of preference at least 50%, 55%, 60%, 65%, 70%, 75%, 80%, 85%, 90%, 95%, 98%, 99% or more amino acid sequence identity to a domain comprising at least one coiled coil as represented by SEQ ID NO: 27; (iii) and an Integrated relational Enzyme database entry EC 2.3.2.13 for protein-glutamine γ-glutamyltransferase.

22. Method according to item 21, wherein said TGase polypeptide has (i) a plastidic transit peptide; (ii) in increasing order of preference at least 50%, 55%, 60%, 65%, 70%, 75%, 80%, 85%, 90%, 95%, 98%, 99% or more amino acid sequence identity to a polypeptide as represented by SEQ ID NO: 45.

23. Method according to item 21 or 22, wherein said TGase polypeptide has in increasing order of preference at least 50%, 55%, 60%, 65%, 70%, 75%, 80%, 85%, 90%, 95%, 98%, 99% or more amino acid sequence identity to a TGase polypeptide as represented by SEQ ID NO: 45 or to any of the polypeptide sequences given in Table A2 herein.

24. Method according to any one of items 21 to 23, wherein said TGase polypeptide is any polypeptide sequence which when used in the construction of a TGase phylogenetic tree, such as the one depicted in FIG. 5, clusters with the clade of TGase polypeptides comprising the polypeptide sequence as represented by SEQ ID NO: 45, rather than with the other clades.

25. Method according to any one of items 21 to 24, wherein said TGase polypeptide is a polypeptide with enzymatic activity consisting in catalyzing the formation of amide linkages, generally in a Ca-dependent fashion, between the primary amine of an amine donor substrate and the y-carboxamide group of peptide-bound endo-glutamine residues in proteins or polypeptides that are the amine acceptors.

26. Method according to any one of items 21 to 25, wherein said nucleic acid sequence encoding a TGase polypeptide is represented by any one of the nucleic acid sequence SEQ ID NOs given in Table A or a portion thereof, or a sequence capable of hybridising with any one of the nucleic acid sequences SEQ ID NOs given in Table A2, or to a complement thereof.

27. Method according to any one of items 21 to 26, wherein said nucleic acid sequence encodes an orthologue or paralogue of any of the polypeptide sequence SEQ ID NOs given in Table A2.

28. Method according to any one of items 21 to 27, wherein said increased expression is effected by any one or more of: T-DNA activation tagging, TILLING, or homologous recombination.

29. Method according to any one of items 21 to 28, wherein said increased expression is effected by introducing and expressing in a plant a nucleic acid sequence encoding a TGase polypeptide.

30. Method according to any one of items 21 to 29, wherein said increased seed yield-related trait is one or more of: increased total seed yield per plant, increased number of filled seeds, and increased harvest index.

31. Method according to any one of items 21 to 30, wherein said nucleic acid sequence is operably linked to a seed-specific promoter.

32. Method according to item 31, wherein said seed-specific promoter is an alpha-globulin promoter, preferably a rice alpha-globulin promoter, more preferably an alpha-globulin promoter as represented by SEQ ID NO: 72.

33. Method according to any one of items 21 to 32, wherein said nucleic acid sequence encoding a TGase polypeptide is from a plant, further preferably from a monocotyledonous plant, more preferably from the family Poaceae, most preferably the nucleic acid sequence is from *Oryza sativa*.

34. Plants, parts thereof (including seeds), or plant cells obtainable by a method according to any one of items 21 to 33, wherein said plant, part or cell thereof comprises an isolated nucleic acid transgene encoding a TGase polypeptide.

35. Construct comprising:

(a) a nucleic acid sequence encoding a TGase polypeptide as defined in any one of items 21 to 27;

(b) one or more control sequences capable of driving expression of the nucleic acid sequence of (a); and optionally (c) a transcription termination sequence.

36. Construct according to item 35, wherein said control sequence is a seed-specific promoter.

37. Construct according to item 36, wherein said seed-specific promoter is an alpha-globulin promoter, preferably a rice alpha-globulin promoter, more preferably an alpha-globulin promoter as represented by SEQ ID NO: 72.

38. Use of a construct according to any one of items 35 to 37, in a method for making plants having increased seed yield-related traits relative to control plants, which increased seed yield-related traits are one or more of: increased total seed yield per plant, increased number of filled seeds, and increased harvest index.

39. Plant, plant part or plant cell transformed with a construct according to any one of items 35 to 37.

40. Method for the production of transgenic plants having increased seed yield-related traits relative to control plants, comprising:

(i) introducing and expressing in a plant, plant part, or plant cell, a nucleic acid sequence encoding a TGase polypeptide as defined in any one of items 1 to 7; and (ii) cultivating the plant cell, plant part, or plant under conditions promoting plant growth and development.

41. Transgenic plant having increased seed yield-related traits relative to control plants, resulting from increased expression of an isolated nucleic acid sequence encoding a TGase polypeptide as defined in any one of items 21 to 27, or a transgenic plant cell or transgenic plant part derived from said transgenic plant.

42. Transgenic plant according to item 34, 39 or 41, wherein said plant is a crop plant or a monocot or a cereal, such as rice, maize, wheat, barley, millet, rye, triticale, sorghum and oats, or a transgenic plant cell derived from said transgenic plant.

43. Harvestable parts comprising an isolated nucleic acid sequence encoding a TGase polypeptide, of a plant according to item 42, wherein said harvestable parts are preferably seeds.

44. Products derived from a plant according to item 42 and/or from harvestable parts of a plant according to item 43.

45. Use of a nucleic acid sequence encoding a TGase polypeptide as defined in any one of items 21 to 27 in increasing seed yield-related traits, comprising one or more of: increased total seed yield per plant, increased number of filled seeds, and increased harvest index.

46. A method for enhancing yield-related traits in plants relative to control plants, comprising modulating expression in a plant of a nucleic acid encoding a TRY-like polypeptide, wherein said TRY-like polypeptide comprises a Myb-like DNA-binding domain (Panther PTHR10641: SF26; Gene3D G3DSA:1.10.10.60).

47. Method according to item 46, wherein said TRY-like polypeptide comprises one or more of motifs 12 to 15 (SEQ ID NO: 229 to SEQ ID NO: 232).

48. Method according to item 46 or 47, wherein said modulated expression is effected by introducing and expressing in a plant a nucleic acid encoding a TRY-like polypeptide.
49. Method according to any one of items 46 to 48, wherein said nucleic acid encoding a TRY-like polypeptide encodes any one of the proteins listed in Table A3 or is a portion of such a nucleic acid, or a nucleic acid capable of hybridising with such a nucleic acid.
50. Method according to any one of items 46 to 49, wherein said nucleic acid sequence encodes an orthologue or paralogue of any of the proteins given in Table A3.
51. Method according to any one of items 46 to 50, wherein said enhanced yield-related traits comprise increased emergence vigour and/or increased yield, relative to control plants.
52. Method according to any one of items 46 to 51, wherein said enhanced yield-related traits are obtained under non-stress conditions or under conditions of nitrogen deficiency.
53. Method according to any one of items 48 to 52, wherein said nucleic acid is operably linked to a root-specific promoter, preferably to a RCc3 promoter, most preferably to a RCc3 promoter from rice, or wherein said nucleic acid is operably linked to a constitutive promoter, preferably to a GOS2 promoter, most preferably to a GOS2 promoter from rice.
54. Method according to any one of items 46 to 53, wherein said nucleic acid encoding a TRY-like polypeptide is of plant origin, preferably from a dicotyledonous plant, further preferably from the family Brassicaceae, more preferably from the genus *Arabidopsis*, most preferably from *Arabidopsis thaliana.*
55. Plant or part thereof, including seeds, obtainable by a method according to any one of items 46 to 48, wherein said plant or part thereof comprises a recombinant nucleic acid encoding a TRY-like polypeptide.
56. Construct comprising:
    (a) nucleic acid encoding a TRY-like polypeptide as defined in items 1 or 2;
    (b) one or more control sequences capable of driving expression of the nucleic acid sequence of (a); and optionally
    (c) a transcription termination sequence.
57. Construct according to item 56, wherein one of said control sequences is a constitutive promoter, preferably a RCc3 promoter, most preferably a RCc3 promoter from rice, or wherein one of said control sequences is a constitutive promoter, preferably a RCc3 promoter, most preferably a RCc3 promoter from rice.
58. Use of a construct according to item 56 or 57 in a method for making plants having increased yield-related traits, particularly increased emergence vigour and/or increased seed yield relative to control plants.
59. Plant, plant part or plant cell transformed with a construct according to item 56 or 57.
60. Method for the production of a transgenic plant having increased yield-related traits, particularly increased emergence vigour and/or increased seed yield relative to control plants, comprising:
    (i) introducing and expressing in a plant a nucleic acid encoding a TRY-like polypeptide as defined in item 1 or 2; and
    (ii) cultivating the plant cell under conditions promoting plant growth and development.
61. Transgenic plant having increased emergence vigour and/or increased yield, relative to control plants, resulting from modulated expression of a nucleic acid encoding a TRY-like polypeptide as defined in item 46 or 47, or a transgenic plant cell derived from said transgenic plant.
62. Transgenic plant according to item 55, 59 or 61, or a transgenic plant cell derived thereof, wherein said plant is a crop plant or a monocot or a cereal, such as rice, maize, wheat, barley, millet, rye, triticale, sorghum emmer, spelt, secale, einkorn, teff, milo and oats.
63. Harvestable parts of a plant according to item 62, wherein said harvestable parts are preferably seeds.
64. Products derived from a plant according to item 62 and/or from harvestable parts of a plant according to item 63.
65. Use of a nucleic acid encoding a TRY-like polypeptide in increasing emergence vigour and/or increasing yield in plants, relative to control plants.
66. A method for increasing seed yield in plants relative to control plants, comprising modulating expression in a plant of a nucleic acid encoding a BZR, BRASSINAZOLE-RESISTANT polypeptide and optionally selecting for plants having increased seed yield.
67. Method according to item 66, wherein said BZR polypeptide comprises:
    (i) a domain having in increasing order of preference at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to the domain located between amino acid coordinates 10-157 in SEQ ID NO: 239 and/or
    (ii) a domain having in increasing order of preference at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to a bHLH-like domain as represented SEQ ID NO: 326 and/or
    (iii) 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more sequence identity to the amino acid sequence of any of the polypeptides of Table A4; and/or
    (iv) a motif as represented by any one of SEQ ID NO: 323, SEQ ID NO: 324, SEQ ID NO: 325, wherein 1, 2, 3 or 4 residues may be substituted by any amino acid.
68. Method according to item 66 or 67, wherein said modulated expression is effected by introducing and expressing in a plant a nucleic acid encoding a BZR polypeptide.
69. Method according to any one of items 66 to 68, wherein said nucleic acid encoding a BZR polypeptide encodes any one of the proteins listed in Table A4 or is a portion of such a nucleic acid, or a nucleic acid capable of hybridising with such a nucleic acid.
70. Method according to any preceding item, wherein said nucleic acid sequence encodes an orthologue or paralogue of any of the proteins given in Table A4.
71. Method according to any one of items 66 to 70, wherein said increased seed yield is selected from the total weight of the seed, the number of filled seed and the thousand kernel weight.
72. Method according to any one of items 66 to 71, wherein said increased seed yield is obtained under non-stress conditions.
73. Method according to any one of items 68 to 72, wherein said nucleic acid is operably linked to a plant derived constitutive promoter, preferably to a GOS2 promoter, most preferably to a GOS2 promoter from rice.

74. Method according to any one of items 66 to 73, wherein said nucleic acid encoding a BZR polypeptide is of plant origin, preferably from a dicotyledonous plant, further preferably from the family Brasicaceae, most preferably from *Arabidopsis thaliana.*

75. Plant or part thereof, including seeds, obtainable by a method according to any one of items 66 to 74, wherein said plant or part thereof comprises a recombinant nucleic acid encoding a BZR polypeptide.

76. An isolated nucleic acid molecule comprising any one of the following features:
   (i) a nucleic acid represented by any one of SEQ ID NO: 250, 252, 254, 256;
   (ii) a nucleic acid or fragment thereof that is complementary to any one of SEQ ID NO: 250, 252, 254, 256;
   (iii) a nucleic acid encoding a BZR polypeptide having, in increasing order of preference, at least 80%, 81%, 82%, 83%, 84%, 85%, 86%, 87%, 88%, 89%, 90%, 91%, 92%, 93%, 94%, 95%, 96%, 97%, 98%, or 99% or more sequence identity to one of SEQ ID NO: 252, 254, 256, 258;
   (iv) a nucleic acid capable of hybridizing under stringent conditions to any one of the nucleic acids given in (i), (ii) or (iii) above.

77. An isolated polypeptide comprising:
   (i) an amino acid sequence having, in increasing order of preference, at least at least 80%, 81%, 82%, 83%, 84%, 85%, 86%, 87%, 88%, 89%, 90%, 91%, 92%, 93%, 94%, 95%, 96%, 97%, 98%, or 99% or more sequence identity to one of SEQ ID NO: 252, 254, 256, 258; and/or
   (ii) derivatives of any of the amino acid sequences given in (i).

78. Construct comprising:
   (i) nucleic acid encoding a BZR polypeptide as defined in items 66, 67 or 77, or a nucleic acid according to item 76;
   (ii) one or more control sequences capable of driving expression of the nucleic acid sequence of (a); and optionally
   (iii) a transcription termination sequence.

79. Construct according to item 78, wherein one of said control sequences is a constitutive promoter, preferably a GOS2 promoter, most preferably a GOS2 promoter from rice.

80. Use of a construct according to item 13 or 14 in a method for making plants having increased seed yield relative to control plants.

81. Plant, plant part or plant cell transformed with a construct according to item 78 or 79.

82. Method for the production of a transgenic plant having increased seed yield relative to control plants, comprising:
   (i) introducing and expressing in a plant a nucleic acid encoding a BZR polypeptide as defined in item 66, 67 or 77, or a nucleic acid according to item 11; and
   (ii) cultivating the plant cell under conditions promoting plant growth and development; and optionally
   (iii) selecting for plants having seed yield.

83. Transgenic plant having increased seed yield resulting from modulated expression of a nucleic acid encoding a BZR polypeptide as defined in item 66, 67 or 77 or a transgenic plant cell derived from said transgenic plant.

84. Transgenic plant according to item 75, 81 or 83, or a transgenic plant cell derived thereof, wherein said plant is a crop plant or a monocot or a cereal, such as rice, maize, wheat, barley, millet, rye, triticale, sorghum and oats.

85. Harvestable parts of a plant according to item 84, wherein said harvestable parts are preferably shoot biomass and/or seeds.

86. Products derived from a plant according to item 85 and/or from harvestable parts of a plant according to item 85.

87. Use of a nucleic acid encoding a BZR polypeptide in increasing seed yield relative to control plants.

DESCRIPTION OF FIGURES

The present invention will now be described with reference to the following figures in which:

FIG. 1 represents the sequence of SEQ ID NO: 2 with conserved putative nuclear localization signals.

FIG. 2 represents multiple alignment of RHL1 polypeptide.

FIG. 7 shows an AlignX (from Vector NTI 10.3, Invitrogen Corporation) multiple sequence alignment of the TGase polypeptides from Table A2. The N-terminal plastidic transit peptide is separated from the rest of the polypeptide (mature polypeptide) by a vertical bar. The putative calcium binding region is boxed, and marked with X's under the consensus sequence. The domain where at least one coiled coil is predicted using the Coils algorithm (and as represented by SEQ ID NO: 70) is marked with X's under the consensus region.

FIG. 8 shows the binary vector for increased expression in *Oryza sativa* plants of a nucleic acid sequence encoding a TGase polypeptide under the control of a promoter functioning in plants.

FIG. 9 represents the sequence of SEQ ID NO: 76 with conserved motifs or domains: the Myb-like DNA-binding domain as identified with HMMPfam (PF00249.17) is indicated in bold, the sequence that is covered by motif 12 is underlined.

FIG. 10 represents a multiple alignment of various TRY-like polypeptide sequences. A dot indicates conserved residues, a colon indicates highly conserved residues and an asterisk stands for perfectly conserved residues. The highest degree of sequence conservation is found in the region of the DNA-binding domain.

FIG. 12 represents a multiple alignment of BZR polypeptides.

EXAMPLES

Figure 3:
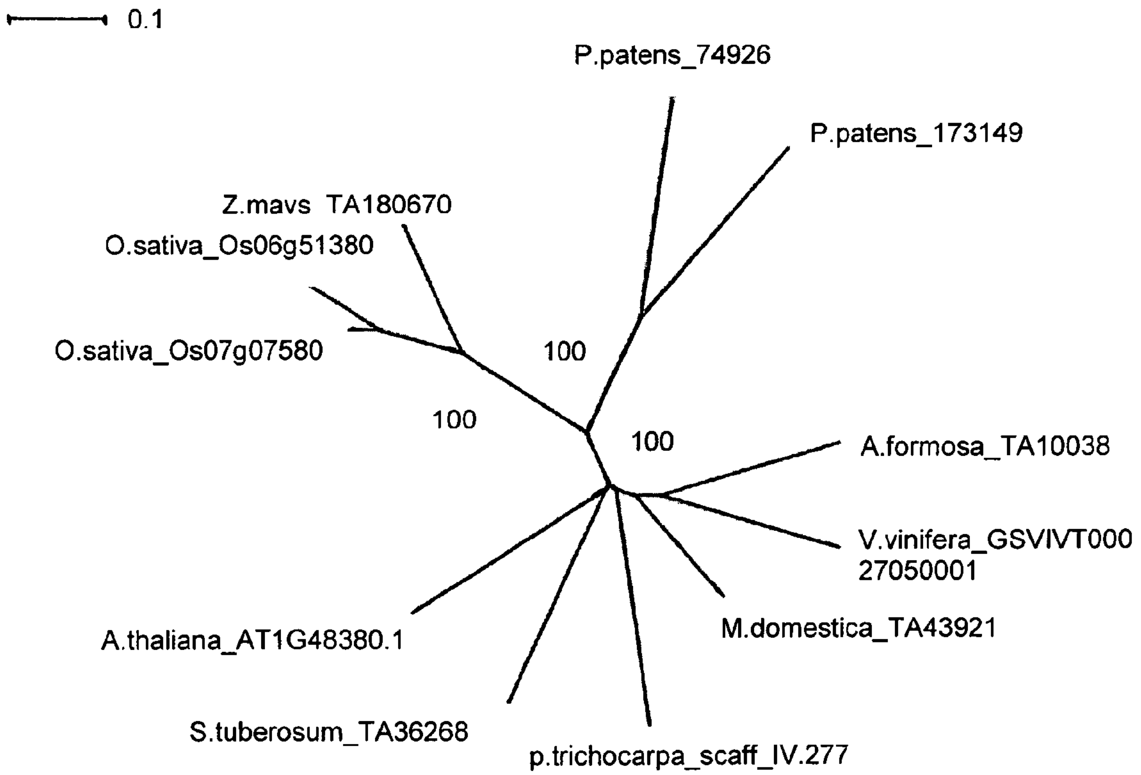
FIG. 3 shows phylogenetic tree of RHL1 polypeptide

The present invention will now be described with reference to the following examples, which are by way of illustration alone. The following examples are not intended to completely define or otherwise limit the scope of the invention.

DNA manipulation: unless otherwise stated, recombinant DNA techniques are performed according to standard protocols described in (Sambrook (2001) Molecular Cloning: a laboratory manual, 3rd Edition Cold Spring Harbor Laboratory Press, CSH, New York) or in Volumes 1 and 2 of Ausubel et al. (1994), Current Protocols in Molecular Biology, Current Protocols. Standard materials and methods for plant molecular work are described in Plant Molecular Biology Labfax (1993) by R. D. D. Croy, published by BIOS Scientific Publications Ltd (UK) and Blackwell Scientific Publications (UK).

Example 1

Identification of Sequences Related to the Nucleic Acid Sequence Used in the Methods of the Invention 1.1. Root Hairless 1 (RHL1)

Sequences (full length cDNA, ESTs or genomic) related to the nucleic acid sequence used in the methods of the present invention were identified amongst those maintained in the Entrez Nucleotides database at the National Center for Biotechnology Information (NCBI) using database sequence search tools, such as the Basic Local Alignment Tool (BLAST) (Altschul et al. (1990) J. Mol. Biol. 215:403-410; and Altschul et al. (1997) Nucleic Acids Res. 25:3389-3402). The program is used to find regions of local similarity between sequences by comparing nucleic acid or polypeptide sequences to sequence databases and by calculating the statistical significance of matches. For example, the polypeptide encoded by the nucleic acid used in the present invention was used for the TBLASTN algorithm, with default settings and the filter to ignore low complexity sequences set off. The output of the analysis was viewed by pairwise comparison, and ranked according to the probability score (E-value), where the score reflect the probability that a particular alignment occurs by chance (the lower the E-value, the more significant the hit). In addition to E-values, comparisons were also scored by percentage identity. Percentage identity refers to the number of identical nucleotides (or amino acids) between the two compared nucleic acid (or polypeptide) sequences over a particular length. In some instances, the default parameters may be adjusted to modify the stringency of the search. For example the E-value may be increased to show less stringent matches. This way, short nearly exact matches may be identified.

Table A1 provides a list of nucleic acid sequences related to the nucleic acid sequence used in the methods of the present invention.

TABLE A1

Examples of RHL1 nucleic acids and polypeptides:

| Name | Source Organism | Nucleic acid SEQ ID NO: | Protein SEQ ID NO: |
|---|---|---|---|
| A. thaliana_AT1G48380.1 (Arath_RHL1) | *Arabidopsis thaliana* | 1 | 2 |
| p. trichocarpa_scaff_44.278 | *Populus trichocarpa* | 3 | 4 |
| p. trichocarpa_scaff_184.3 | *Populus trichocarpa* | 5 | 6 |
| p. trichocarpa_scaff_IV.277 | *Populus trichocarpa* | 7 | 8 |
| O. sativa_Os07g07580 (Orysa_RHL1) | *Oryza sativa* | 9 | 10 |
| O. sativa_Os06g51380 | *Oryza sativa* | 11 | 12 |
| Z. mays_TA180670 | *Zea mays* | 13 | 14 |
| A. formosa_TA10038 | *Aquilegia formosa* | 15 | 16 |
| M. domestica_TA43921 | *Malus domestica* | 17 | 18 |
| P. patens_74926 | *Physcomitrella patens* | 19 | 20 |
| P. patens_173149 | *Physcomitrella patens* | 21 | 22 |
| S. tuberosum_TA36268 | *Solanum tuberosum* | 23 | 24 |
| V. shuttleworthii_TA2694 | *Vitis shuttleworthii* | 25 | 26 |
| V. vinifera_GSVIVT00027050001 | *Vitis vinifera* | 27 | 28 |

In some instances, related sequences have tentatively been assembled and publicly disclosed by research institutions, such as The Institute for Genomic Research (TIGR). The Eukaryotic Gene Orthologs (EGO) database may be used to identify such related sequences, either by keyword search or by using the BLAST algorithm with the nucleic acid or polypeptide sequence of interest.

1.2. Transglutaminases (TGases)

Sequences (full length cDNA, ESTs or genomic) related to the nucleic acid sequence used in the methods of the present invention were identified amongst those maintained in the Entrez Nucleotides database at the National Center for Biotechnology Information (NCBI) using database sequence search tools, such as the Basic Local Alignment Tool (BLAST) (Altschul et al. (1990) J. Mol. Biol. 215:403-410; and Altschul et al. (1997) Nucleic Acids Res. 25:3389-3402). The program is used to find regions of local similarity between sequences by comparing nucleic acid sequence or polypeptide sequences to sequence databases and by calculating the statistical significance of matches. For example, the polypeptide encoded by the nucleic acid sequence of the present invention was used for the TBLASTN algorithm, with default settings and the filter to ignore low complexity sequences set off. The output of the analysis was viewed by pairwise comparison, and ranked according to the probability score (E-value), where the score reflect the probability that a particular alignment occurs by chance (the lower the E-value, the more significant the hit). In addition to E-values, comparisons were also scored by percentage identity. Percentage identity refers to the number of identical nucleotides (or amino acids) between the two compared nucleic acid sequence (or polypeptide) sequences over a particular length. In some instances, the default parameters may be adjusted to modify the stringency of the search. For example the E-value may be increased to show less stringent matches. This way, short nearly exact matches may be identified.

Table A2 provides a list of nucleic acid sequences related to the nucleic acid sequence used in the methods of the present invention.

TABLE A2

| Examples of TGase polypeptide sequences, and encoding nucleic acid sequences: | | | | |
|---|---|---|---|---|
| Name | Source organism | Public database accession number | Nucleic acid sequence SEQ ID NO: | Polypeptide sequence SEQ ID NO: |
| Orysa_TGase | *Oryza sativa* | na | 44 | 45 |
| Arath_TGase | *Arabidopsis thaliana* | NM_105387 | 46 | 47 |
| Horvu_TGase | *Hordeum vulgare* | AK251411 | 48 | 49 |
| Lyces_TGase | *Lycopersicon esculentum* | BT012898 | 50 | 51 |
| Orysa_TGase II | *Oryza sativa* | NM_001052696 | 52 | 53 |
| Picsi_TGAse | *Picea sitchensis* | EF087701 | 54 | 55 |
| Poptr_TGase | *Populus tremuloides* | TA16744_3694 | 56 | 57 |
| Sacof_TGase | *Saccharum officinarum* | CA246119<br>CA254082<br>CA265940 | 58 | 59 |
| Sorbi_TGase | *Sorghum bicolor* | CL187991<br>ER757182.1<br>CW291038 | 60 | 61 |
| Zeama_TGase II | *Zea mays* | DT641696.1,<br>DV540831.1 | 62 | 63 |
| Zeama_TGase III | *Zea mays* | na | 64 | 65 |
| Zeama_tgz15 | *Zea mays* | AJ421525 | 66 | 67 |
| Zeama_tgz21 | *Zea mays* | AJ488103 | 68 | 69 |

In some instances, related sequences have tentatively been assembled and publicly disclosed by research institutions, such as The Institute for Genomic Research (TIGR; beginning with TA). The Eukaryotic Gene Orthologs (EGO) database may be used to identify such related sequences, either by keyword search or by using the BLAST algorithm with the nucleic acid sequence or polypeptide sequence of interest. On other instances, special nucleic acid sequence databases have been created for particular organisms, such as by the Joint Genome Institute.

1.3. Tryptichon (TRY-Like)

Sequences (full length cDNA, ESTs or genomic) related to the nucleic acid sequence used in the methods of the present invention were identified amongst those maintained in the Entrez Nucleotides database at the National Center for Biotechnology Information (NCBI) using database sequence search tools, such as the Basic Local Alignment Tool (BLAST) (Altschul et al. (1990) J. Mol. Biol. 215:403-410; and Altschul et al. (1997) Nucleic Acids Res. 25:3389-3402). The program is used to find regions of local similarity between sequences by comparing nucleic acid or polypeptide sequences to sequence databases and by calculating the statistical significance of matches. For example, the polypeptide encoded by the nucleic acid used in the present invention was used for the TBLASTN algorithm, with default settings and the filter to ignore low complexity sequences set off. The output of the analysis was viewed by pairwise comparison, and ranked according to the probability score (E-value), where the score reflect the probability that a particular alignment occurs by chance (the lower the E-value, the more significant the hit). In addition to E-values, comparisons were also scored by percentage identity. Percentage identity refers to the number of identical nucleotides (or amino acids) between the two compared nucleic acid (or polypeptide) sequences over a particular length. In some instances, the default parameters may be adjusted to modify the stringency of the search. For example the E-value may be increased to show less stringent matches. This way, short nearly exact matches may be identified.

Table A3 provides a list of nucleic acid sequences related to the nucleic acid sequence used in the methods of the present invention.

TABLE A3

| Examples of TRY-like polypeptides: | | |
|---|---|---|
| Name | Nucleic acid SEQ ID NO: | Polypeptide SEQ ID NO: |
| At5g53200 | 75 | 76 |
| A. capillaris_DV853805 | 77 | 78 |
| A. capillaris_DV859458 | 79 | 80 |
| A. hypogaea_CD038483 | 81 | 82 |
| A. sativa_CN818591 | 83 | 84 |
| A. thaliana_At1g01380_CPC-like_ETC1 | 85 | 86 |
| A. thaliana_At1g09710_CPC-like_NA | 87 | 88 |
| A. thaliana_At1g18960_CPC-like_NA | 89 | 90 |
| A. thaliana_At1g58220_CPC-like_NA | 91 | 92 |
| A. thaliana_At1g71030_CPC-like_ATMYBL2 | 93 | 94 |
| A. thaliana_At2g30420_CPC-like_NA | 95 | 96 |
| A. thaliana_At2g46410_CPC-like_CPC | 97 | 98 |
| A. thaliana_At4g01060_CPC-like_ETC3 | 99 | 100 |
| B. gymnorrhiza_TA2541_39984 | 101 | 102 |
| B. napus_CD843377 | 103 | 104 |
| B. napus_EE451172 | 105 | 106 |
| B. napus_EV055366 | 107 | 108 |
| B. napus_TC92601 | 109 | 110 |
| B. napus_TC95812 | 111 | 112 |
| C. canephora_DV693718 | 113 | 114 |
| C. longa_DY390653 | 115 | 116 |
| C. tetragonoloba_EG990179 | 117 | 118 |
| E. esula_DV121180 | 119 | 120 |
| G. hirsutum_DW508052 | 121 | 122 |
| G. hirsutum_TC102183 | 123 | 124 |
| G. hirsutum_TC116960 | 125 | 126 |
| G. hirsutum_TC121748 | 127 | 128 |
| G. max_Glyma11g02060.1 | 129 | 130 |
| G. max_8223 | 131 | 132 |
| G. max_29139 | 133 | 134 |
| G. soja_TA4526_3848 | 135 | 136 |
| H. vulgare_TC189825 | 137 | 138 |
| I. nil_TC6509 | 139 | 140 |
| J. hindsii_x_regia_EL893054 | 141 | 142 |
| J. hindsii_x_regia_TA1295_432290 | 143 | 144 |
| L. japonicus_CB827663 | 145 | 146 |
| L. multiflorum_AU249134 | 147 | 148 |
| L. saligna_DW052030 | 149 | 150 |
| L. serriola_DW108811 | 151 | 152 |
| L. tulipifera_CV004984 | 153 | 154 |
| M. domestica_TC17597 | 155 | 156 |
| M. esculenta_DV443286 | 157 | 158 |

TABLE A3-continued

| Examples of TRY-like polypeptides: | | |
|---|---|---|
| Name | Nucleic acid SEQ ID NO: | Polypeptide SEQ ID NO: |
| M. esculenta_TA9427_3983 | 159 | 160 |
| M. truncatula_CT033771_17.4 | 161 | 162 |
| O. minuta_CB884361 | 163 | 164 |
| O. sativa_LOC_Os01g43230.2 | 165 | 166 |
| P. equestris_CB034844 | 167 | 168 |
| P. glauca_DR564374 | 169 | 170 |
| P. hybrida_EB175070 | 171 | 172 |
| P. menziesii_TA3655_3357 | 173 | 174 |
| P. persica_BU039343 | 175 | 176 |
| P. pinaster_CT579117 | 177 | 178 |
| P. pinaster_TA6535_71647 | 179 | 180 |
| P. sitchensis_TA16538_3332 | 181 | 182 |
| P. sitchensis_TA17447_3332 | 183 | 184 |
| P. taeda_DR096185 | 185 | 186 |
| P. tremula_BU888423 | 187 | 188 |
| P. tremula_DN497189 | 189 | 190 |
| P. tremula_TA11725_113636 | 191 | 192 |
| P. tremula_TA7610_113636 | 193 | 194 |
| P. trichocarpa_562293 | 195 | 196 |
| P. trichocarpa_568212 | 197 | 198 |
| P. trichocarpa_594467 | 199 | 200 |
| P. trichocarpa_674550 | 201 | 202 |
| P. trichocarpa_807368 | 203 | 204 |
| P. vulgaris_CV538421 | 205 | 206 |
| S. bicolor_Sb03g028170.1 | 207 | 208 |
| S. miltiorrhiza_CV166339 | 209 | 210 |
| S. miltiorrhiza_TA1626_226208 | 211 | 212 |
| S. tuberosum_CV505951 | 213 | 214 |
| T. aestivum_BE412359 | 215 | 216 |
| T. androssowii_TA2313_189785 | 217 | 218 |
| Triphysaria_sp_TC9313 | 219 | 220 |
| V. vinifera_GSVIVT00006915001 | 221 | 222 |
| V. vinifera_GSVIVT00010755001 | 223 | 224 |
| V. vinifera_GSVIVT00026045001 | 225 | 226 |
| Z. mays_TC409725 | 227 | 228 |

In some instances, related sequences have tentatively been assembled and publicly disclosed by research institutions, such as The Institute for Genomic Research (TIGR; beginning with TA). The Eukaryotic Gene Orthologs (EGO) database may be used to identify such related sequences, either by keyword search or by using the BLAST algorithm with the nucleic acid sequence or polypeptide sequence of interest. On other instances, special nucleic acid sequence databases have been created for particular organisms, such as by the Joint Genome Institute. Further, access to proprietary databases, has allowed the identification of novel nucleic acid and polypeptide sequences.

1.4. BRASSINAZOLE RESISTANT1 (BZR1)

Sequences (full length cDNA, ESTs or genomic) related BZR nucleic acid sequence were identified amongst those maintained in the Entrez Nucleotides database at the National Center for Biotechnology Information (NCBI) using database sequence search tools, such as the Basic Local Alignment Tool (BLAST) (Altschul et al. (1990) J. Mol. Biol. 215:403-410; and Altschul et al. (1997) Nucleic Acids Res. 25:3389-3402). The program was used to find regions of local similarity between sequences by comparing nucleic acid or polypeptide sequences to sequence databases and by calculating the statistical significance of matches. SEQ ID NO: 2 was used for the TBLASTN algorithm, under default settings and without filters to ignore low complexity sequences. The output of the analysis was viewed by pairwise comparison, and ranked according to the probability score (E-value), where the score reflect the probability that a particular alignment occurs by chance (the lower the E-value, the more significant the hit). In addition to E-values, comparisons were also scored by percentage identity. Percentage identity refers to the number of identical nucleotides (or amino acids) between the two compared nucleic acid (or polypeptide) sequences over a particular length.

Table A4 provides a list of BZR nucleic acid sequences and encoded proteins thereof.

TABLE A4

| Examples of BZR polypeptides: | | | |
|---|---|---|---|
| Name | Plant Source | Nucleic acid SEQ ID NO: | Polypeptide SEQ ID NO: |
| AT3G50750.1 | *Arabidopsis thaliana* | 238 | 239 |
| AT1G19350.1 | *Arabidopsis thaliana* | 240 | 241 |
| AT1G75080.1 | *Arabidopsis thaliana* | 242 | 243 |
| AT1G78700.1 | *Arabidopsis thaliana* | 244 | 245 |
| AT4G18890.1 | *Arabidopsis thaliana* | 246 | 247 |
| AT4G36780.1 | *Arabidopsis thaliana* | 248 | 249 |
| Gm\1762729 | *Glycine max* | 250 | 251 |
| Gm\1765606 | *Glycine max* | 252 | 253 |
| Gm\1768381 | *Glycine max* | 254 | 255 |
| Gm\1768507 | *Glycine max* | 256 | 257 |
| Hv_TA37786_4513 | *Hordeum vulgare* | 258 | 259 |
| Le\LAT61 | *Lycopersicum esculentum* | 260 | 261 |
| Le_DB718708 | *Lycopersicum esculentum* | 262 | 263 |
| Le_TA37112_4081 | *Lycopersicum esculentum* | 264 | 265 |
| Le_TA51962_4081 | *Lycopersicum esculentum* | 266 | 267 |
| Mt_BF635822 | *Medicago truncatula* | 268 | 269 |
| Mt_TA21345_3880 | *Medicago truncatula* | 270 | 271 |
| Mt_TA28179_3880 | *Medicago truncatula* | 272 | 273 |
| Os01g0203000 | *Oryza sativa* | 274 | 275 |
| Os02g0129600 | *Oryza sativa* | 276 | 277 |
| Os06g0552300 | *Oryza sativa* | 278 | 279 |
| Os07g0580500 | *Oryza sativa* | 280 | 281 |
| Pp\17189 | *Physcomitrella patens* | 282 | 283 |
| Pp\172161 | *Physcomitrella patens* | 284 | 285 |
| Pp\82495 | *Physcomitrella patens* | 286 | 287 |
| Ps\WS0287_023 | *Picea sitchensis* | 288 | 289 |
| Pt\WS01123_K11 | *Populus trichocarpa* | 290 | 291 |
| Pt_scaff_178.36 | *Populus trichocarpa* | 292 | 293 |
| Pt_scaff_40.175 | *Populus trichocarpa* | 294 | 295 |
| Pt_scaff_57.215 | *Populus trichocarpa* | 296 | 297 |
| Pt_scaff_II.1237 | *Populus trichocarpa* | 298 | 299 |
| Pt_scaff_IV.340 | *Populus trichocarpa* | 300 | 301 |
| Pt_scaff_VII.1038 | *Populus trichocarpa* | 302 | 303 |
| Pt_scaff_XI.678 | *Populus trichocarpa* | 304 | 305 |
| Pt_scaff_XI.792 | *Populus trichocarpa* | 306 | 307 |
| Sl\FC26BA11 | *Solanum lycopersicum* | 308 | 309 |
| Vv_TA44770_29760 | *Vitis vinifera* | 310 | 311 |
| Zm_AY107201 | *Zea mays* | 312 | 313 |
| Zm_EE158804 | *Zea mays* | 314 | 315 |
| Zm_TA175044_4577 | *Zea mays* | 316 | 317 |
| Zm_TA178991_4577 | *Zea mays* | 318 | 319 |

Example 2

Alignment of Sequences Related to the Nucleic Acid Sequence Used in the Methods of the Invention 2.1. Root Hairless 1 (RHL1)

Alignment of the RHL1 polypeptide sequences of Table A was performed using the Clustal W algorithm of progressive alignment (Larking et al. Bioinformatics. 2007 Nov. 1; 23(21):2947-8. Thompson et al. (1997) Nucleic Acids Res 25:4876-4882; Chenna et al. (2003). Nucleic Acids Res 31:3497-3500). Default values are for the gap open penalty of 10, for the gap extension penalty of 0.1 and the selected weight matrix is Blosum 62. Proteins alignment is given in FIG. 2*a*.

A phylogenetic tree the RHL1 polypeptide sequences of Table A (FIG. 2*b*) was constructed using a neighbour-joining clustering algorithm as provided in the Clustal W programme.

2.2. Transglutaminases (TGases)

Multiple sequence alignment of all the TGase polypeptide sequences in Table A was performed using the AlignX algorithm (from Vector NTI 10.3, Invitrogen Corporation). Results of the alignment are shown in FIG. 7 of the present application. The N-terminal plastidic transit peptide is separated from the rest of the polypeptide by a vertical bar. The putative calcium binding region is boxed, and marked with X's under the consensus sequence. The domain where at least one coiled coil is predicted using the Coils algorithm (and as represented by SEQ ID NO: 70) is marked with X's under the consensus region.

2.3. Tryptichon (TRY-Like)

Alignment of polypeptide sequences was performed using the ClustalW 2.0 algorithm of progressive alignment (Thompson et al. (1997) Nucleic Acids Res 25:4876-4882; Chenna et al. (2003). Nucleic Acids Res 31:3497-3500) with standard setting (slow alignment, similarity matrix: Gonnet, gap opening penalty 10, gap extension penalty: 0.2). Minor manual editing was done to further optimise the alignment. Sequence conservation among TRY-like polypeptides is essentially in the DNA binding domain of the polypeptides, the C-terminus and N-terminus usually being more variable in sequence length and composition. The TRY-like polypeptides are aligned in FIG. 10.

This alignment can be used for determining conserved signature sequences of about 5 to 10 amino acids in length. Preferably the conserved regions of the proteins are used, recognisable by the asterisks (identical residues), the colons (highly conserved substitutions) and the dots (conserved substitutions).

2.4. Brassinazole Resistant1 (BZR1)

Alignment of polypeptide sequences was performed using the AlignX programme from the Vector NTI (Invitrogen) which is based on the popular Clustal W algorithm of progressive alignment (Thompson et al. (1997) Nucleic Acids Res 25:4876-4882; Chenna et al. (2003). Nucleic Acids Res 31:3497-3500). Default values were as follows: gap open penalty of 10; gap extension penalty of 0.1; and the selected weight matrix was Blosum 62 (if polypeptides are aligned). The alignment of BZR polypeptides is shown in FIG. 12. The sequence Pp172161 in the alignment is truncated in the N- and C-terminal. The highly conserved amino acid residues are indicated in the consensus sequence.

Sequence conservation among BZR polypeptides is essentially in the N-terminal part along the BZR1, transcriptional repressor domain. The highly conserved bHLH-like DNA binding domain characteristic of BZR polypeptides is highlighted in FIG. 12. Conserved amino acid motifs such as SAPVTPPLSSP (SEQ ID NO: 323: located at position 405-415 in the consensus sequence) and VKPWEGERIHE (SEQ ID NO: 324: located at position 634-644 in the consensus sequence) and DLELTLG (SEQ ID NO: 325: located at positions 656-662 in the consensus sequence) were identified.

Example 3

Calculation of Global Percentage Identity Between Polypeptide Sequences Useful in Performing the Methods of the Invention 3.1. Root Hairless 1 (RHL1)

Global percentages of similarity and identity between full length polypeptide sequences useful in performing the methods of the invention were determined using one of the methods available in the art, the MatGAT (Matrix Global Alignment Tool) software (BMC Bioinformatics. 2003 4:29. MatGAT: an application that generates similarity/identity matrices using protein or DNA sequences. Campanella J J, Bitincka L, Smalley J; software hosted by Ledion Bitincka). MatGAT software generates similarity/identity matrices for DNA or protein sequences without needing pre-alignment of the data. The program performs a series of pair-wise alignments using the Myers and Miller global alignment algorithm (with a gap opening penalty of 12, and a gap extension penalty of 2), calculates similarity and identity using for example Blosum 62 (for polypeptides), and then places the results in a distance matrix. Sequence similarity is shown in the bottom half of the dividing line and sequence identity is shown in the top half of the diagonal dividing line.

Parameters used in the comparison were:

Scoring matrix: Blosum62

First Gap: 12

Extending gap: 2

Results of the software analysis are shown in Table B1 for the global similarity and identity over the full length of the polypeptide sequences. Percentage identity is given above the diagonal in bold and percentage similarity is given below the diagonal (normal face).

The percentage identity between the RHL1 polypeptide sequences useful in performing the methods of the invention can be as low as 31% amino acid identity compared to SEQ ID NO: 2.

TABLE B1

MatGAT results for global similarity and identity over the full length of the polypeptid sequences.

| Polypeptide nr | Name polypeptide | 1 | 2 | 3 | 4 | 5 | 6 | 7 | 8 | 9 | 10 | 11 |
|---|---|---|---|---|---|---|---|---|---|---|---|---|
| 1 | O. sativa_Os07g07580 | 100 | 88 | 74 | 42 | 42 | 49 | 39 | 40 | 39 | 35 | 34 |
| 2 | O. sativa_Os06g51380 | 88 | 100 | 66 | 36 | 35 | 43 | 34 | 35 | 35 | 31 | 30 |
| 3 | Z. mays_TA180670 | 74 | 66 | 100 | 38 | 37 | 47 | 38 | 37 | 38 | 33 | 31 |
| 4 | A. formosa_TA10038 | 42 | 36 | 38 | 100 | 60 | 62 | 50 | 50 | 49 | 34 | 35 |
| 5 | V. vinifera_GSVIVT00027050001 | 42 | 35 | 37 | 60 | 100 | 65 | 51 | 49 | 49 | 27 | 27 |
| 6 | M. domestica_TA43921 | 49 | 43 | 47 | 62 | 65 | 100 | 58 | 59 | 56 | 41 | 39 |
| 7 | S. tuberosum_TA36268 | 39 | 34 | 38 | 50 | 51 | 58 | 100 | 48 | 50 | 31 | 32 |
| 8 | P. trichocarpa_scaff_IV.277 | 40 | 35 | 37 | 50 | 49 | 59 | 48 | 100 | 49 | 29 | 31 |
| 9 | A. thaliana_AT1G48380.1 | 39 | 35 | 38 | 49 | 49 | 56 | 50 | 49 | 100 | 32 | 31 |
| 10 | P. patens_74926 | 35 | 31 | 33 | 34 | 27 | 41 | 31 | 29 | 32 | 100 | 52 |
| 11 | P. patens_173149 | 34 | 30 | 31 | 35 | 27 | 39 | 32 | 31 | 31 | 52 | 100 |

3.2. Transglutaminases (TGases)

Global percentages of similarity and identity between full length polypeptide sequences useful in performing the methods of the invention were determined using one of the methods available in the art, the MatGAT (Matrix Global Alignment Tool) software (BMC Bioinformatics. 2003 4:29. MatGAT: an application that generates similarity/identity matrices using protein or DNA sequences. Campanella J J, Bitincka L, Smalley J; software hosted by Ledion Bitincka). MatGAT software generates similarity/identity matrices for DNA or protein sequences without needing pre-alignment of the data. The program performs a series of pair-wise alignments using the Myers and Miller global alignment algorithm (with a gap opening penalty of 12, and a gap extension penalty of 2), calculates similarity and identity using for example Blosum 62 (for polypeptides), and then places the results in a distance matrix. Sequence similarity is shown in the bottom half of the dividing line and sequence identity is shown in the top half of the diagonal dividing line.

Parameters used in the comparison were:

Scoring matrix: Blosum62

First Gap: 12

Extending gap: 2

Results of the software analysis are shown in Table B2 for the global similarity and identity over the full length of the polypeptide sequences (excluding the partial polypeptide sequences).

The percentage identity between the full length polypeptide sequences useful in performing the methods of the invention can be as low as 26% amino acid identity compared to SEQ ID NO: 44.

TABLE B

MatGAT results for global similarity and identity over the full length of the polypeptide sequences of Table A.

| | 1 | 2 | 3 | 4 | 5 | 6 | 7 | 8 | 9 | 10 | 11 | 12 | 13 |
|---|---|---|---|---|---|---|---|---|---|---|---|---|---|
| 1. Arath_TGase | | 36 | 41 | **26** | 31 | 33 | 30 | 24 | 24 | 21 | 23 | 18 | 16 |
| 2. Horvu_TGase | 49 | | 40 | **29** | 61 | 30 | 26 | 28 | 27 | 26 | 27 | 22 | 21 |
| 3. Lyces_TGase | 58 | 51 | | **29** | 36 | 30 | 26 | 28 | 28 | 27 | 28 | 21 | 21 |
| 4. Orysa_TGase | 42 | 46 | 45 | | **28** | **26** | **29** | **67** | **62** | **57** | **62** | **40** | **36** |
| 5. Orysa_TGase\II | 43 | 69 | 47 | 42 | | 25 | 23 | 27 | 27 | 26 | 25 | 20 | 20 |
| 6. Picsi_TGAse | 49 | 41 | 42 | 43 | 34 | | 32 | 24 | 22 | 20 | 21 | 17 | 16 |
| 7. Poptr_TGase | 50 | 40 | 39 | 45 | 35 | 51 | | 31 | 29 | 26 | 28 | 23 | 22 |
| 8. Sacof_TGase | 40 | 45 | 45 | 75 | 42 | 41 | 44 | | 88 | 75 | 81 | 48 | 44 |
| 9. Sorbi_TGase | 40 | 46 | 46 | 70 | 41 | 38 | 41 | 91 | | 81 | 87 | 49 | 45 |
| 10. Zeama_TGase\II | 34 | 43 | 42 | 64 | 42 | 34 | 37 | 77 | 82 | | 93 | 49 | 47 |
| 11. Zeama_TGase\III | 38 | 46 | 44 | 70 | 41 | 37 | 39 | 83 | 88 | 93 | | 50 | 46 |
| 12. Zeama_tgz15 | 32 | 37 | 38 | 49 | 37 | 29 | 34 | 56 | 56 | 58 | 57 | | 91 |
| 13. Zeama_tgz21 | 29 | 34 | 35 | 45 | 34 | 27 | 32 | 52 | 51 | 55 | 53 | 91 | |

The percentage amino acid identity can be significantly increased if the most conserved region of the polypeptides are compared. For example, when comparing the amino acid sequence of the coiled coil domain of SEQ ID NO: 2 (as represented by SEQ ID NO: 27), with the coiled coil domain of the polypeptides of Table A, the percentage amino acid identity increased up to 50%.

3.3. Tryptichon (TRY-Like)

Global percentages of similarity and identity between full length polypeptide sequences useful in performing the methods of the invention were determined using one of the methods available in the art, the MatGAT (Matrix Global Alignment Tool) software (BMC Bioinformatics. 2003 4:29. MatGAT: an application that generates similarity/identity matrices using protein or DNA sequences. Campanella J J, Bitincka L, Smalley J; software hosted by Ledion Bitincka). MatGAT software generates similarity/identity matrices for DNA or protein sequences without needing pre-alignment of the data. The program performs a series of pair-wise alignments using the Myers and Miller global alignment algorithm (with a gap opening penalty of 12, and a gap extension penalty of 2), calculates similarity and identity using for example Blosum 62 (for polypeptides), and then places the results in a distance matrix. Sequence similarity is shown in the bottom half of the dividing line and sequence identity is shown in the top half of the diagonal dividing line.

Parameters used in the comparison were:

Scoring matrix: Blosum62

First Gap: 12

Extending gap: 2

Results of the software analysis are shown in Table B3 for the global similarity and identity over the full length of the polypeptide sequences. Percentage identity between At5g53200 and other TRY-like polypeptides is given above the diagonal in bold, for both the full length sequence and for the DNA-binding domain.

The percentage identity between the TRY-like polypeptide sequences useful in performing the methods of the invention can be as low as 12% sequence identity compared to SEQ ID NO: 76. However, the sequence conservation is much higher when the DNA binding is compared. Table B2 shows similarity and identity among the sequences representing the DNA binding domain (sequences that align with the DNA-binding domain as shown in FIG. 9 (residues 30 to 75 in SEQ ID NO: 76). The sequence identity is generally higher than 50%.

TABLE B3

A: MatGAT results for global similarity and identity over the full length of the polypeptide sequences.

| | 1 | 2 | 3 | 4 | 5 | 6 | 7 | 8 | 9 | 10 | 11 | 12 |
|---|---|---|---|---|---|---|---|---|---|---|---|---|
| 1. Pt_scaff_XII.135 | | 38.1 | 57.3 | 19.1 | 36.1 | 15.7 | 43.3 | 15.3 | 13.2 | 15.1 | 51.8 | 52.0 |
| 2. Pt_scaff_64.55 | 52.6 | | 36.5 | 15.5 | 93.2 | 12.9 | 40.7 | 14.8 | 12.3 | 12.8 | 32.1 | 41.2 |
| 3. Pt_scaff_II.1572 | 70.2 | 44.2 | | 20.1 | 36.5 | 16.5 | 44.8 | 16.5 | 17.5 | 14.6 | 47.4 | 48.1 |
| 4. Pt_scaff I.1021 | 29.9 | 22.2 | 30.9 | | 16.0 | 37.8 | 15.5 | 44.3 | 36.1 | 40.8 | 19.1 | 16.0 |
| 5. Pt_scaff VII.231 | 49.5 | 94.6 | 43.3 | 21.1 | | 12.0 | 38.3 | 14.8 | 12.7 | 11.9 | 33.0 | 39.3 |
| 6. AT3G13540 | 22.1 | 17.3 | 25.7 | 51.4 | 17.7 | | 12.4 | 40.4 | 35.2 | 38.2 | 16.9 | 14.1 |
| 7. AT4G01060 | 62.9 | 62.3 | 57.7 | 26.3 | 63.6 | 19.7 | | 12.8 | 14.5 | 14.6 | 36.6 | 45.2 |
| 8. AT5G14750 | 25.1 | 23.6 | 30.5 | 57.1 | 23.6 | 53.4 | 22.2 | | 55.0 | 58.9 | 17.2 | 15.8 |
| 9. AT3G27920 | 24.1 | 19.3 | 27.2 | 50.9 | 21.5 | 49.0 | 21.1 | 64.5 | | 63.8 | 18.8 | 14.0 |
| 10. AT5G40330 | 24.7 | 19.2 | 22.4 | 54.3 | 18.3 | 52.6 | 21.0 | 71.2 | 75.9 | | 17.8 | 14.5 |
| 11. AT2G30420 | 65.2 | 42.9 | 60.7 | 32.0 | 43.8 | 27.7 | 53.6 | 28.6 | 28.9 | 29.2 | | 59.8 |
| 12. AT2G30432 | 72.2 | 53.6 | 60.6 | 24.2 | 51.2 | 20.1 | 66.7 | 28.1 | 22.4 | 24.7 | 66.1 | |
| 13. Os03g29614 | 16.5 | 13.4 | 19.0 | 38.3 | 13.7 | 43.9 | 14.3 | 41.7 | 40.5 | 38.3 | 19.6 | 15.6 |
| 14. Os01g50110 | 21.5 | 16.7 | 21.8 | 44.7 | 16.0 | 57.1 | 18.2 | 46.9 | 48.7 | 44.4 | 21.5 | 17.8 |
| 15. Os01g43180 | 51.4 | 46.7 | 57.9 | 27.8 | 44.9 | 21.7 | 53.3 | 28.6 | 26.8 | 27.4 | 53.6 | 53.3 |
| 16. Os01g43230 | 54.6 | 49.4 | 51.9 | 24.7 | 50.6 | 21.7 | 59.0 | 27.6 | 23.7 | 23.7 | 48.2 | 60.7 |
| 17. AT1G01380 | 67.0 | 59.0 | 61.5 | 28.4 | 59.0 | 19.7 | 79.5 | 22.7 | 20.6 | 21.0 | 56.3 | 69.0 |
| 18. Zm_C1 | 19.8 | 16.1 | 21.6 | 44.3 | 15.4 | 54.2 | 17.2 | 42.9 | 45.8 | 46.9 | 23.8 | 19.8 |
| 19. At5g53200 | 79.2 | 40.6 | 69.8 | 33.5 | 42.5 | 25.7 | 55.7 | 30.5 | 28.1 | 27.9 | 72.3 | 64.2 |
| 20. AT2G46410 | 72.2 | 50.0 | 66.3 | 30.4 | 51.1 | 23.7 | 60.6 | 24.6 | 25.4 | 23.7 | 60.7 | 67.0 |
| 21. Zm_TA175111 | 18.8 | 15.6 | 20.5 | 44.1 | 14.9 | 52.1 | 17.0 | 45.8 | 43.4 | 44.1 | 22.6 | 16.3 |
| 22. Zm_TA218306 | 55.7 | 62.8 | 50.0 | 25.3 | 61.5 | 19.7 | 62.8 | 25.1 | 23.2 | 23.7 | 46.4 | 64.3 |
| 23. Zm_AY135018 | 20.7 | 16.6 | 19.9 | 45.0 | 15.5 | 53.9 | 17.7 | 44.3 | 48.0 | 49.1 | 24.7 | 18.5 |
| 24. Zm_TA175105 | 25.2 | 22.0 | 27.1 | 55.0 | 21.1 | 57.0 | 22.0 | 53.2 | 52.6 | 52.5 | 28.9 | 22.5 |

| | 13 | 14 | 15 | 16 | 17 | 18 | 19 | 20 | 21 | 22 | 23 | 24 |
|---|---|---|---|---|---|---|---|---|---|---|---|---|
| 1. Pt_scaff_XII.135 | 10.3 | 12.7 | 31.5 | 34.0 | 52.6 | 12.8 | **63.0** | 56.0 | 11.8 | 37.1 | 12.2 | 13.8 |
| 2. Pt_scaff_64.55 | 10.6 | 11.3 | 31.5 | 34.9 | 45.8 | 11.4 | **31.1** | 38.3 | 10.4 | 41.8 | 11.1 | 13.3 |
| 3. Pt_scaff_II.1572 | 11.2 | 13.5 | 32.3 | 33.7 | 45.2 | 14.7 | **52.9** | 51.3 | 13.5 | 33.7 | 13.7 | 15.1 |
| 4. Pt_scaff I.1021 | 29.8 | 35.3 | 15.5 | 15.5 | 19.6 | 35.0 | **21.1** | 20.1 | 28.4 | 16.0 | 37.4 | 38.7 |
| 5. Pt_scaff VII.231 | 10.6 | 10.9 | 32.4 | 36.1 | 47.6 | 11.0 | **32.1** | 37.2 | 10.1 | 39.2 | 11.1 | 12.8 |
| 6. AT3G13540 | 33.7 | 45.0 | 14.5 | 15.3 | 13.5 | 33.9 | **16.1** | 14.9 | 36.7 | 14.1 | 36.8 | 41.0 |
| 7. AT4G01060 | 9.7 | 11.6 | 38.3 | 42.4 | 65.9 | 11.0 | **39.8** | 48.9 | 11.5 | 46.3 | 11.8 | 12.8 |
| 8. AT5G14750 | 28.0 | 35.3 | 18.2 | 20.2 | 14.3 | 31.3 | **18.1** | 16.2 | 31.2 | 19.2 | 31.5 | 38.7 |
| 9. AT3G27920 | 28.8 | 35.3 | 16.2 | 15.8 | 13.2 | 32.5 | **18.3** | 15.8 | 32.8 | 15.8 | 31.8 | 35.9 |
| 10. AT5G40330 | 27.1 | 34.2 | 17.1 | 15.8 | 13.7 | 34.3 | **19.0** | 16.0 | 30.6 | 16.4 | 35.6 | 36.3 |
| 11. AT2G30420 | 13.1 | 15.6 | 27.6 | 31.3 | 44.6 | 15.4 | **57.5** | 44.6 | 12.8 | 31.0 | 16.2 | 15.6 |
| 12. AT2G30432 | 9.0 | 12.4 | 28.8 | 35.3 | 51.8 | 11.7 | **56.5** | 44.7 | 10.4 | 32.6 | 10.7 | 13.8 |
| 13. Os03g29614 | | 37.3 | 10.2 | 9.7 | 9.0 | 39.6 | **12.1** | 11.8 | 33.7 | 8.1 | 40.3 | 31.2 |
| 14. Os01g50110 | 48.6 | | 12.7 | 11.6 | 12.0 | 37.4 | **15.3** | 14.2 | 35.1 | 12.4 | 37.5 | 34.5 |
| 15. Os01g43180 | 17.1 | 19.6 | | 54.5 | 35.1 | 11.4 | **27.4** | 33.6 | 13.4 | 49.5 | 11.1 | 15.8 |
| 16. Os01g43230 | 15.0 | 16.4 | 64.5 | | 37.2 | 12.8 | **32.1** | 37.9 | 10.8 | 60.2 | 12.5 | 15.9 |
| 17. AT1G01380 | 14.3 | 18.2 | 52.3 | 59.0 | | 12.7 | **44.4** | 54.3 | 10.1 | 39.8 | 12.1 | 12.8 |
| 18. Zm_C1 | 48.6 | 50.5 | 20.1 | 17.9 | 19.4 | | **13.9** | 13.9 | 34.4 | 10.3 | 81.8 | 37.7 |
| 19. At5g53200 | 18.4 | 22.2 | 55.1 | 50.9 | 57.5 | 20.1 | | **47.7** | **14.2** | **30.2** | **15.9** | **16.1** |

TABLE B3-continued

| | | | | | | | | | | | | |
|---|---|---|---|---|---|---|---|---|---|---|---|---|
| 20. AT2G46410 | 16.5 | 21.8 | 54.2 | 55.3 | 66.0 | 20.1 | 65.1 | | 12.8 | 39.4 | 15.9 | 16.5 |
| 21. Zm_TA175111 | 48.3 | 50.0 | 19.1 | 16.3 | 16.7 | 45.5 | 20.8 | 19.4 | | 9.7 | 36.1 | 48.6 |
| 22. Zm_TA218306 | 13.1 | 17.8 | 57.0 | 72.3 | 59.0 | 16.1 | 50.0 | 57.4 | 17.4 | | 10.7 | 13.3 |
| 23. Zm_AY135018 | 50.8 | 50.2 | 19.9 | 18.8 | 18.5 | 84.6 | 22.5 | 20.3 | 49.7 | 16.6 | | 36.2 |
| 24. Zm_TA175105 | 41.7 | 49.1 | 25.7 | 24.8 | 22.9 | 47.6 | 26.6 | 25.2 | 59.0 | 23.4 | 46.5 | |

B: MatGAT results for global similarity and identity over the DNA binding domain of the polypeptide sequences.

| | 1 | 2 | 3 | 4 | 5 | 6 | 7 | 8 | 9 | 10 | 11 | 12 |
|---|---|---|---|---|---|---|---|---|---|---|---|---|
| 1. Zm_C1 | | 95.7 | 71.7 | 73.9 | 91.3 | 84.8 | 87.0 | 89.1 | 76.1 | 76.1 | 73.9 | 50.0 |
| 2. Zm_AY135018 | 100.0 | | 69.6 | 71.7 | 91.3 | 82.6 | 84.8 | 91.3 | 76.1 | 76.1 | 73.9 | 47.8 |
| 3. Zm_TA175111 | 87.0 | 89.1 | | 91.3 | 67.4 | 71.7 | 67.4 | 71.7 | 73.9 | 71.7 | 71.7 | 41.3 |
| 4. Zm_TA175105 | 91.3 | 91.3 | 93.5 | | 73.9 | 73.9 | 69.6 | 73.9 | 76.1 | 73.9 | 73.9 | 39.1 |
| 5. Os03g29614 | 95.7 | 95.7 | 87.0 | 93.5 | | 82.6 | 84.8 | 89.1 | 71.7 | 71.7 | 69.6 | 45.7 |
| 6. AT3G13540 | 93.5 | 93.5 | 87.0 | 91.3 | 91.3 | | 87.0 | 84.8 | 78.3 | 78.3 | 76.1 | 50.0 |
| 7. Os01g50110 | 91.3 | 91.3 | 84.8 | 89.1 | 89.1 | 91.3 | | 89.1 | 71.7 | 73.9 | 69.6 | 47.8 |
| 8. Pt_scaff_I.1021 | 93.5 | 93.5 | 93.5 | 95.7 | 91.3 | 93.5 | 93.5 | | 80.4 | 82.6 | 78.3 | 50.0 |
| 9. AT5G14750 | 89.1 | 89.1 | 93.5 | 95.7 | 87.0 | 89.1 | 87.0 | 95.7 | | 97.8 | 97.8 | 43.5 |
| 10. AT5G40330 | 89.1 | 89.1 | 93.5 | 95.7 | 87.0 | 89.1 | 87.0 | 95.7 | 100.0 | | 95.7 | 41.3 |
| 11. AT3G27920 | 89.1 | 89.1 | 93.5 | 95.7 | 87.0 | 89.1 | 87.0 | 95.7 | 100.0 | 100.0 | | 43.5 |
| 12. Pt_scaff_XII.135 | 67.4 | 67.4 | 63.0 | 67.4 | 65.2 | 65.2 | 67.4 | 71.7 | 67.4 | 67.4 | 67.4 | |
| 13. Pt_scaff_II.1572 | 71.7 | 71.7 | 69.6 | 71.7 | 69.6 | 69.6 | 71.7 | 76.1 | 71.7 | 71.7 | 71.7 | 97.8 |
| 14. AT2G46410 | 71.7 | 71.7 | 67.4 | 69.6 | 69.6 | 71.7 | 73.9 | 73.9 | 69.6 | 69.6 | 69.6 | 89.1 |
| 15. AT2G30420 | 69.6 | 69.6 | 65.2 | 69.6 | 67.4 | 67.4 | 67.4 | 73.9 | 69.6 | 69.6 | 69.6 | 89.1 |
| 16. AT2G30432 | 65.2 | 65.2 | 60.9 | 65.2 | 63.0 | 63.0 | 63.0 | 69.6 | 69.6 | 69.6 | 69.6 | 95.7 |
| 17. At5g53200 | 69.6 | 69.6 | 65.2 | 69.6 | 67.4 | 67.4 | 67.4 | 73.9 | 69.6 | 69.6 | 69.6 | 97.8 |
| 18. AT4G01060 | 73.9 | 73.9 | 69.6 | 71.7 | 71.7 | 71.7 | 71.7 | 73.9 | 71.7 | 69.6 | 71.7 | 91.3 |
| 19. AT1G01380 | 69.6 | 69.6 | 63.0 | 65.2 | 67.4 | 67.4 | 69.6 | 69.6 | 65.2 | 63.0 | 67.4 | 91.3 |
| 20. Os01g43180 | 71.7 | 71.7 | 69.6 | 73.9 | 69.6 | 69.6 | 69.6 | 73.9 | 73.9 | 73.9 | 73.9 | 89.1 |
| 21. Os01g43230 | 61.2 | 61.2 | 59.2 | 63.3 | 59.2 | 59.2 | 59.2 | 63.3 | 63.3 | 63.3 | 63.3 | 73.5 |
| 22. Zm_TA218306 | 71.7 | 71.7 | 69.6 | 73.9 | 69.6 | 69.6 | 69.6 | 73.9 | 73.9 | 73.9 | 73.9 | 80.4 |
| 23. Pt_scaff_64.55 | 67.4 | 67.4 | 67.4 | 73.9 | 67.4 | 67.4 | 69.6 | 67.4 | 67.4 | 67.4 | 67.4 | 78.3 |
| 24. Pt_scaff_VII.231 | 69.6 | 69.6 | 69.6 | 76.1 | 69.6 | 69.6 | 71.7 | 69.6 | 69.6 | 69.6 | 69.6 | 78.3 |

| | 13 | 14 | 15 | 16 | 17 | 18 | 19 | 20 | 21 | 22 | 23 | 24 |
|---|---|---|---|---|---|---|---|---|---|---|---|---|
| 1. Zm_C1 | 52.2 | 52.2 | 52.2 | 47.8 | **52.2** | 52.2 | 47.8 | 47.8 | 46.9 | 47.8 | 54.3 | 54.3 |
| 2. Zm_AY135018 | 54.3 | 54.3 | 50.0 | 45.7 | **50.0** | 54.3 | 50.0 | 45.7 | 44.9 | 45.7 | 54.3 | 54.3 |
| 3. Zm_TA175111 | 45.7 | 47.8 | 47.8 | 43.5 | **47.8** | 45.7 | 43.5 | 47.8 | 46.9 | 45.7 | 45.7 | 45.7 |
| 4. Zm_TA175105 | 43.5 | 45.7 | 45.7 | 41.3 | **45.7** | 43.5 | 41.3 | 45.7 | 44.9 | 43.5 | 45.7 | 45.7 |
| 5. Os03g29614 | 50.0 | 50.0 | 47.8 | 43.5 | **47.8** | 50.0 | 45.7 | 43.5 | 42.9 | 43.5 | 54.3 | 54.3 |
| 6. AT3G13540 | 50.0 | 52.2 | 54.3 | 47.8 | **52.2** | 50.0 | 50.0 | 52.2 | 51.0 | 52.2 | 52.2 | 52.2 |
| 7. Os01g50110 | 47.8 | 50.0 | 52.2 | 45.7 | **50.0** | 47.8 | 50.0 | 47.8 | 46.9 | 47.8 | 52.2 | 52.2 |
| 8. Pt_scaff_I.1021 | 56.5 | 54.3 | 52.2 | 47.8 | **52.2** | 54.3 | 50.0 | 45.7 | 44.9 | 45.7 | 52.2 | 52.2 |
| 9. AT5G14750 | 50.0 | 47.8 | 52.2 | 50.0 | **52.2** | 45.7 | 43.5 | 50.0 | 46.9 | 50.0 | 45.7 | 45.7 |
| 10. AT5G40330 | 47.8 | 45.7 | 50.0 | 47.8 | **50.0** | 45.7 | 43.5 | 47.8 | 44.9 | 47.8 | 43.5 | 43.5 |
| 11. AT3G27920 | 50.0 | 47.8 | 52.2 | 50.0 | **52.2** | 45.7 | 43.5 | 50.0 | 46.9 | 50.0 | 47.8 | 47.8 |
| 12. Pt_scaff_XII.135 | 87.0 | 73.9 | 78.3 | 73.9 | **78.3** | 67.4 | 78.3 | 65.2 | 53.1 | 63.0 | 65.2 | 65.2 |
| 13. Pt_scaff_II.1572 | | 78.3 | 78.3 | 78.3 | **82.6** | 69.6 | 71.7 | 58.7 | 51.0 | 54.3 | 67.4 | 67.4 |
| 14. AT2G46410 | 87.0 | | 65.2 | 63.0 | **71.7** | 78.3 | 73.9 | 65.2 | 55.1 | 63.0 | 65.2 | 65.2 |
| 15. AT2G30420 | 91.3 | 87.0 | | 87.0 | **84.8** | 60.9 | 67.4 | 56.5 | 53.1 | 56.5 | 58.7 | 58.7 |
| 16. AT2G30432 | 93.5 | 84.8 | 93.5 | | **89.1** | 60.9 | 65.2 | 54.3 | 53.1 | 50.0 | 56.5 | 56.5 |
| 17. At5g53200 | 95.7 | 91.3 | 91.3 | 93.5 | | **63.0** | **69.6** | **58.7** | **53.1** | **54.3** | **60.9** | **60.9** |
| 18. AT4G01060 | 89.1 | 91.3 | 91.3 | 87.0 | 89.1 | | 78.3 | 67.4 | 59.2 | 67.4 | 56.5 | 56.5 |
| 19. AT1G01380 | 89.1 | 91.3 | 84.8 | 84.8 | 87.0 | 91.3 | | 60.9 | 51.0 | 58.7 | 63.0 | 63.0 |
| 20. Os01g43180 | 91.3 | 87.0 | 84.8 | 89.1 | 91.3 | 89.1 | 84.8 | | 73.5 | 78.3 | 58.7 | 58.7 |
| 21. Os01g43230 | 73.5 | 71.4 | 67.3 | 71.4 | 73.5 | 73.5 | 69.4 | 83.7 | | 65.3 | 51.0 | 51.0 |
| 22. Zm_TA218306 | 80.4 | 82.6 | 76.1 | 76.1 | 78.3 | 84.8 | 76.1 | 87.0 | 71.4 | | 58.7 | 58.7 |
| 23. Pt_scaff_64.55 | 76.1 | 82.6 | 69.6 | 69.6 | 71.7 | 78.3 | 80.4 | 80.4 | 65.3 | 82.6 | | 97.8 |
| 24. Pt_scaff_VII.231 | 76.1 | 82.6 | 69.6 | 69.6 | 71.7 | 78.3 | 80.4 | 80.4 | 65.3 | 82.6 | 97.8 | |

3.4. Brassinazole Resistant1 (BZR1)

Global percentages of similarity and identity between full length BZR polypeptide sequences were determined the MatGAT (Matrix Global Alignment Tool) software (BMC Bioinformatics. 2003 4:29. MatGAT: an application that generates similarity/identity matrices using protein or DNA sequences. Campanella J J, Bitincka L, Smalley J; software hosted by Ledion Bitincka). MatGAT software generates similarity/identity matrices for DNA or protein sequences without needing pre-alignment of the data. The program performed a series of pair-wise alignments using the Myers and Miller global alignment algorithm (with a gap opening penalty of 12, and a gap extension penalty of 2) and calculated similarity and identity using for example Blosum 62 (for polypeptides), and then placed the results in a distance matrix. Sequence similarity is shown in the bottom half of the dividing line and sequence identity is shown in the top half of the diagonal dividing line.

Parameters used in the comparison were:

Scoring matrix: Blosum62

First Gap: 12

Extending gap: 2

Results of the software analysis are shown in Table B for the global similarity and identity over the full length of the polypeptide sequences. Percentage identity is given above the diagonal in bold and percentage similarity is given below the diagonal (normal face).

The percentage identity between the BZR polypeptide sequences of table B4 compared to SEQ ID NO: 239 ranges from 22.5% to 88.2%.

TABLE B4

MatGAT results for global similarity and identity over the full length of the polypeptide sequences.

| | 1 | 2 | 3 | 4 | 5 | 6 | 8 | 9 | 10 | 11 | 20 | 21 | 22 | 23 |
|---|---|---|---|---|---|---|---|---|---|---|---|---|---|---|
| 1. AT1G19350.1 | | 88.2 | 40.7 | 51.9 | 39.8 | 25.1 | 65.4 | 41.0 | 54.7 | 54.9 | 40.6 | 23.2 | 41.1 | 56.5 |
| 2. AT1G75080.1 | 92.3 | | 39.4 | 53.4 | 39.3 | 24.0 | 65.7 | 40.9 | 55.4 | 55.5 | 40.6 | 23.0 | 40.5 | 55.1 |
| 3. AT1G78700.1 | 56.1 | 56.5 | | 46.0 | 62.1 | 25.1 | 40.6 | 67.1 | 46.2 | 46.7 | 59.5 | 22.8 | 59.3 | 45.5 |
| 4. AT3G50750.1 | 62.7 | 64.0 | 55.1 | | 47.3 | 33.1 | 54.3 | 42.9 | 58.6 | 60.3 | 40.6 | 22.5 | 40.9 | 57.4 |
| 5. AT4G18890.1 | 54.6 | 53.3 | 72.3 | 61.6 | | 27.9 | 42.1 | 57.2 | 47.0 | 48.7 | 52.2 | 22.1 | 52.2 | 46.2 |
| 6. AT4G36780.1 | 35.2 | 35.4 | 33.2 | 42.0 | 36.6 | | 26.5 | 24.7 | 29.0 | 29.8 | 23.6 | 18.7 | 26.5 | 28.0 |
| 8. Gm\1762729 | 78.5 | 78.0 | 55.7 | 67.2 | 55.6 | 37.0 | | 43.1 | 56.9 | 56.1 | 41.9 | 24.6 | 41.6 | 55.6 |
| 9. Gm\1765606 | 58.8 | 58.6 | 80.8 | 53.6 | 68.3 | 31.1 | 56.6 | | 45.4 | 44.4 | 56.6 | 22.6 | 58.4 | 43.9 |
| 10. Gm\1768381 | 69.9 | 71.7 | 59.1 | 71.3 | 57.4 | 36.1 | 73.3 | 56.9 | | 93.6 | 41.9 | 21.4 | 44.0 | 63.1 |
| 11. Gm\1768507 | 69.9 | 69.3 | 56.6 | 72.1 | 56.5 | 37.7 | 71.4 | 56.6 | 96.1 | | 40.1 | 21.0 | 43.2 | 64.0 |
| 20. Os01g0203000 | 53.4 | 52.1 | 69.9 | 49.9 | 62.2 | 31.2 | 52.1 | 69.6 | 52.6 | 52.1 | | 23.3 | 64.8 | 43.4 |
| 21. Os02g0129600 | 36.9 | 37.2 | 38.2 | 34.8 | 35.3 | 26.2 | 36.1 | 37.2 | 35.9 | 34.0 | 37.4 | | 23.3 | 22.6 |
| 22. Os06g0552300 | 53.5 | 52.7 | 71.0 | 51.5 | 62.3 | 31.8 | 53.5 | 70.7 | 56.3 | 55.2 | 78.4 | 36.6 | | 43.5 |
| 23. Os07g0580500 | 69.6 | 69.0 | 58.5 | 71.1 | 58.1 | 37.2 | 71.1 | 56.3 | 75.2 | 76.3 | 54.2 | 35.1 | 55.2 | |

Example 4

Identification of Domains Comprised in Polypeptide Sequences Useful in Performing the Methods of the Invention

4.1. Root Hairless 1 (RHL1)

Identification of highly conserved sequence motifs in the RHL1 polypeptides of Table A was carried out using the MEME system (Timothy et al; 1998. Journal of Computational Biology, Vol. 5, pp. 211-221, 1998); Timothy et al. 1998. Bioinformatics, Vol. 14, pp. 48-54).

TABLE C1

MEME scan results (major accession numbers) of the polypeptide sequence as represented by SEQ ID NO: 2.

| Motif | Position of motif in SEQ ID NO: 2: Start | E-value** | Sequence* |
|---|---|---|---|
| Motif 1 | 63 | 1.5e-118 | [IV]R[RK][KG][SG]QRK [NS][RK][FY] LFSFPGLLAP |
| Motif 2 | 85 | 3.2e-141 | SGG[KR][IV]G[ED]L[KA] DL[GD]TKNP[ILV] LYLDFPQG[RQ]MKL |
| Motif 3 | 244 | 6.9e-073 | TP[VS]RQSARTAGKK[FL] [KN][FY][AT]ExSS |
| Motif 4 | 155 | 9.6e-072 | GTK[ED]ENPEE[LA][RK]L [DE]FPKE[LF]Q[ENQ][GD] |
| Motif 5 | 34 | 2.3e-061 | [SN][GN][NL]L[LQV][SR] [EDG]xP[AS][KA]PR[SA] [APS]LAPSK[TAG]VL[KR] [HL][HQ]G[KR]D |
| Motif 6 | 177 | 1.1e-036 | HA[ED][CY]DFKGGAGAA [CS]D[ES][KA]Q |
| Motif 7 | 198 | 2.5e-009 | [KSN][KEP]P[GEK][EKT] [KTE][YT][VT][EG] [EPST][ELQ]SP[KE][IT] [ED][SLV][ED][DI][DV] |

TABLE C1-continued

MEME scan results (major accession numbers) of the polypeptide sequence as represented by SEQ ID NO: 2.

| Motif | Position of motif in SEQ ID NO: 2: Start | E-value** | Sequence* |
|---|---|---|---|
| | | | [LS]S[ED][DE][SD][NDS] [LD]K[DK] |
| Motif 8 | 334 | 7.3e-004 | KG[PA]AAKKQRASP[EM] [EA]K[HQ]P[TA]G[KI]K |

*Amino acids given between brackets indicate any of the possible amino acid at such given position.

** E-value: Expectation value. The number of different alignments with scores equivalent to or better than a given Score that are expected to occur in a database search by chance. The lower the E value, the more significant the score.

4.2. Tryptichon (TRY-Like)

The Integrated Resource of Protein Families, Domains and Sites (InterPro) database is an integrated interface for the commonly used signature databases for text- and sequence-based searches. The InterPro database combines these databases, which use different methodologies and varying degrees of biological information about well-characterized proteins to derive protein signatures. Collaborating databases include SWISS-PROT, PROSITE, TrEMBL, PRINTS, ProDom and Pfam, Smart and TIGRFAMs. Pfam is a large collection of multiple sequence alignments and hidden Markov models covering many common protein domains and families. Pfam is hosted at the Sanger Institute server in the United Kingdom. Interpro is hosted at the European Bioinformatics Institute in the United Kingdom.

The results of the InterPro scan of the polypeptide sequence as represented by SEQ ID NO: 76 are presented in Table C2.

TABLE C2

| InterPro scan results (major accession numbers) of the polypeptide sequence as represented by SEQ ID NO: 76. | | | | | |
|---|---|---|---|---|---|
| Method | Accession | Domain | start | stop | E-value |
| HMMPanther | PTHR10641:SF26 | TRIPTYCHON AND CPC | 32 | 106 | 1.20E−60 |
| HMMPanther | PTHR10641 | MYB-RELATED | 32 | 106 | 1.20E−60 |
| Gene3D | G3DSA:1.10.10.60 | no description | 31 | 79 | 3.60E−08 |
| HMMPfam | PF00249 | Myb_DNA-binding | 30 | 75 | 5.00E−07 |
| superfamily | SSF46689 | Homeodomain-like | 26 | 79 | 6.90E−07 |
| HMMSmart | SM00717 | SANT | 29 | 77 | 3.10E−06 |
| ProfileScan | PS50090 | MYB_LIKE | 34 | 71 | 6.307 |

4.3. Brassinazole Resistant1 (BZR1)

The Integrated Resource of Protein Families, Domains and Sites (InterPro) database is an integrated interface for the commonly used signature databases for text- and sequence-based searches. The InterPro database combines these databases, which use different methodologies and varying degrees of biological information about well-characterized proteins to derive protein signatures. Collaborating databases include SWISS-PROT, PROSITE, TrEMBL, PRINTS, ProDom and Pfam, Smart and TIGRFAMs. Pfam is a large collection of multiple sequence alignments and hidden Markov models covering many common protein domains and families. Pfam is hosted at the Sanger Institute server in the United Kingdom. Interpro is hosted at the European Bioinformatics Institute in the United Kingdom.

The results of the InterPro scan of the polypeptide sequence as represented by SEQ ID NO: 239 are presented in Table C3. The Interpro family corresponding to the BZR polypeptide is IPR008540.

TABLE C3

| InterPro scan results (major accession numbers) of the polypeptide sequence as represented by SEQ ID NO: 239. | | | | |
|---|---|---|---|---|
| Database | Accession number | Accession name | Evalue | Amino acid coordinates on SEQ ID NO: 239 |
| Pfam | PF05687 | DUF822 | 7.199xE−89 | 10-157 |

Example 5

Prediction of Secondary Structure Features of TGase

Coiled coils usually contain a repeated seven amino acid residue pattern called a heptad repeat. Coiled coils are important to identify for protein-protein interactions, such as oligomerization, either of identical proteins, of proteins of the same family, or of unrelated proteins. Recently much progress has been made in computational prediction of coiled coils from sequence data. Many algorithms well known to a person skilled in the art are available at the ExPASy Proteomics tools. One of them, COILS, is a program that compares a sequence to a database of known parallel two-stranded coiled-coils and derives a similarity score. By comparing this score to the distribution of scores in globular and coiled-coil proteins, the program then calculates the probability that the sequence will adopt a coiled-coil conformation.

Figure 6:
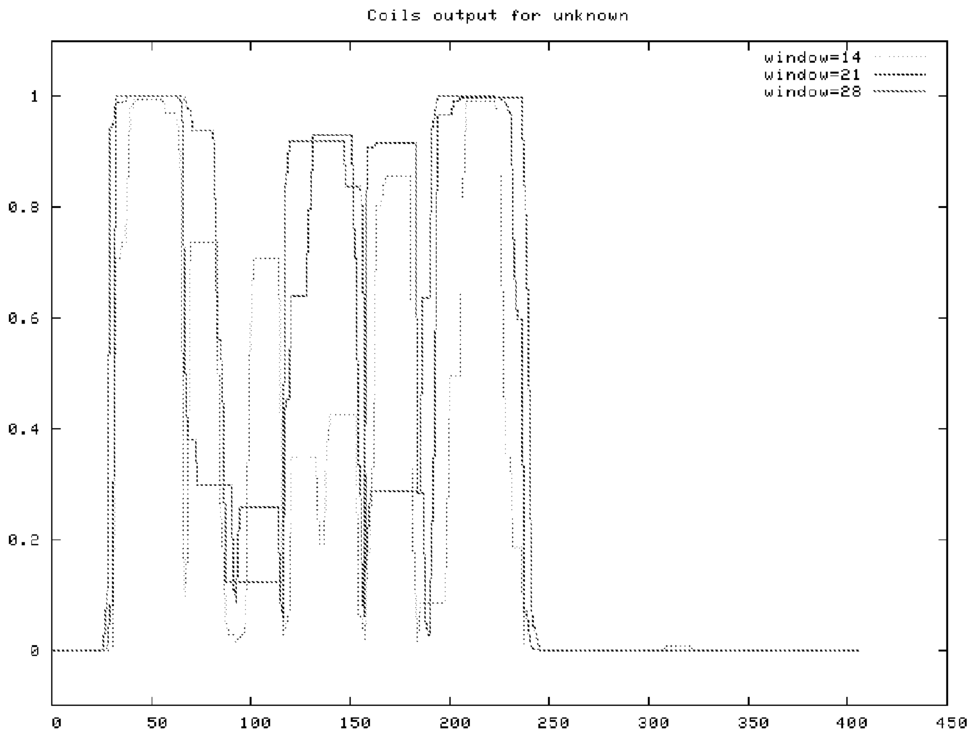
FIG. 6 shows the graphical output of the COILS algorithm predicting at least one coiled coil domain in the polypeptide as represented by SEQ ID NO: 45. The X axis represents the amino acid residue coordinates, the Y axis the probability (ranging from 0 to 1) that a coiled coil domain is present, and the three lines, the three windows (14, 21, 28) examined.
Figure 11:
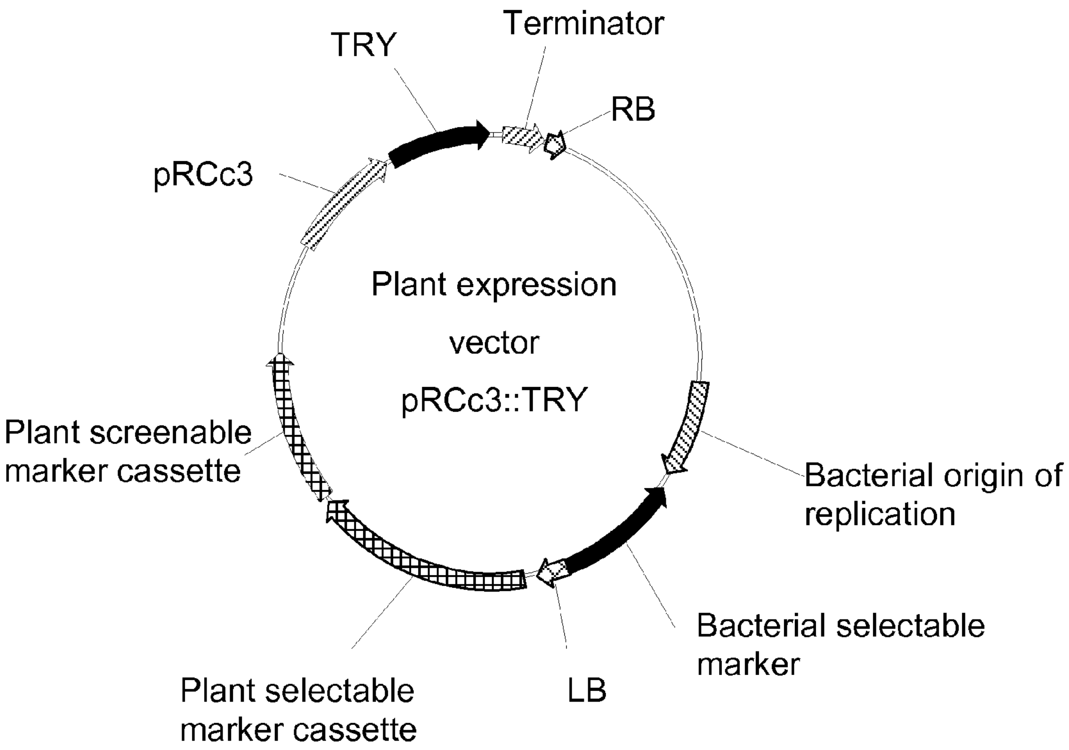
FIG. 11 represents the binary vector for increased expression in *Oryza sativa* of a TRY-like-encoding nucleic acid under the control of a rice RCc3 promoter (pRCc3).
Figure 13:
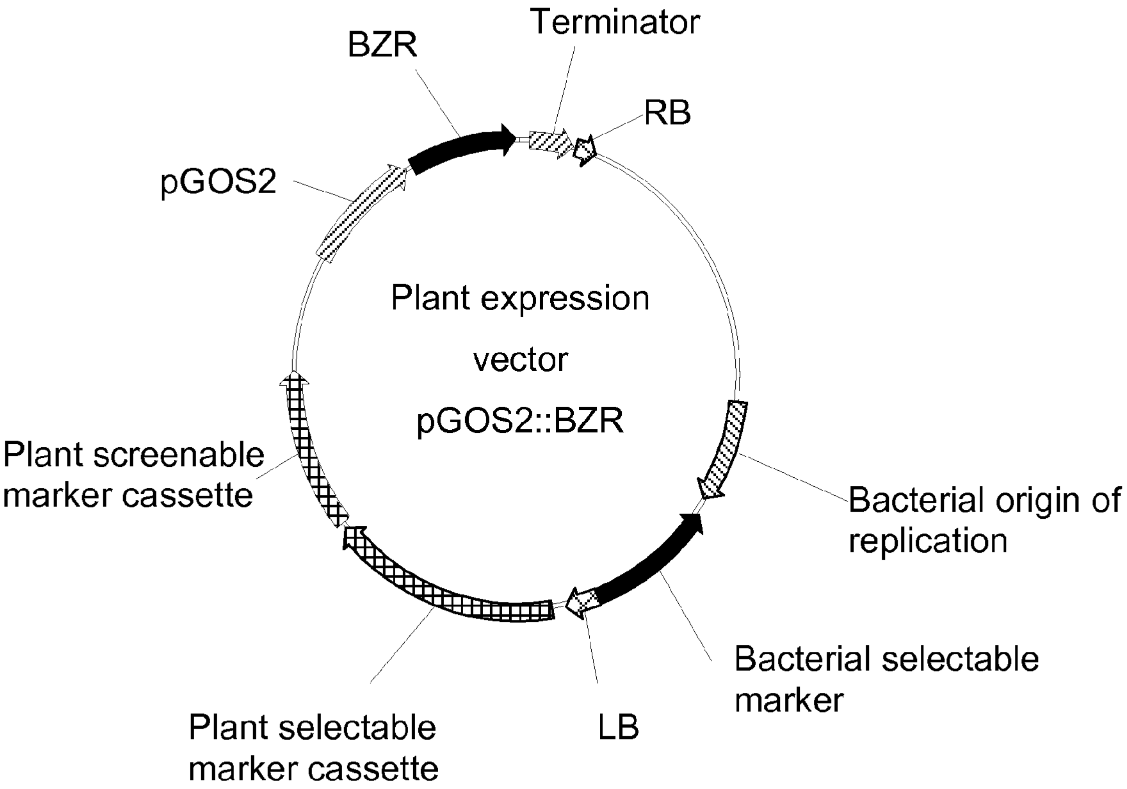
FIG. 13 represents the binary vector for increased expression in *Oryza sativa* of a BZR-encoding nucleic acid under the control of a rice GOS2 promoter (pGOS2).

The TGase polypeptide as represented by SEQ ID NO: 45, has at least one predicted coiled coil domain, with a high probability, in all three windows (14, 21 and 28) examined. In Table D1, the residue coordinates, residues, the three windows and corresponding probability values are shown. In FIG. 6, is the graphical output of the COILS algorithm on the polypeptide as represented by SEQ ID NO: 45, where at least one predicted coiled coil is clearly visible, in all three windows (as represented by the three lines).

TABLE D1

Numerical output of the COILS algorithm on the polypeptide as represented by SEQ ID NO: 45. The residue coordinates (#), residues, the three windows and corresponding probability values are shown. Probabilities above 0.9 are shown in bold.

| # | Residue | Window 14 | Prob | Window 21 | Prob | Window 28 | Prob |
|---|---|---|---|---|---|---|---|
| 29 | R | e | 0.001 | e | 0.082 | e | **0.946** |
| 30 | Q | f | 0.003 | f | 0.082 | f | **0.946** |
| 31 | P | g | 0.003 | g | 0.082 | g | **0.946** |
| 32 | L | a | 0.708 | a | **0.991** | a | **1.000** |
| 33 | D | b | 0.708 | b | **0.991** | b | **1.000** |
| 34 | R | c | 0.708 | c | **0.991** | c | **1.000** |
| 35 | A | d | 0.737 | d | **0.991** | d | **1.000** |
| 36 | A | e | 0.737 | e | **0.993** | e | **1.000** |
| 37 | T | f | 0.737 | f | **0.993** | f | **1.000** |
| 38 | A | g | 0.813 | g | **0.999** | g | **1.000** |
| 39 | L | a | **0.980** | a | **1.000** | a | **1.000** |
| 40 | E | b | **0.980** | b | **1.000** | b | **1.000** |
| 41 | I | c | **0.980** | c | **1.000** | c | **1.000** |
| 42 | L | d | **0.996** | d | **1.000** | d | **1.000** |
| 43 | E | e | **0.996** | e | **1.000** | e | **1.000** |
| 44 | K | f | **0.996** | f | **1.000** | f | **1.000** |
| 45 | K | g | **0.996** | g | **1.000** | g | **1.000** |
| 46 | L | a | **0.996** | a | **1.000** | a | **1.000** |
| 47 | A | b | **0.996** | b | **1.000** | b | **1.000** |
| 48 | E | c | **0.996** | c | **1.000** | c | **1.000** |
| 49 | Q | d | **0.996** | d | **1.000** | d | **1.000** |
| 50 | T | e | **0.996** | e | **1.000** | e | **1.000** |
| 51 | A | f | **0.996** | f | **1.000** | f | **1.000** |
| 52 | E | g | **0.996** | g | **1.000** | g | **1.000** |
| 53 | A | a | **0.996** | a | **1.000** | a | **1.000** |
| 54 | E | b | **0.996** | b | **1.000** | b | **1.000** |
| 55 | K | c | **0.996** | c | **1.000** | c | **1.000** |
| 56 | L | d | **0.996** | d | **1.000** | d | **1.000** |
| 57 | I | e | **0.971** | e | **1.000** | e | **1.000** |
| 58 | R | f | **0.971** | f | **1.000** | f | **1.000** |
| 59 | E | g | **0.971** | g | **1.000** | g | **1.000** |
| 60 | N | a | **0.971** | a | **1.000** | a | **1.000** |
| 61 | Q | b | **0.971** | b | **1.000** | b | **1.000** |
| 62 | R | c | **0.971** | c | **1.000** | c | **1.000** |
| 63 | L | d | **0.971** | d | **1.000** | d | **1.000** |
| 64 | A | e | **0.921** | e | **0.997** | e | **1.000** |
| 65 | S | f | 0.848 | f | **0.989** | f | **1.000** |
| 66 | S | g | 0.231 | g | **0.917** | g | **1.000** |
| 67 | H | a | 0.099 | a | 0.537 | a | **0.999** |
| 68 | V | b | 0.179 | b | 0.379 | b | **0.979** |
| 69 | V | c | 0.662 | c | 0.379 | c | **0.979** |
| 70 | L | d | 0.736 | d | 0.379 | d | **0.979** |
| 71 | R | e | 0.736 | e | 0.379 | e | **0.939** |
| 72 | Q | f | 0.736 | f | 0.379 | f | **0.939** |
| 73 | D | g | 0.736 | g | 0.297 | g | **0.939** |
| 74 | I | a | 0.736 | a | 0.297 | a | **0.939** |
| 75 | V | b | 0.736 | b | 0.297 | b | **0.939** |

TABLE D1-continued

Numerical output of the COILS algorithm on the polypeptide as represented by SEQ ID NO: 45. The residue coordinates (#), residues, the three windows and corresponding probability values are shown. Probabilities above 0.9 are shown in bold.

TABLE D1-continued

Numerical output of the COILS algorithm on the polypeptide as represented by SEQ ID NO: 45. The residue coordinates (#), residues, the three windows and corresponding probability values are shown. Probabilities above 0.9 are shown in bold.

| # | Residue | Window 14 | Prob | Window 21 | Prob | Window 28 | Prob |
|---|---|---|---|---|---|---|---|
| 76 | D | c | 0.736 | c | 0.297 | c | **0.939** |
| 77 | T | d | 0.736 | d | 0.297 | d | **0.939** |
| 78 | E | e | 0.736 | e | 0.297 | e | **0.939** |
| 79 | K | f | 0.736 | f | 0.297 | f | **0.939** |
| 80 | E | g | 0.736 | g | 0.297 | g | **0.939** |
| 81 | M | a | 0.736 | a | 0.297 | a | **0.939** |
| 82 | Q | b | 0.736 | b | 0.297 | b | **0.900** |
| 83 | M | c | 0.736 | c | 0.297 | c | 0.560 |
| 84 | I | d | 0.265 | d | 0.297 | d | 0.560 |
| 85 | R | e | 0.265 | e | 0.297 | e | 0.560 |
| 86 | A | f | 0.151 | f | 0.297 | f | 0.407 |
| 87 | H | g | 0.047 | g | 0.297 | g | 0.123 |
| 88 | L | a | 0.047 | a | 0.297 | a | 0.123 |
| 89 | G | b | 0.026 | b | 0.297 | b | 0.123 |
| 90 | D | c | 0.026 | c | 0.297 | c | 0.123 |
| 91 | V | d | 0.026 | d | 0.108 | d | 0.123 |
| 92 | Q | e | 0.013 | e | 0.108 | e | 0.123 |
| 93 | T | b | 0.009 | b | 0.086 | b | 0.123 |
| 94 | E | c | 0.025 | c | 0.259 | c | 0.123 |
| 95 | T | d | 0.025 | d | 0.259 | d | 0.123 |
| 96 | D | e | 0.025 | e | 0.259 | e | 0.123 |
| 97 | M | f | 0.051 | f | 0.259 | f | 0.123 |
| 98 | H | g | 0.159 | g | 0.259 | g | 0.124 |
| 99 | M | a | 0.517 | a | 0.259 | a | 0.124 |
| 100 | R | b | 0.556 | b | 0.259 | b | 0.124 |
| 101 | D | c | 0.707 | c | 0.259 | c | 0.124 |
| 102 | L | d | 0.707 | d | 0.259 | d | 0.124 |
| 103 | M | e | 0.707 | e | 0.259 | e | 0.124 |
| 104 | E | f | 0.707 | f | 0.259 | f | 0.124 |
| 105 | R | g | 0.707 | g | 0.259 | g | 0.124 |
| 106 | M | a | 0.707 | a | 0.259 | a | 0.124 |
| 107 | R | b | 0.707 | b | 0.259 | b | 0.124 |
| 108 | L | c | 0.707 | c | 0.259 | c | 0.124 |
| 109 | M | d | 0.707 | d | 0.259 | d | 0.124 |
| 110 | E | e | 0.707 | e | 0.259 | e | 0.124 |
| 111 | A | f | 0.707 | f | 0.259 | f | 0.124 |
| 112 | D | g | 0.707 | g | 0.259 | g | 0.124 |
| 113 | I | a | 0.707 | a | 0.259 | a | 0.124 |
| 114 | Q | b | 0.707 | b | 0.259 | b | 0.124 |
| 115 | A | c | 0.561 | c | 0.092 | c | 0.124 |
| 116 | G | d | 0.028 | d | 0.057 | d | 0.124 |
| 117 | D | b | 0.040 | b | 0.424 | b | 0.842 |
| 118 | A | c | 0.042 | c | 0.452 | c | 0.842 |
| 119 | V | d | 0.074 | d | 0.452 | d | **0.918** |
| 120 | K | e | 0.349 | e | 0.639 | e | **0.918** |
| 121 | K | f | 0.349 | f | 0.639 | f | **0.918** |
| 122 | E | g | 0.349 | g | 0.639 | g | **0.918** |
| 123 | L | a | 0.349 | a | 0.639 | a | **0.918** |
| 124 | H | b | 0.349 | b | 0.639 | b | **0.918** |
| 125 | Q | c | 0.349 | c | 0.639 | c | **0.918** |
| 126 | V | d | 0.349 | d | 0.639 | d | **0.918** |
| 127 | H | e | 0.349 | e | 0.639 | e | **0.918** |
| 128 | M | f | 0.349 | f | 0.639 | f | **0.918** |
| 129 | E | g | 0.349 | g | 0.797 | g | **0.918** |
| 130 | A | a | 0.349 | a | 0.797 | a | **0.918** |
| 131 | K | b | 0.349 | b | 0.930 | b | **0.918** |
| 132 | R | c | 0.349 | c | 0.930 | c | **0.918** |
| 133 | L | d | 0.349 | d | 0.930 | d | **0.918** |
| 134 | I | e | 0.190 | e | 0.930 | e | **0.918** |
| 135 | A | f | 0.190 | f | 0.930 | f | **0.918** |
| 136 | E | g | 0.190 | g | 0.930 | g | **0.918** |
| 137 | R | a | 0.190 | a | 0.930 | a | **0.918** |
| 138 | Q | b | 0.376 | b | 0.930 | b | **0.918** |
| 139 | M | c | 0.376 | c | 0.930 | c | **0.918** |
| 140 | L | d | 0.426 | d | 0.930 | d | **0.918** |
| 141 | T | e | 0.426 | e | 0.930 | e | **0.918** |
| 142 | V | f | 0.426 | f | 0.930 | f | **0.918** |
| 143 | E | g | 0.426 | g | 0.930 | g | **0.918** |
| 144 | M | a | 0.426 | a | 0.930 | a | **0.918** |
| 145 | D | b | 0.426 | b | 0.930 | b | **0.918** |
| 146 | K | c | 0.426 | c | 0.930 | c | **0.918** |
| 147 | V | d | 0.426 | d | 0.930 | d | **0.918** |
| 148 | T | e | 0.426 | e | 0.930 | e | 0.838 |
| 149 | K | f | 0.426 | f | 0.930 | f | 0.838 |
| 150 | E | g | 0.426 | g | 0.930 | g | 0.838 |
| 151 | L | a | 0.426 | a | 0.930 | a | 0.838 |
| 152 | H | b | 0.426 | b | 0.708 | b | 0.838 |
| 153 | K | c | 0.426 | c | 0.708 | c | 0.838 |
| 154 | F | d | 0.066 | d | 0.334 | d | 0.838 |
| 155 | S | e | 0.055 | e | 0.334 | e | 0.838 |
| 156 | G | f | 0.055 | f | 0.099 | f | 0.792 |
| 157 | D | g | 0.018 | g | 0.062 | g | 0.492 |
| 158 | S | e | 0.071 | e | 0.755 | e | 0.146 |
| 159 | K | f | 0.176 | f | **0.908** | f | 0.201 |
| 160 | K | g | 0.176 | g | **0.908** | g | 0.288 |
| 161 | L | a | 0.333 | a | **0.908** | a | 0.288 |
| 162 | P | b | 0.333 | b | **0.908** | b | 0.288 |
| 163 | E | c | 0.804 | c | **0.916** | c | 0.288 |
| 164 | L | d | 0.804 | d | **0.916** | d | 0.288 |
| 165 | L | e | 0.804 | e | **0.916** | e | 0.288 |
| 166 | T | f | 0.807 | f | **0.916** | f | 0.288 |
| 167 | E | g | 0.856 | g | **0.916** | g | 0.288 |
| 168 | L | a | 0.856 | a | **0.916** | a | 0.288 |
| 169 | D | b | 0.856 | b | **0.916** | b | 0.288 |
| 170 | G | c | 0.856 | c | **0.916** | c | 0.288 |
| 171 | L | d | 0.856 | d | **0.916** | d | 0.288 |
| 172 | R | e | 0.856 | e | **0.916** | e | 0.288 |
| 173 | K | f | 0.856 | f | **0.916** | f | 0.288 |
| 174 | E | g | 0.856 | g | **0.916** | g | 0.288 |
| 175 | H | a | 0.856 | a | **0.916** | a | 0.288 |
| 176 | Q | b | 0.856 | b | **0.916** | b | 0.288 |
| 177 | S | c | 0.856 | c | **0.916** | c | 0.288 |
| 178 | L | d | 0.856 | d | **0.916** | d | 0.288 |
| 179 | R | e | 0.856 | e | **0.916** | e | 0.288 |
| 180 | S | f | 0.856 | f | **0.916** | f | 0.288 |
| 181 | A | g | 0.405 | g | **0.916** | g | 0.288 |
| 182 | F | a | 0.102 | a | **0.916** | a | 0.288 |
| 183 | E | b | 0.102 | b | **0.916** | b | 0.288 |
| 184 | Y | c | 0.016 | c | 0.283 | c | 0.288 |
| 185 | E | c | 0.085 | c | 0.283 | c | 0.288 |
| 186 | K | d | 0.085 | d | 0.283 | d | 0.638 |
| 187 | N | e | 0.085 | e | 0.283 | e | 0.638 |
| 188 | T | f | 0.085 | f | 0.058 | f | 0.638 |
| 189 | N | g | 0.085 | g | 0.025 | g | 0.638 |
| 190 | I | a | 0.085 | a | 0.026 | a | 0.638 |
| 191 | K | b | 0.085 | b | 0.232 | b | **0.938** |
| 192 | Q | c | 0.085 | c | 0.232 | c | **0.951** |
| 193 | V | d | 0.085 | d | 0.696 | d | **0.988** |
| 194 | E | f | 0.087 | f | **0.967** | f | **1.000** |
| 195 | Q | g | 0.087 | g | **0.967** | g | **1.000** |
| 196 | M | a | 0.087 | a | **0.967** | a | **1.000** |
| 197 | R | b | 0.087 | b | **0.967** | b | **1.000** |
| 198 | T | c | 0.087 | c | **0.967** | c | **1.000** |
| 199 | M | d | 0.203 | d | **0.967** | d | **1.000** |
| 200 | E | e | 0.497 | e | **0.967** | e | **1.000** |
| 201 | M | f | 0.497 | f | **0.967** | f | **1.000** |
| 202 | N | g | 0.497 | g | **0.994** | g | **1.000** |
| 203 | L | a | 0.497 | a | **0.994** | a | **1.000** |
| 204 | M | b | 0.497 | b | **0.994** | b | **1.000** |
| 205 | T | c | 0.497 | c | **0.997** | c | **1.000** |
| 206 | M | d | 0.792 | d | **0.997** | d | **1.000** |
| 207 | T | e | 0.884 | e | **0.997** | e | **1.000** |
| 208 | K | f | **0.993** | f | **0.997** | f | **1.000** |
| 209 | E | g | **0.993** | g | **0.997** | g | **1.000** |
| 210 | A | a | **0.993** | a | **0.997** | a | **1.000** |
| 211 | D | b | **0.993** | b | **0.997** | b | **1.000** |
| 212 | K | c | **0.993** | c | **0.997** | c | **1.000** |
| 213 | L | d | **0.993** | d | **0.997** | d | **1.000** |
| 214 | R | e | **0.993** | e | **0.997** | e | **1.000** |
| 215 | A | f | **0.993** | f | **0.997** | f | **1.000** |
| 216 | D | g | **0.993** | g | **0.997** | g | **1.000** |
| 217 | V | a | **0.993** | a | **0.997** | a | **1.000** |
| 218 | A | b | **0.993** | b | **0.997** | b | **1.000** |
| 219 | N | c | **0.993** | c | **0.997** | c | **1.000** |

TABLE D1-continued

Numerical output of the COILS algorithm on the polypeptide as represented by SEQ ID NO: 45. The residue coordinates (#), residues, the three windows and corresponding probability values are shown. Probabilities above 0.9 are shown in bold.

| # | Residue | Window 14 | Prob | Window 21 | Prob | Window 28 | Prob |
|---|---|---|---|---|---|---|---|
| 220 | A | d | **0.993** | d | **0.997** | d | **1.000** |
| 221 | E | e | **0.993** | e | **0.997** | e | **1.000** |
| 222 | K | f | **0.993** | f | **0.997** | f | **1.000** |
| 223 | R | g | **0.978** | g | **0.997** | g | **0.999** |
| 224 | A | a | **0.978** | a | **0.997** | a | **0.999** |
| 225 | Q | b | **0.978** | b | **0.997** | b | **0.999** |
| 226 | V | c | 0.745 | c | **0.996** | c | **0.999** |
| 227 | A | d | 0.560 | d | **0.996** | d | **0.999** |
| 228 | A | e | 0.348 | e | **0.989** | e | **0.999** |
| 229 | A | f | 0.348 | f | **0.982** | f | **0.999** |
| 230 | Q | g | 0.348 | g | **0.968** | g | **0.999** |
| 231 | A | a | 0.296 | a | **0.968** | a | **0.999** |
| 232 | V | g | 0.184 | g | 0.778 | g | **0.999** |
| 233 | A | a | 0.184 | a | 0.632 | a | **0.999** |
| 234 | A | b | 0.184 | b | 0.598 | b | **0.999** |
| 235 | Q | c | 0.184 | c | 0.598 | c | **0.999** |
| 236 | A | d | 0.184 | d | 0.598 | d | **0.998** |
| 237 | G | e | 0.013 | e | 0.069 | e | 0.840 |
| 238 | V | f | 0.004 | f | 0.069 | f | 0.840 |
| 239 | A | b | 0.001 | b | 0.069 | b | 0.742 |
| 240 | H | c | 0.001 | c | 0.017 | c | 0.383 |
| 241 | V | d | 0.001 | d | 0.007 | d | 0.085 |
| 242 | T | e | 0.001 | e | 0.001 | e | 0.042 |
| 243 | A | f | 0.001 | f | 0.001 | f | 0.042 |
| 244 | S | g | 0.000 | g | 0.001 | g | 0.013 |
| 245 | Q | f | 0.000 | f | 0.001 | f | 0.002 |
| 246 | P | b | 0.000 | b | 0.000 | b | 0.000 |

Example 6

Topology Prediction of the Polypeptide Sequences Useful in Performing the Methods of the Invention 6.1. Transglutaminases (TGases)

Many algorithms can be used to perform prediction of the subcellular localisation of polypeptides, including:

- TargetP 1.1 hosted on the server of the Technical University of Denmark;
- ChloroP 1.1 hosted on the server of the Technical University of Denmark;
- Protein Prowler Subcellular Localisation Predictor version 1.2 hosted on the server of the Institute for Molecular Bioscience, University of Queensland, Brisbane, Australia;
- PENCE Proteome Analyst PA-GOSUB 2.5 hosted on the server of the University of Alberta, Edmonton, Alberta, Canada;
- TMHMM, hosted on the server of the Technical University of Denmark By comparing the polypeptide sequence of SEQ ID NO: 45 with orthologs from other plant species for which subcellular localisation was identified, it is possible to deduce that the subcellular localization of the polypeptide sequence as represented by SEQ ID NO: 45 is the chloroplast (Villalobos et al. (2004) Gene 336: 93-104).

6.2. Tryptichon (TRY-Like)

TargetP 1.1 predicts the subcellular location of eukaryotic proteins. The location assignment is based on the predicted presence of any of the N-terminal pre-sequences: chloroplast transit peptide (cTP), mitochondrial targeting peptide (mTP) or secretory pathway signal peptide (SP). Scores on which the final prediction is based are not really probabilities, and they do not necessarily add to one. However, the location with the highest score is the most likely according to TargetP, and the relationship between the scores (the reliability class) may be an indication of how certain the prediction is. The reliability class (RC) ranges from 1 to 5, where 1 indicates the strongest prediction. TargetP is maintained at the server of the Technical University of Denmark.

For the sequences predicted to contain an N-terminal presequence a potential cleavage site can also be predicted.

A number of parameters were selected, such as organism group (non-plant or plant), cutoff sets (none, predefined set of cutoffs, or user-specified set of cutoffs), and the calculation of prediction of cleavage sites (yes or no).

The results of TargetP 1.1 analysis of the polypeptide sequence as represented by SEQ ID NO: 76 are presented Table E1. The "plant" organism group has been selected, no cutoffs defined, and the predicted length of the transit peptide requested. The subcellular localization of the polypeptide sequence as represented by SEQ ID NO: 76 may be the cytoplasm or nucleus, no transit peptide is predicted.

TABLE E1

TargetP 1.1 analysis of the polypeptide sequence as represented by SEQ ID NO: 76

| | |
|---|---|
| Length (AA) | 106 |
| Chloroplastic transit peptide | 0.048 |
| Mitochondrial transit peptide | 0.348 |
| Secretory pathway signal peptide | 0.046 |
| Other subcellular targeting | 0.822 |
| Predicted Location | / |
| Reliability class | 3 |
| Predicted transit peptide length | / |

When analysed with PSort, the probability for a nuclear localisation is 0.700, therefore the protein is likely a nuclear protein.

Many other algorithms can be used to perform such analyses, including:

- ChloroP 1.1 hosted on the server of the Technical University of Denmark;
- Protein Prowler Subcellular Localisation Predictor version 1.2 hosted on the server of the Institute for Molecular Bioscience, University of Queensland, Brisbane, Australia;
- PENCE Proteome Analyst PA-GOSUB 2.5 hosted on the server of the University of Alberta, Edmonton, Alberta, Canada;
- TMHMM, hosted on the server of the Technical University of Denmark
- PSORT (URL: psort.org)
- PLOC (Park and Kanehisa, Bioinformatics, 19, 1656-1663, 2003).

Example 7

Assay Related to the Polypeptide Sequences Useful in Performing the Methods of the Invention 7.1. Functional Assay of Root Hairless 1 (RHL1)

The binding of an RHL1 polypeptide is assayed in an in vitro assay essentially as described by Sugimoto-Shirasu et al. 2005 PNAS vol. 102_ no. 51, 18736-18741. Briefly, Recombinant RHL1 Pprotein is produced in a bacterial system and purified using standard methods. Purified RHL1 protein is incubated with DNa fragments and binding of the RHL1 protein the DNA fragment is detected using plasmon resonance (SPR).

7.2. Transglutaminases (TGases)

Polypeptides useful in performing the methods of the invention typically catalyze the formation of amide linkages, generally in a Ca-dependent fashion, between the primary amine of an amine donor substrate and the γ-carboxamide group of peptide-bound endo-glutamine residues in proteins or polypeptides that are the amine acceptors. More specifically, TGase activity can be measured using the radiolabeled putrescine method, or the gamma-glutamyl biotin cadaverine method, as described in Villalobos et al. (2004; supra).

A person skilled in the art is well aware of such experimental procedures to measure TGase polypeptide enzymatic activity, including the activity of a TGase polypeptide as represented by SEQ ID NO: 45.

7.3. Functional Assay of Tryptichon (TRY-Like)

TRY-like polypeptides typically have DNA-binding activity. One method for measuring and characterising DNA-binding properties of polypeptides is described in Xue (A CELD-fusion method for rapid determination of the DNA-binding sequence specificity of novel plant DNA-binding proteins. Plant Journal 41, 638-649, 2005).

Example 8

Cloning of the Nucleic Acid Sequence Used in the Methods of the Invention

8.1. Root Hairless 1 (RHL1)

The nucleic acid sequence used in the methods of the invention was amplified by PCR using as template a custom-made *Arabidopsis thaliana* seedlings cDNA library (in pCMV Sport 6.0; Invitrogen, Paisley, UK). PCR was performed using Hifi Taq DNA polymerase in standard conditions, using 200 ng of template in a 50 μl PCR mix. The primers used were: 5'-ggggacaagtttgtacaaaaaagcag-gcttaaacaatggtacgagcttcatcgtc-3' (SEQ ID NO: 40; sense) and 5'-ggggaccactttgtacaa-gaaagctgggtttctggaaaagatttctttaagc-3' (SEQ ID NO: 41; reverse) which include the AttB sites for Gateway recombination. The amplified PCR fragment was purified also using standard methods. The first step of the Gateway procedure, the BP reaction, was then performed, during which the PCR fragment recombines in vivo with the pDONR201 plasmid to produce, according to the Gateway terminology, an "entry clone", pArath_RHL1. Plasmid pDONR201 was purchased from Invitrogen, as part of the Gateway® technology.

The entry clone comprising SEQ ID NO: 1 was then used in an LR reaction with a destination vector used for *Oryza sativa* transformation. This vector contained as functional elements within the T-DNA borders: a plant selectable marker; a screenable marker expression cassette; and a Gateway cassette intended for LR in vivo recombination with the nucleic acid sequence of interest already cloned in the entry clone. A rice GOS2 promoter (SEQ ID NO: 42) for root specific expression was located upstream of this Gateway cassette.

After the LR recombination step, the resulting expression vector pGOS2::Arath_RHL11 (FIG. 3) was transformed into *Agrobacterium* strain LBA4044 according to methods well known in the art.

8.2. Transglutaminases (TGases)

The *Oryza sativa* nucleic acid sequence encoding a TGase polypeptide sequence as represented by SEQ ID NO: 45 was amplified by PCR using as template a cDNA bank constructed using RNA from rice plants at different developmental stages. The following primers, which include the AttB sites for Gateway recombination, were used for PCR amplification: prm02265 (SEQ ID NO: 73, sense): 5'-gggga-caagtttgtacaaaaaagcaggcttcacaatggcataccatggacag-3' and prm02266 (SEQ ID NO: 74, reverse, complementary): 5'-ggggaccactttgtacaagaaagctgggtatttcacctctggcctg-3'. PCR was performed using Hifi Taq DNA polymerase in standard conditions. A PCR fragment of the expected length (including attB sites) was amplified and purified also using standard methods. The first step of the Gateway procedure, the BP reaction, was then performed, during which the PCR fragment recombined in vivo with the pDONR201 plasmid to produce, according to the Gateway terminology, an "entry clone". Plasmid pDONR201 was purchased from Invitrogen, as part of the Gateway® technology.

The entry clone comprising SEQ ID NO: 44 was subsequently used in an LR reaction with a destination vector used for *Oryza sativa* transformation. This vector contained as functional elements within the T-DNA borders: a plant selectable marker; a screenable marker expression cassette; and a Gateway cassette intended for LR in vivo recombination with the nucleic acid sequence of interest already cloned in the entry clone. A rice alpha-globulin promoter (SEQ ID NO: 72) for seed-specific expression was located upstream of this Gateway cassette.

Figure 4:
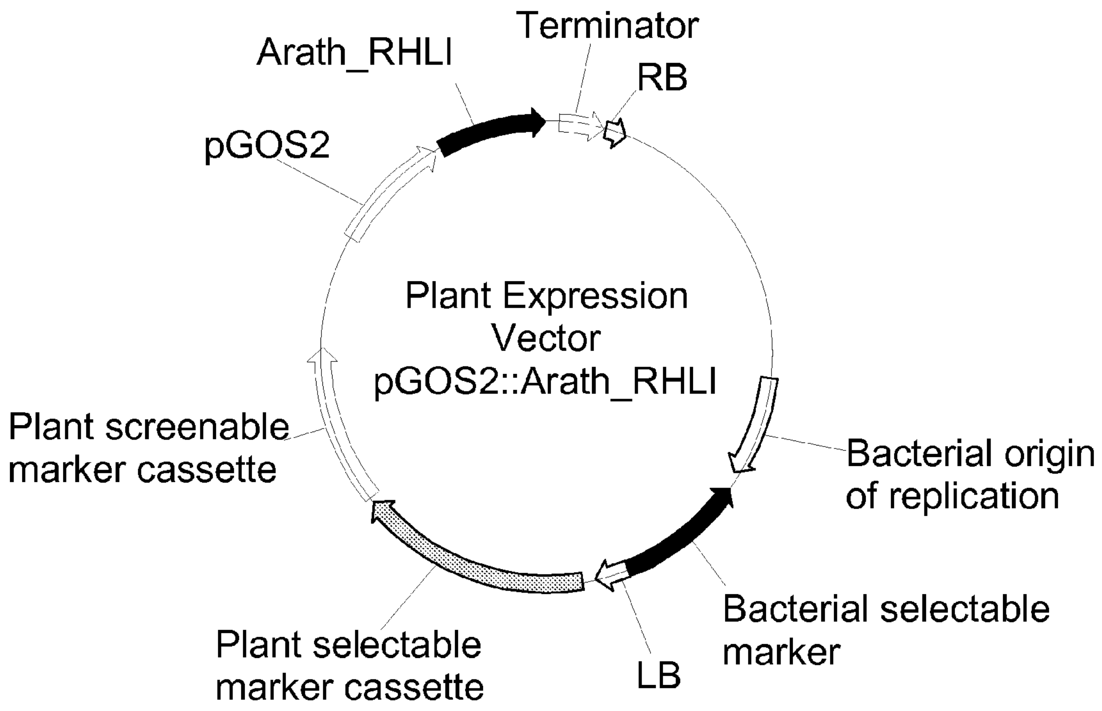
FIG. 4 represents the binary vector for increased expression in *Oryza sativa* of a RHL1-encoding nucleic acid under the control of a rice GOS2 promoter (pGOS2)
Figure 5:
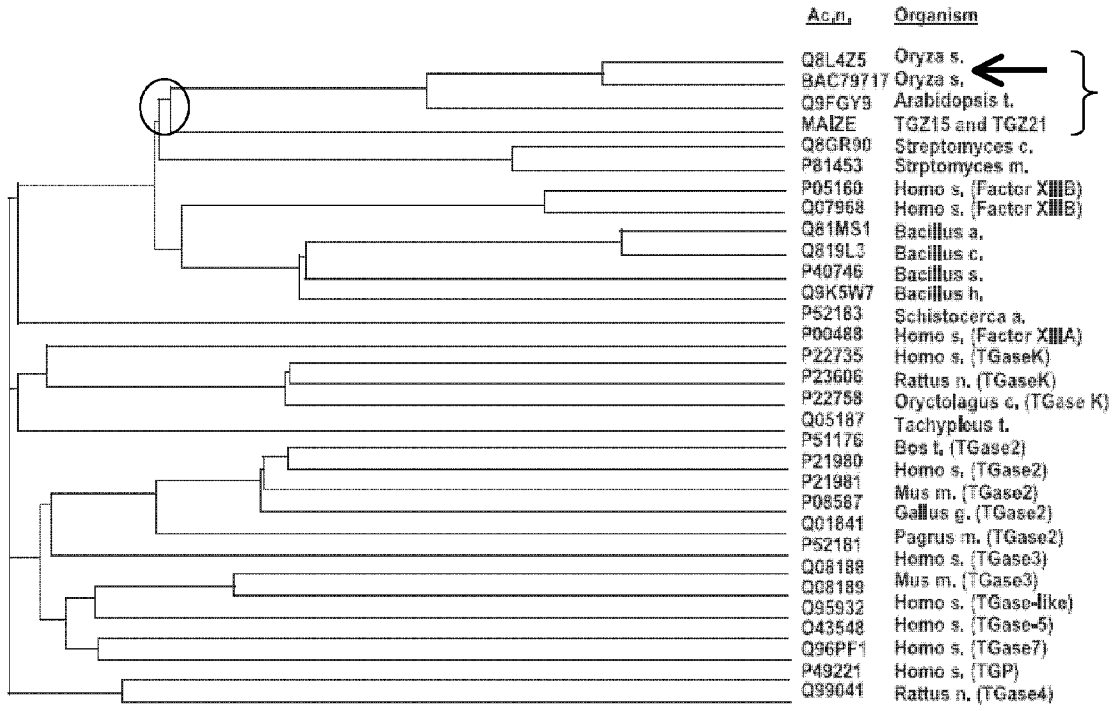
FIG. 5 shows a phylogenetic tree of TGase polypeptides from various source organisms, according to Villalobos et al. (2004; Gene 336: 93-104). TGases useful in performing the methods of the invention (essentially from plants) are shown with a bracket, the clade split with a circle, the arrow points to the *Oryza sativa* TGase polypeptide as represented by SEQ ID NO: 45.

After the LR recombination step, the resulting expression vector pGlob::TGase (FIG. 4) for seed-specific expression, was transformed into *Agrobacterium* strain LBA4044 according to methods well known in the art.

8.3. Tryptichon (TRY-Like)

The nucleic acid sequence used in the methods of the invention was amplified by PCR using as template a custom-made *Arabidopsis thaliana* seedlings cDNA library (in pCMV Sport 6.0; Invitrogen, Paisley, UK). PCR was performed using Hifi Taq DNA polymerase in standard conditions, using 200 ng of template in a 50 μl PCR mix. The primers used were prm09014 (SEQ ID NO: 233; sense, start codon in bold): 5'-ggggacaagtttgtacaaaaaagcag-gcttaaacaatggataacactgaccgtcgt-3' and prm09015 (SEQ ID NO: 234; reverse, complementary): 5'-ggggaccactttgtacaa-gaaagctgggttttttcgttggcttaaaaaca-3', which include the AttB sites for Gateway recombination. The amplified PCR fragment was purified also using standard methods. The first step of the Gateway procedure, the BP reaction, was then performed, during which the PCR fragment recombines in vivo with the pDONR201 plasmid to produce, according to the Gateway terminology, an "entry clone", pTRY-like. Plasmid pDONR201 was purchased from Invitrogen, as part of the Gateway® technology.

The entry clone comprising SEQ ID NO: 75 was then used in an LR reaction with a destination vector used for *Oryza sativa* transformation. This vector contained as functional elements within the T-DNA borders: a plant selectable marker; a screenable marker expression cassette; and a Gateway cassette intended for LR in vivo recombination with the nucleic acid sequence of interest already cloned in the entry clone. A rice GOS2 promoter (SEQ ID NO: 237) for constitutive specific expression was located upstream of this Gateway cassette. In an alternative embodiment, a root specific promoter (RCc3 promoter; SEQ ID NO: 235)

After the LR recombination step, the resulting expression vector pGOS2::TRY-like (FIG. 3) or pRCc3::TRY was transformed into *Agrobacterium* strain LBA4044 according to methods well known in the art.

8.4. Brassinazole Resistant1 (BZR1)

The nucleic acid sequence used in the methods of the invention was amplified by PCR using as template a custom-made *Arabidopsis thaliana* seedlings cDNA library (in pCMV Sport 6.0; Invitrogen, Paisley, UK). PCR was performed using Hifi Taq DNA polymerase in standard conditions, using 200 ng of template in a 50 μl PCR mix. The primers used were (SEQ ID NO: 320; sense): 5'-ggggacaagtttgtacaaaaaagcaggcttaaacaatgacggcatcaggagga-3' and (SEQ ID NO: 321; reverse, complementary): 5'-ggggaccactttgtacaagaaagctgggtaccacgatattaacctagccg-3', which include the AttB sites for Gateway recombination. The amplified PCR fragment was purified also using standard methods. The first step of the Gateway procedure, the BP reaction, was then performed, during which the PCR fragment recombined in vivo with the pDONR201 plasmid to produce, according to the Gateway terminology, an "entry clone", pBZR. Plasmid pDONR201 was purchased from Invitrogen, as part of the Gateway® technology.

The entry clone comprising SEQ ID NO: 238 was then used in an LR reaction with a destination vector used for *Oryza sativa* transformation. This vector contained as functional elements within the T-DNA borders: a plant selectable marker; a screenable marker expression cassette; and a Gateway cassette intended for LR in vivo recombination with the nucleic acid sequence of interest already cloned in the entry clone. A rice GOS2 promoter (SEQ ID NO: 322) for constitutive specific expression was located upstream of this Gateway cassette.

After the LR recombination step, the resulting expression vector pGOS2::BZR (FIG. 3) was transformed into *Agrobacterium* strain LBA4044 according to methods well known in the art.

Example 9

Plant Transformation

Rice Transformation

The *Agrobacterium* containing the expression vector was used to transform *Oryza sativa* plants. Mature dry seeds of the rice japonica cultivar Nipponbare were dehusked. Sterilization was carried out by incubating for one minute in 70% ethanol, followed by 30 minutes in 0.2% $HgCl_2$, followed by a 6 times 15 minutes wash with sterile distilled water. The sterile seeds were then germinated on a medium containing 2,4-D (callus induction medium). After incubation in the dark for four weeks, embryogenic, scutellum-derived calli were excised and propagated on the same medium. After two weeks, the calli were multiplied or propagated by subculture on the same medium for another 2 weeks. Embryogenic callus pieces were sub-cultured on fresh medium 3 days before co-cultivation (to boost cell division activity).

*Agrobacterium* strain LBA4404 containing the expression vector was used for co-cultivation. *Agrobacterium* was inoculated on AB medium with the appropriate antibiotics and cultured for 3 days at 28° C. The bacteria were then collected and suspended in liquid co-cultivation medium to a density ($OD_{600}$) of about 1. The suspension was then transferred to a Petri dish and the calli immersed in the suspension for 15 minutes. The callus tissues were then blotted dry on a filter paper and transferred to solidified, co-cultivation medium and incubated for 3 days in the dark at 25° C. Co-cultivated calli were grown on 2,4-D-containing medium for 4 weeks in the dark at 28° C. in the presence of a selection agent. During this period, rapidly growing resistant callus islands developed. After transfer of this material to a regeneration medium and incubation in the light, the embryogenic potential was released and shoots developed in the next four to five weeks. Shoots were excised from the calli and incubated for 2 to 3 weeks on an auxin-containing medium from which they were transferred to soil. Hardened shoots were grown under high humidity and short days in a greenhouse.

Approximately 35 independent T0 rice transformants were generated for one construct. The primary transformants were transferred from a tissue culture chamber to a greenhouse. After a quantitative PCR analysis to verify copy number of the T-DNA insert, only single copy transgenic plants that exhibit tolerance to the selection agent were kept for harvest of T1 seed. Seeds were then harvested three to five months after transplanting. The method yielded single locus transformants at a rate of over 50% (Aldemita and Hodges 1996, Chan et al. 1993, Hiei et al. 1994).

Corn Transformation

Transformation of maize (*Zea mays*) is performed with a modification of the method described by Ishida et al. (1996) Nature Biotech 14(6): 745-50. Transformation is genotype-dependent in corn and only specific genotypes are amenable to transformation and regeneration. The inbred line A188 (University of Minnesota) or hybrids with A188 as a parent are good sources of donor material for transformation, but other genotypes can be used successfully as well. Ears are harvested from corn plant approximately 11 days after pollination (DAP) when the length of the immature embryo is about 1 to 1.2 mm. Immature embryos are cocultivated with *Agrobacterium tumefaciens* containing the expression vector, and transgenic plants are recovered through organogenesis. Excised embryos are grown on callus induction medium, then maize regeneration medium, containing the selection agent (for example imidazolinone but various selection markers can be used). The Petri plates are incubated in the light at 25° C. for 2-3 weeks, or until shoots develop. The green shoots are transferred from each embryo to maize rooting medium and incubated at 25° C. for 2-3 weeks, until roots develop. The rooted shoots are transplanted to soil in the greenhouse. T1 seeds are produced from plants that exhibit tolerance to the selection agent and that contain a single copy of the T-DNA insert.

Wheat Transformation

Transformation of wheat is performed with the method described by Ishida et al. (1996) Nature Biotech 14(6): 745-50. The cultivar Bobwhite (available from CIMMYT, Mexico) is commonly used in transformation. Immature embryos are co-cultivated with *Agrobacterium tumefaciens* containing the expression vector, and transgenic plants are recovered through organogenesis. After incubation with *Agrobacterium*, the embryos are grown in vitro on callus induction medium, then regeneration medium, containing the selection agent (for example imidazolinone but various selection markers can be used). The Petri plates are incubated in the light at 25° C. for 2-3 weeks, or until shoots develop. The green shoots are transferred from each embryo to rooting medium and incubated at 25° C. for 2-3 weeks, until roots develop. The rooted shoots are transplanted to soil in the greenhouse. T1 seeds are produced from plants that exhibit tolerance to the selection agent and that contain a single copy of the T-DNA insert.

Soybean Transformation

Soybean is transformed according to a modification of the method described in the Texas A&M U.S. Pat. No. 5,164,310. Several commercial soybean varieties are amenable to transformation by this method. The cultivar Jack (available from the Illinois Seed foundation) is commonly used for transformation. Soybean seeds are sterilised for in vitro sowing. The hypocotyl, the radicle and one cotyledon are excised from seven-day old young seedlings. The epicotyl and the remaining cotyledon are further grown to develop axillary nodes.

These axillary nodes are excised and incubated with *Agrobacterium tumefaciens* containing the expression vector. After the cocultivation treatment, the explants are washed and transferred to selection media. Regenerated shoots are excised and placed on a shoot elongation medium. Shoots no longer than 1 cm are placed on rooting medium until roots develop. The rooted shoots are transplanted to soil in the greenhouse. T1 seeds are produced from plants that exhibit tolerance to the selection agent and that contain a single copy of the T-DNA insert.

Rapeseed/Canola Transformation

Cotyledonary petioles and hypocotyls of 5-6 day old young seedling are used as explants for tissue culture and transformed according to Babic et al. (1998, Plant Cell Rep 17: 183-188). The commercial cultivar Westar (Agriculture Canada) is the standard variety used for transformation, but other varieties can also be used. Canola seeds are surface-sterilized for in vitro sowing. The cotyledon petiole explants with the cotyledon attached are excised from the in vitro seedlings, and inoculated with *Agrobacterium* (containing the expression vector) by dipping the cut end of the petiole explant into the bacterial suspension. The explants are then cultured for 2 days on MSBAP-3 medium containing 3 mg/l BAP, 3% sucrose, 0.7% Phytagar at 23° C., 16 hr light. After two days of co-cultivation with *Agrobacterium*, the petiole explants are transferred to MSBAP-3 medium containing 3 mg/l BAP, cefotaxime, carbenicillin, or timentin (300 mg/l) for 7 days, and then cultured on MSBAP-3 medium with cefotaxime, carbenicillin, or timentin and selection agent until shoot regeneration. When the shoots are 5-10 mm in length, they are cut and transferred to shoot elongation medium (MSBAP-0.5, containing 0.5 mg/l BAP). Shoots of about 2 cm in length are transferred to the rooting medium (MS0) for root induction. The rooted shoots are transplanted to soil in the greenhouse. T1 seeds are produced from plants that exhibit tolerance to the selection agent and that contain a single copy of the T-DNA insert.

Alfalfa Transformation

A regenerating clone of alfalfa (*Medicago sativa*) is transformed using the method of (McKersie et al., 1999 Plant Physiol 119: 839-847). Regeneration and transformation of alfalfa is genotype dependent and therefore a regenerating plant is required. Methods to obtain regenerating plants have been described. For example, these can be selected from the cultivar Rangelander (Agriculture Canada) or any other commercial alfalfa variety as described by Brown D C W and A Atanassov (1985. Plant Cell Tissue Organ Culture 4: 111-112). Alternatively, the RA3 variety (University of Wisconsin) has been selected for use in tissue culture (Walker et al., 1978 Am J Bot 65:654-659). Petiole explants are cocultivated with an overnight culture of *Agrobacterium tumefaciens* C58C1 pMP90 (McKersie et al., 1999 Plant Physiol 119: 839-847) or LBA4404 containing the expression vector. The explants are cocultivated for 3 d in the dark on SH induction medium containing 288 mg/L Pro, 53 mg/L thioproline, 4.35 g/L K2SO4, and 100 μm acetosyringinone. The explants are washed in half-strength Murashige-Skoog medium (Murashige and Skoog, 1962) and plated on the same SH induction medium without acetosyringinone but with a suitable selection agent and suitable antibiotic to inhibit *Agrobacterium* growth. After several weeks, somatic embryos are transferred to BOi2Y development medium containing no growth regulators, no antibiotics, and 50 g/L sucrose. Somatic embryos are subsequently germinated on half-strength Murashige-Skoog medium. Rooted seedlings were transplanted into pots and grown in a greenhouse. T1 seeds are produced from plants that exhibit tolerance to the selection agent and that contain a single copy of the T-DNA insert.

Cotton Transformation

Cotton is transformed using *Agrobacterium tumefaciens* according to the method described in U.S. Pat. No. 5,159,135. Cotton seeds are surface sterilised in 3% sodium hypochlorite solution during 20 minutes and washed in distilled water with 500 μg/ml cefotaxime. The seeds are then transferred to SH-medium with 50 μg/ml benomyl for germination. Hypocotyls of 4 to 6 days old seedlings are removed, cut into 0.5 cm pieces and are placed on 0.8% agar. An *Agrobacterium* suspension (approx. 108 cells per ml, diluted from an overnight culture transformed with the gene of interest and suitable selection markers) is used for inoculation of the hypocotyl explants. After 3 days at room temperature and lighting, the tissues are transferred to a solid medium (1.6 g/l Gelrite) with Murashige and Skoog salts with B5 vitamins (Gamborg et al., Exp. Cell Res. 50:151-158 (1968)), 0.1 mg/l 2,4-D, 0.1 mg/l 6-furfurylaminopurine and 750 μg/ml MgCL2, and with 50 to 100 μg/ml cefotaxime and 400-500 μg/ml carbenicillin to kill residual bacteria. Individual cell lines are isolated after two to three months (with subcultures every four to six weeks) and are further cultivated on selective medium for tissue amplification (30° C., 16 hr photoperiod). Transformed tissues are subsequently further cultivated on non-selective medium during 2 to 3 months to give rise to somatic embryos. Healthy looking embryos of at least 4 mm length are transferred to tubes with SH medium in fine vermiculite, supplemented with 0.1 mg/l indole acetic acid, 6 furfurylaminopurine and gibberellic acid. The embryos are cultivated at 30° C. with a photoperiod of 16 hrs, and plantlets at the 2 to 3 leaf stage are transferred to pots with vermiculite and nutrients. The plants are hardened and subsequently moved to the greenhouse for further cultivation.

Example 10

Phenotypic Evaluation Procedure 10.1 Evaluation Setup

Approximately 35 independent TO rice transformants were generated. The primary transformants were transferred from a tissue culture chamber to a greenhouse for growing and harvest of T1 seed. Six events, of which the T1 progeny segregated 3:1 for presence/absence of the transgene, were retained. For each of these events, approximately 10 T1 seedlings containing the transgene (hetero- and homo-zygotes) and approximately 10 T1 seedlings lacking the transgene (nullizygotes) were selected by monitoring visual marker expression. The transgenic plants and the corresponding nullizygotes were grown side-by-side at random positions. Greenhouse conditions were of shorts days (12 hours light), 28° C. in the light and 22° C. in the dark, and a relative humidity of 70%. Plants grown under non-stress conditions are watered at regular intervals to ensure that water and nutrients are not limiting to satisfy plant needs to complete growth and development.

Four T1 events were further evaluated in the T2 generation following the same evaluation procedure as for the T1 generation but with more individuals per event. From the stage of sowing until the stage of maturity the plants were passed several times through a digital imaging cabinet. At each time point digital images (2048×1536 pixels, 16 million colours) were taken of each plant from at least 6 different angles.

Drought Screen

Plants from T2 seeds are grown in potting soil under normal conditions until they approached the heading stage. They were then transferred to a "dry" section where irrigation was withheld. Humidity probes were inserted in randomly chosen pots to monitor the soil water content (SWC). When SWC went below certain thresholds, the plants were automatically re-watered continuously until a normal level was reached again. The plants were then re-transferred again to normal conditions. The rest of the cultivation (plant maturation, seed harvest) was the same as for plants not grown under abiotic stress conditions. Growth and yield parameters are recorded as detailed for growth under normal conditions.

Nitrogen Use Efficiency Screen

Rice plants from T2 seeds were grown in potting soil under normal conditions except for the nutrient solution. The pots were watered from transplantation to maturation with a specific nutrient solution containing reduced N nitrogen (N) content, usually between 7 to 8 times less. The rest of the cultivation (plant maturation, seed harvest) was the same as for plants not grown under abiotic stress. Growth and yield parameters are recorded as detailed for growth under normal conditions.

Salt Stress Screen

Plants are grown on a substrate made of coco fibers and argex (3 to 1 ratio). A normal nutrient solution was used during the first two weeks after transplanting the plantlets in the greenhouse. After the first two weeks, 25 mM of salt (NaCl) was added to the nutrient solution, until the plants were harvested. Seed-related parameters were then measured.

10.2 Statistical Analysis: F Test

A two factor ANOVA (analysis of variants) was used as a statistical model for the overall evaluation of plant phenotypic characteristics. An F test was carried out on all the parameters measured of all the plants of all the events transformed with the gene of the present invention. The F test was carried out to check for an effect of the gene over all the transformation events and to verify for an overall effect of the gene, also known as a global gene effect. The threshold for significance for a true global gene effect was set at a 5% probability level for the F test. A significant F test value points to a gene effect, meaning that it is not only the mere presence or position of the gene that is causing the differences in phenotype.

Because two experiments with overlapping events were carried out, a combined analysis was performed. This is useful to check consistency of the effects over the two experiments, and if this is the case, to accumulate evidence from both experiments in order to increase confidence in the conclusion. The method used was a mixed-model approach that takes into account the multilevel structure of the data (i.e. experiment-event-segregants). P values were obtained by comparing likelihood ratio test to chi square distributions.

10.3 Parameters Measured

Biomass-Related Parameter Measurement

From the stage of sowing until the stage of maturity the plants were passed several times through a digital imaging cabinet. At each time point digital images (2048×1536 pixels, 16 million colours) were taken of each plant from at least 6 different angles.

The plant aboveground area (or leafy biomass) was determined by counting the total number of pixels on the digital images from aboveground plant parts discriminated from the background. This value was averaged for the pictures taken on the same time point from the different angles and was converted to a physical surface value expressed in square mm by calibration. Experiments show that the aboveground plant area measured this way correlates with the biomass of plant parts above ground. The above ground area is the area measured at the time point at which the plant had reached its maximal leafy biomass. The early vigour is the plant (seedling) aboveground area three weeks post-germination. Increase in root biomass is expressed as an increase in total root biomass (measured as maximum biomass of roots observed during the lifespan of a plant); or as an increase in the root/shoot index (measured as the ratio between root mass and shoot mass in the period of active growth of root and shoot).

Early vigour was determined by counting the total number of pixels from aboveground plant parts discriminated from the background. This value was averaged for the pictures taken on the same time point from different angles and was converted to a physical surface value expressed in square mm by calibration. The results described below are for plants three weeks post-germination.

Seed-Related Parameter Measurements

The mature primary panicles were harvested, counted, bagged, barcode-labelled and then dried for three days in an oven at 37° C. The panicles were then threshed and all the seeds were collected and counted. The filled husks were separated from the empty ones using an air-blowing device. The empty husks were discarded and the remaining fraction was counted again. The filled husks were weighed on an analytical balance. The number of filled seeds was determined by counting the number of filled husks that remained after the separation step. The total seed yield was measured by weighing all filled husks harvested from a plant. Total seed number per plant was measured by counting the number of husks harvested from a plant. Thousand Kernel Weight (TKW) is extrapolated from the number of filled seeds counted and their total weight. The Harvest Index (HI) in the present invention is defined as the ratio between the total seed yield and the above ground area ($mm^2$), multiplied by a factor $10^6$. The total number of flowers per panicle as defined in the present invention is the ratio between the total number of seeds and the number of mature primary panicles. The seed fill rate as defined in the present invention is the proportion (expressed as a %) of the number of filled seeds over the total number of seeds (or florets).

Example 11

Results of the Phenotypic Evaluation of the Transgenic Plants 11.1. Root Hairless 1 (RHL1)

The results of the evaluation of transgenic rice plants in T2 generation expressing coding region of an Arath_RHL1 nucleic acid (SEQ ID NO: 1) under the growth conditions of nitrogen limitation of Example 8 are presented below. An increase of at least 5% was observed for emergence vigour (early vigour, EmerVigor), total seed yield (totalweightseeds), number of filled seeds (Nr filled seeds), harvest index (harvestindex), root biomass (Rootmax) and the number of total seeds on a plant (nrtotalseed) (Table F1).

TABLE F1

Evaluation of transgenic plants expressing the Arath_RHL1 gene under nitrogen limitation growth conditions.

| Parameter | % increase in transgenic compared to control plant |
|---|---|
| EmerVigor | 19 |
| RootMax | 7.6 |
| totalweightseeds | 17 |
| Nr filled seeds | 16 |
| harvestindex | 12 |
| nrtotalseed | 11 |

The results of the evaluation of transgenic rice plants in T1 generation expressing the coding region of Orysa_RHL1 nucleic acid (SEQ ID NO: 9) from the constitutive promoter GOS2 (SEQ ID NO: 39) under the non-stress presented below (Table F2).

TABLE F2

Evaluation of transgenic plants expressing an Orysa_RHL1 nucleic acid under non-stress conditions.

| Parameter | % increase in transgenic compared to control plant |
|---|---|
| AreaMax | 8.1 |
| TimetoFlower | 1.25 |
| RootMax | 3.6 |
| totalwgseeds | 16.19 |
| nrfilledseed | 14.9 |
| fillrate | 5.7 |
| harvestindex | 10.0 |
| HeightMax | 2.6 |
| GNbfFlow | 7.4 |
| nrtotalseed | 8.6 |

The results of the evaluation of transgenic rice plants in T1 generation expressing the coding region of Orysa_RHL1 nucleic acid (SEQ ID NO: 9) driven from the root specific promoter Rcc3 (SEQ ID NO: 40) grown under nitrogen limiting conditions as specified above in the Nitrogen use efficiency screen are shown in Table F3. EmerVigor (also refer to as Early vigour) is a yield trait directly correlated with the vigour of the plant in particular at early, seedling stage of development.

TABLE F3

Evaluation of transgenic plants expressing an Orysa_RHL1 nucleic acid under nitrogen limiting conditions.

| Parameter | % increase in transgenic compared to control plant |
|---|---|
| EmerVigor | 16.6 |
| totalwgseeds | 12 |
| nrfilledseed | 15 |

11.2. Transglutaminases (TGases)

The results of the evaluation of T1 and T2 generation transgenic rice plants expressing the nucleic acid sequence encoding a TGase polypeptide as represented by SEQ ID NO: 45, under the control of a seed-specific promoter, and grown under normal growth conditions, are presented below.

There was a significant increase in the early vigor, in the aboveground biomass, in the total seed yield per plant, in the total number of seeds, in the number of filled seeds, in the seed filling rate, and in the harvest index of the transgenic plants compared to corresponding nullizygotes (controls), as shown in Table F4.

TABLE F4

Results of the evaluation of T1 and T2 generation transgenic rice plants expressing the nucleic acid sequence encoding a TGase polypeptide as represented by SEQ ID NO: 45, under the control of a promoter for seed-specific expression.

| Trait | Overall average % increase in 8 events in the T1 generation | Overall average % increase in 4 events in the T2 generation |
|---|---|---|
| Total seed yield per plant | 26% | 15% |
| Total number of filled seeds | 27% | 14% |
| Harvest index | 26% | 14% |

11.3. Tryptichon (TRY-Like)

The evaluation of transgenic rice plants expressing a TRY-like nucleic acid under control of the RCc3 promoter, and grown under conditions of reduced nitrogen availability, revealed an increase of more than 5% for emergence vigour (early vigour), fill rate, harvest index, and total seed yield. These increases were observed in T1 generation plants as well as in T2 generation plants.

The results of the evaluation of transgenic rice plants, expressing a nucleic acid encoding the TRY polypeptide of SEQ ID NO: 76 under control of the constitutive promoter, and grown under non-stress conditions in the T1 and the T2 generation, are presented below in Table E and F respectively. When grown under non-stress conditions, an increase of at least 5% was observed in T1 for seed yield (total weight of seeds, number of filled seeds, number of total seeds).

TABLE F5

Data summary for transgenic rice plants transformed with the pGOS2::TRY construct; for each parameter, the overall percent increase is shown for the T1 generation, for each parameter the p-value is ≤0.05.

| Parameter | Overall increase |
|---|---|
| Nr total seeds | 8.7 |
| totalwgseeds | 17.3 |
| nrfilledseed | 14.5 |

In the T2 generation, a strong increase 5%) was found for above ground biomass (AreaMax and firstpan), early vigour, and seed yield; details are given in Table F:

TABLE F6

Data summary for transgenic rice plants transformed with the pGOS2::TRY construct; for each parameter, the overall percent increase is shown for the T2 generation, for each parameter the p-value is ≤0.05.

| Parameter | Overall increase |
|---|---|
| AreaMax | 5.0 |
| EmerVigor | 20.2 |
| firstpan | 8.3 |
| totalwgseeds | 8.8 |
| nrfilledseed | 7.5 |

11.4. Brassinazole Resistant1 (BZR1)

The results of the evaluation of transgenic rice plants expressing the coding region of the BZR nucleic acid of SEQ ID NO: 1 under non-stress conditions are presented below. An increase of at least 5% was observed for total seed yield, the number of filled seeds per plant, the seed filling rate and the harvest index, and of more than 2.5% for thousand kernel weight compared to control (corresponding nullyzogotes) plants (Table F7).

TABLE F7

| Parameter | Total Seed weight | Number of filled seed | Seed filling rate | Harvest Index | TKW |
|---|---|---|---|---|---|
| % increase in the transgenic compared to the control plant | 17.5 | 14.4 | 5.5 | 11.4 | 3.0 |

The invention claimed is:

1. A method for enhancing seed yield-related traits in plants relative to corresponding wild-type plants, comprising (a) increasing expression in a plant of a nucleic acid encoding a Root Hairless polypeptide by introducing and expressing said nucleic acid in said plant; and (b) selecting for plants having enhanced seed yield-related traits relative to corresponding wild-type plants, wherein the nucleic acid encoding a Root Hairless polypeptide is selected from the group consisting of:

(i) a nucleic acid encoding a polypeptide comprising the amino acid sequence of SEQ ID NO: 2 or SEQ ID NO: 10;

(ii) a nucleic acid comprising the polynucleotide of SEQ ID NO: 1 or SEQ ID NO: 9;

(iii) a nucleic acid encoding a polypeptide comprising an amino acid sequence having at least 80% sequence identity to the amino acid sequence of SEQ ID NO: 2 or SEQ ID NO: 10; and (iv) a nucleic acid capable of hybridizing to the complement of the polynucleotide of the polynucleotide of SEQ ID NO: 1 or SEQ ID NO: 9 under high stringency conditions comprising hybridization at 65° C. in 1×SSC, or at 42° C. in 1×SSC and 50% formamide, followed by washing at 65° C. in 0.3×SSC.

2. The method according to claim 1, wherein said Root Hairless polypeptide comprises one or more of the following:

(i) a motif having at least 80% sequence identity to the amino acid sequence of Motif 1: [IV]R[RK][KG][SG]QRK[NS][RK][FY]LFSFPGLLAP (SEQ ID NO: 29);

(ii) a motif having at least 80% sequence identity to the amino acid sequence of Motif 2: SGG[KR][IV]G[ED]L[KA]DL[GD]TKNP[ILV]LYLDFPQG[RQ]MKL] (SEQ ID NO: 30);

(iii) a motif having at least 80% sequence identity to the amino acid sequence of Motif 3: TP[VS]RQSARTAGKK[FL][KN][FY][AT]ExSS (SEQ ID NO: 31);

(iv) a motif having at least 80% sequence identity to the amino acid sequence of Motif 4: GTK[ED]ENPEE[LA][RK]L[DE]FPKE[LF]Q[ENQ][GD] (SEQ ID NO: 32);

(v) a motif having at least 80% sequence identity to the amino acid sequence of Motif 5: [SN][GN][NL]L[LQV][SR][EDG]xP[AS][KA]PR[SA][APS]LAPSK[TAG]VL[KR][HL][HQ]G[KR]D (SEQ ID NO: 33);

(vi) a motif having at least 80% sequence identity to the amino acid sequence of Motif 6: HA[ED][CY]DFKGGAGAA[CS]D[ES][KA]Q (SEQ ID NO: 34);

(vii) a motif having at least 80% sequence identity to the amino acid sequence of Motif 7: [KSN][KEP]P[GEK][EKT][KTE][YT][VT][EG][EPST][ELQ]SP[KE][IT][ED][SLV][ED][DI][DV][LS]S[ED][DE][SD][NDS][LD]K[DK] (SEQ ID NO: 35);

(viii) a motif having at least 80% sequence identity to the amino acid sequence of Motif 8: KG[PA]AAKKQRASP[EM][EA]K[HQ]P[TA]G[KI]K (SEQ ID NO: 36).

3. The method according to claim 1, wherein said Root Hairless polypeptide comprises the amino acid sequence of SEQ ID NO: 2 or SEQ ID NO: 10.

4. The method according to claim 1, wherein said enhanced seed yield-related traits are obtained under cultivation conditions of nitrogen deficiency.

5. The method according to claim 1, wherein said nucleic acid encoding a Root Hairless polypeptide is operably linked to a constitutive promoter, a GOS2 promoter, or a GOS2 promoter from rice.

6. The method according to claim 1, wherein said nucleic acid encoding a Root Hairless polypeptide is of plant origin, from a dicotyledonous plant, from the family Brassicaceae, or from *Arabidopsis thaliana.*

7. A plant or plant part obtainable by the method according to claim 1, wherein said plant or plant part comprises a recombinant nucleic acid encoding a Root Hairless polypeptide, and wherein said recombinant nucleic acid comprises the polynucleotide of SEQ ID NO: 1 or SEQ ID NO: 9.

8. A method for making plants having an increased seed yield-related trait and/or increased emergence vigor relative to corresponding wild-type plants, comprising:

(a) transforming a plant, plant part, or plant cell with a construct comprising:

(i) a nucleic acid encoding a Root Hairless polypeptide;

(ii) one or more control sequences heterologous to, operably linked to, and capable of driving expression of the nucleic acid sequence of (i); and optionally (iii) a transcription termination sequence, wherein the nucleic acid encoding a Root Hairless polypeptide comprises the polynucleotide of SEQ ID NO: 1 or SEQ ID NO: 9; and (b) selecting for plants having an increased seed yield-related trait and/or increased emergence vigor relative to corresponding wild-type plants.

9. The method of claim 1, wherein the method comprises cultivating the plant under conditions promoting plant growth and development.

10. A transgenic plant having an increased seed yield-related trait and/or increased emergence vigor relative to a corresponding wild-type plant, resulting from increased expression of a nucleic acid encoding a Root Hairless polypeptide operably linked to a heterologous promoter, or a transgenic plant cell derived from said transgenic plant, wherein the nucleic acid encoding a Root Hairless polypeptide comprises the polynucleotide of SEQ ID NO: 1 or SEQ ID NO: 9.

11. The transgenic plant according to claim 10, or a transgenic plant cell derived thereof, wherein said plant is a crop plant, a monocot, a cereal, rice, maize, wheat, barley, millet, rye, triticale, sorghum or oats.

12. Harvestable parts of the transgenic plant according to claim 11, wherein said harvestable parts are shoot biomass and/or seeds.

13. Products derived from the transgenic plant according to claim 11 and/or from harvestable parts of said transgenic plant, wherein said products comprise the nucleic acid encoding a Root Hairless polypeptide comprising the polynucleotide of SEQ ID NO: 1 or SEQ ID NO: 9 operably linked to a heterologous promoter.

14. The method of claim 1, wherein the nucleic acid encoding a Root Hairless polypeptide is selected from the group consisting of:

(i) a nucleic acid encoding a polypeptide comprising the amino acid sequence of SEQ ID NO: 2 or SEQ ID NO: 10;

(ii) a nucleic acid comprising the polynucleotide of SEQ ID NO: 1 or SEQ ID NO: 9; and (iii) a nucleic acid comprising a polynucleotide having at least 90% sequence identity to the polynucleotide of SEQ ID NO: 1 or SEQ ID NO: 9.

15. The method of claim 1, wherein the nucleic acid encoding a Root Hairless polypeptide is capable of hybridizing to the complement of the polynucleotide of the polynucleotide of SEQ ID NO: 1 or SEQ ID NO: 9 under high stringency conditions comprising hybridization at 65° C. in 1×SSC, or at 42° C. in 1×SSC and 50% formamide, followed by washing at 65° C. in 0.3×SSC.

16. The method of claim 1, wherein the plants are monocotyledonous plants.

17. The method of claim 1, wherein the nucleic acid encoding a Root Hairless polypeptide is operably linked to a constitutive promoter or a root-specific promoter, and wherein said promoter is heterologous to said nucleic acid.

18. The method of claim 1, wherein the nucleic acid encoding a Root Hairless polypeptide is operably linked to a GOS2 promoter or an RCc3 promoter.

19. The method of claim 1, wherein the seed yield-related trait is number of filled seed and/or total seed weight.

20. The plant or plant part of claim 7, wherein the plant is a monocotyledonous plant and the plant part is from a monocotyledonous plant.

21. The plant part of claim 7, wherein the plant part is a seed.

* * * * *